US009309240B2

(12) United States Patent
Blench et al.

(10) Patent No.: US 9,309,240 B2
(45) Date of Patent: Apr. 12, 2016

(54) PYRAZOLOPYRIDINE COMPOUNDS, COMPOSITIONS AND METHODS OF USE

(71) Applicant: F. HOFFMANN-LA ROCHE AG, Basel (CH)

(72) Inventors: Toby Blench, Essex (GB); Simon Goodacre, Essex (GB); Yingjie Lai, Cupertino, CA (US); Jun Liang, Palo Alto, CA (US); Calum Macleod, Essex (GB); Steven Magnuson, Dublin, CA (US); Vickie Tsui, Burlingame, CA (US); Karen Williams, Essex (GB); Birong Zhang, Union City, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 13/896,024

(22) Filed: May 16, 2013

(65) Prior Publication Data

US 2013/0252941 A1 Sep. 26, 2013

Related U.S. Application Data

(63) Continuation of application No. PCT/EP2011/070313, filed on Nov. 17, 2011.

(60) Provisional application No. 61/415,782, filed on Nov. 19, 2010.

(51) Int. Cl.
C07D 471/04 (2006.01)
C07D 487/04 (2006.01)

(52) U.S. Cl.
CPC ............ *C07D 471/04* (2013.01); *C07D 487/04* (2013.01)

(58) Field of Classification Search
CPC ........................ C07D 471/04; C07D 487/04
See application file for complete search history.

(56) References Cited

U.S. PATENT DOCUMENTS

| 4,603,139 | A | 7/1986 | King |
| 2004/0092520 | A1 | 5/2004 | Griffith |
| 2004/0097485 | A1 | 5/2004 | Burkitt et al. |
| 2005/0245546 | A1 | 11/2005 | Cristalli |
| 2009/0306071 | A1 | 12/2009 | Young et al. |
| 2010/0160288 | A1 | 6/2010 | Astles et al. |

FOREIGN PATENT DOCUMENTS

| EP | 1 221 444 A1 | 7/2002 |
| WO | 98/14451 A1 | 4/1998 |
| WO | 2004/037823 A1 | 5/2004 |
| WO | 2007/019344 A1 | 2/2007 |
| WO | 2007/019346 A1 | 2/2007 |
| WO | 2007/039797 A1 | 4/2007 |
| WO | 2009/042607 | 4/2009 |
| WO | 2009/061453 A1 | 5/2009 |
| WO | 2009/061453 A8 | 5/2009 |
| WO | 2009/073153 A2 | 6/2009 |
| WO | 2010/019762 A1 | 2/2010 |
| WO | 2010/038060 | 4/2010 |
| WO | 2010/089292 A1 | 8/2010 |
| WO | 2010/094647 A1 | 8/2010 |
| WO | 2011/048082 A1 | 4/2011 |
| WO | 2011/113802 A2 | 9/2011 |
| WO | 2011/134831 A1 | 11/2011 |

OTHER PUBLICATIONS

Sheridan, R.P. "The Most Common Chemical Replacements in Drug-Like Compounds" J. Chem. Inf. Comput. Sci., 2002, vol. 42, pp. 103-108.*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
Anerson et al., "Chemistry of the adenosine monophosphate site of rabbit muscle glycogen phosphorylase. I. Hydrophobic nature and affinity labeling of the allosteric site" Biochemistry 12(10):1895-900 ( 1973).
Barraclough et al., "Inotropic 'A' ring substituted sulmazole and isomazole analogues" J Med Chem. 33(8):2231-9 ( 1990).
Borrmann et al., "Structure-activity relationships of adenine and deazaadenine derivatives as ligands for adenine receptors, a new purinergic receptor family" J Med Chem. 52:5974-89 ( 2009).
Cartwright et al., "Imidazopyridine and pyrimidinopyridine systems from perfluorinated pyridine derivatives" Tetrahedron 63(30) (Jun. 13, 2007).
Database Registry [Online] Chemical Abstracts Service, Columbus, Ohio, US; Jun. 10, 2008, 'Not yet assigned', Database accession No. 1026925-65-4 the whole document.
Database Registry [Online] Chemical Abstracts Service, Columbus, Ohio, US; Aug. 29, 2004, '9H-Purine, 9-(4-cholorphenyl)-8-(2-fluorophenyl)-6-(1-pyrrolidinyl)-', Database accession No. 734532-63-9 the whole document.

(Continued)

Primary Examiner — Kendra D Carter
(74) Attorney, Agent, or Firm — Tamara A. Kale

(57) ABSTRACT

The invention provides compounds of Formula I, stereoisomers or pharmaceutically acceptable salts thereof, wherein A, X, $R^1$, $R^2$, $R^4$ and $R^5$ are defined herein, a pharmaceutical composition that includes a compound of Formula I and a pharmaceutically acceptable carrier, adjuvant or vehicle, and methods of using the compound or composition in therapy.

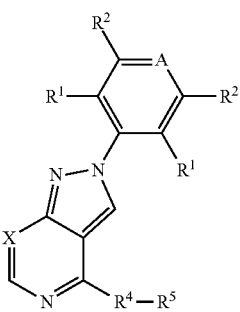

I

16 Claims, No Drawings

(56) References Cited

OTHER PUBLICATIONS

Database Registry [Online] Chemical Abstracts Service, Columbus, Ohio, US; Jun. 8, 2008, 'Not yet assigned', Database accession No. 1026421-43-1 the whole document.
Database Registry [Online] Chemical Abstracts Service, Columbus, Ohio, US; Nov. 10, 2004, '3-Azabicyclo[3.1.0]hexan-6-amine, 3-[9-(4-chlorophenyl)-8-(2,3-dichlorophenyl 1)-9H-purin-6-yl]-N,N-dimethyl-, (1.alpha.-5.alpha.,6.beta.)-', Database accession No. 777853-55-1 the whole document.
Database Registry [Online] Chemical Abstracts Service, Columbus, Ohio, US; Apr. 4, 2003, '9H-Purin-6-amine, 8-(2,4-dichlorophenyl)-', Database accession No. 501657-71-2 the whole document.
Database Registry [Online] Chemical Abstracts Service, Columbus, Ohio, US; Jun. 10, 2008, 'Not yet assigned', Database accession No. 1027012-36-7 the whole document.
Database Registry [Online] Chemical Abstracts Service, Columbus, Ohio, US; Jun. 13, 2008, 'Not yet assigned', Database accession No. 1027914-11-9 the whole document.
Database Registry [Online]Chemical Abstracts Service, Columbus, Ohio, US; Jul. 12, 2818 (2810-87-12), '9H-Purine, 8-(2-chlorophenyl)-6-(4-methyl-1-piperazin yl)-9-[(tetrahydro-2H-piran-4-yl)methyl]-' Database accession No. 1231299-64-1 the whole document.
Database Registry [Online] Chemical Abstracts Service, Columbus, Ohio, US; Sep. 14, 2010, '1H-Imidazo[4,5-c]pyridin-4-amine, 2-(2-clorophenyl)-N-[3-methoxy-4-(3-methyl-1H-1,2,4-triazol-1-yl]phenyl]-1-(methylethyl=-', Database accession No. 1240783-28-1 the whole document.
Geldenhuys et al., "Virtual screening to identify novel antagonists for the G protein-coupled NK3 receptor" J Med Chem. 53:8080-8 (Nov. 2010).
Griffith et al., "Discovery of 1-[9-(4-chlorophenyl)-8-(2-chlorophenyl)-9H-purin-6-yl]-4-ethylaminopiperidine-4-carboxylic acid amide hydrochloride (CP-945,598), a novel, potent, and selective cannabinoid type 1 receptor antagonist" J Med Chem. 52(2):234-7 (Jan. 22, 2009).
Hasnik et al., "Cross-Coupling reactions of Halopurines with Aryl- and alkyltrifluoroborates; The Scope and Limitations in the Synthesis of Modified Purines" Synthesis 9:1309-17 (Mar. 25, 2009).

International Preliminary Report on Patentability for International Patent Application No. PCT/EP2011/065892.
International Preliminary Report on Patentability for International Patent Application No. PCT/EP2011/070313.
International Preliminary Report on Patentability for International Patent Application No. PCT/EP2011/053826.
International Search Report for International Patent Application No. PCT/EP2012/068380.
MacNaught et al., Other Database, (IUPAC ED—Compendium of Chemical Terminology, Blackwell Science, Oxford [U.A.], XP002585005, ISBN: 978-0-86542-684-9), pp. 1 Jan. 1, 1997.
McCloskey et al., "New insights into the design of inhibitors of human S-adenosylmethionine decarboxylase: studies of adenine C8 substitution in structural analogues of S-adenosylmethionine" J Med Chem. 52(5):1388-407 ( 2009).
Medebielle et al., "Electrochemically induced SRNI substitution of fluorinated aryl halides. Application to the synthesis of fluorinated-aryl heterocycles" Electrochimica Acta 42(13):2049-55 ( 1997).
Millen et al., "Computational and experimental evidence for the structural preference of phenolic C-8 purine adducts" J Phys Chem A 112:3742-3753 ( 2008).
Ragan et al., "Development of a practical and Efficient Synthesis of CP-945,598-02,a CB1 Antagonist for the Treatment of Obesity" Organic Process Research and Development 13(2):186-197 (Dec. 22, 2008).
Sahnoun et al., "A site selective C—H arylation of free-(NH2) adenines with aryl chlorides: application to the synthesis of 6,8-disubstituted adenines" Org Biomol Chem. 7(20):4271-8 (Aug. 14, 2009).
Sahnoun et al., "Microwave-assisted Pd(OH)2-catalyzed direct C—H arylation of free-(NH2) adenines with aryl halides" Tetrahedron Letters 49(51):7279-83 (Dec. 15, 2008).
Storr et al., "Pd(0)/Cu(I)-mediated direct arylation of 2'-deoxyadenosines: mechanistic role of Cu(I) and reactivity comparisons with related purine nucleosides" J Org Chem 74(16):5810-21 ( 2009).
Young et al., "Purine derivatives as competitive inhibitors of human erythrocyte membrane phosphatidylinositol 4-kinase" J Med Chem. 33(8):2073-80 (Aug. 1990).
Tadashi et al., "Syntheses of Fused Heterocycles via cycloaddition of Hetaryne Studies on Heteroaromaticity, Part XLVII" Bulletin of the Chemical Society of Japan 44(3) (Jan. 1, 1971).

* cited by examiner

PYRAZOLOPYRIDINE COMPOUNDS, COMPOSITIONS AND METHODS OF USE

CROSS-REFERENCE TO RELATED APPLICATIONS

This application is a continuation application of International Application No. PCT/EP2011/070313, filed Nov. 17, 2011, which claims the benefit of U.S. Provisional Application Ser. No. 61/415,782, filed Nov. 19, 2010, each of which is incorporated by reference herein in its entirety for all purposes.

FIELD OF THE INVENTION

The present invention relates to organic compounds useful for therapy and/or prophylaxis in a patient, and in particular to inhibitors of TYK2 kinase useful for treating diseases mediated by TYK2 kinase.

BACKGROUND OF INVENTION

Cytokine pathways mediate a broad range of biological functions, including many aspects of inflammation and immunity. Janus kinases (JAK), including JAK1, JAK2, JAK3 and TYK2 are cytoplasmic protein kinases that associate with type I and type II cytokine receptors and regulate cytokine signal transduction. Cytokine engagement with cognate receptors triggers activation of receptor associated JAKs and this leads to JAK-mediated tyrosine phosphorylation of signal transducer and activator of transcription (STAT) proteins and ultimately transcriptional activation of specific gene sets. JAK1, JAK2 and TYK2 exhibit broad patterns of gene expression, while JAK3 expression is limited to leukocytes. Cytokine receptors are typically functional as heterodimers, and as a result, more than one type of JAK kinase is usually associated with cytokine receptor complexes. The specific JAKs associated with different cytokine receptor complexes have been determined in many cases through genetic studies and corroborated by other experimental evidence.

JAK1 is functionally and physically associated with the type I interferon (e.g., IFNalpha), type II interferon (e.g., IFNgamma), IL-2 and IL-6 cytokine receptor complexes. JAK1 knockout mice die perinatally due to defects in LIF receptor signaling. Characterization of tissues derived from JAK1 knockout mice demonstrated critical roles for this kinase in the IFN, IL-10, IL-2/IL-4, and IL-6 pathways. A humanized monoclonal antibody targeting the IL-6 pathway (Tocilizumab) was recently approved by the European Commission for the treatment of moderate-to-severe rheumatoid arthritis.

Biochemical and genetic studies have shown an association between JAK2 and single-chain (e.g., EPO), IL-3 and interferon gamma cytokine receptor families. Consistent with this, JAK2 knockout mice die of anemia. Kinase activating mutations in JAK2 (e.g., JAK2 V617F) are associated with myeloproliferative disorders (MPDs) in humans.

JAK3 associates exclusively with the gamma common cytokine receptor chain, which is present in the IL-2, IL-4, IL-7, IL-9, IL-15 and IL-21 cytokine receptor complexes. JAK3 is critical for lymphoid cell development and proliferation and mutations in JAK3 result in severe combined immunodeficiency (SCID). Based on its role in regulating lymphocytes, JAK3 and JAK3-mediated pathways have been targeted for immunosuppressive indications (e.g., transplantation rejection and rheumatoid arthritis).

TYK2 associates with the type I interferon (e.g., IFNalpha), IL-6, IL-10, IL-12 and IL-23 cytokine receptor complexes. Consistent with this, primary cells derived from a TYK2 deficient human are defective in type I interferon, IL-6, IL-10, IL-12 and IL-23 signaling. A fully human monoclonal antibody targeting the shared p40 subunit of the IL-12 and Il-23 cytokines (Ustekinumab) was recently approved by the European Commission for the treatment of moderate-to-severe plaque psoriasis. In addition, an antibody targeting the IL-12 and IL-23 pathways underwent clinical trials for treating Crohn's Disease.

SUMMARY OF INVENTION

One embodiment includes a compound of Formula I:

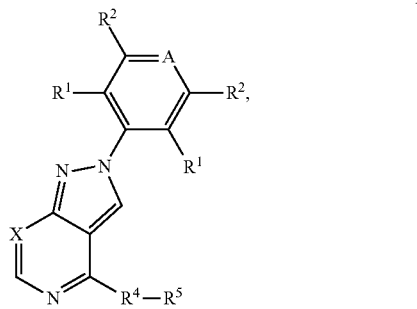

and stereoisomers, tautomers, solvates, prodrugs and pharmaceutically acceptable salts thereof, wherein A, X, $R^1$, $R^2$, $R^4$ and $R^5$ are defined herein.

Another embodiment includes a pharmaceutical composition that includes a compound of Formula I, stereoisomers, tautomers, solvates, prodrugs or pharmaceutically acceptable salts thereof, and a pharmaceutically acceptable carrier, adjuvant or vehicle.

Another embodiment includes a method of inhibiting TYK2 kinase activity in a cell, comprising introducing into said cell an amount effective to inhibit said kinase of a compound of Formula I, stereoisomers, tautomers, solvates, prodrugs or pharmaceutically acceptable salts thereof.

Another embodiment includes a method of treating or lessening the severity of a disease or condition responsive to the inhibition of TYK2 kinase activity in a patient. The method includes administering to the patient a therapeutically effective amount of a compound of Formula I, stereoisomers, tautomers, solvates, prodrugs or pharmaceutically acceptable salts thereof.

Another embodiment includes use of a compound of Formula I, stereoisomers, tautomers, solvates, prodrugs or pharmaceutically acceptable salts thereof, in therapy.

Another embodiment includes a compound of Formula I, stereoisomers, tautomers, solvates, prodrugs or pharmaceutically acceptable salts thereof, in therapy.

Another embodiment includes use of a compound of Formula I, stereoisomers, tautomers, solvates, prodrugs or pharmaceutically acceptable salts thereof, in manufacturing a medicament for treating a disease responsive to the inhibition of TYK2 kinase.

Another embodiment includes a compound of Formula I, stereoisomers, tautomers, solvates, prodrugs or pharmaceutically acceptable salts thereof, for the treatment a disease responsive to the inhibition of TYK2 kinase.

Another embodiment includes use of a compound of Formula I, stereoisomers, tautomers, solvates, prodrugs or pharmaceutically acceptable salts thereof, in the treatment of an immunological or inflammatory disease.

Another embodiment includes methods of preparing a compound of Formula I, stereoisomers, tautomers, solvates, prodrugs or pharmaceutically acceptable salts thereof.

Another embodiment includes a kit for treating a disease or disorder responsive to the inhibition of TYK2 kinase. The kit includes a first pharmaceutical composition comprising a compound of Formula I, stereoisomers, tautomers, solvates, prodrugs or pharmaceutically acceptable salts thereof and instructions for use

DETAILED DESCRIPTION OF THE INVENTION

Reference will now be made in detail to certain embodiments, examples of which are illustrated in the accompanying structures and formulas. While the invention will be described in conjunction with the enumerated embodiments, the invention is intended to cover all alternatives, modifications, and equivalents, which may be included within the scope of the present invention as defined by the claims. One skilled in the art will recognize methods and materials similar or equivalent to those described herein, which could be used in the practice of the present invention.

DEFINITIONS

The term "alkyl" refers to a saturated linear or branched-chain monovalent hydrocarbon radical, wherein the alkyl radical may be optionally substituted independently with one or more substituents described herein. In one example, the alkyl radical is one to eighteen carbon atoms ($C_1$-$C_{18}$). In other examples, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. $C_0$ refers to a bond. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl and 1-octyl.

The term "alkenyl" refers to linear or branched-chain monovalent hydrocarbon radical with at least one site of unsaturation, i.e., a carbon-carbon double bond, wherein the alkenyl radical may be optionally substituted independently with one or more substituents described herein, and includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—$CH=CH_2$), prop-1-enyl (—$CH=CHCH_3$), prop-2-enyl (—$CH_2CH=CH_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The term "alkynyl" refers to a linear or branched monovalent hydrocarbon radical with at least one site of unsaturation, i.e., a carbon-carbon, triple bond, wherein the alkynyl radical may be optionally substituted independently with one or more substituents described herein. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl (—$C\equiv CH$), prop-1-ynyl (—$C\equiv CCH_3$), prop-2-ynyl (propargyl, —$CH_2C\equiv CH$), but-1-ynyl, but-2-ynyl and but-3-ynyl.

"Alkylene" refers to a saturated, branched or straight chain hydrocarbon group having two monovalent radical centers derived by the removal of two hydrogen atoms from the same or two different carbon atoms of a parent alkane. In one example, the divalent alkylene group is one to eighteen carbon atoms ($C_1$-$C_{18}$). In other examples, the divalent alkylene group is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. Example alkylene groups include methylene (—$CH_2$—), 1,1-ethyl (—$CH(CH_3)$—), (1,2-ethyl (—$CH_2CH_2$—), 1,1-propyl (—$CH(CH_2CH_3)$—), 2,2-propyl (—$C(CH_3)_2$—), 1,2-propyl (—$CH(CH_3)CH_2$—), 1,3-propyl (—$CH_2CH_2CH_2$—), 1,1-dimethyleth-1,2-yl (—$C(CH_3)_2CH_2$—), 1,4-butyl (—$CH_2CH_2CH_2CH_2$—), and the like.

"Alkenylene" refers to an unsaturated, branched or straight chain hydrocarbon group having two monovalent radical centers derived by the removal of two hydrogen atoms from the same or two different carbon atoms of a parent alkene. In one example, the alkenylene group is two to eighteen carbon atoms ($C_2$-$C_{18}$). In other examples, the alkenylene group is $C_2$-$C_{12}$, $C_2$-$C_{10}$, $C_2$-$C_8$, $C_2$-$C_6$ or $C_2$-$C_3$. Example alkenylene groups include: 1,2-ethylene (—$CH=CH$—).

"Alkynylene" refers to an unsaturated, branched or straight chain hydrocarbon group having two monovalent radical centers derived by the removal of two hydrogen atoms from the same or two different carbon atoms of a parent alkyne. In one example, the alkynylene radical is two to eighteen carbon atoms ($C_2$-$C_{18}$). In other examples, the alkynylene radical is $C_2$-$C_{12}$, $C_2$-$C_{10}$, $C_2$-$C_8$, $C_2$-$C_6$ or $C_2$-$C_3$. Example alkynylene radicals include: acetylene (—$C\equiv C$—), propargyl (—$CH_2C\equiv C$—), and 4-pentynyl (—$CH_2CH_2CH_2C\equiv C$—).

"Cycloalkyl" refers to a non-aromatic, saturated or partially unsaturated hydrocarbon ring group wherein the cycloalkyl group may be optionally substituted independently with one or more substituents described herein. In one example, the cycloalkyl group is 3 to 12 carbon atoms ($C_3$-$C_{12}$). In other examples, cycloalkyl is $C_3$-$C_8$, $C_3$-$C_{10}$ or $C_5$-$C_{10}$. In other examples, the cycloalkyl group, as a monocycle, is $C_3$-$C_4$, $C_3$-$C_6$ or $C_5$-$C_6$. In another example, the cycloalkyl group, as a bicycle, is $C_7$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane. In another example, the cycloalkyl, as a spiro, is $C_5$-$C_{12}$. Examples of spiro cycloalkyl include, but are not limited to, spiro[2.2]pentane, spiro[2.3]hexane, spiro[2.4]heptane, spiro

[2.5]octane, spiro[3.3]heptane, spiro[3.4]octane, spiro[3.5]nonane, spiro[4.4]nonane and spiro[4.5]decane.

"Aryl" refers to a cyclic aromatic hydrocarbon group optionally substituted independently with one or more substituents described herein. In one example, the aryl group is 6-20 carbon atoms ($C_6$-$C_{20}$). In another example, the aryl group is $C_6$-$C_{10}$. In another example, the aryl group is a $C_6$ aryl group. Aryl includes bicyclic groups comprising an aromatic ring with a fused non-aromatic or partially saturated ring.

Example aryl groups include, but are not limited to, phenyl, naphthalenyl, anthracenyl, indenyl, indanyl, 1,2-dihydronapthalenyl and 1,2,3,4-tetrahydronapthyl. In one example, aryl includes phenyl. Substituted phenyl or substituted aryl means a phenyl group or aryl group substituted with one, two, three, four or five, for example 1-2, 1-3 or 1-4 substituents chosen from groups specified herein. In one example, optional substituents on aryl are selected from halogen (F, Cl, Br, I), hydroxy, protected hydroxy, cyano, nitro, alkyl (for example $C_1$-$C_6$ alkyl), alkoxy (for example $C_1$-$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, alkylsulfonylaminoalkyl, arylsulfonylamino, arylsulfonylaminoalkyl, heterocyclylsulfonylamino, heterocyclylsulfonylaminoalkyl, heterocyclyl, optionally substituted phenyl, or other groups specified. One or more methyne (CH) and/or methylene ($CH_2$) groups in these substituents may in turn be substituted with a similar group as those denoted above. Examples of the term "substituted phenyl" include a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(isopropyl)phenyl, 4-ethylphenyl, 3-(n-propyl) phenyl and the like; a mono or di(alkoxy)phenyl group, for example, 3,4-dimethoxyphenyl, 3-methoxy-4-benzyloxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl) phenyl or (protected aminomethyl)phenyl such as 2-(aminomethyl)phenyl or 2,4-(protected aminomethyl)phenyl; or a mono- or di-(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino. Particular substituted phenyl groups include the 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-6-methyl sulfonyl aminophenyl groups. Fused aryl rings may also be substituted with any, for example 1, 2 or 3, of the substituents specified herein in the same manner as substituted alkyl groups.

"Halo" or "halogen" refer to F, Cl, Br or I.

The terms "heterocycle," "heterocyclyl" and "heterocyclic ring" are used interchangeably herein and refer to: (i) a saturated or partially unsaturated cyclic group (i.e., having one or more double and/or triple bonds within the ring) ("heterocycloalkyl"), or (ii) an aromatic cyclic group ("heteroaryl"), and in each case, which at least one ring atom is a heteroatom independently selected from nitrogen, oxygen, phosphorus and sulfur, the remaining ring atoms being carbon. The heterocyclyl group may be optionally substituted with one or more substituents described below. In one embodiment, heterocyclyl includes monocycles or bicycles having 1 to 9 carbon ring members ($C_1$-$C_9$) with the remaining ring atoms being heteroatoms selected from N, O, S and P. In other examples, heterocyclyl includes monocycles or bicycles having $C_1$-$C_5$, $C_3$-$C_5$ or $C_4$-$C_5$, with the remaining ring atoms being heteroatoms selected from N, O, S and P. In another embodiment, heterocyclyl includes 3-10 membered rings, 3-7-membered rings or 3-6 membered rings, containing one or more heteroatoms independently selected from N, O, S and P. In other examples, heterocyclyl includes monocyclic 3-, 4-, 5-, 6- or 7-membered rings, containing one or more heteroatoms independently selected from N, O, S and P. In another embodiment, heterocyclyl includes bi- or polycyclic, spiro or bridged 4-, 5-, 6-, 7-, 8- and 9-membered ring systems, containing one or more heteroatoms independently selected from N, O, S and P. Examples of bicycle systems include, but are not limited to, [3,5], [4,5], [5,5], [3,6], [4,6], [5,6], or [6,6] systems. Examples of bridged ring systems include, but are not limited to [2.2.1], [2.2.2], [3.2.2] and [4.1.0] arrangements, and having 1 to 3 heteroatoms selected from N, O, S and P. In another embodiment, heterocyclyl includes spiro groups having 1 to 4 heteroatoms selected from N, O, S and P. The heterocyclyl group may be a carbon-linked group or heteroatom-linked group. "Heterocyclyl" includes a heterocyclyl group fused to a cycloalkyl group.

Exemplary heterocyclyl groups include, but are not limited to, oxiranyl, aziridinyl, thiiranyl, azetidinyl, oxetanyl, thietanyl, 1,2-dithietanyl, 1,3-dithietanyl, pyrrolidinyl, piperidinyl, morpholinyl, thiomorpholinyl, thioxanyl, piperazinyl, homopiperazinyl, homopiperidinyl, oxepanyl, thiepanyl, oxazepinyl, oxazepanyl, diazepanyl, 1,4-diazepanyl, diazepinyl, thiazepinyl, thiazepanyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, dioxanyl, 1,3-dioxolanyl, pyrazolinyl, pyrazolidinyl, dithianyl, dithiolanyl, pyrazolidinylimidazolinyl, imidazolidinyl, 3-azabicyco[3.1.0]hexanyl, 3,6-diazabicyclo[3.1.1] heptanyl, 6-azabicyclo[3.1.1]heptanyl, 3-azabicyclo[3.1.1] heptanyl, 3-azabicyclo[4.1.0]heptanyl and azabicyclo[2.2.2] hexanyl. Examples of a heterocyclyl group wherein a ring atom is substituted with oxo (=O) are 2H-pyrazolo[4,3-c] pyridin-4(5H)-onyl, 2H-pyrazolo[3,4-d]pyrimidin-4(5H)-only, pyrimidinonyl and 1,1-dioxo-thiomorpholinyl. The heterocyclyl groups herein are optionally substituted independently with one or more substituents described herein. Heterocycles are described in Paquette, Leo A.; "Principles of Modern Heterocyclic Chemistry" (W. A. Benjamin, New York, 1968), particularly Chapters 1, 3, 4, 6, 7, and 9;

"The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

The term "heteroaryl" refers to an aromatic carbocyclic radical in which at least one ring atom is a heteroatom independently selected from nitrogen, oxygen and sulfur, the remaining ring atoms being carbon.

Heteroaryl groups may be optionally substituted with one or more substituents described herein. In one example, the heteroaryl group contains 1 to 9 carbon ring atoms ($C_1$-$C_9$). In other examples, the heteroaryl group is $C_1$-$C_5$, $C_3$-$C_5$ or $C_4$-$C_5$. In one embodiment, exemplary heteroaryl groups include 5-6-membered rings, or monocyclic aromatic 5-, 6- and 7-membered rings containing one or more heteroatoms independently selected from nitrogen, oxygen, and sulfur. In another embodiment, exemplary heteroaryl groups include fused ring systems of up to 9 carbon atoms wherein at least one aromatic ring contains one or more heteroatoms independently selected from nitrogen, oxygen, and sulfur. "Heteroaryl" includes heteroaryl groups fused with an aryl, cycloalkyl or other heterocyclyl group. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, thiazolopyridinyl, pyrazolopyridinyl, pyrazolo[4,3-c]pyridinyl, pyrazolo[4,3-c]pyrimidinyl, and furopyridinyl.

In certain embodiments, the heterocyclyl or heteroaryl group is C-attached. By way of example and not limitation, carbon bonded heterocyclyls include bonding arrangements at position 2, 3, 4, 5, or 6 of a pyridine (e.g. 2-pyridyl, 3-pyridyl, 4-pyridyl, 5-pyridyl, 6-pyridyl), position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

In certain embodiments, the heterocyclyl or heteroaryl group is N-attached. By way of example and not limitation, the nitrogen bonded heterocyclyl or heteroaryl group include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

"Leaving group" refers to a portion of a first reactant in a chemical reaction that is displaced from the first reactant in the chemical reaction. Examples of leaving groups include, but are not limited to, halogen atoms, alkoxy and sulfonyloxy groups. Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)).

"Treat" and "treatment" includes both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, remission (whether partial or total), whether detectable or undetectable, sustaining remission and suppressing reoccurrence. "Treatment" can also mean prolonging survival as compared to expected survival if not receiving treatment. Those in need of treatment include those already with the condition or disorder as well as those prone to have the condition or disorder, (for example, through a genetic mutation) or those in which the condition or disorder is to be prevented.

The phrase "therapeutically effective amount" means an amount of a compound of the present invention that (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. In the case of cancer, the therapeutically effective amount of the drug may reduce the number of cancer cells; reduce the tumor size; inhibit (i.e., slow to some extent and alternatively stop) cancer cell infiltration into peripheral organs; inhibit (i.e., slow to some extent and alternatively stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR). In the case of immunological disorders, the therapeutic effective amount is an amount sufficient to decrease or alleviate an allergic disorder, the symptoms of an autoimmune and/or inflammatory disease, or the symptoms of an acute inflammatory reaction (e.g. asthma). In some embodiments, a therapeutically effective amount is an amount of a chemical entity described herein sufficient to significantly decrease the activity or number of B-cells.

The term "NSAID" is an acronym for "non-steroidal anti-inflammatory drug" and is a therapeutic agent with analgesic, antipyretic (lowering an elevated body temperature and relieving pain without impairing consciousness) and, in higher doses, with anti-inflammatory effects (reducing inflammation). The term "non-steroidal" is used to distinguish these drugs from steroids, which (among a broad range of other effects) have a similar eicosanoid-depressing, anti-inflammatory action. As analgesics, NSAIDs are unusual in that they are non-narcotic. NSAIDs include aspirin, ibuprofen, and naproxen. NSAIDs are usually indicated for the treatment of acute or chronic conditions where pain and inflammation are present. NSAIDs are generally indicated for the symptomatic relief of the following conditions: rheumatoid arthritis, osteoarthritis, inflammatory arthropathies (e.g. ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic. Most NSAIDs act as non-selective inhibitors of the enzyme cyclooxygenase, inhibiting both the cyclooxygenase-1 (COX-1) and cyclooxygenase-2 (COX-2) isoenzymes. Cyclooxygenase catalyzes the formation of prostaglandins and thromboxane from arachidonic acid (itself derived from the cellular phospholipid bilayer by phospholipase $A_2$). Prostaglandins act (among other things) as messenger molecules in the process of inflammation. COX-2 inhibitors include celecoxib, etoricoxib, lumiracoxib, parecoxib, rofecoxib, rofecoxib, and valdecoxib.

The terms "cancer" and "cancerous" refer to or describe the physiological condition in patients that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is an agent useful in the treatment of a given disorder, for example, cancer or inflammatory disorders. Examples of chemotherapeutic agents include NSAIDs; hormones such as glucocorticoids; corticosteroids such as hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomide, methotrexate (MTX), minocycline, sulfasalazine, cyclophosphamide, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), monoclonal antibodies against B cells such as rituximab (RITUXAN®), T cell costimulation blockers such as abatacept (Orencia), Interleukin 6 (IL-6) blockers such as tocilizumab; hormone antagonists, such as tamoxifen, finasteride0 or LHRH antagonists; radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-$OCH_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; alkylating agents such as thiotepa and cyclophosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e. g., calicheamicin, especially calicheamicin gamma1I and calicheamicin omegaI1 (see, e.g., Nicolaou et al., *Angew. Chem Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine;

mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chlorambucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as fenretinide, retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Additional chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: antiestrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide.

Additional chemotherapeutic agents include therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length $IgG_1\lambda$ antibody genetically modified to recognize interleukin-12 p40 protein.

Chemotherapeutic agents also include "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al., *J. Biol. Chem.* 279(29):30375-30384 (2004)). The anti-EGFR antibody may be conjugated with a cytotoxic agent, thus generating an immunoconjugate (see, e.g., EP659, 439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033,2-propenamide, N-[4-[(3-chloro-4-fluorophenyl)amino]-7-[3-(4-morpholinyl)propoxy]-6-quinazolinyl]-, dihydrochloride, Pfizer Inc.); ZD1839, gefitinib (IRESSA™) 4-(3'-Chloro-4'-fluoroanilino)-7-methoxy-6-(3-morpholinopropoxy) quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6 [5 [[[2methylsulfonyl)ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC™, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804, 396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC™); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include asthma treatment agents, including inhaled corticosteroids such as fluticasone, budesonide, mometasone, flunisolide and beclomethasone; leukotriene modifiers, such as montelukast, zafirlukast and zileuton; long-acting beta agonists, such as salmeterol and formoterol; combinations of the above such as combinations of fluticasone and salmeterol, and combinations of budesonide and formoterol; theophylline; short-acting beta agonists, such as albuterol, levalbuterol and pirbuterol; ipratropium; oral and intravenous corticosteroids, such as prednisone and methylprednisolone; omalizumab; lebrikizumab; antihistamines; and decongestants; cromolyn; and ipratropium.

"Optionally substituted" unless otherwise specified means that a group may be unsubstituted or substituted by one or more (e.g. 0, 1, 2, 3 or 4) of the substituents listed for that group in which said substituents may be the same or different. In an embodiment an optionally substituted group has 1 substituent. In another embodiment an optionally substituted group has 2 substituents. In another embodiment an optionally substituted group has 3 substituents.

The term "prodrug" as used in this application refers to a precursor or derivative form of a pharmaceutically active substance that is less efficacious to the patient or cytotoxic to tumor cells compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

The term "package insert" is used to refer to instructions customarily included in commercial packages of therapeutic products, that contain information about the indications, usage, dosage, administration, contraindications and/or warnings concerning the use of such therapeutic products.

The term "stereoisomers" refers to compounds which have identical chemical constitution, but differ with regard to the arrangement of the atoms or groups in space. Stereoisomers include diastereomers, enantiomers, conformers and the like.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt," as used herein, refers to pharmaceutically acceptable organic or inorganic salts of a compound of Formula I. "Pharmaceutically acceptable salts" include both acid and base addition salts. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion, for example a dihydrochloride or diformate salt.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, tromethamine, dicyclohexylamine, choline, and caffeine.

A "solvate" refers to an association or complex of one or more solvent molecules and a compound of Formula I. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, phthalimido, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include acetyl, trialkylsilyl, dialkylphenylsilyl, benzoyl, benzyl, benzyloxymethyl, methyl, methoxymethyl, triarylmethyl, and tetrahydropyranyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see T. W. Greene and P. Wuts, Protective Groups in Organic Synthesis, Third Ed., John Wiley & Sons, New York, 1999; and P. Kocienski, Protecting Groups, Third Ed., Verlag, 2003.

The term "patient" includes human patients and animal patients. The term "animal" includes companion animals (e.g., dogs, cats and horses), food-source animals, zoo animals, marine animals, birds and other similar animal species. In one example, patient is a human.

The phrase "pharmaceutically acceptable" indicates that the substance or composition must be compatible chemically and/or toxicologically, with the other ingredients comprising a formulation, and/or the mammal being treated therewith.

The terms "compound of this invention," and "compounds of the present invention", unless otherwise indicated, include compounds of Formulas I, stereoisomers, tautomers, solvates, prodrugs and salts (e.g., pharmaceutically acceptable salts) thereof. Unless otherwise stated, structures depicted herein are also meant to include compounds that differ only in the presence of one or more isotopically enriched atoms. For example, compounds of Formula I, wherein one or more hydrogen atoms are replaced deuterium or tritium, or one or more carbon atoms are replaced by a $^{13}C$ or $^{14}C$ carbon atom, or one or more nitrogen atoms are replaced by a $^{15}N$ nitrogen atom, or one or more sulfur atoms are replaced by a $^{33}S$, $^{34}S$ or $^{36}S$ sulfur atom, or one or more oxygen atoms are replaced by a $^{17}O$ or $^{18}O$ oxygen atom are within the scope of this invention.

TYK2 Inhibitor Compounds

In one embodiment, a compound of Formulas I, stereoisomers, tautomers, solvates, prodrugs and pharmaceutically acceptable salts thereof, and pharmaceutical formulations thereof, are provided that are useful in the treatment of diseases, conditions and/or disorders responsive to the inhibition of TYK2.

Another embodiment includes compounds of Formula I:

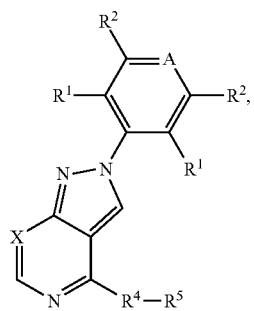

I stereoisomers, tautomers, solvates, prodrugs and pharmaceutically acceptable salts thereof, wherein:

A is $CR^3$ or N;

X is $CR^{15}$ or N;

$R^1$ is independently hydrogen, halogen, $C_1$-$C_6$ alkyl, $C_2$-$C_6$ alkenyl, $C_2$-$C_6$ alkynyl, $C_3$-$C_6$ cycloalkyl, —$CF_3$, —$OR^6$, —$SR^6$, —$OCF_3$, —CN, —$NO_2$, —C(O)$R^6$, —C(O)O$R^6$, —C(O)N$R^6R^7$, —S(O)$_{1-2}R^6$, —S(O)$_{1-2}$N$R^6R^7$, —N$R^6SO_2R^7$, —N$R^6SO_2$N$R^6R^7$, —N$R^6$C(O)$R^7$, —N$R^6$C(O)O$R^7$, —N$R^6$C(O)N$R^6R^7$, —OC(O)N$R^6R^7$, —N$R^6R^7$, 3-6 membered heterocyclyl or phenyl, wherein both $R^1$ cannot be hydrogen at the same time, and wherein said alkyl, alkenyl and alkynyl are independently optionally substituted by halogen, oxo, —CN, —$OR^6$, —N$R^6R^7$ $C_3$-$C_6$ cycloalkyl, 3-6 membered heterocyclyl or phenyl, and said cycloalkyl, heterocyclyl and phenyl are independently optionally substituted by $R^{10}$;

$R^2$ and $R^3$ are each independently hydrogen, $C_1$-$C_6$ alkyl, $C_2$-$C_6$ alkenyl, $C_2$-$C_6$ alkynyl, halogen, —($C_0$-$C_3$ alkylene)CN, —($C_0$-$C_3$ alkylene)O$R^8$, —($C_0$-$C_3$ alkylene)S$R^8$, —($C_0$-$C_3$ alkylene)N$R^8R^9$, —($C_0$-$C_3$ alkylene)CF$_3$, —O($C_0$-$C_3$ alkylene)CF$_3$, —($C_0$-$C_3$ alkylene)NO$_2$, —($C_0$-$C_3$ alkylene)C(O)$R^8$, —($C_0$-$C_3$ alkylene)C(O)O$R^8$, —($C_0$-$C_3$ alkylene)C(O)N$R^8R^9$, —($C_0$-$C_3$ alkylene)N$R^8$C(O)$R^9$, —($C_0$-$C_3$ alkylene)S(O)$_{1-2}R^8$, —($C_0$-$C_3$ alkylene)N$R^8$S(O)$_{1-2}R^9$, —($C_0$-$C_3$ alkylene)S(O)$_{1-2}$N$R^8R^9$, —($C_0$-$C_3$ alkylene)($C_3$-$C_6$ cycloalkyl), —($C_0$-$C_3$ alkylene)(3-6-membered heterocyclyl), —($C_0$-$C_3$ alkylene)(5-6-membered heteroaryl) or —($C_0$-$C_3$ alkylene)phenyl, wherein $R^2$ and $R^3$ are each independently optionally substituted by $R^{10}$;

$R^4$ is hydrogen, —$NR^6$—, —$NR^6R^7$, —$NR^6$C(O)—, —$NR^6$C(O)O—, —$NR^6$C(O)$NR^7$—, —$NR^6$S(O)$_{1-2}$— or —$NR^6$S(O)$_{1-2}$N$R^7$—;

$R^5$ is absent, hydrogen, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3-10-membered heterocyclyl or 5-10-membered heteroaryl, wherein $R^5$ is optionally substituted by $R^{10}$;

$R^6$ and $R^7$ are each independently hydrogen, $C_1$-$C_6$ alkyl, $C_2$-$C_6$ alkenyl, $C_2$-$C_6$ alkynyl, $C_3$-$C_6$ cycloalkyl, 3-10 membered heterocyclyl or phenyl, wherein said alkyl, alkenyl and alkynyl are independently optionally substituted by halogen, oxo, —CN, —$OR^6$, —N$R^6R^7$, $C_3$-$C_6$ cycloalkyl, 3-6 membered heterocyclyl or phenyl, and said cycloalkyl, heterocyclyl and phenyl are independently optionally substituted by $R^{10}$; or $R^6$ and $R^7$ are independently taken together with the atom to which they are attached to form a 3-10 membered heterocyclyl optionally substituted by halogen, oxo, —$OR^{11}$, —$NR^{11}R^{12}$, $C_1$-$C_6$ alkyl, $C_2$-$C_6$ alkenyl or $C_2$-$C_6$ alkynyl, wherein said alkyl, alkenyl and alkynyl are independently optionally substituted by halogen or oxo;

$R^8$ and $R^9$ are each independently hydrogen, $C_1$-$C_6$ alkyl, $C_2$-$C_6$ alkenyl, $C_2$-$C_6$ alkynyl, $C_3$-$C_6$ cycloalkyl, phenyl, 3-10-membered heterocyclyl, wherein said alkyl, alkenyl, alkynyl, cycloalkyl, phenyl and heterocyclyl are independently optionally substituted by $R^{10}$; or $R^8$ and $R^9$ are independently taken together with the atom to which they are attached to form a 3-10 membered heterocyclyl optionally substituted by halogen, oxo, —$OR^{11}$, —$NR^{11}R^{12}$, $C_1$-$C_6$ alkyl, $C_2$-$C_6$ alkenyl or $C_2$-$C_6$ alkynyl, wherein said alkyl, alkenyl and alkynyl are independently optionally substituted by halogen or oxo;

$R^{10}$ is independently hydrogen, oxo, $C_1$-$C_{12}$ alkyl, $C_2$-$C_{12}$ alkenyl, $C_2$-$C_{12}$ alkynyl, halogen, —($C_0$-$C_3$ alkylene)CN, —($C_0$-$C_3$ alkylene)O$R^{11}$, —($C_0$-$C_3$ alkylene)S$R^{11}$, —($C_0$-$C_3$ alkylene)N$R^{11}R^{12}$, —($C_0$-$C_3$ alkylene)CF$_3$, —($C_0$-$C_3$ alkylene)NO$_2$, —($C_0$-$C_3$ alkylene)C═N$R^{11}$($R^{12}$), —($C_0$-$C_3$ alkylene)C═N$R^{11}$(O$R^{12}$), —($C_0$-$C_3$ alkylene)C(O)$R^{11}$, —($C_0$-$C_3$ alkylene)C(O)O$R^{11}$, —($C_0$-$C_3$ alkylene)C(O)N$R^{11}R^{12}$, —($C_0$-$C_3$ alkylene)N$R^{11}$C(O)$R^{12}$, —($C_0$-$C_3$ alkylene)S(O)$_{1-2}R^{11}$, —($C_0$-$C_3$ alkylene)N$R^{11}$S(O)$_{1-2}R^{12}$, —($C_0$-$C_3$ alkylene)S(O)$_{1-2}$N$R^{11}R^{12}$, —($C_0$-$C_3$ alkylene)($C_3$-$C_6$ cycloalkyl), —($C_0$-$C_3$ alkylene)(3-10-membered heterocyclyl), —($C_0$-$C_3$ alkylene)C(O)(3-10-membered heterocyclyl) or —($C_0$-$C_3$ alkylene)($C_6$-$C_{10}$ aryl), wherein $R^{10}$ is independently optionally substituted by halogen, oxo, $C_1$-$C_{12}$ alkyl optionally substituted by oxo or halogen, $C_2$-$C_{12}$ alkenyl optionally substituted by oxo or halogen, $C_2$-$C_{12}$ alkynyl optionally substituted by oxo or halogen, —($C_0$-$C_3$ alkylene)CN, —($C_0$-$C_3$ alkylene)O$R^{13}$, —($C_0$-$C_3$ alkylene)S$R^{13}$, —($C_0$-$C_3$ alkylene)N$R^{13}R^{14}$, —($C_0$-$C_3$ alkylene)CF$_3$, —($C_0$-$C_3$ alkylene)NO$_2$, —($C_0$-$C_3$ alkylene)C(O)$R^{13}$, —($C_0$-$C_3$ alkylene)C(O)O$R^{13}$, —($C_0$-$C_3$ alkylene)C(O)N$R^{13}R^{14}$, —($C_0$-$C_3$ alkylene)N$R^{13}$C(O)$R^{14}$, —($C_0$-$C_3$ alkylene)S(O)$_{1-2}R^{13}$, —($C_0$-$C_3$ alkylene)N$R^{13}$S(O)$_{1-2}R^{14}$, —($C_0$-$C_3$ alkylene)S(O)$_{1-2}$N$R^{13}R^{14}$, —($C_0$-$C_3$ alkylene)($C_3$-$C_6$ cycloalkyl), —($C_0$-$C_3$ alkylene)(3-6-membered heterocyclyl), —($C_0$-$C_3$ alkylene)C(O)(3-6-membered heterocyclyl) or —($C_0$-$C_3$ alkylene)phenyl.

$R^{11}$ and $R^{12}$ are each independently hydrogen, $C_1$-$C_6$ alkyl, $C_2$-$C_6$ alkenyl, $C_2$-$C_6$ alkynyl, $C_3$-$C_6$ cycloalkyl, phenyl or 3-6 membered heterocyclyl, wherein said alkyl, alkenyl, alkynyl, cycloalkyl, phenyl and heterocyclyl are independently optionally substituted by halogen, oxo, —CN, —OR$^{16}$, —NR$^{16}$R$^{17}$ or $C_1$-$C_6$ alkyl optionally substituted by halogen or oxo; or R$^{11}$ and R$^{12}$ are taken together with the atom to which they attached to form a 3-6 membered heterocyclyl optionally substituted by halogen, oxo, —OR$^{16}$, —NR$^{16}$R$^{17}$ or $C_1$-$C_3$ alkyl optionally substituted by halogen, oxo or OH;

R$^{13}$ and R$^{14}$ are each independently hydrogen or $C_1$-$C_6$ alkyl optionally substituted by halogen or oxo; or R$^{13}$ and R$^{14}$ are taken together with the atom to which they attached to form a 3-6 membered heterocyclyl optionally substituted by halogen, oxo or $C_1$-$C_6$ alkyl optionally substituted by halogen or oxo;

R$^{15}$ is hydrogen, halogen, $C_1$-$C_6$ alkyl, $C_2$-$C_6$ alkenyl, $C_2$-$C_6$ alkynyl, —($C_0$-$C_3$ alkylene)CN, —($C_0$-$C_3$ alkylene)OR$^{18}$, —($C_0$-$C_3$ alkylene)SR$^{18}$, —($C_0$-$C_3$ alkylene)NR$^{18}$R$^{19}$, —($C_0$-$C_3$ alkylene)CF$_3$, —O($C_0$-$C_3$ alkylene)CF$_3$, —($C_0$-$C_3$ alkylene)NO$_2$, —($C_0$-$C_3$ alkylene)C(O)R, —($C_0$-$C_3$ alkylene)C(O)OR$^{18}$, —($C_0$-$C_3$ alkylene)C(O)NR$^{18}$R$^{19}$, —($C_0$-$C_3$ alkylene)NR$^{18}$C(O)R$^{19}$, —($C_0$-$C_3$ alkylene)S(O)$_{1-2}$R$^{18}$, —($C_0$-$C_3$ alkylene)NR$^{18}$S(O)$_{1-2}$R$^{19}$, —($C_0$-$C_3$ alkylene)S(O)$_{1-2}$NR$^{18}$R$^{19}$, —($C_0$-$C_3$ alkylene)($C_3$-$C_6$ cycloalkyl), —($C_0$-$C_3$ alkylene)(3-6-membered heterocyclyl) or —($C_0$-$C_3$ alkylene)phenyl, wherein R$^{15}$ is independently optionally substituted by halogen, oxo, —CN, —CF$_3$ or $C_1$-$C_6$ alkyl optionally substituted by oxo or halogen;

R$^{16}$ and R$^{17}$ are each independently hydrogen or $C_1$-$C_6$ alkyl optionally substituted by halogen or oxo; or R$^{16}$ and R$^{17}$ are taken together with the atom to which they attached to form a 3-6 membered heterocyclyl optionally substituted by halogen, oxo or $C_1$-$C_6$ alkyl optionally substituted by oxo or halogen; and R$^{18}$ and R$^{19}$ are each independently hydrogen or $C_1$-$C_6$ alkyl optionally substituted by halogen or oxo.

Another embodiment includes a compound of Formula I, stereoisomers, tautomers, solvates, prodrugs and pharmaceutically acceptable salts thereof, wherein:

A is CR$^3$ or N;

X is CR$^{15}$ or N;

R$^1$ is independently hydrogen, halogen, $C_1$-$C_3$ alkyl, $C_2$-$C_3$ alkenyl, $C_2$-$C_3$ alkynyl, $C_3$-$C_4$ cycloalkyl, —CF$_3$, —OR$^6$, —SR$^6$, —OCF$_3$, —CN, —NO$_2$, —NR$^6$SO$_2$R$^7$, —NR$^6$C(O)R$^7$ or —NR$^6$R$^7$, wherein both R$^1$ cannot be hydrogen at the same time, and wherein said alkyl, alkenyl, alkynyl and cycloalkyl are optionally substituted by halogen, OR$^6$, —NR$^6$R$^7$ or phenyl;

R$^2$ and R$^3$ are each independently hydrogen, $C_1$-$C_6$ alkyl, $C_2$-$C_6$ alkenyl, $C_2$-$C_6$ alkynyl, halogen, —($C_0$-$C_3$ alkylene)CN, —($C_0$-$C_3$ alkylene)OR$^8$, —($C_0$-$C_3$ alkylene)SR$^8$, —($C_0$-$C_3$ alkylene)NR$^8$R$^9$, —($C_0$-$C_3$ alkylene)CF$_3$, —O($C_0$-$C_3$ alkylene)CF$_3$, —($C_0$-$C_3$ alkylene)NO$_2$, —($C_0$-$C_3$ alkylene)C(O)R$^8$, —($C_0$-$C_3$ alkylene)C(O)OR$^8$, —($C_0$-$C_3$ alkylene)C(O)NR$^8$R$^9$, —($C_0$-$C_3$ alkylene)NR$^8$C(O)R$^9$, —($C_0$-$C_3$ alkylene)S(O)$_{1-2}$R$^8$, —($C_0$-$C_3$ alkylene)NR$^8$S(O)$_{1-2}$R$^9$, —($C_0$-$C_3$ alkylene)S(O)$_{1-2}$NR$^8$R$^9$, —($C_0$-$C_3$ alkylene)($C_3$-$C_6$ cycloalkyl), —($C_0$-$C_3$ alkylene)(3-6-membered heterocyclyl), —($C_0$-$C_3$ alkylene)(5-6-membered heteroaryl) or —($C_0$-$C_3$ alkylene)phenyl, wherein R$^2$ and R$^3$ are each independently optionally substituted by R$^{10}$;

R$^4$ is hydrogen, —NH$_2$, —NH—, —NR$^6$R$^7$, —NR$^6$C(O)—, —NR$^6$C(O)O—, —NR$^6$C(O)NR$^7$—, —NR$^6$S(O)$_{1-2}$— or —NR$^6$S(O)$_{1-2}$NR$^7$—;

R$^5$ is absent, hydrogen, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3-10-membered heterocyclyl or 5-10-membered heteroaryl, wherein R$^5$ is optionally substituted by R$^{10}$;

R$^6$ and R$^7$ are each independently hydrogen, $C_1$-$C_3$ alkyl, $C_2$-$C_6$ alkenyl, $C_2$-$C_6$ alkynyl or $C_3$-$C_4$ cycloalkyl, wherein said alkyl, alkenyl, alkynyl and cycloalkyl are independently optionally substituted by halogen, oxo, —OR$^{11}$ or —NR$^{11}$R$^{12}$; or R$^6$ and R$^7$ are independently taken together with the atom to which they are attached to form a 3-6 membered heterocyclyl optionally substituted by halogen, oxo, —NR$^{11}$R$^{12}$ or $C_1$-$C_3$ alkyl;

R$^8$ and R$^9$ are each independently hydrogen, $C_1$-$C_3$ alkyl, $C_3$-$C_6$ cycloalkyl, phenyl, 3-6-membered heterocyclyl or 5-6-membered heteroaryl, wherein said alkyl, cycloalkyl, phenyl, heterocyclyl or heteroaryl are independently optionally substituted by R$^{10}$; or R$^8$ and R$^9$ are independently taken together with the atom to which they are attached to form a 3-6 membered heterocyclyl optionally substituted by halogen, oxo, —NR$^{11}$R$^{12}$ or $C_1$-$C_3$ alkyl;

R$^{10}$ is independently hydrogen, oxo, $C_1$-$C_6$ alkyl, $C_2$-$C_6$ alkenyl, $C_2$-$C_6$ alkynyl, halogen, —($C_0$-$C_3$ alkylene)CN, —($C_0$-$C_3$ alkylene)OR$^{11}$, —($C_0$-$C_3$ alkylene)SR$^{11}$, —($C_0$-$C_3$ alkylene)NR$^{11}$R$^{12}$, —($C_0$-$C_3$ alkylene)CF$_3$, —($C_0$-$C_3$ alkylene)NO$_2$, —C═NH(OR$^{11}$), —($C_0$-$C_3$ alkylene)C(O)R$^{11}$, —($C_0$-$C_3$ alkylene)C(O)OR$^{11}$, —($C_0$-$C_3$ alkylene)C(O)NR$^{11}$R$^{12}$, —($C_0$-$C_3$ alkylene)NR$^{11}$C(O)R$^{12}$, —($C_0$-$C_3$ alkylene)S(O)$_{1-2}$R$^{11}$, —($C_0$-$C_3$ alkylene)NR$^{11}$S(O)$_{1-2}$R$^{12}$, —($C_0$-$C_3$ alkylene)S(O)$_{1-2}$NR$^{11}$R$^{12}$, —($C_0$-$C_3$ alkylene)($C_3$-$C_6$ cycloalkyl), —($C_0$-$C_3$ alkylene)(3-6-membered heterocyclyl), —($C_0$-$C_3$ alkylene)C(O)(3-6-membered heterocyclyl), —($C_0$-$C_3$ alkylene)(5-6-membered heteroaryl) or —($C_0$-$C_3$ alkylene)phenyl, wherein R$^{10}$ is independently optionally substituted by halogen, oxo, —CF$_3$, —($C_0$-$C_3$ alkylene)OR$^{13}$, —($C_0$-$C_3$ alkylene)NR$^{13}$R$^{14}$, —($C_0$-$C_3$ alkylene)C(O)R$^{13}$, —($C_0$-$C_3$ alkylene)S(O)$_{1-2}$R$^{13}$ or $C_1$-$C_3$ alkyl optionally substituted by oxo or halogen;

R$^{11}$ and R$^{12}$ are each independently hydrogen, $C_1$-$C_6$ alkyl, $C_2$-$C_6$ alkenyl, $C_2$-$C_6$ alkynyl, $C_3$-$C_6$ cycloalkyl, phenyl, 5-6 membered heteroaryl or 3-6 membered heterocyclyl, wherein said alkyl, alkenyl, alkynyl, phenyl, heteroaryl and heterocyclyl are independently optionally substituted by halogen, oxo, —CN, —OR$^{16}$, —NR$^{16}$R$^{17}$ or $C_1$-$C_3$ alkyl optionally substituted by halogen or oxo; or R$^{11}$ and R$^{12}$ are taken together with the atom to which they attached to form a 3-6 membered heterocyclyl optionally substituted by halogen, oxo, —OR$^{16}$, —NR$^{16}$R$^{17}$ or $C_1$-$C_3$ alkyl optionally substituted by halogen, oxo or OH;

R$^{13}$ and R$^{14}$ are each independently hydrogen or $C_1$-$C_6$ alkyl optionally substituted by halogen or oxo; or R$^{13}$ and R$^{14}$ are taken together with the atom to which they attached to form a 3-6 membered heterocyclyl optionally substituted by halogen, oxo or $C_1$-$C_3$ alkyl optionally substituted by halogen or oxo;

R$^{15}$ is hydrogen, halogen, $C_1$-$C_6$ alkyl, $C_2$-$C_6$ alkenyl, $C_2$-$C_6$ alkynyl, —($C_0$-$C_3$ alkylene)CN, —($C_0$-$C_3$ alkylene)OR$^{18}$, —($C_0$-$C_3$ alkylene)SR$^{18}$, —($C_0$-$C_3$ alkylene)NR$^{18}$R$^{19}$, —($C_0$-$C_3$ alkylene)CF$_3$, —O($C_0$-$C_3$ alkylene)CF$_3$, —($C_0$-$C_3$ alkylene)NO$_2$, —($C_0$-$C_3$ alkylene)C(O)R$^{18}$, —($C_0$-$C_3$ alkylene)C(O)OR$^{18}$, —($C_0$-$C_3$ alkylene)C(O)NR$^{18}$R$^{19}$, —($C_0$-$C_3$ alkylene)NR$^{18}$C(O)

$R^{19}$, —($C_0$-$C_3$ alkylene)S(O)$_{1-2}R^{18}$, —($C_0$-$C_3$ alkylene)NR$^{18}$S(O)$_{1-2}R^{19}$, —($C_0$-$C_3$ alkylene)S(O)$_{1-2}$NR$^{18}R^{19}$, —($C_0$-$C_3$ alkylene)($C_3$-$C_6$ cycloalkyl), —($C_0$-$C_3$ alkylene)(3-6-membered heterocyclyl), —($C_0$-$C_3$ alkylene)(5-6-membered heteroaryl) or —($C_0$-$C_3$ alkylene)phenyl, wherein $R^{15}$ is independently optionally substituted by halogen, oxo, —CF$_3$ or $C_1$-$C_3$ alkyl optionally substituted by oxo or halogen;

$R^{16}$ and $R^{17}$ are each independently hydrogen or $C_1$-$C_6$ alkyl optionally substituted by halogen or oxo; or $R^{16}$ and $R^{17}$ are taken together with the atom to which they attached to form a 3-6 membered heterocyclyl optionally substituted by halogen, oxo or $C_1$-$C_3$ alkyl optionally substituted by halogen; and $R^{18}$ and $R^{19}$ are each independently hydrogen or $C_1$-$C_6$ alkyl optionally substituted by halogen or oxo.

In certain embodiments, compounds of Formula I, stereoisomers, tautomers, solvates, prodrugs and pharmaceutically acceptable salts thereof, includes compounds other than the compounds 2-(2-ethylphenyl)-N-[4-(trifluoromethoxy)phenyl]-2H-pyrazolo[3,4-d]pyrimidin-4-amine, 2-(2,4-dichlorophenyl)-N-[4-(trifluoromethoxy)phenyl]-2H-Pyrazolo[3,4-d]pyrimidin-4-amine, 2-(2-fluorophenyl)-N-[4-(trifluoromethoxy)phenyl]-2H-Pyrazolo[3,4-d]pyrimidin-4-amine or 2-(2,3-dimethylphenyl)-N-[4-(trifluoromethoxy)phenyl]-2H-Pyrazolo[3,4-d]pyrimidin-4-amine.

In certain embodiments, A is CR$^3$.
In certain embodiments, A is CR$^3$ and X is CR$^{15}$.
In certain embodiments, A is CR$^3$ and X is N.
In certain embodiments, A is N.
In certain embodiments, A is N and X is CR$^{15}$.
In certain embodiments, A is N and X is N.

In certain embodiments, $R^1$ is independently halogen. In one embodiment, $R^1$ is independently F or Cl. In another embodiment, $R^1$ is Cl.

In certain embodiments, $R^1$ is independently halogen, the group —$R^4$-$R^5$ is —NHR$^5$, —NR$^6$C(O)R$^5$, —NR$^6$C(O)OR$^5$ or —NR$^6$C(O)NR$^7R^5$, wherein $R^5$ is other than hydrogen.

In certain embodiments, one $R^1$ is halogen and the other $R^1$ is hydrogen, halogen, $C_1$-$C_3$ alkyl, $C_3$-$C_4$ cycloalkyl, —CF$_3$, —OH, —O($C_1$-$C_3$ alkyl), —SH, —S($C_1$-$C_3$ alkyl), —OCF$_3$, —CN, —NO$_2$, —NHSO$_2$CH$_3$, —NHC(O)R$^7$ or —NR$^6R^7$, wherein said alkyl and cycloalkyl are optionally substituted by halogen, OR$^8$, —NR$^8R^9$ or phenyl.

In certain embodiments, one $R^1$ is halogen and the other $R^1$ is hydrogen, halogen, $C_1$-$C_3$ alkyl, $C_3$-$C_4$ cycloalkyl, —CF$_3$, —OH, —O($C_1$-$C_3$ alkyl), —SH, —S($C_1$-$C_3$ alkyl), —OCF$_3$, —CN, —NO$_2$, —NHSO$_2$CH$_3$, —C(O)OR$^6$, —NHC(O)R$^7$ or —NR$^6R^7$, wherein said alkyl and cycloalkyl are optionally substituted by halogen, OR$^8$, —NR$^8R^9$ or phenyl.

In certain embodiments, one $R^1$ is halogen and the other $R^1$ is hydrogen, halogen, $C_1$-$C_6$ alkyl, $C_2$-$C_6$ alkenyl, $C_2$-$C_6$ alkynyl, $C_3$-$C_6$ cycloalkyl, —CF$_3$, —OR$^6$, —SR$^6$, —OCF$_3$, —CN, —NO$_2$, —C(O)R$^6$, —C(O)OR$^6$, —C(O)NR$^6R^7$, —S(O)$_{1-2}R^6$, —S(O)$_{1-2}$NR$^6R^7$, —NR$^6$SO$_2R^7$, —NR$^6$SO$_2$NR$^6R^7$, —NR$^6$C(O)R$^7$, —NR$^6$C(O)OR$^7$, —NR$^6$C(O)NR$^6R^7$, —OC(O)NR$^6R^7$, —NR$^6R^7$, 3-6 membered heterocyclyl or phenyl, wherein both $R^1$ cannot be hydrogen at the same time, and wherein said alkyl, alkenyl and alkynyl are independently optionally substituted by halogen, oxo, —CN, —OR$^6$, —NR$^6R^7$ $C_3$-$C_6$ cycloalkyl, 3-6 membered heterocyclyl or phenyl, and said cycloalkyl, heterocyclyl and phenyl are independently optionally substituted by R$^{10}$, In certain embodiments, one $R^1$ is halogen and the other $R^1$ is halogen, $C_1$-$C_3$ alkyl, $C_3$-$C_4$ cycloalkyl, —CF$_3$, —OH, —O($C_1$-$C_3$ alkyl), —SH, —S($C_1$-$C_3$ alkyl), —OCF$_3$, —CN, —NO$_2$, —NHSO$_2$CH$_3$, —NHC(O)R$^7$ or —NR$^6R^7$, wherein said alkyl and cycloalkyl are optionally substituted by halogen, OR$^8$, —NR$^8R^9$ or phenyl.

In certain embodiments, $R^1$ is independently halogen, $C_1$-$C_3$ alkyl, $C_3$-$C_4$ cycloalkyl, —CF$_3$, —OH, —O($C_1$-$C_3$ alkyl), —SH, —S($C_1$-$C_3$ alkyl), —OCF$_3$, —CN, —NO$_2$, —NHSO$_2$CH$_3$, —NHC(O)R$^7$ or —NR$^6R^7$, wherein said alkyl and cycloalkyl are optionally substituted by halogen, OR$^8$, —NR$^8R^9$ or phenyl.

In certain embodiments, $R^1$ is independently hydrogen, F, Cl, —CN, —CF$_3$, —CH$_3$, or —OCF$_3$, wherein both $R^1$ cannot be hydrogen at the same time.

In certain embodiments, $R^1$ is independently hydrogen, F, Cl, —CN, —CF$_3$, —CH$_3$, —C(O)OH or —OCF$_3$, wherein both $R^1$ cannot be hydrogen at the same time.

In certain embodiments, $R^1$ is independently hydrogen, F, Cl, —CN, —CF$_3$, —CH$_3$, —C(O)OH or —OCF$_3$, wherein both $R^1$ cannot be hydrogen at the same time; and $R^4$ is —NR$^6$—.

In certain embodiments, $R^2$ is hydrogen or halogen.
In certain embodiments, $R^2$ is hydrogen.
In certain embodiments, $R^2$ is halogen. In certain embodiments, $R^2$ is F or Cl. In certain embodiments, $R^2$ is F.

In certain embodiments, $R^2$ is hydrogen or halogen; and $R^3$ is hydrogen, $C_1$-$C_6$ alkyl, $C_2$-$C_6$ alkenyl, $C_2$-$C_6$ alkynyl, halogen, —($C_0$-$C_3$ alkylene)CN, —($C_0$-$C_3$ alkylene)OR$^8$, —($C_0$-$C_3$ alkylene)SR$^8$, —($C_0$-$C_3$ alkylene)NR$^8R^9$, —($C_0$-$C_3$ alkylene)CF$_3$, —O($C_0$-$C_3$ alkylene)CF$_3$, —($C_0$-$C_3$ alkylene)NO$_2$, —($C_0$-$C_3$ alkylene)C(O)R$^8$, —($C_0$-$C_3$ alkylene)C(O)OR$^8$, —($C_0$-$C_3$ alkylene)C(O)NR$^8R^9$, —($C_0$-$C_3$ alkylene)NR$^8$C(O)R$^9$, —($C_0$-$C_3$ alkylene)S(O)$_{1-2}R^8$, —($C_0$-$C_3$ alkylene)NR$^8$S(O)$_{1-2}R^9$, —($C_0$-$C_3$ alkylene)S(O)$_{1-2}$NR$^8R^9$, —($C_0$-$C_3$ alkylene)($C_3$-$C_6$ cycloalkyl), —($C_0$-$C_3$ alkylene)(3-6-membered heterocyclyl), —($C_0$-$C_3$ alkylene)(5-6-membered heteroaryl) or —($C_0$-$C_3$ alkylene)phenyl, wherein $R^3$ is optionally substituted by R$^{10}$.

In certain embodiments, $R^2$ is hydrogen and $R^3$ is hydrogen, $C_1$-$C_6$ alkyl, $C_2$-$C_6$ alkenyl, $C_2$-$C_6$ alkynyl, halogen, —($C_0$-$C_3$ alkylene)CN, —($C_0$-$C_3$ alkylene)OR$^8$, —($C_0$-$C_3$ alkylene)SR$^8$, —($C_0$-$C_3$ alkylene)NR$^8R^9$, —($C_0$-$C_3$ alkylene)CF$_3$, —O($C_0$-$C_3$ alkylene)CF$_3$, —($C_0$-$C_3$ alkylene)NO$_2$, —($C_0$-$C_3$ alkylene)C(O)R$^8$, —($C_0$-$C_3$ alkylene)C(O)OR$^8$, —($C_0$-$C_3$ alkylene)C(O)NR$^8R^9$, —($C_0$-$C_3$ alkylene)NR$^8$C(O)R$^9$, —($C_0$-$C_3$ alkylene)S(O)$_{1-2}R^8$, —($C_0$-$C_3$ alkylene)NR$^8$S(O)$_{1-2}R^9$, —($C_0$-$C_3$ alkylene)S(O)$_{1-2}$NR$^8R^9$, —($C_0$-$C_3$ alkylene)($C_3$-$C_6$ cycloalkyl), —($C_0$-$C_3$ alkylene)(3-6-membered heterocyclyl), —($C_0$-$C_3$ alkylene)(5-6-membered heteroaryl) or —($C_0$-$C_3$ alkylene)phenyl, wherein $R^3$ is optionally substituted by R$^{10}$.

In certain embodiments, $R^3$ is hydrogen, $C_1$-$C_6$ alkyl, $C_2$-$C_6$ alkenyl, $C_2$-$C_6$ alkynyl, halogen, —CN, —NR$^8R^9$, —NO$_2$, —C(O)R$^8$ or —S(O)$_{1-2}$($C_1$-$C_3$ alkyl), wherein said alkyl, alkenyl and alkynyl are independently optionally substituted by halogen, oxo, —OR$^{11}$ or —NR$^{11}R^{12}$. In one embodiment, R³ is hydrogen, hydroxylmethyl, —C(O)H, ethenyl, —CN, —NH₂, F, Cl, I or —S(O)₂CH₃. In one embodiment, R³ is hydrogen, —NH₂, F or —CN. In one embodiment, R³ is hydrogen. In one embodiment, R³ is —CN.

In certain embodiments, A is CR³, R² is hydrogen or halogen, and R³ is hydrogen, —CN, —NH₂ or F.

In certain embodiments, the portion of Formula I having the structure:

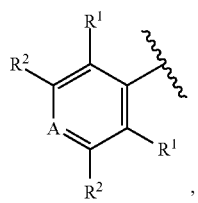

is selected from:

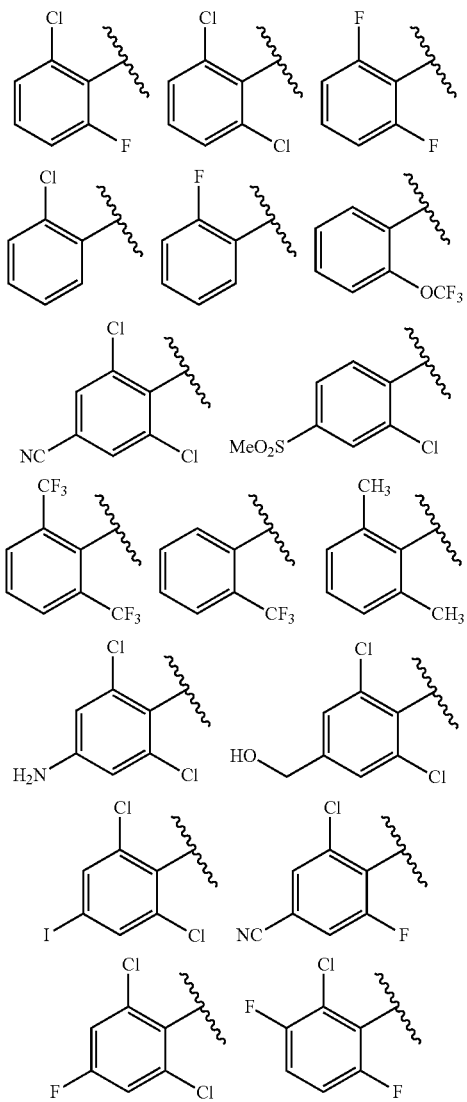

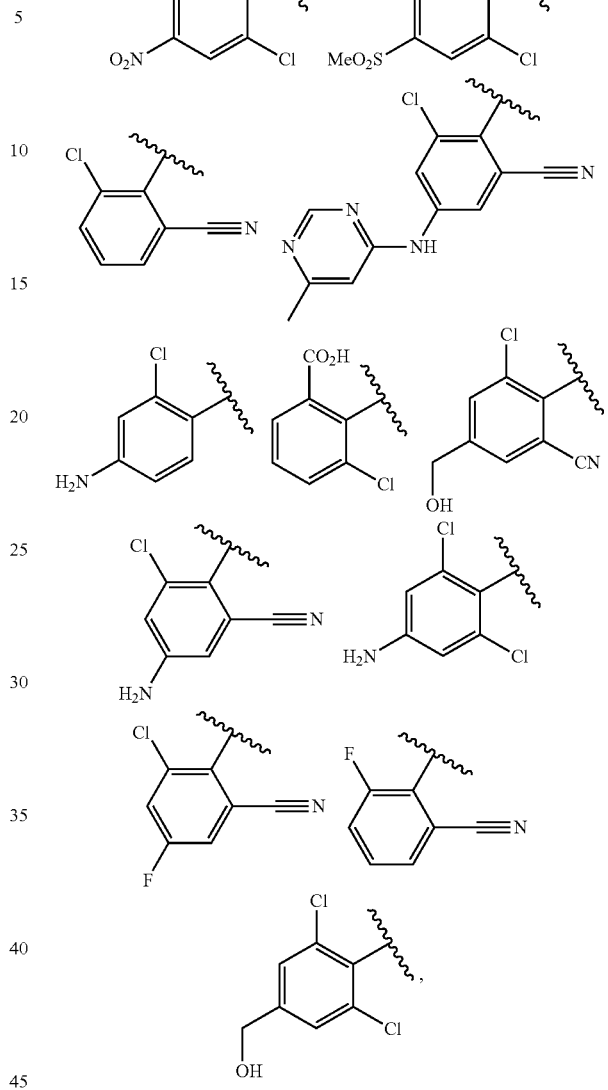

wherein the wavy lines represent the point of attachment in Formula I.

In certain embodiments, R⁴ is hydrogen and R⁵ is absent.
In certain embodiments, R⁴ is —NR⁶—. In certain embodiments, R⁴ is —NR⁶C(O)—. In certain embodiments, R⁴ is —NR⁶C(O)O—. In certain embodiments, R⁴ is —NR⁶C(O)NR⁷—. In certain embodiments, R⁴ is —NH—. In certain embodiments, R⁴ is —NHC(O)—. In certain embodiments, R⁴ is —NHC(O)O—. In certain embodiments, R⁴ is —NHC(O)NH—.

In certain embodiments, R⁴ is —NR⁶—, —NR⁶C(O)—, —NR⁶C(O)O— or —NR⁶C(O)NR⁷—.

In certain embodiments, the group —R⁴-R⁵ is —NHR⁵, —NHC(O)R⁵, —NHC(O)OR⁵ or —NHC(O)NHR⁵.

In certain embodiments, the group —R⁴-R⁵ is —NHR⁵, —NHC(O)R⁵, —NHC(O)OR⁵ or —NHC(O)NHR⁵, wherein R⁵ is other than hydrogen.

In certain embodiments, X is CR¹⁵ and the group —R⁴-R⁵ is —NHR⁵, —NHC(O)R⁵, —NHC(O)OR⁵ or —NHC(O)NR⁷R⁵. In certain embodiments, X is CR¹⁵; R¹⁵ is hydrogen; and the group —R⁴-R⁵ is —NHR⁵, —NHC(O)R⁵, —NHC (O)OR⁵ or —NHC(O)NHR⁵, wherein R⁵ is other than hydrogen. In certain embodiments, A is CR³; X is CR¹⁵; R¹⁵ is hydrogen; and the group —R⁴-R⁵ is —NHR⁵, —NHC(O)R⁵, —NHC(O)OR⁵ or —NHC(O)NHR⁵, wherein R⁵ is other than hydrogen.

In certain embodiments, R⁴ is —NH—, —NHC(O)— or —NHC(O)NH—.

In certain embodiments, R⁴ is —NH₂ and R⁵ absent.

In certain embodiments, R⁵ is other than 4-trifluoromethoxyphenyl. In certain embodiments, X is CR¹⁵ and R⁵ is other than 4-trifluoromethoxyphenyl.

In certain embodiments, R⁵ is hydrogen.

In certain embodiments, R⁴ is —NR⁶R⁷; R⁵ is absent; and R⁶ and R⁷ are independently hydrogen, C₁-C₃ alkyl or C₃-C₄ cycloalkyl, wherein said alkyl and cycloalkyl are independently optionally substituted by halogen, oxo, —OR¹¹ or —NR¹¹R¹².

In certain embodiments, R⁵ is C₁-C₆ alkyl optionally substituted by halogen, oxo, —OR¹¹, —SR¹¹, —C(O)R¹¹ or —NR¹¹R¹². In certain embodiments, R⁵ is methyl, ethyl, isopropyl or tert-butyl.

In certain embodiments, R⁵ is C₃-C₁₀ cycloalkyl optionally substituted by R¹⁰. In certain embodiments, R⁵ is C₃-C₆ cycloalkyl optionally substituted by halogen. In certain embodiments, R⁵ is cyclopropyl optionally substituted by halogen. In certain embodiments, R⁵ is cyclopropyl. In certain embodiments, R⁵ is selected from:

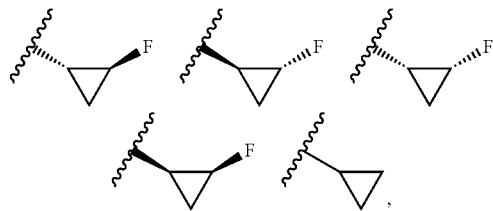

wherein the wavy line represents the point of attachment in Formula I.

In certain embodiments, R⁵ is C₆-C₁₀ aryl optionally substituted by R¹⁰. In certain embodiments, R⁵ is selected from phenyl optionally substituted by R¹⁰.

In certain embodiments, R⁵ is phenyl optionally substituted by R¹⁰. In certain embodiments, R⁵ is phenyl. In certain embodiments, R⁵ is phenyl optionally substituted by —O(CH₂)₂pyrrolidinyl.

In certain embodiments, when X is N, R⁵ is other than 4-methoxyphenyl. In certain embodiments, when X is N, R⁵ is other than phenyl.

In certain embodiments, R⁵ is 3-10-membered heterocyclyl optionally substituted by R¹⁰.

In certain embodiments, R⁵ is 3-7-membered heterocyclyl optionally substituted by R¹⁰. In certain embodiments, said heterocyclyl is pyridinonyl or pyrimidinonyl optionally substituted by R¹⁰. In certain embodiments, said heterocyclyl is pyridinonyl or pyrimidinonyl optionally substituted by C₁-C₆ alkyl. In certain embodiments, said heterocyclyl is 1-methyl-2-oxo-pyridinon-3-yl or pyrimidin-4(3H)-on-2-yl.

In certain embodiments, R⁵ is 5-10-membered heteroaryl optionally substituted by R¹⁰. In certain embodiments, R⁵ is pyridinyl, pyrimidinyl, pyrazolyl, thiazolyl, pyrazinyl, pyridazinyl, oxazolyl or isoxazolyl, wherein said R⁵ is optionally substituted by R¹⁰.

In certain embodiments, R⁵ is pyridinyl, pyrimidinyl, pyrazinyl or pyridazinyl optionally substituted by C₁-C₆ alkyl, C₃-C₆ cycloalkyl, halogen, —CN, —O(C₀-C₃ alkyl), —CF₃, —(C₀-C₃ alkylene)NR¹¹R¹², —NR¹¹C(O)R¹², —C(O)NR¹¹R¹², —C(O)OR¹¹, —(C₀-C₃ alkylene)3-6-membered heterocyclyl, wherein said alkyl is optionally substituted by halogen or OR¹¹ and said heterocyclyl is optionally substituted by oxo, halogen, OR¹¹ or C₁-C₃ alkyl optionally substituted by halogen or OR¹¹.

In certain embodiments, R⁵ is 5-6-membered heteroaryl, wherein R⁵ is optionally substituted by R¹⁰, wherein R¹⁰ is C₁-C₆ alkyl, halogen, —CN, —OR¹¹, —SR¹¹, —NR¹¹R¹², —CF₃, —C(O)R¹¹, —C(O)OR¹¹, —C(O)NR¹¹R¹², —NR¹¹C(O)R¹², —S(O)₁₋₂R¹¹, —NR¹¹S(O)₁₋₂R¹², —S(O)₁₋₂NR¹¹R¹², C₃-C₆ cycloalkyl, 3-6-membered heterocyclyl, —C(O)(3-6-membered heterocyclyl), 5-6-membered heteroaryl or phenyl, wherein R¹⁰ is independently optionally substituted by halogen, C₁-C₃ alkyl, oxo, —CF₃, —OR¹³, —NR¹³R¹⁴, —C(O)R¹³ or —S(O)₁₋₂R¹³. In an example, R⁵ is pyridinyl, pyrimidinyl, pyridazinyl, pyrazinyl, triazinyl, thienyl, pyrazolyl, pyranyl, triazolyl, isoxazolyl, oxazolyl, imidazolyl, thiazolyl or thiadiazolyl, wherein R⁵ is optionally substituted by 1, 2 or 3 R¹⁰.

In certain embodiments, R⁵ is pyridinyl optionally substituted by C₁-C₆ alkyl, C₂-C₆ alkenyl, C₂-C₆ alkynyl, halogen, —(C₀-C₃ alkylene)CN, —(C₀-C₃ alkylene)OR¹¹, —(C₀-C₃ alkylene)SR¹¹, —(C₀-C₃ alkylene)NR¹¹R¹², —(C₀-C₃ alkylene)CF₃, —(C₀-C₃ alkylene)NO₂, —C=NH(OR¹¹), —(C₀-C₃ alkylene)C(O)R¹¹, —(C₀-C₃ alkylene)C(O)OR¹¹, —(C₀-C₃ alkylene)C(O)NR¹¹R¹², —(C₀-C₃ alkylene)NR¹¹C(O)R¹², —(C₀-C₃ alkylene)S(O)₁₋₂R¹¹, —(C₀-C₃ alkylene)NR¹¹S(O)₁₋₂R¹², —(C₀-C₃ alkylene)S(O)₁₋₂NR¹¹R¹², —(C₀-C₃ alkylene)(C₃-C₆ cycloalkyl), —(C₀-C₃ alkylene)(3-6-membered heterocyclyl), —(C₀-C₃ alkylene)C(O)(3-6-membered heterocyclyl), —(C₀-C₃ alkylene)(5-6-membered heteroaryl) or —(C₀-C₃ alkylene)phenyl, wherein R¹⁰ is independently optionally substituted by halogen, C₁-C₃ alkyl, oxo, —CF₃, —(C₀-C₃ alkylene)OR¹³, —(C₀-C₃ alkylene)NR¹³R¹⁴, —(C₀-C₃ alkylene)C(O)R¹³ or —(C₀-C₃ alkylene)S(O)₁₋₂R¹³.

In certain embodiments, R⁵ is selected from:

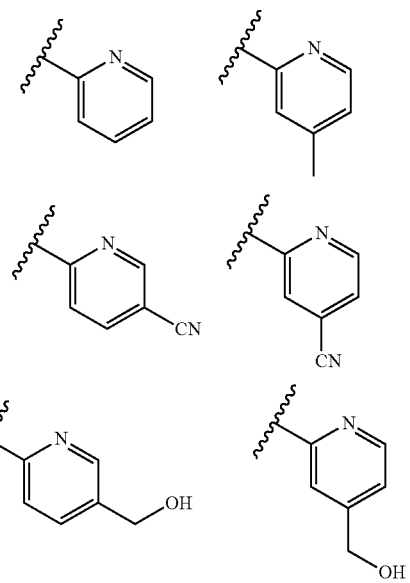

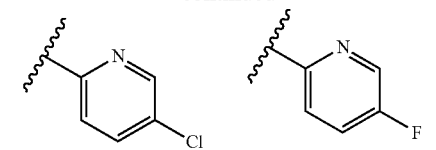
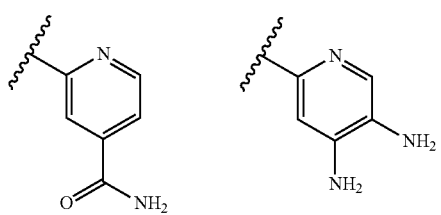
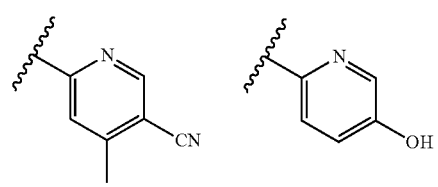
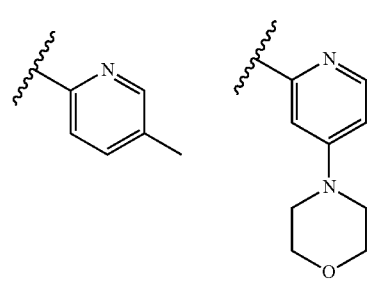
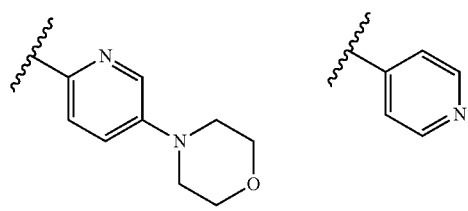
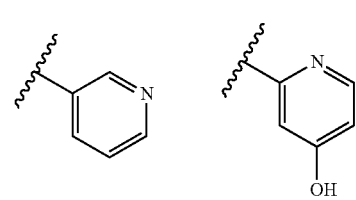
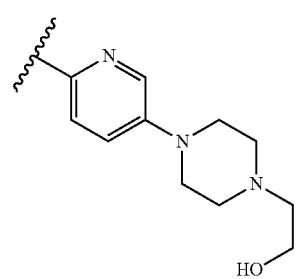
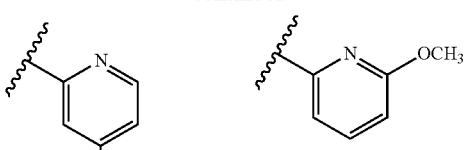
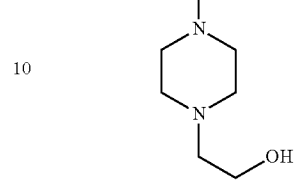
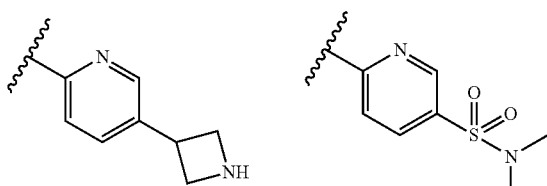
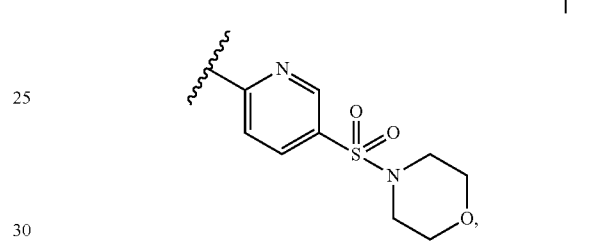
wherein the wavy lines represent the point of attachment in Formula I.
In certain embodiments, R⁵ is selected from:
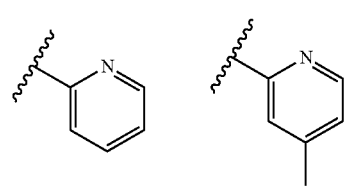
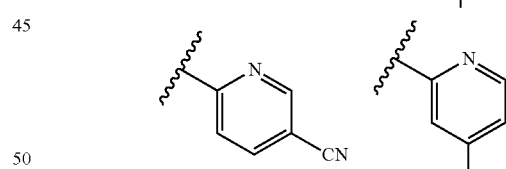
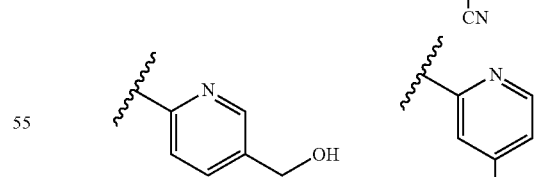
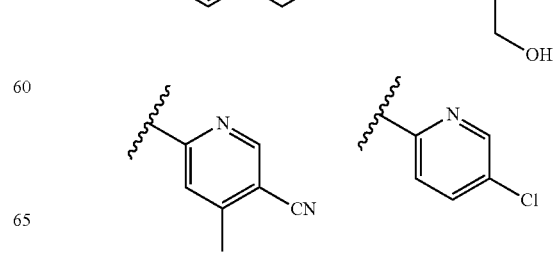

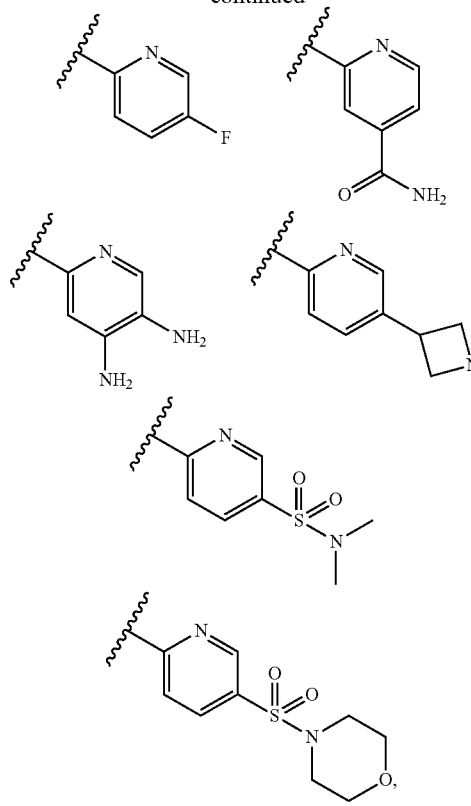

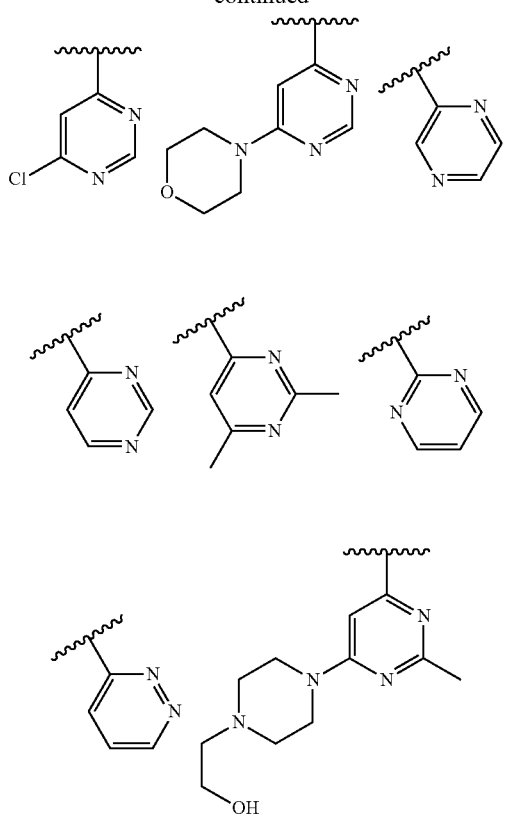

wherein the wavy lines represent the point of attachment in Formula I.

In certain embodiments, $R^5$ is pyrimidinyl, pyridazinyl, or pyrazinyl, optionally substituted by $C_1$-$C_6$ alkyl, $C_2$-$C_6$ alkenyl, $C_2$-$C_6$ alkynyl, halogen, —($C_0$-$C_3$ alkylene)CN, —($C_0$-$C_3$ alkylene)$OR^{11}$, —($C_0$-$C_3$ alkylene)$SR^{11}$, —($C_0$-$C_3$ alkylene)$NR^{11}R^{12}$, —($C_0$-$C_3$ alkylene)$CF_3$, —($C_0$-$C_3$ alkylene)$NO_2$, —C=NH($OR^{11}$), —($C_0$-$C_3$ alkylene)C(O)$R^{11}$, —($C_0$-$C_3$ alkylene)C(O)$OR^{11}$, —($C_0$-$C_3$ alkylene)C(O)$NR^{11}R^{12}$, —($C_0$-$C_3$ alkylene)$NR^{11}$C(O)$R^{12}$, —($C_0$-$C_3$ alkylene)$S(O)_{1-2}R^{11}$, —($C_0$-$C_3$ alkylene)NR $S(O)_{1-2}R^{12}$, —($C_0$-$C_3$ alkylene)$S(O)_{1-2}NR^{11}R^{12}$, —($C_0$-$C_3$ alkylene)($C_3$-$C_6$ cycloalkyl), —($C_0$-$C_3$ alkylene)(3-6-membered heterocyclyl), —($C_0$-$C_3$ alkylene)C(O)(3-6-membered heterocyclyl), —($C_0$-$C_3$ alkylene)(5-6-membered heteroaryl) or —($C_0$-$C_3$ alkylene)phenyl, wherein $R^{10}$ is independently optionally substituted by halogen, $C_1$-$C_3$ alkyl, oxo, —$CF_3$, —($C_0$-$C_3$ alkylene)$OR^{13}$, —($C_0$-$C_3$ alkylene)$NR^{13}R^{14}$, —($C_0$-$C_3$ alkylene)C(O)$R^{13}$ or —($C_0$-$C_3$ alkylene) $S(O)_{1-2}R^{13}$.

In certain embodiments, $R^5$ is selected from:

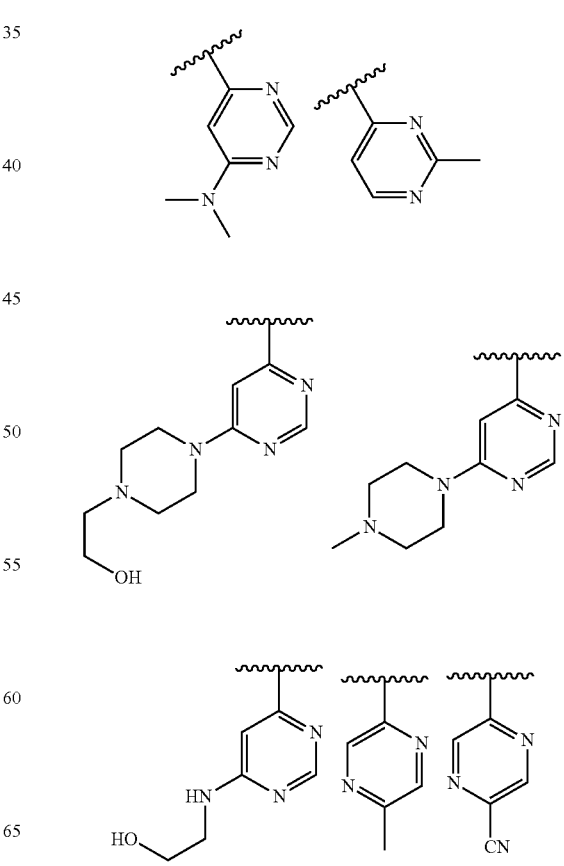

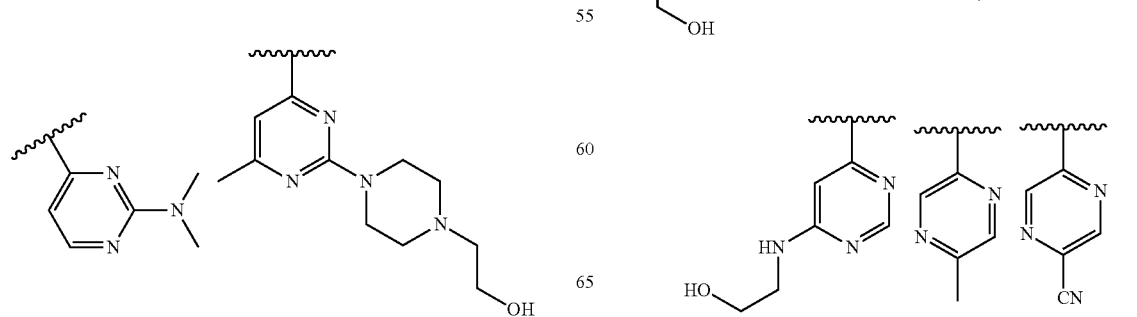

31
-continued
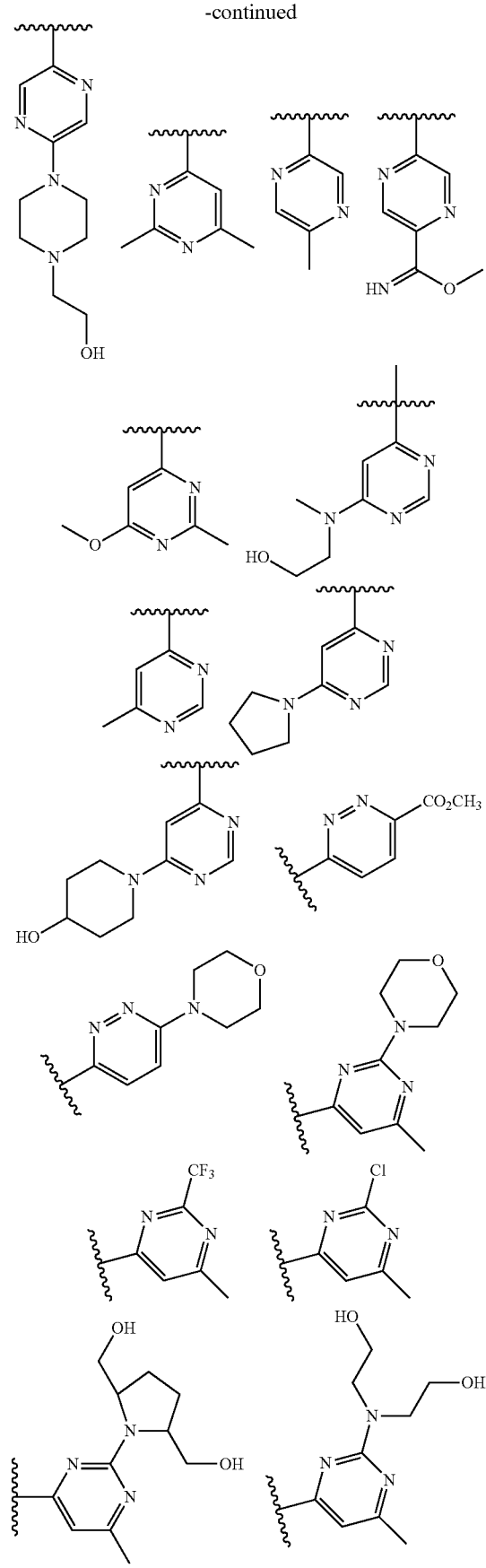
32
-continued
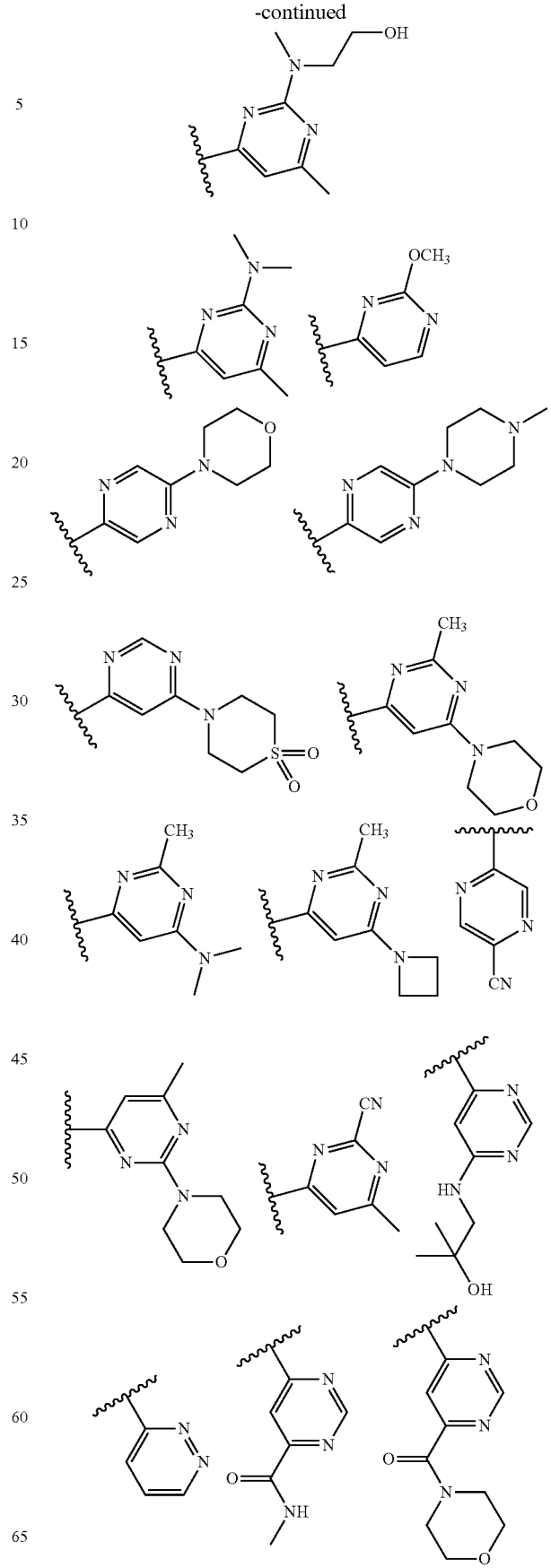

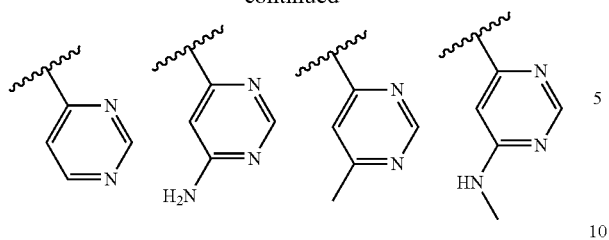
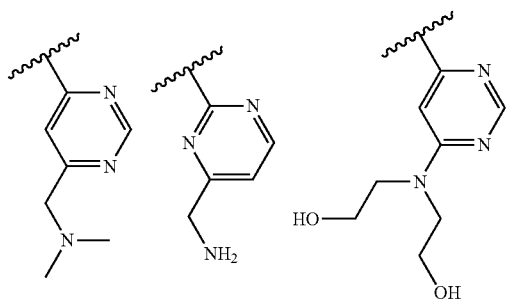
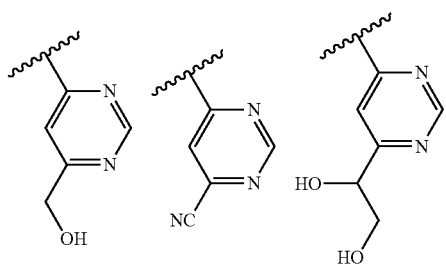
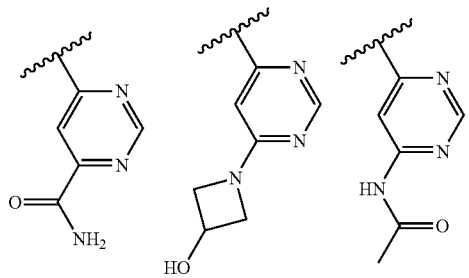
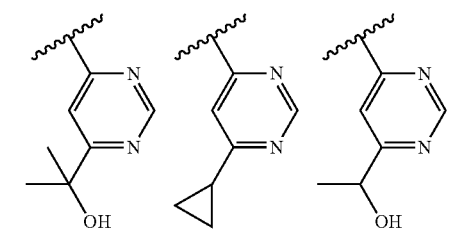
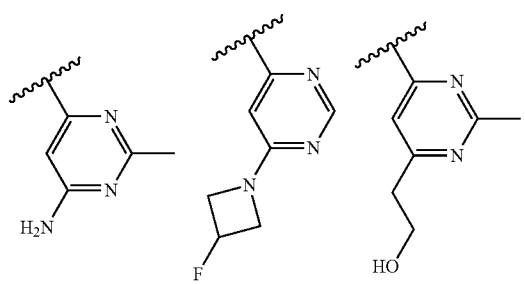
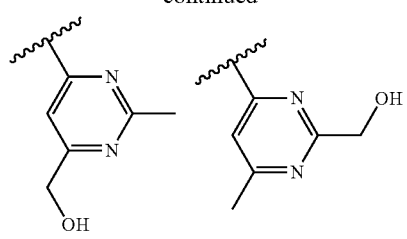
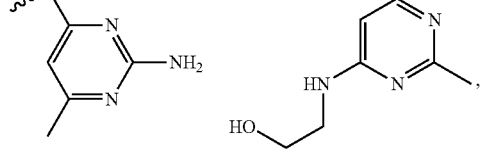
wherein the wavy lines represent the point of attachment in Formula I.
In certain embodiments, $R^5$ is selected from:
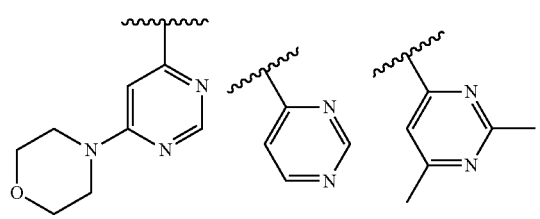
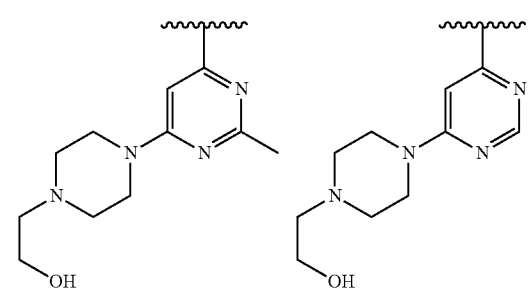
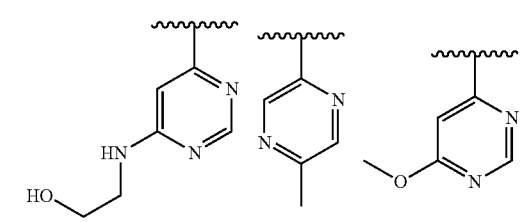
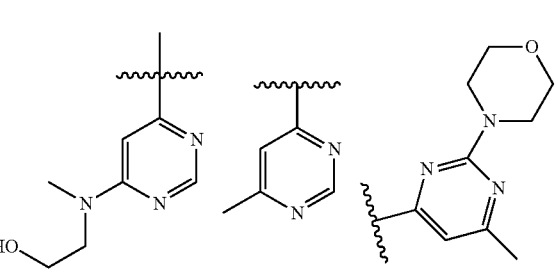

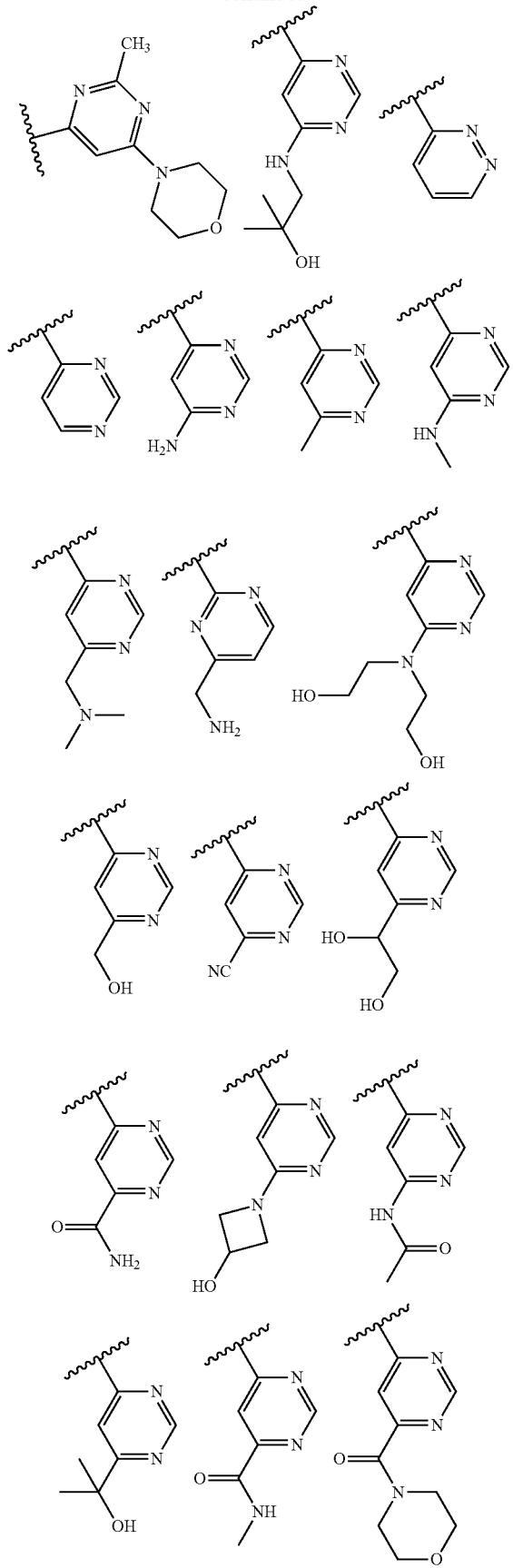
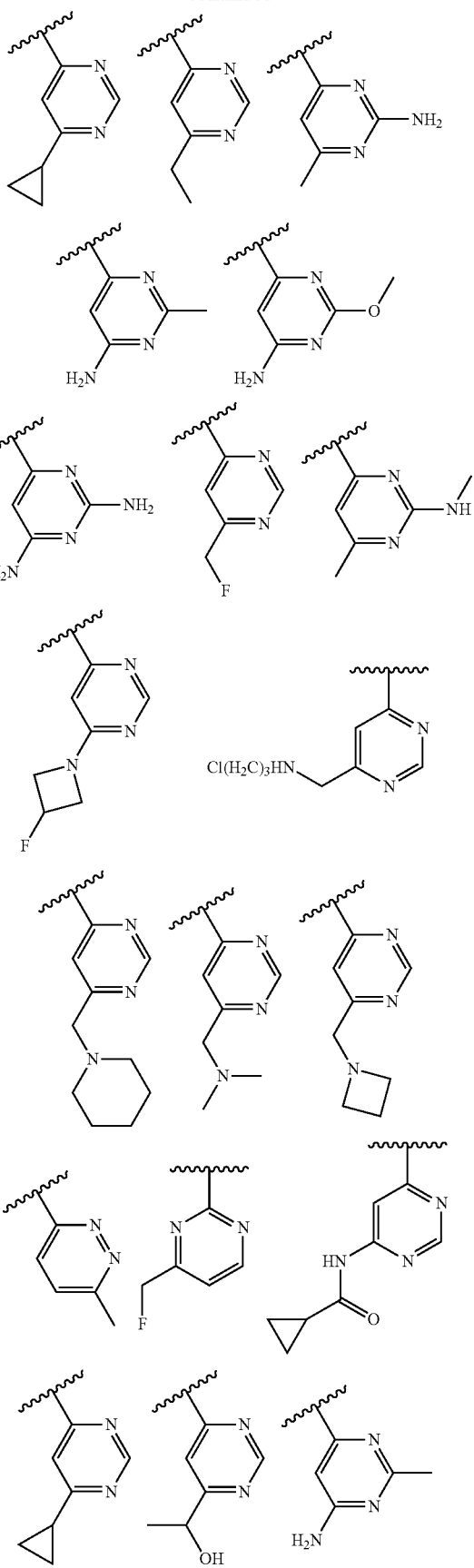

-continued

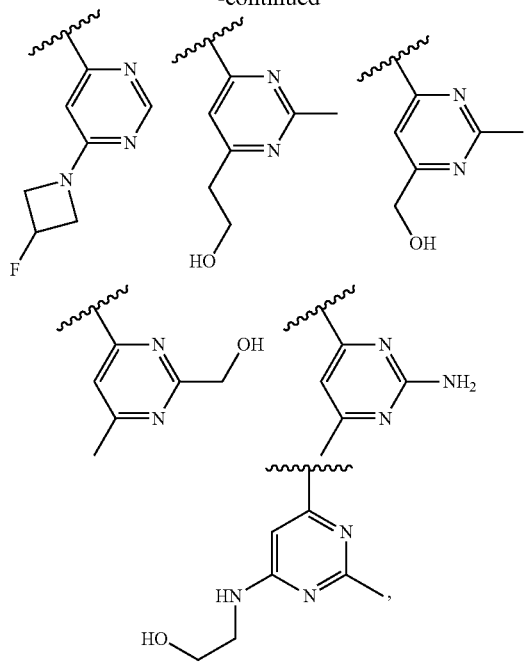

wherein the wavy lines represent the point of attachment in Formula I.

In certain embodiments, $R^5$ is pyrazolyl, isoxazolyl, oxazolyl, imidazolyl, thiazolyl or thiadiazolyl, wherein $R^5$ is optionally substituted by $R^{10}$, wherein $R^{10}$ is $C_1$-$C_6$ alkyl, halogen, —CN, —OR$^{11}$, —SR$^{11}$, —NR$^{11}$R$^{12}$, —CF$_3$, —C(O)R$^{11}$, —C(O)OR$^{11}$, —C(O)NR$^{11}$R$^{12}$, —NR$^{11}$C(O)R$^{12}$, —S(O)$_{1-2}$R$^{11}$, —NR$^{11}$S(O)$_{1-2}$R$^{12}$, —S(O)$_{1-2}$NR$^{11}$R$^{12}$, $C_3$-$C_6$ cycloalkyl, 3-6-membered heterocyclyl, —C(O)(3-6-membered heterocyclyl), 5-6-membered heteroaryl or phenyl, wherein $R^{10}$ is independently optionally substituted by halogen, $C_1$-$C_3$ alkyl, oxo, —CF$_3$, —OR$^{13}$, —NR$^{13}$R$^{14}$, —C(O)R$^{13}$ or —S(O)$_{1-2}$R$^{13}$. In certain embodiments, $R^5$ is pyrazolyl optionally substituted by $R^{10}$.

In certain embodiments, $R^5$ is selected from:

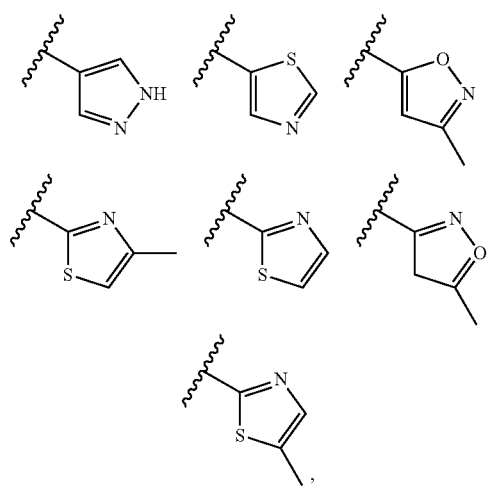

wherein the wavy lines represent the point of attachment in Formula I.

In certain embodiments, $R^5$ is selected from:

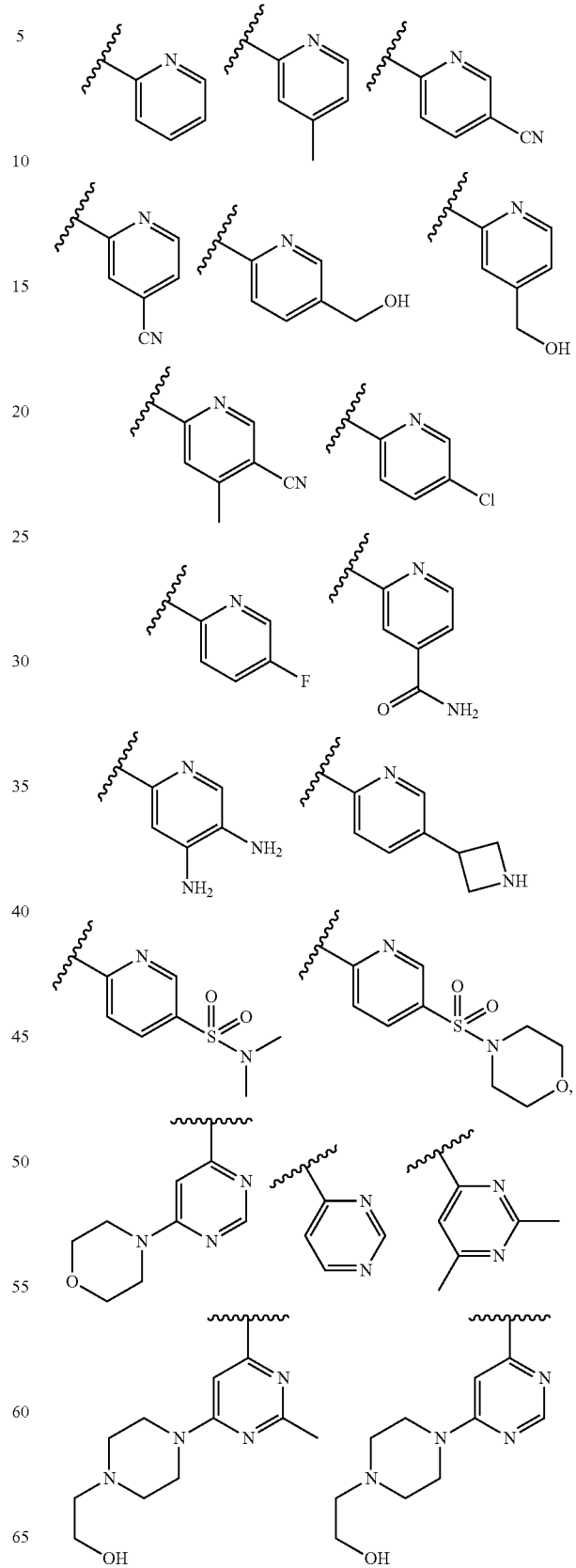

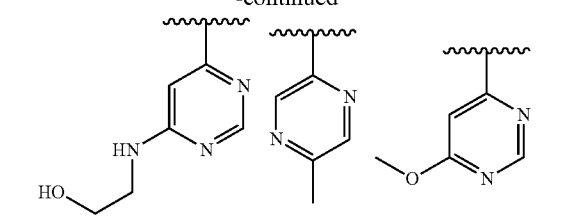
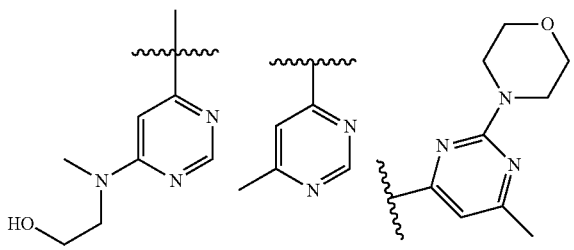
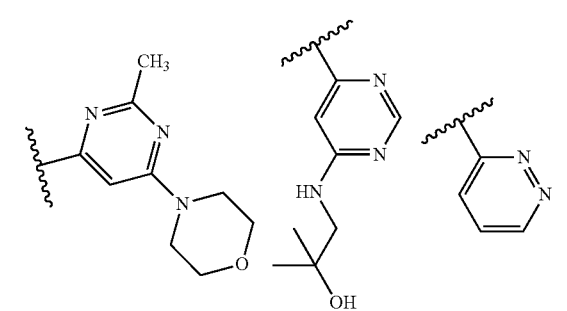
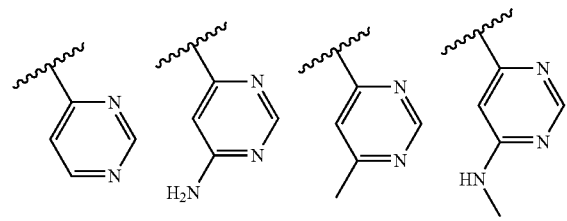
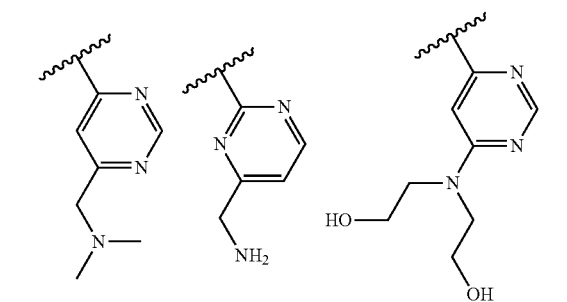
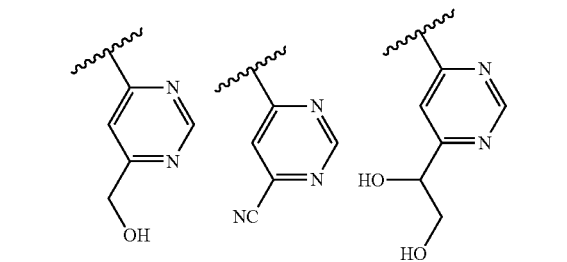
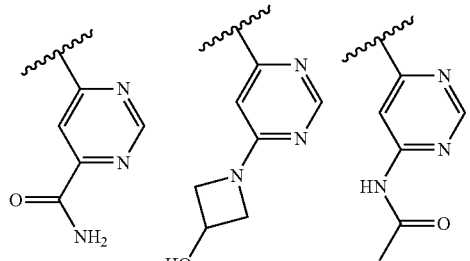
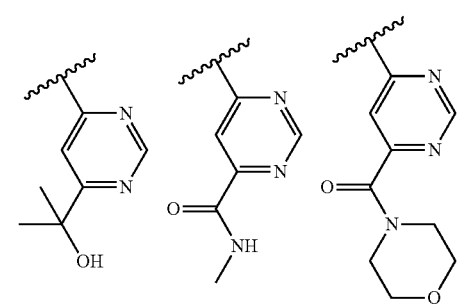
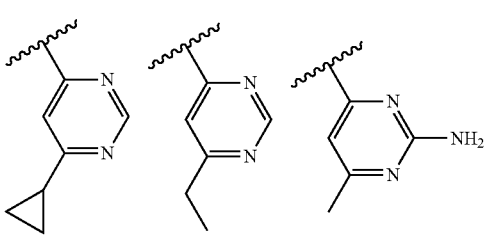
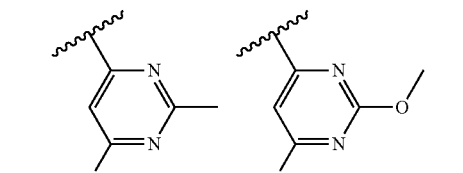
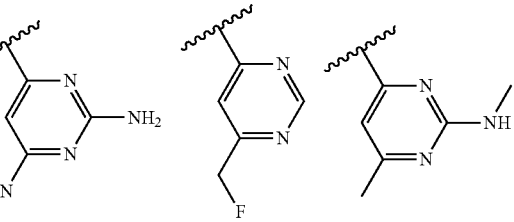
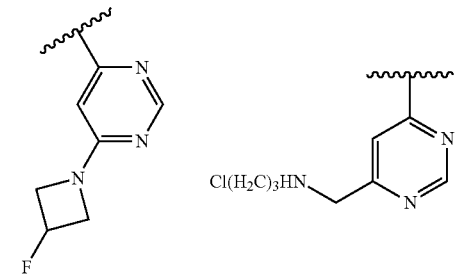

-continued

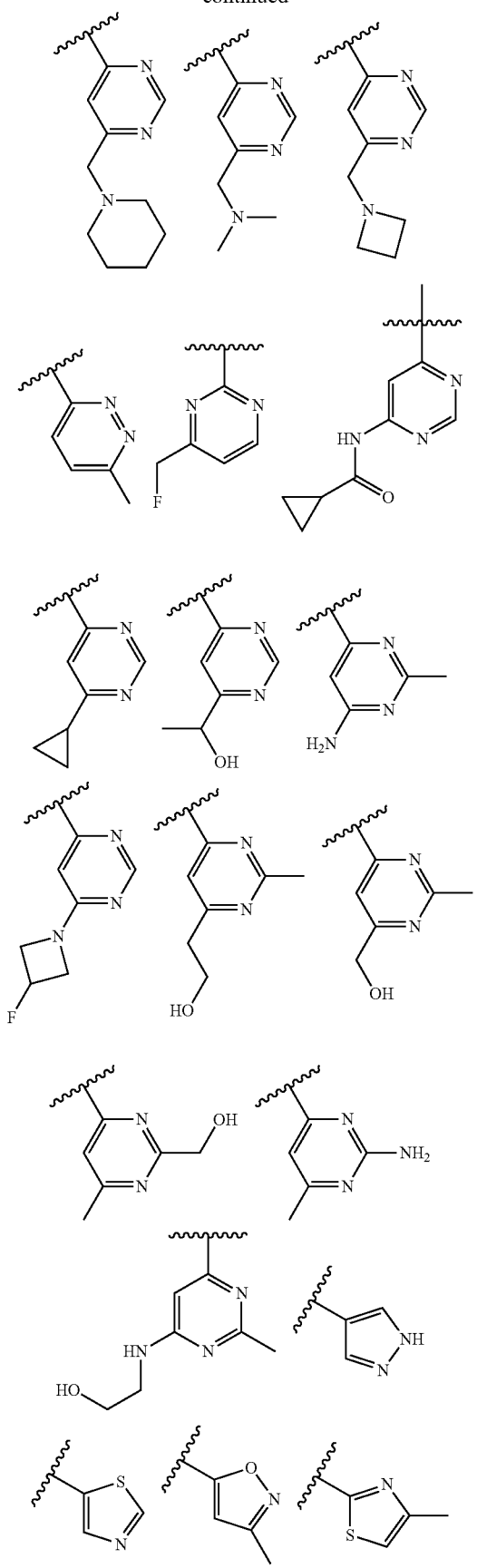

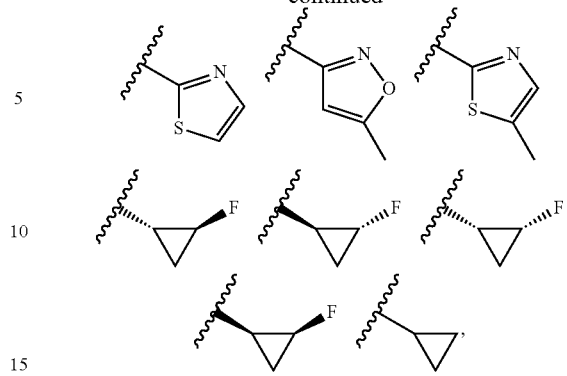

wherein the wavy line represents the point of attachment in Formula I.

In certain embodiments, $R^6$ and $R^7$ are each independently hydrogen or $C_1$-$C_6$ alkyl optionally substituted by $R^{10}$; or $R^6$ and $R^7$ are independently taken together with the atom to which they are attached to form a 3-6 membered heterocyclyl optionally substituted by halogen, oxo, —$OR^{11}$, —$NR^{11}R^{12}$, $C_1$-$C_6$ alkyl, $C_2$-$C_6$ alkenyl or $C_2$-$C_6$ alkynyl, wherein said alkyl, alkenyl and alkynyl are independently optionally substituted by halogen or oxo.

In certain embodiments, $R^6$ and $R^7$ are each independently hydrogen, methyl or ethyl, wherein said methyl and ethyl are independently optionally substituted by $R^{10}$. In certain embodiments, $R^6$ and $R^7$ are each independently hydrogen, methyl or ethyl In certain embodiments, $R^8$ and $R^9$ are each independently hydrogen, $C_1$-$C_6$ alkyl, $C_2$-$C_6$ alkenyl or $C_2$-$C_6$ alkynyl, wherein said alkyl, alkenyl and alkynyl are independently optionally substituted by $R^{10}$; or $R^8$ and $R^9$ are independently taken together with the atom to which they are attached to form a 3-10 membered heterocyclyl optionally substituted by halogen, oxo, —$OR^{11}$, —$NR^{11}R^{12}$, $C_1$-$C_6$ alkyl, $C_2$-$C_6$ alkenyl or $C_2$-$C_6$ alkynyl, wherein said alkyl, alkenyl and alkynyl are independently optionally substituted by halogen or oxo.

In certain embodiments, $R^8$ is hydrogen and $R^9$ $C_1$-$C_6$ alkyl optionally substituted by $R^{10}$. In certain embodiments, $R^8$ is hydrogen and $R^9$ $C_1$-$C_6$ alkyl optionally substituted by oxo or halogen.

In certain embodiments, $R^8$ and $R^9$ are each independently hydrogen, $C_3$-$C_6$ cycloalkyl, phenyl or 3-10-membered heterocyclyl, wherein said alkyl, alkenyl, alkynyl, cycloalkyl, phenyl and heterocyclyl are independently optionally substituted by $R^{10}$. In certain embodiments, $R^8$ is hydrogen and $R^9$ is 3-6-membered heterocyclyl optionally substituted by $R^{10}$. In certain embodiments, $R^8$ is hydrogen and $R^9$ is pyrimidinyl optionally substituted by $R^{10}$.

In certain embodiments, $R^8$ and $R^9$ are hydrogen.

In certain embodiments, $R^{10}$ is independently halogen. In certain embodiments, $R^{10}$ is independently F.

In certain embodiments, $R^{10}$ is independently —CN.

In certain embodiments, $R^{10}$ is independently $C_1$-$C_6$ alkyl, $C_2$-$C_6$ alkenyl or $C_2$-$C_6$ alkynyl, wherein said alkyl, alkenyl and alkynyl are independently optionally substituted by halogen, oxo, —$OR^{13}$ or —$NR^{13}R^{14}$. In certain embodiments, $R^{10}$ is methyl, ethyl, isopropy, —$CH_2OH$, —$CH_2CH_2OH$, —$CH(OH)CH_2OH$, —$C(CH_3)_2OH$, —$CH_2NH_2$, —$CH_2N(CH_3)_2$, —$CF_3$, —$C(O)NH_2$, —$C(O)NHCH_3$, —$C(O)N(CH_3)_2$ or —$C(O)$morpholinyl. In certain embodiments, $R^{10}$ is methyl.

In certain embodiments, $R^{10}$ is independently 3-6 membered heterocyclyl or —C(O)(3-6 membered heterocyclyl), wherein said heterocyclyl is independently optionally substituted by —($C_0$-$C_3$ alkylene)$OR^{13}$, —($C_0$-$C_3$ alkylene)$NR^{13}R^{14}$, halogen, —CN, oxo or $C_1$-$C_6$ alkyl optionally substituted by oxo or halogen. In certain embodiments, said heterocyclyl is morpholinyl, thiomorpholinyl, piperizinyl, piperidinyl or aziridinyl, wherein said heterocyclyl is independently optionally substituted by oxo, —$CH_2OH$, —$CH_2CH_2OH$, —OH, methyl or —$CF_3$. In certain embodiments, $R^{10}$ is independently selected from:

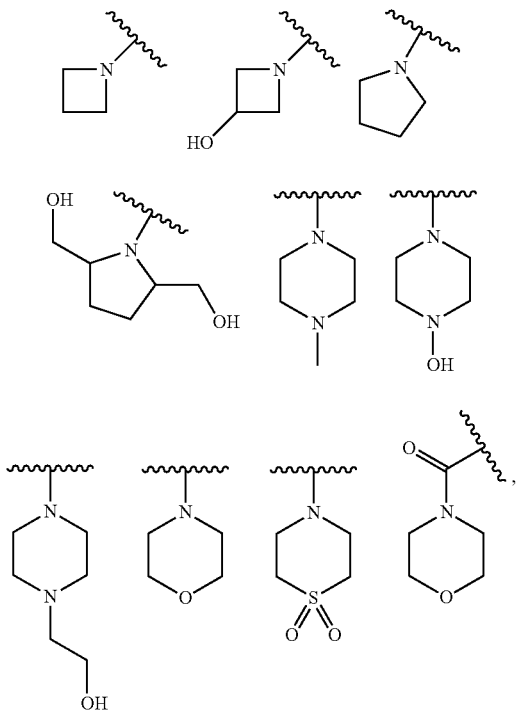

wherein the wavy line represents the point of attachment in Formula I.

In certain embodiments, $R^{10}$ is independently —($C_0$-$C_3$ alkylene)$OR^{11}$ or —($C_0$-$C_3$ alkylene)$SR^{11}$. In certain embodiments, $R^{10}$ is —OH, —$OCH_3$, —$CH_2OH$, —$CH_2CH_2OH$, —CH(OH)$CH_2OH$ or —C($CH_3$)$_2OH$. In certain embodiments, $R^{10}$ is —OH or —$OCH_3$.

In certain embodiments, $R^{10}$ is independently —($C_0$-$C_3$ alkylene)$NR^{11}R^{12}$. In certain embodiments, $R^{10}$ is —$NH_2$, —$NHCH_3$, —NHC(O)$CH_3$, —N($CH_3$)$_2$, —N($CH_2CH_2OH$)$_2$, —$NHCH_2CH_2OH$, —N($CH_3$)$CH_2CH_2OH$, —$NHCH_2C(CH_3)_2OH$, —N($CH_3$)$CH_2C(CH_3)_2OH$, 4-hydroxyaziridin-1-yl, morpholinyl, dioxothiomorpholinyl, piperidinyl, 4-hydroxypiperidinyl, 4-methylpiperazinyl, pyrrolidinyl or 4-(2-hydroxyethyl)piperazinyl.

In certain embodiments, $R^{10}$ is independently —C(O)$NR^{11}R^{12}$. In certain embodiments, $R^{10}$ is —C(O)$NH_2$, —C(O)$NHCH_3$, —C(O)N($CH_3$)$_2$ or —C(O)morpholinyl.

In certain embodiments, $R^{10}$ is independently $C_1$-$C_6$ alkyl, halogen, —CN, —$OR^{11}$, —$SR^{11}$, —$NR^{11}R^{12}$, —$CF_3$, —C=NH($OR^{11}$), —C(O)$OR^{11}$, $C_3$-$C_6$ cycloalkyl, 3-6-membered heterocyclyl, 5-6-membered heteroaryl or phenyl, wherein $R^{10}$ is independently optionally substituted by halogen, oxo, —$CF_3$, —$OR^{13}$, —$NR^{13}R^{14}$, —C(O)$R^{13}$, —S(O)$_{1-2}R^{13}$ or $C_1$-$C_3$ alkyl optionally substituted by oxo or halogen.

In certain embodiments, $R^{10}$ is independently selected from F, —CN, methyl, ethyl, isopropy, —$CH_2OH$, —$CH_2CH_2OH$, —CH(OH)$CH_2OH$, —C($CH_3$)$_2OH$, —$CH_2NH_2$, —$CH_2N(CH_3)_2$, —$CF_3$, —OH, —$OCH_3$, —$NH_2$, —$NHCH_3$, —NHC(O)$CH_3$, —N($CH_3$)$_2$, —N($CH_2CH_2OH$)$_2$, —$NHCH_2CH_2OH$, —N($CH_3$)$CH_2CH_2OH$, —$NHCH_2C(CH_3)_2OH$, —N($CH_3$)$CH_2C(CH_3)_2OH$, —C(O)$NH_2$, —C(O)$NHCH_3$, —C(O)N($CH_3$)$_2$,

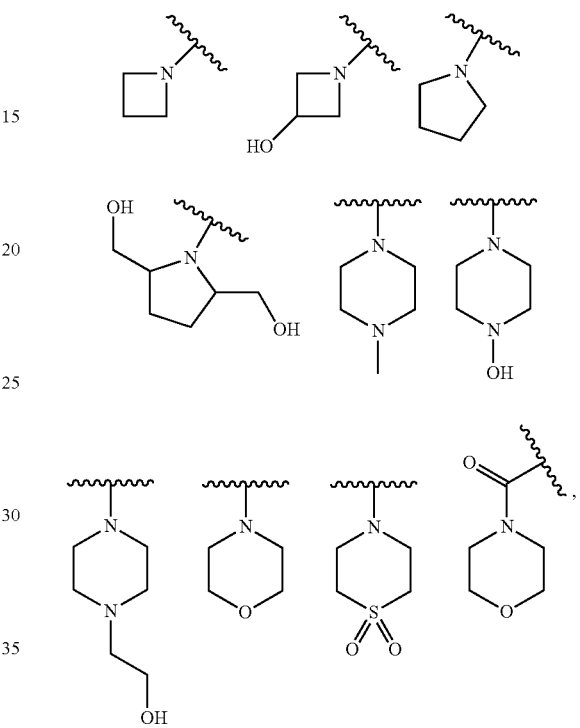

wherein the wavy line represents the point of attachment in Formula I.

In certain embodiments, $R^{10}$ is independently selected from F, Cl, —CN, methyl, ethyl, isopropy, —$CH_2OH$, —$CH_2CH_2OH$, —CH(OH)$CH_2OH$, —C($CH_3$)$_2OH$, —$CH_2NH_2$, —$CH_2N(CH_3)_2$, —$CF_3$, —OH, —$OCH_3$, —$NH_2$, —$NHCH_3$, —NHC(O)$CH_3$, —N($CH_3$)$_2$, —N($CH_2CH_2OH$)$_2$, —$NHCH_2CH_2OH$, —N($CH_3$)$CH_2CH_2OH$, —$NHCH_2C(CH_3)_2OH$, —N($CH_3$)$CH_2C(CH_3)_2OH$, —C(O)$NH_2$, —C(O)$NHCH_3$, —C(O)N($CH_3$)$_2$,

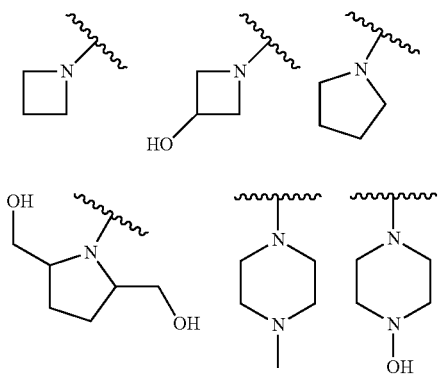

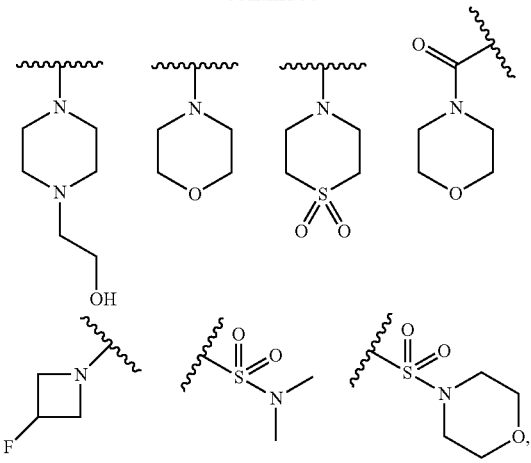

wherein the wavy line represents the point of attachment in Formula I.

In certain embodiments, $R^{11}$ and $R^{12}$ are independently hydrogen or $C_1$-$C_6$ alkyl optionally substituted by halogen, oxo, —CN, —OR$^{16}$ or —NR$^{16}$R$^{17}$, or are taken together with the atom to which they attached to form a 3-6 membered heterocyclyl optionally substituted by halogen, oxo, —OR$^{16}$, —NR$^{16}$R$^{17}$ or $C_1$-$C_3$ alkyl optionally substituted by halogen, oxo or OH.

In certain embodiments, $R^{11}$ and $R^{12}$ are independently hydrogen, methyl, —C(O)CH$_3$, 2-hydroxy-2-methylpropyl or 2-hydroxyethyl, or are taken together with the atom to which they attached to form a azetidinyl, pyrrolidinyl, morpholinyl, dioxothiomorphlinyl, piperazinyl or piperidinyl ring optionally substituted by halogen, oxo or $C_1$-$C_3$ alkyl optionally substituted by oxo, halogen or OH.

In certain embodiments, $R^{11}$ and $R^{12}$ are independently hydrogen, methyl, —C(O)CH$_3$, 2-hydroxy-2-methylpropyl or 2-hydroxyethyl.

In certain embodiments, $R^{13}$ and $R^{14}$ are independently hydrogen or $C_1$-$C_3$ alkyl. In certain embodiments, $R^{13}$ and $R^{14}$ are independently hydrogen or methyl.

In certain embodiments, $R^{15}$ is hydrogen, halogen, —CF$_3$, —CN, —O($C_1$-$C_6$ alkyl) or $C_1$-$C_6$ alkyl, wherein said alkyl is optionally substituted by halogen or oxo. In certain embodiments, $R^{15}$ is methyl. In certain embodiments, $R^{15}$ is halogen. In certain embodiments, $R^{15}$ is F, Cl or Br. In certain embodiments, $R^{15}$ is —O($C_1$-$C_6$ alkyl). In certain embodiments, $R^{15}$ is —OCH$_3$. In certain embodiments, $R^{15}$ is —CN.

In certain embodiments, $R^{15}$ is hydrogen, F, Cl, Br, —CN, —OCH$_3$ or methyl.

In certain embodiments, X is CR$^{15}$, $R^{15}$ is halogen, —CN, —O($C_1$-$C_6$ alkyl) or $C_1$-$C_6$ alkyl, wherein said alkyl is optionally substituted by halogen or oxo, $R^1$ is halogen or —CN, and $R^2$ is hydrogen or F.

In certain embodiments, X is CR$^{15}$, $R^{15}$ is halogen, —CN, —O($C_1$-$C_6$ alkyl) or $C_1$-$C_6$ alkyl, wherein said alkyl is optionally substituted by halogen or oxo, $R^1$ is halogen or —CN, $R^2$ is hydrogen or F, and $R^4$ is —NHR$^5$, —NHC(O)R$^5$, —NHC(O)OR$^5$ or —NHC(O)NHR$^5$.

In certain embodiments, $R^{16}$ and $R^{17}$ are each independently hydrogen or $C_1$-$C_3$ alkyl. In certain embodiments, $R^{16}$ and $R^{17}$ are each independently hydrogen or methyl.

In certain embodiments, $R^{18}$ and $R^{19}$ are independently hydrogen or methyl.

In certain embodiments, A is CR$^3$; X is CH; $R^1$ is independently hydrogen, —CN, —OCH$_3$, —CF$_3$, —OCF$_3$, —CH$_3$, Cl or F, wherein both $R^1$ cannot be hydrogen at the same time; $R^2$ is hydrogen; $R^3$ is hydrogen, halogen or —CN; $R^4$ is —NH—, —NHC(O)—, —NHC(O)NH— or —NHC(O)O—; and $R^5$ is $C_3$-$C_6$ cycloalkyl optionally substituted by $R^{10}$.

In certain embodiments, A is CR$^3$; X is CH; $R^1$ is independently hydrogen, —CN, —OCH$_3$, —CF$_3$, —OCF$_3$, —CH$_3$, Cl or F, wherein both $R^1$ cannot be hydrogen at the same time; $R^2$ is hydrogen; $R^3$ is hydrogen, halogen or —CN; $R^4$ is —NH—, —NHC(O)—, —NHC(O)NH— or —NHC(O)O—; and $R^5$ is pyrimidinyl, pyridinyl, pyridazinyl or pyrazinyl optionally substituted by $R^{10}$.

In certain embodiments, A is CR$^3$; X is CR$^{15}$, one $R^1$ is halogen; $R^2$ is hydrogen; $R^4$ is —NH—, —NHC(O)—, —NHC(O)NH— or —NHC(O)O—; and $R^5$ is pyrimidinyl, pyridinyl, pyridazinyl or pyrazinyl optionally substituted by F, Cl, —CN, methyl, ethyl, isopropy, —CH$_2$OH, —CH$_2$CH$_2$OH, —CH(OH)CH$_2$OH, —C(CH$_3$)$_2$OH, —CH$_2$NH$_2$, —CH$_2$N(CH$_3$)$_2$, —CF$_3$, —OH, —OCH$_3$, —NH$_2$, —NHCH$_3$, —NHC(O)CH$_3$, —N(CH$_3$)$_2$, —N(CH$_2$CH$_2$OH)$_2$, —NHCH$_2$CH$_2$OH, —N(CH$_3$)CH$_2$CH$_2$OH, —NHCH$_2$C(CH$_3$)$_2$OH, —N(CH$_3$)CH$_2$C(CH$_3$)$_2$OH, —C(O)NH$_2$, —C(O)NHCH$_3$, —C(O)N(CH$_3$)$_2$,

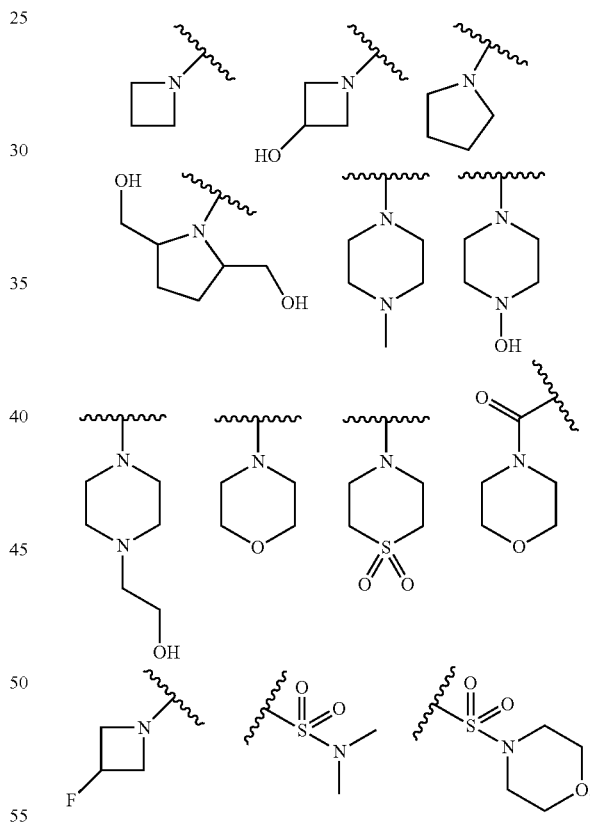

wherein the wavy line represents the point of attachment in Formula I.

In certain embodiments, $R^1$ is independently hydrogen, —CN or halogen, wherein both $R^1$ cannot be hydrogen at the same time and $R^4$ is —NH—, —NR$^6$C(O)—, —NR$^6$C(O)O— or —NR$^6$C(O)NR$^7$—.

Another embodiment includes a compound of Formula I, stereoisomers or pharmaceutically acceptable salts thereof, selected from:

N-(2-(2,6-Dichlorophenyl)-2H-pyrazolo[4,3-c]pyridin-4-yl) cyclopropanecarboxamide;

[2-(2,6-Dichlorophenyl)-2H-pyrazolo[4,3-c]pyridine-4-yl]-(2,6-dimethylpyrimidin-4-yl)amine;
6-[2-(2,6-Dichlorophenyl)-2H-pyrazolo[4,3-c]pyridin-4-ylamino]nicotinonitrile;
N-[2-(2,6-Dichlorophenyl)-2H-pyrazolo[4,3-c]pyridine-4-yl]-N'-methylpyrimidine-4,6-diamine;
[2-(2,6-Dichlorophenyl)-2H-pyrazolo[4,3-c]pyridine-4-yl]-[6-(3-fluoroazetidin-1-yl)pyrimidin-4-yl]amine;
[2-(2,6-Dichlorophenyl)-2H-pyrazolo[4,3-c]pyridine-4-yl] carbamic acid methyl ester;
1-[2-(2,6-Dichlorophenyl)-2H-pyrazolo[4,3-c]pyridine-4-yl]-3-methylurea;
N-[2-(2,6-Dichlorophenyl)-2H-pyrazolo[4,3-c]pyridin-4-yl]-pyridazine-3,6-diamine;
$N^4$-[2-(2,6-Dichlorophenyl)-2H-pyrazolo[4,3-c]pyridine-4-yl]-6-methyl-pyrimidine-2,4-diamine;
N-[2-(2,6-Dichlorophenyl)-2H-pyrazolo[4,3-c]pyridin-4-yl]-2-methoxy-pyrimidine-4,6-diamine;
N-[2-(2,6-Dichlorophenyl)-2H-pyrazolo[4,3-c]pyridin-4-yl]-pyrimidine-2,4,6-triamine;
N-[2-(2,6-Dichlorophenyl)-2H-pyrazolo[4,3-c]pyridin-4-yl]-2-methyl-pyrimidine-4,6-diamine;
$N^4$-[2-(2,6-dichlorophenyl)-2H-pyrazolo[4,3-c]pyridine-4-yl]-6,$N^2$-dimethylpyrimidine-2,4-diamine;
N-[2-(2,6-Dichlorophenyl)-2H-pyrazolo[4,3-c]pyridin-4-yl]-pyrimidine-4,6-diamine;
Cyclopropanecarboxylic acid [2-(2-chloro-6-fluorophenyl)-2H-pyrazolo[4,3-c]pyridin-4-yl]amide;
6-[2-(2-Chloro-6-fluorophenyl)-2H-pyrazolo[4,3-c]pyridin-4-ylamino]isonicotinonitrile;
4-Bromo-2-(2-chloro-6-fluorophenyl)-2H-pyrazolo[4,3-c]pyridine;
[2-(2,6-Dichloro-4-methanesulfonylphenyl)-2H-pyrazolo[4,3-c]pyridin-4-yl]-(2,6-dimethylpyrimidin-4-yl)amine;
3,5-Dichloro-4-[4-(2,6-dimethylpyrimidin-4-ylamino)pyrazolo[4,3-c]pyridin-2-yl]benzonitrile;
3,5-Dichloro-4-[4-(6-hydroxymethyl-pyrimidin-4-ylamino)-pyrazolo[4,3-c]pyridin-2-yl]-benzonitrile;
3,5-Dichloro-4-[4-(6-fluoromethyl-pyrimidin-4-ylamino)-pyrazolo[4,3-c]pyridin-2-yl]-benzonitrile;
4-[4-(6-Azetidin-1-ylmethylpyrimidin-4-ylamino)pyrazolo[4,3-c]pyridin-2-yl]-3,5-dichlorobenzonitrile;
3,5-Dichloro-4-[4-(4-fluoromethylpyrimidin-2-ylamino)pyrazolo[4,3-c]pyridin-2-yl]benzonitrile;
4-[4-(6-Amino-2-methylpyrimidin-4-ylamino)pyrazolo[4,3-c]pyridin-2-yl]-3,5-dichlorobenzonitrile;
4-[4-(6-Aminopyrimidin-4-ylamino)-pyrazolo[4,3-c]pyridin-2-yl]-3,5-dichloro-benzonitrile;
N-(6-((2-(2,6-dichloro-4-cyanophenyl)-2H-pyrazolo[4,3-c]pyridin-4-yl)amino]pyrimidin-4-yl)-cyclopropanecarboxamide;
[2-(2,6-Dichloro-4-fluorophenyl)-2H-pyrazolo[4,3-c]pyridin-4-yl]-(6-methylpyrimidin-4-yl)amine;
{6-[2-(2,6-Dichloro-4-fluorophenyl)-2H-pyrazolo[4,3-c]pyridine-4-yl]-(4-methylpyridin-2-yl)}methanol;
[2-(2,6-Dichloro-4-fluorophenyl)-2H-pyrazolo[4,3-c]pyridin-4-yl]-(6-fluoromethylpyrimidin-4-yl)amine;
3,5-Dichloro-4-[7-chloro-4-(6-methylpyrimidin-4-ylamino)pyrazolo[4,3-c]pyridin-2-yl]benzonitrile;
{6-[7-Chloro-2-(2,6-dichlorophenyl)-2H-pyrazolo[4,3-c]pyridin-4-ylamino]-pyrimidin-4-yl}-methanol;
N-[7-Chloro-2-(2,6-dichlorophenyl)-2H-pyrazolo[4,3-c]pyridin-4-yl]-pyrimidine-4,6-diamine;
3,5-Dichloro-4-[7-fluoro-4-(6-methyl-pyrimidin-4-ylamino)-pyrazolo[4,3-c]pyridin-2-yl]-benzonitrile;
4-[4-(6-Amino-pyrimidin-4-ylamino)-7-fluoro-pyrazolo[4,3-c]pyridin-2-yl]-3,5-dichlorobenzonitrile;
[2-(2,6-Dichlorophenyl)-7-fluoro-2H-pyrazolo[4,3-c]pyridin-4-yl]-(6-methyl-pyrimidin-4-yl)-amine;
4-[7-Bromo-4-(6-methyl-pyrimidin-4-ylamino)-pyrazolo[4,3-c]pyridin-2-yl]-3,5-dichlorobenzonitrile;
{6-[7-Bromo-2-(2,6-dichloro-phenyl)-2H-pyrazolo[4,3-c]pyridin-4-ylamino]-pyrimidin-4-yl}-methanol;
[7-Bromo-2-(2,6-dichlorophenyl)-2H-pyrazolo[4,3-c]pyridin-4-yl]-(6-methylpyrimidin-4-yl)-amine;
2-(2,6-Dichlorophenyl)-4-(6-methylpyrimidin-4-ylamino)-2H-pyrazolo[4,3-c]pyridine-7-carbonitrile;
4-(6-Aminopyrimidin-4-ylamino)-2-(2,6-dichlorophenyl)-2H-pyrazolo[4,3-c]pyridine-7-carbonitrile;
N-[7-Bromo-2-(2,6-dichlorophenyl)-2H-pyrazolo[4,3-c]pyridin-4-yl]-pyrimidine-4,6-diamine;
{6-[2-(2,6-Dichlorophenyl)-7-methoxy-2H-pyrazolo[4,3-c]pyridin-4-ylamino]-pyrimidin-4-yl}-methanol;
[2-(2,6-Dichloro-4-fluorophenyl)-7-fluoro-2H-pyrazolo[4,3-c]pyridin-4-yl]-(6-methylpyrimidin-4-yl)-amine;
[2-(2,6-Dichlorophenyl)-2H-pyrazolo[4,3-c]pyridine-4-yl] pyrimidin-4-ylamine;
2-[2-(2,6-Dichlorophenyl)-2H-pyrazolo[4,3-c]pyridin-4-ylamino]isonicotinonitrile;
[2-(2,6-Dichlorophenyl)-2H-pyrazolo[4,3-c]pyridine-4-yl]-(6-methylpyrimidin-4-yl)amine;
[2-(2,6-Dichlorophenyl)-2H-pyrazolo[4,3-c]pyridin-4-yl]-(6-morpholin-4-ylpyrimidin-4-yl)amine;
{6-[2-(2,6-Dichlorophenyl)-2H-pyrazolo[4,3-c]pyridin-4-ylamino]pyrimidin-4-yl}methanol;
2-(4-(6-((2-(2,6-dichlorophenyl)-2H-pyrazolo[4,3-c]pyridin-4-yl)amino)pyrimidin-4-yl)piperazin-1-yl)ethan-1-ol;
1-{6-[2-(2,6-Dichlorophenyl)-2H-pyrazolo[4,3-c]pyridin-4-ylamino]pyrimidin-4-yl}azetidin-3-ol;
{2-[2-(2,6-Dichlorophenyl)-2H-pyrazolo[4,3-c]pyridin-4-ylamino]pyridin-4-yl}methanol;
[2-(2,6-Dichlorophenyl)-2H-pyrazolo[4,3-c]pyridin-4-yl]-(5-fluoropyridin-2-yl)amine;
6-[2-(2,6-Dichlorophenyl)-2H-pyrazolo[4,3-c]pyridin-4-ylamino]-4-methylnicotinonitrile;
6-[2-(2,6-Dichlorophenyl)-2H-pyrazolo[4,3-c]pyridin-4-ylamino]pyrimidine-4-carbonitrile;
2-[2-(2,6-Dichloro-phenyl)-2H-pyrazolo[4,3-c]pyridin-4-ylamino]-isonicotinamide;
[2-(2,6-Dichlorophenyl)-2H-pyrazolo[4,3-c]pyridin-4-yl]-(6-methoxypyrimidin-4-yl)amine;
[2-(2,6-Dichlorophenyl)-2H-pyrazolo[4,3-c]pyridin-4-yl]-(6-methylpyridazin-3-yl)amine;
[2-(2,6-Dichlorophenyl)-2H-pyrazolo[4,3-c]pyridin-4-yl]-(5-methylpyrazin-2-yl)amine;
6-[2-(2,6-Dichloro-phenyl)-2H-pyrazolo[4,3-c]pyridin-4-ylamino]-pyrimidine-4-carboxylic acid amide;
N-{6-[2-(2,6-Dichloro-phenyl)-2H-pyrazolo[4,3-c]pyridin-4-ylamino]-pyrimidin-4-yl}-acetamide;
2-{6-[2-(2,6-Dichlorophenyl)-2H-pyrazolo[4,3-c]pyridin-4-ylamino]pyrimidin-4ylamino}ethanol;
1-{6-[2-(2,6-Dichlorophenyl)-2H-pyrazolo[4,3-c]pyridin-4-ylamino]pyrimidin-4-ylamino}-2-methylpropan-2-ol;
[2-(2-Chloro-6-fluorophenyl)-2H-pyrazolo[4,3-c]pyridine-4-yl]-(6-methylpyrimidin-4-yl)amine;
[2-(2-Chloro-6-fluorophenyl)-2H-pyrazolo[4,3-c]pyridine-4-yl]-(2,6-dimethylpyrimidin-4-yl)amine;
{6-[2-(2-Chloro-6-fluoro-phenyl)-2H-pyrazolo[4,3-c]pyridin-4-ylamino]-pyrimidin-4-yl}-methanol;
{6-[2-(2,6-Dichloro-4-methanesulphonylphenyl)-2H-pyrazolo[4,3-c]pyridine-4-ylamino]pyrimidin-4-yl}methanol;
N-(2-(2,6-dichloro-4-(methylsulfonyl)phenyl)-2H-pyrazolo[4,3-c]pyridin-4-yl)cyclopropanecarboxamide;

3,5-Dichloro-4-[4-(6-methylpyrimidin-4-ylamino)pyrazolo [4,3-c]pyridin-2-yl]benzonitrile;
N-(2-(2,6-dichloro-4-cyanophenyl)-2H-pyrazolo[4,3-c]pyridin-4-yl)cyclopropanecarboxamide;
3,5-Dichloro-4-[4-(6-ethyl-pyrimidin-4-ylamino)-pyrazolo [4,3-c]pyridin-2-yl]-benzonitrile;
3,5-Dichloro-4-[4-(6-cyclopropylpyrimidin-4-ylamino) pyrazolo[4,3-c]pyridin-2-yl]benzonitrile;
3,5-Dichloro-4-[4-(6-dimethylaminomethylpyrimidin-4-ylamino)pyrazolo[4,3-c]pyridine-2-yl]benzonitrile;
3,5-Dichloro-4-[4-(6-piperidin-1-ylmethylpyrimidin-4-ylamino)pyrazolo[4,3-c]pyridine-2-yl]benzonitrile;
[2-(2,6-Dichloro-4-fluorophenyl)-2H-pyrazolo[4,3-c]pyridine-4-yl]-(4-methylpyridin-2-yl)amine;
[2-(2,6-dichloro-4-fluorophenyl)-2H-pyrazolo[4,3-c]pyridine-4-yl]-(2,6-dimethylpyrimidin-4-yl)amine;
(5-Chloropyridin-2-yl)-[2-(2,6-dichloro-4-fluorophenyl)-2H-pyrazolo[4,3-c]pyridine-4-yl]amine;
3,5-Dichloro-4-[7-chloro-4-(6-hydroxymethylpyrimidin-4-ylamino)pyrazolo[4,3-c]pyridin-2-yl]benzonitrile;
3,5-Dichloro-4-[7-fluoro-4-(6-hydroxymethyl-pyrimidin-4-ylamino)-pyrazolo[4,3-c]pyridin-2-yl]-benzonitrile;
{6-[2-(2,6-Dichloro-phenyl)-7-fluoro-2H-pyrazolo[4,3-c] pyridin-4-ylamino]-pyrimidin-4-yl}-methanol;
{6-[2-(2,6-Dichloro-4-fluoro-phenyl)-7-fluoro-2H-pyraolo [4,3-c]pyridin-4-ylamino]-pyrimdin-4-yl}-methanol;
N4-(2-(2-chloro-3,6-difluorophenyl)-2H-pyrazolo[4,3-c] pyridin-4-yl)pyrimidine-4,6-diamine;
2-((6-(2-(2-chloro-3,6-difluorophenyl)-2H-pyrazolo[4,3-c] pyridin-4-ylamino)pyrimidin-4-yl)(methyl)amino)ethanol;
2-(4-(6-(2-(2-chloro-3,6-difluorophenyl)-2H-pyrazolo[4,3-c]pyridin-4-ylamino)pyrimidin-4-yl)piperazin-1-yl)ethanol;
3-(2-(2-chloro-3,6-difluorophenyl)-2H-pyrazolo[4,3-c]pyridin-4-ylamino)-1-methylpyridin-2(1H)-one;
2-(2-(2-chloro-3,6-difluorophenyl)-2H-pyrazolo[4,3-c]pyridin-4-ylamino)pyrimidin-4(3H)-one;
2-(4-amino-2,6-dichlorophenyl)-N-(6-methylpyrimidin-4-yl)-2H-pyrazolo[4,3-c]pyridin-4-amine;
N4-(2-(4-amino-2,6-dichlorophenyl)-2H-pyrazolo[4,3-c] pyridin-4-yl)pyrimidine-4,6-diamine; and
3-chloro-2-(4-(6-methylpyrimidin-4-ylamino)-2H-pyrazolo [4,3-c]pyridin-2-yl)benzonitrile.

Another embodiment includes a compound of Formula I or a stereoisomer or pharmaceutically acceptable salt thereof, selected from:
N-(2-(2,6-Dichlorophenyl)-2H-pyrazolo[4,3-c]pyridin-4-yl) cyclopropanecarboxamide;
[2-(2,6-Dichlorophenyl)-2H-pyrazolo[4,3-c]pyridine-4-yl]-(2,6-dimethylpyrimidin-4-yl)amine;
6-[2-(2,6-Dichlorophenyl)-2H-pyrazolo[4,3-c]pyridin-4-ylamino]nicotinonitrile;
N-[2-(2,6-Dichlorophenyl)-2H-pyrazolo[4,3-c]pyridine-4-yl]-N'-methylpyrimidine-4,6-diamine;
[2-(2,6-Dichlorophenyl)-2H-pyrazolo[4,3-c]pyridine-4-yl]-[6-(3-fluoroazetidin-1-yl)pyrimidin-4-yl]amine;
[2-(2,6-Dichlorophenyl)-2H-pyrazolo[4,3-c]pyridine-4-yl] carbamic acid methyl ester;
1-[2-(2,6-Dichlorophenyl)-2H-pyrazolo[4,3-c]pyridine-4-yl]-3-methylurea;
N-[2-(2,6-Dichlorophenyl)-2H-pyrazolo[4,3-c]pyridin-4-yl]-pyridazine-3,6-diamine;
$N^4$-[2-(2,6-Dichlorophenyl)-2H-pyrazolo[4,3-c]pyridin-4-yl]-6-methyl-pyrimidine-2,4-diamine;
N-[2-(2,6-Dichlorophenyl)-2H-pyrazolo[4,3-c]pyridin-4-yl]-2-methoxy-pyrimidine-4,6-diamine;
N-[2-(2,6-Dichlorophenyl)-2H-pyrazolo[4,3-c]pyridin-4-yl]-pyrimidine-2,4,6-triamine;
N-[2-(2,6-Dichlorophenyl)-2H-pyrazolo[4,3-c]pyridin-4-yl]-2-methyl-pyrimidine-4,6-diamine;
$N^4$-[2-(2,6-dichlorophenyl)-2H-pyrazolo[4,3-c]pyridin-4-yl]-6,$N^2$-dimethylpyrimidine-2,4-diamine;
N-[2-(2,6-Dichlorophenyl)-2H-pyrazolo[4,3-c]pyridin-4-yl]-pyrimidine-4,6-diamine;
Cyclopropanecarboxylic acid [2-(2-chloro-6-fluorophenyl)-2H-pyrazolo[4,3-c]pyridin-4-yl]amide;
6-[2-(2-Chloro-6-fluorophenyl)-2H-pyrazolo[4,3-c]pyridin-4-ylamino]isonicotinonitrile;
4-Bromo-2-(2-chloro-6-fluorophenyl)-2H-pyrazolo[4,3-c] pyridine;
[2-(2,6-Dichloro-4-methanesulfonylphenyl)-2H-pyrazolo[4,3-c]pyridin-4-yl]-(2,6-dimethylpyrimidin-4-yl)amine;
3,5-Dichloro-4-[4-(2,6-dimethylpyrimidin-4-ylamino)pyrazolo[4,3-c]pyridin-2-yl]benzonitrile;
3,5-Dichloro-4-[4-(6-hydroxymethyl-pyrimidin-4-ylamino)-pyrazolo[4,3-c]pyridin-2-yl]-benzonitrile;
3,5-Dichloro-4-[4-(6-fluoromethyl-pyrimidin-4-ylamino)-pyrazolo[4,3-c]pyridin-2-yl]-benzonitrile;
4-[4-(6-Azetidin-1-ylmethylpyrimidin-4-ylamino)pyrazolo [4,3-c]pyridin-2-yl]-3,5-dichlorobenzonitrile;
3,5-Dichloro-4-[4-(4-fluoromethylpyrimidin-2-ylamino) pyrazolo[4,3-c]pyridin-2-yl]benzonitrile;
4-[4-(6-Amino-2-methylpyrimidin-4-ylamino)pyrazolo[4,3-c]pyridin-2-yl]-3,5-dichlorobenzonitrile;
4-[4-(6-Aminopyrimidin-4-ylamino)-pyrazolo[4,3-c]pyridin-2-yl]-3,5-dichloro-benzonitrile;
N-(6-((2-(2,6-dichloro-4-cyanophenyl)-2H-pyrazolo[4,3-c] pyridin-4-yl)amino]pyrimidin-4-yl)-cyclopropanecarboxamide;
[2-(2,6-Dichloro-4-fluorophenyl)-2H-pyrazolo[4,3-c]pyridin-4-yl]-(6-methylpyrimidin-4-yl)amine;
{6-[2-(2,6-Dichloro-4-fluorophenyl)-2H-pyrazolo[4,3-c]pyridine-4-yl]-(4-methylpyridin-2-yl)}methanol;
[2-(2,6-Dichloro-4-fluorophenyl)-2H-pyrazolo[4,3-c]pyridin-4-yl]-(6-fluoromethylpyrimidin-4-yl)amine;
3,5-Dichloro-4-[7-chloro-4-(6-methylpyrimidin-4-ylamino) pyrazolo[4,3-c]pyridin-2-yl]benzonitrile;
{6-[7-Chloro-2-(2,6-dichlorophenyl)-2H-pyrazolo[4,3-c] pyridin-4-ylamino]-pyrimidin-4-yl}-methanol;
N-[7-Chloro-2-(2,6-dichlorophenyl)-2H-pyrazolo[4,3-c]pyridin-4-yl]-pyrimidine-4,6-diamine;
3,5-Dichloro-4-[7-fluoro-4-(6-methyl-pyrimidin-4-ylamino)-pyrazolo[4,3-c]pyridin-2-yl]-benzonitrile;
4-[4-(6-Amino-pyrimidin-4-ylamino)-7-fluoro-pyrazolo[4,3-c]pyridin-2-yl]-3,5-dichlorobenzonitrile;
[2-(2,6-Dichlorophenyl)-7-fluoro-2H-pyrazolo[4,3-c]pyridin-4-yl]-(6-methyl-pyrimidin-4-yl)-amine;
4-[7-Bromo-4-(6-methyl-pyrimidin-4-ylamino)-pyrazolo[4,3-c]pyridin-2-yl]-3,5-dichlorobenzonitrile;
{6-[7-Bromo-2-(2,6-dichloro-phenyl)-2H-pyrazolo[4,3-c] pyridin-4-ylamino]-pyrimidin-4-yl}-methanol;
[7-Bromo-2-(2,6-dichlorophenyl)-2H-pyrazolo[4,3-c]pyridin-4-yl]-(6-methylpyrimidin-4-yl)-amine;
2-(2,6-Dichlorophenyl)-4-(6-methylpyrimidin-4-ylamino)-2H-pyrazolo[4,3-c]pyridine-7-carbonitrile;
4-(6-Aminopyrimidin-4-ylamino)-2-(2,6-dichlorophenyl)-2H-pyrazolo[4,3-c]pyridine-7-carbonitrile;
N-[7-Bromo-2-(2,6-dichlorophenyl)-2H-pyrazolo[4,3-c]pyridin-4-yl]-pyrimidine-4,6-diamine;
{6-[2-(2,6-Dichlorophenyl)-7-methoxy-2H-pyrazolo[4,3-c] pyridin-4-ylamino]-pyrimidin-4-yl}-methanol;
[2-(2,6-Dichloro-4-fluorophenyl)-7-fluoro-2H-pyrazolo[4,3-c]pyridin-4-yl]-(6-methylpyrimidin-4-yl)-amine;

[2-(2,6-Dichlorophenyl)-2H-pyrazolo[4,3-c]pyridine-4-yl] pyrimidin-4-ylamine;
2-[2-(2,6-Dichlorophenyl)-2H-pyrazolo[4,3-c]pyridin-4-ylamino]isonicotinonitrile;
[2-(2,6-Dichlorophenyl)-2H-pyrazolo[4,3-c]pyridin-4-yl]-(6-methylpyrimidin-4-yl)amine;
[2-(2,6-Dichlorophenyl)-2H-pyrazolo[4,3-c]pyridin-4-yl]-(6-morpholin-4-ylpyrimidin-4-yl)amine;
{6-[2-(2,6-Dichlorophenyl)-2H-pyrazolo[4,3-c]pyridin-4-ylamino]pyrimidin-4-yl}methanol;
2-(4-(6-((2-(2,6-dichlorophenyl)-2H-pyrazolo[4,3-c]pyridin-4-yl)amino)pyrimidin-4-yl)piperazin-1-yl)ethan-1-ol;
1-{6-[2-(2,6-Dichlorophenyl)-2H-pyrazolo[4,3-c]pyridin-4-ylamino]pyridin-4-yl}azetidin-3-ol;
{2-[2-(2,6-Dichlorophenyl)-2H-pyrazolo[4,3-c]pyridin-4-ylamino]pyridin-4-yl}methanol;
[2-(2,6-Dichlorophenyl)-2H-pyrazolo[4,3-c]pyridin-4-yl]-(5-fluoropyridin-2-yl)amine;
6-[2-(2,6-Dichlorophenyl)-2H-pyrazolo[4,3-c]pyridin-4-ylamino]-4-methylnicotinonitrile;
6-[2-(2,6-Dichlorophenyl)-2H-pyrazolo[4,3-c]pyridin-4-ylamino]pyrimidine-4-carbonitrile;
2-[2-(2,6-Dichloro-phenyl)-2H-pyrazolo[4,3-c]pyridin-4-ylamino]-isonicotinamide;
[2-(2,6-Dichlorophenyl)-2H-pyrazolo[4,3-c]pyridin-4-yl]-(6-methoxypyrimidin-4-yl)amine;
[2-(2,6-Dichlorophenyl)-2H-pyrazolo[4,3-c]pyridin-4-yl]-(6-methylpyridazin-3-yl)amine;
[2-(2,6-Dichlorophenyl)-2H-pyrazolo[4,3-c]pyridin-4-yl]-(5-methylpyrazin-2-yl)amine;
6-[2-(2,6-Dichloro-phenyl)-2H-pyrazolo[4,3-c]pyridin-4-ylamino]-pyrimidine-4-carboxylic acid amide;
N-{6-[2-(2,6-Dichloro-phenyl)-2H-pyrazolo[4,3-c]pyridin-4-ylamino]-pyrimidin-4-yl}-acetamide;
2-{6-[2-(2,6-Dichlorophenyl)-2H-pyrazolo[4,3-c]pyridin-4-ylamino]pyrimidin-4ylamino}ethanol;
1-{6-[2-(2,6-Dichlorophenyl)-2H-pyrazolo[4,3-c]pyridin-4-ylamino}pyrimidin-4-ylamino}-2-methylpropan-2-ol;
[2-(2-Chloro-6-fluorophenyl)-2H-pyrazolo[4,3-c]pyridine-4-yl]-(6-methylpyrimidin-4-yl)amine;
[2-(2-Chloro-6-fluorophenyl)-2H-pyrazolo[4,3-c]pyridine-4-yl]-(2,6-dimethylpyrimidin-4-yl)amine;
{6-[2-(2-Chloro-6-fluoro-phenyl)-2H-pyrazolo[4,3-c]pyridin-4-ylamino]-pyrimidin-4-yl}-methanol;
{6-[2-(2,6-Dichloro-4-methanesulphonylphenyl)-2H-pyrazolo[4,3-c]pyridine-4-ylamino]pyrimidin-4-yl}methanol;
N-(2-(2,6-dichloro-4-(methylsulfonyl)phenyl)-2H-pyrazolo[4,3-c]pyridin-4-yl)cyclopropanecarboxamide;
3,5-Dichloro-4-[4-(6-methylpyrimidin-4-ylamino)pyrazolo[4,3-c]pyridin-2-yl]benzonitrile;
N-(2-(2,6-dichloro-4-cyanophenyl)-2H-pyrazolo[4,3-c]pyridin-4-yl)cyclopropanecarboxamide;
3,5-Dichloro-4-[4-(6-ethyl-pyrimidin-4-ylamino)-pyrazolo[4,3-c]pyridin-2-yl]-benzonitrile;
3,5-Dichloro-4-[4-(6-cyclopropylpyrimidin-4-ylamino)pyrazolo[4,3-c]pyridin-2-yl]benzonitrile;
3,5-Dichloro-4-[4-(6-dimethylaminomethylpyrimidin-4-ylamino)pyrazolo[4,3-c]pyridin-2-yl]benzonitrile;
3,5-Dichloro-4-[4-(6-piperidin-1-ylmethylpyrimidin-4-ylamino)pyrazolo[4,3-c]pyridine-2-yl]benzonitrile;
[2-(2,6-Dichloro-4-fluorophenyl)-2H-pyrazolo[4,3-c]pyridine-4-yl]-(4-methylpyridin-2-yl)amine;
[2-(2,6-dichloro-4-fluorophenyl)-2H-pyrazolo[4,3-c]pyridine-4-yl]-(2,6-dimethylpyrimidin-4-yl)amine;
(5-Chloropyridin-2-yl)-[2-(2,6-dichloro-4-fluorophenyl)-2H-pyrazolo[4,3-c]pyridine-4-yl]amine;
3,5-Dichloro-4-[7-chloro-4-(6-hydroxymethylpyrimidin-4-ylamino)pyrazolo[4,3-c]pyridin-2-yl]benzonitrile;
3,5-Dichloro-4-[7-fluoro-4-(6-hydroxymethyl-pyrimidin-4-ylamino)-pyrazolo[4,3-c]pyridin-2-yl]-benzonitrile;
{6-[2-(2,6-Dichloro-phenyl)-7-fluoro-2H-pyrazolo[4,3-c]pyridin-4-ylamino]-pyrimidin-4-yl}-methanol;
{6-[2-(2,6-Dichloro-4-fluoro-phenyl)-7-fluoro-2H-pyraolo[4,3-c]pyridin-4-ylamino]-pyrimdin-4-yl}-methanol;
N4-(2-(2-chloro-3,6-difluorophenyl)-2H-pyrazolo[4,3-c]pyridin-4-yl)pyrimidine-4,6-diamine;
2-((6-(2-(2-chloro-3,6-difluorophenyl)-2H-pyrazolo[4,3-c]pyridin-4-ylamino)pyrimidin-4-yl)(methyl)amino)ethanol;
2-(4-(6-(2-(2-chloro-3,6-difluorophenyl)-2H-pyrazolo[4,3-c]pyridin-4-ylamino)pyrimidin-4-yl)piperazin-1-yl)ethanol;
3-(2-(2-chloro-3,6-difluorophenyl)-2H-pyrazolo[4,3-c]pyridin-4-ylamino)-1-methylpyridin-2(1H)-one;
2-(2-(2-chloro-3,6-difluorophenyl)-2H-pyrazolo[4,3-c]pyridin-4-ylamino)pyrimidin-4(3H)-one;
2-(4-amino-2,6-dichlorophenyl)-N-(6-methylpyrimidin-4-yl)-2H-pyrazolo[4,3-c]pyridin-4-amine;
N4-(2-(4-amino-2,6-dichlorophenyl)-2H-pyrazolo[4,3-c]pyridin-4-yl)pyrimidine-4,6-diamine;
3-chloro-2-(4-(6-methylpyrimidin-4-ylamino)-2H-pyrazolo[4,3-c]pyridin-2-yl)benzonitrile;
3-Chloro-2-[7-fluoro-4-(6-methylpyrimidin-4-ylamino)pyrazolo[4,3-c]pyridin-2-yl]-5-hydroxymethyl benzonitrile;
{3,5-Dichloro-4-[7-fluoro-4-(6-methylpyrimidin-4-ylamino)pyrazolo[4,3-c]pyridin-2-yl]phenyl}methanol;
{4-[2-(2-Chloro-6-fluoro-phenyl)-7-fluoro-2H-pyrazolo[4,3-c]pyridin-4-ylamino]-6-methyl-pyrimidin-2-yl}-methanol;
4-[4-(6-Aminopyrimidin-4-ylamino)-7-chloropyrazolo[4,3-c]pyridin-2-yl]-3,5-dichlorobenzonitrile;
N-[2-(2,6-Dichlorophenyl)-7-fluoro-2H-pyrazolo[4,3-c]pyridin-4-yl]pyrimidine-4,6-diamine;
N-{6-[2-(2,6-Dichlorophenyl)-7-fluoro-2H-pyrazolo[4,3-c]pyridin-4-ylamino]-pyrimidin-4-yl}-acetamide;
1-{6-[2-(2,6-Dichlorophenyl)-2H-pyrazolo[4,3-c]pyridin-4-ylamino]-pyrimidin-4-yl}-ethanol;
(6-Cyclopropylpyrimidin-4-yl)-[2-(2,6-dichlorophenyl)-2H-pyrazolo[4,3-c]pyridin4-yl]-amine;
3-Chloro-2-[7-fluoro-4-(6-methylpyrimidin-4-ylamino)-pyrazolo[4,3-c]pyridin-2-yl]-benzonitrile;
3-Chloro-2-{7-fluoro-4-[6-(1-hydroxyethyl)-pyrimidin-4-ylamino]-pyrazolo[4,3-c]pyridin-2-yl}-benzonitrile;
2-[4-(6-Amino-2-methylpyrimid-4-ylamino)-7-fluoropyrazolo[4,3-c]pyridin-2-yl]-3-chlorobenzonitrile;
2-[4-(5-Azetidin-3-yl-pyridin-2-ylamino)-7-fluoropyrazolo[4,3-c]pyridin-2-yl]-3-chlorobenzonitrile;
[2-(4-Amino-2,6-dichlorophenyl)-7-fluoro-2H-pyrazolo[4,3-c]pyridin-4-yl]-(6-methylpyrimidin-4-yl)-amine;
5-Amino-3-chloro-2-[7-fluoro-4-(6-methylpyrimidin-4-ylamino)-pyrazolo[4,3-c]pyridin-2-yl]benzonitrile;
5-Amino-2-[4-(6-aminopyrimidin-4-ylamino)-7-fluoropyrazolo[4,3-c]pyridin-2-yl]-3-chlorobenzonitrile;
N-[2-(2,6-Dichlorophenyl)-7-methyl-2H-pyrazolo[4,3-c]pyridin-4-yl]-pyrimidine-4,6-diamine;
3-Chloro-5-fluoro-2-[7-fluoro-4-(6-methylpyrimidin-4-ylamino)-pyrazolo[4,3-c]pyridin-2-yl]benzonitrile;
2-[4-(6-Amino-2-methylpyrimidin-4-ylamino)-7-fluoropyrazolo[4,3-c]pyridin-2-yl]-3-chloro-5-fluorobenzonitrile;
3-Chloro-5-fluoro-2-{7-fluoro-4-[6-(3-fluoroazetidin-1-yl)pyrimidin-4-ylamino]pyrazolo[4,3-c]pyridin-2-yl}benzonitrile;
3-Chloro-5-fluoro-2-{7-fluoro-4-[6-(2-hydroxyethylamino)-2-methylpyrimidin-4-ylamino]pyrazolo[4,3-c]pyridin-2-yl}benzonitrile;
2-[4-(2,6-Dimethylpyrimidin-4-ylamino)-7-fluoropyrazolo[4,3-c]pyridin-2-yl]-3-fluorobenzonitrile;
N-[2-(2-Chloro-6-fluorophenyl)-7-fluoro-2H-pyrazolo[4,3-c]pyridin-4-yl]-2-methylpyrimidine-4,6-diamine;

[2-(2-Chloro-6-fluorophenyl)-7-fluoro-2H-pyrazolo[4,3-c]pyridin-4-yl]-(2,6-dimethylpyrimidin-4-yl)amine;
{6-[2-(2-Chloro-6-fluorophenyl)-7-fluoro-2H-pyrazolo[4,3-c]pyridin-4-ylamino]-2-methylpyrimidin-4-yl}-methanol;
3,5-Dichloro-4-[7-fluoro-4-(6-hydroxymethylpyrimidin-4-ylamino)-pyrazolo)-[4,3-c]pyridin-2-yl]-benzonitrile;
3,5-Dichloro-4-{7-fluoro-4-[6-(1-hydroxyethyl)-pyrimidin-4-ylamino]-pyrazolo)-[4,3-c]pyridin-2-yl}-benzonitrile;
[7-Chloro-2-(2,6-dichlorophenyl)-2H-pyrazolo[4,3-c]pyridin-4-yl]-(6-methylpyrimidin-4-yl)-amine;
2-(2,6-Dichlorophenyl)-4-(6-hydroxymethylpyrimidin-4-ylamino)-2H-pyrazolo[4,3-c]pyridine-7-carbonitrile;
3-Chloro-2-[7-fluoro-4-(-6-hydroxymethylpyrimidin-4-ylamino)-pyrazolo[4,3-c]pyridin-2-yl]-benzonitrile;
N-{6-[2-(2-Chloro-6-cyanophenyl)-7-fluoro-2H-pyrazolo[4,3-c]pyridin-4-ylamino]-pyrimidin-4-yl}-acetamide;
2-[4-(6-Aminopyrimidin-4-ylamino)-7-fluoropyrazolo[4,3-c]pyridin-2-yl]-3-chlorobenzonitrile;
N-(2-(2-chloro-6-cyanophenyl)-7-fluoro-2H-pyrazolo[4,3-c]pyridine-4-yl)cyclopropanecarboxamide;
3-Chloro-2-[4-(2,6-dimethylpyrimidin-4-ylamino)-7-fluoropyrazolo[4,3-c]pyridin-2-yl]benzonitrile;
2-[4-(2-Amino-6-methylpyrimidin-4-ylamino)-7-fluoropyrazolo[4,3-c]pyridin-2-yl]-3-chlorobenzonitrile;
3-Chloro-2-[7-fluoro-4-(2-hydroxymethyl-6-methylpyrimidin-4-ylamino)-pyrazolo[4,3-c]pyridin-2-yl]-benzonitrile;
3-Chloro-2-[7-fluoro-4-(6-hydroxymethyl-2-methylpyrimidin-4-ylamino)-pyrazolo[4,3-c]pyridin-2-yl]-benzonitrile;
3-Chloro-2-[4-(6-cyclopropylpyrimidin-4-ylamino)-7-fluoropyrazolo[4,3-c]pyridin-2-yl]-benzonitrile;
N-[2-(4-Amino-2,6-dichlorophenyl)-7-fluoro-2H-pyrazolo[4,3-c]pyridin-4-yl]-benzene-1,3-diamine;
{6-[2-(4-Amino-2,6-dichlorophenyl)-7-fluoro-2H-pyrazolo[4,3-c]pyridin-4-ylamino)-pyrimidin-4-yl}-methanol;
N-(2-(4-amino-2,6-dichlorophenyl)-7-fluoro-2H-pyrazolo[4,3-c]pyridine-4-yl)cyclopropanecarboxamide;
N-(2-(4-amino-2-chloro-6-cyanophenyl)-7-fluoro-2H-pyrazolo[4,3-c]pyridine-4-yl)cyclopropanecarboxamide;
2-(2,6-dichlorophenyl)-7-methyl-N-(6-methylpyrimidin-4-yl)-2H-pyrazolo[4,3-c]pyridine-4-amine;
3-Chloro-5-fluoro-2-[7-fluoro-4-(6-hydroxymethyl-pyrimidin-4-ylamino)-pyrazolo[4,3-c]pyridin-2-yl]-benzonitrile;
2-[4-(6-Aminopyrimidin-4-ylamino)-7-fluoropyrazolo[4,3-c]pyridin-2-yl]-3-chloro-5-fluorobenzonitrile;
3-Chloro-2-[4-(6-cyclopropylpyrimidin-4-ylamino)-7-fluoropyrazolo[4,3-c]pyridin-2-yl]-5-fluorobenzonitrile;
N-(2-(2-chloro-6-cyano-4-fluorophenyl)-7-fluoro-2H-pyrazolo[4,3-c]pyridine-4-yl)cyclopropanecarboxamide;
3-Chloro-2-[4-(2,6-dimethylpyrimidin-4-ylamino)-7-fluoropyrazolo[4,3-c]pyridin-2-yl]-5-fluorobenzonitrile;
2-[4-(2-Amino-6-methylpyrimidin-4-ylamino)-7-fluoropyrazolo[4,3-c]pyridin-2-yl]-3-chloro-5-fluoro-benzonitrile;
3-Chloro-5-fluoro-2-[7-fluoro-4-(2-hydroxymethyl-6-methylpyrimidin-4-ylamino)-pyrazolo[4,3-c]pyridin-2-yl]-benzonitrile;
3-Chloro-5-fluoro-2-[7-fluoro-4-(6-hydroxymethyl-2-methylpyrimidin-4-ylamino)-pyrazolo[4,3-c]pyridin-2-yl]-benzonitrile;
2-[4-(6-Aminopyrimidin-4-ylamino)-7-fluoropyrazolo[4,3-c]pyridin-2-yl]-3-fluorobenzonitrile;
2-[4-(6-Amino-2-methylpyrimidin-4-ylamino)-7-fluoropyrazolo[4,3-c]pyridin-2-yl]-3-fluorobenzonitrile;
2-[4-(2-Amino-6-methylpyrimidin-4-ylamino)-7-fluoropyrazolo[4,3-c]pyridin-2-yl]-3-fluorobenzonitrile;
3-Fluoro-2-[7-fluoro-4-(6-hydroxymethyl-2-methylpyrimidin-4-ylamino)-pyrazolo[4,3-c]pyridin-2-yl]-benzonitrile;
3-Fluoro-2-[7-fluoro-4-(2-hydroxymethyl-6-methylpyrimidin-4-ylamino)-pyrazolo[4,3-c]pyridin-2-yl]-benzonitrile;
{6-[2-(2-Chloro-6-fluorophenyl)-7-fluoro-2H-pyrazolo[4,3-c]pyridin-4-ylamino]pyrimidin-4-yl}methanol;
$N^4$-[2-(2-Choro-6-fluorophenyl)-7-fluoro-2H-pyrazolo[4,3-c]pyridine-4-yl]-6-methylpyrimidine-2,4-diamine;
2-{6-[2-(2-Chloro-6-fluorophenyl)-7-fluoro-2H-pyrazolo[4,3-c]pyridin-4-ylamino]-2-methylpyrimidin-4-ylamino}-ethanol;
N-{6-[2-(2-Chloro-6-fluorophenyl)-7-fluoro-2H-pyrazolo[4,3-c]pyridin-4-ylamino]-pyrimidin-4-yl}-acetamide;
(5-Azetidin-3-yl-pyridin-2-yl)-[2-(2-chloro-6-fluorophenyl)-7-fluoro-2H-pyrazolo[4,3-c]pyridin-4-yl]-amine;
2-(4-(6-aminopyrimidin-4-ylamino)-7-chloro-2H-pyrazolo[4,3-c]pyridin-2-yl)-3-chlorobenzonitrile;
3-chloro-2-(4-(6-(hydroxymethyl)pyrimidin-4-ylamino)-2H-pyrazolo[4,3-c]pyridin-2-yl)benzonitrile;
3-chloro-2-(7-chloro-4-(6-(hydroxymethyl)pyrimidin-4-ylamino)-2H-pyrazolo[4,3-c]pyridin-2-yl)benzonitrile;
5-amino-2-(4-(6-aminopyrimidin-4-ylamino)-2H-pyrazolo[4,3-c]pyridin-2-yl)-3-chlorobenzonitrile;
2-(4-(6-aminopyrimidin-4-ylamino)-2H-pyrazolo[4,3-c]pyridin-2-yl)-3-chlorobenzoic acid;
2-(4-(6-aminopyrimidin-4-ylamino)-2H-pyrazolo[4,3-c]pyridin-2-yl)-3-fluorobenzonitrile;
3-fluoro-2-(4-(6-methylpyrimidin-4-ylamino)-2H-pyrazolo[4,3-c]pyridin-2-yl)benzonitrile;
3-chloro-5-(6-methylpyrimidin-4-ylamino)-2-(4-(6-methylpyrimidin-4-ylamino)-2H-pyrazolo[4,3-c]pyridin-2-yl)benzonitrile;
2-(4-amino-2,6-dichlorophenyl)-N-(2,6-dimethylpyrimidin-4-yl)-2H-pyrazolo[4,3-c]pyridin-4-amine;
N-(7-chloro-2-(2-chloro-6-cyanophenyl)-2H-pyrazolo[4,3-c]pyridin-4-yl)cyclopropanecarboxamide;
N-(2-(2-chloro-6-cyanophenyl)-2H-pyrazolo[4,3-c]pyridin-4-yl)cyclopropanecarboxamide;
N-(2-(4-amino-2,6-dichlorophenyl)-2H-pyrazolo[4,3-c]pyridin-4-yl)cyclopropanecarboxamide;
2-(4-amino-2-chlorophenyl)-N-(5-(morpholinosulfonyl)pyridin-2-yl)-2H-pyrazolo[4,3-c]pyridin-4-amine;
6-(2-(4-amino-2-chlorophenyl)-2H-pyrazolo[4,3-c]pyridin-4-ylamino)-N,N-dimethylpyridine-3-sulfonamide; and
5-amino-3-chloro-2-(4-(6-methylpyrimidin-4-ylamino)-2H-pyrazolo[4,3-c]pyridin-2-yl)benzonitrile.

The compounds of Formula I may contain asymmetric or chiral centers, and, therefore, exist in different stereoisomeric forms. It is intended that all stereoisomeric forms of the compounds of Formula I, including but not limited to: diastereomers, enantiomers, and atropisomers as well as mixtures thereof such as racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention. Both the single positional isomers and mixture of positional isomers, e.g., resulting from the N-oxidation of the pyrimidinyl and pyrrozolyl rings, or the E and Z forms of compounds of Formula I (for example oxime moieties), are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention, as defined by the claims, embrace both solvated and unsolvated forms.

In an embodiment, compounds of Formula I may exist in different tautomeric forms, and all such forms are embraced within the scope of the invention, as defined by the claims. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of Formula I, which are identical to those recited herein, but for the fact that one or more atoms are replaced by an atom having an atomic mass or mass number different from the atomic mass or mass number usually found in nature. All isotopes of any particular atom or element as specified are contemplated within the scope of the invention. Exemplary isotopes that can be incorporated into compounds of Formula I include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Certain isotopically-labeled compounds of Formula I (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). Positron emitting isotopes such as $^{15}O$, $^{3}N$, $^{11}C$, and $^{18}F$ are useful for positron emission tomography (PET) studies to examine substrate receptor occupancy. Isotopically labeled compounds of Formula I can generally be prepared by following procedures analogous to those disclosed in the Schemes and/or in the Examples herein below, by substituting an isotopically labeled reagent for a non-isotopically labeled reagent.

Synthesis of TYK2 Inhibitor Compounds

Compounds of Formula I may be synthesized by synthetic routes described herein. In certain embodiments, processes well-known in the chemical arts can be used, in addition to, or in light of, the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), Beilsteins Handbuch der organischen Chemie, 4, Aufl. ed. Springer-Verlag, Berlin, including supplements (also available via the Beilstein online database)), or *Comprehensive Heterocyclic Chemistry*, Editors Katrizky and Rees, Pergamon Press, 1984.

Compounds of Formula I may be prepared singly or as compound libraries comprising at least 2, for example 5 to 1,000 compounds, or 10 to 100 compounds of Formula I. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of Formula I, enantiomers, diastereiomers or pharmaceutically acceptable salts thereof.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Compounds of the invention may be prepared from commercially available starting materials using the general methods illustrated herein.

For illustrative purposes, reaction Schemes 1-4 depicted below provide routes for synthesizing the compounds of Formula I, as well as key intermediates. For a more detailed description of the individual reaction steps, see the Examples section below. Those skilled in the art will appreciate that other synthetic routes may be available and used. Although specific starting materials and reagents are depicted in the Schemes and discussed below, other starting materials and reagents may be available for substitution to provide a variety of derivatives and/or reaction conditions. In addition, many of the compounds prepared by the methods described below can be further modified in light of this disclosure using conventional chemistry well known to those skilled in the art.

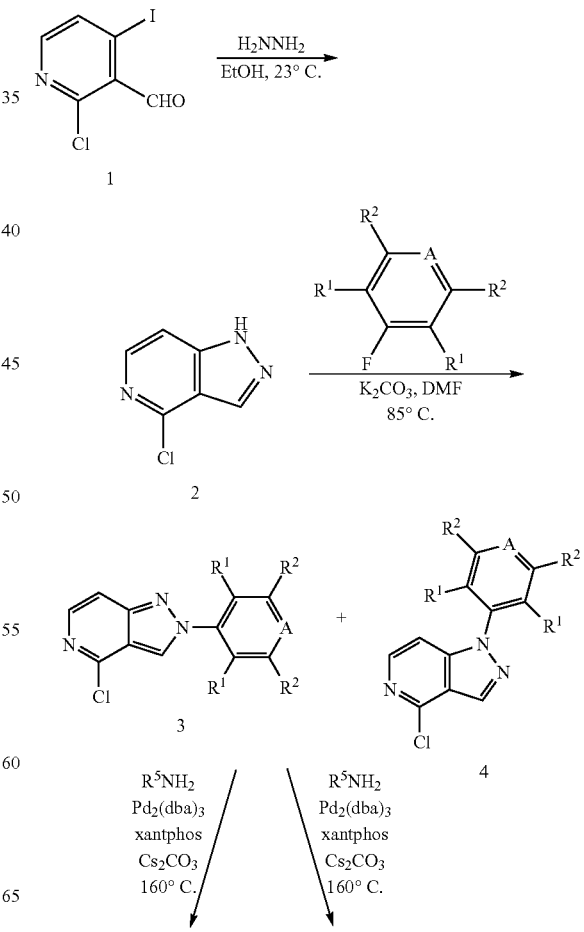

Scheme 1 (Method 1)

-continued

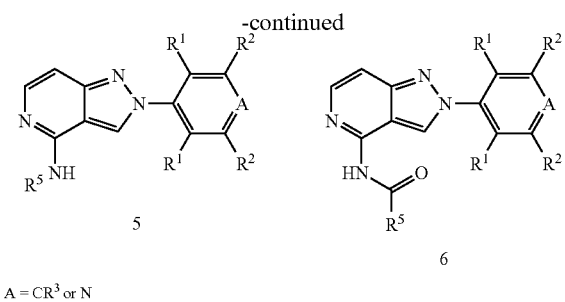

A = CR³ or N

Scheme 1 (Method 1) shows the preparation of compounds of formulas 5 and 6, wherein $R^1$, $R^2$, A, $R^5$ are as defined in Formula I. Commercially available 2-chloro-3-formyl-4-iodopyridine was treated with hydrazine in ethanol at 23° C. to give pyrazole 2. Upon heating of pyrazole 2 with an aryl fluoride in the presence of $K_2CO_3$, both 3 and its regio-isomer 4 were produced. This mixture could be separated via column chromatography on silica gel. Intermediate 3 could be coupled to an amine or amide under Pd-catalyzed conditions to provide products such as 5 or 6.

An alternative procedure is shown in Scheme 2 (Method 2), wherein X, A, $R^1$, $R^2$ and $R^5$ are as defined for Formula I. Synthesis started with commercially available 4-chloropyridine 7, which was deprotonated with LDA, followed by quenching with DMF to provide aldehyde 8. 4-chloropyridine-3-carboxaldehyde 8 was treated with sodium azide to displace 4-chloride to give 9. When azide 9 was condensed with an aniline in the presence of $TiCl_4$, the resulting imine intermediate was not isolated, but was directly heated in toluene to effect ring closure that yielded 10. This was followed by N-oxide formation with hydrogen peroxide in the presence of catalytic amount of methyl rhenium trioxide. Subsequently, the N-oxide was treated with $POCl_3$ or $POBr_3$ to give chloride or bromide 11. Under Pd-catalyzed conditions, 11 could then be coupled to an amine or amide to provide products 5 or 6.

Scheme 2 (Method 2)

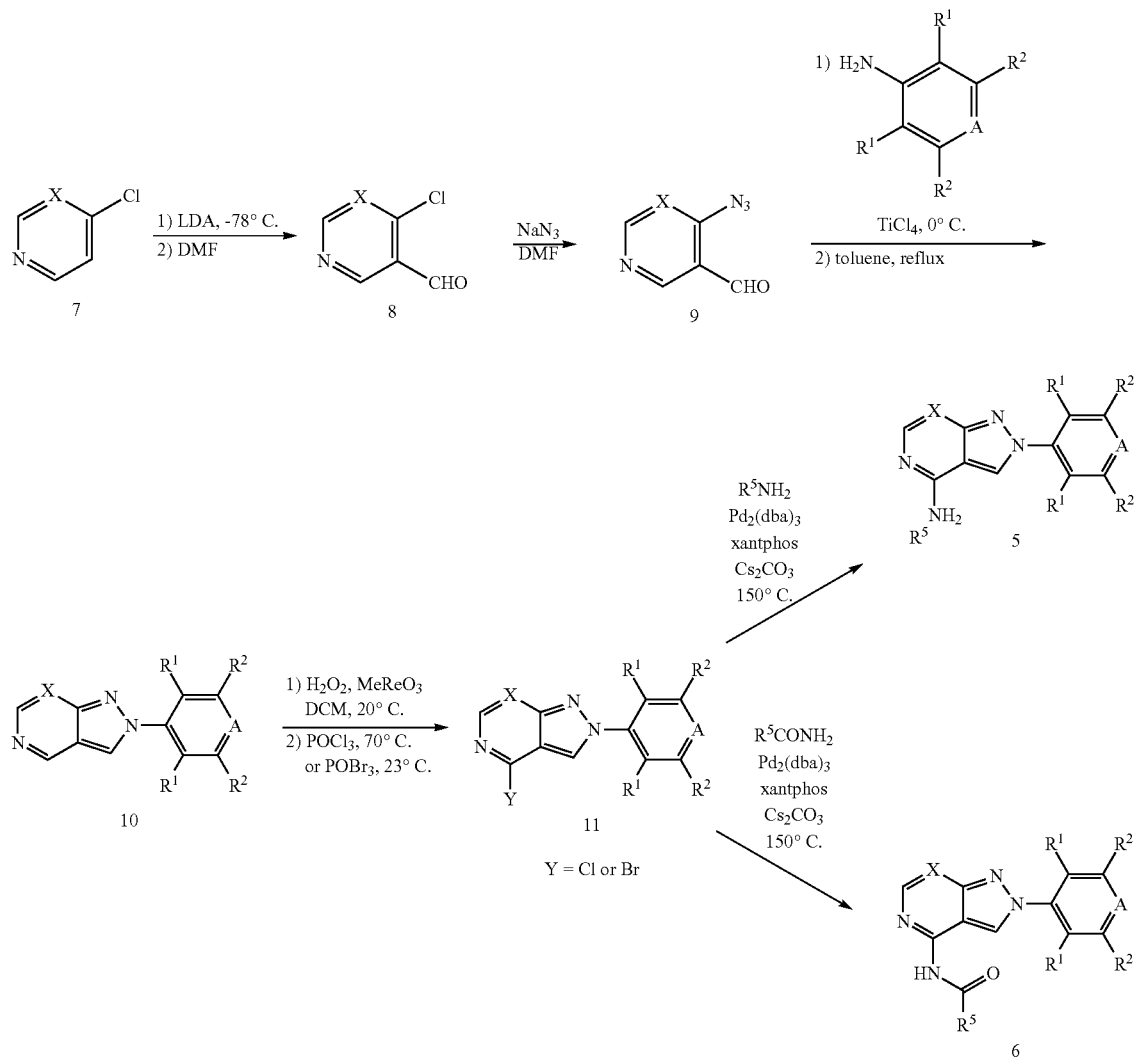

Scheme 3 (Method 3)
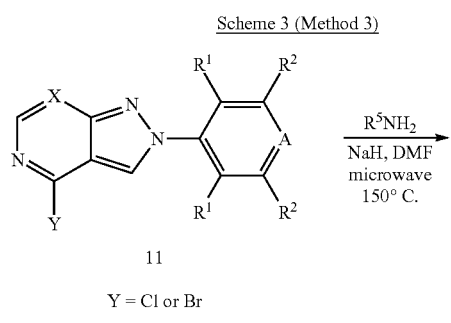
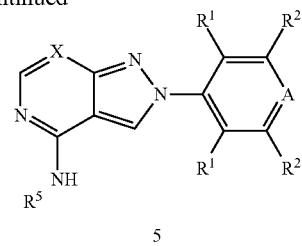
For some substrates, the amine could be coupled with intermediate 11 through a SNAr-type reaction in the presence of a base, such as sodium hydride, as outlined in Scheme 3 (Method 3).
Scheme 4 (Method 4)
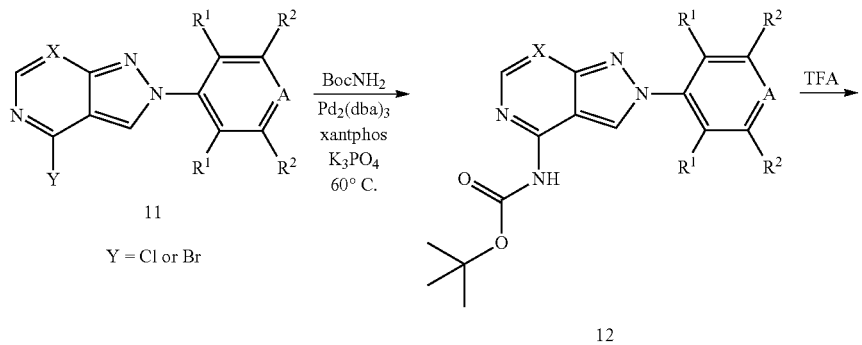
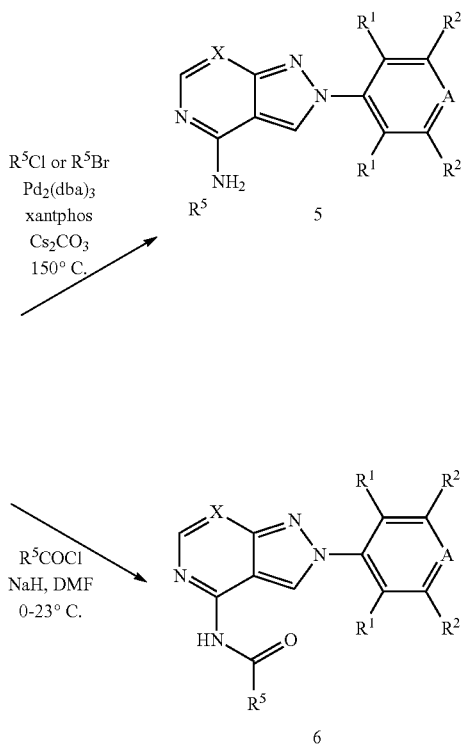

Final products 5 or 6 could also be prepared according to Scheme 4 (Method 4). Intermediate 11 from Scheme 2 could be coupled with tert-butyl carbamate via Pd-catalyzed reaction, followed by treatment with trifluoroacetic acid to provide amino intermediate 13. Intermediate 13 could then be transformed to 5 via a Pd-catalyzed coupling reaction with an aryl- or heteroaryl-chloride or bromide. The amino intermediate 13 could also be coupled to an acid chloride to give amide 6.

It will be appreciated that where appropriate functional groups exist, compounds of various formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

In each of the exemplary Schemes it may be advantageous to separate reaction products from one another and/or from starting materials. Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g. an enantiomer, substantially free of its stereoisomer may be obtained by resolution of the racemic mixture using a method such as formation of diastereomers using optically active resolving agents (Eliel, E. and Wilen, S., *Stereochemistry of Organic Compounds*, John Wiley & Sons, Inc., New York, 1994; Lochmuller, C. H., *J. Chromatogr.*, 113(3):283-302 (1975)). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: *Drug Stereochemistry, Analytical Methods and Pharmacology*, Irving W. Wainer, Ed., Marcel Dekker, Inc., New York (1993).

Diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, the substrate to be resolved is reacted with one enantiomer of a chiral compound to form a diastereomeric pair (Eliel, E. and Wilen, S., *Stereochemistry of Organic Compounds*, John Wiley & Sons, Inc., New York, 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g. (–) menthyl chloroformate in the presence of base, or Mosher ester, α-methoxy-α-(trifluoromethyl)phenyl acetate (Jacob, *J. Org. Chem.* 47:4165 (1982)), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase (*Chiral Liquid Chromatography* W. J. Lough, Ed., Chapman and Hall, New York, (1989); Okamoto, *J. of Chromatogr.* 513:375-378 (1990)). Enriched or purified enantiomers can be distinguished by methods used to distinguish other chiral molecules with asymmetric carbon atoms, such as optical rotation and circular dichroism.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of Formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends on the particular use and the concentration of compound, and can range anywhere from about 3 to about 8. In one example, a compound of Formula I is formulated in an acetate buffer, at pH 5. In another embodiment, the compounds of Formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular patient being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit TYK2 kinase activity. For example, such amount may be below the amount that is toxic to normal cells, or the patient as a whole.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Sustained-release preparations may be prepared. Suitable examples of sustained-release preparations include semipermeable matrices of solid hydrophobic polymers containing a compound of Formula I, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

In one example, the pharmaceutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 5-100 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal, inhaled and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, aerosols, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 25 mg, 50 mg, 100 mg, 250 mg or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

In one embodiment, the pharmaceutical composition also includes an additional chemotherapeutic agent selected from an anti-proliferative agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, or an agent for treating immunodeficiency disorders.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

Another embodiment includes a pharmaceutical composition comprising a compound of Formula I, or a stereoisomer or pharmaceutically acceptable salt thereof, for use in the treatment of an immunological or inflammatory disease. Another embodiment includes a pharmaceutical composition comprising a compound of Formula I, or a stereoisomer or pharmaceutically acceptable salt thereof for use in the treatment of psoriasis or inflammatory bowel disease.

Indications and Methods of Treatment

The compounds of the invention inhibit TYK2 kinase activity. Accordingly, the compounds of the invention are useful for reducing inflammation in particular patient tissue and cells. Compounds of the invention are useful for inhibiting TYK2 kinase activity in cells that overexpress TYK2 kinase. Alternatively, compounds of the invention are useful for inhibiting TYK2 kinase activity in cells in which, for example, the type I interferon, IL-6, IL-10, IL-12 and IL-23 signaling pathway is disruptive or abnormal, for example by binding to TYK2 kinase and inhibiting its activity. Alternatively, the compounds of the invention can be used for the treatment of immunological or inflammatory disorders.

Another embodiment includes a method of treating or lessening the severity of a disease or condition responsive to the inhibition of TYK2 kinase activity in a patient. The method includes the step of administering to a patient a therapeutically effective amount of a compound of Formula I, stereoisomers, tautomers or salts thereof.

In one embodiment, a compound of Formula I is administered to a patient in a therapeutically effective amount to treat or lessen the severity of a disease or condition responsive to the inhibition of TYK2 kinase activity, and said compound is at least 15 fold, alternatively 10 fold, alternatively 5 fold or more selective in inhibiting TYK2 kinase activity over inhibiting each of the other Janus kinase activities.

Another embodiment includes a compound of Formula I, stereoisomers, tautomers or salts thereof for use in therapy.

Another embodiment includes a compound of Formula I, stereoisomers, tautomers or salts thereof for use in treating an immunological or inflammatory disease.

Another embodiment includes a compound of Formula I, stereoisomers, tautomers or salts thereof for use in treating psoriasis or inflammatory bowel disease.

Another embodiment includes the use of a compound of Formula I, stereoisomers, tautomers or salts thereof for treating an immunological or inflammatory disease.

Another embodiment includes the use of a compound of Formula I, stereoisomers, tautomers or salts thereof for treating psoriasis or inflammatory bowel disease.

Another embodiment includes the use of a compound of Formula I, stereoisomers, tautomers or salts thereof in the preparation of a medicament for the treatment of an immunological or inflammatory disease.

Another embodiment includes the use of a compound of Formula I, stereoisomers, tautomers or salts thereof in the preparation of a medicament for the treatment of psoriasis or inflammatory bowel disease.

In one embodiment, the disease or condition is cancer, stroke, diabetes, hepatomegaly, cardiovascular disease, multiple sclerosis, Alzheimer's disease, cystic fibrosis, viral disease, autoimmune diseases, immunological disease, atherosclerosis, restenosis, psoriasis, allergic disorders, inflammatory disease, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, liver disease, pathologic immune conditions involving T cell activation, CNS disorders or a myeloproliferative disorder.

In one embodiment, the disease or condition is cancer.

In one embodiment, the disease or condition is an immunological disorder.

In one embodiment, the disease is a myeloproliferative disorder.

In one embodiment, the myeloproliferative disorder is polycythemia vera, essential thrombocytosis, myelofibrosis or chronic myelogenous leukemia (CML).

In one embodiment, the disease is asthma.

In one embodiment, the cancer is breast, ovary, cervix, prostate, testis, penile, genitourinary tract, seminoma, esophagus, larynx, gastric, stomach, gastrointestinal, skin, keratoacanthoma, follicular carcinoma, melanoma, lung, small cell lung carcinoma, non-small cell lung carcinoma (NSCLC), lung adenocarcinoma, squamous carcinoma of the lung, colon, pancreas, thyroid, papillary, bladder, liver, biliary passage, kidney, bone, myeloid disorders, lymphoid disorders, hairy cells, buccal cavity and pharynx (oral), lip, tongue, mouth, salivary gland, pharynx, small intestine, colon, rectum, anal, renal, prostate, vulval, thyroid, large intestine, endometrial, uterine, brain, central nervous system, cancer of the peritoneum, hepatocellular cancer, head cancer, neck cancer, Hodgkin's or leukemia.

In one embodiment, the cardiovascular disease is restenosis, cardiomegaly, atherosclerosis, myocardial infarction or congestive heart failure.

In one embodiment, the neurodegenerative disease is Alzheimer's disease, Parkinson's disease, amyotrophic lateral sclerosis, Huntington's disease, and cerebral ischemia, and neurodegenerative disease caused by traumatic injury, glutamate neurotoxicity or hypoxia.

In one embodiment, the inflammatory disease is asthma, inflammatory bowel disease, Crohn's disease, ulcerative colitis, rheumatoid arthritis, psoriasis, allergic rhinitis, atopic dermatitis, contact dermatitis or delayed hypersensitivity reactions. In one embodiment, the inflammatory disease is inflammatory bowel disease. In one embodiment, the inflammatory disease is psoriasis. In one embodiment, the inflammatory disease is asthma.

In one embodiment, the autoimmune disease is lupus or multiple sclerosis.

In one embodiment, the disease is asthma, inflammatory bowel disease, Crohn's disease, pouchitis, microscopic colitis, ulcerative colitis, rheumatoid arthritis, psoriasis, allergic rhinitis, atopic dermatitis, contact dermatitis, delayed hypersensitivity reactions, lupus or multiple sclerosis.

Evaluation of drug-induced immunosuppression by the compounds of the invention may be performed using in vivo functional tests, such as rodent models of induced arthritis and therapeutic or prophylactic treatment to assess disease score, T cell-dependent antibody response (TDAR), and delayed-type hypersensitivity (DTH). Other in vivo systems including murine models of host defense against infections or tumor resistance (Burleson G R, Dean J H, and Munson A E. *Methods in Immunotoxicology*, Vol. 1. Wiley-Liss, New York, 1995) may be considered to elucidate the nature or mechanisms of observed immunosuppression. The in vivo test systems can be complemented by well-established in vitro or ex vivo functional assays for the assessment of immune competence. These assays may comprise B or T cell proliferation in response to mitogens or specific antigens, measurement of signaling through one or more of the Janus kinase pathways in B or T cells or immortalized B or T cell lines, measurement of cell surface markers in response to B or T cell signaling, natural killer (NK) cell activity, mast cell activity, mast cell degranulation, macrophage phagocytosis or kill activity, and neutrophil oxidative burst and/or chemotaxis. In each of these tests determination of cytokine production by particular effector cells (e.g., lymphocytes, NK, monocytes/macrophages, neutrophils) may be included. The in vitro and ex vivo assays can be applied in both preclinical and clinical testing using lymphoid tissues and/or peripheral blood (House R V. "Theory and practice of cytokine assessment in immunotoxicology" (1999) Methods 19:17-27; Hubbard A K. "Effects of xenobiotics on macrophage function: evaluation in vitro" (1999) Methods; 19:8-16; Lebrec H, et al (2001) Toxicology 158:25-29).

Collagen-induced arthritis (CIA) is an animal model of human rheumatoid arthritis (RA). Joint inflammation, which develops in animals with CIA, strongly resembles inflammation observed in patients with rheumatoid arthritis (RA). Blocking tumor necrosis factor (TNF) is an efficacious treatment of CIA, just as it is a highly efficacious therapy in treatment of RA patients. CIA is mediated by both T-cells and antibodies (B-cells). Macrophages are believed to play an important role in mediating tissue damage during disease development. CIA is induced by immunizing animals with collagen emulsified in Complete Freund's Adjuvant (CFA). It is most commonly induced in the DBA/1 mouse strain, but the disease can also be induced in Lewis rats.

The T-cell Dependent Antibody Response (TDAR) is An assay for immune function testing when potential immunotoxic effects of compounds need to be studied. The IgM-Plaque Forming Cell (PFC) assay, using Sheep Red Blood Cells (SRBC) as the antigen, is currently a widely accepted and validated standard test. TDAR is an assay for adult exposure immunotoxicity detection in mice based on the US National Toxicology Program (NTP) database (M. I. Luster et al (1992) Fundam. Appl. Toxicol. 18:200-210). The utility of this assay stems from the fact that it is a holistic measurement involving several important components of an immune response. A TDAR is dependent on functions of the following cellular compartments: (1) antigen-presenting cells, such as macrophages or dendritic cells; (2) T-helper cells, which are critical players in the genesis of the response, as well as in isotype switching; and (3) B-cells, which are the ultimate effector cells and are responsible for antibody production. Chemically-induced changes in any one compartment can cause significant changes in the overall TDAR (M. P. Holsapple In: G. R. Burleson, J. H. Dean and A. E. Munson, Editors, *Modern Methods in Immunotoxicology*, Volume 1, Wiley-Liss Publishers, New York, N.Y. (1995), pp. 71-108). Usually, this assay is performed either as an ELISA for measurement of soluble antibody (R. J. Smialowizc et al (2001) Toxicol. Sci. 61:164-175) or as a plaque (or antibody) forming cell assay (L. Guo et al (2002) Toxicol. Appl. Pharmacol. 181:219-227) to detect plasma cells secreting antigen specific antibodies. The antigen of choice is either whole cells (e.g. sheep erythrocytes) or soluble protein antigens (T. Miller et al (1998) Toxicol. Sci. 42:129-135).

A compound of Formula I may be administered by any route appropriate to the disease or condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary, and intranasal. For local immunosuppressive treatment, the compounds may be administered by intralesional administration, including perfusing or otherwise contacting the graft with the inhibitor before transplantation. It will be appreciated that the route may vary with for example the condition of the recipient. Where the compound of Formula I is administered orally, it may be formulated as a pill, capsule, tablet, etc. with a pharmaceutically acceptable carrier or excipient. Where the compound of Formula I is administered parenterally, it may be formulated with a pharmaceutically acceptable parenteral vehicle and in a unit dosage injectable form, as detailed below.

A dose to treat human patients may range from about 5 mg to about 1000 mg of a compound of Formula I. A typical dose may be about 5 mg to about 300 mg of a compound of Formula I. A dose may be administered once a day (QD), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Combination Therapy

The compounds of Formula I may be employed alone or in combination with other therapeutic agents for the treatment of a disease or disorder described herein, such as an immunologic disorder (e.g. psoriasis or inflammation) or a hyperproliferative disorder (e.g., cancer). In certain embodiments, a compound of Formula I is combined in a pharmaceutical combination formulation, or dosing regimen as combination therapy, with a second therapeutic compound that has anti-inflammatory or anti-hyperproliferative properties or that is useful for treating an inflammation, immune-response disorder, or hyperproliferative disorder (e.g., cancer). The second therapeutic agent may be a NSAID or other anti-inflammatory agent. The second therapeutic agent may be a chemotherapeutic agent. The second therapeutic agent of the pharmaceutical combination formulation or dosing regimen for example has complementary activities to the compound of Formula I such that they do not adversely affect each other. Such compounds are suitably present in combination in amounts that are effective for the purpose intended. In one embodiment, a composition of this invention comprises a compound of Formula I, or a stereoisomer, geometric isomer, tautomer, solvate, metabolite, or pharmaceutically acceptable salt or prodrug thereof, in combination with a therapeutic agent such as an NSAID.

Another embodiment, therefore, includes a method of treating or lessening the severity of a disease or condition responsive to the inhibition of TYK2 kinase in a patient, comprising administering to said patient a therapeutically effective amount of a compound of Formula I, and further comprising, administering a second therapeutic agent.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein for example there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

In a particular embodiment of therapy, a compound of Formula I, or a stereoisomer, geometric isomer, tautomer, solvate, metabolite, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I, or a stereoisomer, geometric isomer, tautomer, solvate, metabolite, or pharmaceutically acceptable salt or prodrug thereof, and the use of at least one other cancer treatment method, or immunological disorder method. The amounts of the compound(s) of Formula I and the other pharmaceutically active immunologic or chemotherapeutic agent(s) and the relative timings of administration will be selected in order to achieve the desired combined therapeutic effect.

In one embodiment, compounds of the present invention are coadministered with any of anti-IBD agents, including but not limited to anti-inflammatory drugs, such as sulfasalazine, mesalamine or corticosteroids, such as budesonide, prednisone, cortisone or hydrocortisone, immune suppressing agents, such as azathioprine, mercaptopurine, infliximab, adalimumab, certolizumab pegol, methotrexate, cyclosporine or natalizumab, antibiotics, such as metronidazole or ciprofloxacin, anti-diarrheals, such as psyllium powder, loperamide or methylcellulose, laxatives, pain relievers, such as NSAIDs or acetaminophen, iron supplements, vitamin B supplements, vitamin D supplements and any combination of the above. In another example, compounds of the present invention are administered with (e.g. before, during or after) other anti-IBD therapies, such as surgery.

In one embodiment, compounds of the present invention are coadministered with any of anti-psoriasis agents, including but not limited to topical corticosteroids, vitamin D analogues, such as calcipotriene or calcitriol, anthralin, topical retinoids, such as tazarotene, calcineurin inhibitors, such as tacrolimus or pimecrolimus, salicylic acid, coal tar, NSAIDs, moisturizing creams and ointments, oral or injectible retinoids, such as acitretin, methotrexate, cyclosporine, hydroxyurea. immunomodulator drugs, such as alefacept, etanercept, infliximab or ustekinumab, thioguanine, and any combinations of the above. In another example, compounds of the present invention are administered with (e.g. before, during or after) other anti-psoriasis therapies, such as light therapy, sunlight therapy, UVB therarpy, narrow-band UVB therapy, Goeckerman therapy, photochemotherapy, such as psoralen plus ultraviolet A (PUVA), excimer and pulsed dye laser therapy, or in any combination of antipsoriasis agents and anti-psoriasis therapies.

In one embodiment, compounds of the present invention are coadministered with any of anti-asthmtic agents, including but not limited to beta2-adrenergic agonists, inhaled and oral corticosteroids, leukotriene receptor antagonist, and omalizumab. In another embodiment, compounds of the present invention are coadministered with an anti-asthmtic agent selected from a NSAID, combinations of fluticasone and salmeterol, combinations of budesonide and formoterol, omalizumab, lebrikizumab and corticosteroid selected from fluticasone, budesonide, mometasone, flunisolide and beclomethasone.

Methods and Articles of Manufacture

Another embodiment includes a method of manufacturing a compound of Formula I. The method includes:

(a) reacting a compound of formula (i) with a compound of formula (ii):

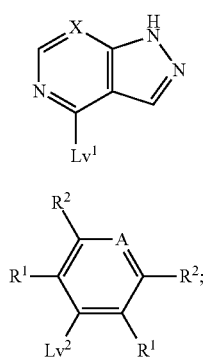

wherein $Lv^1$ and $Lv^2$ are independently a leaving group, for example $Lv^1$ is chloro and $Lv^2$ is fluoro, and X, A, $R^1$ and $R^2$ are as defined for Formula I, under conditions sufficient to form a compound of formula (iii):

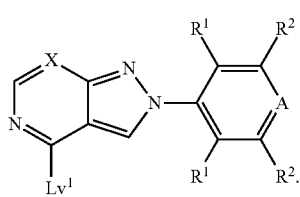

In one example, the conditions for reacting compounds of formulae (i) and (ii) include heating at elevated temperatures of about 50-150° C., alternatively about 75-100° C., and optionally heating in the presence of a base, such as an nonnucleophilic base, for example carbonate base such as potassium carbonate, and optionally including solvent, for example a polar aprotic solvent, for example DMF.

The method of manufacturing a compound of Formula I includes and alternative process including:

(c) reacting a compound of formula (iv) with a compound of formula (v):

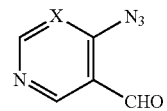

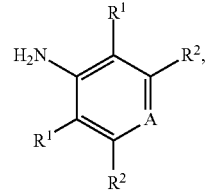

wherein X, A, $R^1$ and $R^2$ are as defined for Formula I, under conditions sufficient to form a compound of formula (vii):

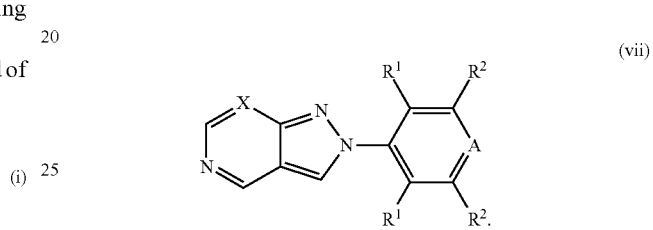

In one example, the conditions for reacting compounds of formulae (iv) and (v) include contacting said compounds with a catalyst, for example a lewis acid catalyst, such as a transition metal catalyst, for example, metal halides such as titanium halides (e.g. $TiCl_4$ or $TiBr_4$) or vanadium tetrachloride, or other lewis acid catalysts such as $AlCl_3$. The conditions optionally include cooling during reaction with the catalyst for a period of time, and further include optionally heating at elevated temperatures of about 50-150° C., alternatively about 75-100° C., in a solvent, for example an aprotic solvent, for example chloroform, carbon tetrachloride, dichloromethane, toluene or xylene, or the like.

The method of manufacturing a compound of Formula I further includes oxidizing a compound of formula vii to form a compound of formula viii, followed by halogenation to form the compound of formula iii, or directly halogenating vii to form compound iii, wherein Lv is a halogen. Oxidation conditions include contacting compound vii with peroxide and a catalyst, for example a ruthenium oxide such as $MeRuO_3$.

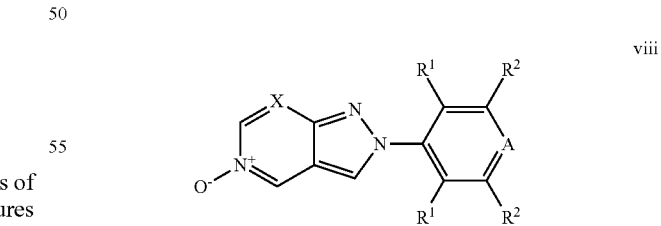

Halogenation of compound viii with a halogenating reagent, for example a phosphorous oxyhalide, such as $POBr_3$ or $POCl_3$, forms a compound of formula iii, wherein Lv is a halogen.

The method of manufacturing a compound of Formula I further includes reacting the compound of formula iii with a compound of the formula $H-R^4-R^5$ under conditions sufficient to form the product, such as a compound of Formula I;

and optionally further functionalizing said product, for example by forming a pharmaceutically acceptable salt thereof by reacting with an acid, such as hydrochloric or formic acid.

In certain embodiments, the conditions for reacting a compound of formula iii with a compound of the formula H—$R^4$-$R^5$ include transition metal catalyzed reaction conditions. In one embodiment, the transition metal catalyst is selected from a platinum, palladium or copper catalyst. In one embodiment, the catalyst is a Pd(0) catalyst. Pd(0) catalysts for use in the method include tetrakis(tri-optionally substituted phenyl) phosphine palladium(0) catalyst, wherein said optional substituents on phenyl are selected from —OMe, —$CF_3$, —$OCF_3$, -Me and -Et and dipalladium(0) catalysts, such as tris(dibenzylideneacetone)dipalladium(0). In certain embodiments, the conditions include heating the reactants under basic conditions, for example, in the presence of an inorganic base, for example, a cesium, potassium, ammonium, or sodium carbonate or bicarbonate base, for example $Cs_2CO_3$. In certain embodiments, the conditions further include ligands to the transition metal catalyst. In one embodiment, a bidentate ligand is included, for example, the bidentate ligand xantphos is added.

Another embodiment includes a kit for treating a disease or disorder responsive to the inhibition of a TYK2 kinase. The kit includes:
(a) a first pharmaceutical composition comprising a compound of Formula I; and
(b) instructions for use.
In another embodiment, the kit further includes:
(c) a second pharmaceutical composition, which includes a chemotherapeutic agent.

In one embodiment, the instructions include instructions for the simultaneous, sequential or separate administration of said first and second pharmaceutical compositions to a patient in need thereof.

In one embodiment, the first and second compositions are contained in separate containers.

In one embodiment, the first and second compositions are contained in the same container.

Containers for use include, for example, bottles, vials, syringes, blister pack, etc. The containers may be formed from a variety of materials such as glass or plastic. The container includes a compound of Formula I or formulation thereof which is effective for treating the condition and may have a sterile access port (for example the container may be an intravenous solution bag or a vial having a stopper pierceable by a hypodermic injection needle). The container includes a composition comprising at least one compound of Formula I. The label or package insert indicates that the composition is used for treating the condition of choice, such as cancer. In one embodiment, the label or package inserts indicates that the composition comprising the compound of Formula I can be used to treat a disorder. In addition, the label or package insert may indicate that the patient to be treated is one having a disorder characterized by overactive or irregular kinase activity. The label or package insert may also indicate that the composition can be used to treat other disorders.

The article of manufacture may comprise (a) a first container with a compound of Formula I contained therein; and (b) a second container with a second pharmaceutical formulation contained therein, wherein the second pharmaceutical formulation comprises a chemotherapeutic agent. The article of manufacture in this embodiment of the invention may further comprise a package insert indicating that the first and second compounds can be used to treat patients at risk of stroke, thrombus or thrombosis disorder. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare other compounds of Formula I, and alternative methods for preparing the compounds of Formula I are within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

BIOLOGICAL EXAMPLES

Compounds of Formula I may be assayed for the ability to modulate the activity of protein kinases, tyrosine kinases, additional serine/threonine kinases, and/or dual specificity kinases in vitro and in vivo. In vitro assays include biochemical and cell-based assays that determine inhibition of the kinase activity. Alternate in vitro assays quantify the ability of the compound of Formula I to bind to kinases and may be measured either by radiolabelling the compound of Formula I prior to binding, isolating the compound of Formula I/kinase complex and determining the amount of radiolabel bound, or by running a competition experiment where a compound of Formula I is incubated with known radiolabeled ligands. These and other useful in vitro assays are well known to those of skill in the art.

In an embodiment, the compounds of Formula I can be used to control, modulate or inhibit tyrosine kinase activity, for example TYK2 kinase activity, additional serine/threonine kinases, and/or dual specificity kinases. Thus, they are useful as pharmacological standards for use in the development of new biological tests, assays and in the search for new pharmacological agents.

Example A

JAK1, JAK2 and TYK2 Inhibition Assay Protocol

The activity of the isolated JAK1, JAK2 or TYK2 kinase domain was measured by monitoring phosphorylation of a peptide derived from JAK3 (Val-Ala-Leu-Val-Asp-Gly-Tyr-Phe-Arg-Leu-Thr-Thr) fluorescently labeled on the N-terminus with 5-carboxyfluorescein using the Caliper LabChip technology (Caliper Life Sciences, Hopkinton, Mass.). To determine the inhibition constants (Ki) of Examples 1-165, compounds were diluted serially in DMSO and added to 50 µL kinase reactions containing 1.5 nM JAK1, 0.2 nM purified JAK2 or 1 nM purified TYK2 enzyme, 100 mM Hepes pH7.2, 0.015% Brij-35, 1.5 uM peptide substrate, 25 uM ATP, 10 mM $MgCl_2$, 4 mM DTT at a final DMSO concentration of 2%. Reactions were incubated at 22° C. in 384-well polypropylene microtiter plates for 30 minutes and then stopped by addition of 25 μL of an EDTA containing solution (100 mM Hepes pH 7.2, 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip 3000 according to the manufacturer's specifications. Ki values were then determined using the Morrison tight binding model. Morrison, J. F., *Biochim. Biophys. Acta.* 185:269-296 (1969); William, J. W. and Morrison, J. F., *Meth. Enzymol.*, 63:437-467 (1979).

Example B

JAK3 Inhibition Assay Protocol

The activity of the isolated JAK3 kinase domain was measured by monitoring phosphorylation of a peptide derived from JAK3 (Leu-Pro-Leu-Asp-Lys-Asp-Tyr-Tyr-Val-Val-Arg) fluorescently labeled on the N-terminus with 5-carboxyfluorescein using the Caliper LabChip technology (Caliper Life Sciences, Hopkinton, Mass.). To determine the inhibition constants (Ki) of Examples 1-165, compounds were diluted serially in DMSO and added to 50 μL kinase reactions containing 5 nM purified JAK3 enzyme, 100 mM Hepes pH7.2, 0.015% Brij-35, 1.5 uM peptide substrate, 5 uM ATP, 10 mM $MgCl_2$, 4 mM DTT at a final DMSO concentration of 2%. Reactions were incubated at 22° C. in 384-well polypropylene microtiter plates for 30 minutes and then stopped by addition of 25 μL of an EDTA containing solution (100 mM Hepes pH 7.2, 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip 3000 according to the manufacturer's specifications. Ki values were then determined using the Morrison tight binding model. Morrison, J. F., *Biochim. Biophys. Acta.* 185:269-296 (1969); William, J. W. and Morrison, J. F., *Meth. Enzymol.*, 63:437-467 (1979).

Example C

Cell-Based Pharmacology Assays

The activities of compounds 1-89 were determined in cell-based assays that are designed to measure Janus kinase dependent signaling. Compounds were serially diluted in DMSO and incubated with NK92 cells (American Type Culture Collection (ATCC); Manassas, Va.) in 384-well microtiter plates in RPMI medium at a final cell density of 50,000 cells per well and a final DMSO concentration of 0.2%. Human recombinant IL-12 (R&D systems; Minneapolis, Minn.) was then added at a final concentration of 30 ng/ml to the microtiter plates containing the NK92 cells and compound and the plates were incubated for 45 min at 37° C. Alternatively, compounds were serially diluted in DMSO and incubated with TF-1 cells (American Type Culture Collection (ATCC); Manassas, Va.) in 384-well microtiter plates in Opti-MEM medium without phenol red, 1% Charcoal/Dextran stripped FBS, 0.1 mM NEAA, 1 mM sodium pyruvate (Invitrogen Corp.; Carlsbad, Calif.) at a final cell density of 100,000 cells per well and a final DMSO concentration of 0.2%. Human recombinant EPO (Invitrogen Corp.; Carlsbad, Calif.) was then added at a final concentration of 10 Units/ml to the microtiter plates containing the TF-1 cells and compound and the plates were incubated for 30 min at 37° C. Compound-mediated effects on STAT4 or STAT5 phosphorylation were then measured in the lysates of incubated cells using the Meso Scale Discovery (MSD) technology (Gaithersburg, Md.) according to the manufacturer's protocol and $EC_{50}$ values were determined.

The compounds of Examples 1-89 were tested in the above assays and found to have $K_i$ values for TYK2 inhibition (Example A) of less than about 500 nM. The compounds of Examples 1-165 were tested in the above assays and found to have $K_i$ values for TYK2 inhibition (Example A) of less than about 500 nM. Examples of the TYK2 inhibition (Example A) are shown in the below Table 1.

TABLE 1

| Example | Tyk2 Ki (nM) |
| --- | --- |
| 1 | 1.3 |
| 2 | 2 |
| 3 | 3 |
| 6 | 5.2 |
| 7 | 3.3 |
| 15 | 1.6 |
| 30 | 5.6 |
| 34 | 0.4 |
| 37 | 0.4 |
| 40 | 1.1 |
| 49 | 1.9 |
| 53 | 1 |
| 67 | 14.9 |
| 69 | 2 |
| 81 | 2.2 |
| 96 | 0.8 |
| 101 | 105 |
| 151 | 0.1 |
| 158 | 1.8 |

PREPARATIVE EXAMPLES

Abbreviations

'BuOH tert-Butanol
DAST Diethylaminosulfur trifluoride
DCE Dichloroethane
DCM Dichloromethane
DIPEA Diisopropylethylamine
DMA N,N-dimethylacetamide
DMAP 4-Dimethylaminopyridine
DME Ethyleneglycol dimethyl ether
DMF N,N-Dimethylformamide
DMSO Dimethylsulfoxide
HATU O-(7-Azabenzotriazol-1-yl)-N,N,N',N'-tetramethyluronium hexafluorophosphate
HCl Hydrochloric acid
HPLC High Pressure Liquid Chromatography
IMS Industrial methylated spirits
IPA Propan-2-ol
LCMS Liquid Chromatography Mass Spectrometry
mCPBA 3-Chloroperbenzoic acid
MeOH Methanol
$NH_2$ cartridge Isolute® silica-based sorbent with a chemically bonded Aminopropyl functional group
NMP N-Methyl-2-pyrrolidinone
RPHPLC Reverse phase high pressure liquid chromatography
RT Retention time
Sat. aq. Saturated aqueous
SCX-2 Isolute® silica-based sorbent with a chemically bonded propylsulfonic acid functional group
TFA Trifluoroacetic acid
THF Tetrahydrofuran
$Pd_2(dba)_3$ Tris(dibenzylideneacetone)dipalladium(0)

Xantphos 4,5-Bis(diphenylphosphino)-9,9-dimethylxanthene
Amgen catalyst PdCl$_2${P$^t$Bu$_2$(Ph-p-NMe$_2$)}$_2$
KP-NH Biotage PK-NH Flash SNAP Cartridge®
NMP 1-Methyl-2-pyrrolidinone
PdCl$_2$(dppf)$_2$.DCM 1-1'-Bis(diphenylphosphino)ferrocene-palladium(II)dichloride dichloromethane complex
Pd(dppf)Cl$_2$.CHCl$_3$ 1,1'-Bis(diphenylphosphino)ferrocene-palladium(II)dichloride chloroform complex
Pd(PPh$_3$)$_4$ Tetrakis(triphenylphosphine) palladium (0)
TBME tert-Butyl methyl ether General Experimental Conditions Compounds of this invention can be prepared with commercially available starting materials using the general methods illustrated herein. Specifically, 2-chloro-3-formyl-4-iodopyridine and 3-bromo-4-chloropyridine were purchased from Matrix Scientific (Columbia, S.C.). 1,3-dichloro2-fluorobenzene was purchased from Alfa Aesar (Ward Hill, Mass.). 4-chloropyridine-3-carboaldehyde was purchased from Frontier Scientific (Logan, Utah). 4-chloro-3-fluoropyridine, 2,6-dichloroaniline, 2,6-dichloro4-nitroaniline, 4-amino-3,5-dichlorobenzonitrile were purchased from Aldrich (St. Louis, Mo.). 3,4-dichloropyridine and 2,6-dichloro-4-fluoroaniline were purchased from Apollo Scientific (Stockport, Cheshire, UK).

LCMS Analytical Methods

Method A: Experiments performed on Agilent 6110 quadrupole LC/MS system, with UV detector monitoring at 220 nm and 254 nm, and mass spectrometry scanning 110-800 amu in ESI+ ionization mode. Column: XBridge C18, 4.6×50 mm, 3.5 mm; mobile phase: A water (0.01% ammonia), B CH$_3$CN; gradient: 5%-95% B in 8.0 min; flow rate: 1.2 mL/min; oven temperature 40° C.

Method B: Experiments performed on a Waters Micromass ZQ2000 quadrupole mass spectrometer linked to a Waters Acquity UPLC system with a PDA UV detector. The spectrometer has an electrospray source operating in positive and negative ion mode. This system uses an Acquity BEH C18 1.7 um 100×2.1 mm column, maintained at 40° C. or an Acquity BEH Shield RP18 1.7 µm 100×2.1 mm column, maintained at 40° C. and a 0.4 ml/minute flow rate. The initial solvent system was 95% water containing 0.1% formic acid (solvent A) and 5% acetonitrile containing 0.1% formic acid (solvent B) for the first 0.4 minute followed by a gradient up to 5% solvent A and 95% solvent B over the next 5.6 minutes. This was maintained for 0.8 minute before returning to 95% solvent A and 5% solvent B over the next 1.2 minutes. Total run time was 8 minutes.

Method C: Experiments performed on a Waters Platform LC quadrupole mass spectrometer linked to a Hewlett Packard HP1100 LC system with a diode array and a Sedex 85 evaporative light scattering detector. The spectrometer has an electrospray source operating in positive and negative ion mode. This system uses a Phenomenex Luna 3 micron C18(2) 30×4.6 mm column and a 2 ml/minute flow rate. The initial solvent system was 95% water containing 0.1% formic acid (solvent A) and 5% acetonitrile containing 0.1% formic acid (solvent B) for the first 0.5 minute followed by a gradient up to 5% solvent A and 95% solvent B over the next 4.0 minutes. This was maintained for 1 minute before returning to 95% solvent A and 5% solvent B over the next 0.5 minute. Total run time was 6 minutes.

Method D: Experiments performed on a Waters ZMD quadrupole mass spectrometer linked to a Waters 1525 LC system with a Waters 996 diode array detector and a Sedex 85 evaporative light scattering detector. The spectrometer has an electrospray source operating in positive and negative ion mode. This system uses a Luna 3 micron C18(2) 30×4.6 mm column and a 2 ml/minute flow rate. The initial solvent system was 95% water containing 0.1% formic acid (solvent A) and 5% acetonitrile containing 0.1% formic acid (solvent B) for the first 0.5 minute followed by a gradient up to 5% solvent A and 95% solvent B over the next 4.0 minutes. This was maintained for 1 minute before returning to 95% solvent A and 5% solvent B over the next 0.5 minute. Total run time was 6 minutes Method E: Experiments performed on Agilent 1200 LC/MS system, with UV detector monitoring at 220 nm and 254 nm, and mass spectrometry scanning 110-800 amu in ESI+ ionization mode. Column: Agilent ZORBAX SD-C18, 2.1×30 mm, 1.8 µm; mobile phase: A water with 0.05% TFA, B CH$_3$CN with 0.05% TFA; gradient: 3%-95% B in 8.5 min; flow rate: 0.4 mL/min; Column temperature 40° C.

Method F: Experiments performed on a VG Platform II quadrupole mass spectrometer linked to a Hewlett Packard HP1050 LC system with diode array detector and 100 position autosampler, using a Phenomenex Luna 3 µm C$_{18}$(2) 30×4.6 mm and a 2 mL/minute flow rate. The mobile phase consisted of formic acid 0.1% in water (solvent A) and formic acid 0.1% in acetonitrile (solvent B). The initial solvent system was 95% solvent A and 5% solvent B for the first 0.3 minute followed by a gradient up to 5% solvent A and 95% solvent B over the next 4 minutes. The final solvent system was held constant for a further 1 minute.

Method G: Experiments were performed on a Waters Quattro Micro triple quadrupole mass spectrometer with an electrospray source operating in positive and negative ion mode linked to a Hewlett Packard HP1100 LC system. Detection was achieved using a PDA detector. The LC column was a Higgins Clipeus 5 micron C18 100×3.0 mm maintained at 22° C. The flow rate was 1 mL/minute. The initial solvent system was 95% water containing 0.1% formic acid (solvent A) and 5% acetonitrile containing 0.1% formic acid (solvent B) for 1 minute followed by a gradient up to 5% solvent A and 95% solvent B over the next 14 minutes. The final solvent system was held constant for a further 5 minutes.

$^1$H NMR spectra were recorded at ambient temperature using a Varian Unity Inova (400 MHz) spectrometer with a triple resonance 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

Microwave experiments were carried out using a Biotage Initiator 60™ which uses a single-mode resonator and dynamic field tuning. Temperature from 40-250° C. can be achieved, and pressures of up to 30 bar can be reached.

Method 1

Example 1

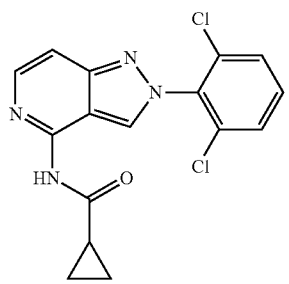

N-(2-(2,6-Dichlorophenyl)-2H-pyrazolo[4,3-c]pyridin-4-yl)cyclopropanecarboxamide

77

Step 1

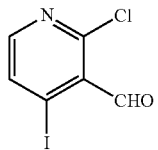

2-Chloro-4-iodonicotinaldehyde

A mixture of 2-chloro-3-iodopyridine (5.0 g, 21 mmol) in dry THF (30 mL) was slowly added to a cold (−78° C.) solution of lithium diisopropylamide (15 mL, 30 mmol) in dry THF (50 mL). The resulting mixture was stirred for 3 h at this temperature. Ethyl formate (4.0 g, 54 mmol) was then added. Stirring was continued for 1.5 h at the same temperature. Water (10 mL) was added to quench the reaction, and then the resulting mixture was warmed to room temperature. 2M HCl (50 mL) was added and then the THF was removed under reduced pressure. The aqueous residue was extracted with ethyl acetate (2×50 mL). The combined organic extracts were washed with brine, dried over $Na_2SO_4$ and concentrated under reduced pressure. The residue was purified on silica gel (diethyl ether:petroleum ether=1:4) to give the desired product 2-chloro-4-iodonicotinaldehyde as a yellow solid (3.0 g, 54% yield). $^1$H NMR (500 MHz, $CDCl_3$): δ 10.22 (s, 1H), 8.09 (d, J=5.0 Hz, 1H), 7.95 (d, J=5.0 Hz, 1H).

Step 2

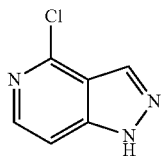

4-Chloro-1H-pyrazolo[4,3-c]pyridine

To a mixture of 2-chloro-4-iodonicotinaldehyde (1.0 g, 3.7 mmol) in ethanol (6.0 mL) was added 3.0 mL of hydrazine (excess). The mixture was stirred at room temperature for 15 h and then concentrated under reduced pressure. The residue was diluted with water (30 mL) and extracted with dichloromethane (300 mL). The organic extract was washed with brine, dried over $Na_2SO_4$, and concentrated under reduced pressure. The residue was dissolved in dichloromethane (5 mL) and stirred for 5 min. The precipitated solid was isolated by filtration and dried to give the desired intermediate 4-chloro-1H-pyrazolo[4,3-c]pyridine as a grey solid (110 mg, 19% yield), which was used in the next step without further purification. LCMS(ESI) m/z: 154.1 [M+H$^+$]

78

Step 3

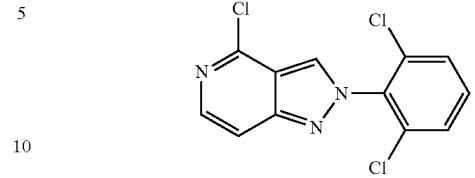

4-Chloro-2-(2,6-dichlorophenyl)-2H-pyrazolo[4,3-c]pyridine

A mixture of 4-chloro-1H-pyrazolo[4,3-c]pyridine (150 mg, 0.990 mmol), 1,6-dichloro-2-fluorobenzene (300 mg, 1.80 mmol) and potassium carbonate (450 mg, 3.26 mmol) in dry DMF (3.0 mL) was heated at 85° C. for 20 h. The reaction was quenched with water (30 mL) and extracted with ethyl acetate (3×20 mL). The combined organic extracts were washed with brine, dried over $Na_2SO_4$ and concentrated under reduced pressure. The residue was purified on silica gel (ethyl acetate:petroleum ether=1:10) to give 4-chloro-2-(2,6-dichlorophenyl)-2H-pyrazolo[4,3-c]pyridine as a white solid (10 mg, 3.5% yield) and 4-chloro-1-(2,6-dichlorophenyl)-1H-pyrazolo[4,3-c]pyridine as a white solid (30 mg, 11% yield).

4-Chloro-2-(2,6-dichlorophenyl)-2H-pyrazolo[4,3-c]pyridine: $^1$H-NMR ($CDCl_3$): δ 8.31 (d, J=0.5 Hz, 1H), 8.13 (d, J=6.0 Hz, 1H), 7.64-7.56 (m, 3H), 7.49 (m, 1H). LCMS(ESI) m/z: 298.0 [M+H$^+$].

4-Chloro-1-(2,6-dichlorophenyl)-1H-pyrazolo[4,3-c]pyridine, $^1$H-NMR ($CDCl_3$): δ 8.44 (d, J=0.5 Hz, 1H), 8.24 (d, J=6.0 Hz, 1H), 7.57-7.47 (m, 3H), 7.00 (d, J=6.0 Hz, 1H). LCMS(ESI) m/z: 298.0 [M+H$^+$].

Step 4

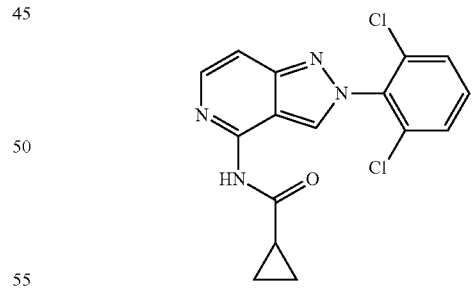

N-(2-(2,6-Dichlorophenyl)-2H-pyrazolo[4,3-c]pyridin-4-yl)cyclopropanecarboxamide A suspension of 4-chloro-2-(2,6-dichlorophenyl)-2H-pyrazolo[4,3-c]pyridine (25 mg, 0.084 mmol), cyclopropanecarboxamide (16 mg, 0.19 mmol), Xantphos (14 mg, 0.024 mmol), $Pd_2(dba)_3$ (14 mg, 0.016 mmol) and $Cs_2CO_3$ (152 mg, 0.470 mmol) in dry dioxane (4.0 mL) was sealed in a microwave vial after degassing with nitrogen. The mixture was irradiated at 160° C. for 60 minutes in the microwave and then cooled to room temperature. The solid material was removed via filtration and the filtrate was purified via prep-HPLC (Gilson GX 281, Shim-pack PRC-ODS 250 mm×20 mm×2, gradient: CH$_3$CN/10 mm/L NH$_4$HCO$_3$, 17 min) to afford N-(2-(2,6-dichlorophenyl)-2H-pyrazolo[4,3-c]pyridin-4-yl) cyclopropanecarboxamide (10 mg, 35% yield) as a white solid. $^1$H NMR (400 MHz, DMSO-d$_6$): δ 11.19 (br, 1H), 8.90 (s, 1H), 7.99 (d, J=6.5 Hz, 1H), 7.79-7.67 (m, 3H), 7.39 (d, J=6.0 Hz, 1H), 2.13 (m, 1H), 0.92-0.86 (m, 4H). LCMS (Method A): RT=5.50 min, m/z: 347.0 [M+H$^+$].

Method 1

Example 2

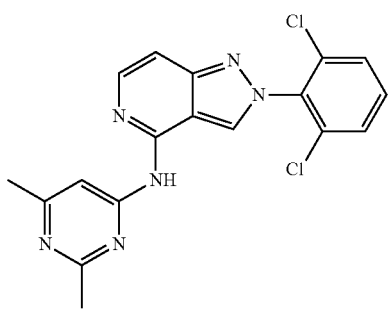 [SMILES: Cc1cc(Nc2nccc3nn(-c4c(Cl)cccc4Cl)cc23)nc(C)n1]

[2-(2,6-Dichlorophenyl)-2H-pyrazolo[4,3-c]pyridine-4-yl]-(2,6-dimethylpyrimidin-4-yl)amine In a similar procedure as shown in Example 1, this compound was prepared in 11% yield. $^1$H NMR (400 MHz, DMSO-d$_6$): δ 10.57 (br s, 1H), 9.16 (s, 1H), 8.34 (s, 1H), 7.99 (d, J=6.5 Hz, 1H), 7.83-7.70 (m, 3H), 7.22 (d, J=6.5 Hz, 1H), 2.49 (s, 3H), 2.41 (s, 3H). LCMS (Method A): RT=5.24 min, m/z: 385.0 [M+H$^+$].

Alternatively, Example 2 could also be prepared by Method 2:

Step 1

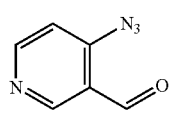 [SMILES: [N-]=[N+]=Nc1ccncc1C=O]

4-Azidopyridine-3-carbaldehyde

Sodium azide (1.07 g, 16.5 mmol) was added to a mixture of 4-chloro-3-formylpyridine (2.22 g, 15.7 mmol) in DMF (15 mL) and the reaction mixture was stirred for 18 hours. Ethyl acetate was added and the organic layers were washed with water and brine. The combined organic phases were dried over anhydrous magnesium sulfate, filtered and concentrated under reduced pressure. The residue was purified by silica gel flash chromatography (0-60% ethyl acetate in cyclohexane) to afford the title compound as a white solid (2.02 g, 87% yield). $^1$H NMR (300 MHz, CDCl$_3$): δ 10.35 (s, 1H), 8.99 (s, 1H), 8.72 (d, J=5.6 Hz, 1H), 7.20 (d, J=5.6 Hz, 1H).

Step 2

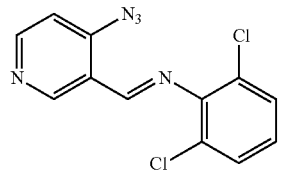 [SMILES: [N-]=[N+]=Nc1ccncc1/C=N/c1c(Cl)cccc1Cl]

[1-(4-Azidopyridin-3-yl)meth-(E)-ylidene]-(2,6-dichlorophenyl)amine

Titanium tetrachloride (1M, 4.3 mL, 4.3 mmol) was added to a cooled (0° C.) mixture of 4-azidopyridine-3-carbaldehyde (1.06 g, 7.2 mmol), 2,6-dichloroaniline (1.17 g, 7.2 mmol) and triethylamine (3.0 mL, 21.6 mmol) in DCM (24 mL) under nitrogen. The resultant mixture was stirred for 3 hours at 0° C. before warming to room temperature and stirring for a further 3 hours. The reaction mixture was concentrated under reduced pressure. The residue was suspended in toluene and filtered though a pad of Celite®. The filtrate was concentrated to dryness under reduced pressure to afford the title compound as a yellow solid. This crude material was employed in the next step without further purification or analysis.

Step 3

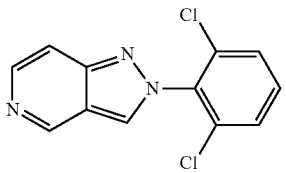 [SMILES: Clc1cccc(Cl)c1-n1cc2cnccc2n1]

2-(2,6-Dichlorophenyl)-2H-pyrazolo[4,3-c]pyridine

A mixture of [1-(4-azidopyridin-3-yl)meth-(E)-ylidene]-(2,6-dichlorophenyl)amine (7.2 mmol) in toluene (20 mL) was heated to 105° C. for 18 hours. The reaction mixture was cooled and concentrated under reduced pressure. The resultant residue was purified by silica gel flash chromatography (0-70% ethyl acetate in cyclohexane) to afford the title compound as a yellow solid (1.30 g, 68% yield). $^1$H NMR (300 MHz, CDCl$_3$): δ 9.31 (d, J=1.4 Hz, 1H), 8.36 (d, J=6.4 Hz, 1H), 8.30 (d, J=1.0 Hz, 1H), 7.65 (dt, J=6.4, 1.2 Hz, 1H), 7.54-7.52 (m, 2H), 7.46 (dd, J=9.5, 6.4 Hz, 1H). LCMS (Method D): RT=3.46 min, m/z: 264 [M+H$^+$].

Step 4

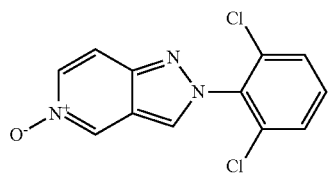

2-(2,6-Dichlorophenyl)-2H-pyrazolo[4,3-c]pyridine 5-oxide

A dried solution of mCPBA (7.2 mmol) in DCM (20 mL) was added to a cooled (0° C.) solution of 2-(2,6-dichlorophenyl)-2H-pyrazolo[4,3-c]pyridine (1.28 g, 4.8 mmol) in DCM (30 mL) under nitrogen. The reaction mixture was stirred for 1 hour, warmed to room temperature, and stirred for a further 2 hours. Sodium thiosulfate (sat. aq.) was added and the layers were partitioned. The organic layer was washed with sodium hydrogen carbonate (sat. aq.) and brine, dried over anhydrous magnesium sulfate, and concentrated to under reduced pressure. The residue was purified by silica gel flash chromatography (5-10% methanol in DCM) to afford the title compound as a white solid (1.22 g, 91% yield). $^1$H NMR (400 MHz, DMSO-$d_6$): δ 8.90 (dd, J=1.8, 0.9 Hz, 1H), 8.84 (d, J=1.0 Hz, 1H), 7.95 (dd, J=7.5, 1.8 Hz, 1H), 7.84 (dt, J=7.5, 1.0 Hz, 1H), 7.81-7.78 (m, 2H), 7.70 (dd, J=9.0, 7.3 Hz, 1H).

Step 5

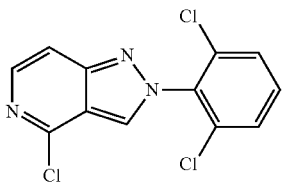 [SMILES: Clc1cccc(Cl)c1-n1cc2c(Cl)nccc2n1]

4-Chloro-2-(2,6-dichlorophenyl)-2H-pyrazolo[4,3-c]pyridine 2-(2,6-Dichlorophenyl)-2H-pyrazolo[4,3-c]pyridine 5-oxide (1.12 g, 4 mmol) was slowly added to phosphorous oxychloride (8 mL). Tetrabutylammonium chloride (1.11 g, 4 mmol) was then added. The reaction mixture was heated at 80° C. for 5 hours and then cooled to room temperature. The reaction was poured into a mixture of ethyl acetate and sodium hydrogen carbonate (sat. aq.) and the layers were partitioned. The organic layer was washed with sodium hydrogen carbonate (sat. aq.) and brine, dried over anhydrous sodium sulfate, and concentrated under reduced pressure. The resultant residue was purified by silica gel flash chromatography (20% ethyl acetate in cyclohexane) to afford the title compound as a white solid (590 mg, 49% yield). $^1$H NMR (400 MHz, DMSO-$d_6$): δ 9.33 (d, J=1.0 Hz, 1H), 8.11 (d, J=6.0 Hz, 1H), 7.83 (d, J=1.3 Hz, 1H), 7.82-7.81 (m, 1H), 7.75-7.71 (m, 1H). LCMS (Method D): RT=3.42 min, m/z: 298 [M+H$^+$].

Step 6

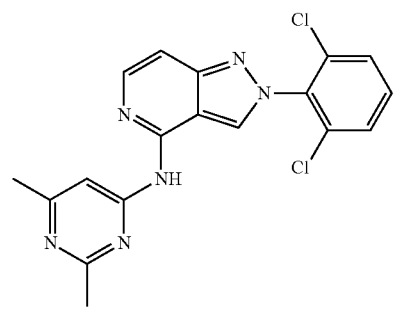 [SMILES: Cc1cc(Nc2nccc3nn(-c4c(Cl)cccc4Cl)cc23)nc(C)n1]

[2-(2,6-Dichlorophenyl)-2H-pyrazolo[4,3-c]pyridine-4-yl]-(2,6-dimethylpyrimidin-4-yl)amine A suspension of 4-chloro-2-(2,6-dichlorophenyl)-2H-pyrazolo[4,3-c]pyridine (200 mg, 0.57 mmol), 4-amino-2,6-dimethylpyrimidine (95 mg, 0.77 mmol), Pd$_2$(dba)$_3$ (16 mg, 0.018 mmol), Xantphos (39 mg, 0.067 mmol) and cesium carbonate (437 mg, 1.34 mmol) in dioxane (5 mL) was sealed in a microwave vial, purged with nitrogen and irradiated at 150° C. for 25 minutes in the microwave. The reaction mixture was cooled and partitioned between ethyl acetate and water. The organic layer was washed with brine, dried over anhydrous sodium sulfate, and concentrated under reduced pressure. The residue was purified by silica gel flash chromatography (60-80% ethyl acetate in cyclohexane) to afford the title compound as a yellow solid (189 mg, 73% yield). $^1$H NMR (400 MHz, DMSO-$d_6$): δ 10.52 (br s, 1H), 9.16 (s, 1H), 8.34 (s, 1H), 7.99 (d, J=6.4 Hz, 1H), 7.83 (d, J=1.0 Hz, 1H), 7.81 (s, 1H), 7.71 (dd, J=9.0, 7.3 Hz, 1H), 7.21 (d, J=6.4 Hz, 1H), 3.32 (s, 3H), 2.41 (s, 3H). LCMS (Method B): RT=2.93 min, m/z: 385 [M+H$^+$].

Method 2

Example 3

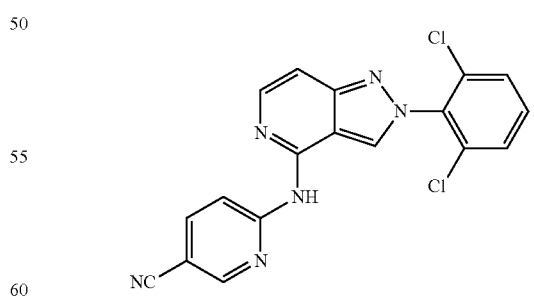

6-[2-(2,6-Dichlorophenyl)-2H-pyrazolo[4,3-c]pyridin-4-ylamino]nicotinonitrile

Sodium hydride (12 mg, 0.30 mmol) was added to a solution of 6-amino-3-pyridinecarbonitrile (36 mg, 0.30 mmol) in DMF (2 mL) and the resultant mixture was stirred for 5 minutes before 4-chloro-2-(2,6-dichlorophenyl)-2H-pyrazolo[4,3-c]pyridine (80 mg, 0.27 mmol) was added. The reaction vial was sealed, purged with nitrogen and irradiated in a microwave at 150° C. for 10 minutes. The reaction mixture was cooled and partitioned between ethyl acetate and water. The organic layer was washed with brine, dried over anhydrous sodium sulfate, and concentrated under reduced pressure. The residue was purified by silica gel flash chromatography (40% ethyl acetate in cyclohexane) to afford the title compound as a yellow solid (53 mg, 52% yield). $^1$H NMR (400 MHz, DMSO-$d_6$): δ 9.57 (d, J=0.9 Hz, 1H), 8.98 (dd, J=2.3, 0.8 Hz, 1H), 8.47 (dd, J=8.7, 2.3 Hz, 1H), 8.04 (d, J=7.3 Hz, 1H), 7.89-7.83 (m, 2H), 7.77 (dd, J=9.1, 7.2 Hz, 1H), 7.65-7.61 (m, 2H). LCMS (Method B): RT=3.05 min, m/z: 381 [M+H$^+$].

Method 2

Example 4

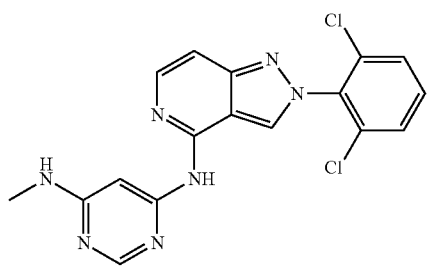 [SMILES: CNc1cc(Nc2nccc3nn(-c4c(Cl)cccc4Cl)cc23)ncn1]

N-[2-(2,6-Dichlorophenyl)-2H-pyrazolo[4,3-c]pyridine-4-yl]-N'-methylpyrimidine-4,6-diamine Step 1

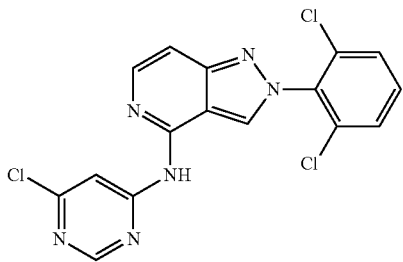 [SMILES: Clc1cc(Nc2nccc3nn(-c4c(Cl)cccc4Cl)cc23)ncn1]

(6-Chloropyrimidin-4-yl)-[2-(2,6-dichlorophenyl)-2H-pyrazolo[4,3-c]pyridine-4-yl]amine Following the procedure described above for [2-(2,6-dichlorophenyl)-2H-pyrazolo[4,3-c]pyridine-4-yl]-(2,6-dimethylpyrimidin-4-yl)amine, 4-chloro-2-(2,6-dichlorophenyl)-2H-pyrazolo[4,3-c]pyridine and 4-amino-6-chloropyrimidine were reacted to afford the title compound as a yellow solid (244 mg, 57% yield). $^1$H NMR (400 MHz, DMSO-$d_6$): δ 11.14 (br s, 1H), 9.15 (s, 1H), 8.76 (s, 1H), 8.70 (s, 1H), 8.04 (d, J=6.4 Hz, 1H), 7.81 (d, J=8.1 Hz, 2H), 7.71 (t, J=8.1 Hz, 1H), 7.30 (d, J=6.4 Hz, 1H). LCMS (Method D): RT=2.40 min, m/z: 391 [M+H$^+$].

Step 2

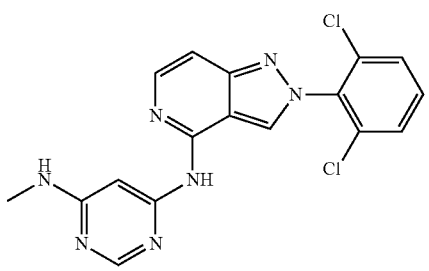 [SMILES: CNc1cc(Nc2nccc3nn(-c4c(Cl)cccc4Cl)cc23)ncn1]

N-[2-(2,6-Dichlorophenyl)-2H-pyrazolo[4,3-c]pyridine-4-yl]-N'-methylpyrimidine-4,6-diamine A solution of (6-chloropyrimidin-4-yl)-[2-(2,6-dichlorophenyl)-2H-pyrazolo[4,3-c]pyridine-4-yl]amine (80 mg, 0.20 mmol) and methylamine (2M in THF, 300 μL, 0.60 mmol) in NMP (2.0 mL) was sealed in a microwave vial, purged with nitrogen and irradiated at 160° C. for 30 minutes in the microwave. Further methylamine (300 μL, 0.20 mmol) was added and the reaction mixture was irradiated at 170° C. for 30 minutes. The resultant mixture was cooled and partitioned between ethyl acetate and water. The organic layer was washed with brine, dried over anhydrous sodium sulfate, and concentrated under reduced pressure. The residue was purified by silica gel flash chromatography (4-5% methanol in DCM) to afford the title compound as a white solid (35.0 mg, 45% yield). $^1$H NMR (400 MHz, DMSO-$d_6$): δ 10.03 (br s, 1H), 9.14 (s, 1H), 8.21 (s, 1H), 7.91 (d, J=6.3 Hz, 1H), 7.80 (d, J=8.1 Hz, 2H), 7.70 (dd, J=9.0, 7.4 Hz, 1H), 7.23 (br s, 1H), 7.13 (d, J=6.4 Hz, 1H), 2.81 (d, J=4.7 Hz, 3H). LCMS (Method B): RT=2.99 min, m/z: 386 [M+H$^+$].

Method 2

Example 5

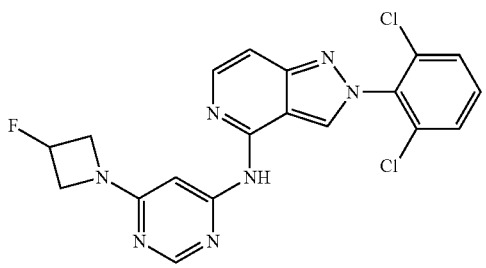 [SMILES: FC1CN(c2cc(Nc3nccc4nn(-c5c(Cl)cccc5Cl)cc34)ncn2)C1]

[2(2,6-Dichlorophenyl)-2H-pyrazolo[4,3-c]pyridine-4-yl]-[6-(3-fluoroazetidin-1-yl)pyrimidin-4-yl]amine Following the procedure described for N-[2-(2,6-dichlorophenyl)-2H-pyrazolo[4,3-c]pyridine-4-yl]-N'-methylpyrimidine-4,6-diamine, (6-chloropyrimidin-4-yl)-[2-(2,6-dichlorophenyl)-2H-pyrazolo[4,3-c]pyridine-4-yl]amine and 3-fluoroazetidine with added DIPEA (103 μL, 0.6 mmol) were reacted to afford the title compound as a yellow solid (81 mg, 93% yield). ¹H NMR (400 MHz, DMSO-d₆): δ 10.28 (br s, 1H), 9.14 (s, 1H), 8.29 (s, 1H), 7.94 (s, 1H), 7.80 (d, J=8.1 Hz, 2H), 7.70 (dd, J=9.1, 7.3 Hz, 2H), 7.16 (br s, 1H), 5.62-5.46 (m, 1H), 4.38 (ddd, J=21.3, 10.5, 5.9 Hz, 2H), 4.14 (d, J=10.5 Hz, 1H), 4.08 (d, J=10.5 Hz, 1H). LCMS (Method B): RT=3.16 min, m/z: 430 [M+H⁺].

Method 2

Example 6

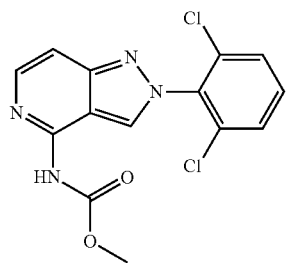 [SMILES: COC(=O)Nc1nccc2nn(-c3c(Cl)cccc3Cl)cc12]

[2-(2,6-Dichlorophenyl)-2H-pyrazolo[4,3-c]pyridine-4-yl]carbamic acid methyl ester Step 1

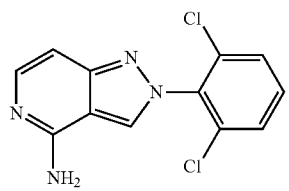 [SMILES: Nc1nccc2nn(-c3c(Cl)cccc3Cl)cc12]

2-(2,6-Dichlorophenyl)-2H-pyrazolo[4,3-c]pyridine-4-ylamine

Following the procedure described for N-[2-(2,6-dichlorophenyl)-2H-pyrazolo[4,3-c]pyridine-4-yl]-N'-methylpyrimidine-4,6-diamine, 4-chloro-2-(2,6-dichlorophenyl)-2H-pyrazolo[4,3-c]pyridine and 33% aqueous ammonia (1.5 mL) were reacted to afford the title compound as a white solid (139 mg, 53% yield). ¹H NMR (400 MHz, DMSO-d₆): δ 8.66 (d, J=0.9 Hz, 1H), 7.79-7.77 (m, 2H), 7.67 (dd, J=9.0, 7.3 Hz, 1H), 7.58 (d, J=6.5 Hz, 1H), 7.10 (br s, 2H), 6.74 (dd, J=6.5, 1.0 Hz, 1H). LCMS (Method B): RT=2.54 min, m/z: 279 [M+H⁺].

Step 2

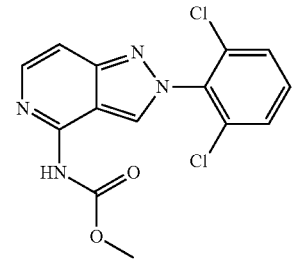 [SMILES: COC(=O)Nc1nccc2nn(-c3c(Cl)cccc3Cl)cc12]

[2-(2,6-Dichlorophenyl)-2H-pyrazolo[4,3-c]pyridine-4-yl]carbamic acid methyl ester DIPEA (51 μL, 0.3 mmol) and then methyl chloroformate (19 μL, 0.25 mmol) were added to a solution of 2-(2,6-dichlorophenyl)-2H-pyrazolo[4,3-c]pyridine-4-ylamine (60 mg, 0.21 mmol) in DCM (2 mL). The reaction was stirred at room temperature until completion as determined by TLC. The mixture was partitioned between DCM and water. The organic layer was washed with brine, dried over anhydrous sodium sulfate, and concentrated under reduced pressure. The residue was purified by silica gel flash chromatography (40-50% ethyl acetate in cyclohexane) to afford the title compound as a white solid (35 mg, 49% yield). ¹H NMR (400 MHz, DMSO-d₆): δ 9.54 (d, J=0.9 Hz, 1H), 7.97 (d, J=7.3 Hz, 1H), 7.86 (d, J=1.4 Hz, 1H), 7.84 (d, J=0.6 Hz, 1H), 7.80-7.78 (m, 1H), 7.72 (dd, J=7.3, 0.9 Hz, 1H), 3.97 (s, 3H). LCMS (Method B): RT=2.71 min, m/z: 337 [M+H⁺].

Method 2

Example 7

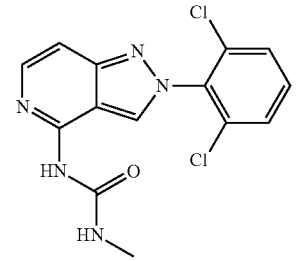 [SMILES: CNC(=O)Nc1nccc2nn(-c3c(Cl)cccc3Cl)cc12]

1-[2-(2,6-Dichlorophenyl)-2H-pyrazolo[4,3-c]pyridine-4-yl]-3-methylurea

Following the procedure described for [2-(2,6-dichlorophenyl)-2H-pyrazolo[4,3-c]pyridine-4-yl]carbamic acid methyl ester, 2-(2,6-dichlorophenyl)-2H-pyrazolo[4,3-c]pyridine-4-ylamine and methyl isocyanate were reacted to afford the title compound as a white solid (78% yield). ¹H NMR (400 MHz, DMSO-d₆): δ 10.06 (br s, 1H), 9.75-9.70 (m, 1H), 9.04 (d, J=0.9 Hz, 1H), 7.85 (d, J=6.5 Hz, 1H), 7.83-7.76 (m, 2H), 7.70 (dd, J=9.0, 7.3 Hz, 1H), 7.17 (dd, J=6.5, 0.9 Hz, 1H), 2.84 (d, J=4.6 Hz, 3H). LCMS (Method B): RT=2.69 min, m/z: 336 [M+H⁺].

Method 2

Example 8

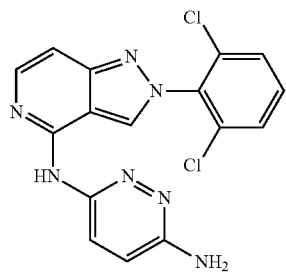 [SMILES: Nc1ccc(Nc2nccc3nn(-c4c(Cl)cccc4Cl)cc23)nn1]

N-[2-(2,6-Dichlorophenyl)-2H-pyrazolo[4,3-c]pyridin-4-yl]-pyridazine-3,6-diamine A mixture of 2-(2,6-dichlorophenyl)-2H-pyrazolo[4,3-c]pyridine-4-ylamine (100 mg, 0.36 mmol), 3-amino-6-chloropyridazine (57 mg, 0.44 mmol), $Pd_2(dba)_3$ (8 mg, 0.009 mmol), Xantphos (21 mg, 0.036 mmol) and cesium carbonate (234 mg, 0.72 mmol) in dioxane (2.5 mL) was degassed with argon then heated at 150° C. for 30 minutes in a microwave reactor. The reaction mixture was partitioned between ethyl acetate and water. The organic layer was washed with brine, dried over anhydrous sodium sulfate, and concentrated under reduced pressure. The residue was purified by silica gel flash chromatography (4-7% methanol in DCM) to afford the title compound as a beige solid (17 mg, 13% yield). $^1$H NMR (400 MHz, DMSO-$d_6$): δ 9.45 (d, J=0.9 Hz, 1H), 7.95-7.89 (m, 2H), 7.86-7.84 (m, 2H), 7.76 (dd, J=9.1, 7.2 Hz, 1H), 7.62 (d, J=9.7 Hz, 1H), 7.57-7.53 (m, 1H). LCMS (Method B): RT=2.56 min, m/z: 372 [M+H$^+$].

Method 2

Example 9

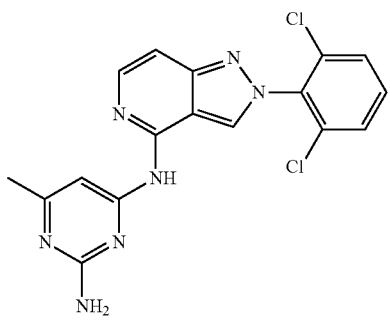 [SMILES: Cc1cc(Nc2nccc3nn(-c4c(Cl)cccc4Cl)cc23)nc(N)n1]

N$^4$-[2-(2,6-Dichlorophenyl)-2H-pyrazolo[4,3-c]pyridin-4-yl]-6-methyl-pyrimidine-2,4-diamine

Step 1

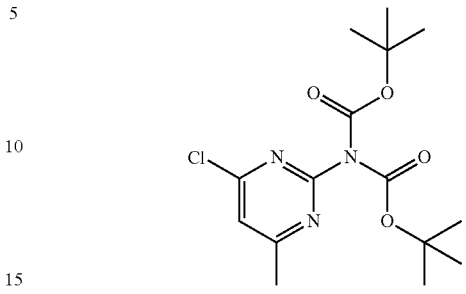

(4-Chloro-6-methyl-pyrimidin-2-yl)-bis-carbamic acid tert-butyl ester

DMAP (43 mg, 0.35 mmol) was added to a mixture of 2-amino-6-chloro-4-methylpyrimidine (1.0 g, 7.0 mmol) and di-tert-butyl-dicarbonate (3.3 g, 15.0 mmol) in THF (40 mL). The reaction was stirred at room temperature for 18 hours and then concentrated under reduced pressure. The residue purified by silica gel chromatography (20% ethyl acetate in cyclohexane) to afford the title compound as an off-white solid (1.64 g, 68% yield). $^1$H NMR (400 MHz, CDCl$_3$): δ 7.12 (d, J=0.6 Hz, 1H), 2.54 (d, J=0.5 Hz, 3H), 1.47 (s, 18H).

Step 2

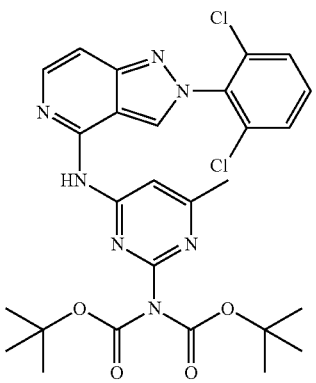 [SMILES: Cc1cc(Nc2nccc3nn(-c4c(Cl)cccc4Cl)cc23)nc(N(C(=O)OC(C)(C)C)C(=O)OC(C)(C)C)n1]

{4-[2-(2,6-Dichlorophenyl)-2H-pyrazolo[4,3-c]pyridin-4-ylamino]-6-methyl-pyrimidin-2-yl}-bis-carbamic acid tert-butyl ester Following the procedure described for N-[2-(2,6-dichlorophenyl)-2H-pyrazolo[4,3-c]pyridin-4-yl]-pyridazine-3,6-diamine, 2-(2,6-dichlorophenyl)-2H-pyrazolo[4,3-c]pyridine-4-ylamine and (4-chloro-6-methyl-pyrimidin-2-yl)-bis-carbamic acid tert-butyl ester were reacted to afford the title compound as a pale yellow solid (126 mg, 60% yield). LCMS (Method D): RT=3.15 min, m/z: 586 [M+H$^+$].

Step 3

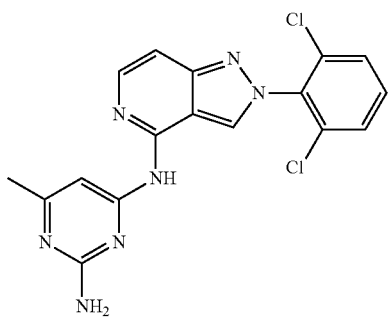 [SMILES: Cc1cc(Nc2nccc3nn(-c4c(Cl)cccc4Cl)cc23)nc(N)n1]

N⁴-[2-(2,6-Dichlorophenyl)-2H-pyrazolo[4,3-c]pyridin-4-yl]-6-methyl-pyrimidine-2,4-diamine TFA (1 mL) was added to a solution of {4-[2-(2,6-dichlorophenyl)-2H-pyrazolo[4,3-c]pyridin-4-ylamino]-6-methyl-pyrimidin-2-yl}-bis-carbamic acid tert-butyl ester (121 mg, 0.21 mmol) in DCM (3 mL) and stirred at room temperature for 1.5 hours. The reaction mixture was concentrated under reduced pressure and the residue was partitioned between DCM and sodium bicarbonate (sat. aq.). The organic layer was dried over anhydrous sodium sulfate and concentrated under reduced pressure. The residue was purified by silica gel chromatography (2% methanol in ethyl acetate) to afford the title compound as a white solid (23 mg, 28% yield). ¹H NMR (400 MHz, DMSO-d₆): δ 9.62 (d, J=0.9 Hz, 1H), 8.05 (d, J=7.2 Hz, 1H), 7.86 (d, J=1.5 Hz, 1H), 7.84 (d, J=0.6 Hz, 1H), 7.81-7.75 (m, 2H), 6.75 (d, J=0.9 Hz, 1H), 2.55-2.50 (obs. m, 3H). LCMS (Method B): RT=2.68 min, m/z: 386 [M+H⁺].

Method 2

Example 10

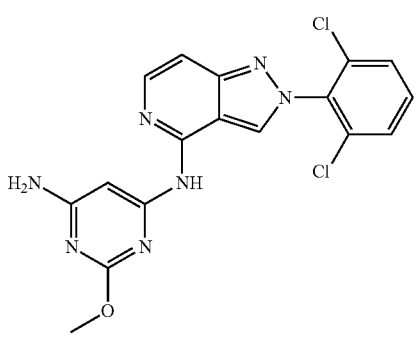 [SMILES: COc1nc(N)cc(Nc2nccc3nn(-c4c(Cl)cccc4Cl)cc23)n1]

N-[2-(2,6-Dichlorophenyl)-2H-pyrazolo[4,3-c]pyridin-4-yl]-2-methoxy-pyrimidine-4,6-diamine

Step 1

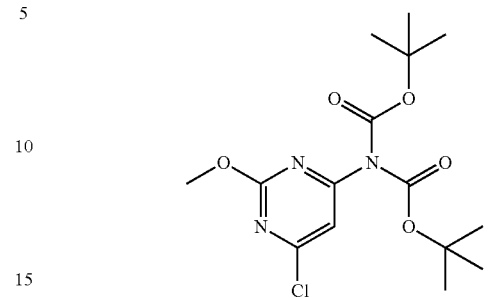

(6-Chloro-2-methoxy-pyrimidin-4-yl)-bis-carbamic acid tert-butyl ester

Following the procedure described for (4-chloro-6-methyl-pyrimidin-2-yl)-bis-carbamic acid tert-butyl ester, 6-chloro-2-methoxy-pyrimidin-4-ylamine and di-tert-butyl-dicarbonate were reacted to afford the title compound as a colourless oil (336 mg, 89% yield). ¹H NMR (400 MHz, CDCl₃): δ 7.49 (s, 1H), 3.94 (s, 3H), 1.56 (s, 18H).

Step 2

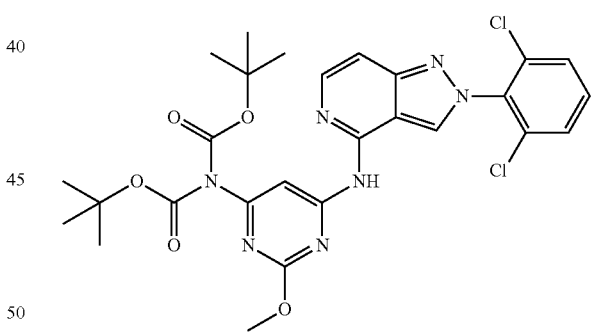

{4-[2-(2,6-Dichlorophenyl)-2H-pyrazolo[4,3-c]pyridin-4-ylamino]-4-methoxy-pyrimidin-6-yl}-carbamic acid tert-butyl ester Following the procedure described for N-[2-(2,6-dichlorophenyl)-2H-pyrazolo[4,3-c]pyridin-4-yl]-pyridazine-3,6-diamine, 2-(2,6-dichlorophenyl)-2H-pyrazolo[4,3-c]pyridine-4-ylamine and (6-chloro-2-methoxy-pyrimidin-4-yl)-bis-carbamic acid tert-butyl ester were reacted to afford the title compound as a white solid (82 mg, 38% yield). LCMS (Method D): RT=3.11 min, m/z: 602 [M+H⁺].

Step 3

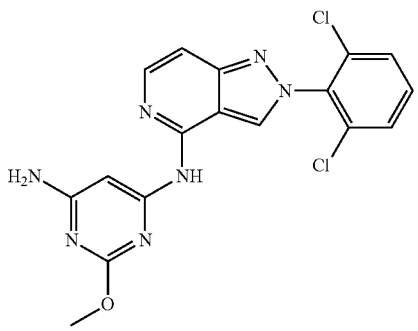 [SMILES: COc1nc(N)cc(Nc2nccc3nn(-c4c(Cl)cccc4Cl)cc23)n1]

N-[2-(2,6-Dichlorophenyl)-2H-pyrazolo[4,3-c]pyridin-4-yl]-2-methoxy-pyrimidine-4,6-diamine Following the procedure described for $N^4$-[2-(2,6-dichlorophenyl)-2H-pyrazolo[4,3-c]pyridin-4-yl]-6-methyl-pyrimidine-2,4-diamine, {4-[2-(2,6-dichlorophenyl)-2H-pyrazolo[4,3-c]pyridin-4-ylamino]-4-methoxy-pyrimidin-6-yl}-carbamic acid tert-butyl ester was reacted to afford the title compound as a white solid (20 mg, 35% yield). $^1$H NMR (400 MHz, DMSO-$d_6$): δ 9.89 (s, 1H), 9.16 (s, 1H), 7.91 (d, J=6.4 Hz, 1H), 7.85-7.77 (m, 2H), 7.70 (dd, J=9.0, 7.3 Hz, 1H), 7.41 (s, 1H), 7.13 (d, J=6.3 Hz, 1H), 6.72 (s, 2H), 3.79 (s, 3H). LCMS (Method B): RT=2.68 min, m/z: 386 [M+H$^+$].

Method 2

Example 11

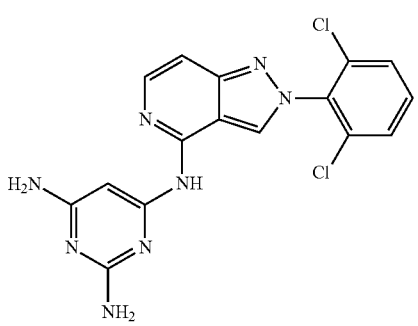 [SMILES: Nc1cc(Nc2nccc3nn(-c4c(Cl)cccc4Cl)cc23)nc(N)n1]

N-[2-(2,6-Dichlorophenyl)-2H-pyrazolo[4,3-c]pyridin-4-yl]-pyrimidine-2,4,6-triamine

Step 1

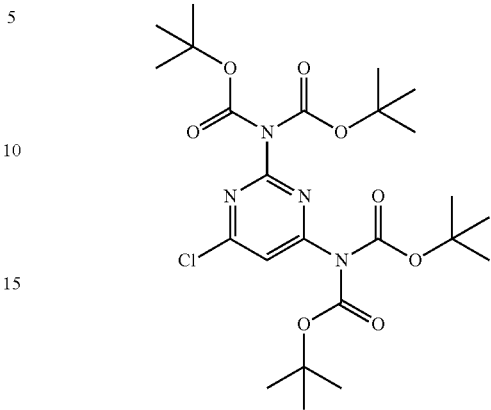

(2-bis-tert-Butoxycarbonylamino-6-chloro-pyrimidin-4-yl)-bis-carbamic acid tert-butyl ester DMAP (12 mg, 0.10 mmol) was added to a mixture of 4-chloro-2,6-diaminopyrimidine (145 mg, 1.0 mmol) and di-tert-butyl-dicarbonate (960 mg, 4.4 mmol) in THF (6 mL) and the resultant mixture stirred at room temperature for 18 hours. The reaction mixture was concentrated to dryness under reduced pressure and the resultant residue purified by silica gel chromatography (10% ethyl acetate in cyclohexane) to afford the title compound as a colourless oil (quant. yield). $^1$H NMR (400 MHz, CDCl$_3$): δ 7.77 (s, 1H), 1.43 (s, 26H).

Step 2

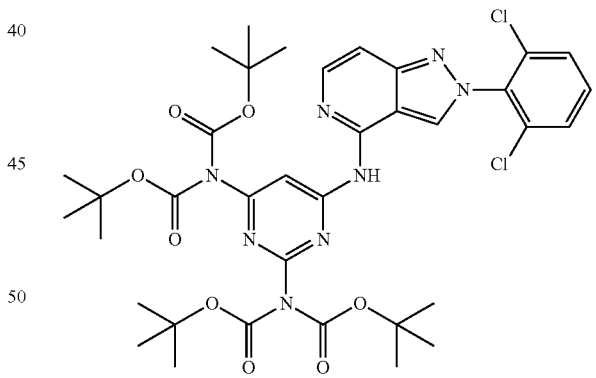

{2-bis-tert-Butoxycarbonylamino-6-[2-(2,6-dichlorophenyl)-2H-pyrazolo[4,3-c]pyridin-4-ylamino]-pyrimidin-4-yl}-bis-carbamic acid tert-butyl ester Following the procedure described for N-[2-(2,6-dichlorophenyl)-2H-pyrazolo[4,3-c]pyridin-4-yl]-pyridazine-3,6-diamine, 2-(2,6-dichlorophenyl)-2H-pyrazolo[4,3-c]pyridine-4-ylamine and (2-bis-tert-butoxycarbonylamino-6-chloro-pyrimidin-4-yl)-bis-carbamic acid tert-butyl ester were reacted to afford the title compound as a white solid (176 mg, 62% yield). LCMS (Method D): RT=3.95 min, m/z: 787 [M+H$^+$].

Step 3

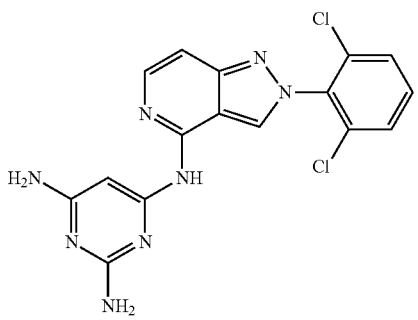 [SMILES: Nc1cc(Nc2nccc3nn(-c4c(Cl)cccc4Cl)cc23)nc(N)n1]

N-[2-(2,6-Dichloro-phenyl)-2H-pyrazolo[4,3-c]pyridin-4-yl]-pyrimidine-2,4,6-triamine Following the procedure described for $N^4$-[2-(2,6-dichlorophenyl)-2H-pyrazolo[4,3-c]pyridin-4-yl]-6-methyl-pyrimidine-2,4-diamine, {2-bis-tert-butoxycarbonylamino-6-[2-(2,6-dichlorophenyl)-2H-pyrazolo[4,3-c]pyridin-4-ylamino]-pyrimidin-4-yl}-bis-carbamic acid tert-butyl ester was reacted to afford the title compound as a pale yellow solid (30 mg, 35% yield). $^1$H NMR (400 MHz, DMSO-d$_6$): δ 9.44 (s, 1H), 7.91 (d, J=7.2 Hz, 1H), 7.86 (d, J=1.3 Hz, 1H), 7.84 (s, 2H), 7.76 (dd, J=9.2, 7.2 Hz, 1H), 7.62-7.61 (m, 1H). LCMS (Method B): RT=2.59 min, m/z: 387 [M+H$^+$].

Method 2

Example 12

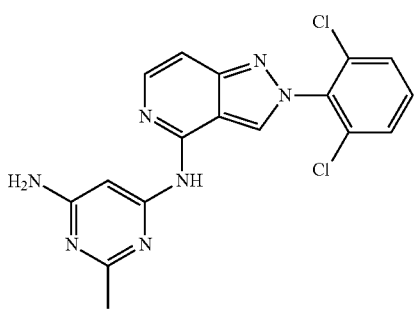 [SMILES: Cc1nc(N)cc(Nc2nccc3nn(-c4c(Cl)cccc4Cl)cc23)n1]

N-[2-(2,6-Dichlorophenyl)-2H-pyrazolo[4,3-c]pyridin-4-yl]-2-methyl-pyrimidine-4,6-diamine Step 1

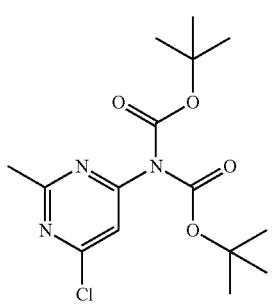 [SMILES: Cc1nc(Cl)cc(N(C(=O)OC(C)(C)C)C(=O)OC(C)(C)C)n1]

(6-Chloro-2-methyl-pyrimidin-4-yl)-bis-carbamic acid tert-butyl ester

Following the procedure described for (4-chloro-6-methyl-pyrimidin-2-yl)-bis-carbamic acid tert-butyl ester, 6-chloro-2-methyl-pyrimidin-4-ylamine and di-tert-butyl-dicarbonate were reacted to afford the title compound as a white solid (1.45 g, quant. yield). $^1$H NMR (400 MHz, CDCl$_3$): δ 7.66 (d, J=0.7 Hz, 1H), 2.58 (d, J=0.6 Hz, 3H), 1.56 (s, 18H).

Step 2

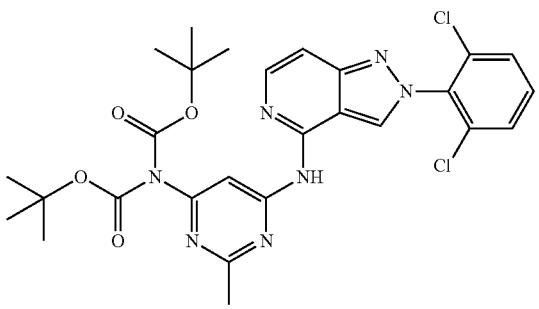 [SMILES: Cc1nc(Nc2nccc3nn(-c4c(Cl)cccc4Cl)cc23)cc(N(C(=O)OC(C)(C)C)C(=O)OC(C)(C)C)n1]

{6-[2-(2,6-Dichlorophenyl)-2H-pyrazolo[4,3-c]pyridin-4-ylamino]-2-methyl-pyrimidin-4-yl}-carbamic acid tert-butyl ester Following the procedure described for N-[2-(2,6-dichlorophenyl)-2H-pyrazolo[4,3-c]pyridin-4-yl]-pyridazine-3,6-diamine, 2-(2,6-dichlorophenyl)-2H-pyrazolo[4,3-c]pyridine-4-ylamine and (6-chloro-2-methyl-pyrimidin-4-yl)-bis-carbamic acid tert-butyl ester were reacted to afford the title compound as a white solid (116 mg, 55% yield). LCMS (Method D): RT=3.05 min, m/z: 586 [M+H$^+$].

Step 3

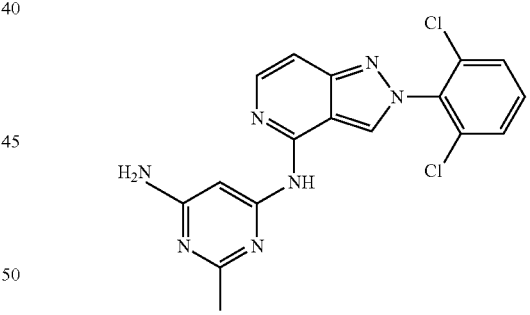

N-[2-(2,6-Dichlorophenyl)-2H-pyrazolo[4,3-c]pyridin-4-yl]-2-methyl-pyrimidine-4,6-diamine Following the procedure described for $N^4$-[2-(2,6-dichloro-phenyl)-2H-pyrazolo[4,3-c]pyridin-4-yl]-6-methyl-pyrimidine-2,4-diamine, {6-[2-(2,6-dichlorophenyl)-2H-pyrazolo[4,3-c]pyridin-4-ylamino]-2-methyl-pyrimidin-4-yl}-carbamic acid tert-butyl ester was reacted to afford the title compound as a white solid (40 mg, 55% yield). $^1$H NMR (400 MHz, DMSO-d$_6$): δ 9.93 (s, 1H), 9.16 (s, 1H), 7.90 (d, J=6.4 Hz, 1H), 7.84-7.78 (m, 2H), 7.70 (dd, J=9.0, 7.3 Hz, 1H), 7.57 (s, 1H), 7.12 (d, J=6.4 Hz, 1H), 6.59 (s, 2H), 2.28 (s, 3H). LCMS (Method B): RT=2.90 min, m/z: 386 [M+H$^+$].

Method 2

Example 13

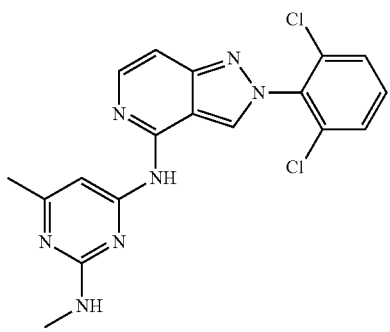 [SMILES: CNc1nc(C)cc(Nc2nccc3nn(-c4c(Cl)cccc4Cl)cc23)n1]

N⁴-[2-(2,6-Dichlorophenyl)-2H-pyrazolo[4,3-c]pyridin-4-yl]-6,N²-dimethylpyrimidine-2,4-diamine Step 1

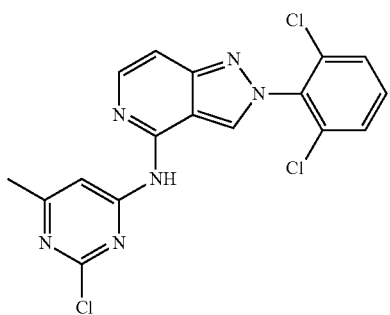 [SMILES: Cc1cc(Nc2nccc3nn(-c4c(Cl)cccc4Cl)cc23)nc(Cl)n1]

(2-Chloro-6-methylpyrimidin-4-yl)-[2-(2,6-dichlorophenyl)-2H-pyrazolo[4,3-c]pyridin-4-yl]amine Following the procedure described above for [2-(2,6-dichlorophenyl)-2H-pyrazolo[4,3-c]pyridine-4-yl]-(2,6-dimethylpyrimidin-4-yl)amine, 4-chloro-2-(2,6-dichlorophenyl)-2H-pyrazolo[4,3-c]pyridine and 2-chloro-6-methylpyrimidin-4-ylamine were reacted to afford the title compound as a yellow solid (256 mg, 57% yield). $^1$H NMR (400 MHz, DMSO-$d_6$): δ 11.06 (s, 1H), 9.14 (s, 1H), 8.51 (s, 1H), 8.02 (d, J=6.4 Hz, 1H), 7.84-7.80 (m, 2H), 7.73-7.68 (m, 1H), 7.30 (d, J=6.4 Hz, 1H), 2.46 (s, 3H). LCMS (Method D): RT=2.50 min, m/z: 407 [M+H⁺].

Step 2

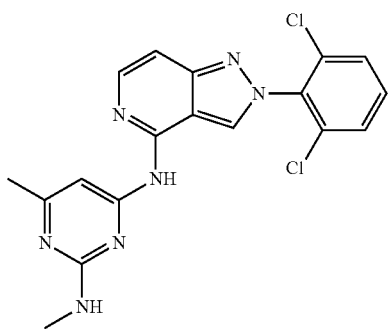 [SMILES: CNc1nc(C)cc(Nc2nccc3nn(-c4c(Cl)cccc4Cl)cc23)n1]

N⁴-[2-(2,6-Dichlorophenyl)-2H-pyrazolo[4,3-c]pyridin-4-yl]-6,N²-dimethylpyrimidine-2,4-diamine Following the procedure described for N-[2-(2,6-dichlorophenyl)-2H-pyrazolo[4,3-c]pyridine-4-yl]-N'-methylpyrimidine-4,6-diamine, (2-chloro-6-methylpyrimidin-4-yl)-[2-(2,6-dichlorophenyl)-2H-pyrazolo[4,3-c]pyridin-4-yl]amine and methylamine were reacted to afford the title compound as a yellow solid (24 mg, 33% yield). $^1$H NMR (400 MHz, DMSO-$d_6$): δ 9.88 (s, 1H), 9.16 (s, 1H), 7.94 (d, J=6.4 Hz, 1H), 7.81-7.80 (m, 2H), 7.70 (dd, J=9.0, 7.3 Hz, 1H), 7.65 (s, 1H), 7.15 (dd, J=6.4, 1.0 Hz, 1H), 2.82 (d, J=4.8 Hz, 3H), 2.25 (s, 3H). LCMS (Method B): RT=2.90 min, m/z: 400 [M+H⁺].

Method 2

Example 14

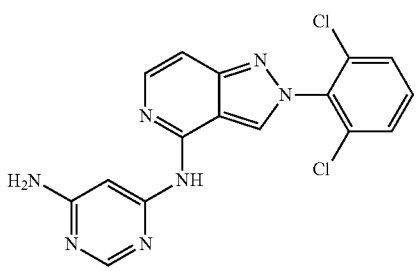

N-[2-(2,6-Dichlorophenyl)-2H-pyrazolo[4,3-c]pyridin-4-yl]-pyrimidine-4,6-diamine Step 1

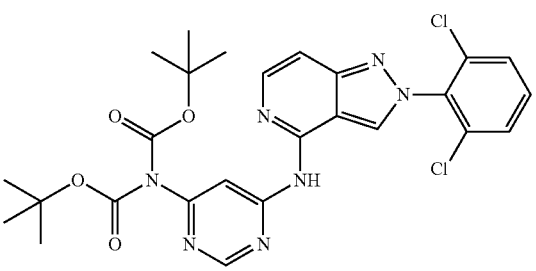

{6-[2-(2,6-Dichlorophenyl)-2H-pyrazolo[4,3-c]pyridin-4-ylamino]-pyrimidin-4-yl}-carbamic acid tert-butyl ester Following the procedure described for N-[2-(2,6-dichlorophenyl)-2H-pyrazolo[4,3-c]pyridin-4-yl]-pyridazine-3,6-diamine, 2-(2,6-dichlorophenyl)-2H-pyrazolo[4,3-c]pyridine-4-ylamine and (6-chloro-pyrimidin-4-yl)-bis-carbamic acid tert-butyl ester were reacted to afford the title compound as a yellow glass (453 mg, 55% yield). LCMS (Method D): RT=2.98 min, m/z: 572 [M+H⁺].

Step 2

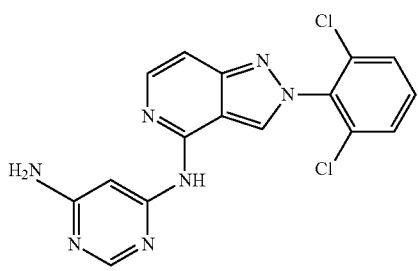 [SMILES: Nc1cc(Nc2nccc3nn(-c4c(Cl)cccc4Cl)cc23)ncn1]

N-[2-(2,6-Dichlorophenyl)-2H-pyrazolo[4,3-c]pyridin-4-yl]-pyrimidine-4,6-diamine Following the procedure described for $N^4$-[2-(2,6-dichloro-phenyl)-2H-pyrazolo[4,3-c]pyridin-4-yl]-6-methyl-pyrimidine-2,4-diamine, {6-[2-(2,6-dichlorophenyl)-2H-pyrazolo[4,3-c]pyridin-4-ylamino]-pyrimidin-4-yl}-carbamic acid tert-butyl ester was reacted to afford the title compound as a white solid (148 mg, 50% yield). $^1$H NMR (400 MHz, DMSO-$d_6$): δ 10.02 (br s, 1H), 9.15 (s, 1H), 8.14 (s, 1H), 7.92 (d, J=6.4 Hz, 1H), 7.84-7.79 (m, 2H), 7.72-7.71 (m, 2H), 7.15 (d, J=6.4 Hz, 1H), 6.71 (br s, 2H). LCMS (Method B): RT=2.85 min, m/z: 372 [M+H$^+$].

Method 2

Example 15

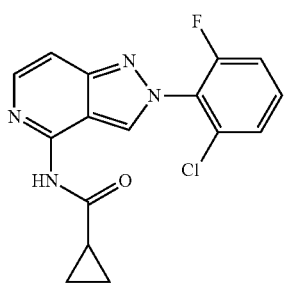

N-(2-(2-chloro-6-fluorophenyl)-2H-pyrazolo[4,3-c]pyridin-4-yl)cyclopropanecarboxamide Step 1

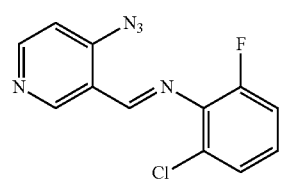 [SMILES: [N-]=[N+]=Nc1ccncc1/C=N/c1c(F)cccc1Cl]

[1-(4-Azidopyridin-3-yl)meth-(E)-ylidene]-(2-chloro-6-fluorophenyl)amine

Triethylamine (7.1 mL, 51 mmol) was added to a cooled (0° C.) mixture of 4-azidopyridine-3-carbaldehyde (2.52 g, 17 mmol) and 2-chloro-6-fluoroaniline (2.47 g, 17 mmol) in DCM (60 mL) under nitrogen. Titanium tetrachloride (1 M, 10.2 mL, 10.2 mmol) was then added and the resulting mixture was stirred for 1 hour at 0° C. before warming to room temperature and stirring for a further 4 hours. The reaction mixture was concentrated under reduced pressure. The residue was suspended in toluene and filtered through a pad of Celite®. The filtrate was concentrated to dryness under reduced pressure to afford the title compound as a yellow solid. This crude material was employed in the next step without further purification or analysis.

Step 2

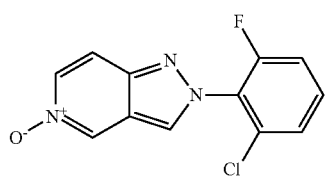 [SMILES: [O-][n+]1ccc2nn(-c3c(F)cccc3Cl)cc2c1]

2-(2-Chloro-6-fluorophenyl)-2H-pyrazolo[4,3-c]pyridine

A solution of [1-(4-azidopyridin-3-yl)meth-(E)-ylidene]-(2-chloro-6-fluorophenyl)amine (17 mmol) in toluene (50 mL) was heated at 105° C. for 18 hours. The reaction mixture was cooled and concentrated under reduced pressure. The residue was purified by silica gel flash chromatography (60-70% ethyl acetate in cyclohexane) to afford the title compound as a yellow solid (2.29 g, 54% yield). $^1$H NMR (400 MHz, CDCl$_3$): δ 9.31 (d, J=1.5 Hz, 1H), 8.38-8.33 (m, 2H), 7.65 (dd, J=6.4, 1.4 Hz, 1H), 7.52 (td, J=8.3, 5.6 Hz, 1H), 7.45-7.41 (m, 1H), 7.30-7.24 (m, 1H). LCMS (Method C): RT=1.42, m/z: 248 [M+H$^+$].

Step 3

2-(2-Chloro-6-fluorophenyl)-2H-pyrazolo[4,3-c]pyridine 5-oxide mCPBA (2.38 g, 13.88 mmol) was added to a cooled 0° C. solution of 2-(2-chloro-6-fluorophenyl)-2H-pyrazolo[4,3-c]pyridine (2.27 g, 9.2 mmol) in DCM (55 mL) under nitrogen. The reaction was stirred for 3 hours, warmed to room temperature, and stirred for an additional 2 hours. Sodium thiosulfate (sat. aq.) was added and the layers were partitioned. The organic layer was washed with sodium hydrogen carbonate (sat. aq.) and brine, dried over anhydrous magnesium sulfate, and concentrated under reduced pressure. The residue was purified by silica gel flash chromatography (5-10% methanol in DCM) to afford the title compound as a beige solid (2.13 g, 88% yield). $^1$H NMR (400 MHz, DMSO-d$_6$): δ 8.90 (dd, J=1.8, 0.9 Hz, 1H), 8.87 (s, 1H), 7.95 (dd, J=7.5, 1.8 Hz, 1H), 7.83 (dt, J=7.5, 1.0 Hz, 1H), 7.74 (td, J=8.3, 5.8 Hz, 1H), 7.65-7.63 (m, 2H).

Step 4

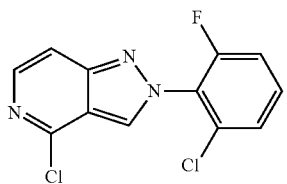 [SMILES: Fc1cccc(Cl)c1-n1cc2c(Cl)nccc2n1]

4-Chloro-2-(2-chloro-6-fluorophenyl)-2H-pyrazolo[4,3-c]pyridine 2-(2-Chloro-6-fluorophenyl)-2H-pyrazolo[4,3-c]pyridine 5-oxide (2.13 g, 8.1 mmol) was added to a solution of tetrabutylammonium chloride (2.24 g, 8.1 mmol) in phosphorous oxychloride (16 mL) and the reaction mixture was heated at 85° C. for 5 hours. The reaction mixture was cooled to room temperature and poured into a mixture of ethyl acetate and sodium hydrogen carbonate (sat. aq.). The organic phase was separated, washed with sodium hydrogen carbonate (sat. aq.) and brine, dried over anhydrous sodium sulfate, and concentrated under reduced pressure. The residue was purified by silica gel flash chromatography (20% ethyl acetate in cyclohexane) to afford the title compound as a white solid (606 mg, 27% yield). $^1$H NMR (400 MHz, CDCl$_3$): δ 8.36 (s, 1H), 8.12 (d, J=6.3 Hz, 1H), 7.57 (d, J=6.5 Hz, 1H), 7.55-7.50 (m, 1H), 7.45 (d, J=8.3 Hz, 1H), 7.27 (m, 1H). LCMS (Method D): RT=3.29 min, m/z: 282 [M+H$^+$].

Step 5

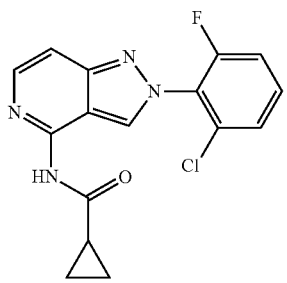

Cyclopropanecarboxylic acid [2-(2-chloro-6-fluorophenyl)-2H-pyrazolo[4,3-c]pyridin-4-yl]amide A mixture of 4-chloro-2-(2-chloro-6-fluorophenyl)-2H-pyrazolo[4,3-c]pyridine (76 mg, 0.27 mmol), cyclopropylcarboxamide (26 mg, 0.31 mmol), Pd$_2$(dba)$_3$ (7 mg, 0.007 mmol), Xantphos (16 mg, 0.027 mmol) and cesium carbonate (176 mg, 0.54 mmol) in dioxane (2 mL) was sealed in a microwave vial, purged with nitrogen, and irradiated at 150° C. for 20 minutes in the microwave. The reaction mixture was cooled and partitioned between ethyl acetate and water. The organic layer was washed with brine, dried over anhydrous sodium sulfate, and concentrated under reduced pressure. The residue was purified by silica gel flash chromatography (50% ethyl acetate in cyclohexane) to afford the title compound as a yellow solid (38 mg, 43% yield). $^1$H NMR (400 MHz, DMSO-d$_6$): δ 11.15 (br s, 1H), 8.94 (s, 1H), 8.00 (d, J=6.3 Hz, 1H), 7.73 (td, J=8.3, 5.8 Hz, 1H), 7.67-7.66 (m, 1H), 7.64-7.52 (m, 2H), 7.36 (d, J=6.3 Hz, 1H), 2.18-2.12 (m, 1H), 0.93-0.86 (m, 4H). LCMS (Method B): RT=2.77 min, m/z: 331 [M+H$^+$].

Method 3

Example 16

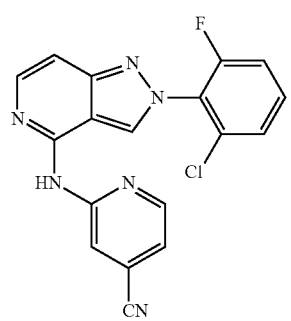

6-[2-(2-Chloro-6-fluorophenyl)-2H-pyrazolo[4,3-c]pyridin-4-ylamino]isonicotinonitrile Sodium hydride (12 mg, 0.30 mmol) was added to a solution of 2-amino-4-cyanopyridine (36 mg, 0.30 mmol) in DMF (2 mL) in a microwave vial and stirred for 5 minutes. 4-Chloro-2-(2-chloro-6-fluorophenyl)-2H-pyrazolo[4,3-c]pyridine (76 mg, 0.27 mmol) was added and then the vial was sealed, purged with nitrogen and irradiated at 150° C. for 10 minutes in the microwave. The reaction mixture was cooled and partitioned between ethyl acetate and water. The organic layer was washed with brine, dried over anhydrous sodium sulfate, and concentrated under reduced pressure. The residue was purified by silica gel flash chromatography (50% ethyl acetate in cyclohexane) to afford the title compound as a yellow solid (10 mg, 10% yield). $^1$H NMR (400 MHz, DMSO-d$_6$): δ 9.61 (s, 1H), 8.77 (dd, J=5.2, 0.9 Hz, 1H), 7.99 (d, J=7.3 Hz, 1H), 7.85 (s, 1H), 7.81-7.80 (m, 2H), 7.73 (d, J=8.2 Hz, 1H), 7.67 (t, J=9.0 Hz, 1H), 7.58 (dd, J=7.3, 0.9 Hz, 1H). LCMS (Method B): RT=2.98 min, m/z: 365 [M+H$^+$].

Method 4

Example 17

Step 1

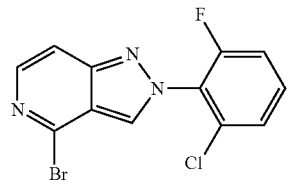 [SMILES: Fc1cccc(Cl)c1-n1cc2c(Br)nccc2n1]

4-Bromo-2-(2-chloro-6-fluorophenyl)-2H-pyrazolo[4,3-c]pyridine

To a suspension of 2-(2-chloro-6-fluorophenyl)-2H-pyrazolo[4,3-c]pyridine 5-oxide (740 mg, 2.8 mmol) in DCE (18 mL) at 0° C. was added phosphorus oxybromide (2.4 g, 8.4 mmol). The reaction mixture was stirred at 0° C. for 15 minutes, warmed to room temperature, and stirred for an additional 4.5 h. The resultant mixture was diluted with DCM, washed with sodium carbonate (sat. aq.) and then with brine. The organic phase was dried over anhydrous magnesium sulphate and concentrated under reduced pressure. The residue was purified by silica gel flash chromatography (0-30% ethyl acetate in cyclohexane) to afford the title compound as a white solid (230 mg, 25% yield). LCMS (Method C): RT=3.44 min, m/z: 327 [M+H$^+$].

Step 2

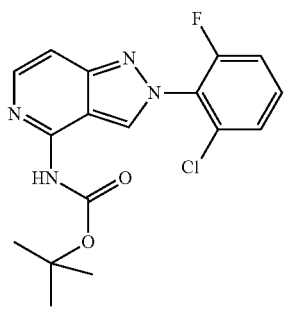 [SMILES: CC(C)(C)OC(=O)Nc1nccc2nn(-c3c(F)cccc3Cl)cc12]

[2-(2-Chloro-6-fluorophenyl)-2H-pyrazolo[4,3-c]pyridin-4-yl]-carbamic acid tert-butyl ester A mixture of 4-bromo-2-(2-chloro-6-fluorophenyl)-2H-pyrazolo[4,3-c]pyridine (166 mg, 0.51 mmol), tert-butyl carbamate (297 mg, 2.54 mmol), Pd$_2$(dba)$_3$ (23 mg, 0.025 mmol), Xantphos (29 mg, 0.05 mmol) and potassium phosphate tribasic (216 mg, 1.02 mmol) in toluene (5 mL) and water (1 mL) was degassed with argon then heated at 60° C. for 1.5 hours. The reaction mixture was cooled to room temperature and then filtered through Celite® washing with ethyl acetate. The filtrate was washed with water and brine, dried over magnesium sulfate and concentrated under reduced pressure. The resultant residue was purified by silica gel flash chromatography (0-35% ethyl acetate in cyclohexane) to afford the title compound as a yellow solid (137 mg, 74% yield). LCMS (Method C): RT=2.30 min, m/z: 348 [M–C$_4$H$_7$$^+$].

Step 3

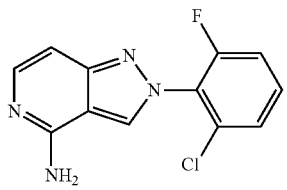

2-(2-Chloro-6-fluorophenyl)-2H-pyrazolo[4,3-c]pyridin-4-ylamine

To a solution of [2-(2-chloro-6-fluorophenyl)-2H-pyrazolo[4,3-c]pyridin-4-yl]-carbamic acid tert-butyl ester (137 mg) in DCM (1 mL)) at 0° C. was added TFA (1 mL). The reaction mixture was stirred at room temperature for 1 hour then concentrated under reduced pressure. The resultant residue was partitioned between ethyl acetate and sodium bicarbonate (sat. aq.). The organic layer was dried over anhydrous magnesium sulfate, filtered and concentrated to give a colourless oil. Trituration with diethyl ether gave the title compound as a white solid (100 mg, 91% yield). LCMS (Method C): RT=0.34 min and 1.79 min, m/z: 263 [M+H$^+$].

Step 4

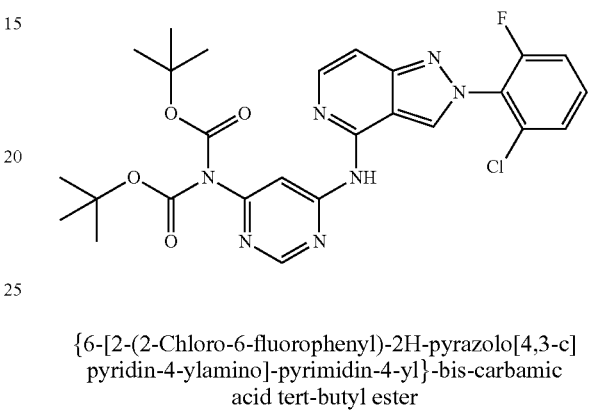

{6-[2-(2-Chloro-6-fluorophenyl)-2H-pyrazolo[4,3-c]pyridin-4-ylamino]-pyrimidin-4-yl}-bis-carbamic acid tert-butyl ester A suspension of 2-(2-chloro-6-fluorophenyl)-2H-pyrazolo[4,3-c]pyridin-4-ylamine (100 mg, 0.38 mmol), 6-chloro-pyrimidin-4-yl)-bis-carbamic acid tert-butyl ester (153 mg, 0.46 mmol), Pd$_2$(dba)$_3$ (8 mg, 0.009 mmol), Xantphos (22 mg, 0.04 mmol) and cesium carbonate (248 mg, 0.76 mmol) in dioxane (2.5 mL) was sealed in a microwave reaction vial, purged with nitrogen and irradiated at 150° C. for 30 minutes in the microwave. The reaction mixture was cooled and partitioned between ethyl acetate and water. The organic layer was washed with brine, dried over anhydrous magnesium sulfate, and concentrated under reduced pressure. The residue was purified by silica gel flash chromatography (40% ethyl acetate in cyclohexane) to afford the title compound as a pale beige solid (65 mg, 31% yield). LCMS (Method C): RT=2.93 min, m/z: 556 [M+H$^+$].

Step 5

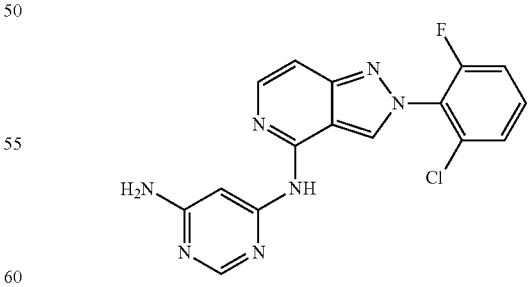

N-[2-(2-Chloro-6-fluorophenyl)-2H-pyrazolo[4,3-c]pyridin-4-yl]-pyrimidine-4,6-diamine.HCl A suspension of {6-[2-(2-Chloro-6-fluoro-phenyl)-2H-pyrazolo[4,3-c]pyridin-4-ylamino]-pyrimidin-4-yl}-bis-carbamic acid tert-butyl ester (65 mg, 0.12 mmol) in HCl (1.25 N in IPA, 1.5 ml) was sealed in a reaction vial, purged with nitrogen and stirred at 50° C. for 18 h. The reaction mixture was cooled, diluted with IPA and the resultant solid was filtered. The white solid was further washed with IPA and dried to afford the title compound as an off-white solid (35 mg, 84% yield). $^1$H NMR (400 MHz, DMSO-d$_6$+TFA-d): δ 9.68 (s, 1H), 8.50 (s, 1H), 7.91 (d, J=7.2 Hz, 1H), 7.75-7.70 (m, 1H), 7.65-7.56 (m, 2H), 7.44 (d, J=7.2 Hz, 1H) 6.71 (s, 1H). LCMS (Method B): RT=2.71 min, m/z: 355 [M+H$^+$].

Method 2

Example 18

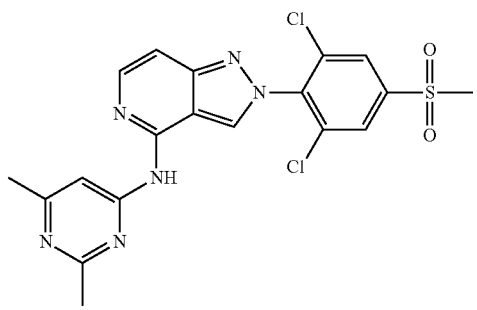

[2-(2,6-Dichloro-4-methanesulfonylphenyl)-2H-pyrazolo[4,3-c]pyridin-4-yl]-(2,6-dimethylpyrimidin-4-yl)amine Step 1

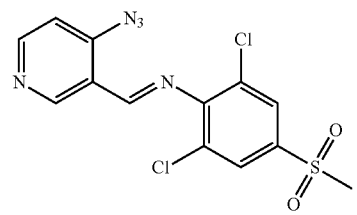 [SMILES: CS(=O)(=O)c1cc(Cl)c(/N=C/c2cnccc2N=[N+]=[N-])c(Cl)c1]

[1-(4-Azidopyridin-3-yl)meth-(E)-ylidene]-(2,6-dichloro-4-methanesulfonylphenyl)amine Triethylamine (1.7 mL, 12.6 mmol) was added to a cooled (0° C.) mixture of 4-azidopyridine-3-carbaldehyde (621 mg, 4.2 mmol) and 2,6-dichloro-4-(methylsulfonyl)aniline (1 g, 4.2 mmol) in DCM (15 mL) under nitrogen. Titanium tetrachloride (1 M, 2.5 mL, 2.5 mmol) was then added and the resulting mixture was stirred for 1 hour, warmed to room temperature, and stirred for an additional 4 hours. The reaction mixture was concentrated to dryness under reduced pressure. The residue was suspended in toluene and filtered though a pad of Celite®. The filtrate was concentrated to dryness under reduced pressure to afford the title compound as a yellow solid. This crude material was employed in the next step without further purification or analysis.

Step 2

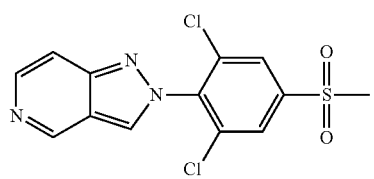 [SMILES: CS(=O)(=O)c1cc(Cl)c(-n2cc3cnccc3n2)c(Cl)c1]

2-(2,6-Dichloro-4-methanesulfonylphenyl)-2H-pyrazolo[4,3-c]pyridine

A mixture of [1-(4-azidopyridin-3-yl)meth-(E)-ylidene]-(2,6-dichloro-4-methanesulfonylphenyl)amine (4.21 mmol) in toluene (15 mL) was heated to 105° C. for 18 hours. The reaction mixture was allowed to cool and then concentrated under reduced pressure. The residue was recrystallised from ethyl acetate and the solid was collected by filtration to afford the title compound as a beige solid (0.75 g, 52% yield). $^1$H NMR (300 MHz, DMSO-d$_6$): δ 9.38 (d, J=1.4 Hz, 1H) 9.15 (d, J=1.0 Hz, 1H), 8.34 (s, 2H) 8.31 (d, J=6.4 Hz, 1H) 7.68 (dt, J=6.4, 1.2 Hz, 1H) 3.49 (s, 3H). LCMS (Method D): RT=1.72 min, m/z: 342 [M+H$^+$].

Step 3

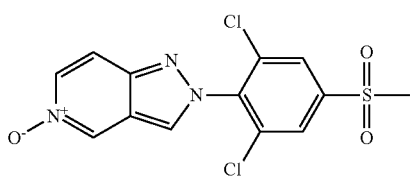 [SMILES: CS(=O)(=O)c1cc(Cl)c(-n2cc3c[n+]([O-])ccc3n2)c(Cl)c1]

2-(2,6-Dichloro-4-methanesulfonylphenyl)-2H-pyrazolo[4,3-c]pyridine-5-oxide mCPBA (569 mg, 3.3 mmol) was added to a cooled (0° C.) solution of 2-(2,6-dichloro-4-methanesulfonylphenyl)-2H-pyrazolo[4,3-c]pyridine (752 mg, 2.2 mmol) in DCM (20 mL) under nitrogen. The reaction was stirred for 1 hour, warmed to room temperature, and stirred for an additional 2 hours. Further mCPBA (150 mg) was added and the reaction mixture was stirred at room temperature for 4 hours before adding sodium thiosulfate (aq.). The organic layer was separated, washed with sodium hydrogen carbonate (sat. aq.) and brine, dried over anhydrous magnesium sulfate, and concentrated under reduced pressure. The residue was purified by silica gel flash chromatography (5-10% methanol in DCM) to afford the title compound as a white solid (640 mg, 81% yield). $^1$H NMR (300 MHz, DMSO-d$_6$): δ 8.94 (dd, J=1.8, 0.9 Hz, 1H), 8.88 (d, J=1.0 Hz, 1H), 8.33 (s, 2H), 7.96 (dd, J=7.5, 1.8 Hz, 1H), 7.86 (dt, J=7.5, 1.0 Hz, 1H), 3.48 (s, 3H). LCMS (Method D): RT=2.13 min, m/z: 358 [M+H$^+$].

Step 4

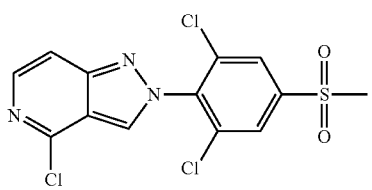 [SMILES: CS(=O)(=O)c1cc(Cl)c(-n2cc3c(Cl)nccc3n2)c(Cl)c1]

4-Chloro-2-(2,6-dichloro-4-methanesulfonylphenyl)-2H-pyrazolo[4,3-c]pyridine

2-(2,6-Dichloro-4-methanesulfonylphenyl)-2H-pyrazolo[4,3-c]pyridine-5-oxide (640 mg, 1.79 mmol) was added to a solution of tetrabutylammonium chloride (497 mg, 1.79 mmol) in phosphorous oxychloride (5 mL) and the reaction mixture was heated at 85° C. for 4 hours. The reaction mixture was cooled and partitioned between ethyl acetate and sodium hydrogen carbonate (sat. aq.). The organic phase was washed with sodium hydrogen carbonate (sat. aq.) and brine, dried over anhydrous sodium sulfate, and concentrated to dryness under reduced pressure. The residue was purified by silica gel flash chromatography (40% ethyl acetate in cyclohexane) to afford the title compound as a white solid (238 mg, 35% yield). $^1$H NMR (300 MHz, DMSO-$d_6$): δ 9.35 (d, J=1.0 Hz, 1H), 8.36 (s, 2H), 8.14 (d, J=6.3 Hz, 1H), 7.76 (dd, J=6.3, 1.0 Hz, 1H), 3.49 (s, 3H). LCMS (Method D): RT=3.19 min, m/z: 376 [M+H$^+$].

Step 5

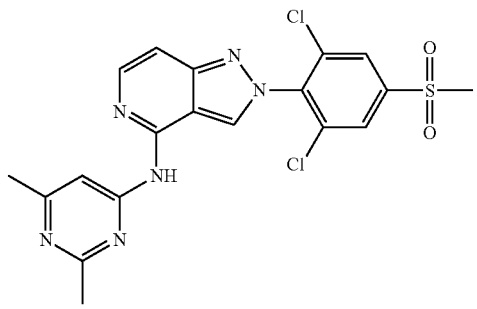

[2-(2,6-Dichloro-4-methanesulfonylphenyl)-2H-pyrazolo[4,3-c]pyridin-4-yl]-(2,6-dimethylpyrimidin-4-yl)amine

A suspension of 4-chloro-2-(2,6-dichloro-4-methanesulfonylphenyl)-2H-pyrazolo[4,3-c]pyridine (75 mg, 0.20 mmol), 4-amino-2,6-dimethylpyrimidine (27 mg, 0.22 mmol), Pd$_2$(dba)$_3$ (5 mg, 0.005 mmol), Xantphos (12 mg, 0.02 mmol) and cesium carbonate (130 mg, 0.40 mmol) in dioxane (2 mL) was sealed in a microwave vial, purged with nitrogen, and irradiated at 150° C. for 30 minutes in the microwave. The reaction mixture was cooled and partitioned between ethyl acetate and water. The organic layer was washed with brine, dried over anhydrous sodium sulfate, and concentrated under reduced pressure. The residue was purified by silica gel flash chromatography (0-1% methanol in ethyl acetate) to afford the title compound as a yellow solid (55 mg, 59% yield). $^1$H NMR (400 MHz, DMSO-$d_6$): δ 10.60 (br s, 1H), 9.21 (s, 1H), 8.32 (s, 2H), 8.30 (s, 1H), 7.99 (d, J=6.4 Hz, 1H), 7.21 (d, J=6.4 Hz, 1H), 3.48 (s, 3H), 2.49 (s, 3H), 2.40 (s, 3H). LCMS (Method B): RT=2.80 min, m/z: 463 [M+H$^+$].

Method 2

Example 19

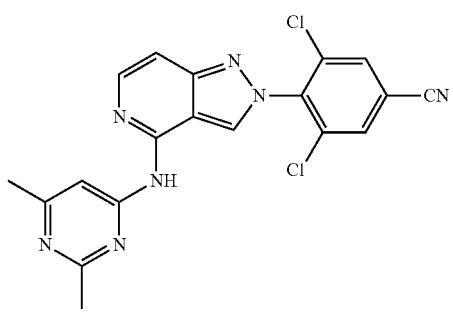 [SMILES: Cc1cc(Nc2nccc3nn(-c4c(Cl)cc(C#N)cc4Cl)cc23)nc(C)n1]

3,5-Dichloro-4-[4-(2,6-dimethylpyrimidin-4-ylamino)pyrazolo[4,3-c]pyridin-2-yl]benzonitrile

Step 1

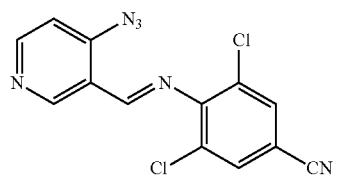 [SMILES: N#Cc1cc(Cl)c(/N=C/c2cnccc2N=[N+]=[N-])c(Cl)c1]

4-{[1-(4-Azidopyridin-3-yl)meth-(E)-ylidene]amino}-3,5-dichlorobenzonitrile

Triethylamine (8.9 mL, 64.2 mmol) was added to a cooled (0° C.) mixture of 4-azidopyridine-3-carbaldehyde (3.2 g, 21.4 mmol) and 4-amino-3,5-dichlorobenzonitrile (4.0 g, 21.4 mmol) in DCM (80 mL) under nitrogen. Titanium tetrachloride (1M, 12.8 mL, 12.8 mmol) was added and then the reaction mixture was stirred for 1 hour at 0° C. After warming to room temperature, the reaction was stirred for an additional 2 h and then concentrated under reduced pressure. The residue was suspended in toluene and filtered though a pad of Celite®. The filtrate was concentrated to dryness under reduced pressure to afford the title compound as an orange solid. This crude material was employed in the next step without further purification or analysis.

Step 2

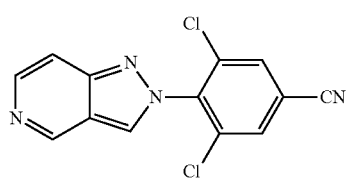 [SMILES: N#Cc1cc(Cl)c(-n2cc3cnccc3n2)c(Cl)c1]

3,5-Dichloro-4-pyrazolo[4,3-c]pyridine-2-ylbenzonitrile

A mixture of 4-{[1-(4-azidopyridin-3-yl)meth-(E)-ylidene]amino}-3,5-dichlorobenzonitrile (21.4 mmol) in toluene (80 mL) was heated to 105° C. for 1 hour. The reaction mixture was cooled and concentrated under reduced pressure. The resultant residue was purified by silica gel flash chromatography (0-100% ethyl acetate in cyclohexane) to afford the title compound as a yellow solid (4.10 g, 66% yield). $^1$H NMR (300 MHz, CDCl$_3$): δ 9.36 (d, J=1.4 Hz, 1H), 8.39 (d, J=6.5 Hz, 1H), 8.35 (d, J=1.0 Hz, 1H), 7.85 (s, 2H), 7.68-7.66 (m, 1H). LCMS (Method D): RT=1.66 min, m/z: 289 [M+H$^+$].

Step 3

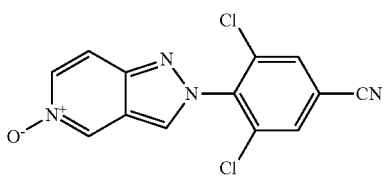 [SMILES: N#Cc1cc(Cl)c(-n2cc3c[n+]([O-])ccc3n2)c(Cl)c1]

3,5-Dichloro-4-(5-oxypyrazolo[4,3-c]pyridine-2-yl)benzonitrile

Aqueous hydrogen peroxide (30% aq., 0.4 mL, 4.15 mmol) was added to a solution of 3,5-dichloro-4-pyrazolo[4,3-c]pyridine-2-ylbenzonitrile (600 mg, 2.08 mmol) and methyltrioxorhenium (2.6 mg, 0.01 mmol) in DCM (1.0 mL). The reaction mixture was stirred at room temperature for 2 hours and then concentrated to dryness under reduced pressure to afford the title compound as a yellow solid (633 mg, quant. yield). $^1$H NMR (300 MHz, CDCl$_3$): δ 9.12-9.02 (m, 1H), 8.32 (s, 1H), 8.08 (d, J=7.5 Hz, 1H), 7.87 (s, 2H), 7.80-7.74 (m, 1H). LCMS (Method D): RT=2.26 min, m/z: 305 [M+H$^+$].

Step 4

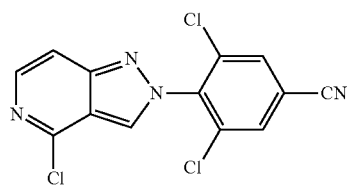 [SMILES: N#Cc1cc(Cl)c(-n2cc3c(Cl)nccc3n2)c(Cl)c1]

3,5-Dichloro-4-(4-chloropyrazolo[4,3-c]pyridin-2-yl)benzonitrile

A solution of 3,5-dichloro-4-(5-oxypyrazolo[4,3-c]pyridine-2-yl)benzonitrile (305 mg, 1.0 mmol) and phosphorous oxychloride (3.0 mL) was heated at 85° C. for 1 hour. The reaction mixture was allowed to cool and then partitioned between ethyl acetate and sodium hydrogen carbonate (sat. aq.). The organic layer was washed with sodium hydrogen carbonate (sat. aq.) and brine, dried over anhydrous sodium sulfate, and concentrated under reduced pressure. The resultant residue was purified by silica gel flash chromatography (0-30% ethyl acetate in cyclohexane) to afford the title compound as a white solid (137 mg, 42% yield). $^1$H NMR (300 MHz, CDCl$_3$): δ 8.32 (d, J=1.0 Hz, 1H), 8.15 (d, J=6.3 Hz, 1H), 7.86 (s, 2H), 7.58 (dd, J=6.3, 1.0 Hz, 1H). LCMS (Method C): RT=3.35, m/z: 323 [M+H$^+$].

Step 5

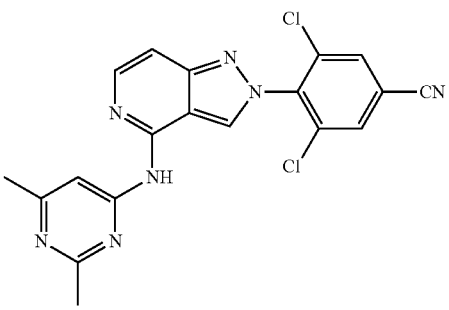

3,5-Dichloro-4-[4-(2,6-dimethylpyrimidin-4-ylamino)pyrazolo[4,3-c]pyridin-2-yl]benzonitrile A suspension of 3,5-dichloro-4-(4-chloropyrazolo[4,3-c]pyridin-2-yl)benzonitrile (65 mg, 0.20 mmol), 4-amino-2,6-dimethylpyrimidine (27 mg, 0.22 mmol), Pd$_2$(dba)$_3$ (5 mg, 0.005 mmol), Xantphos (12 mg, 0.02 mmol) and cesium carbonate (91 mg, 0.28 mmol) in dioxane (2 mL) was sealed in a reaction vial, purged with nitrogen, and heated at 90° C. for 18 hours. The reaction mixture was cooled, filtered, and concentrated under reduced pressure. The residue was purified by silica gel flash chromatography (30-100% ethyl acetate in cyclohexane), then by HPLC (gradient: 25 to 98% acetonitrile in water with 0.1% ammonium hydroxide), to afford the title compound as a white solid (22 mg, 27% yield). $^1$H NMR (400 MHz, DMSO-d$_6$): δ 9.41 (d, J=0.9 Hz, 1H), 8.51 (s, 2H), 8.08 (d, J=6.9 Hz, 1H), 7.67 (s, 1H), 7.54 (dd, J=6.9, 1.0 Hz, 1H), 2.73 (s, 3H), 2.58 (s, 3H). LCMS (Method B): RT=3.00 min, m/z: 410.15 [M+H$^+$].

Method 2

Example 20

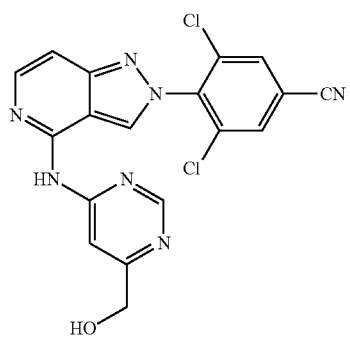 [SMILES: N#Cc1cc(Cl)c(-n2cc3c(Nc4cc(CO)ncn4)nccc3n2)c(Cl)c1]

3,5-Dichloro-4-[4-(6-hydroxymethyl-pyrimidin-4-ylamino)-pyrazolo[4,3-c]pyridin-2-yl]-benzonitrile Following the procedure described for 3,5-dichloro-4-[4-(2,6-dimethylpyrimidin-4-ylamino)pyrazolo[4,3-c]pyridin-2-yl]benzonitrile, (6-amino-pyrimidin-4-yl)-methanol and 3,5-dichloro-4-(4-chloropyrazolo[4,3-c]pyridin-2-yl)benzonitrile were reacted to afford the title compound as a pale yellow solid (70 mg, 37% yield). $^1$H NMR (400 MHz, DMSO-d$_6$): δ 10.76 (s, 1H), 9.22 (s, 1H), 8.70 (s, 2H), 8.49 (s, 2H), 8.00 (d, J=6.4 Hz, 1H), 7.25-7.22 (m, 1H), 5.61 (t, J=5.7 Hz, 1H), 4.53 (d, J=5.8 Hz, 2H). LCMS (Method D): RT=2.05 min, m/z: 412 [M+H$^+$].

Method 2

Example 21

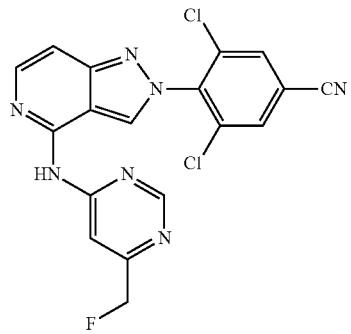 [SMILES: N#Cc1cc(Cl)c(-n2cc3c(Nc4cc(CF)ncn4)nccc3n2)c(Cl)c1]

3,5-Dichloro-4-[4-(6-fluoromethyl-pyrimidin-4-ylamino)-pyrazolo[4,3-c]pyridin-2-yl]-benzonitrile To a suspension of 3,5-dichloro-4-[4-(6-hydroxymethyl-pyrimidin-4-ylamino)-pyrazolo[4,3-c]pyridin-2-yl]-benzonitrile (70 mg, 0.17 mmol) in DCM (5 mL) at −25° C. was added DAST (34 μL, 0.25 mmol). The reaction mixture was warmed to room temperature over 1 hour. The reaction mixture was partitioned between DCM and sodium bicarbonate (sat. aq.). The organic layer was dried over anhydrous sodium sulfate and concentrated under reduced pressure. The residue was purified by silica gel chromatography (0-100% ethyl acetate in cyclohexane) then by HPLC (5 to 98% acetonitrile in water with 0.1% ammonium hydroxide) to afford the title compound as a white solid (10 mg, 14% yield). $^1$H NMR (400 MHz, DMSO-d$_6$): δ 10.96 (s, 1H), 9.23 (s, 1H), 8.81 (s, 1H), 8.69 (s, 1H), 8.49 (s, 2H), 8.02 (d, J=6.4 Hz, 1H), 7.27 (d, J=6.4 Hz, 1H), 5.50 (d, J=46.3 Hz, 2H). LCMS (Method B): RT=2.96 min, m/z: 414 [M+H$^+$].

Method 2

Example 22

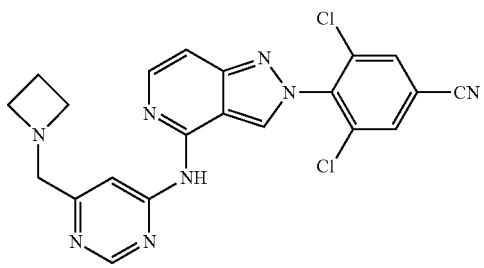 [SMILES: N#Cc1cc(Cl)c(-n2cc3c(Nc4cc(CN5CCC5)ncn4)nccc3n2)c(Cl)c1]

4-[4-(6-Azetidin-1-ylmethylpyrimidin-4-ylamino)pyrazolo[4,3-c]pyridin-2-yl]-3,5-dichlorobenzonitrile Step 1

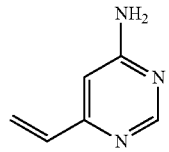

6-Vinylpyrimidin-4-ylamine

A mixture of 4-amino-6-chloropyrimidine (2.5 g, 19.2 mmol), 1,1'-bis(diphenylphosphino)ferrocene palladium dichloride (810 mg, 1.2 mmol), sodium carbonate (8.14 g, 76.8 mmol) and vinyl borane pinacol ester (3.9 mL, 23 mmol) in dioxane (11.5 mL) and water (11.5 mL) under nitrogen, was heated at 100° C. for 20 hours then cooled to ambient temperature. The reaction mixture was partitioned between ethyl acetate and water. The organic layer was dried over anhydrous sodium sulfate and concentrated under reduced pressure. The residue was purified by silica gel flash chromatography (0-10% methanol in DCM) to afford the title compound as a yellow solid (1.87 g, 80% yield). $^1$H NMR (300 MHz, DMSO-d$_6$): δ 8.30 (s, 1H), 6.83 (s, 2H), 6.57 (dd, J=17.2, 10.5 Hz, 1H), 6.36 (s, 1H), 6.26 (dd, J=17.2, 2.1 Hz, 1H), 5.48 (dd, J=10.5, 2.1 Hz, 1H).

Step 2

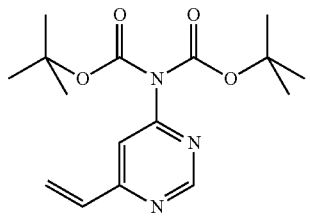 [SMILES: C=Cc1cc(N(C(=O)OC(C)(C)C)C(=O)OC(C)(C)C)ncn1]

(6-Vinylpyrimidin-4-yl)bis-carbamic acid tert-butyl ester

Sodium hexamethyldisilazane (1M in THF, 24.7 mL, 24.7 mmol) was added to a solution of 6-vinylpyrimidin-4-ylamine (1.87 g, 15.5 mmol) in THF (26 mL) under nitrogen, over 10 minutes. Di-tert-butyl-dicarbonate (5.05 g, 23.2 mmol) in THF (10 mL) was added and the reaction mixture was stirred at ambient temperature for 2.5 hours. The mixture was partitioned between ethyl acetate and water. The organic layer was washed with brine, dried over anhydrous sodium sulfate, and concentrated to dryness under reduced pressure. The resultant residue was purified by silica gel flash chromatography (0-50% ethyl acetate in DCM) to afford the title compound (1.57 g, 46% yield). $^1$H NMR (300 MHz, CDCl$_3$): δ 8.84 (d, J=1.2 Hz, 1H), 7.62 (d, J=1.3 Hz, 1H), 6.71 (dd, J=17.3, 10.6 Hz, 1H), 6.46 (dd, J=17.3, 1.3 Hz, 1H), 5.66 (dd, J=10.6, 1.3 Hz, 1H), 1.53 (s, 18H).

Step 3

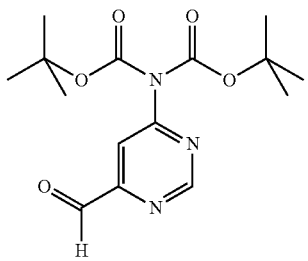 [SMILES: CC(C)(C)OC(=O)N(C(=O)OC(C)(C)C)c1cc(C=O)ncn1]

(6-Formylpyrimidin-4-yl)bis-carbamic acid tert-butyl ester

Ozone was bubbled through a solution of (6-vinylpyrimidin-4-yl)bis-carbamic acid tert-butyl ester (1.53 g, 4.8 mmol) in DCM (40 mL) and methanol (10 mL) at −78° C. for 1 hour, before purging the reaction mixture with air and nitrogen. Triphenylphosphine (1.25 g, 4.8 mmol) was added and the reaction was stirred at room temperature for 18 hours. The mixture was concentrated under reduced pressure and the residue was purified by silica gel flash chromatography (0-50% ethyl acetate in cyclohexane) to afford the title compound as a yellow solid (965 mg, 58% yield). $^1$H NMR (300 MHz, CDCl$_3$): δ 10.03 (s, 1H), 9.09 (d, J=1.3 Hz, 1H), 8.24 (d, J=1.3 Hz, 1H), 1.57 (s, 18H).

Step 4

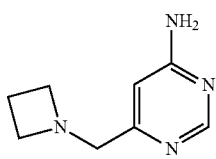 [SMILES: Nc1cc(CN2CCC2)ncn1]

6-Azetidin-1-ylmethylpyrimidin-4-ylamine

A solution of (6-formylpyrimidin-4-yl)bis-carbamic acid tert-butyl ester (200 mg, 0.62 mmol) and azetidine (33 mg, 0.68 mmol) in DCE (5 mL) was stirred at room temperature for 1.5 hours. Sodium triacetoxyborohydride (198 mg, 0.43 mmol) was added and the reaction mixture was stirred at room temperature for 18 hours. TFA (5 mL) was added, the reaction was stirred for a further 1 hour, and then the mixture was concentrated under reduced pressure. The residue was purified by SCX-2 chromatography (washing with methanol and eluting with 2M ammonia in methanol) to afford the title compound as a yellow solid (89 mg, 88% yield). $^1$H NMR (300 MHz, CDCl$_3$): δ 8.50 (s, 1H), 6.53 (s, 1H), 4.86 (br s, 2H), 3.60 (s, 2H), 3.37 (t, J=7.1 Hz, 4H), 2.17 (t, J=7.1 Hz, 2H).

Step 5

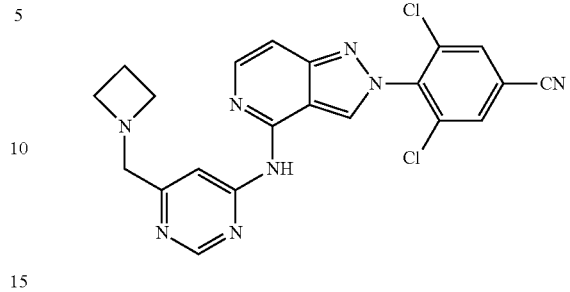

4-[4-(6-Azetidin-1-ylmethylpyrimidin-4-ylamino)pyrazolo[4,3-c]pyridin-2-yl]-3,5-dichlorobenzonitrile Following the procedure described for 3,5-dichloro-4-[4-(2,6-dimethylpyrimidin-4-ylamino)pyrazolo[4,3-c]pyridin-2-yl]benzonitrile, 3,5-dichloro-4-(4-chloropyrazolo[4,3-c]pyridin-2-yl)benzonitrile and 6-azetidin-1-ylmethylpyrimidin-4-ylamine were reacted to afford the title compound as a yellow solid (14 mg, 17% yield). $^1$H NMR (400 MHz, DMSO-d$_6$): δ 9.66 (d, J=0.9 Hz, 1H), 9.16 (d, J=1.2 Hz, 1H), 8.54 (s, 2H), 8.11 (d, J=7.3 Hz, 1H), 7.70 (dd, J=7.3, 0.9 Hz, 1H), 7.50 (s, 1H), 4.80 (s, 2H), 4.29 (m, 2H), 4.20 (m, 2H), 2.55-2.52 (m, 1H), 2.41 (m, 1H). LCMS (Method B): RT=2.29 min, m/z: 451 [M+H$^+$].

Method 2

Example 23

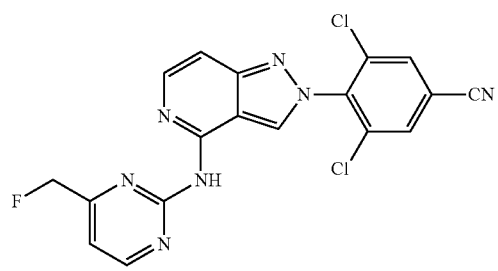 [SMILES: N#Cc1cc(Cl)c(-n2cc3c(Nc4nccc(CF)n4)nccc3n2)c(Cl)c1]

3,5-Dichloro-4-[4-(4-fluoromethylpyrimidin-2-ylamino)pyrazolo[4,3-c]pyridin-2-yl]benzonitrile Step 1

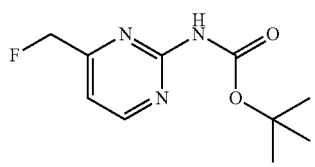 [SMILES: CC(C)(C)OC(=O)Nc1nccc(CF)n1]

(4-Fluoromethylpyrimidin-2-yl)carbamic acid tert-butyl ester

A solution of (4-hydroxymethylpyrimidin-2-yl)carbamic acid tert-butyl ester (450 mg, 2.0 mmol) in DCM (10 mL) at 0° C. was treated with DAST (396 µL, 3.0 mmol) and stirred for 10 minutes. The reaction mixture was partitioned between DCM and sodium bicarbonate (sat. aq.). The organic layer was dried over anhydrous sodium sulfate and concentrated under reduced pressure. The residue was purified by silica gel chromatography (50% ethyl acetate in cyclohexane) to afford the title compound as a white solid (144 mg, 32% yield). $^1$H NMR (300 MHz, CDCl$_3$): δ 8.64 (d, J=5.1 Hz, 1H), 7.53 (s, 1H), 7.15-7.12 (m, 1H), 5.45-5.44 (m, 1H), 5.33-5.32 (m, 1H), 1.54 (s, 9H).

Step 2

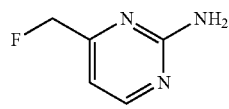

4-Fluoromethylpyrimidin-2-ylamine

A mixture of (4-fluoromethylpyrimidin-2-yl)carbamic acid tert-butyl ester (140 mg, 0.62 mmol) and TFA (2 mL) in DCM (2 mL) was stirred at room temperature for 1 hour then concentrated under reduced pressure. The residue was purified by SCX-2 chromatography (washing with methanol and eluting with 2M ammonia in methanol) to afford the title compound as a yellow solid (78 mg, quant. yield). $^1$H NMR (400 MHz, CDCl$_3$): δ 8.34 (d, J=5.1 Hz, 1H), 6.79-6.78 (m, 1H), 5.33-5.30 (m, 1H), 5.21-5.19 (m, 1H), 5.13 (s, 2H).

Step 3

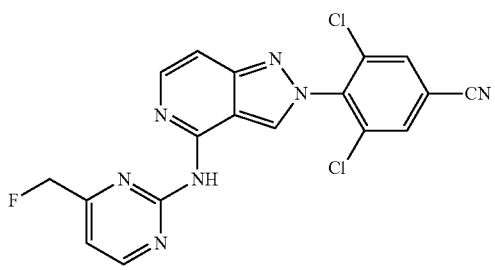 [SMILES: N#Cc1cc(Cl)c(-n2cc3c(Nc4nccc(CF)n4)nccc3n2)c(Cl)c1]

3,5-Dichloro-4-[4-(4-fluoromethylpyrimidin-2-ylamino)pyrazolo[4,3-c]pyridin-2-yl]benzonitrile Following the procedure described for 3,5-dichloro-4-[4-(2,6-dimethylpyrimidin-4-ylamino)pyrazolo[4,3-c]pyridin-2-yl]benzonitrile, 3,5-dichloro-4-(4-chloropyrazolo[4,3-c]pyridin-2-yl)benzonitrile and 4-fluoromethylpyrimidin-2-ylamine were reacted to afford the title compound as a yellow solid (6 mg, 5% yield). $^1$H NMR (400 MHz, DMSO-d$_6$): δ 9.74-9.73 (m, 1H), 8.98 (d, J=5.2 Hz, 1H), 8.53 (s, 2H), 8.07 (s, 1H), 8.05 (s, 1H), 7.62 (dd, J=7.3, 0.9 Hz, 1H), 7.55-7.52 (m, 1H), 5.78-5.75 (m, 1H), 5.66-5.63 (m, 1H). LCMS (Method B): RT=3.04 min, m/z: 414 [M+H$^+$].

Method 4

Example 24

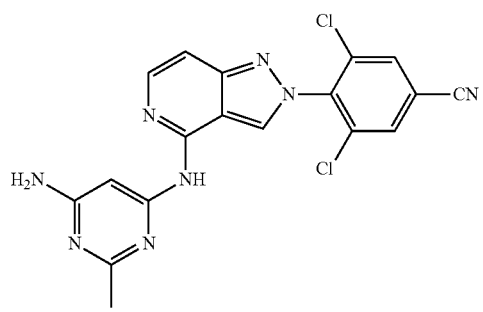 [SMILES: Cc1nc(N)cc(Nc2nccc3nn(-c4c(Cl)cc(C#N)cc4Cl)cc23)n1]

4-[4-(6-Amino-2-methylpyrimidin-4-ylamino)pyrazolo[4,3-c]pyridin-2-yl]-3,5-dichlorobenzonitrile Step 1

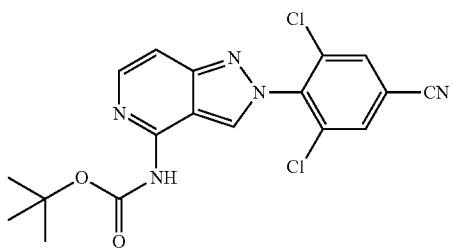 [SMILES: CC(C)(C)OC(=O)Nc1nccc2nn(-c3c(Cl)cc(C#N)cc3Cl)cc12]

[2-(2,6-Dichloro-4-cyanophenyl)-2H-pyrazolo[4,3-c]pyridin-4-yl]carbamic acid tert-butyl ester A mixture of 3,5-dichloro-4-(4-chloro-pyrazolo[4,3-c]pyridin-2-yl)-benzonitrile (3.23 g, 10 mmol), tert-butyl carbamate (5.85 mg, 50 mmol), Pd$_2$(dba)$_3$ (458 mg, 0.5 mmol), Xantphos (576 mg, 1.0 mmol) and potassium phosphate tribasic (4.24 g, 20 mmol) in toluene (100 mL) and water (20 mL) was degassed with argon then heated at 90° C. for 30 minutes. The reaction was cooled to room temperature and then filtered through Celite® using ethyl acetate to wash the filter pad. The filtrate was washed with water and sodium bicarbonate (sat. aq.), dried over sodium sulfate and concentrated under reduced pressure. The resultant residue was purified by silica gel flash chromatography (0-50% ethyl acetate in cyclohexane) to afford the title compound as an off-white solid (5.0 g, contaminated with residual tert-butyl carbamate). LCMS (Method D): RT=2.44 min, m/z: 348 [M−C$_4$H$_7^+$].

Step 2

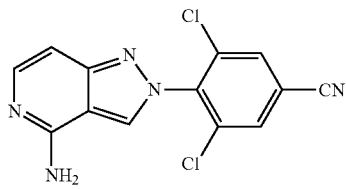 [SMILES: N#Cc1cc(Cl)c(-n2cc3c(N)nccc3n2)c(Cl)c1]

4-(4-Aminopyrazolo[4,3-c]pyridin-2-yl)-3,5-dichlorobenzonitrile

A mixture of [2-(2,6-dichloro-4-cyano-phenyl)-2H-pyrazolo[4,3-c]pyridin-4-yl]carbamic acid tert-butyl ester (5.0 g, contaminated with residual tert-butyl carbamate) and HCl (4 N in dioxane, 40 mL, 160 mmol) was stirred at 50° C. for 6 h then concentrated to dryness under reduced pressure. The resultant residue was partitioned between ethyl acetate and sodium bicarbonate (sat. aq.). The organic layer was separated, washed with brine, dried over anhydrous sodium sulfate, filtered and concentrated to dryness under reduced pressure to afford the title compound as a yellow solid (1.17 g, 39% yield over 2 steps). $^1$H NMR (400 MHz, CDCl$_3$): δ 8.95 (s, 1H), 8.48 (s, 2H), 7.58 (d, J=6.9 Hz, 1H), 7.27-7.22 (m, 1H), 7.19-7.14 (m, 1H), 6.91-6.88 (m, 1H). LCMS (Method D): RT=1.95 min, m/z: 304 [M+H$^+$].

Step 3

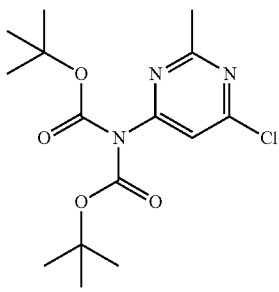 [SMILES: Cc1nc(Cl)cc(N(C(=O)OC(C)(C)C)C(=O)OC(C)(C)C)n1]

(6-Chloro-2-methylpyrimidin-4-yl)bis-carbamic acid tert-butyl ester

Lithium hexamethyldisilazane (1M in THF, 1.85 mL, 1.85 mmol) was added to a cooled (0° C.) solution of 6-chloro-2-methylpyrimidin-4-ylamine (106 mg, 0.74 mmol) in THF (5 mL). The mixture was stirred for 15 minutes and then di-tert-butyl dicarbonate (354 mg, 1.62 mmol) was added. The reaction was warmed to room temperature and stirred for 18 hours. The mixture was partitioned between ethyl acetate and sodium bicarbonate (sat. aq.). The organic layer was washed with brine, dried over anhydrous sodium sulfate, and concentrated under reduced pressure. The residue was purified by silica gel flash chromatography (0-20% ethyl acetate in pentane) to afford the title compound as a colourless oil (quant. yield). $^1$H NMR (300 MHz, CDCl$_3$): δ 7.66 (d, J=0.6 Hz, 1H), 2.58 (d, J=0.6 Hz, 3H), 1.56 (s, 9H), 1.53 (s, 9H).

Step 4

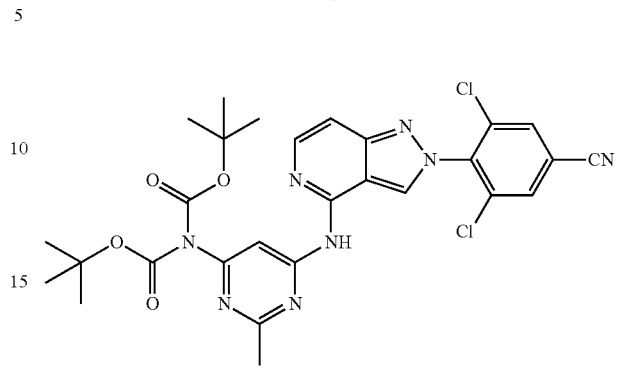

{6-[2-(2,6-Dichloro-4-cyanophenyl)-2H-pyrazolo[4,3-c]pyridin-4-ylamino]-2-methylpyrimidin-4-yl}bis-carbamic acid tert-butyl ester Following the procedure described for 3,5-dichloro-4-[4-(2,6-dimethylpyrimidin-4-ylamino)pyrazolo[4,3-c]pyridin-2-yl]benzonitrile, 4-(4-aminopyrazolo[4,3-c]pyridin-2-yl)-3,5-dichlorobenzonitrile and (6-chloro-2-methylpyrimidin-4-yl)bis-carbamic acid tert-butyl ester were reacted to afford the title compound as a yellow solid (47 mg, 23% yield). LCMS (Method D): RT=3.12 min, m/z: 611 [M+H$^+$].

Step 5

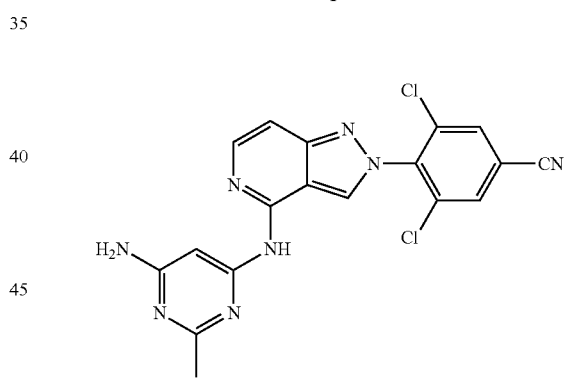

4-[4-(6-Amino-2-methylpyrimidin-4-ylamino)pyrazolo[4,3-c]pyridin-2-yl]-3,5-dichlorobenzonitrile A mixture of {6-[2-(2,6-dichloro-4-cyanophenyl)-2H-pyrazolo[4,3-c]pyridin-4-ylamino]-2-methylpyrimidin-4-yl}bis-carbamic acid tert-butyl ester (47 mg, 0.08 mmol) and TFA (2 mL) in DCM (2 mL) was stirred at room temperature for 2 hours and then concentrated under reduced pressure. The residue was partitioned between ethyl acetate and sodium bicarbonate (sat. aq.). The organic layer was washed with brine, dried over anhydrous sodium sulfate, and concentrated under reduced pressure. The residue was purified by silica gel flash chromatography (0-10% methanol in DCM) to afford the title compound as a yellow solid (18 mg, 56% yield). $^1$H NMR (400 MHz, CDCl$_3$): δ 10.01 (s, 1H), 9.21 (s, 1H), 8.48 (s, 2H), 7.91 (d, J=6.4 Hz, 1H), 7.54 (s, 1H), 7.14-7.10 (m, 1H), 6.59 (s, 2H), 2.27 (s, 3H). LCMS (Method B): RT=2.98 min, m/z: 411 [M+H⁺].

Method 4

Example 25

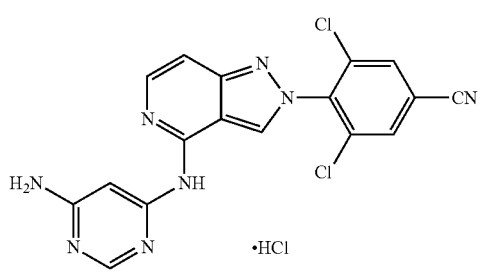 [SMILES: N#Cc1cc(Cl)c(-n2cc3c(Nc4cc(N)ncn4)nccc3n2)c(Cl)c1 ; Cl]

4-[4-(6-Aminopyrimidin-4-ylamino)-pyrazolo[4,3-c]pyridin-2-yl]-3,5-dichloro-benzonitrile.HCl Step 1

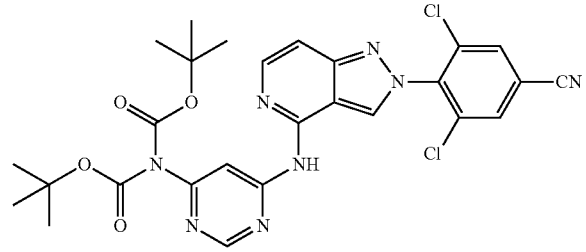 [SMILES: CC(C)(C)OC(=O)N(C(=O)OC(C)(C)C)c1cc(Nc2nccc3nn(-c4c(Cl)cc(C#N)cc4Cl)cc23)ncn1]

{6-[2-(2,6-Dichloro-4-cyanophenyl)-2H-pyrazolo[4,3-c]pyridin-4-ylamino]-pyrimidin-4-yl}bis-carbamic acid tert-butyl ester Following the procedure described for 3,5-dichloro-4-[4-(2,6-dimethylpyrimidin-4-ylamino)pyrazolo[4,3-c]pyridin-2-yl]benzonitrile, 4-(4-aminopyrazolo[4,3-c]pyridin-2-yl)-3,5-dichlorobenzonitrile and (6-chloropyrimidin-4-yl)bis-carbamic acid tert-butyl ester were reacted to afford the title compound as a yellow solid (280 mg, 17% yield). LCMS (Method B): RT=4.37 min, m/z: 597 [M+H⁺].

Step 2

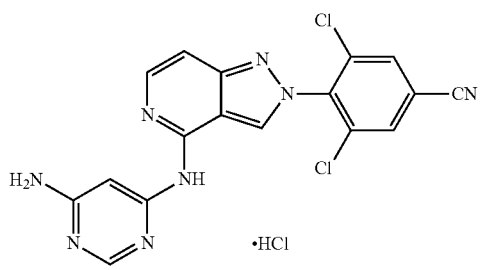 [SMILES: N#Cc1cc(Cl)c(-n2cc3c(Nc4cc(N)ncn4)nccc3n2)c(Cl)c1 ; Cl]

4-[4-(6-Aminopyrimidin-4-ylamino)-pyrazolo[4,3-c]pyridin-2-yl]-3,5-dichloro-benzonitrile.HCl A suspension of {6-[2-(2,6-dichloro-4-cyanophenyl)-2H-pyrazolo[4,3-c]pyridin-4-ylamino]-pyrimidin-4-yl}bis-carbamic acid tert-butyl ester (280 mg, 0.47 mmol) and HCl (4 N in dioxane, 4.0 mL, 16 mmol) was stirred at 50° C. for 4 h. The reaction mixture was diluted with IPA and the resultant solid was filtered. The pale pink solid was further washed with IPA and dried to afford the title compound as an off-white solid (121 mg, 58% yield). ¹H NMR (400 MHz, DMSO-$d_6$): δ 9.88 (br s, 1H), 8.48 (s, 2H), 8.41 (s, 1H), 7.91 (d, J=7.1 Hz, 1H), 7.40 (d, J=7.1 Hz, 1H), 6.77 (br s, 1H). LCMS (Method B): RT=2.85 min, m/z: 397 [M+H⁺].

Method 2

Example 26

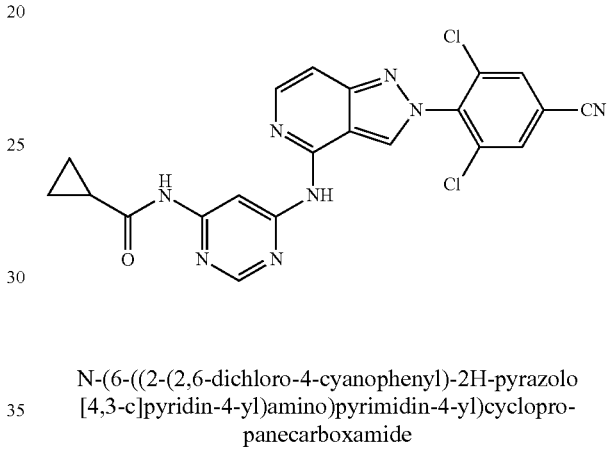

N-(6-((2-(2,6-dichloro-4-cyanophenyl)-2H-pyrazolo[4,3-c]pyridin-4-yl)amino)pyrimidin-4-yl)cyclopropanecarboxamide Step 1

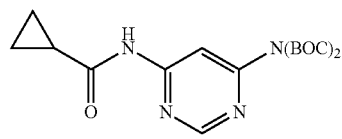

[6-(Cyclopropanecarbonyl-amino)-pyrimidin-4-yl]-bis-carbamic acid tert-butyl ester A mixture of (6-chloro-pyrimidin-4-yl)-bis-carbamic acid tert-butyl ester (327 mg, 1.0 mmol), cyclopropanecarboxylic acid amide (127 mg, 1.5 mmol), Pd₂(dba)₃ (27 mg, 0.03 mmol), Xantphos (36 mg, 0.06 mmol) and cesium carbonate (652 mg, 2.0 mmol) in dioxane (2 mL) was sealed in a reaction vial, purged with nitrogen, and heated at 70° C. for 18 hours. The reaction mixture was cooled and partitioned between ethyl acetate and water. The organic layer was separated and washed with brine, dried over Na₂SO₄, filtered and concentrated. The residue was purified by silica gel flash chromatography (0-75% diethyl ether in pentane), to afford the title compound as a colourless oil (300 mg, 79% yield). LCMS (Method D): RT=3.72 min, m/z: 379 [M+H⁺].

Step 2

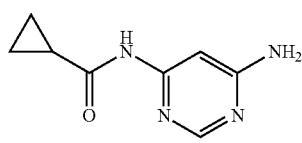 [SMILES: Nc1cc(NC(=O)C2CC2)ncn1]

Cyclopropanecarboxylic acid
(6-aminopyrimidin-4-yl)-amide

To a solution of [6-(cyclopropanecarbonyl-amino)-pyrimidin-4-yl]-bis-carbamic acid tert-butyl ester (300 mg, 0.79 mmol) in DCM (3 mL) was added TFA (3 mL). The reaction mixture was stirred at room temperature for 2 hours then concentrated under reduced pressure. The resultant residue was partitioned between ethyl acetate and sodium hydrogen carbonate (sat. aq.). The organic layer was separated and washed with brine, dried over $Na_2SO_4$, filtered and concentrated to afford the title compound as a white solid (123 mg, 87% yield). LCMS (Method D): RT=1.02 min, m/z: 179 [M+H$^+$].

Step 3

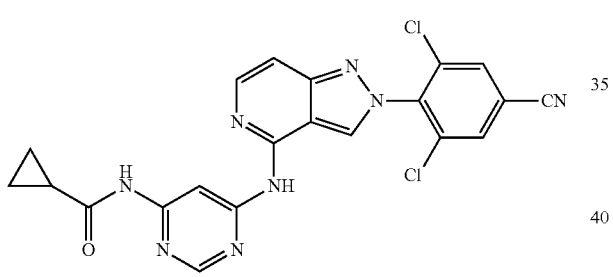

Cyclopropanecarboxylic acid {6-[2-(2,6-dichloro-4-cyanophenyl)-2H-pyrazolo[4,3-c]pyridin-4-ylamino]-pyrimidin-4-yl}-amide A suspension of 3,5-dichloro-4-(4-chloropyrazolo[4,3-c]pyridin-2-yl)benzonitrile (132 mg, 0.41 mmol), cyclopropanecarboxylic acid (6-amino-pyrimidin-4-yl)-amide (80 mg, 0.45 mmol), $Pd_2(dba)_3$ (19 mg, 0.02 mmol), Xantphos (24 mg, 0.04 mmol) and cesium carbonate (266 mg, 0.82 mmol) in dioxane (2 mL) was sealed in a microwave vial after degassing with nitrogen. The mixture was irradiated at 150° C. for 30 minutes in the microwave and then cooled to room temperature. The reaction mixture was partitioned between ethyl acetate and water. The organic layer was separated and washed with brine, dried over $Na_2SO_4$, filtered and concentrated. The residue was purified by silica gel flash chromatography (0-100% ethyl acetate in cyclohexane), then by HPLC (gradient: 5 to 98% acetonitrile in water with 0.1% ammonium hydroxide), to afford the title compound as an off-white solid (49 mg, 26% yield). $^1$H NMR (400 MHz, DMSO-$d_6$+d-TFA): δ 9.47 (s, 1H), 8.79 (d, 1H), 8.47 (s, 2H), 8.09 (d, J=0.9 Hz, 1H), 7.99 (d, J=7.6 Hz, 1H), 7.55 (dd, J=7.6, 0.9 Hz, 1H), 2.10-2.02 (m, 1H), 0.93-0.90 (m, 4H). LCMS (Method B): RT=3.17 min, m/z: 465 [M+H$^+$].

Method 2

Example 27

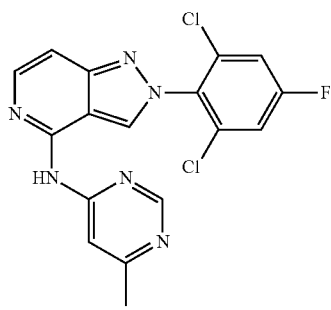

[2-(2,6-Dichloro-4-fluorophenyl)-2H-pyrazolo[4,3-c]pyridin-4-yl]-(6-methylpyrimidin-4-yl)amine

Step 1

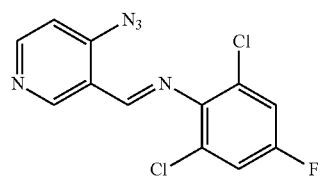 [SMILES: [N-]=[N+]=Nc1ccncc1/C=N/c1c(Cl)cc(F)cc1Cl]

[1-(4-Azidopyridin-3-yl)meth-(E)-ylidene]-(2,6-dichloro-4-fluorophenyl)amine

Titanium tetrachloride (1M, 4.0 mL, 4.15 mmol) was added to a cooled (0° C.) mixture of 4-azidopyridine-3-carbaldehyde (1.0 g, 6.75 mmol), 2,6-dichloro-4-fluorophenylamine (1.22 g, 6.75 mmol) and triethylamine (2.8 mL, 20.3 mmol) in DCM (24 mL), under nitrogen. The reaction was stirred for 30 minutes at 0° C., warmed to room temperature, stirred for an additional 2 h, and concentrated under reduced pressure. The residue was dissolved in toluene and filtered though a pad of Celite®. The filtrate was concentrated to dryness under reduced pressure to afford the title compound as a yellow solid (2.09 g, quant.). This crude material was employed in the next step without further purification or analysis.

Step 2

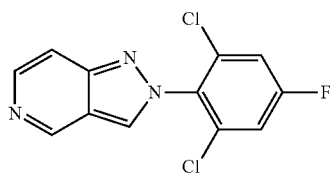 [SMILES: Fc1cc(Cl)c(-n2cc3cnccc3n2)c(Cl)c1]

2-(2,6-Dichloro-4-fluorophenyl)-2H-pyrazolo[4,3-c]pyridine

A mixture of [1-(4-azidopyridin-3-yl)meth-(E)-ylidene]-(2,6-dichloro-4-fluorophenyl)amine (2.09 g, 6.75 mmol) in toluene (20 mL) was heated to 105° C. for 45 minutes. The reaction was cooled and concentrated under reduced pressure. The residue was purified by silica gel flash chromatography (50-100% ethyl acetate in cyclohexane) to afford the title compound as a yellow solid (1.60 g, 84% yield). $^1$H NMR (300 MHz, CDCl$_3$): δ 9.38 (s, 1H), 8.45-8.30 (m, 2H), 7.70 (d, J=6.5 Hz, 1H), 7.32 (d, J=7.7 Hz, 2H).

Step 3

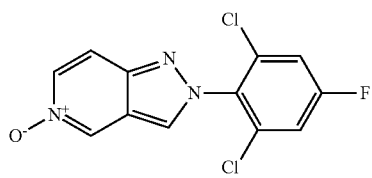 [SMILES: [O-][n+]1ccc2nn(-c3c(Cl)cc(F)cc3Cl)cc2c1]

2-(2,6-Dichloro-4-fluorophenyl)-2H-pyrazolo[4,3-c]pyridine-5-oxide

To a cooled (0° C.) solution of 2-(2,6-dichloro-4-fluorophenyl)-2H-pyrazolo[4,3-c]pyridine (1.6 g, 5.67 mmol) in DCM (30 mL) under nitrogen, was added mCPBA (1.47 g, 8.51 mmol). The reaction mixture was stirred at 0° C. for 2 hours, warmed to room temperature, and stirred for a further 16 hours. Sodium thiosulfate (sat. aq.) was added and the organic layer was separated, washed with sodium hydrogen carbonate (sat. aq.) and brine, dried over anhydrous magnesium sulfate, and concentrated to dryness under reduced pressure. The residue was purified by silica gel flash chromatography (5-10% methanol in DCM) to afford the title compound as a white solid (1.4 g, 83% yield). $^1$H NMR (300 MHz, DMSO-d$_6$): δ 8.90 (s, 1H), 8.82 (s, 1H), 7.98-7.87 (m, 3H), 7.83 (d, J=7.5 Hz, 1H).

Step 4

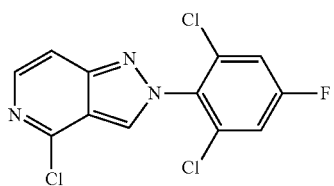 [SMILES: Fc1cc(Cl)c(-n2cc3c(Cl)nccc3n2)c(Cl)c1]

4-Chloro-2-(2,6-dichloro-4-fluorophenyl)-2H-pyrazolo[4,3-c]pyridine 2-(2,6-Dichloro-4-fluorophenyl)-2H-pyrazolo[4,3-c]pyridine-5-oxide (1.4 g, 4.7 mmol) was slowly added to phosphorous oxychloride (10 mL). Tetrabutylammonium chloride (1.31 g, 4.7 mmol) was then added and the reaction mixture was heated at 85° C. for 45 minutes. The mixture was cooled and concentrated under reduced pressure. The residue was partitioned between ethyl acetate and sodium hydrogen carbonate. The organic layer was washed with sodium hydrogen carbonate (sat. aq.) and brine, dried over anhydrous sodium sulfate, and concentrated under reduced pressure. The residue was purified by silica gel flash chromatography (10-20% ethyl acetate in cyclohexane) to afford the title compound as a white solid (706 mg, 47% yield). $^1$H NMR (300 MHz, DMSO-d$_6$): δ 9.28 (s, 1H), 8.11 (d, J=6.3 Hz, 1H), 7.94 (d, J=8.4 Hz, 2H), 7.72 (d, J=6.3 Hz, 1H).

Step 5

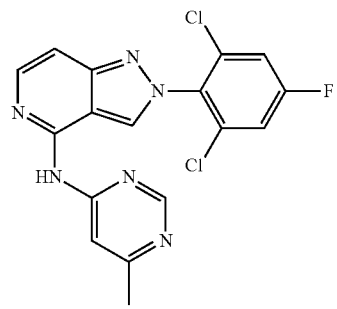

[2-(2,6-Dichloro-4-fluorophenyl)-2H-pyrazolo[4,3-c]pyridin-4-yl]-(6-methylpyrimidin-4-yl)amine A suspension of 4-chloro-2-(2,6-dichloro-4-fluorophenyl)-2H-pyrazolo[4,3-c]pyridine (70 mg, 0.22 mmol), 6-methylpyrimidin-4-ylamine (26 mg, 0.24 mmol), Pd$_2$(dba)$_3$ (10 mg, 0.011 mmol), Xantphos (12.8 mg, 0.022 mmol) and cesium carbonate (144 mg, 0.44 mmol) in dioxane (3 ml) was sealed in a microwave vial, purged with nitrogen and irradiated at 150° C. for 25 minutes in the microwave. The reaction mixture was cooled and partitioned between ethyl acetate and water. The organic layer was washed with brine, dried over anhydrous sodium sulfate, and concentrated under reduced pressure. The resultant residue was purified by silica gel flash chromatography (50-100% ethyl acetate in cyclohexane), then further triturated with diethyl ether:pentane (1:1) to afford the title compound as a yellow solid (53 mg, 62% yield). $^1$H NMR (400 MHz, DMSO-d$_6$): δ 10.65 (br s, 1H), 9.15 (s, 1H), 8.70 (s, 1H), 8.51 (s, 1H), 8.00 (d, J=6.4 Hz, 1H), 7.93 (d, J=8.4 Hz, 2H), 7.23 (d, J=6.4 Hz, 1H), 2.46 (s, 3H). LCMS (Method B): RT=2.94 min, m/z: 389 [M+H$^+$].

Method 2

Example 28

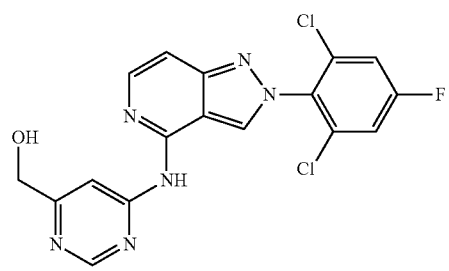 [SMILES: OCc1cc(Nc2nccc3nn(-c4c(Cl)cc(F)cc4Cl)cc23)ncn1]

{6-[2-(2,6-Dichloro-4-fluorophenyl)-2H-pyrazolo[4,3-c]pyridine-4-yl]-(4-methylpyridin-2-yl)}methanol Following the procedure described for 3,5-dichloro-4-[4-(2,6-dimethylpyrimidin-4-ylamino)pyrazolo[4,3-c]pyridin-2-yl]benzonitrile, (6-amino-pyrimidin-4-yl)-methanol and 4-chloro-2-(2,6-dichloro-4-fluorophenyl)-2H-pyrazolo[4,3- c]pyridine were reacted to afford the title compound as a pale yellow solid (35 mg, 39% yield). $^1$H NMR (400 MHz, DMSO-$d_6$): $^1$H NMR (400 MHz, DMSO-$d_6$+d-TFA): δ 9.50 (d, J=0.9 Hz, 1H), 9.02 (d, J=1.1 Hz, 1H), 8.06 (d, J=7.3 Hz, 1H), 7.95 (d, J=8.3 Hz, 2H), 7.62-7.61 (m, 2H), 4.65 (s, 2H). LCMS (Method B): RT=2.80 min, m/z: 405 [M+H$^+$].

Method 2

Example 29

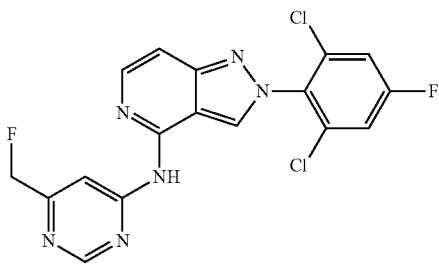 [SMILES: FCc1cc(Nc2nccc3nn(-c4c(Cl)cc(F)cc4Cl)cc23)ncn1]

[2-(2,6-Dichloro-4-fluorophenyl)-2H-pyrazolo[4,3-c]pyridin-4-yl]-(6-fluoromethylpyrimidin-4-yl)amine DAST (9 µL, 0.066 mmol) was added to a solution of {6-[2-(2,6-dichloro-4-fluorophenyl)-2H-pyrazolo[4,3-c]pyridine-4-yl]-(4-methylpyridin-2-yl)}methanol (18 mg, 0.044 mmol) in DCM (5 mL) and stirred at room temperature for 30 minutes. The reaction mixture was partitioned between DCM and sodium hydrogen carbonate (sat. aq.). The organic layer was washed with water and brine, dried over anhydrous sodium sulfate, filtered and concentrated to dryness under reduced pressure. The resultant residue was purified by silica gel flash chromatography (20-60% ethyl acetate in pentane) to afford the title compound as a yellow solid (7.5 mg, 22% yield). $^1$H NMR (400 MHz, CD$_3$OD): δ 8.94 (s, 1H), 8.77 (s, 1H), 7.82-7.81 (m, 2H), 7.59 (d, J=8.1 Hz, 2H), 7.09 (s, 1H), 5.48 (s, 1H), 5.37 (s, 1H). LCMS (Method B): RT=3.05 min, m/z: 407 [M+H$^+$].

Method 2

Example 30

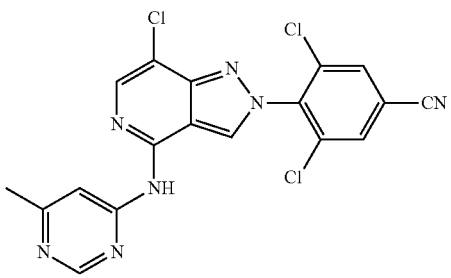 [SMILES: Cc1cc(Nc2ncc(Cl)c3nn(-c4c(Cl)cc(C#N)cc4Cl)cc23)ncn1]

3,5-Dichloro-4-[7-chloro-4-(6-methylpyrimidin-4-ylamino)pyrazolo[4,3-c]pyridin-2-yl]benzonitrile Step 1

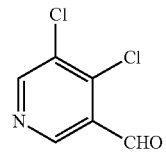

4,5-Dichloropyridine-3-carbaldehyde

To a solution of diisopropylamine (9.7 mL, 69.1 mmol) in THF (60 mL) at −30° C. was added n-butyllithium (2.5 M in hexanes, 27.6 mL, 69.1 mmol). The reaction mixture was stirred for 15 minutes then cooled to −78° C. A solution of 3,4-dichloropyridine (8.53 g, 57.6 mmol) in THF (20 mL) was added dropwise over 20 minutes then the mixture was stirred at −78° C. for 2.5 hours. DMF (5.4 mL, 69.1 mmol) was added and the reaction was warmed to room temperature. The reaction mixture was quenched with ammonium chloride (sat. aq., 300 mL) and extracted with ethyl acetate (3×100 mL). The combined organic extracts were dried over anhydrous sodium sulfate and concentrated under reduced pressure. The residue was purified by silica gel flash chromatography (0-30% ethyl acetate in pentane) to afford the title compound as a white solid (6.78 g, 67% yield). $^1$H NMR (400 MHz, CDCl$_3$): δ 10.49 (s, 1H), 8.92 (s, 1H), 8.82 (s, 1H).

Step 2

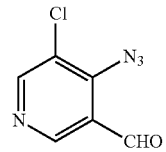

4-Azido-5-chloropyridine-3-carbaldehyde

A mixture of 4,5-dichloropyridine-3-carbaldehyde (6.78 g, 38.5 mmol) and sodium azide (2.62 g, 40.4 mmol) in DMF (25 mL) was stirred at room temperature for 18 hours. The reaction mixture was quenched with brine (250 mL) and extracted with ethyl acetate (3×100 mL). The combined organic extracts were dried over anhydrous sodium sulphate and concentrated under reduced pressure. The residue was purified by silica gel flash chromatography (0-40% ethyl acetate in pentane) to afford the title compound as a yellow solid (6.7 g, 96% yield). $^1$H NMR (400 MHz, CDCl$_3$): δ 10.36 (s, 1H), 8.84 (s, 1H), 8.65 (s, 1H).

Step 3

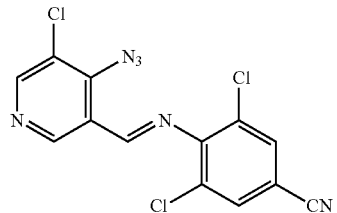 [SMILES: N#Cc1cc(Cl)c(/N=C/c2cncc(Cl)c2N=[N+]=[N-])c(Cl)c1]

4-{[1-(4-Azido-5-chloropyridin-3-yl)meth-(E)-ylidene]amino}-3,5-dichlorobenzonitrile

125

To a cooled (0° C.) solution of 4-azido-5-chloropyridine-3-carbaldehyde (2.0 g, 10.95 mmol), 4-amino-3,5-dichlorobenzonitrile (2.05 g, 10.95 mmol) and triethylamine (4.6 mL, 6.57 mmol) in DCM (48 mL) was added titanium tetrachloride (1M in DCM, 6.6 mL, 6.57 mmol) dropwise over 10 minutes. The reaction mixture was stirred for 20 minutes, warmed to room temperature, and stirred for an additional 30 minutes. The resultant mixture was concentrated to dryness under reduced pressure to afford the title compound which was used without further purification.

Step 4

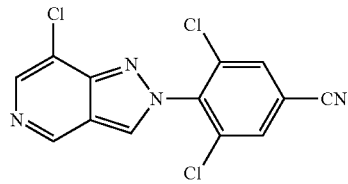

3,5-Dichloro-4-(7-chloropyrazolo[4,3-c]pyridin-2-yl)benzonitrile

A suspension of 4-{[1-(4-azido-5-chloropyridin-3-yl)meth-(E)-ylidene]amino}-3,5-dichlorobenzonitrile (3.8 g, 10.95 mmol) in toluene (45 mL) was heated to reflux for 18 hours and then cooled to room temperature. The precipitated solid was removed by filtration and washed sequentially with toluene, ethyl acetate and DCM. The filtrate was concentrated under reduced pressure. The residue was purified by silica gel flash chromatography (0-100% ethyl acetate in cyclohexane) and then triturated with diethyl ether to afford the title compound as an off-white solid (2.5 g, 71% yield). $^1$H NMR (400 MHz, CDCl$_3$): δ 9.30 (s, 1H), 8.46 (s, 1H), 8.42 (s, 1H), 7.86 (s, 2H).

Step 5

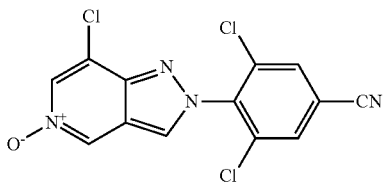

3,5-Dichloro-4-(7-chloro-5-oxypyrazolo[4,3-c]pyridin-2-yl)benzonitrile

To a solution of 3,5-dichloro-4-(7-chloropyrazolo[4,3-c]pyridin-2-yl)benzonitrile (2.5 g, 7.73 mmol) and methyltrioxorhenium (9.6 mg, 0.04 mmol) in DCM (5 mL) was added hydrogen peroxide (30% aq., 1.5 mL, 15.46 mmol) and the reaction mixture stirred at room temperature for 66 hours. More methyltrioxorhenium (10 mg, 0.04 mmol) was added and the mixture stirred for 2 hours. Catalytic manganese dioxide was added and then the mixture was stirred for 1 hour and concentrated under reduced pressure. The residue was triturated with toluene and concentrated to dryness under reduced pressure to afford the title compound as a beige solid (2.52 g, 96% yield) that was used in the next step without further purification.

Step 6

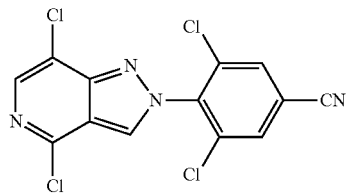 [SMILES: N#Cc1cc(Cl)c(-n2cc3c(Cl)ncc(Cl)c3n2)c(Cl)c1]

3,5-Dichloro-4-(4,7-dichloropyrazolo[4,3-c]pyridin-2-yl)benzonitrile

To a suspension of 3,5-dichloro-4-(7-chloro-5-oxypyrazolo[4,3-c]pyridin-2-yl)benzonitrile (2.52 g, 7.4 mmol) in DCE (60 mL) was added phosphorus oxychloride (3.4 mL, 37.1 mmol) dropwise over 20 minutes. The reaction mixture was heated at 70° C. for 3 hours, cooled to room temperature, and concentrated under reduced pressure. The residue was partitioned between ethyl acetate and sodium bicarbonate (sat. aq.). The organic layer was dried over anhydrous sodium sulfate and concentrated under reduced pressure. The residue was purified by silica gel flash chromatography (0-100% ethyl acetate in pentane) to afford the title compound as a white solid (1.17 g, 44% yield). $^1$H NMR (400 MHz, CDCl$_3$): δ 8.36 (s, 1H), 8.17 (s, 1H), 7.85 (s, 2H).

Step 7

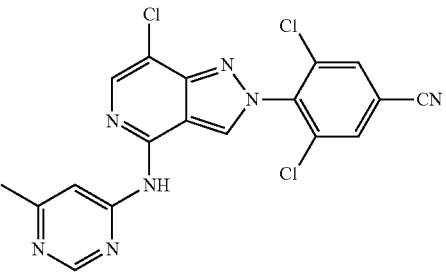

3,5-Dichloro-4-[7-chloro-4-(6-methylpyrimidin-4-ylamino)pyrazolo[4,3-c]pyridin-2-yl]benzonitrile A suspension of 3,5-dichloro-4-(4,7-dichloropyrazolo[4,3-c]pyridin-2-yl)benzonitrile (70 mg, 0.20 mmol), 6-methylpyrimidin-4-ylamine (23 mg, 0.22 mmol), Pd$_2$(dba)$_3$ (9 mg, 0.01 mmol), Xantphos (12 mg, 0.02 mmol) and cesium carbonate (130 mg, 0.40 mmol) in dioxane (3 mL) was sealed in a microwave vial, purged with nitrogen and irradiated at 150° C. for 30 minutes in the microwave. The reaction mixture was cooled and partitioned between ethyl acetate and water. The organic layer was dried over anhydrous sodium sulfate and concentrated under reduced pressure. The residue was purified by silica gel flash chromatography (0-80% ethyl acetate in pentane), then further triturated with ethyl acetate to afford the title compound as a yellow solid (37 mg, 43% yield). $^1$H NMR (400 MHz, DMSO-$d_6$): δ 10.90 (s, 1H), 9.33 (s, 1H), 8.71 (d, J=1.2 Hz, 1H), 8.51 (s, 2H), 8.37 (s, 1H), 8.08 (s, 1H), 2.45 (s, 3H). LCMS (Method B): RT=3.69 min, m/z: 430 [M+H$^+$].

Method 2

Example 31

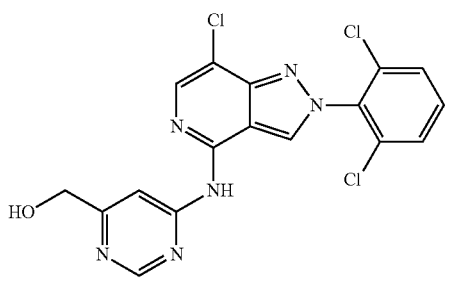 [SMILES: OCc1cc(Nc2ncc(Cl)c3nn(-c4c(Cl)cccc4Cl)cc23)ncn1]

{6-[7-Chloro-2-(2,6-dichlorophenyl)-2H-pyrazolo[4,3-c]pyridin-4-ylamino]-pyrimidin-4-yl}-methanol Step 1

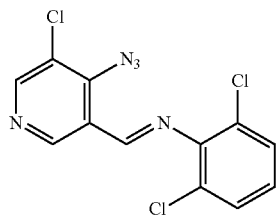

[1-(4-Azido-5-chloropyridin-3-yl)-meth-(E)-ylidene]-(2,6-dichlorophenyl)-amine

Following the procedure described for 4-{[1-(4-azido-5-chloropyridin-3-yl)meth-(E)-ylidene]amino}-3,5-dichlorobenzonitrile, 4-azido-5-chloropyridine-3-carbaldehyde and 2,6-dichloroaniline were reacted to afford the title compound as a beige solid that was used without purification.

Step 2

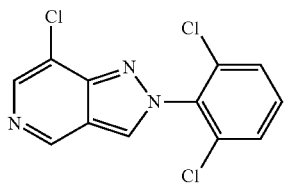 [SMILES: Clc1cccc(Cl)c1-n1cc2cncc(Cl)c2n1]

7-Chloro-2-(2,6-dichlorophenyl)-2H-pyrazolo[4,3-c]pyridine

Following the procedure described for 3,5-dichloro-4-(7-chloropyrazolo[4,3-c]pyridin-2-yl)benzonitrile, [1-(4-azido-5-chloropyridin-3-yl)-meth-(E)-ylidene]-(2,6-dichlorophenyl)-amine was heated under reflux in toluene to afford the title compound as a brown solid (2.7 g, 66% yield). LCMS (Method D): RT=2.96 min, m/z: 298 [M+H$^+$].

Step 3

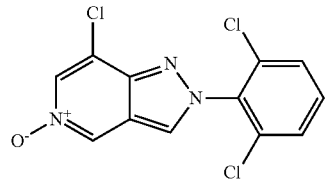 [SMILES: [O-][n+]1cc(Cl)c2nn(-c3c(Cl)cccc3Cl)cc2c1]

7-Chloro-2-(2,6-dichlorophenyl)-2H-pyrazolo[4,3-c]pyridine-5-oxide

To a solution of 7-chloro-2-(2,6-dichlorophenyl)-2H-pyrazolo[4,3-c]pyridine (2.7 g, 9.0 mmol) and methyltrioxorhenium (31 mg, 0.09 mmol) in DCM (6 mL) was added hydrogen peroxide (30% aq., 1.75 mL, 18.0 mmol) and the resulting mixture stirred at room temperature for 18 hours. A catalytic amount of MnO$_2$ was added to the mixture and stirring was continued for 1 hour. The reaction mixture was concentrated under reduced pressure. The residue was triturated in toluene to afford the title compound as a beige solid (2.5 g, 89% yield). LCMS (Method D): RT=2.57 min, m/z: 314 [M+H$^+$].

Step 4

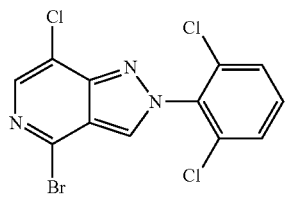 [SMILES: Clc1cccc(Cl)c1-n1cc2c(Br)ncc(Cl)c2n1]

4-Bromo-7-chloro-2-(2,6-dichlorophenyl)-2H-pyrazolo[4,3-c]pyridine

To a cooled (0° C.) suspension of 7-chloro-2-(2,6-dichlorophenyl)-2H-pyrazolo[4,3-c]pyridine-5-oxide (2.5 g, 8.0 mmol) in DCE (50 mL) was added phosphorus oxybromide (6.8 g, 24.0 mmol). The reaction mixture was stirred at 0° C. for 30 minutes, warmed to room temperature, and stirred for a further 18 hours. The reaction mixture was partitioned between DCM and sodium carbonate (sat. aq.). The organic layer was washed with brine, dried over anhydrous sodium sulfate, and concentrated under reduced pressure. The residue was purified by silica gel flash chromatography (0-50% ethyl acetate in cyclohexane) to afford the title compound as a white solid (850 mg, 28% yield). LCMS (Method D): RT=3.92 min, m/z: 377 [M+H$^+$].

Step 5

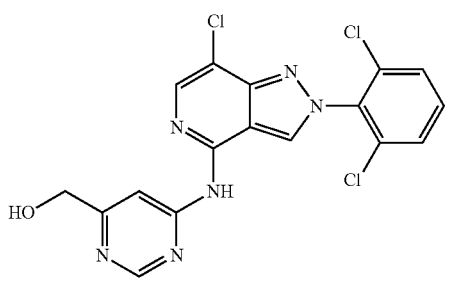 [SMILES: OCc1cc(Nc2ncc(Cl)c3nn(-c4c(Cl)cccc4Cl)cc23)ncn1]

{6-[7-Chloro-2-(2,6-dichlorophenyl)-2H-pyrazolo[4,3-c]pyridin-4-ylamino]-pyrimidin-4-yl}-methanol A suspension of 4-bromo-7-chloro-2-(2,6-dichlorophenyl)-2H-pyrazolo[4,3-c]pyridine (200 mg, 0.53 mmol), (6-amino-pyrimidin-4-yl)-methanol (73 mg, 0.58 mmol), Pd$_2$(dba)$_3$ (24 mg, 0.025 mmol), Xantphos (31 mg, 0.05 mmol) and cesium carbonate (347 mg, 1.1 mmol) in dioxane (3 mL) was sealed in a microwave vial, purged with nitrogen, and irradiated in a microwave reactor at 150° C. for 30 min. The reaction mixture was cooled and partitioned between ethyl acetate and water. The organic layer was washed with brine, dried over anhydrous sodium sulfate, and concentrated under reduced pressure. The residue was purified by NH$_2$ silica gel flash chromatography (0-2% methanol in ethyl acetate), to afford the title compound as a pale yellow solid (57 mg, 34% yield). $^1$H (400 MHz, DMSO-d$_6$+d-TFA): δ 9.36 (s, 1H), 9.04 (s, 1H), 8.27 (bs, 1H), 8.16 (s, 1H), 7.80 (d, J=1.2 Hz, 1H), 7.78 (s, 1H), 7.70 (dd, J=9.0, 7.3 Hz, 1H), 4.67 (s, 2H). LCMS (Method B): RT=3.19 min, m/z: 421 [M+H$^+$].

Method 4

Example 32

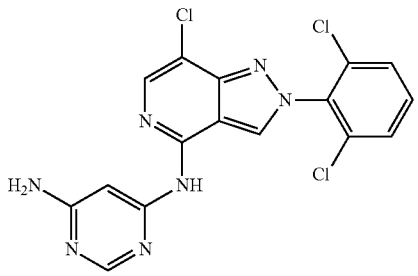 [SMILES: Nc1cc(Nc2ncc(Cl)c3nn(-c4c(Cl)cccc4Cl)cc23)ncn1]

N-[7-Chloro-2-(2,6-dichlorophenyl)-2H-pyrazolo[4,3-c]pyridin-4-yl]-pyrimidine-4,6-diamine Step 1

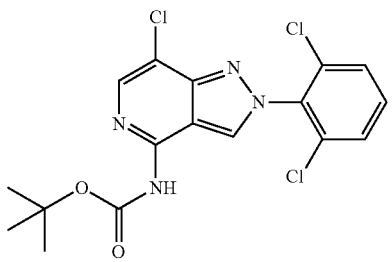 [SMILES: CC(C)(C)OC(=O)Nc1ncc(Cl)c2nn(-c3c(Cl)cccc3Cl)cc12]

[7-Chloro-2-(2,6-dichlorophenyl)-2H-pyrazolo[4,3-c]pyridin-4-yl]-carbamic acid tert-butyl ester A mixture of 4-bromo-7-chloro-2-(2,6-dichlorophenyl)-2H-pyrazolo[4,3-c]pyridine (400 mg, 1.06 mmol), tert-butyl carbamate (619 mg, 5.3 mmol), Pd$_2$(dba)$_3$ (48 mg, 0.05 mmol), Xantphos (61 mg, 0.1 mmol) and potassium phosphate tribasic (449 mg, 2.1 mmol) in toluene (10 mL) and water (2.0 mL) was purged with argon and heated at 70° C. for 3 hours. The reaction mixture was filtered through Celite® and washed with ethyl acetate. The filtrate was washed with water and brine, dried over sodium sulphate, and concentrated under reduced pressure. The residue was purified by silica gel flash chromatography (0-50% ethyl acetate in cyclohexane) to afford the title compound as a yellow solid (531 mg, contaminated with residual tert-butyl carbamate). LCMS (Method D): RT=3.76 min, m/z: 413 [M+H$^+$].

Step 2

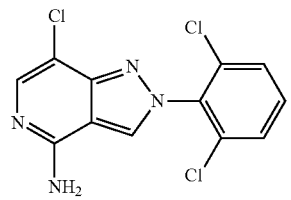 [SMILES: Nc1ncc(Cl)c2nn(-c3c(Cl)cccc3Cl)cc12]

7-Chloro-2-(2,6-dichlorophenyl)-2H-pyrazolo[4,3-c]pyridin-4-ylamine

A solution of [7-chloro-2-(2,6-dichlorophenyl)-2H-pyrazolo[4,3-c]pyridin-4-yl]-carbamic acid tert-butyl ester (531 mg, contaminated with residual tert-butyl carbamate) and TFA (10 mL) in DCM (10 mL) was stirred at room temperature for 2 h and then concentrated under reduced pressure. The residue was partitioned between ethyl acetate and sodium bicarbonate (sat. aq.). The organic layer was washed with brine, dried over anhydrous sodium sulfate, and concentrated to dryness under reduced pressure to afford the title compound as a beige solid (100 g, 30% yield over 2 steps). LCMS (Method D): RT=2.15 min, m/z: 313 [M+H$^+$].

Step 3

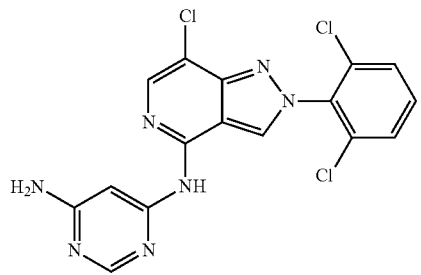

N-[7-Chloro-2-(2,6-dichlorophenyl)-2H-pyrazolo[4,3-c]pyridin-4-yl]-pyrimidine-4,6-diamine A suspension of 7-chloro-2-(2,6-dichlorophenyl)-2H-pyrazolo[4,3-c]pyridin-4-ylamine (100 mg, 0.32 mmol), (6-chloropyrimidin-4-yl)bis-carbamic acid tert-butyl ester (115 mg, 0.35 mmol), Pd$_2$(dba)$_3$ (15 mg, 0.016 mmol), Xantphos (18 mg, 0.032 mmol) and cesium carbonate (209 mg, 0.64 mmol) in dioxane (1 mL) was sealed in a microwave vial, purged with nitrogen, and irradiated in a microwave reactor at 150° C. for 30 min. The reaction mixture was cooled, diluted with DCM and MeOH and loaded onto an SCX-2 cartridge which was washed with MeOH. The products were eluted with a 2M methanolic solution of ammonia. The solvents were removed under reduced pressure and the resultant residue was taken up in a 1.25M solution of HCl in isopropyl alcohol. The reaction mixture was stirred at 50° C. for 3 hours then concentrated. The resultant residue was partitioned between ethyl acetate and sodium bicarbonate (sat. aq.). The organic phase was washed with brine, dried over anhydrous sodium sulfate, concentrated under reduced pressure. The residue was purified by NH$_2$ silica gel flash chromatography (0-100% ethyl acetate in cyclohexane) to afford the title compound as a white solid (30 mg, 23% yield). $^1$H (400 MHz, DMSO-d$_6$+d-TFA): δ 9.21 (s, 1H), 8.49 (s, 1H), 8.01 (s, 1H), 7.78 (d, J=1.2 Hz, 1H), 7.76 (s, 1H), 7.68 (dd, J=9.2, 7.2 Hz, 1H), 7.19 (bs, 1H). LCMS (Method B): RT=3.23 min, m/z: 406 [M+H$^+$].

Method 2

Example 33

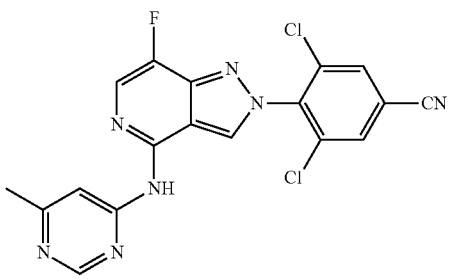

3,5-Dichloro-4-[7-fluoro-4-(6-methyl-pyrimidin-4-ylamino)-pyrazolo[4,3-c]pyridin-2-yl]-benzonitrile Step 1

4-Chloro-5-fluoro-pyridine-3-carbaldehyde

To a solution of diisopropylamine (6.4 mL, 45.6 mmol) in THF (50 mL) at −30° C. was added n-butyllithium (2.5 M in hexanes, 18.2 mL, 45.6 mmol) over 15 minutes and the resulting mixture stirred for 15 minutes then cooled to −78° C. A solution of 4-chloro-3-fluoro-pyridine (5.0 g, 38.0 mmol) in THF (10 mL) was added dropwise over 15 minutes then the resulting mixture was stirred at −78° C. for 18 hours. DMF (3.5 mL, 45.6 mmol) was added and the reaction was warmed to room temperature. The mixture was quenched with ammonium chloride (sat. aq., 300 mL) and extracted with ethyl acetate (3×100 mL). The combined organic extracts were dried over anhydrous sodium sulfate and concentrated to dryness under reduced pressure. The residue was purified by silica gel flash chromatography (0-40% ethyl acetate in cyclohexane) to afford the title compound as a pale orange solid (5.1 g, 84% yield). $^1$H NMR (300 MHz, CDCl$_3$): δ 10.47 (s, 1H), 8.88 (s, 1H), 8.70 (s, 1H).

Step 2

4-Azido-5-fluoro-pyridine-3-carbaldehyde

A mixture of 4-chloro-5-fluoro-pyridine-3-carbaldehyde (4.15 g, 26.0 mmol) and sodium azide (1.86 g, 28.6 mmol) in DMF (15 mL) was stirred at room temperature for 18 hours. The reaction mixture was quenched with brine (200 mL) and extracted with ethyl acetate (3×75 mL). The combined organic extracts were dried over anhydrous sodium sulfate and concentrated under reduced pressure. The residue was purified by silica gel flash chromatography (0-50% ethyl acetate in cyclohexane) to afford the title compound as an off-white solid (3.61 g, 84% yield). $^1$H NMR (300 MHz, CDCl$_3$): δ 10.32 (s, 1H), 8.79 (s, 1H), 8.58 (d, J=3.0 Hz, 1H).

Step 3

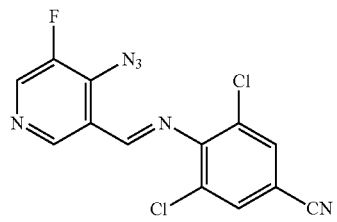

4-{[1-(4-Azido-5-fluoro-pyridin-3-yl)-meth-(E)-ylidene]-amino}-3,5-dichloro-benzonitrile To a cooled (0° C.) solution of 4-azido-5-fluoro-pyridine-3-carbaldehyde (2.0 g, 12.0 mmol), 4-amino-3,5-dichlorobenzonitrile (2.25 g, 12.0 mmol) and triethylamine (5.0 mL, 36.1 mmol) in DCM (48 mL) was added titanium tetrachloride (1M in DCM, 7.2 mL, 7.2 mmol) dropwise over 20 minutes. The reaction mixture was stirred for 20 minutes, warmed to room temperature, and stirred for a further 30 minutes. The resultant mixture was concentrated to dryness

Step 4

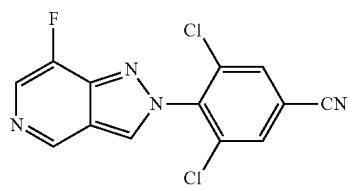 [SMILES: N#Cc1cc(Cl)c(-n2cc3cncc(F)c3n2)c(Cl)c1]

3,5-Dichloro-4-(7-fluoro-pyrazolo[4,3-c]pyridin-2-yl)-benzonitrile

A suspension of 4-{[1-(4-azido-5-fluoro-pyridin-3-yl)-meth-(E)-ylidene]-amino}-3,5-dichlorobenzonitrile (4.0 g, 12.0 mmol) in toluene (50 mL) was heated under reflux for 1 hour and then cooled to room temperature. The precipitated solid was removed by filtration and washed sequentially with toluene, ethyl acetate, and 1:1 ethyl acetate:DCM. The filtrate was concentrated under reduced pressure and the residue was purified by silica gel flash chromatography (0-100% ethyl acetate in cyclohexane) to afford the title compound as an off-white solid (2.77 g, 75% yield). $^1$H NMR (300 MHz, CDCl$_3$): δ 9.11 (d, J=2.2 Hz, 1H), 8.36 (d, J=2.4 Hz, 1H), 8.24 (d, J=3.4 Hz, 1H), 7.85 (s, 2H).

Step 5

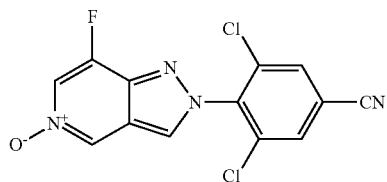 [SMILES: N#Cc1cc(Cl)c(-n2cc3c[n+]([O-])cc(F)c3n2)c(Cl)c1]

3,5-Dichloro-4-(7-fluoro-5-oxy-pyrazolo[4,3-c]pyridin-2-yl)-benzonitrile

To a solution of 3,5-dichloro-4-(7-fluoro-pyrazolo[4,3-c]pyridin-2-yl)-benzonitrile (1.0 g, 3.26 mmol) and methyltrioxorhenium (24 mg, 0.10 mmol) in DCM (5 mL) was added hydrogen peroxide (30% aq., 0.6 mL, 6.51 mmol) and the resulting mixture stirred at room temperature for 3 hours. The reaction mixture was diluted with DCM and washed with sodium bicarbonate (sat. aq.). The organic layer was dried over anhydrous sodium sulfate and concentrated under reduced pressure. The residue was purified by silica gel flash chromatography (80-100% ethyl acetate in cyclohexane and then 0-10% methanol in DCM) to afford the title compound as a white solid (889 mg, 84% yield). $^1$H NMR (300 MHz, CDCl$_3$): δ 8.64 (d, J=1.4 Hz, 1H), 8.18 (d, J=2.3 Hz, 1H), 8.02 (dd, J=5.4, 1.4 Hz, 1H), 7.86 (s, 2H).

Step 6

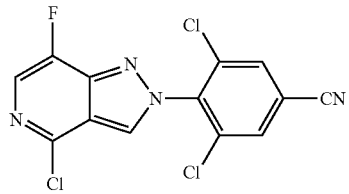 [SMILES: N#Cc1cc(Cl)c(-n2cc3c(Cl)ncc(F)c3n2)c(Cl)c1]

3,5-Dichloro-4-(4-chloro-7-fluoro-pyrazolo[4,3-c]pyridin-2-yl)-benzonitrile To a suspension of 3,5-dichloro-4-(7-fluoro-5-oxy-pyrazolo[4,3-c]pyridin-2-yl)-benzonitrile (889 mg, 2.7 mmol) in DCE (25 mL) was added phosphorus oxychloride (1.25 mL, 13.7 mmol) dropwise over 90 minutes. The reaction mixture was heated at 70° C. for 3 hours, cooled to room temperature, and concentrated under reduced pressure. The residue was partitioned between ethyl acetate and sodium bicarbonate (sat. aq.). The organic phase was dried over anhydrous sodium sulfate and concentrated under reduced pressure. The residue was purified by silica gel flash chromatography (0-100% ethyl acetate in cyclohexane) to afford the title compound as a white solid (456 mg, 49% yield). $^1$H NMR (300 MHz, CDCl$_3$): δ 8.35 (d, J=2.2 Hz, 1H), 8.02 (d, J=3.0 Hz, 1H), 7.86 (s, 2H).

Step 7

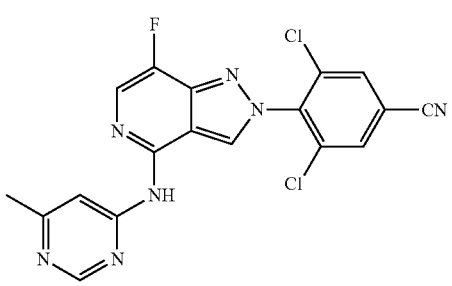 [SMILES: Cc1cc(Nc2ncc(F)c3nn(-c4c(Cl)cc(C#N)cc4Cl)cc23)ncn1]

3,5-Dichloro-4-[7-fluoro-4-(6-methyl-pyrimidin-4-ylamino)-pyrazolo[4,3-c]pyridin-2-yl]-benzonitrile Following the procedure described for 3,5-dichloro-4-[7-chloro-4-(6-methylpyrimidin-4-ylamino)pyrazolo[4,3-c]pyridin-2-yl]benzonitrile, 3,5-dichloro-4-(4-chloro-7-fluoro-pyrazolo[4,3-c]pyridin-2-yl)-benzonitrile and 6-methylpyrimidin-4-ylamine were reacted to afford the title compound as a white solid (35 mg, 41% yield). $^1$H NMR (400 MHz, DMSO-d$_6$): δ 10.79 (s, 1H), 9.33 (d, J=2.6 Hz, 1H), 8.69 (d, J=1.2 Hz, 1H), 8.51 (s, 2H), 8.34 (s, 1H), 8.00 (d, J=3.5 Hz, 1H), 2.44 (s, 3H). LCMS (Method B): RT=3.39 min, m/z: 416 [M+H$^+$].

Method 4

Example 34

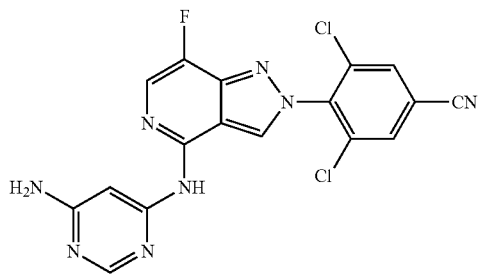 [SMILES: N#Cc1cc(Cl)c(-n2cc3c(Nc4cc(N)ncn4)ncc(F)c3n2)c(Cl)c1]

4-[4-(6-Amino-pyrimidin-4-ylamino)-7-fluoro-pyrazolo[4,3-c]pyridin-2-yl]-3,5-dichlorobenzonitrile·HCl

Step 1

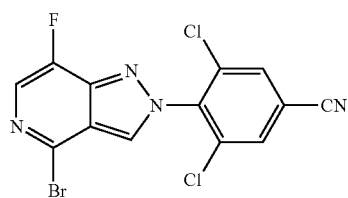 [SMILES: N#Cc1cc(Cl)c(-n2cc3c(Br)ncc(F)c3n2)c(Cl)c1]

3,5-Dichloro-4-(4-bromo-7-fluoro-pyrazolo[4,3-c]pyridin-2-yl)-benzonitrile

To a suspension of 3,5-dichloro-4-(7-fluoro-5-oxy-pyrazolo[4,3-c]pyridin-2-yl)-benzonitrile (1.0 mg, 3.1 mmol) in DCE (20 mL) at 0° C. was added phosphorus oxybromide (2.4 g, 9.2 mmol). The reaction mixture was stirred at 0° C. for 30 minutes, warmed to room temperature, and stirred for an additional 3 h. The reaction mixture was diluted with DCM and washed with sodium bicarbonate (sat. aq.). The organic phase was dried over anhydrous sodium sulphate and concentrated under reduced pressure. The residue was purified by silica gel flash chromatography (0-50% ethyl acetate in cyclohexane) to afford the title compound as a white solid (370 mg, 31% yield). LCMS (Method D): RT=3.66 min, m/z: 387 [M+H$^+$].

Step 2

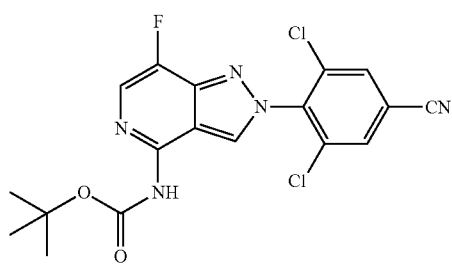 [SMILES: CC(C)(C)OC(=O)Nc1ncc(F)c2nn(-c3c(Cl)cc(C#N)cc3Cl)cc12]

2-(2,6-Dichloro-4-cyanophenyl)-7-fluoro-2H-pyrazolo[4,3-c]pyridin-4-yl]-carbamic acid tert-butyl ester A mixture of 3,5-dichloro-4-(4-bromo-7-fluoro-pyrazolo[4,3-c]pyridin-2-yl)-benzonitrile (370 mg, 0.96 mmol), tert-butyl carbamate (559 mg, 4.8 mmol), Pd$_2$(dba)$_3$ (44 mg, 0.05 mmol), Xantphos (55 mg, 0.1 mmol) and potassium phosphate tribasic (405 mg, 1.9 mmol) in toluene (10 mL) and water (2.0 mL) was purged with argon and heated at 60° C. for 1.5 hour. The reaction mixture was filtered through Celite® and washed with ethyl acetate. The filtrate was washed with water and brine, dried over sodium sulphate, and concentrated under reduced pressure. The residue was purified by silica gel flash chromatography (0-50% ethyl acetate in cyclohexane) to afford the title compound as a yellow solid (568 mg, contaminated with residual tert-butyl carbamate). LCMS (Method D): RT=3.51 min, m/z: 366 [M-C$_4$H$_8^+$].

Step 3

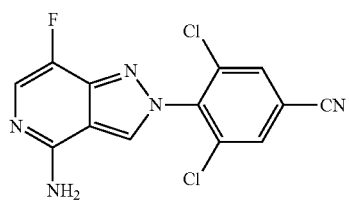 [SMILES: N#Cc1cc(Cl)c(-n2cc3c(N)ncc(F)c3n2)c(Cl)c1]

4-(4-Amino-7-fluoropyrazolo[4,3-c]pyridin-2-yl)-3,5-dichlorobenzonitrile

A mixture of 2-(2,6-dichloro-4-cyanophenyl)-7-fluoro-2H-pyrazolo[4,3-c]pyridin-4-yl]-carbamic acid tert-butyl ester (568 mg, contaminated with residual tert-butyl carbamate) and HCl (4 N in dioxane, 5.0 mL, 20 mmol) was stirred at room temperature for 18 h and then concentrated under reduced pressure. The residue was partitioned between ethyl acetate and sodium bicarbonate (sat. aq.). The organic layer was washed with brine, dried over anhydrous sodium sulfate, and concentrated to dryness under reduced pressure to afford the title compound as a beige solid (272 g, 88% yield over 2 steps). LCMS (Method D): RT=2.04 min, m/z: 322 [M+H$^+$].

Step 4

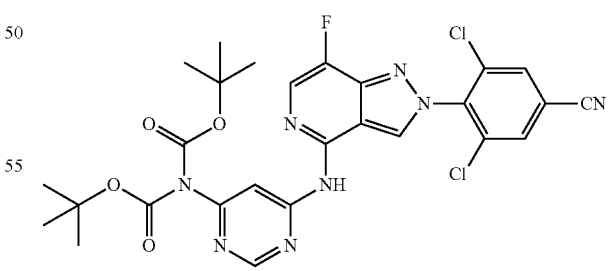

{6-[2-(2,6-Dichloro-4-cyanophenyl)-2H-pyrazolo[4,3-c]pyridin-4-ylamino]-7-fluoropyrimidin-4-yl}bis-carbamic acid tert-butyl ester Following the procedure described for 3,5-dichloro-4-[4-(2,6-dimethylpyrimidin-4-ylamino)pyrazolo[4,3-c]pyridin- 2-yl]benzonitrile, 4-(4-amino-7-fluoropyrazolo[4,3-c]pyridin-2-yl)-3,5-dichlorobenzonitrile and (6-chloropyrimidin-4-yl)bis-carbamic acid tert-butyl ester were reacted to afford the title compound an off-white solid (166 mg, 32% yield). LCMS (Method D): RT=4.14 min, m/z: 615 [M+H$^+$].

Step 5

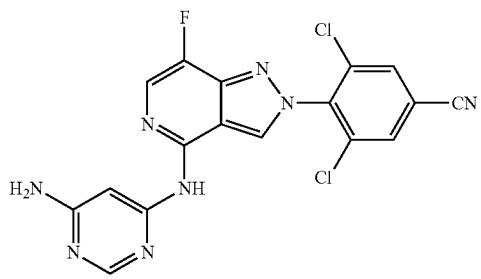 [SMILES: N#Cc1cc(Cl)c(-n2cc3c(Nc4cc(N)ncn4)ncc(F)c3n2)c(Cl)c1]

4-[4-(6-Amino-pyrimidin-4-ylamino)-7-fluoro-pyrazolo[4,3-c]pyridin-2-yl]-3,5-dichlorobenzonitrile A suspension of {6-[2-(2,6-dichloro-4-cyanophenyl)-2H-pyrazolo[4,3-c]pyridin-4-ylamino]-7-fluoropyrimidin-4-yl}bis-carbamic acid tert-butyl ester (166 mg, 0.27 mmol) and HCl (4 N in dioxane, 5.0 mL, 20 mmol) was stirred at room temperature for 18 h. The reaction mixture was partitioned between ethyl acetate and sodium bicarbonate (sat. aq.). The organic phase was washed with brine, dried over anhydrous sodium sulfate, concentrated under reduced pressure. The residue was purified by silica gel flash chromatography (50-100% ethyl acetate in cyclohexane) to afford the title compound as a white solid (29 mg, 26% yield). $^1$H NMR (400 MHz, DMSO-d$_6$): δ 10.19 (br s, 1H), 9.31 (d, J=2.6 Hz, 1H), 8.49 (s, 2H), 8.13-8.12 (m, 1H), 7.87 (d, J=3.5 Hz, 1H), 7.55 (d, J=1.3 Hz, 1H), 6.69 (br s, 2H). LCMS (Method D): RT=2.35 min, m/z: 415 [M+H$^+$].

Step 6

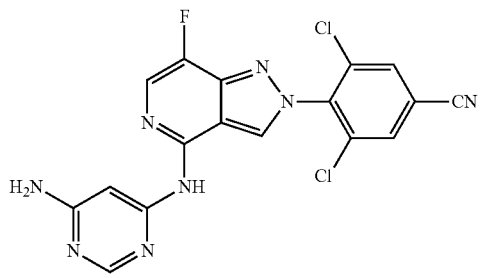

4-[4-(6-Aminopyrimidin-4-ylamino)-7-fluoro-pyrazolo[4,3-c]pyridin-2-yl]-3,5-dichlorobenzonitrile hydrochloride salt A mixture of 4-[4-(6-aminopyrimidin-4-ylamino)-7-fluoropyrazolo[4,3-c]pyridin-2-yl]-3,5-dichlorobenzonitrile (77 mg, 0.19 mmol) and HCl (4 N in dioxane, 5.0 mL, 20 mmol) was stirred at room temperature for 2 hours. The reaction mixture was concentrated under reduced pressure and the residue was dried to afford the title compound as an off-white solid (81 mg, 96% yield). $^1$H NMR (400 MHz, DMSO-d$_6$): δ 9.45 (d, J=2.3 Hz, 1H), 8.57 (s, 1H), 8.50 (s, 2H), 8.03 (d, J=3.3 Hz, 1H), 7.25 (br s, 1H). LCMS (Method B): RT=3.16 min, m/z: 415 [M+H$^+$].

Method 2

Example 35

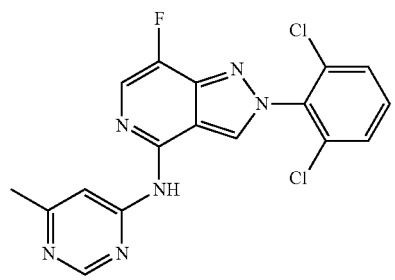 [SMILES: Cc1cc(Nc2ncc(F)c3nn(-c4c(Cl)cccc4Cl)cc23)ncn1]

[2-(2,6-Dichlorophenyl)-7-fluoro-2H-pyrazolo[4,3-c]pyridin-4-yl]-(6-methyl-pyrimidin-4-yl)-amine Step 1

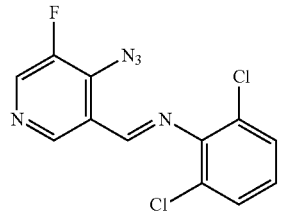 [SMILES: [N-]=[N+]=Nc1c(F)cncc1/C=N/c1c(Cl)cccc1Cl]

1-(4-Azido-5-fluoropyridin-3-yl)-meth-(E)-ylidene]-(2,6-dichlorophenyl)-amine

To a cooled (0° C.) solution of 4-azido-5-fluoropyridine-3-carbaldehyde (4.98 g, 30.0 mmol), 2,6-dichloroaniline (4.86 g, 30.0 mmol) and triethylamine (12.5 mL, 90.0 mmol) in DCM (100 mL) under nitrogen was added titanium tetrachloride (1M in DCM, 18 mL, 18.0 mmol) dropwise over 20 minutes. The reaction mixture was stirred for 2 hours, warmed to room temperature, and stirred for a further 4 hours. The resulting mixture was concentrated under reduced pressure. The residue was suspended in toluene and filtered though a pad of Celite®. The filtrate was concentrated to dryness under reduced pressure to afford the title compound as a yellow solid. This crude material was employed in the next step without further purification or analysis.

Step 2

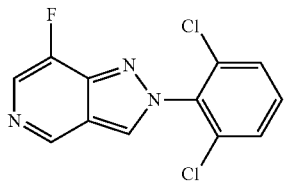 [SMILES: Fc1cncc2cn(-c3c(Cl)cccc3Cl)nc12]

2-(2,6-Dichlorophenyl)-7-fluoro-2H-pyrazolo[4,3-c]pyridine

A mixture of 1-(4-azido-5-fluoropyridin-3-yl)-meth-(E)-ylidene]-(2,6-dichloro-phenyl)-amine (30.0 mmol) in toluene (100 mL) was heated to 105° C. for 18 hours. The reaction mixture was cooled and concentrated under reduced pressure. The resultant residue was triturated with diethylether to afford the title compound as a beige solid (5.44 g, 64% yield). LCMS (Method D): RT=2.81 min, m/z: 282 [M)+H+].

Step 3

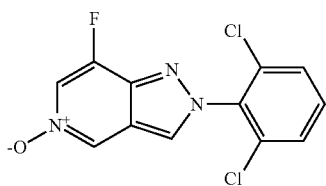

2-(2,6-Dichlorophenyl)-7-fluoro-2H-pyrazolo[4,3-c]pyridine 5-oxide

To a cooled (0° C.) solution of 2-(2,6-dichlorophenyl)-7-fluoro-2H-pyrazolo[4,3-c]pyridine (5.4 g, 19.1 mmol) in DCM (100 mL) was added mCPBA (5.2 g, 30.0 mmol). The reaction mixture was stirred for 1.5 hours, warmed to room temperature, and stirred for a further 16 hours. Sodium thiosulfate (sat. aq.) was added and the layers were partitioned. The organic layer was washed with sodium hydrogen carbonate (sat. aq.) and brine, dried over anhydrous sodium sulfate, and concentrated under reduced pressure. The residue was triturated with ether to afford the title compound as a beige solid (5.04 g, 89% yield). LCMS (Method C): RT=2.45 min, m/z: 298 [M+H+].

Step 4

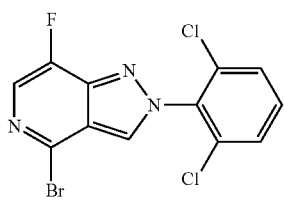

4-Bromo-2-(2,6-dichlorophenyl)-7-fluoro-2H-pyrazolo[4,3-c]pyridine

To a cooled (0° C.) solution of 2-(2,6-dichlorophenyl)-7-fluoro-2H-pyrazolo[4,3-c]pyridine 5-oxide (2.5 g, 8.4 mmol) in DCE (55 mL) under nitrogen was added phosphorous oxybromide (7.2 g, 25.2 mmol). The reaction mixture was stirred for 30 minutes, warmed to room temperature, and stirred for a further 4 hours. The reaction was quenched with sodium carbonate (sat. aq.) and the layers were partitioned. The organic layer was washed with brine, dried over anhydrous sodium sulfate, and concentrated under reduced pressure. The resultant residue was purified by silica gel flash chromatography (20% ethyl acetate in cyclohexane) to afford the title compound as a white solid (927 mg, 31% yield). LCMS (Method D): RT=3.74 min, m/z: 360 [M+H+].

Step 5

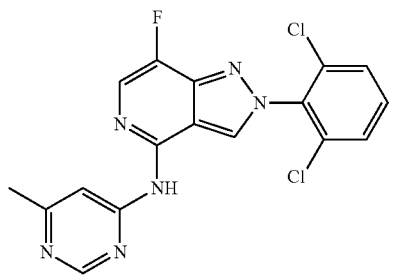 [SMILES: Cc1cc(Nc2ncc(F)c3nn(-c4c(Cl)cccc4Cl)cc23)ncn1]

[2-(2,6-Dichlorophenyl)-7-fluoro-2H-pyrazolo[4,3-c]pyridin-4-yl]-(6-methyl-pyrimidin-4-yl)-amine A suspension of 4-bromo-2-(2,6-dichlorophenyl)-7-fluoro-2H-pyrazolo[4,3c]pyridine (271 mg, 0.75 mmol), 4-amino-6-methylpyrimidine (90 mg, 0.083 mmol), $Pd_2(dba)_3$ (17 mg, 0.019 mmol), Xantphos (43 mg, 0.075 mmol) and cesium carbonate (489 mg, 1.5 mmol) in dioxane (10 mL) was sealed in a microwave vial, purged with nitrogen and irradiated at 150° C. for 1 hour in the microwave. The reaction mixture was cooled and partitioned between ethyl acetate and water. The organic layer was washed with brine, dried over anhydrous sodium sulfate, and concentrated under reduced pressure. The residue was purified by silica gel flash chromatography (50-60% ethyl acetate in cyclohexane) to afford the title compound as a yellow solid (227 mg, 78% yield). $^1$H NMR (400 MHz, DMSO-$d_6$): δ 10.70 (s, 1H), 9.27 (d, J=2.6 Hz, 1H), 8.69 (d, J=1.3 Hz, 1H), 8.37 (s, 1H), 7.98 (d, J=3.4 Hz, 1H), 7.85 (d, J=1.4 Hz, 1H), 7.85 (s, 1H), 7.74 (dd, J=7.5 and 9.2 Hz, 1H), 2.44 (s, 3H). LCMS (Method B): RT=3.28 min, m/z: 389 [M+H+].

Method 2

Example 36

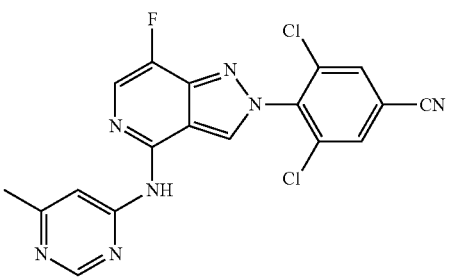

4-[7-Bromo-4-(6-methyl-pyrimidin-4-ylamino)-pyrazolo[4,3-c]pyridin-2-yl]-3,5-dichlorobenzonitrile Step 1

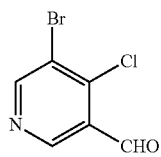

5-Bromo-4-chloro-pyridine-3-carbaldehyde

Following the procedure described for 4,5-dichloropyridine-3-carbaldehyde, 3-bromo-4-chloropyridine and DMF were reacted to afford the title compound as a white solid (3.74 g, 73% yield). $^1$H NMR (300 MHz, CDCl$_3$): δ 10.48 (d, J=0.4 Hz, 1H), 8.95-8.92 (m, 2H).

Step 2

4-Azido-5-bromo-pyridine-3-carbaldehyde

Following the procedure described for 4-azido-5-chloro-pyridine-3-carbaldehyde, 5-bromo-4-chloropyridine-3-carbaldehyde and sodium azide were reacted to afford the title compound as a pale yellow solid (3.18 g, 83% yield). $^1$H NMR (400 MHz, CDCl$_3$): δ 10.30 (s, 1H), 8.85 (s, 1H), 8.79 (s, 1H).

Step 3

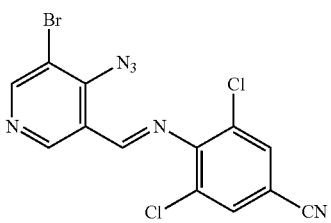

4-{1-(4-Azido-5-bromo-pyridin-3-yl)-meth-(E)-ylidene]-amino}-3,5-dichlorobenzonitrile Following the procedure described for 4-{[1-(4-azido-5-chloropyridin-3-yl)meth-(E)-ylidene]amino}-3,5-dichlorobenzonitrile, 4-azido-5-bromo-pyridine-3-carbaldehyde and 4-amino-3,5-dichlorobenzonitrile were reacted to afford the title compound as a beige solid (quant. yield) that was used without purification.

Step 4

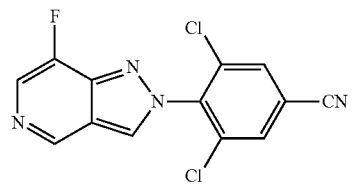

4-(7-Bromo-pyrazolo[4,3-c]pyridin-2-yl)-3,5-dichlorobenzonitrile

Following the procedure described for 3,5-dichloro-4-(7-chloropyrazolo[4,3-c]pyridin-2-yl)benzonitrile, 4-{[1-(4-azido-5-bromo-pyridin-3-yl)-meth-(E)-ylidene]-amino}-3,5-dichlorobenzonitrile was heated under reflux in toluene to afford the title compound as a beige solid (3.57 g, 70% yield). $^1$H NMR (300 MHz, methanol-d$_4$): δ 9.26 (s, 1H), 9.06 (s, 1H), 8.46 (s, 1H), 8.20 (s, 2H).

Step 5

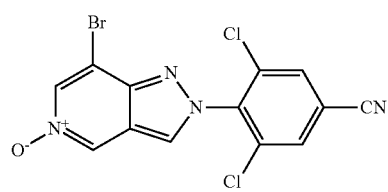

4-(7-Bromo-5-oxy-pyrazolo[4,3-c]pyridin-2-yl)-3,5-dichlorobenzonitrile

To a solution of 4-(7-bromo-pyrazolo[4,3-c]pyridin-2-yl)-3,5-dichlorobenzonitrile (1.5 g, 4.1 mmol) and methyltrioxorhenium (5.1 mg, 0.02 mmol) in DCM (2.8 mL) was added hydrogen peroxide (30% aq., 0.8 mL, 8.2 mmol) and the resulting mixture stirred at room temperature for 18 hours. Additional methyltrioxorhenium (10 mg, 0.04 mmol) was added, the mixture stirred for 24 hours and then catalytic manganese dioxide was added. After stirring for an additional hour the mixture was partitioned between DCM and brine. The organic layer was dried over anhydrous sodium sulfate and concentrated to dryness under reduced pressure. The residue was purified by silica gel chromatography (0-10% methanol in DCM) to afford the title compound as a yellow solid (295 mg, 19% yield). $^1$H NMR (300 MHz, CDCl$_3$): δ 8.84 (s, 1H), 8.29 (s, 2H), 7.85 (s, 2H).

Step 6

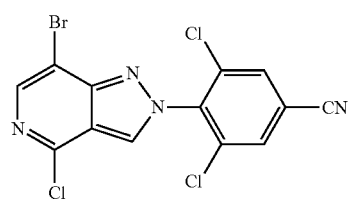 [SMILES: N#Cc1cc(Cl)c(-n2cc3c(Cl)ncc(Br)c3n2)c(Cl)c1]

4-(7-Bromo-4-chloro-pyrazolo[4,3-c]pyridin-2-yl)-3,5-dichlorobenzonitrile

Following the procedure described for 3,5-dichloro-4-(4,7-dichloropyrazolo[4,3-c]pyridin-2-yl)benzonitrile, 4-(7-bromo-5-oxy-pyrazolo[4,3-c]pyridin-2-yl)-3,5-dichlorobenzonitrile and phosphorus oxychloride were reacted to afford the title compound as a white solid (101 mg, 33% yield). $^1$H NMR (300 MHz, CDCl$_3$): δ 8.40 (s, 1H), 8.31 (s, 1H), 7.86 (s, 2H).

Step 7

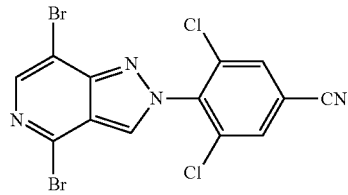 [SMILES: N#Cc1cc(Cl)c(-n2cc3c(Br)ncc(Br)c3n2)c(Cl)c1]

3,5-Dichloro-4-(4,7-dibromo-pyrazolo[4,3-c]pyridin-2-yl)-benzonitrile

A mixture of 3,5-dichloro-4-(4-chloro-7-fluoro-pyrazolo[4,3-c]pyridin-2-yl)-benzonitrile (99 mg, 0.25 mmol) and trimethylsilyl bromide (161 μL, 1.22 mmol) in propionitrile (5 mL) was heated under reflux for 22 hours then concentrated under reduced pressure. The residue was partiti0oned between ethyl acetate and sodium bicarbonate (sat. aq.). The organic layer was dried over anhydrous sodium sulphate and concentrated under reduced pressure. The resultant solid was purified by silica gel chromatography (0-40% ethyl acetate in cyclohexane) to afford the title compound as a white solid (83 mg, 75% yield). $^1$H NMR (300 MHz, CDCl$_3$): δ 8.33 (s, 1H), 8.29 (s, 1H), 7.85 (s, 2H).

Step 8

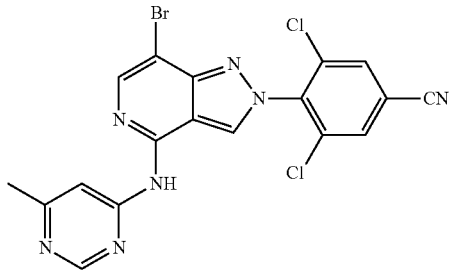

4-[7-Bromo-4-(6-methyl-pyrimidin-4-ylamino)-pyrazolo[4,3-c]pyridin-2-yl]-3,5-dichlorobenzonitrile A suspension of 3,5-dichloro-4-(4,7-dibromo-pyrazolo[4,3-c]pyridin-2-yl)-benzonitrile (70 mg, 0.16 mmol), 6-methylpyrimidin-4-ylamine (18 mg, 0.17 mmol), Pd$_2$(dba)$_3$ (7 mg, 0.008 mmol), Xantphos (9 mg, 0.016 mmol) and cesium carbonate (104 mg, 0.31 mmol) in dioxane (3 mL) was sealed in a microwave vial, purged with nitrogen, and heated at 90° C. for 3.5 hours. The reaction mixture was cooled and partitioned between ethyl acetate and water. The organic layer was dried over anhydrous sodium sulfate and concentrated under reduced pressure. The resultant residue was purified by silica gel flash chromatography (0-100% ethyl acetate in cyclohexane), then futher triturated with diethyl ether then ethyl acetate to afford the title compound as a white solid (42 mg, 57% yield). $^1$H NMR (400 MHz, DMSO-d6): δ 10.90 (s, 1H), 9.35 (s, 1H), 8.71 (d, J=1.2 Hz, 1H), 8.50 (s, 2H), 8.37 (s, 1H), 8.17 (s, 1H), 2.45 (s, 3H). LCMS (Method B): RT=3.75 min, m/z: 476 [M+H$^+$].

Method 2

Example 37

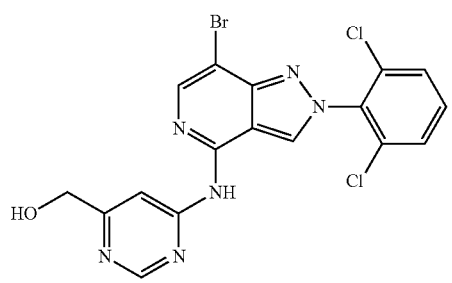

{6-[7-Bromo-2-(2,6-dichloro-phenyl)-2H-pyrazolo[4,3-c]pyridin-4-ylamino]-pyrimidin-4-yl}-methanol Step 1

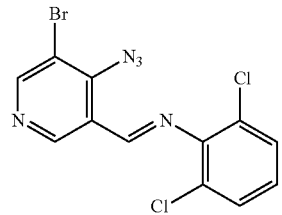 [SMILES: [N-]=[N+]=Nc1c(Br)cncc1/C=N/c1c(Cl)cccc1Cl]

[1-(4-Azido-5-bromopyridin-3-yl)-meth-(E)-ylidene]-(2,6-dichlorophen yl)-amine

Following the procedure described for 4-{[1-(4-azido-5-chloropyridin-3-yl)meth-(E)-ylidene]amino}-3,5-dichlorobenzonitrile, 4-azido-5-bromopyridine-3-carbaldehyde and 2,6-dichloroaniline were reacted to afford the title compound as a beige solid that was used without purification.

Step 2

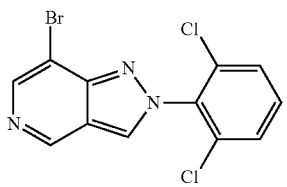

7-Bromo-2-(2,6-dichlorophenyl)-2H-pyrazolo[4,3-c]pyridine

Following the procedure described for 3,5-dichloro-4-(7-chloropyrazolo[4,3-c]pyridin-2-yl)benzonitrile, [1-(4-azido-5-bromopyridin-3-yl)-meth-(E)-ylidene]-(2,6-dichlorophenyl)-amine was heated under reflux in toluene to afford the title compound as a brown solid (7.5 g, 81% yield). LCMS (Method D): RT=2.90 min, m/z: 344 [M+H$^+$].

Step 3

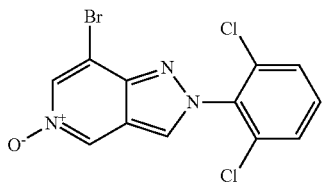

7-Bromo-2-(2,6-dichlorophenyl)-2H-pyrazolo[4,3-c]pyridine-5-oxide

To a solution of 7-bromo-2-(2,6-dichlorophenyl)-2H-pyrazolo[4,3-c]pyridine (3.43 g, 10 mmol) and methyltrioxorhenium (249 mg, 1.0 mmol) in DCM (35 mL) was added hydrogen peroxide (30% aq., 1.95 mL, 20 mmol) and the resulting mixture stirred at room temperature for 18 hours. The reaction mixture was partitioned between DCM and sodium bicarbonate (sat. aq.). The organic layer was washed with brine, dried over anhydrous sodium sulfate, and concentrated under reduced pressure. The residue was purified by silica gel chromatography (0-5% methanol in DCM) to afford the title compound as a beige solid (1.7 g, 47% yield). LCMS (Method D): RT=2.46 min, m/z: 360 [M+H$^+$].

Step 4

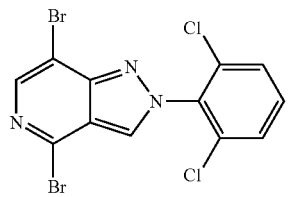

4,7-Dibromo-2-(2,6-dichlorophenyl)-2H-pyrazolo[4,3-c]pyridine

To a cooled (0° C.) suspension of 7-bromo-2-(2,6-dichlorophenyl)-2H-pyrazolo[4,3-c]pyridine-5-oxide (1.7 g, 4.7 mmol) in DCE (30 mL) was added phosphorus oxybromide (4.0 g, 14.1 mmol). The reaction mixture was stirred at 0° C. for 15 minutes, warmed to room temperature, and stirred for a further 2.25 hours. The reaction mixture was partitioned between DCM and sodium carbonate (sat. aq.). The organic layer was washed with brine, dried over anhydrous sodium sulfate, and concentrated under reduced pressure. The residue was purified by silica gel flash chromatography (0-20% ethyl acetate in cyclohexane) to afford the title compound as a white solid (1.07 g, 54% yield). LCMS (Method D): RT=3.93 min, m/z: 422 [M+H$^+$].

Step 5

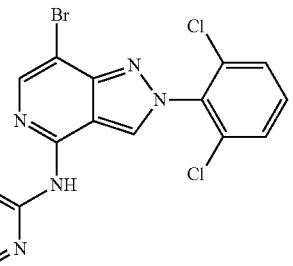

{6-[7-Bromo-2-(2,6-dichlorophenyl)-2H-pyrazolo[4,3-c]pyridin-4-ylamino]-pyrimidin-4-yl}-methanol A suspension of 4,7-dibromo-2-(2,6-dichlorophenyl)-2H-pyrazolo[4,3-c]pyridine (317 mg, 0.75 mmol), (6-amino-pyrimidin-4-yl)-methanol (104 mg, 0.83 mmol), Pd$_2$(dba)$_3$ (17 mg, 0.019 mmol), Xantphos (43 mg, 0.075 mmol) and cesium carbonate (489 mg, 1.5 mmol) in dioxane (11 mL) was sealed in a microwave vial, purged with nitrogen, and irradiated in a microwave reactor at 150° C. for 1 hour. The reaction mixture was cooled and partitioned between ethyl acetate and water. The organic layer was washed with brine, dried over anhydrous sodium sulfate, and concentrated under reduced pressure. The residue was purified by silica gel flash chromatography (50-100% ethyl acetate in cyclohexane), to afford the title compound as a white solid (229 mg, 66% yield). $^1$H NMR (400 MHz, DMSO-d$_6$): δ 10.84 (br s, 1H), 9.31 (s, 1H), 8.72 (d, J=1.2 Hz, 1H), 8.61-8.60 (m, 1H), 8.16 (s, 1H), 7.85 (d, J=1.2 Hz, 1H), 7.83 (s, 1H), 7.74 (dd, J=7.2, 1.6 Hz, 1H), 5.60 (t, J=5.8 Hz, 1H), 4.53 (d, J=5.7 Hz, 2H). LCMS (Method D): RT=3.21 min, m/z: 467 [M+H$^+$].

Method 2

Example 38

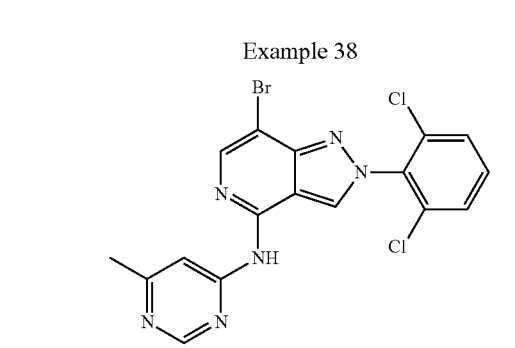

[7-Bromo-2-(2,6-dichlorophenyl)-2H-pyrazolo[4,3-c]pyridin-4-yl]-(6-methylpyrimidin-4-yl)-amine A suspension of 4,7-dibromo-2-(2,6-dichlorophenyl)-2H-pyrazolo[4,3-c]pyridine (317 mg, 0.75 mmol), 6-methylpyrimidin-4-ylamine (90 mg, 0.83 mmol), Pd$_2$(dba)$_3$ (17 mg, 0.019 mmol), Xantphos (43 mg, 0.075 mmol) and cesium carbonate (489 mg, 1.5 mmol) in dioxane (11 mL) was sealed in a microwave vial, purged with nitrogen, and irradiated in a microwave reactor at 150° C. for 1 hour. The reaction mixture was cooled and partitioned between ethyl acetate and water. The organic layer was washed with brine, dried over anhydrous sodium sulfate, and concentrated under reduced pressure. The residue was purified by silica gel flash chromatography (50-60% ethyl acetate in cyclohexane), to afford the title compound as a yellow solid (215 mg, 64% yield). $^1$H NMR (400 MHz, DMSO-$d_6$): δ 10.80 (s, 1H), 9.29 (s, 1H), 8.72 (d, J=1.3 Hz, 1H), 8.40 (s, 1H), 8.17 (s, 1H), 7.85 (d, J=0.9 Hz, 1H), 7.82 (s, 1H), 7.74 (dd, J=7.1 and 9.0 Hz, 1H), 2.46 (s, 3H). LCMS (Method B): RT=3.60 min, m/z: 449 [M+H$^+$].

Method 2

Example 39

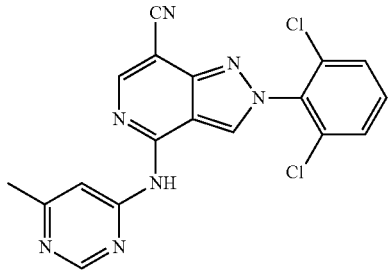 [SMILES: Cc1cc(Nc2ncc(C#N)c3nn(-c4c(Cl)cccc4Cl)cc23)ncn1]

2-(2,6-Dichlorophenyl)-4-(6-methylpyrimidin-4-ylamino)-2H-pyrazolo[4,3-c]pyridine-7-carbonitrile A suspension of [7-bromo-2-(2,6-dichlorophenyl)-2H-pyrazolo[4,3-c]pyridin-4-yl]-(6-methylpyrimidin-4-yl)-amine (100 mg, 0.22 mmol), Zn(CN)$_2$ (52 mg, 0.44 mmol), and Pd(PPh$_3$)$_4$ (25 mg, 0.022 mmol), in DMA (1.0 mL) was sealed in a microwave vial, purged with nitrogen, and irradiated in a microwave reactor at 150° C. for 30 minutes. The reaction mixture was cooled and partitioned between ethyl acetate and water. The organic layer was washed with brine, dried over anhydrous sodium sulfate, and concentrated under reduced pressure. The resultant residue was purified by silica gel flash chromatography (0-70% ethyl acetate in cyclohexane), to afford the title compound as an off-white solid (15 mg, 17% yield). $^1$H NMR (400 MHz, DMSO-$d_6$): δ 11.32 (br s, 1H), 9.36 (s, 1H), 8.80 (d, J=1.0 Hz, 1H), 8.61 (s, 1H), 8.46 (s, 1H), 7.86 (d, J=1.0 Hz, 1H), 7.83 (s, 1H), 7.74 (dd, J=7.4, 1.8 Hz, 1H), 2.50 (s, 3H). LCMS (Method B): RT=3.84 min, m/z: 396 [M+H$^+$].

Method 4

Example 40

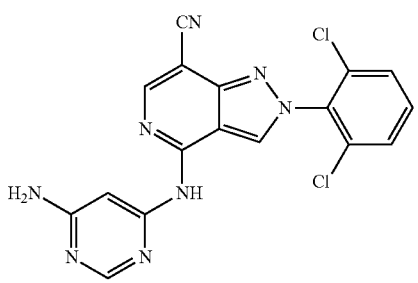

4-(6-Aminopyrimidin-4-ylamino)-2-(2,6-dichlorophenyl)-2H-pyrazolo[4,3-c]pyridine-7-carbonitrile Step 1

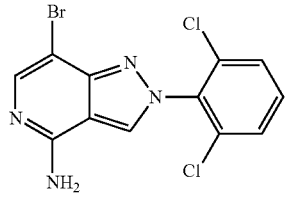

7-Bromo-2-(2,6-dichlorophenyl)-2H-pyrazolo[4,3-c]pyridin-4-ylamine

A solution of 4,7-dibromo-2-(2,6-dichlorophenyl)-2H-pyrazolo[4,3-c]pyridine (730 mg, 1.73 mmol) in NMP (6.5 mL) and 33% aqueous ammonia (3.5 mL) was sealed in a microwave vial and irradiated in a microwave reactor at 160° C. for 2 hours. The reaction mixture was cooled and partitioned between ethyl acetate and water. The organic layer was washed with brine, dried over anhydrous sodium sulfate, and concentrated under reduced pressure. The residue was triturated with ether to afford the title compound as a beige solid (515 mg, 84% yield). LCMS (Method C): RT=2.00 min, m/z: 357 [M+H$^+$].

Step 2

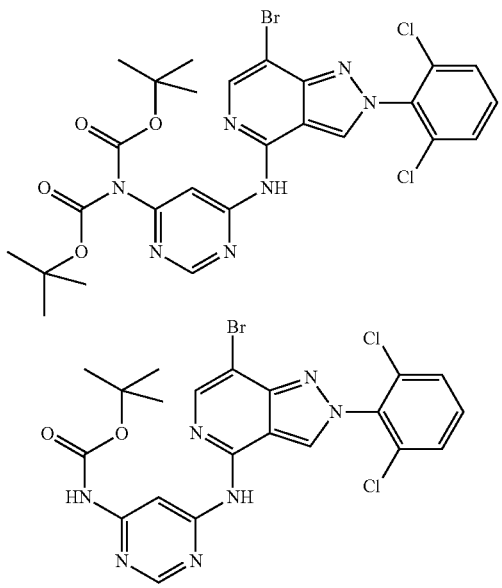

{6-[7-Bromo-2-(2,6-dichlorophenyl)-2H-pyrazolo[4,3-c]pyridin-4-ylamino]-pyrimidin-4-yl}-bis-carbamic acid tert-butyl ester and {6-[7-Bromo-2-(2,6-dichlorophenyl)-2H-pyrazolo[4,3-c]pyridin-4-ylamino]-pyrimidin-4-yl}-carbamic acid tert-butyl ester A suspension of 4,7-dibromo-2-(2,6-dichlorophenyl)-2H-pyrazolo[4,3-c]pyridine (515 mg, 1.45 mmol), (6-chloropyrimidin-4-yl)-bis-carbamic acid tert-butyl ester (560 mg, 1.7 mmol), Pd$_2$(dba)$_3$ (33 mg, 0.036 mmol), Xantphos (83 mg, 0.144 mmol) and cesium carbonate (939 mg, 2.88 mmol) in dioxane (10 mL) was sealed in a microwave vial, purged with nitrogen, and irradiated in a microwave reactor at 150° C. for 30 minutes. The reaction mixture was cooled and partitioned between ethyl acetate and water. The organic layer was washed with brine, dried over anhydrous sodium sulfate, and concentrated under reduced pressure. The residue was purified by silica gel flash chromatography (20-100% ethyl acetate in cyclohexane), to afford the first title compound as a white solid (315 mg, 33% yield); LCMS (Method D): RT=4.32 min, m/z: 650 [M+H⁺]. The second title compound was also obtained as a yellow solid (97 mg, 12% yield); LCMS (Method D): RT=3.10 min, m/z: 550 [M+H⁺].

Step 3

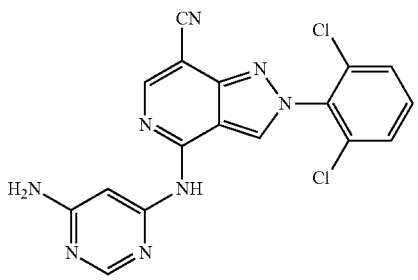 [SMILES: N#Cc1cnc(Nc2cc(N)ncn2)c2cn(-c3c(Cl)cccc3Cl)nc12]

4-(6-Amino-pyrimidin-4-ylamino)-2-(2,6-dichlorophenyl)-2H-pyrazolo[4,3-c]pyridine-7-carbonitrile A suspension of {6-[7-bromo-2-(2,6-dichlorophenyl)-2H-pyrazolo[4,3-c]pyridin-4-ylamino]-pyrimidin-4-yl}-bis-carbamic acid tert-butyl ester (141 mg, 0.22 mmol), $Zn(CN)_2$ (52 mg, 0.44 mmol), and $Pd(PPh_3)_4$ (25 mg, 0.022 mmol) in DMA (3 mL) was sealed in a microwave vial, purged with nitrogen, and irradiated in a microwave reactor at 150° C. for 30 minutes. The reaction mixture was cooled and partitioned between ethyl acetate and water. The organic layer was washed with brine, dried over anhydrous sodium sulfate, and concentrated under reduced pressure. The resultant residue was purified by silica gel flash chromatography (0-2% methanol in ethyl acetate), to afford the title compound as an off-white solid (33 mg, 38% yield). ¹H NMR (400 MHz, DMSO-$d_6$): δ 10.77 (s, 1H), 9.35 (s, 1H), 8.51 (s, 1H), 8.20 (d, J=0.9 Hz, 1H), 7.85 (d, J=0.9 Hz, 1H), 7.83 (s, 1H), 7.74 (dd, J=7.0 and 8.8 Hz, 1H), 7.62 (s, 1H), 6.89 (br s, 2H). LCMS (Method B): RT=3.04 min, m/z: 397 [M+H⁺].

Method 4

Example 41

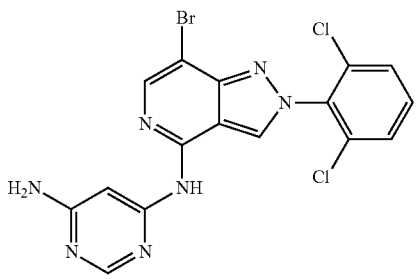

N-[7-Bromo-2-(2,6-dichlorophenyl)-2H-pyrazolo[4,3-c]pyridin-4-yl]-pyrimidine-4,6-diamine A solution of {6-[7-bromo-2-(2,6-dichlorophenyl)-2H-pyrazolo[4,3-c]pyridin-4-ylamino]-pyrimidin-4-yl}-carbamic acid tert-butyl ester (95 mg, 0.18 mmol) in DCM (2 mL) and TFA (1 mL) was stirred at room temperature for 3 hours. The solvent was removed and the residue partitioned between DCM and $NaHCO_3$ (sat. aq.). The organic layer was washed with brine, dried over anhydrous sodium sulfate, and concentrated under reduced pressure. The residue was purified by silica gel flash chromatography (70-90% ethyl acetate in cyclohexane), to afford the title compound as a white solid (23 mg, 29% yield). ¹H NMR (400 MHz, DMSO-$d_6$): δ 10.22 (s, 1H), 9.29 (s, 1H), 8.15 (d, J=0.9 Hz, 1H), 8.04 (s, 1H), 7.84 (d, J=1.2 Hz, 1H), 7.82 (s, 1H), 7.73 (dd, J=7.1 and 9.0 Hz, 1H), 7.59 (d, J=1.2 Hz, 1H), 6.74 (br s, 2H). LCMS (Method B): RT=3.25 min, m/z: 450 [M+H⁺].

Method 2

Example 42

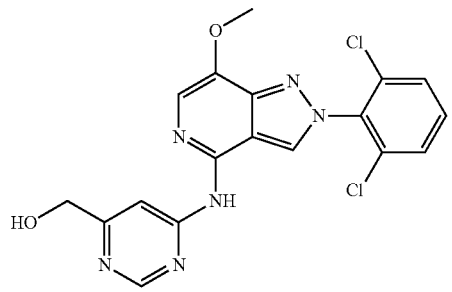 [SMILES: COc1cnc(Nc2cc(CO)ncn2)c2cn(-c3c(Cl)cccc3Cl)nc12]

{6-[2-(2,6-Dichlorophenyl)-7-methoxy-2H-pyrazolo[4,3-c]pyridin-4-ylamino]-pyrimidin-4-yl}-methanol Step 1

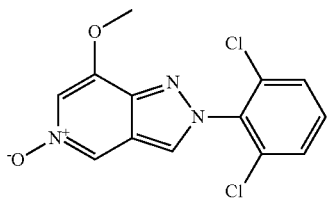

2-(2,6-Dichloro-phenyl)-7-methoxy-2H-pyrazolo[4,3-c]pyridine 5-oxide

A suspension of 2-(2,6-dichlorophenyl)-7-fluoro-2H-pyrazolo[4,3-c]pyridine-5-oxide (1.5 g, 5 mmol) and potassium methoxide (525 mg, 7.5 mmol) in methanol (10 mL) was sealed in a microwave vial, purged with nitrogen and irradiated at 150° C. for 30 minutes in the microwave. The reaction mixture was cooled and partitioned between ethyl acetate and water. The organic layer was washed with brine, dried over anhydrous sodium sulfate, and concentrated under reduced pressure. The residue was triturated with ether to afford the title compound as a beige solid (1.32 g, 85% yield). LCMS (Method D): RT=2.31 min, m/z: 310 [M+H⁺].

Step 2

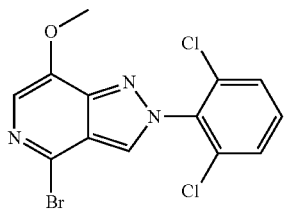 [SMILES: COc1cnc(Br)c2cn(-c3c(Cl)cccc3Cl)nc12]

4-Bromo-2-(2,6-dichlorophenyl)-7-methoxy-2H-pyrazolo[4,3-c]pyridine

To a cooled (0° C.) solution of 2-(2,6-dichlorophenyl)-7-methoxy-2H-pyrazolo[4,3-c]pyridine 5-oxide (1.3 g, 4.2 mmol) in DCE (30 mL) under nitrogen was added phosphorous oxybromide (2.4 g, 8.4 mmol). The reaction mixture was stirred for 30 minutes, warmed to room temperature, and stirred for a further 4 hours. Further phosphorous oxybromide (1.8 g, 6.3 mmol) was added and the reaction mixture was stirred for a further 16 hours. The temperature was raised to 80° C. and stirred for 2 hours. The resultant mixture was cooled, quenched with sodium carbonate (sat. aq.) and the layers were partitioned. The organic layer was washed with brine, dried over anhydrous sodium sulfate, and concentrated under reduced pressure. The resultant residue was purified by silica gel flash chromatography (30-40% ethyl acetate in cyclohexane) to afford the title compound as a white solid (143 mg, 9% yield). LCMS (Method D): RT=3.52 min, m/z: 372 [M+H⁺].

Step 3

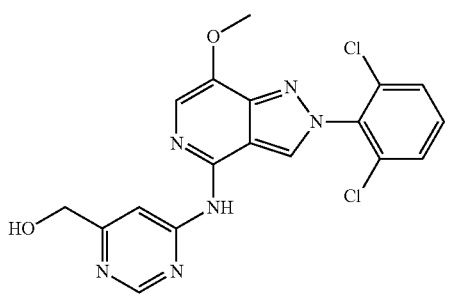 [SMILES: COc1cnc(Nc2cc(CO)ncn2)c2cn(-c3c(Cl)cccc3Cl)nc12]

{6-[2-(2,6-Dichlorophenyl)-7-methoxy-2H-pyrazolo[4,3-c]pyridin-4-ylamino]-pyrimidin-4-yl}-methanol A suspension of 4-bromo-2-(2,6-dichlorophenyl)-7-methoxy-2H-pyrazolo[4,3-c]pyridine (135 mg, 0.36 mmol), (6-aminopyrimidin-4-yl)methanol (50 mg, 0.4 mmol), Pd₂(dba)₃ (8 mg, 0.009 mmol), Xantphos (43 mg, 0.036 mmol) and cesium carbonate (235 mg, 0.72 mmol) in dioxane (3 mL) was sealed in a microwave vial, purged with nitrogen and irradiated at 150° C. for 1 hour in the microwave. The reaction mixture was cooled and partitioned between ethyl acetate and water. The organic layer was washed with brine, dried over anhydrous sodium sulfate, and concentrated under reduced pressure. The residue was purified by silica gel flash chromatography (0-2% methanol in ethyl acetate) to afford the title compound as a yellow solid (62 mg, 41% yield). $^1$H NMR (400 MHz, DMSO-$d_6$): δ 10.42 (s, 1H), 9.11 (s, 1H), 8.64 (d, J=0.9 Hz, 1H), 8.58 (d, J=1.2 Hz, 1H), 7.83 (d, J=1.3 Hz, 1H), 7.80 (s, 1H), 7.72 (dd, J=7.5, 9.2 Hz, 1H), 7.58 (s, 1H), 5.54 (t, J=6.0 Hz, 1H), 4.50 (d, J=6.0 Hz, 2H), 3.97 (s, 3H). LCMS (Method B): RT=2.75 min, m/z: 417 [M+H⁺].

Method 2

Example 43

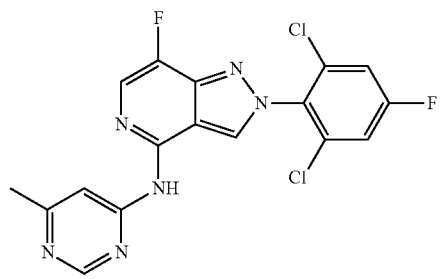 [SMILES: Cc1cc(Nc2ncc(F)c3nn(-c4c(Cl)cc(F)cc4Cl)cc23)ncn1]

[2-(2,6-Dichloro-4-fluorophenyl)-7-fluoro-2H-pyrazolo[4,3-c]pyridin-4-yl]-(6-methylpyrimidin-4-yl)-amine Step 1

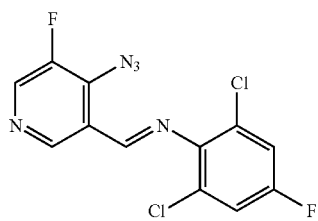 [SMILES: [N-]=[N+]=Nc1c(F)cncc1/C=N/c1c(Cl)cc(F)cc1Cl]

[1-(4-Azido-5-fluoropyridin-3-yl)-meth-(E)-ylidene]-(2,6-dichloro-4-fluorophenyl)-amine To a cooled (0° C.) solution of 4-azido-5-fluoro-pyridine-3-carbaldehyde (2.44 g, 14.7 mmol), 2,6-dichloro-4-fluorophenylamine (2.65 g, 14.7 mmol) and triethylamine (6.1 mL, 44 mmol) in DCM (50 mL) was added titanium tetrachloride (1M in DCM, 8.8 mL, 8.8 mmol) dropwise. The reaction mixture was stirred at 0° C. for 1 hour, warmed to room temperature, and stirred for a further 4 hours. The mixture was concentrated under reduced pressure. The residue was dissolved in toluene and filtered through Celite®.

The filtrate was concentrated under to dryness under reduced pressure to afford the title compound that was used without further purification.

Step 2

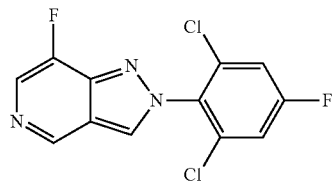 [SMILES: Fc1cc(Cl)c(-n2cc3cncc(F)c3n2)c(Cl)c1]

2-(2,6-Dichloro-4-fluorophenyl)-7-fluoro-2H-pyrazolo[4,3-c]pyridine

A suspension of [1-(4-azido-5-fluoropyridin-3-yl)-meth-(E)-ylidene]-(2,6-dichloro-4-fluorophenyl)-amine (14.7 mmol) in toluene (40 mL) was heated under reflux for 16 hours then allowed to cool to room temperature. The reaction mixture was concentrated under reduced pressure. The residue was purified by silica gel flash chromatography (0-50% ethyl acetate in cyclohexane) to afford the title compound as an off-white solid (3.38 g, 77% yield). LCMS (Method D): RT=2.84 min, m/z: 300 [M+H$^+$].

Step 3

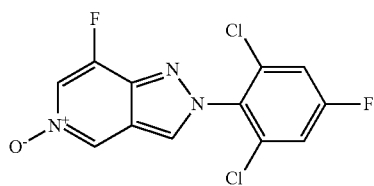 [SMILES: [O-][n+]1cc(F)c2nn(-c3c(Cl)cc(F)cc3Cl)cc2c1]

2-(2,6-Dichloro-4-fluorophenyl)-7-fluoro-2H-pyrazolo[4,3-c]pyridine-5-oxide

To a cooled (0° C.) solution of 2-(2,6-dichloro-4-fluorophenyl)-7-fluoro-2H-pyrazolo[4,3-c]pyridine (3.37 g, 11.2 mmol) in DCM (50 mL) under nitrogen, was added mCPBA (2.9 g, 16.8 mmol). The reaction mixture was stirred at 0° C. for 2 hours, warmed to room temperature, and stirred for a further 5 hours. The reaction was washed with sodium thiosulfate (sat. aq.), sodium hydrogen carbonate (sat. aq.), and brine. The organic layer was then dried over anhydrous sodium sulphate and concentrated under reduced pressure. The residue was purified by trituration with diethyl ether to afford the title compound as an off-white solid (2.98 g, 84% yield). LCMS (Method D): RT=2.48 min, m/z: 316 [M+H$^+$].

Step 4

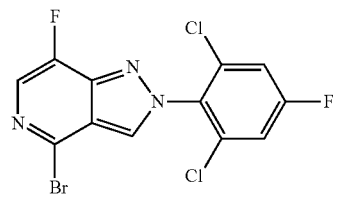 [SMILES: Fc1cc(Cl)c(-n2cc3c(Br)ncc(F)c3n2)c(Cl)c1]

4-Bromo-2-(2,6-dichloro-4-fluorophenyl)-7-fluoro-2H-pyrazolo[4,3-c]pyridine

To a cooled (0° C.) suspension of 2-(2,6-dichloro-4-fluorophenyl)-7-fluoro-2H-pyrazolo[4,3-c]pyridine-5-oxide (2.95 g, 9.3 mmol) in DCE (50 mL) was added phosphorus oxybromide (8.0 g, 28 mmol). The reaction mixture was stirred at 0° C. for 1 hour, warmed to room temperature, and stirred for a further 3 hours. The reaction mixture was diluted with DCM and washed with sodium carbonate (sat. aq.). The organic layer was dried over anhydrous sodium sulfate and concentrated under reduced pressure. The residue was purified by silica gel flash chromatography (0-20% ethyl acetate in cyclohexane) to afford the title compound as a white solid (1.0 g, 28% yield). LCMS (Method D): RT=3.82 min, m/z: 380 [M+H$^+$].

Step 5

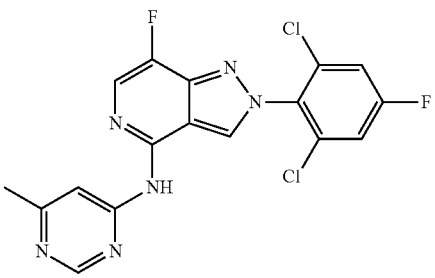 [SMILES: Cc1cc(Nc2ncc(F)c3nn(-c4c(Cl)cc(F)cc4Cl)cc23)ncn1]

[2-(2,6-Dichloro-4-fluorophenyl)-7-fluoro-2H-pyrazolo[4,3-c]pyridin-4-yl]-(6-methylpyrimidin-4-yl)-amine Following the procedure described for 3,5-dichloro-4-[7-chloro-4-(6-methylpyrimidin-4-ylamino)pyrazolo[4,3-c]pyridin-2-yl]benzonitrile, 4-bromo-2-(2,6-dichloro-4-fluorophenyl)-7-fluoro-2H-pyrazolo[4,3-c]pyridine and 6-methylpyrimidin-4-ylamine were reacted to afford the title compound as a white solid (38 mg, 36% yield). $^1$H NMR (400 MHz, DMSO-d$_6$): δ 10.72 (s, 1H), 9.26 (d, J=2.6 Hz, 1H), 8.69 (d, J=1.2 Hz, 1H), 8.36 (s, 1H), 7.98 (d, J=3.5 Hz, 1H), 7.96 (s, 1H), 7.94 (s, 1H), 2.44 (s, 3H). LCMS (Method B): RT=3.44 min, m/z: 407 [M+H$^+$].

Additional Examples 44-89, made according to the general synthetic method given, are shown in the below Table 2.

TABLE 2

| Example | Structure | Name | Synth. Method | LCMS (ESI) m/z | LCMS Method | R$_T$ (min) | NMR |
|---|---|---|---|---|---|---|---|
| 44 | 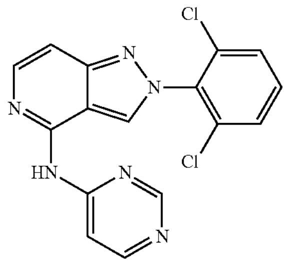 [SMILES: Clc1cccc(Cl)c1-n1cc2c(Nc3ccncn3)nccc2n1] | [2-(2,6-Dichlorophenyl)-2H-pyrazolo[4,3-c]pyridine-4-yl]pyrimidin-4-ylamine | 2 | 357 | B | 2.71 | $^1$H NMR (400 MHz, DMSO-d$_6$): δ 10.76 (br s, 1H), 9.16 (s, 1H), 8.84 (s, 1H), 8.64-8.62 (m, 2H), 8.00 (d, J = 6.4 Hz, 1H), 7.82 (d, J = 8.1 Hz, 2H), 7.72 (dd, J = 9.0, 7.3 Hz, 1H), 7.26 (d, J = 6.4 Hz, 1H). |
| 45 | 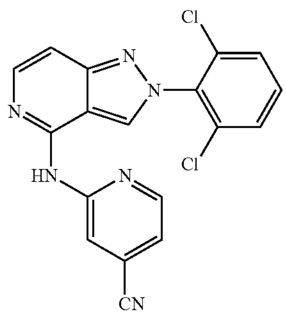 [SMILES: N#Cc1ccnc(Nc2nccc3nn(-c4c(Cl)cccc4Cl)cc23)c1] | 2-[2-(2,6-Dichlorophenyl)-2H-pyrazolo[4,3-c]pyridin-4-ylamino]isonicotinonitrile | 2 | 381 | B | 3.07 | $^1$H NMR (400 MHz, DMSO-d$_6$): δ 9.54 (d, J = 0.9 Hz, 1H), 8.78 (dd, J = 5.3, 0.9 Hz, 1H), 8.00 (d, J = 7.3 Hz, 1H), 7.87 (d, J = 1.5 Hz, 1H), 7.85-7.84 (m, 2H), 7.79-7.78 (m, 2H), 7.61 (dd, J = 7.3, 0.9 Hz, 1H). |
| 46 | 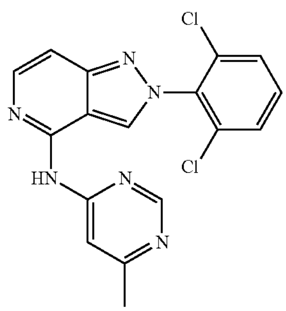 [SMILES: Cc1cc(Nc2nccc3nn(-c4c(Cl)cccc4Cl)cc23)ncn1] | [2-(2,6-Dichlorophenyl)-2H-pyrazolo[4,3-c]pyridine-4-yl]-(6-methylpyrimidin-4-yl)amine | 2 | 371 | B | 2.83 | $^1$H NMR (400 MHz, DMSO-d$_6$): δ 10.61 (br s, 1H), 9.15 (s, 1H), 8.69 (s, 1H), 8.51 (s, 1H), 7.99 (d, J = 6.4 Hz, 1H), 7.81 (d, J = 8.1 Hz, 2H), 7.70 (dd, J = 9.0, 7.3 Hz, 1H), 7.22 (d, J = 6.4 Hz, 1H), 3.31 (s, 3H). |
| 47 | 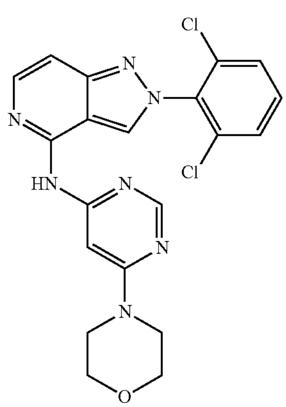 [SMILES: Clc1cccc(Cl)c1-n1cc2c(Nc3cc(N4CCOCC4)ncn3)nccc2n1] | [2-(2,6-Dichlorophenyl)-2H-pyrazolo[4,3-c]pyridin-4-yl]-(6-morpholin-4-ylpyrimidin-4-yl)amine | 2 | 442 | B | 3.17 | $^1$H NMR (400 MHz, DMSO-d$_6$): δ 10.24 (br s, 1H), 9.15 (s, 1H), 8.31 (s, 1H), 8.10 (s, 1H), 7.96 (d, J = 6.4 Hz, 1H), 7.80 (d, J = 8.1 Hz, 2H), 7.70 (t, J = 8.1 Hz, 1H), 7.15 (d, J = 6.4 Hz, 1H), 3.71 (d, J = 5.1 Hz, 4H), 3.58 (d, J = 5.0 Hz, 4H). |

TABLE 2-continued

| Example | Structure | Name | Synth. Method | LCMS (ESI) m/z | LCMS Method | R$_T$ (min) | NMR |
|---|---|---|---|---|---|---|---|
| 48 | 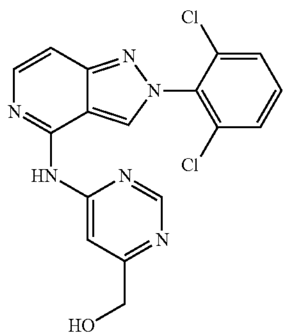 [SMILES: OCc1cc(Nc2nccc3nn(-c4c(Cl)cccc4Cl)cc23)ncn1] | {6-[2-(2,6-Dichlorophenyl)-2H-pyrazolo[4,3-c]pyridin-4-ylamino]pyrimidin-4-yl}methanol | 2 | 387 | B | 2.66 | $^1$H NMR (400 MHz, DMSO-d$_6$): δ 9.53 (d, J = 0.9 Hz, 1H), 9.04 (d, J = 1.1 Hz, 1H), 8.08 (d, J = 7.3 Hz, 1H), 7.88-7.83 (m, 2H), 7.77 (dd, J = 9.1, 7.2 Hz, 1H), 7.64 (dd, J = 7.3, 0.9 Hz, 1H), 7.62 (s, 1H), 4.66 (s, 2H) |
| 49 | 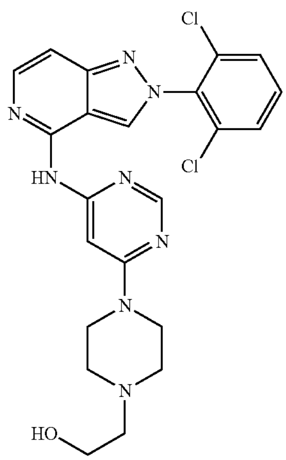 [SMILES: OCCN1CCN(c2cc(Nc3nccc4nn(-c5c(Cl)cccc5Cl)cc34)ncn2)CC1] | 2-(4-(6-((2-(2,6-dichlorophenyl)-2H-pyrazolo[4,3-c]pyridin-4-yl)amino)-pyrimidin-4-yl)piperazin-1-yl)ethan-1-ol | 2 | 485 | B | 2.35 | $^1$H NMR (400 MHz, DMSO-d$_6$): δ 10.19 (br s, 1H), 9.15 (s, 1H), 8.28 (s, 1H), 8.09 (s, 1H), 7.96 (d, J = 6.4 Hz, 1H), 7.81 (d, J = 8.1 Hz, 2H), 7.70 (dd, J = 9.0, 7.3 Hz, 1H), 7.15 (d, J = 6.4 Hz, 1H), 4.45 (br s, 1H), 3.67-3.55 (m, 6H), 2.60-2.52 (m, 4H), 2.50-2.42 (m, 2H). |
| 50 | 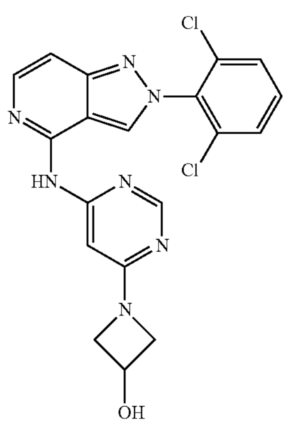 [SMILES: OC1CN(c2cc(Nc3nccc4nn(-c5c(Cl)cccc5Cl)cc34)ncn2)C1] | 1-{6-[2-(2,6-Dichlorophenyl)-2H-pyrazolo[4,3-c]pyridin-4-ylamino]pyrimidin-4-yl}azetidin-3-ol | 2 | 428 | B | 2.86 | $^1$H NMR (400 MHz, DMSO-d$_6$): δ 10.19 (br s, 1H), 9.14 (s, 1H), 8.24 (s, 1H), 7.94 (d, J = 6.4 Hz, 1H), 7.80 (d, J = 8.1 Hz, 2H), 7.70 (dd, J = 9.0, 7.3 Hz, 1H), 7.59 (s, 1H), 7.15 (d, J = 6.4 Hz, 1H), 5.75 (br s, 1H), 4.66-4.58 (m, 1H), 4.25 (t, J = 7.8 Hz, 2H), 3.77 (dd, J = 9.0, 4.4 Hz, 2H). |
| 51 | 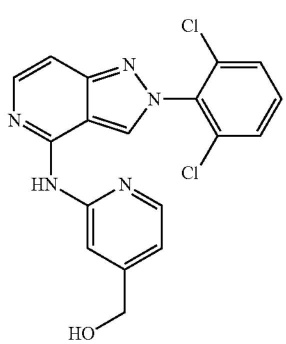 [SMILES: OCc1ccnc(Nc2nccc3nn(-c4c(Cl)cccc4Cl)cc23)c1] | {2-[2-(2,6-Dichlorophenyl)-2H-pyrazolo[4,3-c]pyridin-4-ylamino]pyridin-4-yl}methanol | 2 | 386 | B | 2.98 | $^1$H NMR (400 MHz, DMSO-d$_6$): δ 9.44 (d, J = 0.9 Hz, 1H), 8.45 (d, J = 5.4 Hz, 1H), 7.98 (d, J = 7.3 Hz, 1H), 7.84-7.82 (m, 2H), 7.74 (dd, J = 9.1, 7.2 Hz, 1H), 7.52-7.48 (m, 2H), 7.28 (d, J = 5.5 Hz, 1H), 4.67 (s, 2H). |

| Example | Structure | Name | Synth. Method | LCMS (ESI) m/z | LCMS Method | R$_T$ (min) | NMR |
|---|---|---|---|---|---|---|---|
| 52 | 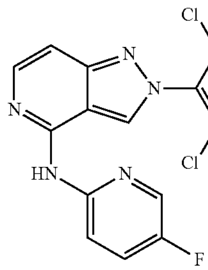 | [2-(2,6-Dichlorophenyl)-2H-pyrazolo[4,3-c]pyridin-4-yl]-(5-fluoropyridin-2-yl)amine | 2 | 374 | B | 3.14 | $^1$H NMR (400 MHz, DMSO-d$_6$): δ 10.30 (s, 1H), 9.11 (s, 1H), 8.71 (dd, J = 9.3, 4.2 Hz, 1H), 8.33 (d, J = 3.1 Hz, 1H), 7.89 (d, J = 6.4 Hz, 1H), 7.83-7.81 (m, 2H), 7.81-7.67 (m, 2H), 7.11-7.09 (m, 1H). |
| 53 | 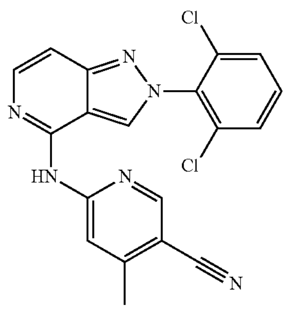 [SMILES: Cc1cc(Nc2nccc3nn(-c4c(Cl)cccc4Cl)cc23)ncc1C#N] | 6-[2-(2,6-Dichlorophenyl)-2H-pyrazolo[4,3-c]pyridin-4-ylamino]-4-methyl-nicotinonitrile | 2 | 395 | B | 3.21 | $^1$H NMR (400 MHz, DMSO-d$_6$): δ 10.75 (s, 1H), 9.15 (s, 1H), 8.72 (s, 1H), 8.67 (s, 1H), 7.98 (d, J = 6.4 Hz, 1H), 7.85-7.77 (m, 2H), 7.71 (dd, J = 9.0, 7.3 Hz, 1H), 7.22 (d, J = 6.4 Hz, 1H), 3.31 (s, 3H). |
| 54 | 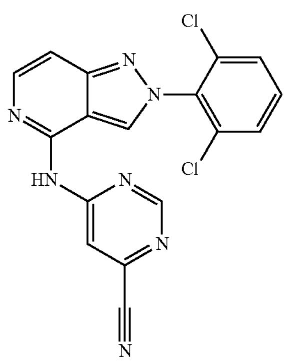 [SMILES: N#Cc1cc(Nc2nccc3nn(-c4c(Cl)cccc4Cl)cc23)ncn1] | 6-[2-(2,6-Dichlorophenyl)-2H-pyrazolo[4,3-c]pyridin-4-ylamino]pyrimidine-4-carbonitrile | 2 | 382 | B | 3.58 | $^1$H NMR (400 MHz, DMSO-d$_6$): δ 9.62 (s, 1H), 9.24 (d, J = 1.2 Hz, 1H), 8.10 (d, J = 7.2 Hz, 1H), 8.07 (d, J = 1.2 Hz, 1H), 7.87 (d, J = 1.3 Hz, 1H), 7.85 (s, 1H), 7.77-7.75 (m, 2H). |
| 55 | 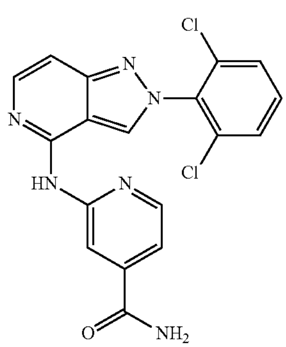 [SMILES: NC(=O)c1ccnc(Nc2nccc3nn(-c4c(Cl)cccc4Cl)cc23)c1] | 2-[2-(2,6-Dichlorophenyl)-2H-pyrazolo[4,3-c]pyridin-4-ylamino]-isonicotinamide | 2 | 399 | B | 2.92 | $^1$H NMR (400 MHz, DMSO-d$_6$): δ 9.52 (s, 1H), 8.12 (d, J = 6.7 Hz, 1H), 7.90 (d, J = 7.3 Hz, 1H), 7.85 (d, J = 1.3 Hz, 1H), 7.83 (s, 1H), 7.78-7.73 (m, 1H), 7.71-7.68 (m, 1H), 7.54 (d, J = 7.3 Hz, 1H), 7.47 (dd, J = 6.7, 1.6 Hz, 1H). |

TABLE 2-continued

| Example | Structure | Name | Synth. Method | LCMS (ESI) m/z | LCMS Method | R$_T$ (min) | NMR |
|---|---|---|---|---|---|---|---|
| 56 | 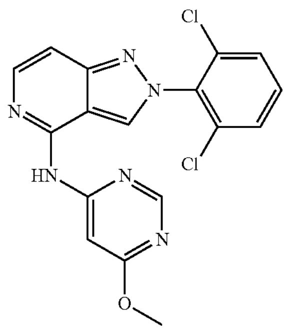 [SMILES: COc1cc(Nc2nccc3nn(-c4c(Cl)cccc4Cl)cc23)ncn1] | [2-(2,6-Dichlorophenyl)-2H-pyrazolo[4,3-c]pyridin-4-yl]-(6-methoxypyrimidin-4-yl)amine | 2 | 387 | B | 3.02 | $^1$H NMR (400 MHz, DMSO-d$_6$): δ 10.62 (s, 1H), 9.16 (s, 1H), 8.52 (s, 1H), 8.11 (s, 1H), 7.98 (d, J = 6.4 Hz, 1H), 7.82-7.79 (m, 2H), 7.71 (dd, J = 9.1, 7.3 Hz, 1H), 7.21 (d, J = 6.4 Hz, 1H), 3.93 (s, 3H). |
| 57 | 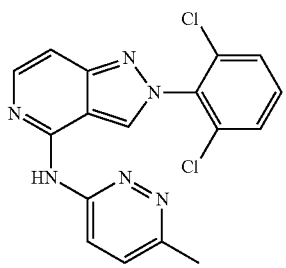 [SMILES: Cc1ccc(Nc2nccc3nn(-c4c(Cl)cccc4Cl)cc23)nn1] | [2-(2,6-Dichlorophenyl)-2H-pyrazolo[4,3-c]pyridin-4-yl](6-methylpyridazin-3-yl)amine | 2 | 371 | B | 2.83 | $^1$H NMR (400 MHz, DMSO-d$_6$): δ 9.50 (s, 1H), 8.08 (d, J = 7.3 Hz, 1H), 7.87-7.85 (m, 3H), 7.78-7.76 (m, 2H), 7.56 (d, J = 7.3 Hz, 1H), 2.70 (s, 3H). |
| 58 | 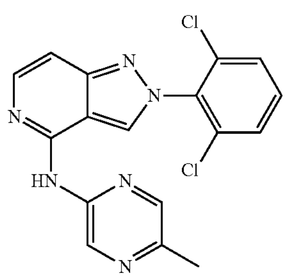 [SMILES: Cc1cnc(Nc2nccc3nn(-c4c(Cl)cccc4Cl)cc23)cn1] | [2-(2,6-Dichlorophenyl)-2H-pyrazolo[4,3-c]pyridin-4-yl]-(5-methylpyrazin-2-yl)amine | 2 | 371 | B | 2.92 | $^1$H NMR (400 MHz, DMSO-d$_6$): δ 14.56 (s, 1H), 9.53 (d, J = 0.9 Hz, 1H), 8.73 (d, J = 1.4 Hz 1H), 8.47-8.45 (m, 1H), 7.98 (d, J = 7.3 Hz, 1H), 7.85 (d, J = 1.3 Hz, 1H), 7.84 (s, 1H), 7.76 (dd, J = 9.1, 7.2 Hz, 1H), 7.55 (dd, J = 7.3, 0.9 Hz, 1H), 2.60 (s, 3H). |
| 59 | 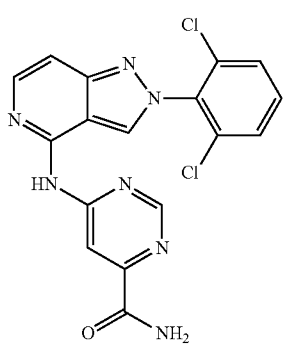 [SMILES: NC(=O)c1cc(Nc2nccc3nn(-c4c(Cl)cccc4Cl)cc23)ncn1] | 6-[2-(2,6-Dichlorophenyl)-2H-pyrazolo[4,3-c]pyridin-4-ylamino]-pyrimidine-4-carboxylic acid amide | 2 | 400 | B | 2.72 | $^1$H NMR (400 MHz, DMSO-d$_6$): δ 11.01 (s, 1H), 9.17 (s, 1H), 9.12 (s, 1H), 8.90 (d, J = 1.2 Hz, 1H), 8.20 (s, 1H), 8.07-8.01 (m, 1H), 7.88 (s, 1H), 7.85-7.78 (m, 2H), 7.71 (dd, J = 9.0, 7.3 Hz, 1H), 7.32-7.26 (m, 1H). |

| Example | Structure | Name | Synth. Method | LCMS (ESI) m/z | LCMS Method | R_T (min) | NMR |
|---|---|---|---|---|---|---|---|
| 60 | 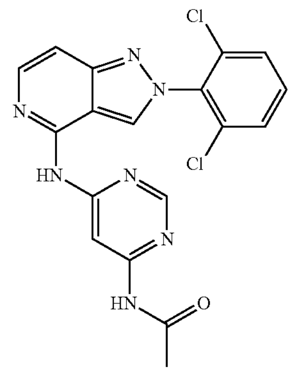 [SMILES: CC(=O)Nc1cc(Nc2nccc3nn(-c4c(Cl)cccc4Cl)cc23)ncn1] | N-{6-[2-(2,6-Dichloro-phenyl)-2H-pyrazolo[4,3-c]pyridin-4-ylamino]-pyrimidin-4-yl}-acetamide | 2 | 414 | B | 2.88 | $^1$H NMR (400 MHz, DMSO-d$_6$): δ 10.63 (s, 1H), 10.55 (s, 1H), 9.23 (s, 1H), 9.13 (s, 1H), 8.53 (d, J = 1.1 Hz, 1H), 7.94 (d, J = 6.4 Hz, 1H), 7.82-7.79 (m, 2H), 7.71 (dd, J = 9.0, 7.3 Hz, 1H), 7.22 (d, J = 6.4 Hz, 1H), 2.13 (s, 3H). |
| 61 | 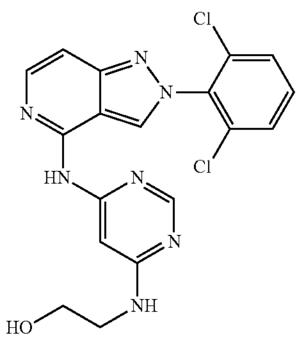 [SMILES: OCCNc1cc(Nc2nccc3nn(-c4c(Cl)cccc4Cl)cc23)ncn1] | 2-{6-[2-(2,6-Dichlorophenyl)-2H-pyrazolo[4,3-c]pyridin-4-ylamino]pyrimidin-4ylamino}ethanol | 2 | 416 | B | 2.86 | $^1$H NMR (400 MHz, DMSO-d$_6$): δ 10.02 (br s, 1H), 9.14 (s, 1H), 8.20 (s, 1H), 7.91 (d, J = 6.4 Hz, 1H), 7.83-7.75 (m, 3H), 7.70 (dd, J = 9.0, 7.3 Hz, 1H), 7.30 (br s, 1H), 7.14 (s, 1H), 4.72 (br s, 1H), 3.57-3.47 (m, 2H), 3.40-3.34 (m, 2H). |
| 62 | 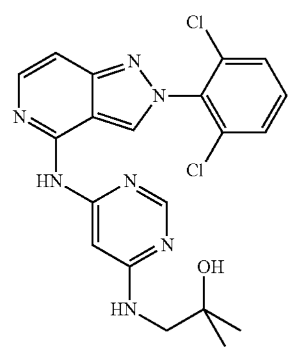 [SMILES: CC(C)(O)CNc1cc(Nc2nccc3nn(-c4c(Cl)cccc4Cl)cc23)ncn1] | 1-{6-[2-(2,6-Dichlorophenyl)-2H-pyrazolo[4,3-c]pyridin-4-ylamino]pyrimidin-4-ylamino}-2-methylpropan-2-ol | 2 | 444 | B | 3.04 | $^1$H NMR (400 MHz, DMSO-d$_6$): δ 10.02 (s, 1H), 9.15 (d, J = 1.0 Hz, 1H), 8.18 (s, 1H), 7.93 (d, J = 6.4 Hz, 1H), 7.84-7.81 (m, 4H), 7.73-7.69 (m, 1H), 7.14 (dd, J = 6.4. 1.0 Hz, 1H), 4.61 (s, 2H), 1.13 (s, 6H). |
| 63 | 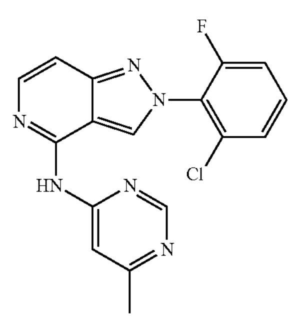 | [2-(2-Chloro-6-fluorophenyl)-2H-pyrazolo[4,3-c]pyridine-4-yl]-(6-methylpyrimidin-4-yl)amine | 2 | 355 | B | 2.72 | $^1$H NMR (400 MHz, DMSO-d$_6$): δ 10.66 (br s, 1H), 9.24 (s, 1H), 8.72 (s, 1H), 8.54 (s, 1H), 8.02 (d, J = 6.4 Hz, 1H), 7.80-7.72 (m, 1H), 7.74-7.60 (m, 2H), 7.24 (d, J = 6.4 Hz, 1H), 2.47 (s, 3H). |

TABLE 2-continued

| Example | Structure | Name | Synth. Method | LCMS (ESI) m/z | LCMS Method | R$_T$ (min) | NMR |
|---|---|---|---|---|---|---|---|
| 64 | 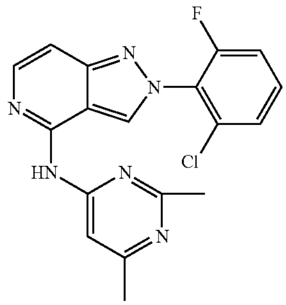 [SMILES: Cc1cc(Nc2nccc3nn(-c4c(F)cccc4Cl)cc23)nc(C)n1] | [2-(2-Chloro-6-fluorophenyl)-2H-pyrazolo[4,3-c]pyridine-4-yl]-(2,6-dimethyl-pyrimidin-4-yl)amine | 2 | 369 | B | 2.83 | $^1$H NMR (400 MHz, DMSO-d$_6$): δ 10.53 (br s, 1H), 9.21 (s, 1H), 8.33 (s, 1H), 7.97 (d, J = 6.4 Hz, 1H), 7.75-7.73 (m, 1H), 7.71-7.57 (m, 2H), 7.19 (d, J = 6.4 Hz, 1H), 3.31 (s, 3H), 2.40 (s, 3H). |
| 65 | 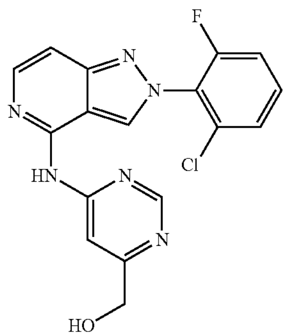 [SMILES: OCc1cc(Nc2nccc3nn(-c4c(F)cccc4Cl)cc23)ncn1] | {6-[2-(2-Chloro-6-fluoro-phenyl)-2H-pyrazolo[4,3-c]pyridin-4-ylamino]-pyrimidin-4-yl}-methanol | 2 | 470 | B | 2.56 | $^1$H NMR (400 MHz, DMSO-d$_6$): δ 10.63 (br s, 1H), 9.17 (s, 1H), 8.67 (d, J = 10.2, 2H), 7.95 (d, J = 7.6 Hz, 1H), 7.74-7.54 (m, 3H), 7.18 (d, J = 6.6 Hz, 1H), 5.55 (t, J = 6.0 Hz, 1H), 4.48 (d, J = 6.0 Hz, 2H). |
| 66 | 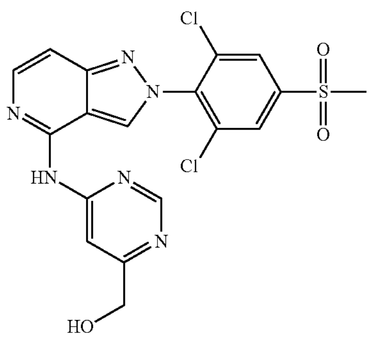 [SMILES: CS(=O)(=O)c1cc(Cl)c(-n2cc3c(Nc4cc(CO)ncn4)nccc3n2)c(Cl)c1] | {6-[2-(2,6-Dichloro-4-methane-sulphonyl-phenyl)-2H-pyrazolo[4,3-c]pyridine-4-ylamino]pyrimidin-4-yl}methanol | 2 | 465 | B | 2.54 | $^1$H NMR (400 MHz, DMSO-d$_6$): δ 10.76 (br s, 1H), 9.22 (s, 1H), 8.70 (s, 2H), 8.33 (s, 2H), 8.00 (d, J = 6.4 Hz, 1H), 7.25 (d, J = 6.4 Hz, 1H), 5.59 (br t, J = 5.8 Hz, 1H), 4.53 (d, J = 5.8 Hz, 2H), 3.48 (s, 3H). |
| 67 | 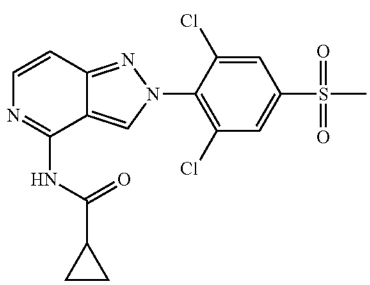 [SMILES: CS(=O)(=O)c1cc(Cl)c(-n2cc3c(NC(=O)C4CC4)nccc3n2)c(Cl)c1] | N-(2-(2,6-dichloro-4-methane-sulphonyl-phenyl)-2H-pyrazolo[4,3-c]pyridine-4-yl)cyclopropane-carboxamide | 2 | 425.14 | B | 2.74 | $^1$H NMR (400 MHz, DMSO-d$_6$): δ 11.17 (br s, 1H), 9.00 (s, 1H), 8.28 (s, 2H), 7.99 (d, J = 6.3 Hz, 1H), 7.39 (d, J = 6.3 Hz, 1H), 3.45 (s, 3H), 2.16-2.08 (m, 1H), 0.91-0.84 (m, 4H). |
| 68 | 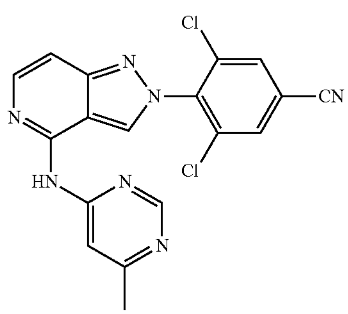 [SMILES: Cc1cc(Nc2nccc3nn(-c4c(Cl)cc(C#N)cc4Cl)cc23)ncn1] | 3,5-Dichloro-4-[4-(6-methylpyrimidin-4-ylamino)pyrazolo[4,3-c]pyridin-2-yl]benzonitrile | 2 | 396 | B | 2.86 | $^1$H NMR (400 MHz, DMSO-d$_6$): δ 9.53 (d, J = 0.9 Hz, 1H), 9.05 (d, J = 1.1 Hz, 1H), 8.54 (s, 2H), 8.06 (d, J = 7.1 Hz, 1H), 7.60 (dd, J = 7.2, 0.9 Hz, 1H), 7.55 (br s, 1H), 5.75 (s, 1H), 2.59 (s, 3H). |

TABLE 2-continued

| Example | Structure | Name | Synth. Method | LCMS (ESI) m/z | LCMS Method | R_T (min) | NMR |
|---|---|---|---|---|---|---|---|
| 69 | 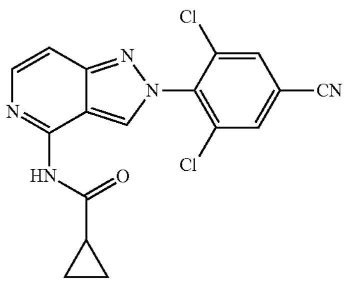 [SMILES: N#Cc1cc(Cl)c(-n2cc3c(NC(=O)C4CC4)nccc3n2)c(Cl)c1] | N-(2-(2,6-dichloro-4-cyanophenyl)-2H-pyrazolo[4,3-c]pyridin-4-yl)cyclopropane-carboxamide | 2 | 372 | B | 2.93 | $^1$H NMR (400 MHz, DMSO-d$_6$): δ 11.17 (br s, 1H), 8.99 (s, 1H), 8.44 (s, 2H), 7.99 (d, J = 6.3 Hz, 1H), 7.37 (d, J = 6.3 Hz, 1H), 2.14-2.12 (m, 1H), 0.89-0.84 (m, 4H). |
| 70 | 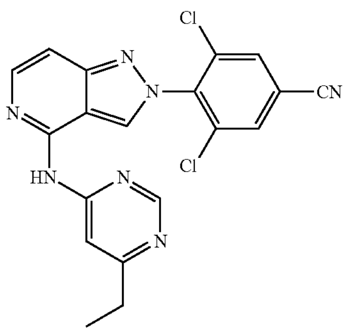 [SMILES: CCc1cc(Nc2nccc3nn(-c4c(Cl)cc(C#N)cc4Cl)cc23)ncn1] | 3,5-Dichloro-4-[4-(6-ethyl-pyrimidin-4-ylamino)-pyrazolo[4,3-c]pyridin-2-yl]-benzonitrile | 2 | 409 | B | 3.02 | $^1$H NMR (400 MHz, DMSO-d$_6$ + d-TFA): δ 9.49 (d, J = 0.9 Hz, 1H), 8.99 (d, J = 0.9 Hz, 1H), 8.47 (s, 2H), 7.99 (d, J = 7.0 Hz, 1H), 7.52 (dd, J = 7.54, 0.9 Hz, 1H), 7.40 (br s, 1H), 2.80 (q, J = 7.3, 2H), 1.23 (t, J = 6.9 Hz, 3H). |
| 71 | 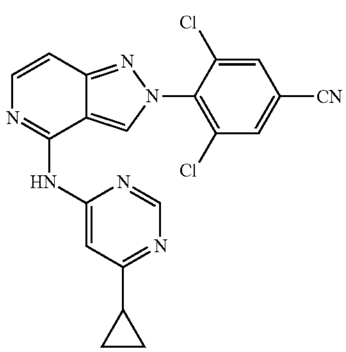 [SMILES: N#Cc1cc(Cl)c(-n2cc3c(Nc4cc(C5CC5)ncn4)nccc3n2)c(Cl)c1] | 3,5-Dichloro-4-[4-(6-cyclopropyl-pyrimidin-4-ylamino)pyrazolo[4,3-c]pyridin-2-yl]benzonitrile | 2 | 422 | B | 3.20 | $^1$H NMR (400 MHz, DMSO-d$_6$ + d-TFA): δ 9.53 (s, 1H), 8.87 (d, 1H), 8.47 (s, 2H), 7.99 (d, J = 7.5 Hz, 1H), 7.55 (dd, J = 7.5, 0.9 Hz, 1H), 7.32 (d, J = 0.9, 1H), 2.29-2.21 (m, 1H), 1.14-1.05 (m, 4H). |
| 72 | 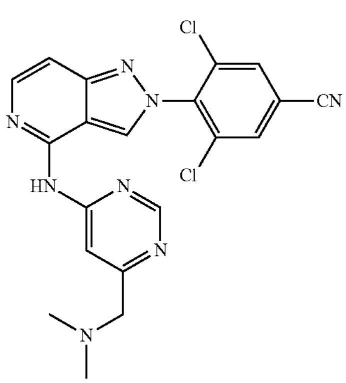 [SMILES: CN(C)Cc1cc(Nc2nccc3nn(-c4c(Cl)cc(C#N)cc4Cl)cc23)ncn1] | 3,5-Dichloro-4-[4-(6-dimethyl-aminomethyl-pyrimidin-4-ylamino)pyrazolo[4,3-c]pyridine-2-yl]benzonitrile | 2 | 439 | B | 2.25 | $^1$H NMR (400 MHz, DMSO-d$_6$ + d-TFA): δ 9.65 (d, J = 0.9 Hz, 1H), 9.21 (d, J = 1.2 Hz, 1H), 8.53 (s, 2H), 8.12 (d, J = 7.3 Hz, 1H), 7.71 (dd, J = 7.3, 0.9 Hz, 1H), 7.57 (s, 1H), 4.67 (s, 2H), 2.93 (s, 6H). |

| Example | Structure | Name | Synth. Method | LCMS (ESI) m/z | LCMS Method | R$_T$ (min) | NMR |
|---|---|---|---|---|---|---|---|
| 73 | 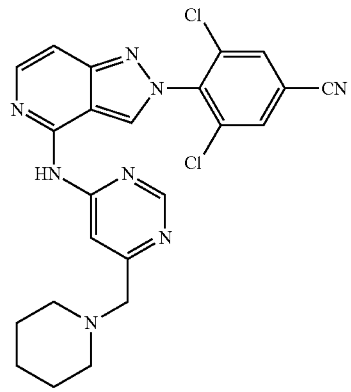 [SMILES: N#Cc1cc(Cl)c(-n2cc3c(Nc4cc(CN5CCCCC5)ncn4)nccc3n2)c(Cl)c1] | 3,5-Dichloro-4-[4-(6-piperidin-1-ylmethyl-pyrimidin-4-ylamino}pyrazolo[4,3-c]pyridine-2-yl)benzonitrile | 2 | 479 | B | 2.40 | $^1$H NMR (400 MHz, DMSO-d$_6$ + d-TFA): δ 9.65 (d, J = 0.9 Hz, 1H), 9.21 (d, J = 1.1 Hz, 1H), 8.54 (s, 2H), 8.12 (d, J = 7.3 Hz, 1H), 7.71 (dd, J = 7.3, 0.9 Hz, 1H), 7.57 (d, J = 1.1 Hz, 1H), 4.65 (s, 2H), 3.53-3.44 (m, 2H), 3.09-2.99 (m, 2H), 1.84-1.66 (m, 6H). |
| 74 | 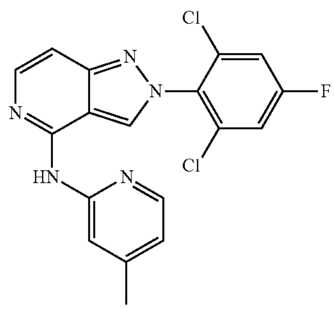 [SMILES: Cc1ccnc(Nc2nccc3nn(-c4c(Cl)cc(F)cc4Cl)cc23)c1] | [2-(2,6-Dichloro-4-fluorophenyl)-2H-pyrazolo[4,3-c]pyridine-4-yl]-(4-methylpyridin-2-yl)amine | 2 | 389 | B | 3.39 | $^1$H NMR (400 MHz, DMSO-d$_6$ + d-TFA): δ 9.48 (d, J = 0.9 Hz, 1H), 8.43 (d, J = 5.3 Hz, 1H), 8.00 (d, J = 7.3 Hz, 1H), 7.95 (d, J = 8.3 Hz, 2H), 7.50 (dd, J = 7.3, 0.9 Hz, 1H), 7.31 (s, 1H), 7.26 (d, J = 5.4 Hz, 1H), 2.47 (s, 3H). |
| 75 | 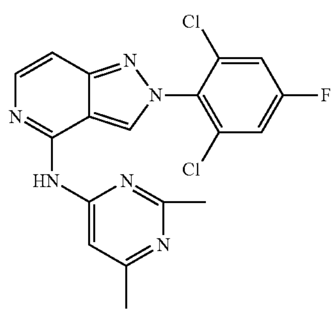 [SMILES: Cc1cc(Nc2nccc3nn(-c4c(Cl)cc(F)cc4Cl)cc23)nc(C)n1] | [2-(2,6-dichloro-4-fluorophenyl)-2H-pyrazolo[4,3-c]pyridine-4-yl]-(2,6-dimethyl-pyrimidin-4-yl)amine | 2 | 403 | B | 3.08 | $^1$H NMR (400 MHz, CD$_3$OD): δ 9.42 (s, 1H), 8.10 (d, J = 7.2 Hz, 1H), 7.69 (d, J = 7.3 Hz, 1H), 7.66 (d, J = 8.1 Hz, 2H), 7.47 (s, 1H), 2.93 (s, 3H), 2.68 (s, 3H). |
| 76 | 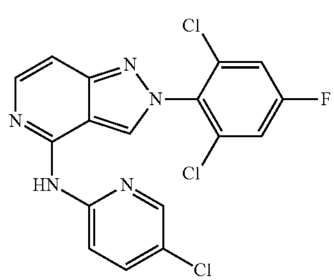 [SMILES: Fc1cc(Cl)c(-n2cc3c(Nc4ccc(Cl)cn4)nccc3n2)c(Cl)c1] | (5-Chloropyridin-2-yl)-[2-(2,6-dichloro-4-fluorophenyl)-2H-pyrazolo[4,3-c]pyridine-4-yl]amine | 2 | 408 | B | 3.44 | $^1$H NMR (400 MHz, CD$_3$OD): δ 8.75 (s, 1H), 8.33 (s, 1H), 7.74 (dd, J = 8.8, 2.7 Hz, 1H), 7.75-7.60 (br s, 2H), 7.55 (d, J = 8.0 Hz, 2H), 6.88 (s, 1H). |

TABLE 2-continued

| Example | Structure | Name | Synth. Method | LCMS (ESI) m/z | LCMS Method | R_T (min) | NMR |
|---|---|---|---|---|---|---|---|
| 77 | 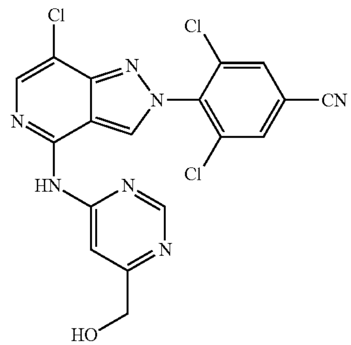 | 3,5-Dichloro-4-[7-chloro-4-(6-hydroxymethyl-pyrimidin-4-ylamino)pyrazolo[4,3-c]pyridin-2-yl]benzonitrile | 2 | 446 | B | 3.32 | $^1$H NMR (400 MHz, DMSO-d$_6$): δ 10.94 (s, 1H), 9.34 (s, 1H), 8.72 (d, J = 1.2 Hz, 1H), 8.58 (s, 1H), 8.51 (s, 2H), 8.08 (s, 1H), 5.61 (t, J = 5.8 Hz, 1H), 4.53 (d, J = 5.8 Hz, 2H). |
| 78 | 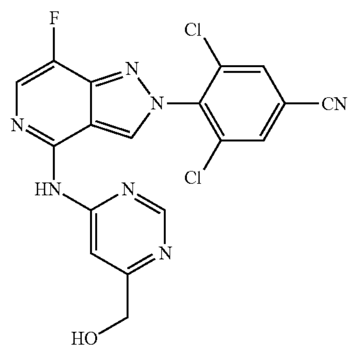 [SMILES: N#Cc1cc(Cl)c(-n2cc3c(Nc4cc(CO)ncn4)ncc(F)c3n2)c(Cl)c1] | 3,5-Dichloro-4-[7-fluoro-4-(6-hydroxymethyl-pyrimidin-4-ylamino)-pyrazolo[4,3-c]pyridin-2-yl]-benzonitrile | 2 | 430 | B | 3.11 | $^1$H NMR (400 MHz, DMSO-d$_6$): δ 10.83 (s, 1H), 9.34 (d, J = 2.6 Hz, 1H), 8.70 (d, J = 1.2 Hz, 1H), 8.55 (d, J = 1.2 Hz, 1H), 8.51 (s, 2H), 8.00 (d, J = 3.4 Hz, 1H), 5.59 (t, J = 5.8 Hz, 1H), 4.52 (d, J = 5.8 Hz, 2H). |
| 79 | 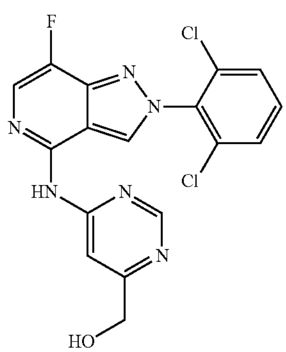 [SMILES: OCc1cc(Nc2ncc(F)c3nn(-c4c(Cl)cccc4Cl)cc23)ncn1] | {6-[2-(2,6-Dichloro-phenyl)-7-fluoro-2H-pyrazolo[4,3-c]pyridin-4-ylamino]-pyrimidin-4-yl}-methanol | 2 | 405 | B | 2.98 | $^1$H NMR (400 MHz, DMSO-d$_6$): δ 10.73 (s, 1H), 9.28 (d, J = 2.6 Hz, 1H), 8.69 (d, J = 1.4 Hz, 1H), 8.59 (d, J = 1.2 Hz, 1H), 7.98 (d, J = 3.5 Hz, 1H), 7.85 (d, J = 1.3 Hz, 1H), 7.83 (s, 1H), 7.74 (dd, J = 7.1, 8.9 Hz, 1H), 5.59 (t, J = 5.7 Hz, 1H), 4.52 (d, J = 5.7 Hz, 2H) |
| 80 | 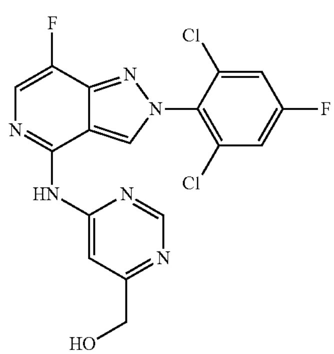 [SMILES: OCc1cc(Nc2ncc(F)c3nn(-c4c(Cl)cc(F)cc4Cl)cc23)ncn1] | 6-[2-(2,6-Dichloro-4-fluoro-phenyl)-7-fluoro-2H-pyrazolo[4,3-c]pyridin-4-ylamino]-pyrimdin-4-yl}-methanol | 2 | 423 | B | 3.15 | $^1$H NMR (400 MHz, CD$_3$OD): δ 10.76 (s, 1H), 9.27 (d, J = 2.6 Hz, 1H), 8.69 (d, J = 1.4 Hz, 1H), 8.57-8.56 (m, 1H), 7.98 (d, J = 3.6 Hz, 1H), 7.96 (s, 1H), 7.94 (s, 1H), 5.59 (t, J = 6.0 Hz, 1H), 4.52 (d, J = 5.8 Hz, 2H). |

TABLE 2-continued

| Example | Structure | Name | Synth. Method | LCMS (ESI) m/z | LCMS Method | R$_T$ (min) | NMR |
|---|---|---|---|---|---|---|---|
| 81 | 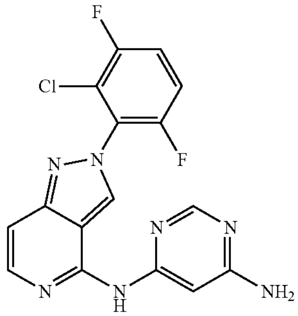 [SMILES: Nc1cc(Nc2nccc3nn(-c4c(F)ccc(F)c4Cl)cc23)ncn1] | N4-(2-(2-chloro-3,6-difluorophenyl)-2H-pyrazolo[4,3-c]pyridin-4-yl)pyrimidine-4,6-diamine | 2 | 374 | E | 3.50 | $^1$H NMR (400 MHz, DMSO) δ 10.07 (s, 1H), 9.24 (s, 1H), 8.22 (s, OH), 8.14 (s, 1H), 7.91 (s, 1H), 7.84 (td, J = 9.1, 4.6, 1H), 7.71 (dt, J = 13.6, 6.8, 2H), 7.13 (s, 1H), 6.67 (s, 2H). |
| 82 | 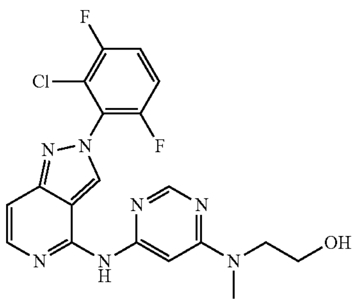 [SMILES: CN(CCO)c1cc(Nc2nccc3nn(-c4c(F)ccc(F)c4Cl)cc23)ncn1] | 2-((6-(2-(2-chloro-3,6-difluorophenyl)-2H-pyrazolo[4,3-c]pyridin-4-ylamino)pyrimidin-4-yl)(methyl)amino)ethanol | 2 | 431 | E | 3.73 | $^1$H NMR (400 MHz, DMSO) δ 10.17 (s, 1H), 9.25 (s, 1H), 8.25 (s, 1H), 7.95 (d, J = 3.9, 1H), 7.78 (dtd, J = 54.5, 9.2, 4.5, 2H), 7.13 (d, J = 6.3, 1H), 4.74 (s, 1H), 3.63 (s, 5H), 3.10 (s, 4H). |
| 83 | 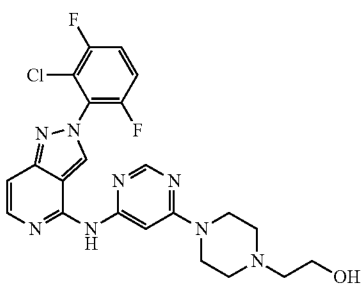 [SMILES: OCCN1CCN(c2cc(Nc3nccc4nn(-c5c(F)ccc(F)c5Cl)cc34)ncn2)CC1] | 2-(4-(6-(2-(2-chloro-3,6-difluorophenyl)-2H-pyrazolo[4,3-c]pyridin-4-ylamino)pyrimidin-4-yl)piperazin-1-yl)ethanol | 2 | 487 | E | 3.33 | $^1$H NMR (400 MHz, DMSO) δ 10.25 (s, 1H), 9.26 (s, 1H), 8.28 (s, 1H), 8.07 (s, 1H), 7.97 (d, J = 6.3, 1H), 7.85 (d, J = 4.2, 1H), 7.71 (d, J = 4.3, 1H), 7.14 (d, J = 6.3, 1H), 4.43 (t, J = 5.0, 1H), 3.73-3.47 (m, 7H), 2.45 (t, J = 6.1, 2H). |
| 84 | 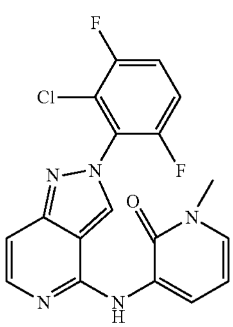 [SMILES: Cn1cccc(Nc2nccc3nn(-c4c(F)ccc(F)c4Cl)cc23)c1=O] | 3-(2-(2-chloro-3,6-difluorophenyl)-2H-pyrazolo[4,3-c]pyridin-4-ylamino)-1-methylpyridin-2(1H)-one | 2 | 388 | E | 3.21 | $^1$H NMR (400 MHz, DMSO) δ 9.37 (s, 1H), 8.86-8.58 (m, 2H), 8.04-7.76 (m, 2H), 7.71 (td, J = 9.2, 4.5, 1H), 7.36 (dd, J = 6.8, 1.5, 1H), 7.06 (d, J = 6.4, 1H), 6.34 (t, J = 7.1, 1H), 3.57 (s, 3H). |
| 85 | 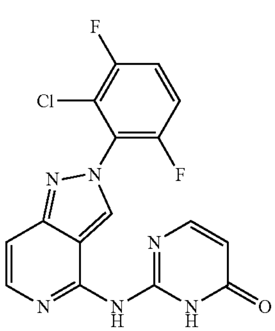 [SMILES: O=c1ccnc(Nc2nccc3nn(-c4c(F)ccc(F)c4Cl)cc23)[nH]1] | 2-(2-(2-chloro-3,6-difluorophenyl)-2H-pyrazolo[4,3-c]pyridin-4-ylamino)pyrimidin-4(3H)-one | 2 | 375 | E | 3.64 | $^1$H NMR (400 MHz, DMSO) δ 14.39-13.52 (m, 1H), 12.15-11.41 (m, 1H), 9.05 (s, 1H), 7.77 (dddd, J = 22.9, 18.4, 9.2, 4.6, 4H), 7.06 (s, 1H), 6.48 (s, 0H), 5.89 (d, J = 5.7, 1H). |

TABLE 2-continued

| Example | Structure | Name | Synth. Method | LCMS (ESI) m/z | LCMS Method | R$_T$ (min) | NMR |
|---|---|---|---|---|---|---|---|
| 86 | 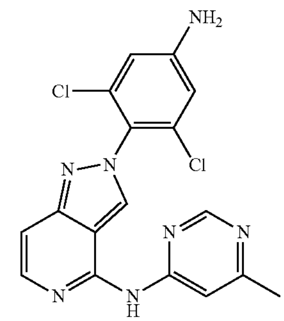 [SMILES: Cc1cc(Nc2nccc3nn(-c4c(Cl)cc(N)cc4Cl)cc23)ncn1] | 2-(4-amino-2,6-dichlorophenyl)-N-(6-methylpyrimidin-4-yl)-2H-pyrazolo[4,3-c]pyridin-4-amine | 2 | 386 | E | 3.38 | $^1$H NMR (400 MHz, DMSO) δ 10.49 (s, 1H), 8.99 (s, 1H), 8.72 (d, J = 26.3, 1H), 8.53 (d, J = 10.0, 1H), 7.95 (d, J = 6.4, 1H), 7.18 (d, J = 6.4, 1H), 6.85-6.74 (m, 2H), 6.17 (d, J = 22.4, 2H), 2.45 (s, 3H). |
| 87 | 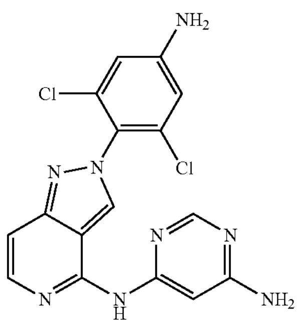 [SMILES: Nc1cc(Cl)c(-n2cc3c(Nc4cc(N)ncn4)nccc3n2)c(Cl)c1] | N4-(2-(4-amino-2,6-dichloro-phenyl)-2H-pyrazolo[4,3-c]pyridin-4-yl)pyrimidine-4,6-diamine | 2 | 387 | E | 3.32 | $^1$H NMR (400 MHz, DMSO) δ 9.89 (s, 1H), 8.98 (s, 1H), 8.27 (s, 1H), 8.13 (s, 1H), 7.87 (d, J = 5.6, 1H), 7.72 (s, 1H), 7.08 (d, J = 5.0, 1H), 6.78 (s, 3H), 6.65 (s, 3H), 6.19 (s, 3H). |
| 88 | 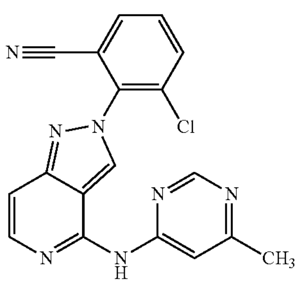 [SMILES: Cc1cc(Nc2nccc3nn(-c4c(Cl)cccc4C#N)cc23)ncn1] | 3-chloro-2-(4-(6-methylpyrimidin-4-ylamino)-2H-pyrazolo[4,3-c]pyridin-2-yl)benzonitrile | 2 | 362 | E | 3.29 | $^1$H NMR (400 MHz, DMSO) δ 11.95 (s, 1H), 8.70 (d, J = 18.5, 1H), 8.61-8.25 (m, 1H), 8.07-7.61 (m, 2H), 7.40 (d, J = 16.6, 1H), 6.02-5.70 (m, 1H). |
| 89 | 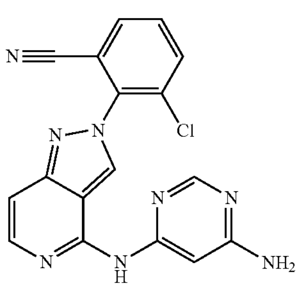 [SMILES: N#Cc1cccc(Cl)c1-n1cc2c(Nc3cc(N)ncn3)nccc2n1] | 2-(4-(6-aminopyrimidin-4-ylamino)-2H-pyrazolo[4,3-c]pyridin-2-yl)-3-chlorobenzonitrile | 2 | 364 | E | 3.26 | $^1$H NMR (400 MHz, DMSO) δ 10.12 (s, 1H), 9.34 (s, 1H), 8.31-8.06 (m, 3H), 8.06-7.78 (m, 2H), 7.71 (s, 1H), 7.16 (d, J = 6.4, 1H), 6.68 (s, 2H). |

Method 2

Example 90

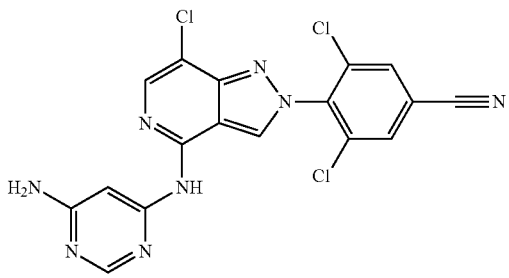 [SMILES: N#Cc1cc(Cl)c(-n2cc3c(Nc4cc(N)ncn4)ncc(Cl)c3n2)c(Cl)c1]

4-[4-(6-Aminopyrimidin-4-ylamino)-7-chloropyrazolo[4,3-c]pyridin-2-yl]-3,5-dichlorobenzonitrile

Step 1

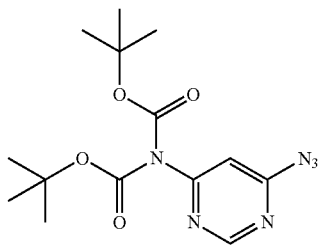 [SMILES: CC(C)(C)OC(=O)N(C(=O)OC(C)(C)C)c1cc(N=[N+]=[N-])ncn1]

(6-Azidopyrimidin-4-yl)-bis-carbamic acid tert-butyl ester

To a mixture of (6-chloropyrimidin-4-yl)-bis-carbamic acid tert-butyl ester (2.0 g, 6.0 mmol) in DMF (10 mL) was added sodium azide (780 mg, 12.0 mmol). The resultant mixture was heated at 70° C. for 4 hours. After allowing to cool to room temperature, the crude mixture was partitioned between water and EtOAc. The organic layer was washed with brine (×2), dried (sodium sulfate) and concentrated to dryness. The resultant residue was purified by column chromatography on silica gel eluting with 20% EtOAc in cyclohexane to afford the title compound as a pale yellow solid (1.33 g, 66% yield). $^1$H NMR (400 MHz, DMSO-d$_6$): δ 8.63 (s, 1H), 7.18 (s, 1H), 1.53 (s, 18H).

Step 2

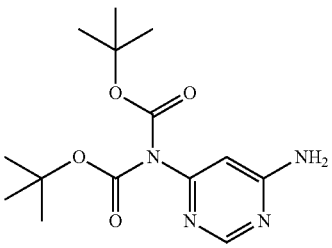 [SMILES: CC(C)(C)OC(=O)N(C(=O)OC(C)(C)C)c1cc(N)ncn1]

(6-Aminopyrimidin-4-yl)-bis-carbamic acid tert-butyl ester

A suspension of (6-azidopyrimidin-4-yl)-bis-carbamic acid tert-butyl ester (1.33 g, 4.0 mmol) and 5% Pd/C (1.0 g) in IMS (10 mL) and EtOAc (3.0 mL) was stirred under a hydrogen atmosphere for 18 hours at room temperature. The reaction mixture was then filtered through Celite® washing with EtOAc. The filtrate was concentrated to dryness under reduced pressure and the resultant residue was triturated with diethyl ether to afford the title compound as a white solid (1.21 g, 95% yield). $^1$H NMR (400 MHz, DMSO-d$_6$): δ 8.17 (s, 1H), 6.96 (br s, 2H), 6.49 (s, 1H), 1.45 (s, 18H).

Step 3

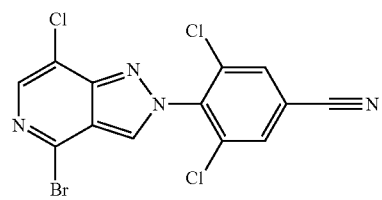

4-(4-Bromo-7-chloropyrazolo[4,3-c]pyridin-2-yl)-3,5-dichlorobenzonitrile

A mixture of 3,5-dichloro-4-(4,7-dichloropyrazolo[4,3-c]pyridin-2-yl)benzonitrile (250 mg, 0.70 mmol) and bromotrimethylsilane (0.462 mL, 3.50 mmol) in propionitrile (4.0 mL) was heated under reflux for 4 hours. The resultant mixture was cooled and concentrated under reduced pressure. The residue was partitioned between ethyl acetate and saturated aqueous sodium bicarbonate solution. The layers were separated and the organic layer was washed with brine, dried over anhydrous sodium sulfate, filtered and concentrated to afford the title compound as a beige solid (273 mg, 97% yield). $^1$H NMR (400 MHz, CDCl$_3$): δ 8.30 (s, 1H), 8.16 (s, 1H), 7.85 (s, 2H).

Step 4

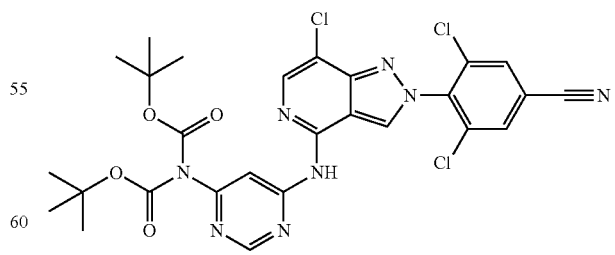

{6-[7-Chloro-2-(2,6-dichloro-4-cyanophenyl)-2H-pyrazolo[4,3-c]pyridin-4-ylamino]-pyrimidin-4-yl}-bis-carbamic acid tert-butyl ester A mixture of 4-(4-bromo-7-chloropyrazolo[4,3-c]pyridin-2-yl)-3,5-dichlorobenzonitrile (270 mg, 0.67 mmol), (6-aminopyrimidin-4-yl)-bis-carbamic acid tert-butyl ester (230 mg, 0.74 mmol), Pd$_2$(dba)$_3$ (31 mg, 0.034 mmol), Xantphos (39 mg, 0.067 mmol) and cesium carbonate (439 mg, 1.35 mmol) in dioxane (3.0 mL) was de-gassed and purged with nitrogen and the reaction mixture was heated at 70° C. for 18 hours. The resultant mixture was cooled and partitioned between ethyl acetate and water. The layers were separated and the organic layer was washed with brine, dried over anhydrous sodium sulfate, filtered and concentrated under reduced pressure. The residue was purified by silica gel flash chromatography (0-50% ethyl acetate in cyclohexane) to afford the title compound as a beige solid (321 mg, 76% yield). $^1$H NMR (400 MHz, CDCl$_3$): δ 8.62-8.57 (m, 2H), 8.39 (s, 1H), 8.06 (s, 1H), 7.88-7.81 (m, 3H), 1.55 (s, 18H).

Step 5

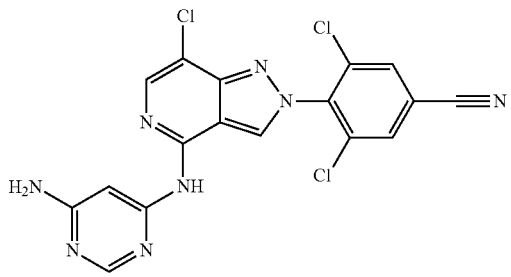 [SMILES: N#Cc1cc(Cl)c(-n2cc3c(Nc4cc(N)ncn4)ncc(Cl)c3n2)c(Cl)c1]

4-[4-(6-Aminopyrimidin-4-ylamino)-7-chloropyrazolo[4,3-c]pyridin-2-yl]-3,5-dichlorobenzonitrile A solution of {6-[7-chloro-2-(2,6-dichloro-4-cyanophenyl)-2H-pyrazolo[4,3-c]pyridin-4-ylamino]-pyrimidin-4-yl}-bis-carbamic acid tert-butyl ester (321 mg, 0.51 mmol) in HCl (4 N in dioxane, 10.0 mL, 40 mmol) was heated at 50° C. for 18 hours. The resultant mixture was concentrated under reduced pressure and the residue was partitioned between ethyl acetate and saturated aqueous sodium bicarbonate solution. The layers were separated and the organic layer was washed with brine, dried over anhydrous sodium sulfate, filtered and concentrated under reduced pressure. The residue was purified by KP-NH flash chromatography (0-100% ethyl acetate in cyclohexane) to afford the title compound as an off-white solid (176 mg, 80% yield). $^1$H NMR (400 MHz, DMSO-d$_6$): 9.35 (s, 1H), 8.57 (s, 1H), 8.50 (s, 2H), 8.10 (s, 1H), 7.26 (br s, 1H). LCMS (Method B): RT=3.28 min, m/z: 431 [M+H$^+$].

Method 4

Example 91

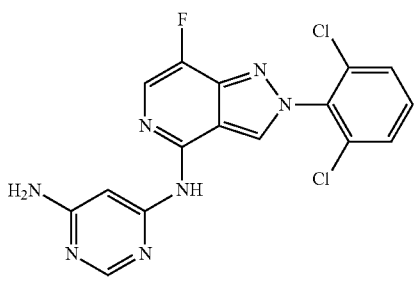 [SMILES: Nc1cc(Nc2ncc(F)c3nn(-c4c(Cl)cccc4Cl)cc23)ncn1]

N-[2-(2,6-Dichlorophenyl)-7-fluoro-2H-pyrazolo[4,3-c]pyridin-4-yl]pyrimidine-4,6-diamine Step 1

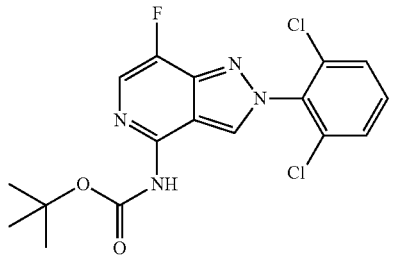

[2-(2,6-Dichlorophenyl)-7-fluoro-2H-pyrazolo[4,3-c]pyridin-4-yl]-carbamic acid tert-butyl ester A suspension of 4-bromo-2-(2,6-dichlorophenyl)-7-fluoro-2H-pyrazolo[4,3-c]pyridine (635 mg, 1.75 mmol), tert-butyl carbamate (614 mg, 5.25 mmol), Pd$_2$(dba)$_3$ (40 mg, 0.044 mmol), Xantphos (101 mg, 0.175 mmol) and potassium phosphate tribasic (742 mg, 3.5 mmol) in toluene (15 mL) and water (3 mL) was de-gassed and purged with argon and the reaction mixture was heated at 70° C. for 5 h. The mixture was cooled and partitioned between ethyl acetate and water. The layers were separated and the organic layer was washed with brine, dried over anhydrous sodium sulfate, filtered and concentrated under reduced pressure. The resultant residue was purified by silica gel flash chromatography (20% ethyl acetate in cyclohexane) to afford the title compound as a pale yellow solid (396 mg, 57% yield). $^1$H NMR (400 MHz, DMSO-d$_6$): δ 10.19 (s, 1H), 9.05 (s, 1H), 7.92 (d, J=3.1 Hz, 1H), 7.80 (d, J=8.2 Hz, 2H), 7.72 (d, J=7.9 Hz, 1H), 1.48 (s, 9H).

Step 2

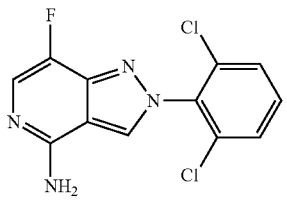 [SMILES: Nc1ncc(F)c2nn(-c3c(Cl)cccc3Cl)cc12]

2-(2,6-Dichlorophenyl)-7-fluoro-2H-pyrazolo[4,3-c]pyridin-4-ylamine

TFA (2.0 ml) was added to a mixture of [2-(2,6-dichlorophenyl)-7-fluoro-2H-pyrazolo[4,3-c]pyridin-4-yl]-carbamic acid tert-butyl ester (390 mg, 1 mmol) in DCM (5 mL) and the reaction mixture was stirred at room temperature for 3.5 h. The volatiles were removed under reduced pressure and the resultant residue was dissolved in DCM and washed with saturated aqueous sodium bicarbonate solution (×2) and brine. The organic layer was dried over anhydrous sodium sulfate, filtered and concentrated under reduced pressure to afford the title compound as an off-white solid (226 mg, 74% yield). $^1$H NMR (400 MHz, DMSO-d$_6$): δ 8.74 (d, J=3.0 Hz, 1H), 7.82-7.78 (m, 2H), 7.72-7.68 (m, 1H), 7.53 (d, J=4.3 Hz, 1H), 6.86 (br s, 2H).

Step 3

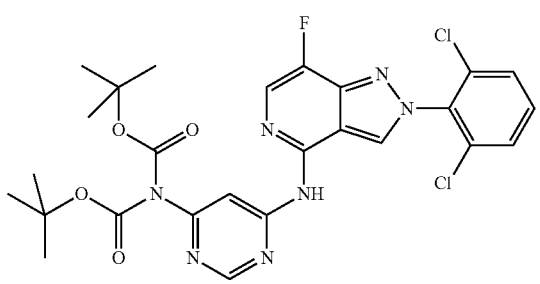 [SMILES: CC(C)(C)OC(=O)N(C(=O)OC(C)(C)C)c1cc(Nc2ncc(F)c3nn(-c4c(Cl)cccc4Cl)cc23)ncn1]

{6-[2-(2,6-Dichlorophenyl)-7-fluoro-2H-pyrazolo[4,3-c]pyridin-4-ylamino]-pyrimidin-4-yl}-bis-carbamic acid tert-butyl ester A suspension of 2-(2,6-dichlorophenyl)-7-fluoro-2H-pyrazolo[4,3-c]pyridin-4-ylamine (223 mg, 0.75 mmol), (6-chloropyrimidin-4-yl)-bis-carbamic acid tert-butyl ester (297 mg, 0.9 mmol), Pd$_2$(dba)$_3$ (34 mg, 0.038 mmol), Xantphos (86 mg, 0.15 mmol) and cesium carbonate (489 mg, 1.5 mmol) in dioxane (3.0 mL) was de-gassed and purged with nitrogen and the reaction mixture was heated at 150° C. in the microwave for 25 minutes. The mixture was partitioned between ethyl acetate and water and the layers were separated. The organic layer was washed with brine, dried over anhydrous sodium sulfate, filtered and concentrated to afford the title compound as a pale yellow solid (155 mg, 35% yield). $^1$H NMR (400 MHz, DMSO-d$_6$): δ 10.99 (br s, 1H), 9.29-9.26 (m, 1H), 8.68 (s, 1H), 8.58 (s, 1H), 7.95 (d, J=3.2 Hz, 1H), 7.85-7.81 (m, 2H), 7.77-7.71 (m, 1H), 1.49 (s, 18H).

Step 4

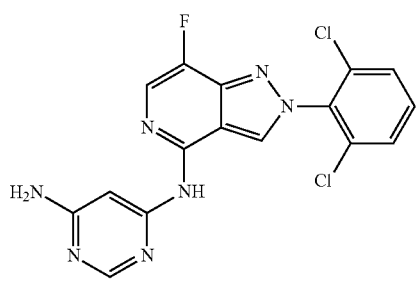

N-[2-(2,6-Dichlorophenyl)-7-fluoro-2H-pyrazolo[4,3-c]pyridin-4-yl]pyrimidin-4,6-diamine TFA (2.0 mL) was added to a mixture of {6-[2-(2,6-dichlorophenyl)-7-fluoro-2H-pyrazolo[4,3-c]pyridin-4-ylamino]-pyrimidin-4-yl}-bis-carbamic acid tert-butyl ester (150 mg, 0.25 mmol) in DCM (5.0 mL) and the reaction mixture was stirred at room temperature for 2 h. The volatiles were concentrated under reduced pressure and the residue was partitioned between DCM and saturated aqueous sodium bicarbonate solution. The layers were separated and the organic layer was washed with brine, dried over anhydrous sodium sulfate, filtered and concentrated under reduced pressure. The resultant residue was purified by silica gel flash chromatography (80-100% ethyl acetate in cyclohexane) to afford the title compound as a white solid (52 mg, 53% yield). $^1$H NMR (400 MHz, DMSO-d$_6$): δ 10.19 (br s, 1H), 9.26 (d, J=2.6 Hz, 1H), 8.15 (s, 1H), 7.87 (d, J=3.5 Hz, 1H), 7.84-7.81 (m, 2H), 7.73 (dd, J=9.0, 7.3 Hz, 1H), 7.56 (br s, 1H), 6.81 (s, 2H). LCMS (Method B): RT=3.10 min, m/z: 390 [M+H$^+$].

Method 2

Example 92

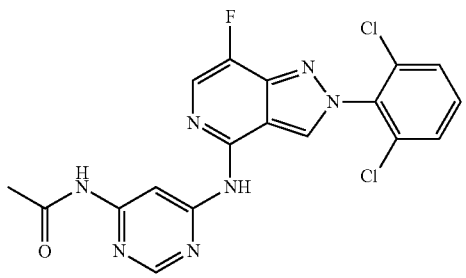 [SMILES: CC(=O)Nc1cc(Nc2ncc(F)c3nn(-c4c(Cl)cccc4Cl)cc23)ncn1]

N-{6-[2-(2,6-Dichlorophenyl)-7-fluoro-2H-pyrazolo[4,3-c]pyridin-4-ylamino]-pyrimidin-4-yl}-acetamide A mixture of 4-bromo-2-(2,6-dichlorophenyl)-7-fluoro-2H-pyrazolo[4,3-c]pyridine (320 mg, 0.89 mmol), N-(6-aminopyrimidin-4-yl)-acetamide (152 mg, 1.0 mmol), Pd$_2$(dba)$_3$ (20 mg, 0.022 mmol), Xantphos (52 mg, 0.089 mmol) and cesium carbonate (580 mg, 1.78 mmol) in dioxane (10 mL) was de-gassed and purged with nitrogen and the reaction mixture was heated at 150° C. in the microwave for 1 h. The resultant mixture was partitioned between ethyl acetate and water and the layers were separated. The organic layer was washed with brine, dried over anhydrous sodium sulfate, filtered and concentrated under reduced pressure. The residue was purified by silica gel flash chromatography (80-100% ethyl acetate in cyclohexane) to afford an off-white solid. This was re-purified by HPLC [gradient: 5 to 98% acetonitrile (0.1% ammonium hydroxide) in water (0.1% ammonium hydroxide)], to afford the title compound as a white solid (31 mg, 10% yield). $^1$H NMR (400 MHz, DMSO-d$_6$): δ 10.65-10.61 (m, 2H), 9.26 (d, J=2.6 Hz, 1H), 9.08 (d, J=1.1 Hz, 1H), 8.53 (d, J=1.1 Hz, 1H), 7.92 (d, J=3.4 Hz, 1H), 7.83-7.81 (m, 2H), 7.74 (dd, J=9.1, 7.3 Hz, 1H), 2.14 (s, 3H). LCMS (Method B): RT=3.20 min, m/z: 432 [M+H$^+$].

Method 2

Example 93

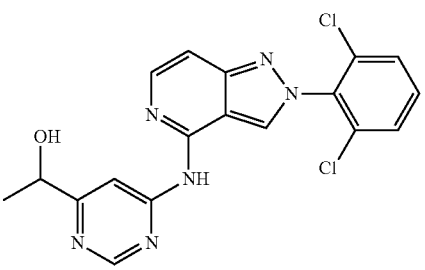 [SMILES: CC(O)c1cc(Nc2nccc3nn(-c4c(Cl)cccc4Cl)cc23)ncn1]

1-{6-[2-(2,6-Dichlorophenyl)-2H-pyrazolo[4,3-c]pyridin-4-ylamino]-pyrimidin-4-yl}-ethanol

Step 1

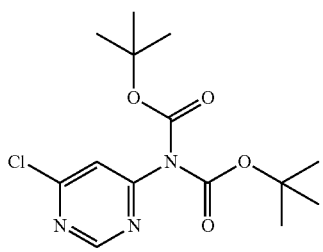 [SMILES: CC(C)(C)OC(=O)N(C(=O)OC(C)(C)C)c1cc(Cl)ncn1]

(6-Chloropyrimidin-4-yl)-bis-carbamic acid tert-butyl ester

4-Amino-6-chloropyrimidine (10.0 g, 77.2 mmol) was suspended in THF (450 mL) and di-tert-butyl dicarbonate (36.4 g, 162 mmol) was added, followed by DMAP (471 mg, 3.86 mmol). The resultant yellow solution was stirred at room temperature for 6 h. The mixture was concentrated under reduced pressure and the residue was dried under reduced pressure overnight. This was purified by silica gel flash chromatography (0-30% ethyl acetate in cyclohexane) to afford the title compound as a white solid (22.9 g, 90% yield). $^1$H NMR (300 MHz, CDCl$_3$): δ 8.66 (d, J=1.0 Hz, 1H), 7.84 (d, J=1.0 Hz, 1H), 1.55 (s, 18H).

An Alte Step 2

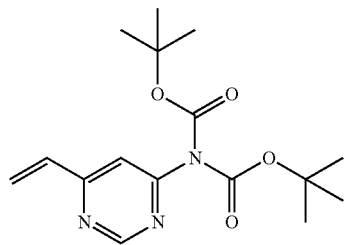 [SMILES: C=Cc1cc(N(C(=O)OC(C)(C)C)C(=O)OC(C)(C)C)ncn1]

(6-Vinylpyrimidin-4-yl)-bis-carbamic acid tert-butyl ester 4,4,5,5-Tetramethyl-2-vinyl-[1,3,2]dioxaborolane (1.24 mL, 7.28 mmol) was added to a mixture of (6-chloropyrimidin-4-yl)-bis-carbamic acid tert-butyl ester (2.0 g, 6.08 mmol), PdCl$_2$(dppf)$_2$·DCM (2.56 g, 0.31 mmol) and sodium carbonate (2.58 g, 24.3 mmol) in dioxane (4.0 mL) and water (4.0 mL). The reaction mixture was heated at 70° C. for 5.5 hours. The resultant mixture was cooled to room temperature and partitioned between ethyl acetate and water. The layers were separated and the organic layer was dried over anhydrous magnesium sulfate, filtered and concentrated under reduced pressure. The residue was purified by silica gel flash chromatography (0-50% ethyl acetate in cyclohexane) to afford the title compound (1.6 g, 84% yield). $^1$H NMR (300 MHz, CDCl$_3$): δ 8.86 (d, J=1.2 Hz, 1H), 7.63 (d, J=1.2 Hz, 1H), 6.72 (dd, J=17.3, 10.6 Hz, 1H), 6.47 (dd, J=17.3, 1.3 Hz, 1H), 5.67 (dd, J=10.6, 1.3 Hz, 1H), 1.55 (s, 18H).

Step 3

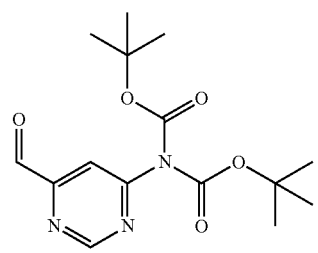 [SMILES: CC(C)(C)OC(=O)N(C(=O)OC(C)(C)C)c1cc(C=O)ncn1]

(6-Formylpyrimidin-4-yl)-bis-carbamic acid tert-butyl ester

Ozone gas was bubbled through a solution of (6-vinylpyrimidin-4-yl)-bis-carbamic acid tert-butyl ester (500 mg, 1.56 mmol) in DCM (60 mL), at −78° C. to give a blue solution. After 1 hour, the reaction mixture was purged with nitrogen and then triphenylphosphine (406 mg, 1.56 mmol) was added. The reaction mixture was stirred at room temperature for 2 hours and then concentrated under reduced pressure. The residue was purified by silica gel flash chromatography (0-30% ethyl acetate in cyclohexane) to afford the title compound as a yellow solid (243 mg, 48% yield). $^1$H NMR (300 MHz, CDCl$_3$): δ 10.03 (s, 1H), 9.10 (d, J=1.3 Hz, 1H), 8.24 (d, J=1.3 Hz, 1H), 1.58 (s, 18H).

Step 4

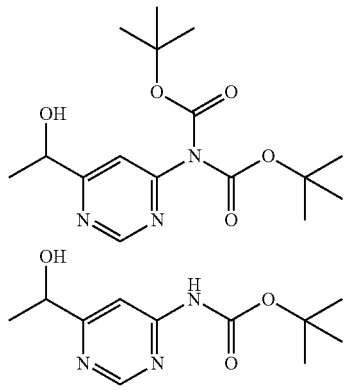

[6-(1-Hydroxyethyl)-pyrimidin-4-yl)-bis-carbamic acid tert-butyl ester and [6-(1-Hydroxyethyl)-pyrimidin-4-yl)-carbamic acid tert-butyl ester Methyl magnesium bromide (3 N in diethyl ether, 0.98 mL, 2.94 mmol) was added to a solution of (6-formylpyrimidin-4-yl)-bis-carbamic acid tert-butyl ester (760 mg, 2.35 mmol) in diethyl ether (30 mL), at −12° C. The reaction mixture was stirred at −12° C. for 15 minutes, then at room temperature overnight. The mixture was cooled to −5° C. and quenched with saturated aqueous ammonium chloride solution. The layers were separated and the aqueous layer was extracted with ethyl acetate. The combined organic extracts were dried over anhydrous magnesium sulfate, filtered and concentrated under reduced pressure. The residue was purified by silica gel flash chromatography (0-100% ethyl acetate in cyclohexane) to afford the first title compound (200 mg, 25% yield); $^1$H NMR (300 MHz, CDCl$_3$): δ 10.01 (s, 1H), 8.98 (d, J=1.3 Hz, 1H), 8.85 (d, J=1.3 Hz, 1H), 8.42 (d, J=1.3 Hz, 1H), 7.71 (dd, J=1.3, 0.7 Hz, 1H), 4.88-4.79 (m, 1H), 3.57 (d, J=5.1 Hz, 1H), 1.55 (s, 18H), 1.51 (d, J=6.6 Hz, 3H). The second title compound was also obtained (198 mg, 25% yield); $^1$H NMR (300 MHz, CDCl$_3$): δ 8.77 (d, J=1.3 Hz, 1H), 8.13 (br s, 1H), 7.94 (s, 1H), 4.87-4.77 (m, 1H), 3.73 (d, J=5.1 Hz, 1H), 1.55 (s, 9H), 1.52 (d, J=6.6 Hz, 3H).

Step 5

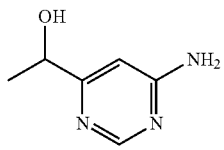

1-(6-Aminopyrimidin-4-yl)-ethanol

A solution of [6-(1-hydroxyethyl)-pyrimidin-4-yl)-bis-carbamic acid tert-butyl ester and [6-(1-hydroxyethyl)-pyrimidin-4-yl)-carbamic acid tert-butyl ester (200 mg+198 mg, 1.45 mmol) in DCM (6.0 mL) was cooled to 0° C. and TFA (6.0 mL) was added. The reaction mixture was stirred at 0° C. for 15 minutes, then at room temperature for 2 hours. The mixture was concentrated under reduced pressure and the residue was partitioned between saturated aqueous sodium bicarbonate solution and 2-methyltetrahydrofuran (×2). The aqueous layer was then extracted with ethyl acetate. The combined organic layers were dried over anhydrous magnesium sulfate, filtered and concentrated under reduced pressure. The residue was purified by silica gel flash chromatography (0-20% methanol in DCM) to afford the title compound as a colorless oil (195 mg, 96% yield). $^1$H NMR (300 MHz, DMSO-d$_6$): δ 8.60 (s, 1H), 8.54 (br s, 2H), 6.67 (s, 1H), 4.73-4.65 (m, 1H), 1.37 (d, J=6.6 Hz, 3H).

Step 6

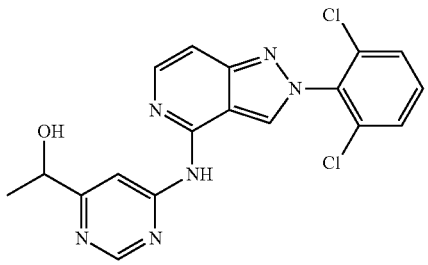 [SMILES: CC(O)c1cc(Nc2nccc3nn(-c4c(Cl)cccc4Cl)cc23)ncn1]

1-{6-[2-(2,6-Dichlorophenyl)-2H-pyrazolo[4,3-c]pyridin-4-ylamino]-pyrimidin-4-yl}-ethanol A mixture of 4-chloro-2-(2,6-dichlorophenyl)-2H-pyrazolo[4,3-c]pyridine (133 mg, 0.445 mmol), 1-(6-aminopyrimidin-4-yl)-ethanol (65 mg, 0.467 mmol), Pd$_2$(dba)$_3$ (20 mg, 0.022 mmol), Xantphos (26 mg, 0.045 mmol) and cesium carbonate (290 mg, 0.89 mmol) in dioxane (3.5 mL) was de-gassed and purged with nitrogen and the reaction mixture was heated at 150° C. in the microwave for 30 minutes. The resultant mixture was filtered and washed with dioxane. The filtrate was concentrated under reduced pressure and the resultant residue was purified by silica gel flash chromatography (0-100% ethyl acetate in cyclohexane) to afford a yellow solid. This was re-purified by HPLC [gradient: 5 to 98% acetonitrile (0.1% ammonium hydroxide) in water (0.1% ammonium hydroxide)], to afford the title compound as a white solid (31 mg, 21% yield). $^1$H NMR (400 MHz, DMSO-d$_6$): δ 9.53 (d, J=0.9 Hz, 1H), 9.07 (d, J=1.1 Hz, 1H), 8.09 (d, J=7.3 Hz, 1H), 7.88-7.86 (m, 2H), 7.78 (dd, J=9.2, 7.1 Hz, 1H), 7.68-7.61 (m, 2H), 4.83-4.76 (m, 1H), 1.46 (d, J=6.7 Hz, 3H). LCMS (Method B): RT=2.74 min, m/z: 401 [M+H$^+$].

Method 2

Example 94

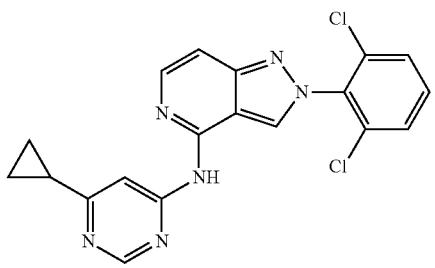 [SMILES: Clc1cccc(Cl)c1-n1cc2c(Nc3cc(C4CC4)ncn3)nccc2n1]

(6-Cyclopropylpyrimidin-4-yl)-[2-(2,6-dichlorophenyl)-2H-pyrazolo[4,3-c]pyridin4-yl]-amine Step 1

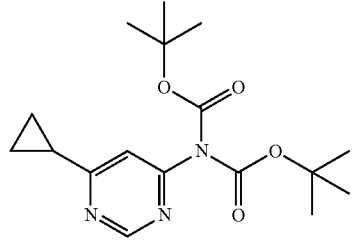 [SMILES: CC(C)(C)OC(=O)N(C(=O)OC(C)(C)C)c1cc(C2CC2)ncn1]

(6-Cyclopropylpyrimidin-4-yl)-bis-carbamic acid tert-butyl ester

A mixture of (6-chloropyrimidin-4-yl)-bis-carbamic acid tert-butyl ester (200 mg, 0.60 mmol), cyclopropyl boronic acid (80 mg, 0.94 mmol) and cesium carbonate (410 mg, 1.26 mmol) in toluene (6.0 mL) and water (0.6 mL) was de-gassed and purged with argon (×3). Amgen catalyst (36 mg, 0.05 mmol) was then added and the reaction mixture was heated at 140° C., in the microwave for 30 minutes. The resultant mixture was diluted with acetic acid and water. The layers were separated and the organic layer was washed with brine, dried over anhydrous magnesium sulfate, filtered and concentrated under reduced pressure. The residue was purified by silica gel flash chromatography (5-10% acetic acid in cyclohexane) to afford the title compound as a white solid (130 mg, 64% yield). $^1$H NMR (400 MHz, CDCl$_3$): δ 8.72 (d, J=1.2 Hz, 1H), 7.49 (d, J=1.2 Hz, 1H), 2.02-1.94 (m, 1H), 1.54 (s, 18H), 1.17-1.12 (m, 2H), 1.11-1.04 (m, 2H).

Step 2

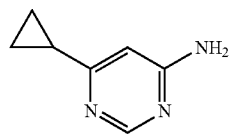

6-Cyclopropylpyrimidin-4-ylamine

A mixture of (6-cyclopropylpyrimidin-4-yl)-bis-carbamic acid tert-butyl ester (256 mg, 0.764 mmol) and (6-cyclopropylpyrimidin-4-yl)-carbamic acid tert-butyl ester (10 mg, 0.043 mmol) in HCl (4 N in dioxane, 3.0 mL, 12 mmol) was heated at 55° C. for 3 hours. Additional HCl (4 N in dioxane, 1.0 mL, 4 mmol) was added and the reaction mixture was heated at 70° C. for another 1.5 hour, then stirred at room temperature overnight. The resultant mixture was partitioned between saturated aqueous sodium bicarbonate solution and ethyl acetate. The organic layer was washed with brine, dried over anhydrous magnesium sulfate, filtered and concentrated under reduced pressure. The residue was purified by silica gel flash chromatography (2-5% methanol in DCM) to afford the title compound (84 mg, 78% yield). $^1$H NMR (400 MHz, methanol-d$_4$): δ 8.17 (d, J=1.1 Hz, 1H), 6.36 (d, J=1.2 Hz, 1H), 4.61 (br s, 2H), 1.90-1.81 (m, 1H), 1.03-0.94 (m, 4H).

Step 3

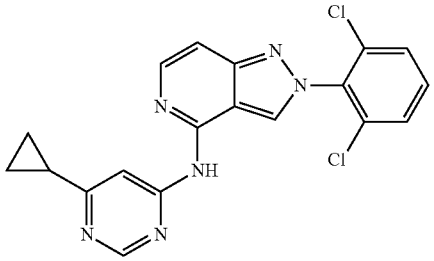 [SMILES: Clc1cccc(Cl)c1-n1cc2c(Nc3cc(C4CC4)ncn3)nccc2n1]

(6-Cyclopropylpyrimidin-4-yl)-[2-(2,6-dichlorophenyl)-2H-pyrazolo[4,3-c]pyridin4-yl]-amine A mixture of 4-chloro-2-(2,6-dichlorophenyl)-2H-pyrazolo[4,3-c]pyridine (52 mg, 0.175 mmol), 6-cyclopropylpyrimidin-4-ylamine (26 mg, 0.193 mmol), Pd$_2$(dba)$_3$ (8 mg, 0.0088 mmol), Xantphos (10.1 mg, 0.0175 mmol) and cesium carbonate (114 mg, 0.35 mmol) in dioxane (1.5 mL) was de-gassed and purged with nitrogen and the reaction mixture was heated at 120° C. in the microwave for 1 hour. The resultant mixture was filtered and washed with dioxane. The filtrate was concentrated under reduced pressure and the resultant residue was purified by silica gel flash chromatography (0-100% ethyl acetate in cyclohexane) to afford the title compound as a yellow solid (30 mg, 43% yield). $^1$H NMR (400 MHz, DMSO-d$_6$): δ 9.56 (d, J=0.9 Hz, 1H), 8.94 (d, J=1.0 Hz, 1H), 8.05 (d, J=7.3 Hz, 1H), 7.87-7.83 (m, 2H), 7.79-7.74 (m, 1H), 7.62 (dd, J=7.3, 0.9 Hz, 1H), 7.39 (s, 1H), 2.34-2.26 (m, 1H), 1.19-1.12 (m, 4H). LCMS (Method B): RT=3.17 min, m/z: 397 [M+H$^+$].

Method 2

Example 95

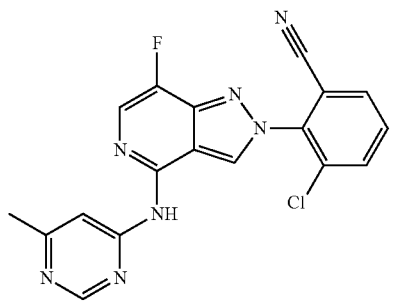 [SMILES: Cc1cc(Nc2ncc(F)c3nn(-c4c(Cl)cccc4C#N)cc23)ncn1]

3-Chloro-2-[7-fluoro-4-(6-methylpyrimidin-4-ylamino)-pyrazolo[4,3-c]pyridin-2-yl]-benzonitrile Step 1

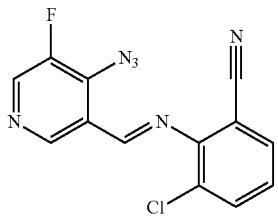 [SMILES: N#Cc1cccc(Cl)c1/N=C/c1cncc(F)c1N=[N+]=[N-]]

2-{[1-(4-Azido-5-fluoropyridin-3-yl)-meth-(E)-ylidene]-amino}-3-chlorobenzonitrile A solution of 4-azido-5-fluoropyridine-3-carbaldehyde (2.86 g, 17.2 mmol) and 2-amino-3-chlorobenzonitrile (2.62 g, 17.2 mmol) in DCM (60 mL) was cooled to 0° C. under an atmosphere of nitrogen. Triethylamine (7.2 mL, 51.6 mmol) was added, followed by dropwise additiona of titanium (IV) chloride solution (1 N in DCM, 10.3 mL, 10.3 mmol). The reaction mixture was stirred at 0° C. for 2 hours, then at room temperature overnight. The resultant mixture was concentrated under reduced pressure and the residue was dissolved in ethyl acetate and filtered through a pad of Celite®. The filtrate was concentrated under reduced pressure and the residue obtained was used in the following step without further purification.

Step 2

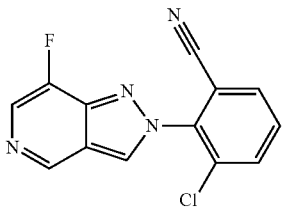

3-Chloro-2-(7-fluoropyrazolo[4,3-c]pyridin-2-yl)-benzonitrile

A solution of 2-{[1-(4-azido-5-fluoropyridin-3-yl)-meth-(E)-ylidene]-amino}-3-chlorobenzonitrile (5.16 g, 17.2 mmol) in toluene (60 mL) was heated at 105° C. for 5 hours. The resultant mixture was cooled to room temperature and concentrated under reduced pressure. The residue was purified by silica gel flash chromatography (0-5% methanol in DCM) to afford the title compound as a beige solid (2.57 g, 55% yield). $^1$H NMR (400 MHz, DMSO-d$_6$): δ 9.42 (d, J=2.6 Hz, 1H), 9.26 (d, J=2.5 Hz, 1H), 8.33 (d, J=3.8 Hz, 1H), 8.24-8.19 (m, 2H), 7.92 (t, J=8.1 Hz, 1H).

Step 3

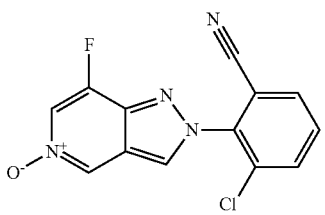 [SMILES: N#Cc1cccc(Cl)c1-n1cc2c[n+]([O-])cc(F)c2n1]

3-Chloro-2-(7-fluoro-5-oxypyrazolo[4,3-c]pyridin-2-yl)-benzonitrile

3-Chloro-2-(7-fluoropyrazolo[4,3-c]pyridin-2-yl)-benzonitrile (2.49 g, 9.1 mmol) was dissolved in DCM (30 mL) and methyltrioxorhenium (227 mg, 0.91 mmol) was added, followed by 30% aqueous hydrogen peroxide solution (1.2 mL, 18 mmol) dropwise. The reaction mixture was stirred at room temperature overnight. The resultant mixture was partitioned between DCM and saturated aqueous sodium bicarbonate solution. The layers were separated and the organic layer was washed with brine, dried over anhydrous sodium sulfate, filtered and concentrated under reduced pressure. The residue was dissolved in the minimum amount of methanol and precipitated with an excess of diethyl ether. The solid was filtered and dried to afford the title compound as a beige solid (2.25 g, 86% yield). $^1$H NMR (400 MHz, DMSO-d$_6$): δ 9.14 (d, J=2.5 Hz, 1H), 8.93 (s, 1H), 8.38 (d, J=6.3 Hz, 1H), 8.21-8.16 (m, 2H), 7.91 (t, J=8.1 Hz, 1H).

Step 4

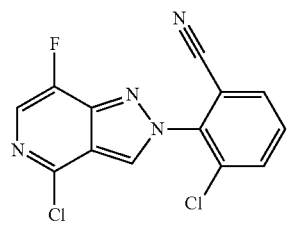 [SMILES: N#Cc1cccc(Cl)c1-n1cc2c(Cl)ncc(F)c2n1]

3-Chloro-2-(4-chloro-7-fluoropyrazolo[4,3-c]pyridin-2-yl)-benzonitrile

3-Chloro-2-(7-fluoro-5-oxypyrazolo[4,3-c]pyridin-2-yl)-benzonitrile (2.25 g, 25 mmol) was suspended in DCE (40 mL), under an atmosphere of nitrogen and phosphorus oxychloride (2.3 mL, 25 mmol) was added. The reaction mixture was heated at 70° C. for 4 hours. The resultant mixture was cooled to room temperature and was carefully quenched by the addition of 1 N aqueous sodium carbonate solution. DCM was added and the layers were separated. The organic layer was washed with brine, dried over anhydrous sodium sulfate, filtered and concentrated under reduced pressure. The residue was purified by silica gel flash chromatography (30-40% ethyl acetate in cyclohexane) to afford the title compound as a yellow solid (893 mg, 37% yield). $^1$H NMR (400 MHz, DMSO-d$_6$): δ 9.62 (d, J=2.4 Hz, 1H), 8.28-8.23 (m, 3H), 7.95 (t, J=8.1 Hz, 1H).

Step 5

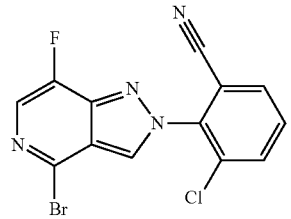 [SMILES: N#Cc1cccc(Cl)c1-n1cc2c(Br)ncc(F)c2n1]

2-(4-Bromo-7-fluoropyrazolo[4,3-c]pyridin-2-yl)-3-chlorobenzonitrile

3-Chloro-2-(4-chloro-7-fluoropyrazolo[4,3-c]pyridin-2-yl)-benzonitrile (890 mg, 2.9 mmol) was suspended in propionitrile (30 mL), under an atmosphere of nitrogen and bromotrimethylsilane (2.0 mL, 15 mmol) was added. The reaction mixture was heated at 110° C. for 3.5 hours. The resultant mixture was cooled to room temperature and partitioned between ethyl acetate and saturated aqueous sodium bicarbonate solution. The layers were separated and the organic layer was washed with brine, dried over anhydrous sodium sulfate, filtered and concentrated under reduced pressure. The residue was triturated with diethyl ether to afford the title compound as a yellow solid (980 mg, 96% yield). $^1$H NMR (400 MHz, DMSO-d$_6$): δ 9.54 (d, J=2.5 Hz, 1H), 8.25-8.21 (m, 3H), 7.94 (t, J=8.1 Hz, 1H).

Step 6

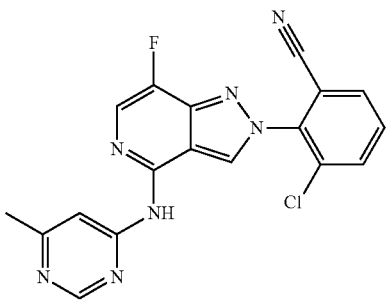

3-Chloro-2-[7-fluoro-4-(6-methylpyrimidin-4-ylamino)-pyrazolo[4,3-c]pyridin-2-yl]-benzonitrile A mixture of 2-(4-bromo-7-fluoropyrazolo[4,3-c]pyridin-2-yl)-3-chlorobenzonitrile (158 mg, 0.45 mmol), 4-amino-6-methylpyrimidine (55 mg, 0.5 mmol), $Pd_2(dba)_3$ (10 mg, 0.011 mmol), Xantphos (26 mg, 0.045 mmol) and cesium carbonate (293 mg, 0.9 mmol) in dioxane (3 mL) was de-gassed and purged with nitrogen and the reaction mixture was heated at 150° C. in the microwave for 30 minutes. The resultant mixture was partitioned between ethyl acetate and water. The layers were separated and the organic layer was washed with brine, dried over anhydrous sodium sulfate, filtered and concentrated under reduced pressure. The residue was purified by silica gel flash chromatography (80-90% ethyl acetate in cyclohexane) to afford the title compound as a beige solid (81 mg, 47% yield). $^1$H NMR (400 MHz, DMSO-$d_6$): δ 10.83 (s, 1H), 9.48 (d, J=2.6 Hz, 1H), 8.71 (d, J=1.2 Hz, 1H), 8.38 (s, 1H), 8.23-8.20 (m, 2H), 8.03 (d, J=3.5 Hz, 1H), 7.92 (t, J=8.1 Hz, 1H), 2.46 (s, 3H). LCMS (Method B): RT=3.04 min, m/z: 380 [M+H$^+$].

Method 2

Example 96

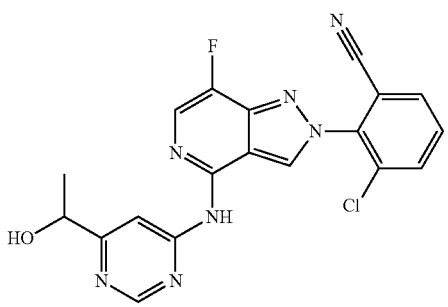 [SMILES: CC(O)c1cc(Nc2ncc(F)c3nn(-c4c(Cl)cccc4C#N)cc23)ncn1]

3-Chloro-2-{7-fluoro-4-[6-(1-hydroxyethyl)-pyrimidin-4-ylamino]-pyrazolo[4,3-c]pyridin-2-yl}-benzonitrile A mixture of 2-(4-bromo-7-fluoropyrazolo[4,3-c]pyridin-2-yl)-3-chlorobenzonitrile (211 mg, 0.61 mmol), 1-(6-aminopyrimidin-4-yl)-ethanol (92 mg, 0.66 mmol), $Pd_2(dba)_3$ (14 mg, 0.015 mmol), Xantphos (35 mg, 0.06 mmol) and cesium carbonate (391 mg, 1.2 mmol) in dioxane (4.0 mL) was de-gassed and purged with nitrogen and the reaction mixture was heated at 150° C. in the microwave for 30 minutes. The resultant mixture was partitioned between ethyl acetate and water. The layers were separated and the organic layer was washed with brine, dried over anhydrous sodium sulfate, filtered and concentrated under reduced pressure. The residue was purified by silica gel flash chromatography (ethyl acetate) to afford the title compound as a beige solid (61 mg, 25% yield). $^1$H NMR (400 MHz, DMSO-$d_6$): δ 10.84 (s, 1H), 9.47 (d, J=2.5 Hz, 1H), 8.72 (d, J=1.2 Hz, 1H), 8.59 (s, 1H), 8.24-8.21 (m, 2H), 8.02 (d, J=3.5 Hz, 1H), 7.90 (t, J=8.1 Hz, 1H), 5.54 (d, J=4.6 Hz, 1H), 4.70-4.63 (m, 1H), 1.39 (d, J=6.6 Hz, 3H). LCMS (Method B): RT=2.92 min, m/z: 410 [M+H$^+$].

Method 2

Example 97

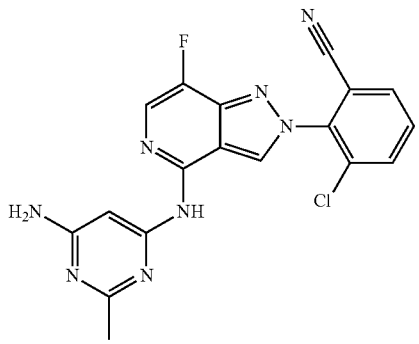 [SMILES: Cc1nc(N)cc(Nc2ncc(F)c3nn(-c4c(Cl)cccc4C#N)cc23)n1]

2-[4-(6-Amino-2-methylpyrimid-4-ylamino)-7-fluoropyrazolo[4,3-c]pyridin-2-yl]-3-chlorobenzonitrile hydrochloride salt Step 1

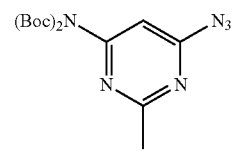

(6-Azido-2-methylpyrimidin-4-yl)-bis-carbamic acid tert-butyl ester

To a mixture of (6-chloro-2-methylpyrimidin-4-yl)-bis-carbamic acid tert-butyl ester (2.0 g, 5.8 mmol) in DMSO (10 mL) was added sodium azide (757 mg, 11.6 mmol). The resultant mixture was heated at 50° C. for 16 hours. After cooling to room temperature, the crude mixture was partitioned between water and EtOAc. The aqueous layer was washed with EtOAc (×2). The combined organic extracts were washed with brine (×2), dried ($Na_2SO_4$) and concentrated to dryness to afford the title compound as an oil (1.64 g, 80% yield). LCMS (Method D): RT=3.76 min, m/z: 351 [M+H$^+$].

Step 2

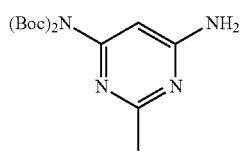

(6-Amino-2-methylpyrimidin-4-yl)-bis-carbamic acid tert-butyl ester

A suspension of (6-azido-2-methylpyrimidin-4-yl)-bis-carbamic acid tert-butyl ester (1.64 g, 4.7 mmol) and 5% Pd/C (0.5 g) in IMS (36 mL) and EtOAc (12 mL) was stirred under an atmosphere of hydrogen for 18 hours at room temperature. The reaction mixture was then filtered through Celite® washing with EtOAc. The filtrate was concentrated to dryness under reduced pressure and the resultant residue was purified by column chromatography on silica gel eluting with 0-60% EtOAc in Pet. Ether (40-60° C.) to afford the title compound as a white solid (0.74 g, 49% yield). LCMS (Method D): RT=2.72 min, m/z: 325 [M+H$^+$].

Step 3

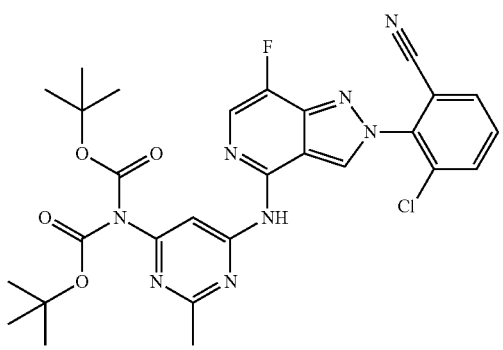 [SMILES: Cc1nc(Nc2ncc(F)c3nn(-c4c(Cl)cccc4C#N)cc23)cc(N(C(=O)OC(C)(C)C)C(=O)OC(C)(C)C)n1]

{6-[2-(2-Chloro-6-cyanophenyl)-7-fluoro-2H-pyrazolo[4,3-c]pyridin-4-ylamino]-2-methylpyrimidin-4-yl}-bis-carbamic acid tert-butyl ester A mixture of 2-(4-bromo-7-fluoropyrazolo[4,3-c]pyridin-2-yl)-3-chlorobenzonitrile (351 mg, 1.0 mmol), (6-amino-2-methylpyrimidin-4-yl)-bis-carbamic acid tert-butyl ester (389 mg, 1.2 mmol), Pd$_2$(dba)$_3$ (23 mg, 0.025 mmol), Xantphos (58 mg, 0.1 mmol) and cesium carbonate (452 mg, 2.0 mmol) in dioxane (8.0 mL) was de-gassed and purged with nitrogen. The reaction mixture was heated at 80° C. in a sealed vial for 6 hours. After cooling to room temperature, the resultant mixture was partitioned between ethyl acetate and water. The layers were separated and the organic layer was washed with brine, dried over anhydrous sodium sulfate, filtered and concentrated under reduced pressure. The residue was purified by silica gel flash chromatography (70% ethyl acetate in cyclohexane) to afford the title compound as a yellow solid (577 mg, 97% yield). $^1$H NMR (400 MHz, DMSO-d$_6$): δ 10.98 (s, 1H), 9.48 (d, J=2.5 Hz, 1H), 8.40 (s, 1H), 8.22 (s, 1H), 8.20 (s, 1H), 7.96 (d, J=3.4 Hz, 1H), 7.94-7.88 (m, 1H), 1.49 (s, 18H).

Step 4

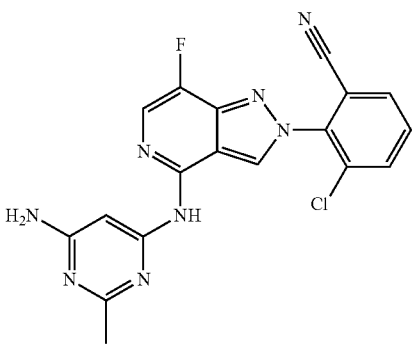 [SMILES: Cc1nc(N)cc(Nc2ncc(F)c3nn(-c4c(Cl)cccc4C#N)cc23)n1]

2-[4-(6-Amino-2-methylpyrimid-4-ylamino)-7-fluoro-pyrazolo[4,3-c]pyridin-2-yl]-3-chlorobenzonitrile hydrochloride salt {6-[2-(2-chloro-6-cyanophenyl)-7-fluoro-2H-pyrazolo[4,3-c]pyridin-4-ylamino]-2-methylpyrimidin-4-yl}-bis-carbamic acid tert-butyl ester (574 mg, 0.97 mmol) was dissolved in a solution of HCl (1.25 N in propan-2-ol, 35 mL) and the reaction mixture was heated at 50° C. for 4 hours. The resultant mixture was allowed to cool to room temperature, filtered and dried to afford the title compound as a yellow solid (357 mg, 85% yield). $^1$H NMR (400 MHz, DMSO-d$_6$): δ 9.61 (d, J=2.5 Hz, 1H), 8.23 (s, 1H), 8.21 (s, 1H), 8.07 (d, J=3.5 Hz, 1H), 7.94 (t, J=8.1 Hz, 1H), 7.55 (s, 1H), 2.52 (s, 3H). LCMS (Method B): RT=3.02 min, m/z: 395 [M+H$^+$].

Method 2

Example 98

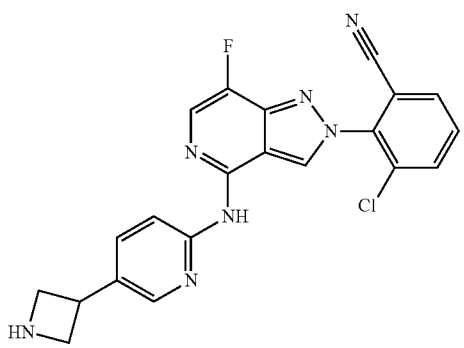 [SMILES: N#Cc1cccc(Cl)c1-n1cc2c(Nc3ccc(C4CNC4)cn3)ncc(F)c2n1]

2-[4-(5-Azetidin-3-yl-pyridin-2-ylamino)-7-fluoro-pyrazolo[4,3-c]pyridin-2-yl]-3-chlorobenzonitrile hydrochloride salt

Step 1

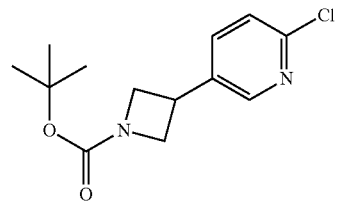 [SMILES: CC(C)(C)OC(=O)N1CC(c2ccc(Cl)nc2)C1]

3-(6-Chloropyridin-3-yl)-azetidine-1-carboxylic acid tert-butyl ester

To a de-gassed suspension of zinc powder (912 mg, 14 mmol) in DMA (2.3 mL) was added drop-wise a solution of chlorotrimethylsilane and 1,2-dibromoethane (0.1 mL, 7:5 v/v ratio) and the resultant mixture was stirred at room temperature for 15 minutes. To this mixture was then added dropwise to a solution of 3-iodoazetidine-1-carboxylic acid tert-butyl ester (3.2 g, 11.3 mmol) in DMA (8.0 mL) and the resultant mixture was stirred at room temperature for 15 minutes. In a separate flask, $PdCl_2(dppf)_2$·DCM (196 mg, 0.24 mmol) and then copper iodide (92 mg, 0.48 mmol) were added to a degassed solution of 2-chloro-4-iodopyridine in DMA (20 mL). After allowing to age for 30 minutes, the zinc suspension above was added to the iodopyridine solution and the reaction mixture was allowed to stir at room temperature for 2 hours. The resultant mixture was quenched by adding saturated ammonium chloride solution and was then extracted with TBME (×2). The combined organic washings were dried over anhydrous sodium sulfate, filtered and concentrated under reduced pressure. The residue was purified by silica gel flash chromatography (0-25% ethyl acetate in cyclohexane) to afford the title compound as a white solid (1.2 g, 56%). LCMS (Method F): RT=3.71 min, m/z: 414 [M+H$^+$].

Step 2

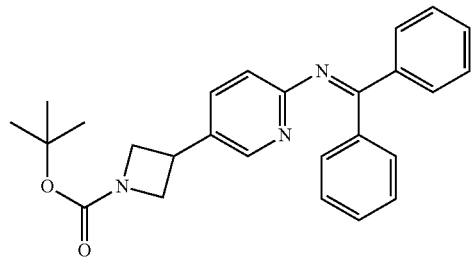 [SMILES: CC(C)(C)OC(=O)N1CC(c2ccc(N=C(c3ccccc3)c3ccccc3)nc2)C1]

3-[6-(Benzhydrylideneamino)-pyridin-3-yl]-azetidine-1-carboxylic acid tert-butyl ester A mixture of 3-(6-chloropyridin-3-yl)-azetidine-1-carboxylic acid tert-butyl ester (274 mg, 1.0 mmol), benzophenone imine (0.2 mL, 1.2 mmol), $Pd_2(dba)_3$ (22 mg, 0.025 mmol), Xantphos (58 mg, 0.10 mmol) and cesium carbonate (652 mg, 2.0 mmol) in dioxane (10 mL) was de-gassed and purged with nitrogen and the reaction mixture was heated at 80° C. in a sealed vial overnight. The resultant mixture was allowed to cool to room temperature, before being partitioned between ethyl acetate and water. The layers were separated and the organic layer was washed with brine, dried over anhydrous sodium sulfate, filtered and concentrated under reduced pressure. The residue was purified by silica gel flash chromatography (30-40% ethyl acetate in cyclohexane) to afford the title compound as a yellow solid (293 mg, 70% yield). LCMS (Method C): RT=3.31 min, m/z: 269 [M+H$^+$].

Step 3

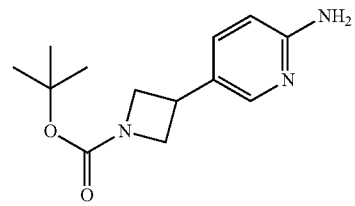 [SMILES: CC(C)(C)OC(=O)N1CC(c2ccc(N)nc2)C1]

3-(6-Aminopyridin-3-yl)-azetidine-1-carboxylic acid tert-butyl ester

To a solution of 3-[6-(benzhydrylideneamino)-pyridin-3-yl]-azetidine-1-carboxylic acid tert-butyl ester (400 mg, 0.97 mmol) in THF (20 mL) was added citric acid (10 mL, 10% aqueous) and the reaction mixture was stirred at room temperature overnight. The resultant mixture was quenched by adding sodium hydrogen carbonate solution and was then extracted with ethyl acetate (×2). The combined organic washings were washed with brine, dried over anhydrous sodium sulfate, filtered and concentrated under reduced pressure. The residue was purified by silica gel flash chromatography (70-100% ethyl acetate in cyclohexane) to afford the title compound as a white solid (183 mg, 76%). LCMS (Method C): RT=1.85 min, m/z: 250 [M+H$^+$].

Step 4

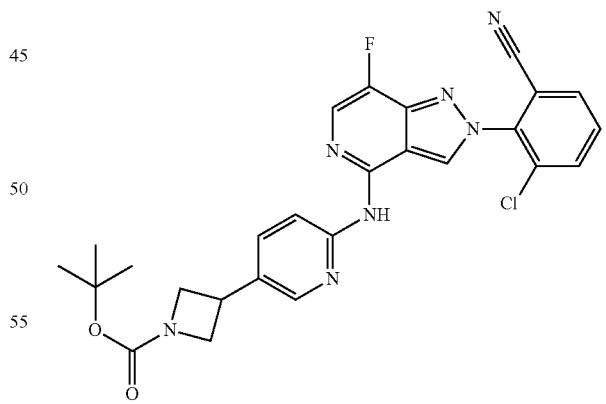

3-{6-[2-(2-Chloro-6-cyanophenyl)-7-fluoro-2H-pyrazolo[4,3-c]pyridin-4-ylamino]-pyridin-3-yl}-azetidine-1-carboxylic acid tert-butyl ester A mixture of 2-(4-bromo-7-fluoropyrazolo[4,3-c]pyridin-2-yl)-3-chlorobenzonitrile (106 mg, 0.3 mmol), 3-(6-aminopyridin-3-yl)-azetidine-1-carboxylic acid tert-butyl ester (57 mg, 0.35 mmol), Pd$_2$(dba)$_3$ (7 mg, 0.0075 mmol), Xantphos (17 mg, 0.03 mmol) and cesium carbonate (196 mg, 0.6 mmol) in dioxane (3.0 mL) was degassed and purged with nitrogen. The reaction mixture was heated at 80° C. overnight. After cooling to room temperature, the resultant mixture was partitioned between ethyl acetate and water. The layers were separated and the organic layer was washed with brine, dried over anhydrous sodium sulfate, filtered and concentrated under reduced pressure. The residue was purified by silica gel flash chromatography (50-60% ethyl acetate in cyclohexane) to afford the title compound as a brown solid (100 mg, 64% yield). LCMS (Method C): RT=2.54 min, m/z: 520 [M+H$^+$].

Step 5

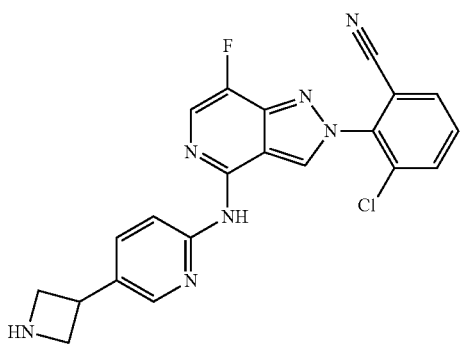 [SMILES: N#Cc1cccc(Cl)c1-n1cc2c(Nc3ccc(C4CNC4)cn3)ncc(F)c2n1]

2-[4-(5-Azetidin-3-yl-pyridin-2-ylamino)-7-fluoropyrazolo[4,3-c]pyridin-2-yl]-3-chlorobenzonitrile hydrochloride salt To a round bottomed flask containing 3-{6-[2-(2-chloro-6-cyanophenyl)-7-fluoro-2H-pyrazolo[4,3-c]pyridin-4-ylamino]-pyridin-3-yl}-azetidine-1-carboxylic acid tert-butyl ester (98 mg, 0.19 mmol), was added a solution of HCl (1.25 N in propan-2-ol, 10 mL) and the suspension was stirred at room temperature for 16 hours and then heated at 50° C. for 4 hours. The reaction mixture was cooled to room temperature, concentrated under reduced pressure and the resultant solid was triturated with diethyl ether, filtered and dried. The crude residue obtained was purified by HPLC [gradient: 20 to 98% MeOH (0.1% NH$_4$OH) in water (0.1% NH$_4$OH)] and freeze dried to afford the free base of the title compound which was dissolved in a solution of HCl (1.25 N in propan-2-ol, 5.0 mL), stirred for 4 hours and was then concentrated under reduced pressure. The resultant residue was triturated with diethyl ether, filtered and dried to yield the title compound as a white solid (30 mg, 35% yield). $^1$H NMR (400 MHz, DMSO-d$_6$): δ 10.00 (d, J=2.5 Hz, 1H), 8.50 (d, J=2.5 Hz, 1H), 8.31 (dd, J=8.7, 2.5 Hz, 1H), 8.26-8.22 (m, 2H), 8.18 (d, J=4.9 Hz, 1H), 7.96 (t, J=8.1 Hz, 1H), 7.75 (d, J=8.9, 1H), 4.39-4.28 (m, 3H), 4.24-4.14 (m, 2H). LCMS (Method B): RT=2.29 min, m/z: 420 [M+H$^+$].

Method 2

Example 99

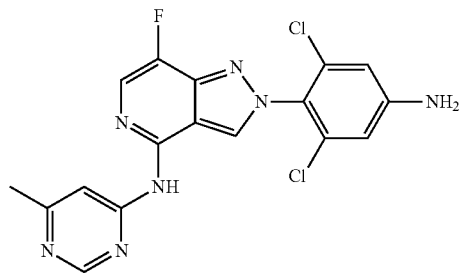

[2-(4-Amino-2,6-dichlorophenyl)-7-fluoro-2H-pyrazolo[4,3-c]pyridin-4-yl]-(6-methylpyrimidin-4-yl)-amine Step 1

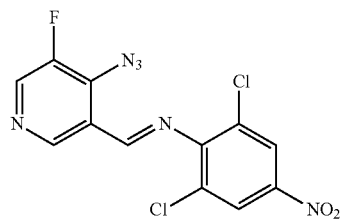 [SMILES: [N-]=[N+]=Nc1c(F)cncc1/C=N/c1c(Cl)cc([N+](=O)[O-])cc1Cl]

[1-(4-Azido-5-fluoropyridin-3-yl)-meth-(E)-ylidene]-(2,6-dichloro-4-nitrophenyl)-amine A solution of 4-azido-5-fluoropyridine-3-carbaldehyde (3.00 g, 18.07 mmol) and 2,6-dichloro-4-nitroaniline (3.74 g, 18.07 mmol) in DCM (60 mL) was cooled to 0° C., under an atmosphere of nitrogen. Triethylamine (7.56 mL, 54.2 mmol) was added, followed by dropwise addition of titanium (IV) chloride solution (1 N in DCM, 10.8 mL, 10.8 mmol). The reaction mixture was stirred at 0° C. for 3 hours, then allowed to reach room temperature over 1 hour. The resultant mixture was concentrated under reduced pressure and the residue was dissolved in ethyl acetate and filtered through a pad of Celite®. The filtrate was concentrated under reduced pressure to afford the crude title compound as a yellow/brown solid (5.89 g, 92% yield). LCMS (Method C): RT=4.08 min, m/z: 327 [M+H$^+$–N$_2$].

Step 2

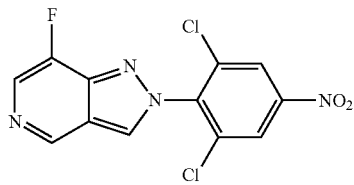 [SMILES: O=[N+]([O-])c1cc(Cl)c(-n2cc3cncc(F)c3n2)c(Cl)c1]

2-(2,6-Dichloro-4-nitrophenyl)-7-fluoro-2H-pyrazolo[4,3-c]pyridine

A suspension of [1-(4-azido-5-fluoropyridin-3-yl)-meth-(E)-ylidene]-(2,6-dichloro-4-nitrophenyl)-amine (5.89 g, 16.6 mmol) in toluene (80 mL) was heated at 105° C. for 4 hours. The resultant mixture was cooled to room temperature and concentrated under reduced pressure. The residue was purified by silica gel flash chromatography (0-5% methanol in DCM) to afford the title compound (4.78 g, 81% yield). $^1$H NMR (300 MHz, CDCl$_3$): δ 9.13 (d, J=2.2 Hz, 1H), 8.43 (s, 2H), 8.39 (d, J=2.4 Hz, 1H), 8.26 (d, J=3.4 Hz, 1H).

Step 3

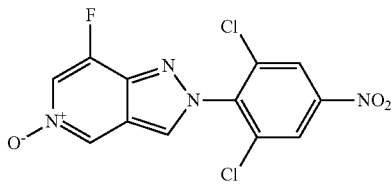 [SMILES: O=[N+]([O-])c1cc(Cl)c(-n2cc3c[n+]([O-])cc(F)c3n2)c(Cl)c1]

2-(2,6-Dichloro-4-nitrophenyl)-7-fluoro-2H-pyrazolo[4,3-c]pyridine 5-oxide 2-(2,6-Dichloro-4-nitrophenyl)-7-fluoro-2H-pyrazolo[4,3-c]pyridine (4.78 g, 14.62 mmol) was dissolved in DCM (90 mL) and a solution of meta-chloroperbenzoic acid (3.78 g, 21.93 mmol) in DCM (60 mL, which had been pre-dried over anhydrous sodium sulfate and passed through a phase separator), was added at 0° C. The reaction mixture was stirred at 0° C. for 1 hour and then at room temperature for 4 hours. Another portion of meta-chloroperbenzoic acid (1.26 g, 7.30 mmol) in DCM (20 mL, dried as above) was added and the reaction mixture was stirred for a further 1.25 hour at room temperature. The resultant mixture was sequentially washed with saturated aqueous sodium thiosulfate solution, saturated aqueous sodium bicarbonate solution and brine. The combined aqueous extracts were further extracted with DCM and the combined organic layers were dried over anhydrous sodium sulfate, filtered and concentrated under reduced pressure. The residue was triturated with diethyl ether (×3) and the solid was collected by filtration and dried under reduced pressure to afford the title compound as a pale yellow solid (4.20 g, 84% yield). $^1$H NMR (300 MHz, CDCl$_3$): δ 8.64 (d, J=1.4 Hz, 1H), 8.42 (s, 2H), 8.20 (d, J=2.3 Hz, 1H), 8.02 (dd, J=5.4, 1.4 Hz, 1H).

Step 4

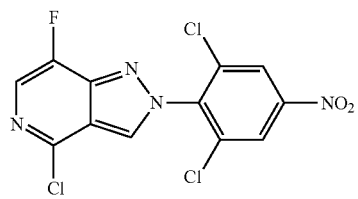 [SMILES: O=[N+]([O-])c1cc(Cl)c(-n2cc3c(Cl)ncc(F)c3n2)c(Cl)c1]

4-Chloro-2-(2,6-dichloro-4-nitrophenyl)-7-fluoro-2H-pyrazolo[4,3-c]pyridine 2-(2,6-Dichloro-4-nitrophenyl)-7-fluoro-2H-pyrazolo[4,3-c]pyridine 5-oxide (4.20 g, 12.24 mmol) was suspended in DCE (60 mL), under an atmosphere of nitrogen and phosphorus oxychloride (3.61 mL, 39.2 mmol) was added. The reaction mixture was heated at 70° C. for 95 minutes. The resultant mixture was cooled to room temperature and was carefully quenched by the addition of 10% aqueous sodium carbonate solution. The layers were separated and the aqueous layer was extracted with DCM (×4). The combined organic layers were filtered to remove insoluble solids, dried over anhydrous sodium sulfate, filtered and concentrated under reduced pressure. The residue was purified by silica gel flash chromatography (0-50% ethyl acetate in cyclohexane) to afford the title compound as a pale yellow solid (1.78 g, 40% yield). $^1$H NMR (300 MHz, CDCl$_3$): δ 8.43 (s, 2H), 8.37 (d, J=2.2 Hz, 1H), 8.03 (d, J=3.0 Hz, 1H).

Step 5

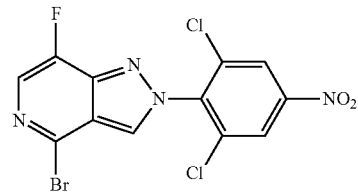 [SMILES: O=[N+]([O-])c1cc(Cl)c(-n2cc3c(Br)ncc(F)c3n2)c(Cl)c1]

4-Bromo-2-(2,6-dichloro-4-nitrophenyl)-7-fluoro-2H-pyrazolo[4,3-c]pyridine

4-Chloro-2-(2,6-dichloro-4-nitrophenyl)-7-fluoro-2H-pyrazolo[4,3-c]pyridine (1.78 g, 4.93 mmol) was suspended in propionitrile (30 mL), under an atmosphere of nitrogen and bromo trimethylsilane (5.1 mL, 38.3 mmol) was added. The reaction mixture was heated at 105° C. overnight. The resultant mixture was cooled to room temperature and partitioned between ethyl acetate and saturated aqueous sodium bicarbonate solution. The layers were separated and the aqueous layer was further extracted with ethyl acetate (×2). The combined organic layers were dried over anhydrous sodium sulfate, filtered and concentrated under reduced pressure. The residue was triturated with pentane and the solid obtained was dried under reduced pressure to afford the title compound as a pale yellow solid (2.06 g, quantitative yield). $^1$H NMR (300 MHz, CDCl$_3$): δ 8.44 (s, 2H), 8.33 (d, J=2.2 Hz, 1H), 8.05 (d, J=3.0 Hz, 1H).

Step 6

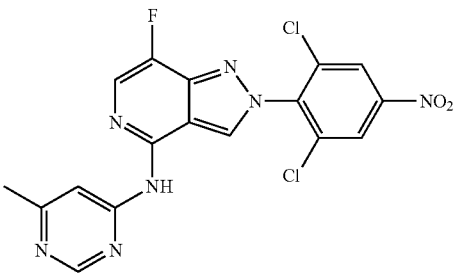 [SMILES: Cc1cc(Nc2ncc(F)c3nn(-c4c(Cl)cc([N+](=O)[O-])cc4Cl)cc23)ncn1]

[2-(2,6-Dichloro-4-nitrophenyl)-7-fluoro-2H-pyrazolo[4,3-c]pyridin-4-yl]-(6-methylpyrimidin-4-yl)-amine A mixture of 4-bromo-2-(2,6-dichloro-4-nitrophenyl)-7-fluoro-2H-pyrazolo[4,3-c]pyridine (200 mg, 0.49 mmol), 4-amino-6-methylpyrimidine (60 mg, 0.55 mmol), Pd$_2$(dba)$_3$ (11 mg, 0.012 mmol), Xantphos (28 mg, 0.049 mmol) and cesium carbonate (321 mg, 0.99 mmol) in dioxane (3 mL) was de-gassed and purged with nitrogen. The reaction mixture was heated at 150° C. in the microwave for 30 minutes. The resultant mixture was partitioned between ethyl acetate and water. The aqueous layer was further extracted with ethyl acetate (×4) and the combined organic layers were dried over anhydrous sodium sulfate, filtered and concentrated under reduced pressure. The residue was purified by silica gel flash chromatography (50-100% ethyl acetate in cyclohexane) to afford the title compound as a pale yellow solid (173 mg, 72% yield). $^1$H NMR (300 MHz, CDCl$_3$): δ 8.69 (s, 1H), 8.44-8.40 (m, 3H), 8.25 (s, 1H), 7.91 (d, J=3.2 Hz, 1H), 7.80 (br s, 1H), 2.55 (s, 3H).

Method 2

Example 100

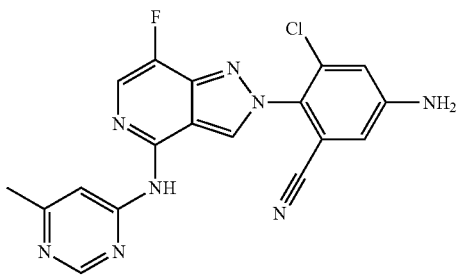

5-Amino-3-chloro-2-[7-fluoro-4-(6-methylpyrimidin-4-ylamino)-pyrazolo-ylamino)[4,3-c]pyridin-2-yl]benzonitrile Step 7

Step 1

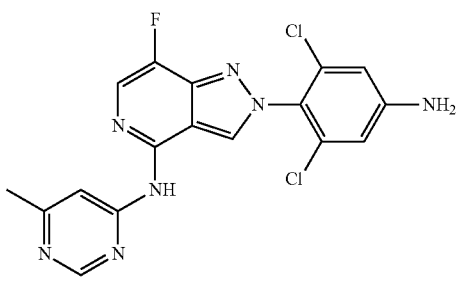 [SMILES: Cc1cc(Nc2ncc(F)c3nn(-c4c(Cl)cc(N)cc4Cl)cc23)ncn1]

[2-(4-Amino-2,6-dichlorophenyl)-7-fluoro-2H-pyrazolo[4,3-c]pyridin-4-yl]-(6-methylpyrimidin-4-yl)-amine

[2-(2,6-Dichloro-4-nitrophenyl)-7-fluoro-2H-pyrazolo[4,3-c]pyridin-4-yl]-(6-methylpyrimidin-4-yl)-amine (173 mg, 0.40 mmol) was dissolved in ethanol (10 mL) and THF (4.0 mL) and water (1.0 mL) were added, followed by iron powder (325 mesh, 112 mg, 2.0 mmol) and ammonium chloride (86 mg, 1.6 mmol). The reaction mixture was heated at 70° C. for 4 hours. More iron powder (112 mg) and ammonium chloride (100 mg) were added and the mixture was heated at 70° C. for another 5 hours. The resultant mixture was cooled and filtered through Celite®. The filtrate was concentrated under reduced pressure and the residue was triturated with water. The solid obtained was dried under reduced pressure and purified by silica gel flash chromatography (0-5% methanol in DCM) to afford the title compound as an off-white solid (120 mg, 74% yield). $^1$H NMR (400 MHz, DMSO-d$_6$): δ 10.62 (s, 1H), 9.13 (d, J=2.6 Hz, 1H), 8.71 (d, J=1.2 Hz, 1H), 8.42 (s, 1H), 7.96 (d, J=3.5 Hz, 1H), 6.83 (s, 2H), 6.30 (s, 2H), 2.46 (s, 3H). LCMS (Method B): RT=3.00 min, m/z: 404 [M+H$^+$].

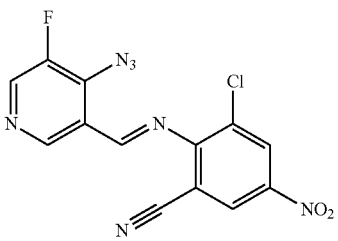 [SMILES: N#Cc1cc([N+](=O)[O-])cc(Cl)c1/N=C/c1cncc(F)c1N=[N+]=[N-]]

2-{[1-(4-Azido-5-fluoropyridin-3-yl)-meth-(E)-ylidene]-amino}-3-chloro-5-nitrobenzonitrile Following the procedure described for [1-(4-azido-5-fluoropyridin-3-yl)-meth-(E)-ylidene]-(2,6-dichloro-4-nitrophenyl)-amine (Example 99, Step 1), 2-amino-3-chloro-5-nitrobenzonitrile was stirred at room temperature to afford the title compound which was used without purification (6.07 g, quantitative yield). LCMS (Method C): RT=3.69 min, m/z: 318 [M+H$^+$–N$_2$].

Step 2

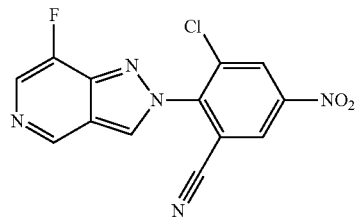 [SMILES: N#Cc1cc([N+](=O)[O-])cc(Cl)c1-n1cc2cncc(F)c2n1]

3-Chloro-2-(7-fluoro-pyrazolo[4,3-c]pyridin-2-yl)-5-nitrobenzonitrile

Following the procedure described for 2-(2,6-dichloro-4-nitrophenyl)-7-fluoro-2H-pyrazolo[4,3-c]pyridine, 2-{[1-(4-azido-5-fluoropyridin-3-yl)-meth-(E)-ylidene]-amino}-3-chloro-5-nitrobenzonitrile was heated at 107° C. for 3.5 hours. After purification by silica gel chromatography (0-5% methanol in DCM), the product was triturated 5 times with diethyl ether/cyclohexane (1:1) to afford the title compound as a yellow solid (3.31 g, 58% yield). LCMS (Method C): RT=2.89 min, m/z: 318 [M+H$^+$].

Step 3

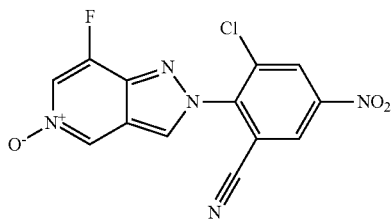 [SMILES: N#Cc1cc([N+](=O)[O-])cc(Cl)c1-n1cc2c[n+]([O-])cc(F)c2n1]

3-Chloro-2-(7-fluoro-5-oxypyrazolo[4,3-c]pyridin-2-yl)-5-nitrobenzonitrile

Methyl trioxorhenium (VII) (0.26 g, 1.04 mmol) was added to a solution of 3-chloro-2-(7-fluoro-pyrazolo[4,3-c]pyridin-2-yl)-5-nitrobenzonitrile (3.31 g, 10.4 mmol) in DCM (35 mL). Aqueous hydrogen peroxide solution (27%, 1.48 mL, 20.6 mmol) was then added dropwise and the reaction mixture was stirred at room temperature overnight. Additional methyl trioxorhenium (50 mg) and hydrogen peroxide solution (0.3 mL) were added and the reaction mixture was stirred at room temperature for 4 hours. The resultant solid was decanted and the remaining solution was washed with saturated aqueous sodium bicarbonate. The aqueous layer was then extracted with DCM and 10% methanol in DCM (×3). The combined organic washings were dried over anhydrous sodium sulfate, filtered and concentrated under reduced pressure. The residue was combined with the solid that was decanted from solution above and purified by silica gel flash chromatography (0-10% methanol in DCM) to afford the title compound as a pale yellow solid (2.75 g, 79% yield). LCMS (Method C): RT=2.45 min, m/z: 334 [M+H$^+$].

Step 4

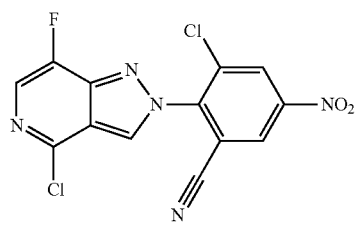 [SMILES: N#Cc1cc([N+](=O)[O-])cc(Cl)c1-n1cc2c(Cl)ncc(F)c2n1]

3-Chloro-2-(4-chloro-7-fluoropyrazolo[4,3-c]pyridin-2-yl)-5-nitrobenzonitrile

Following the procedure described for 4-chloro-2-(2,6-dichloro-4-nitrophenyl)-7-fluoro-2H-pyrazolo[4,3-c]pyridine, 3-chloro-2-(7-fluoro-5-oxypyrazolo[4,3-c]pyridin-2-yl)-5-nitrobenzonitrile was heated at 70° C. overnight to afford the title compound as a pale yellow solid (1.47 g, 51% yield). LCMS (Method C): RT=3.57 min, m/z: 352 [M+H$^+$].

Step 5

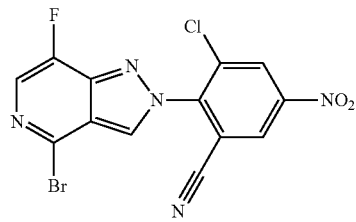 [SMILES: N#Cc1cc([N+](=O)[O-])cc(Cl)c1-n1cc2c(Br)ncc(F)c2n1]

2-(4-Bromo-7-fluoropyrazolo[4,3-c]pyridin-2-yl)-3-chloro-5-nitrobenzonitrile

Following the procedure described for 4-bromo-2-(2,6-dichloro-4-nitrophenyl)-7-fluoro-2H-pyrazolo[4,3-c]pyridine, 3-chloro-2-(4-chloro-7-fluoropyrazolo[4,3-c]pyridin-2-yl)-5-nitrobenzonitrile was heated at 100° C. overnight to afford the title compound as a pale yellow solid (1.38 g, 83% yield). LCMS (Method C): RT=3.62 min, m/z: 396 [M+H$^+$].

Step 6

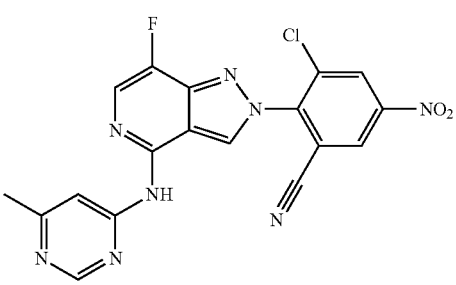 [SMILES: Cc1cc(Nc2ncc(F)c3nn(-c4c(Cl)cc([N+](=O)[O-])cc4C#N)cc23)ncn1]

3-Chloro-2-[7-fluoro-4-(6-methylpyrimidin-4-ylamino)-pyrazolo[4,3-c]pyridin-2-yl]-5-nitrobenzonitrile Following the procedure described for [2-(2,6-dichloro-4-nitrophenyl)-7-fluoro-2H-pyrazolo[4,3-c]pyridin-4-yl]-(6-methylpyrimidin-4-yl)-amine, 2-(4-bromo-7-fluoropyrazolo[4,3-c]pyridin-2-yl)-3-chloro-5-nitrobenzonitrile was heated at 80° C. overnight to afford the title compound as a pale yellow solid (43 mg, 20% yield). LCMS (Method C): RT=2.56 min, m/z: 425 [M+H$^+$].

205

Step 7

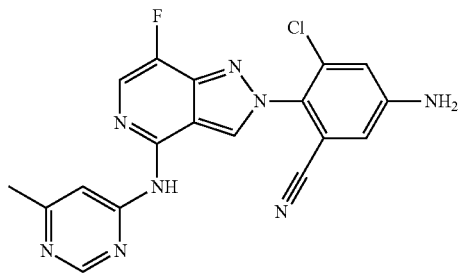 [SMILES: Cc1cc(Nc2ncc(F)c3nn(-c4c(Cl)cc(N)cc4C#N)cc23)ncn1]

5-Amino-3-chloro-2-[7-fluoro-4-(6-methylpyrimidin-4-ylamino)-pyrazolo[4,3-c]pyridin-2-yl]benzonitrile Following the procedure described for [2-(4-amino-2,6-dichlorophenyl)-7-fluoro-2H-pyrazolo[4,3-c]pyridin-4-yl]-(6-methylpyrimidin-4-ylamino)-amine, 3-chloro-2-[7-fluoro-4-(6-methylpyrimidin-4-ylamino)-pyrazolo[4,3-c]pyridin-2-yl]-5-nitrobenzonitrile was heated at 70° C. for 7 h to afford the title compound as a pale yellow solid (27 mg, 30% yield). $^1$H NMR (400 MHz, DMSO-$d_6$): δ 10.68 (s, 1H), 9.26 (d, J=2.6 Hz, 1H), 8.68 (d, J=1.2 Hz, 1H), 8.37 (s, 1H), 7.97 (d, J=3.5 Hz, 1H), 7.13-7.08 (m, 2H), 6.48 (s, 2H), 2.43 (s, 3H). LCMS (Method B): RT=2.88 min, m/z: 395 [M+H$^+$].

Method 2

Example 101

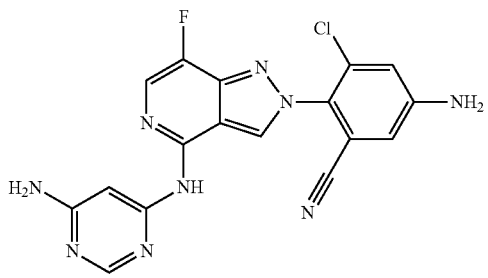 [SMILES: N#Cc1cc(N)cc(Cl)c1-n1cc2c(Nc3cc(N)ncn3)ncc(F)c2n1]

5-Amino-2-[4-(6-aminopyrimidin-4-ylamino)-7-fluoropyrazolo[4,3-c]pyridin-2-yl]-3-chlorobenzonitrile formate salt Step 1

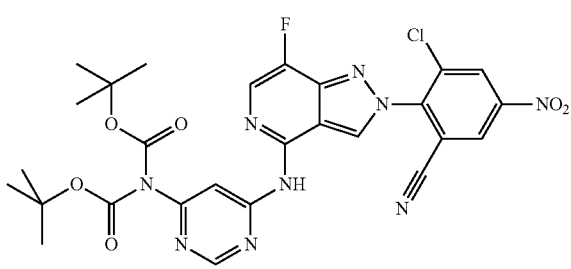

206

-continued

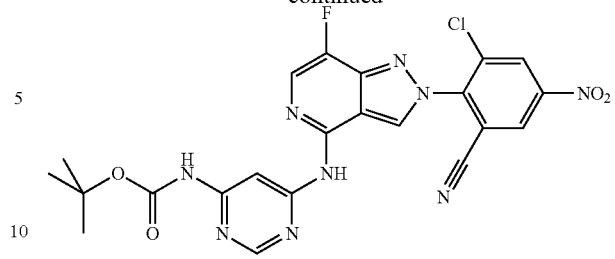

{6-[2-(2-Chloro-6-cyano-4-nitrophenyl)-7-fluoro-2H-pyrazolo[4,3-c]pyridin-4-ylamino]-pyrimidin-4-yl}-bis-carbamic acid tert-butyl ester and {6-[2-(2-chloro-6-cyano-4-nitrophenyl)-7-fluoro-2H-pyrazolo[4,3-c]pyridin-4-ylamino]-pyrimidin-4-yl}-carbamic acid tert-butyl ester Following the procedure described for [2-(2,6-dichloro-4-nitrophenyl)-7-fluoro-2H-pyrazolo[4,3-c]pyridin-4-yl]-(6-methylpyrimidin-4-yl)-amine, 2-(4-bromo-7-fluoropyrazolo[4,3-c]pyridin-2-yl)-3-chloro-5-nitrobenzonitrile and (6-amino-pyrimidin-4-yl)-bis-carbamic acid tert-butyl ester were heated at 80° C. overnight to afford the first title compound as a pale yellow solid (60 mg, 13% yield). $^1$H NMR (400 MHz, CDCl$_3$): δ 8.71 (d, J=2.5 Hz, 1H), 8.66-8.64 (m, 2H), 8.56-8.54 (m, 2H), 8.13 (d, J=2.6 Hz, 1H), 7.98 (br s, 1H), 1.56 (s, 18H). The second title compound was also obtained as a pale yellow solid (55 mg, 14% yield). $^1$H NMR (400 MHz, CDCl$_3$): δ 8.71-8.68 (m, 2H), 8.62 (d, J=2.5 Hz, 1H), 8.57 (d, J=2.4 Hz, 1H), 8.51 (s, 1H), 8.19 (d, J=2.8 Hz, 1H), 8.03 (br s, 1H), 7.95 (br s, 1H), 1.56 (s, 9H).

Step 2

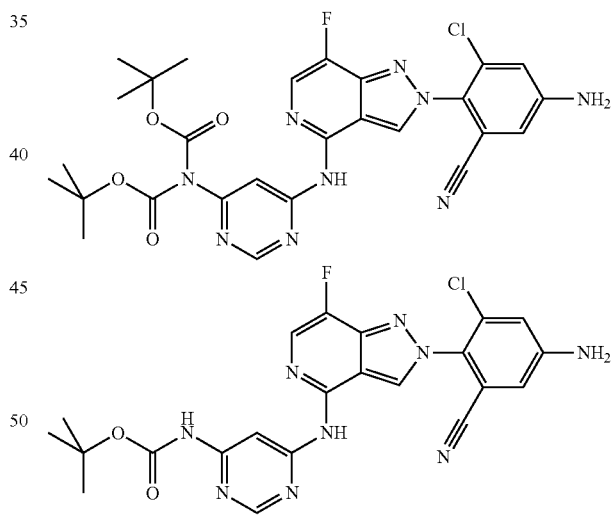

{6-[2-(4-Amino-2-chloro-6-cyanophenyl)-7-fluoro-2H-pyrazolo[4,3-c]pyridin-4-ylamino]-pyrimidin-4-yl}-bis-carbamic acid tert-butyl ester and {6-[2-(4-amino-2-chloro-6-cyanophenyl)-7-fluoro-2H-pyrazolo[4,3-c]pyridin-4-ylamino]-pyrimidin-4-yl}-carbamic acid tert-butyl ester Following the procedure described for [2-(4-amino-2,6-dichlorophenyl)-7-fluoro-2H-pyrazolo[4,3-c]pyridin-4-yl]-(6-methylpyrimidin-4-yl)-amine, {6-[2-(2-chloro-6-cyano-4-nitrophenyl)-7-fluoro-2H-pyrazolo[4,3-c]pyridin-4-ylamino]-pyrimidin-4-yl}-bis-carbamic acid tert-butyl ester and {6-[2-(2-chloro-6-cyano-4-nitrophenyl)-7-fluoro-2H- pyrazolo[4,3-c]pyridin-4-ylamino]-pyrimidin-4-yl}-carbamic acid tert-butyl ester were heated at 70° C. overnight to afford the a mixture of the two title compounds as a pale yellow solid (66 mg, 60% yield). LCMS (Method C): RT=3.97 min, m/z: 595 [M+H⁺], RT=3.07 min, m/z: 495 [M+H⁺].

Step 3

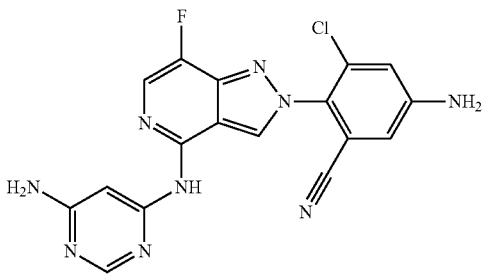 [SMILES: N#Cc1cc(N)cc(Cl)c1-n1cc2c(Nc3cc(N)ncn3)ncc(F)c2n1]

5-Amino-2-[4-(6-aminopyrimidin-4-ylamino)-7-fluoropyrazolo[4,3-c]pyridin-2-yl]-3-chlorobenzonitrile formate salt A mixture of {6-[2-(4-amino-2-chloro-6-cyanophenyl)-7-fluoro-2H-pyrazolo[4,3-c]pyridin-4-ylamino]-pyrimidin-4-yl}-bis-carbamic acid tert-butyl ester and {6-[2-(4-amino-2-chloro-6-cyanophenyl)-7-fluoro-2H-pyrazolo[4,3-c]pyridin-4-ylamino]-pyrimidin-4-yl}-carbamic acid tert-butyl ester (66 mg, ~0.12 mmol) in HCl (4 N in dioxane, 5.0 mL, 20 mmol) was stirred at room temperature overnight. Additional HCl (4 N in dioxane, 1.0 mL, 10 mmol) was added and the reaction mixture was heated at 40° C. for 7 hours. The resultant suspension was concentrated under reduced pressure and the residue was triturated with diethyl ether. The solid obtained was dried under vacuum and was purified by HPLC [gradient: 5 to 60% acetonitrile (0.1% formic acid) in water (0.1% formic acid)], to afford the title compound as a white solid (30 mg, 59% yield). ¹H NMR (400 MHz, DMSO-d₆): δ 10.20 (s, 1H), 9.04 (d, J=2.4 Hz, 1H), 8.16 (d, J=1.1 Hz, 1H), 8.06 (d, J=3.0 Hz, 1H), 7.51 (d, J=1.1 Hz, 1H), 7.09 (d, J=2.5 Hz, 1H), 7.06 (d, J=2.5 Hz, 1H), 6.69 (s, 2H); 6.44 (s, 2H). LCMS (Method B): RT=2.70 min, m/z: 396 [M+H⁺].

Method 2

Example 102

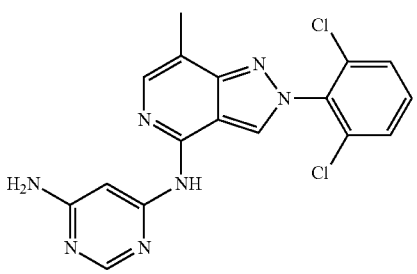 [SMILES: Cc1cnc(Nc2cc(N)ncn2)c2cn(-c3c(Cl)cccc3Cl)nc12]

N-[2-(2,6-Dichlorophenyl)-7-methyl-2H-pyrazolo[4,3-c]pyridin-4-yl]-pyrimidine-4,6-diamine Step 1

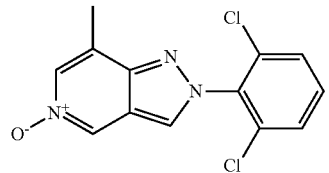 [SMILES: Cc1c[n+]([O-])cc2cn(-c3c(Cl)cccc3Cl)nc12]

2-(2,6-Dichlorophenyl)-7-methyl-2H-pyrazolo[4,3-c]pyridine-5-oxide

Trimethylboroxine (0.348 mL, 2.5 mmol) was added to a suspension of 7-bromo-2-(2,6-dichlorophenyl)-2H-pyrazolo[4,3-c]pyridine-5-oxide (720 mg, 2.0 mmol), potassium carbonate (829 mg, 6.0 mmol) and Pd(PPh₃)₄ (228 mg, 0.2 mmol) in dioxane (11 mL) and the reaction mixture was heated at 80° C., under an atmosphere of nitrogen overnight. Additional trimethylboroxine (0.278 mL) was added and the reaction mixture was heated at 80° C. for another 2 hours. The resultant mixture was cooled to room temperature and filtered. The solid was washed with ethyl acetate and methanol (9:1). The filtrate was concentrated under reduced pressure to give a brown solid. This was purified by silica gel flash chromatography (0-20% methanol in ethyl acetate) to afford the title compound as a pale yellow solid (405 mg, 69% yield). LCMS (Method F): RT=2.30 min, m/z: 294 [M+H⁺].

Step 2

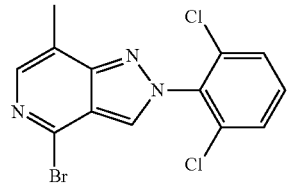 [SMILES: Cc1cnc(Br)c2cn(-c3c(Cl)cccc3Cl)nc12]

4-Bromo-2-(2,6-dichlorophenyl)-7-methyl-2H-pyrazolo[4,3-c]pyridine

Phosphorus(V) oxybromide (921 mg, 3.43 mmol) was slowly added to a suspension of 2-(2,6-dichlorophenyl)-7-methyl-2H-pyrazolo[4,3-c]pyridine-5-oxide (404 mg, 1.37 mmol) in DCE (9.0 mL) at 0° C., under an atmosphere of nitrogen. The reaction mixture was stirred at 0° C. for 30 minutes and then at room temperature overnight. The orange suspension was poured onto saturated aqueous sodium carbonate solution and was stirred for 10 minutes. This was extracted with DCM and the organic layer was washed with brine, dried over anhydrous magnesium sulfate, filtered and concentrated under reduced pressure. The residue was purified by silica gel flash chromatography (0-30% ethyl acetate in cyclohexane) to afford the title compound as a white solid (185 mg, 38% yield). ¹H NMR (300 MHz, DMSO-d₆): δ 9.20 (s, 1H), 7.90-7.89 (m, 1H), 7.84-7.80 (m, 2H), 7.76-7.72 (m, 1H), 2.45 (d, J=1.2 Hz, 3H).

Step 3

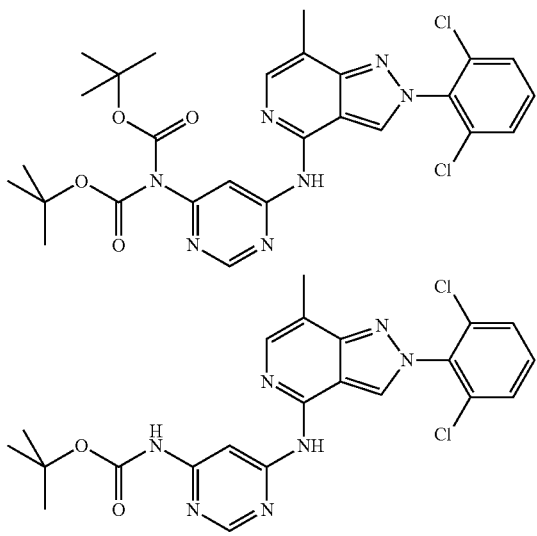

{6-[2-(2,6-Dichlorophenyl)-7-methyl-2H-pyrazolo[4,3-c]pyridin-4-ylamino]-pyrimidin-4-yl}-bis-carbamic acid tert-butyl ester and {6-[2-(2,6-dichlorophenyl)-7-methyl-2H-pyrazolo[4,3-c]pyridin-4-ylamino]-pyrimidin-4-yl}-carbamic acid tert-butyl ester A mixture of 4-bromo-2-(2,6-dichlorophenyl)-7-methyl-2H-pyrazolo[4,3-c]pyridine (95 mg, 0.27 mmol), (6-aminopyrimidin-4-yl)-bis-carbamic acid tert-butyl ester (99 mg, 0.32 mmol), Pd$_2$(dba)$_3$ (6 mg, 0.006 mmol), Xantphos (15 mg, 0.027 mmol) and cesium carbonate (174 mg, 0.53 mmol) in dioxane (2.0 mL) was de-gassed and purged with nitrogen and the reaction mixture was heated at 150° C. in the microwave for 1 hour. The resultant mixture was diluted with dioxane and filtered. The solid was washed with dioxane and the filtrate was concentrated under reduced pressure. The residue obtained was dried under a high vacuum to yield a crude mixture of the two title compounds as a yellow solid. LCMS (Method C): RT=3.08 min, m/z: 586 [M+H$^+$], RT=2.66 min, m/z: 486 [M+H$^+$]. This crude residue was employed directly in next step without further purification.

Step 4

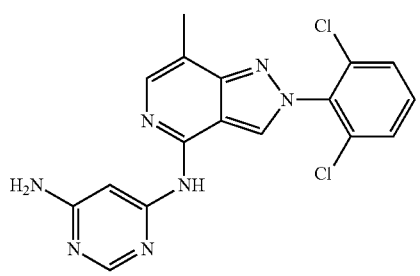 [SMILES: Cc1cnc(Nc2cc(N)ncn2)c2cn(-c3c(Cl)cccc3Cl)nc12]

N-[2-(2,6-Dichlorophenyl)-7-methyl-2H-pyrazolo[4,3-c]pyridin-4-yl]-pyrimidine-4,6-diamine TFA (1.5 mL) was slowly added to the crude mixture of {6-[2-(2,6-dichlorophenyl)-7-methyl-2H-pyrazolo[4,3-c]pyridin-4-ylamino]-pyrimidin-4-yl}-bis-carbamic acid tert-butyl ester and {6-[2-(2,6-dichlorophenyl)-7-methyl-2H-pyrazolo[4,3-c]pyridin-4-ylamino]-pyrimidin-4-yl}-carbamic acid tert-butyl ester in DCM (1.5 mL) at 0° C., under an atmosphere of nitrogen. The reaction mixture was stirred with warming to room temperature over 2 hours. The resultant mixture was concentrated under reduced pressure and the residue was triturated with diethyl ether. The pale yellow solid formed was filtered and washed with diethyl ether to afford the crude title compound (30 mg). The filtrate was concentrated under reduced pressure to afford impure title compound as an yellow oil (220 mg). The two batches were separately dissolved in ethyl acetate, then combined and washed with saturated aqueous sodium bicarbonate solution. The organic layer was dried over anhydrous magnesium sulfate, filtered and concentrated to afford the crude residue. This was purified by silica gel flash chromatography (0-10% methanol in DCM), then further purified by HPLC (gradient: 5 to 98% acetonitrile (0.1% ammonium hydroxide) in water (0.1% ammonium hydroxide)], to afford the title compound as a white powder (14 mg, 14% yield). $^1$H NMR (400 MHz, DMSO-d$_6$): δ 9.38 (s, 1H), 8.51 (d, J=0.9 Hz, 1H), 7.89-7.85 (m, 2H), 7.81-7.74 (m, 2H), 6.51 (br s, 1H), 2.45 (d, J=1.3 Hz, 3H). LCMS (Method B): RT=3.05 min, m/z: 386 [M+H$^+$].

Method 2

Example 103

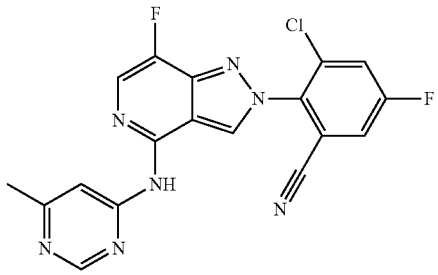 [SMILES: Cc1cc(Nc2ncc(F)c3nn(-c4c(Cl)cc(F)cc4C#N)cc23)ncn1]

3-Chloro-5-fluoro-2-[7-fluoro-4-(6-methylpyrimidin-4-ylamino)-pyrazolo[4,3-c]pyridin-2-yl]-benzonitrile

Step 1

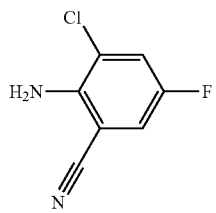 [SMILES: N#Cc1cc(F)cc(Cl)c1N]

2-Amino-3-chloro-5-fluorobenzonitrile

A mixture of 2-bromo-6-chloro-4-fluoroaniline (6.0 g, 26.7 mmol), zinc cyanide (11.42 g, 97.6 mmol) and Pd(PPh$_3$)$_4$ (2.16 g, 1.92 mmol) in anhydrous DMF (84 mL) was heated at 80° C., under an atmosphere of argon for 24 hours. The reaction mixture was cooled and diluted with brine. This mixture was extracted with ethyl acetate (×3) and the combined organic layers were washed with water (×2), dried, filtered and concentrated under reduced pressure. The residue was purified by silica gel flash chromatography (0-20% ethyl acetate in cyclohexane) to afford the title compound as a pale yellow solid (3.29 g, 72% yield). $^1$H NMR (300 MHz, CDCl$_3$): δ 7.27 (dd, J=7.9, 2.9 Hz, 1H), 7.08 (dd, J=7.6, 2.9 Hz, 1H), 4.67 (br s, 2H).

Alternative Procedure for 2-Amino-3-Chloro-5-fluorobenzonitrile

To a solution of 2-amino-5-fluorobenzonitrile (15.0 g, 110 mmol) in anhydrous acetonitrile (300 mL) was added N-chlorosuccinimide (16.0 g, 120 mmol) portionwise. The reaction mixture was heated at 80° C. for 18 hours under nitrogen. The resultant mixture was allowed to cool, concentrated under reduced pressure and then partitioned between EtOAc and water. The aqueous layer was extracted with ethyl acetate and the combined organic extracts were dried, filtered and concentrated under reduced pressure. The crude residue was purified by silica gel flash chromatography (10-20% diethyl ether in pentane) to afford the title compound as an off-white solid (9.6 g, 51% yield). $^1$H NMR (300 MHz, CDCl$_3$): δ 7.27 (dd, J=7.9, 2.9 Hz, 1H), 7.08 (dd, J=7.6, 2.9 Hz, 1H), 4.67 (br s, 2H).

Step 2

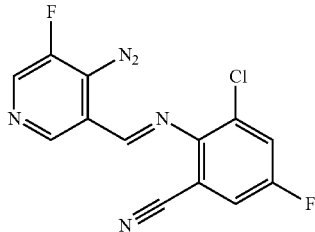

2-{[1-(4-Azido-5-fluoropyridin-3-yl)-meth-(E)-ylidene]-amino}-3-chloro-5-fluorobenzonitrile A solution of 4-azido-5-fluoro-3-pyridinecarboxaldehyde (1.0 g, 6.02 mmol) and 2-amino-3-chloro-5-fluorobenzonitrile (1.03 g, 6.02 mmol) in anhydrous DCM (20 mL) was cooled in an icebath and triethylamine (2.52 mL, 18.07 mmol) was added, followed by titanium (IV) chloride (1 N in DCM, 3.6 mL, 3.6 mmol). The reaction mixture was stirred at 0° C. for 3 hours and then at room temperature overnight. The resultant mixture was concentrated under reduced pressure and the residue was suspended in ethyl acetate and filtered through a pad of Celite®. The filtrate was concentrated under reduced pressure to afford the title compound as a pale brown solid (1.67 g, 89% yield), which was used directly in the next step without purification. LCMS (Method C): RT=3.74 min, m/z: 291 [M+H$^+$–N$_2$].

Step 3

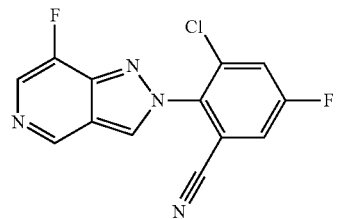 [SMILES: N#Cc1cc(F)cc(Cl)c1-n1cc2cncc(F)c2n1]

3-Chloro-5-fluoro-2-(7-fluoropyrazolo[4,3-c]pyridin-2-yl)-benzonitrile

A solution of 2-{[1-(4-azido-5-fluoropyridin-3-yl)-meth-(E)-ylidene]-amino}-3-chloro-5-fluorobenzonitrile (1.67 g, 5.25 mmol) in anhydrous toluene (25 mL) was heated under reflux for 4.5 hours. The resultant mixture was allowed to cool to room temperature and concentrated under reduced pressure. The residue was purified by silica gel flash chromatography (0-5% methanol in DCM) to afford the title compound as a yellow solid (1.41 g, 93% yield). LCMS (Method C): RT=2.71 min, m/z: 291 [M+H$^+$].

Step 4

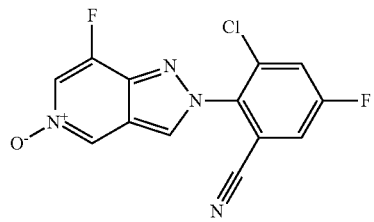 [SMILES: N#Cc1cc(F)cc(Cl)c1-n1cc2c[n+]([O-])cc(F)c2n1]

3-Chloro-5-fluoro-2-(7-fluoro-5-oxypyrazolo[4,3-c]pyridin-2-yl)-benzonitrile

3-Chloro-5-fluoro-2-(7-fluoropyrazolo[4,3-c]pyridin-2-yl)-benzonitrile (1.41 g, 4.84 mmol) was dissolved in DCM (16 mL) and methyltrioxorhenium (VI) (0.13 g, 0.48 mmol), followed by hydrogen peroxide (27% aqueous solution, 0.69 mL, 9.59 mmol) were added. The reaction mixture was stirred at room temperature overnight. Additional methyltrioxorhenium (VI) (0.025 g) and hydrogen peroxide solution (0.15 mL) were added and the reaction mixture was stirred at room temperature for 5 hours. The resulting mixture was washed with saturated aqueous sodium bicarbonate solution and the aqueous layer was separated and extracted into DCM (×4). The combined organic layers were dried, filtered and concentrated under reduced pressure. The residue was triturated with diethyl ether (×2) and the solid obtained was filtered and dried under reduced pressure to afford the title compound as a yellow solid (1.21 g, 82% yield). LCMS (Method C): RT=2.35 min, m/z: 307 [M+H$^+$].

Step 5

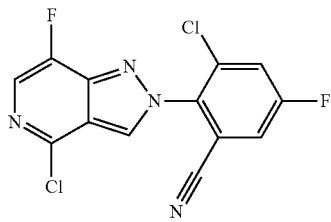 [SMILES: N#Cc1cc(F)cc(Cl)c1-n1cc2c(Cl)ncc(F)c2n1]

3-Chloro-2-(4-chloro-7-fluoropyrazolo[4,3-c]pyridin-2-yl)-5-fluorobenzonitrile

3-Chloro-5-fluoro-2-(7-fluoro-5-oxypyrazolo[4,3-c]pyridin-2-yl)-benzonitrile (1.21 g, 3.95 mmol) was suspended in DCE (19 mL) and phosphorus oxychloride (1.2 mL, 12.7 mmol) was added. The reaction mixture was heated at 70° C. overnight. The resultant mixture was cooled and saturated aqueous sodium bicarbonate solution was added cautiously. DCM was added and the layers were separated. The aqueous layer was extracted with DCM (×3) and the combined organic layers were dried, filtered and concentrated under reduced pressure. The residue was purified by silica gel flash chromatography (0-50% ethyl acetate in cyclohexane) to afford the title compound as a yellow solid (0.55 g, 43% yield). LCMS (Method C): RT=3.51 min, m/z: 325 [M+H$^+$].

Step 6

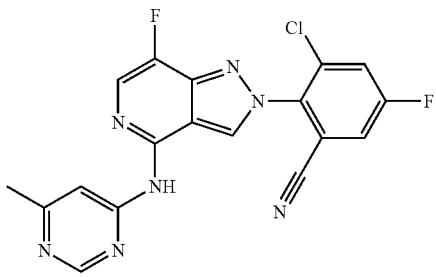 [SMILES: Cc1cc(Nc2ncc(F)c3nn(-c4c(Cl)cc(F)cc4C#N)cc23)ncn1]

3-Chloro-5-fluoro-2-[7-fluoro-4-(6-methylpyrimidin-4-ylamino)-pyrazolo[4,3-c]pyridin-2-yl]-benzonitrile A mixture of 3-chloro-2-(4-chloro-7-fluoropyrazolo[4,3-c]pyridin-2-yl)-5-fluorobenzonitrile (80 mg, 0.28 mmol), 6-methylpyrimidin-4-ylamine (30 mg, 0.27 mmol), Pd$_2$(dba)$_3$ (11 mg, 0.012 mmol), Xantphos (14 mg, 0.028 mmol) and cesium carbonate (160 mg, 0.49 mmol) in dioxane (1.8 mL) was de-gassed and purged with nitrogen. The reaction mixture was heated at 150° C. in the microwave for 30 minutes. The resultant mixture was diluted with ethyl acetate and washed with water. The organic layer was dried over anhydrous magnesium sulfate, filtered and concentrated under reduced pressure. The residue was purified by silica gel flash chromatography (0-100% ethyl acetate in cyclohexane) to afford the title compound (35 mg, 36% yield). $^1$H NMR (400 MHz, DMSO-d$_6$): δ 10.84 (s, 1H), 9.44 (d, J=2.6 Hz, 1H), 8.69 (d, J=1.2 Hz, 1H), 8.37-8.30 (m, 3H), 8.01 (d, J=3.5 Hz, 1H), 2.44 (s, 3H). LCMS (Method B): RT=3.20 min, m/z: 398 [M+H$^+$].

Method 2

Example 104

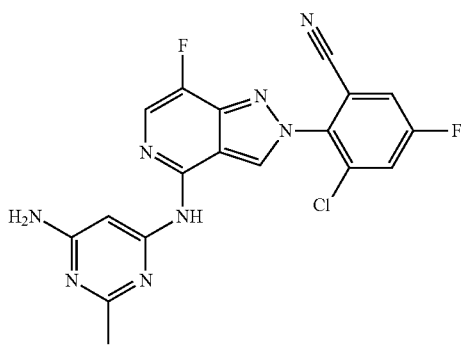 [SMILES: Cc1nc(N)cc(Nc2ncc(F)c3nn(-c4c(Cl)cc(F)cc4C#N)cc23)n1]

2-[4-(6-Amino-2-methylpyrimidin-4-ylamino)-7-fluoropyrazolo[4,3-c]pyridin-2-yl]-3-chloro-5-fluorobenzonitrile hydrochloride salt Step 1

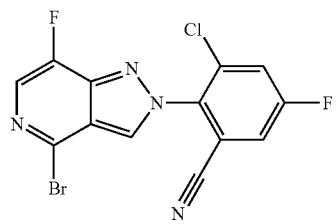 [SMILES: N#Cc1cc(F)cc(Cl)c1-n1cc2c(Br)ncc(F)c2n1]

2-(4-Bromo-7-fluoropyrazolo[4,3-c]pyridin-2-yl)-3-chloro-5-fluorobenzonitrile

3-Chloro-2-(4-chloro-7-fluoropyrazolo[4,3-c]pyridin-2-yl)-5-fluorobenzonitrile (735 mg, 2.26 mmol) was suspended in propionitrile (44 mL), under an atmosphere of nitrogen and bromotrimethylsilane (0.82 mL, 5.64 mmol) was added. The reaction mixture was heated at 80° C. for 5 hours. The resultant mixture was cooled to room temperature and partitioned between ethyl acetate and saturated aqueous sodium bicarbonate solution. The layers were separated and the organic layer was dried over anhydrous sodium sulfate, filtered and concentrated under reduced pressure to afford the title compound as a beige solid (834 mg, 100% yield). $^1$H NMR (300 MHz, CDCl$_3$): δ 8.38 (d, J=2.3 Hz, 1H), 8.03 (d, J=3.0 Hz, 1H), 7.65 (dd, J=7.6, 2.8 Hz, 1H), 7.56 (dd, J=7.0, 2.8 Hz, 1H).

Step 2

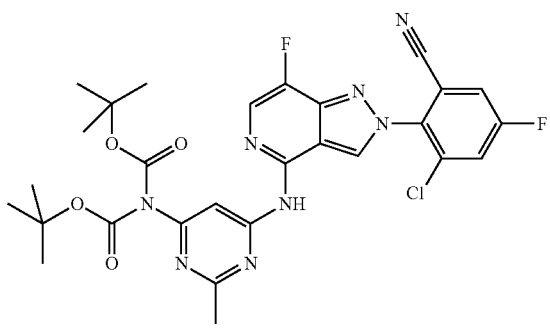 [SMILES: Cc1nc(Nc2ncc(F)c3nn(-c4c(Cl)cc(F)cc4C#N)cc23)cc(N(C(=O)OC(C)(C)C)C(=O)OC(C)(C)C)n1]

{6-[2-(2-Chloro-6-cyano-4-fluorophenyl)-7-fluoro-2H-pyrazolo[4,3-c]pyridin-4-ylamino]-2-methylpyrimidin-4-yl}bis-carbamic acid tert-butyl ester A mixture of 2-(4-bromo-7-fluoropyrazolo[4,3-c]pyridin-2-yl)-3-chloro-5-fluorobenzonitrile (365 mg, 1.0 mmol), (6-amino-2-methylpyrimidin-4-yl)-bis-carbamic acid tert-butyl ester (389 mg, 1.2 mmol), $Pd_2(dba)_3$ (22 mg, 0.025 mmol), Xantphos (58 mg, 0.1 mmol) and cesium carbonate (652 mg, 2.0 mmol) in dioxane (10 mL) was de-gassed and purged with nitrogen. The reaction mixture was heated at 80° C. in a sealed vial overnight. After cooling, the resultant mixture was diluted with ethyl acetate and washed with water. The organic layer was washed with brine, dried over anhydrous sodium sulfate, filtered and concentrated under reduced pressure. The residue was purified by silica gel flash chromatography (20-40% ethyl acetate in cyclohexane) to afford a crude residue which was further purified by silica gel flash chromatography (30% ethyl acetate in cyclohexane) to afford the title compound (296 mg, 48% yield). $^1$H NMR (400 MHz, DMSO-$d_6$): δ 10.97 (s, 1H), 9.43 (d, J=2.5 Hz, 1H), 8.36 (s, 1H), 8.34-8.29 (m, 2H), 7.94 (d, J=3.3 Hz, 1H), 2.45 (s, 3H), 1.47 (s, 18H).

Step 2

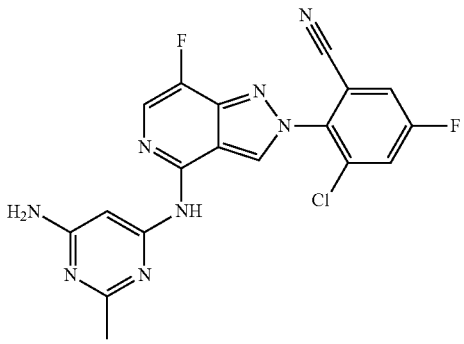 [SMILES: Cc1nc(N)cc(Nc2ncc(F)c3nn(-c4c(Cl)cc(F)cc4C#N)cc23)n1]

2-[4-(6-Amino-2-methylpyrimidin-4-ylamino)-7-fluoropyrazolo[4,3-c]pyridin-2-yl]-3-chloro-5-fluorobenzonitrile hydrochloride salt To {6-[2-(2-Chloro-6-cyano-4-fluorophenyl)-7-fluoro-2H-pyrazolo[4,3-c]pyridin-4-ylamino]-2-methylpyrimidin-4-yl}bis-carbamic acid tert-butyl ester (296 mg, 0.48 mmol) was added HCl (1.25 N in propan-2-ol, 10 mL) and the reaction mixture was heated at 50° C. overnight. After cooling, the solvent was concentrated under reduced pressure and diethyl ether was then added. The precipitate was filtered off and dried to afford the title compound as a beige solid (208 mg, 97% yield). $^1$H NMR (400 MHz, DMSO-$d_6$): δ 9.52 (d, J=2.4 Hz, 1H), 8.39-8.31 (m, 2H), 8.06 (d, J=3.3 Hz, 1H), 7.56 (br s, 1H), 2.51 (s, 3H). LCMS (Method B): RT=3.10 min, m/z: 413 [M+H$^+$].

Method 2

Example 105

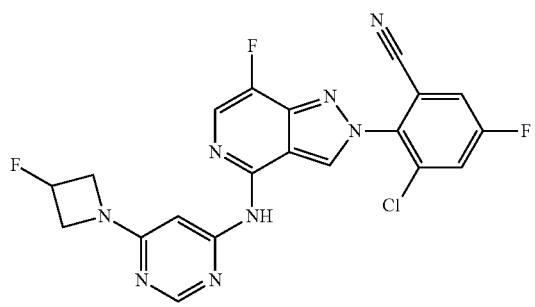 [SMILES: N#Cc1cc(F)cc(Cl)c1-n1cc2c(Nc3cc(N4CC(F)C4)ncn3)ncc(F)c2n1]

3-Chloro-5-fluoro-2-{7-fluoro-4-[6-(3-fluoroazetidin-1-yl)pyrimidin-4-ylamino]pyrazolo[4,3-c]pyridin-2-yl}benzonitrile hydrochloride salt

Step 1

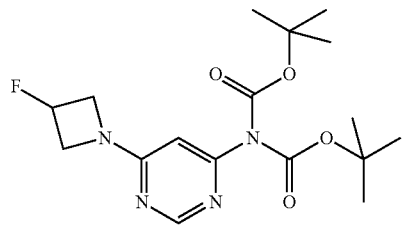 [SMILES: CC(C)(C)OC(=O)N(C(=O)OC(C)(C)C)c1cc(N2CC(F)C2)ncn1]

[6-(3-Fluoroazetidin-1-yl)pyrimidin-4-yl]bis carbamic acid tert butyl ester (6-Chloropyrimidin-4-yl)-bis-carbamic acid tert-butyl ester (2.3 g, 7.0 mmol) and 3-fluoroazetidine hydrochloride (916 mg, 8.2 mmol) were dissolved in NMP (14 mL) and DIPEA (1.8 mL, 10.5 mmol) was added. The reaction mixture was heated at 80° C. overnight. Further DIPEA (1.0 mL, 6.0 mmol) was added and the reaction mixture was heated at 80° C. for another 3 hours. After cooling to room temperature, the mixture was partitioned between ethyl acetate and water. The layers were separated and the organic layer was washed with brine, dried over anhydrous sodium sulfate, filtered and concentrated under reduced pressure. The residue was purified by silica gel flash chromatography (40-50% ethyl acetate in cyclohexane) to afford the title compound as a white solid (945 mg, 37% yield). $^1$H NMR (400 MHz, DMSO-$d_6$): δ 8.33

(d, J=1.1 Hz, 1H), 6.51 (d, J=1.1 Hz, 1H), 5.62-5.42 (m, 1H), 4.43-4.31 (m, 2H), 4.16-4.04 (m, 2H), 1.46 (s, 18H).

Step 2

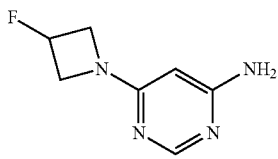 [SMILES: Nc1cc(N2CC(F)C2)ncn1]

6-(3-Fluoroazetidin-1-yl)pyrimidin-4-ylamine

[6-(3-Fluoroazetidin-1-yl)pyrimidin-4-yl]bis carbamic acid tert butyl ester (940 mg, 2.55 mmol) was dissolved in DCM (10 mL) and TFA (2.5 mL) was added. The reaction mixture was stirred at room temperature overnight. The solvent was removed under reduced pressure and the residue was dissolved in DCM and washed with saturated aqueous sodium hydrogen carbonate solution. The organic layer was dried over anhydrous sodium sulfate, filtered and concentrated under reduced pressure to afford the title compound as a white solid (158 mg, 37% yield). $^1$H NMR (400 MHz, DMSO-$d_6$): δ 7.93 (d, J=1.0 Hz, 1H), 6.28 (s, 2H), 5.57-5.37 (m, 1H), 5.27 (d, J=1.1 Hz, 1H), 4.26-4.13 (m, 2H), 3.98-3.87 (m, 2H).

Step 3

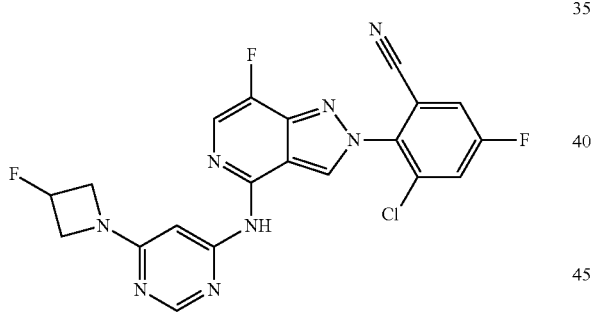

3-Chloro-5-fluoro-2-{7-fluoro-4-[6-(3-fluoroazetidin-1-yl)pyrimidin-4-ylamino]pyrazolo[4,3-c]pyridin-2-yl}benzonitrile hydrochloride salt A mixture of 2-(4-chloro-7-fluoropyrazolo[4,3-c]pyridin-2-yl)-5-fluorobenzonitrile (185 mg, 0.5 mmol), 6-(3-fluoroazetidin-1-yl)pyrimidin-4-ylamine (100 mg, 0.6 mmol), Pd$_2$(dba)$_3$ (11 mg, 0.0125 mmol), Xantphos (29 mg, 0.05 mmol) and cesium carbonate (326 mg, 1.0 mmol) in dioxane (5 mL) was de-gassed and purged with nitrogen. The reaction mixture was heated at 80° C. in a sealed vial overnight. After cooling, the resultant mixture was diluted with ethyl acetate and washed with water. The organic layer was washed with brine, dried over anhydrous sodium sulfate, filtered and concentrated under reduced pressure. The residue was purified by silica gel flash chromatography (90-100% ethyl acetate in cyclohexane) to afford crude product. This crude product was triturated with diethyl ether and the solid obtained was collected by filtration. To this solid was added HCl (5 mL, 1.25 N in propan-2-ol,) and the resultant mixture was stirred at room temperature for 2 hours. The solid was filtered off and dried to afford the title compound as an off-white solid (95 mg, 39% yield). $^1$H NMR (400 MHz, DMSO-$d_6$): δ 12.53 (bs, 1H), 9.74 (s, 1H), 8.59 (s, 1H), 8.35-8.30 (m, 2H), 8.04 (d, J=3.6 Hz, 1H), 6.69 (br s, 1H), 5.69-5.47 (m, 1H), 4.61-4.47 (m, 2H), 4.37-4.24 (m, 2H). LCMS (Method B): RT=3.31 min, m/z: 457 [M+H$^+$].

Method 2

Example 106

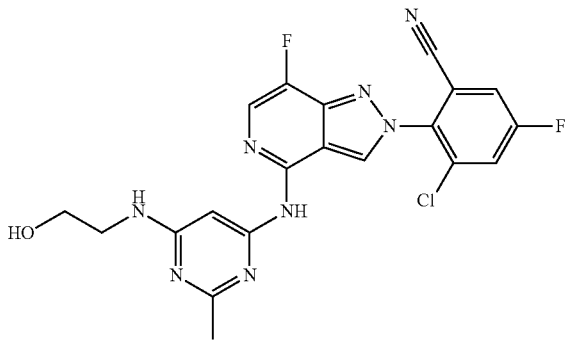 [SMILES: Cc1nc(NCCO)cc(Nc2ncc(F)c3nn(-c4c(Cl)cc(F)cc4C#N)cc23)n1]

3-Chloro-5-fluoro-2-{7-fluoro-4-[6-(2-hydroxyethylamino)-2-methylpyrimidin-4-ylamino]pyrazolo[4,3-c]pyridin-2-yl}benzonitrile hydrochloride salt Step 1

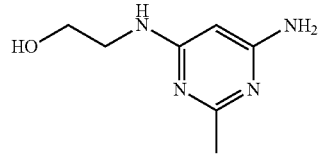

2-(6-Amino-2-methylpyrimidin-4-ylamino)ethanol

A mixture of 6-chloro-2-methylpyrimidin-4-ylamine (717 mg, 5.0 mmol) and ethanolamine (0.602 mL, 10.0 mmol) were heated at 250° C. in a microwave for 30 seconds. After cooling, the residue was dissolved in ethyl acetate, containing a small amount of methanol and was washed with brine. The organic layer was dried over anhydrous sodium sulfate, filtered and concentrated under reduced pressure to afford the title compound as a white solid (334 mg, 40% yield). $^1$H NMR (400 MHz, DMSO-$d_6$): δ 6.45 (br s, 1H), 5.98 (br s, 2H), 5.25 (s, 1H), 3.47 (t, J=6.0 Hz, 2H), 3.23-3.14 (m, 2H), 2.12 (s, 3H).

Step 2

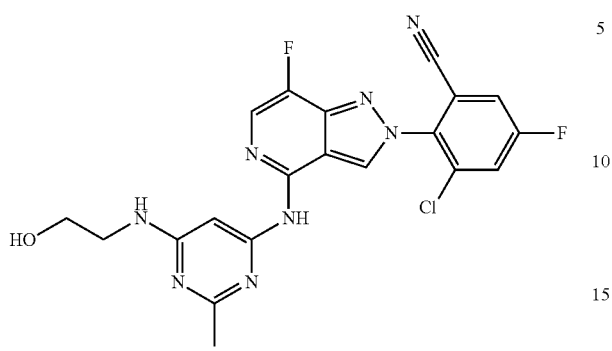

3-Chloro-5-fluoro-2-{7-fluoro-4-[6-(2-hydroxyethylamino)-2-methylpyrimidin-4-ylamino]pyrazolo[4,3-c]pyridin-2-yl}benzonitrile hydrochloride salt A mixture of 2-(4-chloro-7-fluoropyrazolo[4,3-c]pyridin-2-yl)-5-fluorobenzonitrile (185 mg, 0.5 mmol), 2-(6-amino-2-methylpyrimidin-4-ylamino)ethanol (101 mg, 0.6 mmol), Pd$_2$(dba)$_3$ (11 mg, 0.0125 mmol), Xantphos (29 mg, 0.05 mmol) and cesium carbonate (326 mg, 1.0 mmol) in dioxane (5 mL) was de-gassed and purged with nitrogen. The reaction mixture was heated at 80° C. in a sealed vial overnight. After cooling, the resultant mixture was diluted with ethyl acetate and washed with water. The organic layer was washed with brine, dried over anhydrous sodium sulfate, filtered and concentrated under reduced pressure. The residue was purified by silica gel flash chromatography (0-2% methanol in ethyl acetate) to afford crude product. This was dissolved in 1.25 N HCl in propan-2-ol solution (10 mL) and was stirred at room temperature for 1 hour. The solvent was concentrated under reduced pressure, and diethyl ether was added and the mixture was stirred for 5 minutes. The precipitate was filtered off and dried to afford the title compound as an off-white solid (68 mg, 28% yield). $^1$H NMR (400 MHz, DMSO-d$_6$): δ 9.52 (br s, 1H), 8.35-8.29 (m, 2H), 8.07 (s, 1H), 7.13 (br s, 1H), 3.66-3.59 (m, 2H), 3.59-3.49 (m, 2H), 2.59 (s, 3H). LCMS (Method B): RT=3.13 min, m/z: 457 [M+H$^+$].

Method 2

Example 107

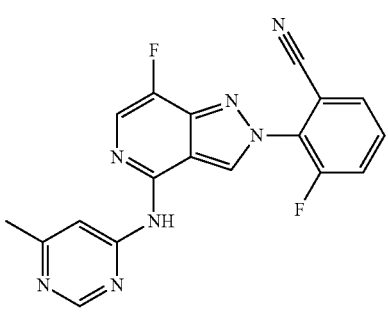 [SMILES: Cc1cc(Nc2ncc(F)c3nn(-c4c(F)cccc4C#N)cc23)ncn1]

3-Fluoro-2-[7-fluoro-4-(6-methylpyrimidin-4-ylamino)pyrazolo[4,3-c]pyridin-2-yl]benzonitrile hydrochloride salt Step 1

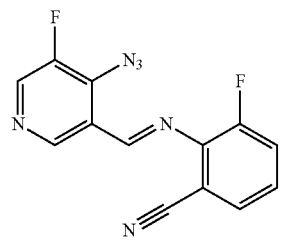 [SMILES: N#Cc1cccc(F)c1/N=C/c1cncc(F)c1N=[N+]=[N-]]

2-{[1-(4-Azido-5-fluoropyridin-3-yl)meth-(E)-ylidene]amino}-3-fluorobenzonitrile A solution of 4-azido-5-fluoropyridine-3-carbaldehyde (3.66 g, 22.1 mmol) and 2-amino-3-fluorobenzonitrile (3.0 g, 22.05 mmol) in DCM (73 mL) was cooled to 0° C. under an atmosphere of nitrogen. Triethylamine (9.1 mL, 66.0 mmol) was added, followed by dropwise addition of titanium (IV) chloride solution (1 N in DCM, 13.15 mL, 13.15 mmol). The reaction mixture was stirred at 0° C. for 2 hours, then at room temperature overnight. The resultant mixture was concentrated under reduced pressure to afford the title compound as a beige residue (5.19 g, 83% yield). This material was used in the next step without purification. LCMS (Method C): RT=3.49 min, m/z: 257 [M−N$_2$].

Step 2

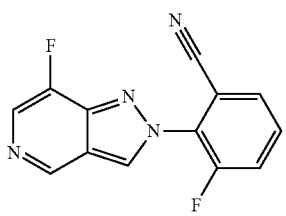 [SMILES: N#Cc1cccc(F)c1-n1cc2cncc(F)c2n1]

3-Fluoro-2-(7-fluoropyrazolo[4,3-c]pyridin-2-yl)-benzonitrile

A solution of 2-{[1-(4-azido-5-fluoropyridin-3-yl)meth-(E)-ylidene]amino}-3-fluorobenzonitrile (5.19 g, 18.2 mmol) in toluene (90 mL) was heated under reflux for 4 hours. The resultant mixture was cooled to room temperature and concentrated under reduced pressure. The residue was purified by silica gel flash chromatography (50-100% ethyl acetate in cyclohexane) to afford the title compound as a beige solid (4.02 g, 86% yield). LCMS (Method C): RT=2.41 min, m/z: 257 [M+H$^+$].

Step 3

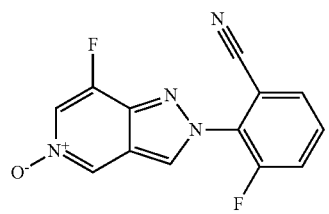

3-Fluoro-2-(7-fluoro-5-oxypyrazolo[4,3-c]pyridin-2-yl)-benzonitrile

3-Fluoro-2-(7-fluoropyrazolo[4,3-c]pyridin-2-yl)-benzonitrile (4.02 g, 15.7 mmol) was dissolved in DCM (50 mL) and methyltrioxorhenium (391 mg, 1.57 mmol) was added, followed by 27% aqueous hydrogen peroxide solution (2.25 mL, 31.4 mmol) dropwise. The reaction mixture was stirred at room temperature overnight. The resultant white suspension was diluted with more DCM and washed with saturated aqueous sodium bicarbonate solution. The layers were separated and the organic layer was washed with saturated aqueous sodium bicarbonate solution, dried over anhydrous magnesium sulfate, filtered and concentrated under reduced pressure. The residue was triturated with diethyl ether and the solid obtained was filtered and dried to afford the title compound as an orange solid (4.05 g, 95% yield). LCMS (Method C): RT=2.13 min, m/z: 273 [M+H$^+$].

Step 4

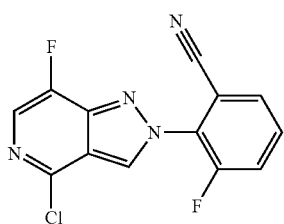

2-(4-Chloro-7-fluoropyrazolo[4,3-c]pyridin-2-yl)-3-fluorobenzonitrile

3-Fluoro-2-(7-fluoro-5-oxypyrazolo[4,3-c]pyridin-2-yl)-benzonitrile (4.05 g, 14.89 mmol) was suspended in DCE (71 mL) under an atmosphere of nitrogen and phosphorus oxychloride (4.4 mL, 47.72 mmol) was added. The reaction mixture was heated at 70° C. overnight. The resultant mixture was cooled to room temperature, concentrated under reduced pressure and azeotroped with toluene. The residue was partitioned between ethyl acetate and aqueous sodium hydrogen carbonate solution. The aqueous layer was extracted with ethyl acetate (×2) and DCM (×2). The combined organic layers were dried over anhydrous magnesium sulfate, filtered and concentrated under reduced pressure. The residue was purified by silica gel flash chromatography (0-50% ethyl acetate in cyclohexane) to afford the title compound as a brown solid (1.45 g, 33% yield). LCMS (Method F): RT=3.24 min, m/z: 291 [M+H$^+$].

Step 5

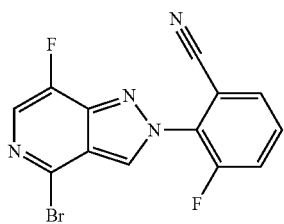

2-(4-Bromo-7-fluoropyrazolo[4,3-c]pyridin-2-yl)-3-fluorobenzonitrile 2-(4-Chloro-7-fluoropyrazolo[4,3-c]pyridin-2-yl)-3-fluorobenzonitrile (520 mg, 1.79 mmol) was suspended in propionitrile (35 mL), under an atmosphere of nitrogen and bromotrimethylsilane (0.646 mL, 6.76 mmol) was added. The reaction mixture was heated at 80° C. for 4.5 hours. The resultant mixture was cooled to room temperature and concentrated under reduced pressure. The residue was partitioned between ethyl acetate and saturated aqueous sodium bicarbonate solution. The layers were separated and the organic layer was dried over anhydrous magnesium sulfate, filtered and concentrated under reduced pressure to afford the title compound as a solid (600 mg, 100% yield). This was used in the next step without purification. LCMS (Method F): RT=3.30 min, m/z: 335 [M+H$^+$].

Step 6

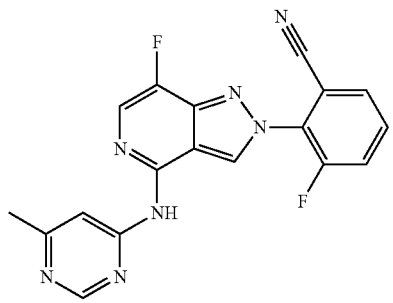

3-Fluoro-2-[7-fluoro-4-(6-methylpyrimidin-4-ylamino)-pyrazolo[4,3-c]pyridin-2-yl]-benzonitrile A mixture of 2-(4-bromo-7-fluoropyrazolo[4,3-c]pyridin-2-yl)-3-fluorobenzonitrile (85 mg, 0.25 mmol), 4-amino-6-methylpyrimidine (31 mg, 0.28 mmol), Pd$_2$(dba)$_3$ (12 mg, 0.013 mmol), Xantphos (15 mg, 0.026 mmol) and cesium carbonate (166 mg, 0.51 mmol) in dioxane (1.8 mL) was de-gassed and purged with nitrogen and the reaction mixture was heated at 150° C. in a sealed vial for 30 minutes. The resultant mixture was diluted with dioxane and filtered. The filtrate was concentrated under reduced pressure and the residue was purified by silica gel flash chromatography (10-100% ethyl acetate in cyclohexane) to afford the title compound as a brown solid (47 mg, 51% yield). LCMS (Method C): RT=2.25 min, m/z: 364 [M+H$^+$].

Step 7

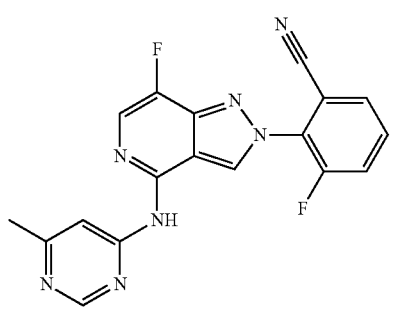

3-Fluoro-2-[7-fluoro-4-(6-methylpyrimidin-4-ylamino)pyrazolo[4,3-c]pyridin-2-yl]benzonitrile hydrochloride salt A solution of 3-fluoro-2-[7-fluoro-4-(6-methylpyrimidin-4-ylamino)-pyrazolo[4,3-c]pyridin-2-yl]-benzonitrile (46 mg, 0.13 mmol) in 1.25 N HCl in propan-2-ol solution (2.5 mL) was heated at 50° C. for 2 hours. The resultant mixture was concentrated under reduced pressure and the residue was dried at 50° C. under high vacuum overnight to afford the title compound as an off-white solid (60 mg, 100% yield). $^1$H NMR (400 MHz, DMSO-d$_6$): δ 9.64 (br s, 1H), 9.06 (s, 1H), 8.39 (br s, 1H), 8.15 (d, J=3.5 Hz, 1H), 8.11-8.02 (m, 2H), 7.97-7.90 (m, 1H), 2.61 (s, 3H). LCMS (Method B): RT=2.92 min, m/z: 364 [M+H$^+$].

Method 2

Example 108

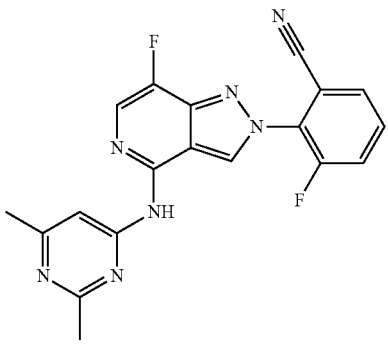 [SMILES: Cc1cc(Nc2ncc(F)c3nn(-c4c(F)cccc4C#N)cc23)nc(C)n1]

2-[4-(2,6-Dimethylpyrimidin-4-ylamino)-7-fluoropyrazolo[4,3-c]pyridin-2-yl]-3-fluorobenzonitrile hydrochloride salt Step 1

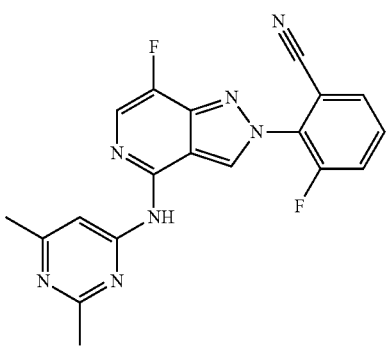 [SMILES: Cc1cc(Nc2ncc(F)c3nn(-c4c(F)cccc4C#N)cc23)nc(C)n1]

2-[4-(2,6-Dimethylpyrimidin-4-ylamino)-7-fluoropyrazolo[4,3-c]pyridin-2-yl]-3-fluorobenzonitrile.HCl A mixture of 2-(4-bromo-7-fluoropyrazolo[4,3-c]pyridin-2-yl)-3-fluorobenzonitrile (131 mg, 0.39 mmol), 2,6-dimethylpyrimidin-4-ylamine (48 mg, 0.39 mmol), Pd$_2$(dba)$_3$ (18 mg, 0.019 mmol), Xantphos (22 mg, 0.039 mmol) and cesium carbonate (254 mg, 0.78 mmol) in dioxane (2.5 mL) was de-gassed and purged with nitrogen and the reaction mixture was heated at 150° C. in a microwave for 30 minutes. The resultant mixture was filtered and the solid washed with dioxane. The filtrate was concentrated under reduced pressure and the residue was purified by silica gel flash chromatography (20-100% ethyl acetate in cyclohexane) to afford a yellow solid. This was further purified by HPLC [gradient: 10 to 90% acetonitrile (0.1% ammonium hydroxide) in water (0.1% ammonium hydroxide], to afford the free base of the title compound. To this was added HCl (1.25 N in propan-2-ol, 2.5 mL) and the suspension was heated at 50° C. for 1.5 hours. The resultant mixture was concentrated under reduced pressure and the residue was dried under high vacuum, at 50° C. overnight, to afford the title compound as a white solid (46 mg, 26% yield). $^1$H NMR (400 MHz, DMSO-d$_6$): δ 9.58 (s, 1H), 8.36 (br s, 1H), 8.14 (d, J=3.3 Hz, 1H), 8.10-8.00 (m, 2H), 7.97-7.90 (m, 1H), 2.69 (s, 3H), 2.63 (s, 3H). LCMS (Method B): RT=2.89 min, m/z: 378 [M+H$^+$].

Method 2

Example 109

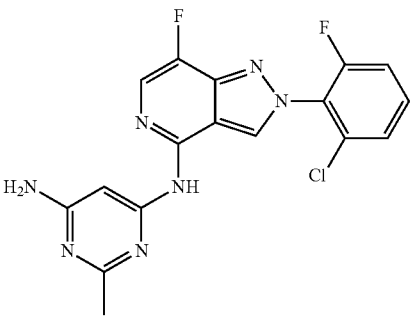 [SMILES: Cc1nc(N)cc(Nc2ncc(F)c3nn(-c4c(F)cccc4Cl)cc23)n1]

N-[2-(2-Chloro-6-fluorophenyl)-7-fluoro-2H-pyrazolo[4,3-c]pyridin-4-yl]-2-methylpyrimidine-4,6-diamine hydrochloride salt Step 1

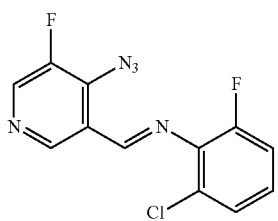 [SMILES: [N-]=[N+]=Nc1c(F)cncc1/C=N/c1c(F)cccc1Cl]

[1-(4-Azido-5-fluoropyridin-3-yl)meth-(E)-ylidene]-(2-chloro-6-fluorophenyl)amine A solution of 4-azido-5-fluoropyridine-3-carbaldehyde (10.0 g, 60.0 mmol) and 2-chloro-6-fluorophenylamine (8.7 g, 60.0 mmol) in DCM (200 mL) was cooled to 0° C. under an atmosphere of nitrogen. Triethylamine (25 mL, 180 mmol) was added, followed by titanium (IV) chloride solution (1 N in DCM, 36 mL, 36 mmol) dropwise. The reaction mixture was stirred at 0° C. then allowed to reach room temperature overnight. The resultant mixture was concentrated under reduced pressure and the residue was suspended in toluene and filtered through a pad of Celite®. The filtrate was concentrated under reduced pressure to afford the title compound which was used in the next step without purification.

Step 2

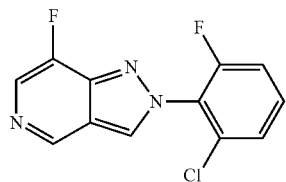

2-(2-Chloro-6-fluorophenyl)-7-fluoro-2H-pyrazolo[4,3-c]pyridine

A solution of [1-(4-azido-5-fluoropyridin-3-yl)meth-(E)-ylidene]-(2-chloro-6-fluorophenyl)amine (~60 mmol) in toluene (250 mL) was heated under reflux for 3 hours. The resultant mixture was cooled to room temperature and concentrated under reduced pressure. The residue was triturated with diethyl ether and the solid obtained was collected by filtration and dried to afford the title compound as an off-white solid (9.96 g, 63% yield over two steps). $^1$H NMR (400 MHz, DMSO-$d_6$): δ 9.32 (d, J=2.7 Hz, 1H), 9.20 (d, J=2.6 Hz, 1H), 8.29 (d, J=3.8 Hz, 1H), 7.81-7.74 (m, 1H), 7.72-7.60 (m, 2H).

Step 3

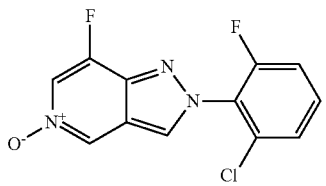 [SMILES: [O-][n+]1cc(F)c2nn(-c3c(F)cccc3Cl)cc2c1]

2-(2-Chloro-6-fluorophenyl)-7-fluoro-2H-pyrazolo[4,3-c]pyridine 5 oxide 2-(2-Chloro-6-fluorophenyl)-7-fluoro-2H-pyrazolo[4,3-c]pyridine (9.95 g, 37.5 mmol) was suspended in DCM (150 mL) at 0° C. and meta-chloroperbenzoic acid (12.9 g, 75 mmol) was added. The reaction mixture was stirred at 0° C. for 2 hours then allowed to reach room temperature and stirred for another 3 hours. The resultant mixture was quenched with saturated aqueous sodium thiosulfate solution and the layers were separated. The organic layer was washed with saturated aqueous sodium bicarbonate solution and brine, dried over anhydrous sodium sulfate, filtered and concentrated under reduced pressure. The residue was triturated with diethyl ether and the solid obtained was filtered off and dried to afford the title compound as a white solid (7.22 g, 68% yield). $^1$H NMR (400 MHz, DMSO-$d_6$): δ 9.04 (d, J=2.6 Hz, 1H), 8.88 (d, J=1.4 Hz, 1H), 8.35 (dd, J=6.4, 1.5 Hz, 1H), 7.82-7.73 (m, 1H), 7.72-7.62 (m, 2H).

Step 4

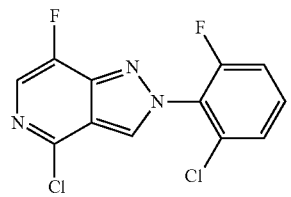 [SMILES: Fc1cccc(Cl)c1-n1cc2c(Cl)ncc(F)c2n1]

4-Chloro-2-(2-chloro-6-fluorophenyl)-7-fluoro-2H-pyrazolo[4,3-c]pyridine 2-(2-Chloro-6-fluorophenyl)-7-fluoro-2H-pyrazolo[4,3-c]pyridine 5 oxide (7.2 g, 25.6 mmol) was suspended in DCE (130 mL) under an atmosphere of nitrogen and phosphorus oxychloride (7.2 mL, 77.0 mmol) was added. The reaction mixture was heated at 70° C. for 5 hours and then allowed to cool to room temperature. The resultant mixture was poured cautiously onto saturated aqueous sodium carbonate solution, with stirring, and the layers were separated. The organic layer was washed with brine, dried over anhydrous sodium sulfate, filtered and concentrated under reduced pressure. The residue was purified by silica gel flash chromatography (20% ethyl acetate in cyclohexane) to afford the title compound as a white solid (3.08 g, 40% yield). $^1$H NMR (400 MHz, DMSO-$d_6$): δ 9.54 (d, J=2.5 Hz, 1H), 8.22 (d, J=3.4 Hz, 1H), 7.86-7.78 (m, 1H), 7.76-7.66 (m, 2H).

Step 5

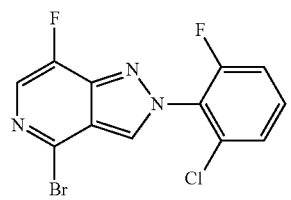 [SMILES: Fc1cccc(Cl)c1-n1cc2c(Br)ncc(F)c2n1]

4-Bromo-2-(2-chloro-6-fluorophenyl)-7-fluoro-2H-pyrazolo[4,3-c]pyridine

4-Chloro-2-(2-chloro-6-fluorophenyl)-7-fluoro-2H-pyrazolo[4,3-c]pyridine (3.05 g, 10.1 mmol) was suspended in propionitrile (60 mL) under an atmosphere of nitrogen and bromotrimethylsilane (4.0 mL, 30.0 mmol) was added. The reaction mixture was heated at 100° C. overnight. The resultant mixture was cooled to room temperature, diluted with ethyl acetate and washed with saturated aqueous sodium bicarbonate solution. The layers were separated and the organic layer was washed with brine, dried over anhydrous sodium sulfate, filtered and concentrated under reduced pressure to afford the title compound as a beige solid (3.5 g, 100% yield). This was used directly in the next step without further purification. $^1$H NMR (400 MHz, DMSO-$d_6$): δ 9.46 (d, J=2.5 Hz, 1H), 8.21 (d, J=3.4 Hz, 1H), 7.85-7.77 (m, 1H), 7.74-7.64 (m, 2H).

Step 6

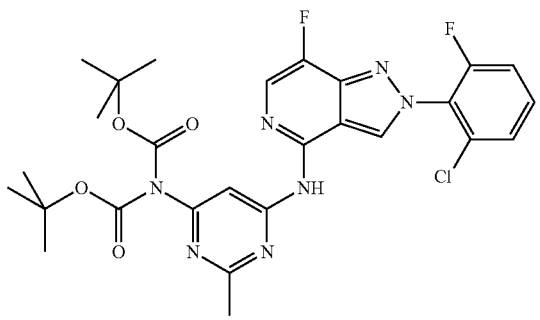 [SMILES: Cc1nc(Nc2ncc(F)c3nn(-c4c(F)cccc4Cl)cc23)cc(N(C(=O)OC(C)(C)C)C(=O)OC(C)(C)C)n1]

{6-[2-(2-Chloro-6-fluorophenyl)-7-fluoro-2H-pyrazolo[4,3-c]pyridin-4-ylamino]-2-methylpyrimidin-4-yl}bis carbamic acid tert-butyl ester A mixture of 4-bromo-2-(2-chloro-6-fluorophenyl)-7-fluoro-2H-pyrazolo[4,3-c]pyridine (175 mg, 0.5 mmol), (6-amino-2-methylpyrimidin-4-yl)-bis-carbamic acid tert-butyl ester (194 mg, 0.6 mmol), Pd$_2$(dba)$_3$ (11 mg, 0.013 mmol), Xantphos (29 mg, 0.05 mmol) and cesium carbonate (326 mg, 1.0 mmol) in dioxane (5 mL) was de-gassed and purged with nitrogen and the reaction mixture was heated at 80° C. in a sealed vial overnight. The resultant mixture was allowed to cool to room temperature, before being partitioned between ethyl acetate and water. The layers were separated and the organic layer was washed with brine, dried over anhydrous sodium sulfate, filtered and concentrated under reduced pressure. The residue was purified by silica gel flash chromatography (40% ethyl acetate in cyclohexane) to afford the title compound as a yellow glass (278 mg, 95% yield). $^1$H NMR (400 MHz, DMSO-d$_6$): δ 10.88 (s, 1H), 9.35 (d, J=2.5 Hz, 1H), 8.42 (s, 1H), 7.93 (d, J=3.4 Hz, 1H), 7.82-7.74 (m, 1H), 7.73-7.62 (m, 2H), 2.47 (s, 3H), 1.49 (s, 18H).

Step 7

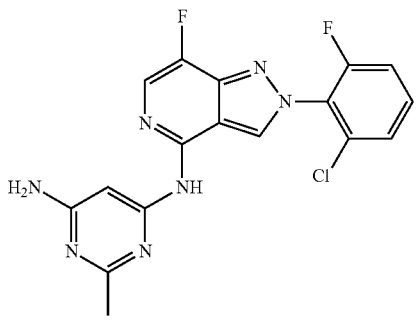 [SMILES: Cc1nc(N)cc(Nc2ncc(F)c3nn(-c4c(F)cccc4Cl)cc23)n1]

N-[2-(2-Chloro-6-fluorophenyl)-7-fluoro-2H-pyrazolo[4,3-c]pyridin-4-yl]-2-methylpyrimidine-4,6-diamine hydrochloride salt To {6-[2-(2-chloro-6-fluorophenyl)-7-fluoro-2H-pyrazolo[4,3-c]pyridin-4-ylamino]-2-methylpyrimidin-4-yl}bis carbamic acid tert-butyl ester (271 mg, 0.46 mmol) in propan-2-ol was added HCl (1.25 N in propan-2-ol, 6.0 mL), and the reaction mixture was heated at 50° C. for 4 hours. The resultant mixture was concentrated under reduced pressure and the residue was triturated with diethyl ether and stirred for 1 hour. The solid obtained was collected by filtration and dried to afford the title compound (174 mg, 82% yield). $^1$H NMR (400 MHz, DMSO-d$_6$): δ 9.54 (d, J=2.5 Hz, 1H), 8.06 (d, J=3.6 Hz, 1H), 7.85-7.78 (m, 1H), 7.75-7.64 (m, 2H), 7.53 (br s, 1H), 2.54 (s, 3H). LCMS (Method B): RT=3.13 min, m/z: 388 [M+H$^+$].

Method 2

Example 110

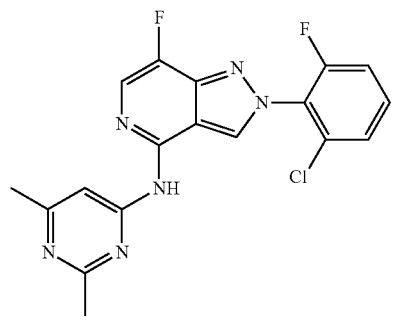 [SMILES: Cc1cc(Nc2ncc(F)c3nn(-c4c(F)cccc4Cl)cc23)nc(C)n1]

[2-(2-Chloro-6-fluorophenyl)-7-fluoro-2H-pyrazolo[4,3-c]pyridin-4-yl]-(2,6-dimethylpyrimidin-4-yl)amine hydrochloride salt A mixture of 4-bromo-2-(2-chloro-6-fluorophenyl)-7-fluoro-2H-pyrazolo[4,3-c]pyridine (172 mg, 0.5 mmol), 4-amino-2,6-dimethylpyrimidine (74 mg, 0.6 mmol), Pd$_2$(dba)$_3$ (11 mg, 0.013 mmol), Xantphos (29 mg, 0.05 mmol) and cesium carbonate (326 mg, 1.0 mmol) in dioxane (5 mL) was de-gassed and purged with nitrogen and the reaction mixture was heated at 80° C. in a sealed vial overnight. The resultant mixture was allowed to cool to room temperature, before being partitioned between ethyl acetate and water. The layers were separated and the organic layer was washed with brine, dried over anhydrous sodium sulfate, filtered and concentrated under reduced pressure. The residue was purified by silica gel flash chromatography (ethyl acetate). The resultant residue was stirred with HCl (1.25 N in propan-2-ol, 5.0 mL) for 1 hour. The solid obtained was collected by filtration and dried to afford the title compound as an off-white solid (142 mg, 67% yield). $^1$H NMR (400 MHz, DMSO-d$_6$): δ 9.36 (s, 1H), 8.15 (br s, 1H), 8.11 (d, J=3.4 Hz, 1H), 7.81-7.73 (m, 1H), 7.73-7.62 (m, 2H), 2.65 (s, 3H), 2.59 (s, 3H). LCMS (Method B): RT=3.14 min, m/z: 387 [M+H$^+$].

Method 2

Example 111

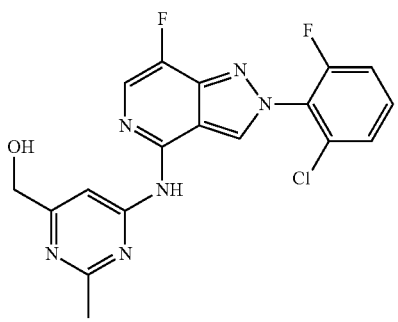 [SMILES: Cc1nc(CO)cc(Nc2ncc(F)c3nn(-c4c(F)cccc4Cl)cc23)n1]

{6-[2-(2-Chloro-6-fluorophenyl)-7-fluoro-2H-pyrazolo[4,3-c]pyridin-4-ylamino]-2-methylpyrimidin-4-yl}-methanol hydrochloride salt Step 1

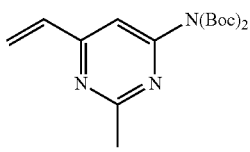

(2-Methyl-6-vinyl-aminopyrimidin-4-yl)-bis-carbamic acid tert-butyl ester

To a solution of (2-methyl-6-chloro-aminopyrimidin-4-yl)-bis-carbamic acid tert-butyl ester (1.50 g, 4.4 mmol), potassium vinyltrifluoroborate (884 mg, 6.6 mmol) and triethylamine (3.3 mL, 22 mmol) in nPrOH (40 mL) was added Pd(dppf)Cl$_2$.CHCl$_3$ (180 mg, 0.22 mmol). The reaction mixture was degassed with nitrogen and then heated at 100° C. for 30 minutes in a sealed vial. The resulting mixture was allowed to cool and was then partitioned between ethyl acetate and saturated sodium bicarbonate. The organic layer was washed with brine, dried over anhydrous sodium sulfate, filtered and concentrated in vacuo. The resultant residue was purified by column chromatography on silica gel eluting with 10% ethyl acetate in cyclohexane to afford the title compound as an oil (1.99 g, 93% yield). $^1$H NMR (400 MHz, CDCl$_3$): δ 7.45 (s, 1H), 6.70 (dd, J=17.3, 1.3 Hz, 1H), 6.42 (dd, J=17.3, 10.7 Hz, 1H), 5.64 (dd, J=10.7, 1.3 Hz, 1H), 2.61 (s, 3H), 1.54 (s, 18H).

Step 2

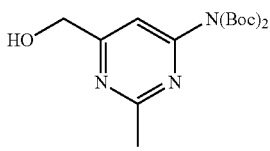

(6-Hydroxymethyl-2-methyl-aminopyrimidin-4-yl)-bis-carbamic acid tert-butyl ester Ozone gas was bubbled through a solution of (2-methyl-6-vinyl-aminopyrimidin-4-yl)-bis-carbamic acid tert-butyl ester (1.98 g, 5.9 mmol), in DCM (50 mL) and MeOH (12 mL), at −78° C. for 60 minutes (until a permanent blue color resulted). The flow of ozone was stopped and then sodium borohydride (448 mg, 11.8 mmol) was added at −78° C. The reaction mixture was allowed to stir at −78° C. for 10 minutes and was then allowed to warm to room temperature and further stirred for 60 minutes. The resulting mixture was then partitioned between DCM and water. The organic layer was washed with brine, dried over anhydrous sodium sulfate, filtered and concentrated in vacuo. The resultant residue was purified by column chromatography on silica gel eluting with 40-60% ethyl acetate in cyclohexane to afford the title compound as an oil (1.69 g, 84% yield). LCMS (Method E): RT=3.19 min, m/z: 340 [M+H$^+$].

Step 3

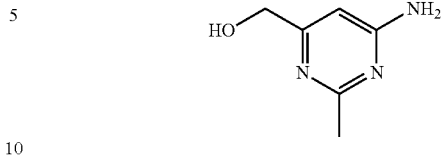

(6-Amino-2-methylpyrimidin-4-yl)-methanol

TFA (5 mL) was added to a solution of (6-hydroxymethyl-2-methyl-aminopyrimidin-4-yl)-bis-carbamic acid tert-butyl ester (1.68 g, 5.0 mmol) in DCM (20 mL) and the reaction mixture was stirred at room temperature for 16 hours. The resulting mixture was concentrated in vacuo. The crude residue was dissolved in methanol and loaded onto an Isolute® SCX-2 cartridge which was washed with MeOH and the product was then eluted with ammonia (2 N in MeOH). The combined methanolic ammonia fractions were concentrated in vacuo and the resultant residue was triturated with diethyl ether to afford the title compound as a pale pink solid (540 mg, 78% yield). $^1$H NMR (400 MHz, DMSO-d$_6$): δ 6.64 (br s, 2H), 6.34 (s, 1H), 5.26 (t, J=5.9 Hz, 1H), 4.25 (d, J=5.9 Hz, 2H), 2.25 (s, 3H).

Step 4

{6-[2-(2-Chloro-6-fluorophenyl)-7-fluoro-2H-pyrazolo[4,3-c]pyridin-4-ylamino]-2-methylpyrimidin-4-yl}-methanol hydrochloride salt

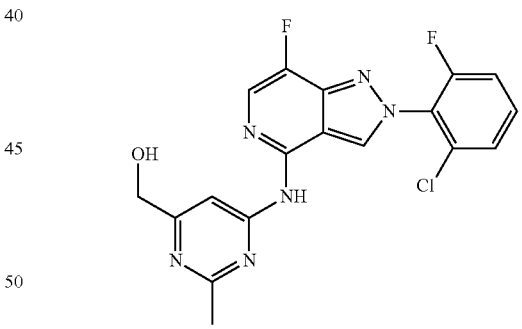

A mixture of 4-bromo-2-(2-chloro-6-fluorophenyl)-7-fluoro-2H-pyrazolo[4,3-c]pyridine (172 mg, 0.5 mmol), 4-amino-2,6-dimethylpyrimidine (83 mg, 0.6 mmol), Pd$_2$(dba)$_3$ (11 mg, 0.013 mmol), Xantphos (29 mg, 0.05 mmol) and cesium carbonate (326 mg, 1.0 mmol) in dioxane (5 mL) was de-gassed and purged with nitrogen and the reaction mixture was heated at 80° C. in a sealed vial overnight. The resultant mixture was allowed to cool to room temperature, before being partitioned between ethyl acetate and water. The layers were separated and the organic layer was washed with brine, dried over anhydrous sodium sulfate, filtered and concentrated under reduced pressure. The residue was purified by silica gel flash chromatography (80-100% ethyl acetate in cyclohexane). The resultant residue was stirred with HCl (1.25 N in propan-2-ol, 5.0 mL) for 1 hour. The resultant mixture was concentrated under reduced pressure and the solid obtained was triturated with diethyl ether, filtered and dried to afford the title compound as a white solid (153 mg, 70% yield). $^1$H NMR (400 MHz, DMSO-$d_6$): δ 12.25 (br s, 1H), 9.48 (s, 1H), 8.25 (br s, 1H), 8.15 (d, J=3.6 Hz, 1H), 7.83-7.76 (m, 1H), 7.74-7.66 (m, 2H), 4.70 (s, 2H), 2.67 (s, 3H). LCMS (Method B): RT=2.96 min, m/z: 403 [M+H$^+$].

Method 2

Example 112

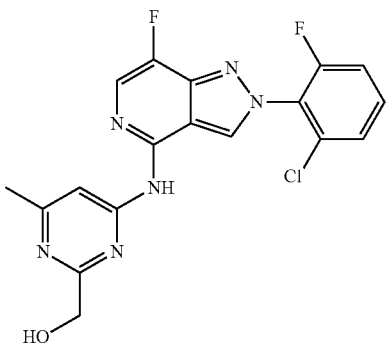 [SMILES: Cc1cc(Nc2ncc(F)c3nn(-c4c(F)cccc4Cl)cc23)nc(CO)n1]

{4-[2-(2-Chloro-6-fluoro-phenyl)-7-fluoro-2H-pyrazolo[4,3-c]pyridin-4-ylamino]-6-methyl-pyrimidin-2-yl}-methanol hydrochloride salt A mixture of 4-bromo-2-(2-chloro-6-fluorophenyl)-7-fluoro-2H-pyrazolo[4,3-c]pyridine (100 mg, 0.29 mmol), (4-amino-6-methylpyrimidin-2-yl)-methanol (42 mg, 0.31 mmol), Pd$_2$(dba)$_3$ (13 mg, 0.015 mmol), Xantphos (17 mg, 0.03 mmol) and cesium carbonate (189 mg, 0.58 mmol) in dioxane (2.0 mL) was de-gassed and purged with nitrogen and the reaction mixture was heated under microwave irradiation at 150° C. for 45 minutes. The resultant mixture was allowed to cool to room temperature and was then filtered through a pad of Celite® washing with further dioxane and then ethyl acetate. The combined washings were concentrated under reduced pressure and the resultant residue was purified by silica gel flash chromatography (40-100% ethyl acetate in cyclohexane). The resultant residue was further purified by HPLC (gradient: 10 to 98% MeOH (0.1% NH$_4$OH) in water (0.1% NH$_4$OH)], to afford the free base of the title compound. To this crude residue was added a solution of HCl (1.25 N in propan-2-ol, 2.0 mL) and the resulting mixture was stirred at room temperature for 1 hour. The resultant mixture was concentrated under reduced pressure and dried in vacuo to afford the title compound as a white solid (42 mg, 33% yield). $^1$H NMR (400 MHz, DMSO-$d_6$): δ 12.24 (br s, 1H), 9.45 (s, 1H), 8.14 (d, J=3.3 Hz, 1H), 8.12 (br s, 1H), 7.83-7.75 (m, 1H), 7.74-7.63 (m, 2H), 4.71 (s, 2H), 2.63 (s, 3H). LCMS (Method B): RT=3.03 min, m/z: 403 [M+H$^+$].

Method 2

Example 113

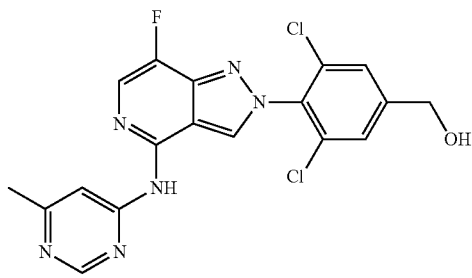 [SMILES: Cc1cc(Nc2ncc(F)c3nn(-c4c(Cl)cc(CO)cc4Cl)cc23)ncn1]

{3,5-Dichloro-4-[7-fluoro-4-(6-methylpyrimidin-4-ylamino)pyrazolo[4,3-c]pyridin-2-yl]phenyl}methanol hydrochloride salt Step 1

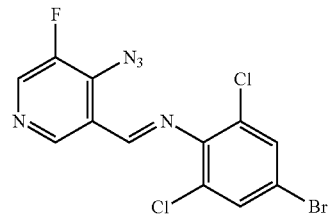 [SMILES: [N-]=[N+]=Nc1c(F)cncc1/C=N/c1c(Cl)cc(Br)cc1Cl]

[1-(4-Azido-5-fluoropyridin-3-yl)meth-(E)-ylidene]-(4-bromo-2,6-dichlorophenyl)amine A solution of 4-azido-5-fluoropyridine-3-carbaldehyde (10.0 g, 60.0 mmol) and 4-bromo-2,6-dichlorophenylamine (14.4 g, 60.0 mmol) in DCM (200 mL) was cooled to 0° C., under an atmosphere of nitrogen. Triethylamine (25 mL, 180 mmol) was added, followed by dropwise addition of titanium (IV) chloride solution (1 N in DCM, 36 mL, 36 mmol). The reaction mixture was stirred at 0° C. then allowed to reach room temperature overnight. The resultant mixture was concentrated under reduced pressure and the residue was suspended in toluene and filtered through a pad of Celite®. The filtrate was concentrated under reduced pressure to afford the title compound (quantitative yield). This was used in the next step without further purification.

Step 2

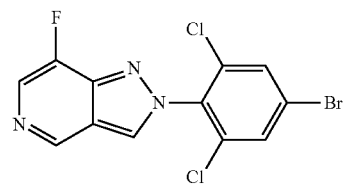 [SMILES: Fc1cncc2cn(-c3c(Cl)cc(Br)cc3Cl)nc12]

2-(4-Bromo-2,6-dichlorophenyl)-7-fluoro-2H-pyrazolo[4,3-c]pyridine

A solution of [1-(4-azido-5-fluoropyridin-3-yl)meth-(E)-ylidene]-(4-bromo-2,6-dichlorophenyl)amine (~60 mmol) in toluene (200 mL) was heated at 105° C. for 2 hours. The resultant mixture was cooled to room temperature and concentrated under reduced pressure. The residue was triturated with diethyl ether and the solid obtained was collected by filtration and dried to afford the title compound (14.5 g, 67% yield over two steps). $^1$H NMR (400 MHz, DMSO-$d_6$): δ 9.25 (d, J=2.7 Hz, 1H), 9.20 (d, J=2.6 Hz, 1H), 8.28 (dd, J=3.8, 0.5 Hz, 1H), 8.19 (s, 2H).

Step 3

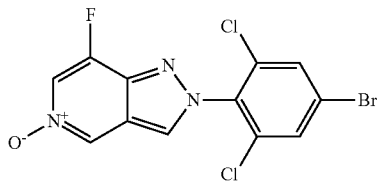 [SMILES: [O-][n+]1cc(F)c2nn(-c3c(Cl)cc(Br)cc3Cl)cc2c1]

2-(4-Bromo-2,6-dichlorophenyl)-7-fluoro-2H-pyrazolo[4,3-c]pyridine 5 oxide 2-(4-Bromo-2,6-dichlorophenyl)-7-fluoro-2H-pyrazolo[4,3-c]pyridine (14.5 g, 40 mmol) was suspended in DCM (160 mL), at 0° C. and meta-chloroperbenzoic acid (12.4 g, 72 mmol) was added. The reaction mixture was stirred at 0° C. for 2 hours then allowed to reach room temperature and stirred overnight. Additional meta-chloroperbenzoic acid (5 g, 30 mmol) was added and the reaction mixture was stirred at room temperature for another 3 hours. The resultant mixture was quenched with saturated aqueous sodium thiosulfate solution and the layers were separated. The organic layer was washed with saturated aqueous sodium bicarbonate solution and brine, dried over anhydrous sodium sulfate, filtered and concentrated under reduced pressure. The residue was triturated with diethyl ether and the solid obtained was filtered and dried to afford the title compound as a beige solid (12.9 g, 86% yield). $^1$H NMR (400 MHz, DMSO-$d_6$): δ 8.98 (d, J=2.6 Hz, 1H), 8.88 (d, J=1.4 Hz, 1H), 8.33 (dd, J=6.3, 1.5 Hz, 1H), 8.19 (s, 2H).

Step 4

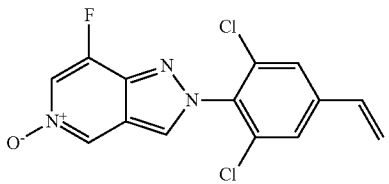 [SMILES: C=Cc1cc(Cl)c(-n2cc3c[n+]([O-])cc(F)c3n2)c(Cl)c1]

2-(2,6-Dichloro-4-vinylphenyl)-7-fluoro-2H-pyrazolo[4,3-c]pyridine 5 oxide

Triethylamine (3.5 mL, 25 mmol) was added to a mixture of 2-(4-bromo-2,6-dichlorophenyl)-7-fluoro-2H-pyrazolo[4,3-c]pyridine 5 oxide (1.88 g, 5.0 mmol), potassium vinyl trifluoroborate (1.0 g, 7.5 mmol) and Pd(dppf)Cl$_2$.CHCl$_3$ (408 mg, 0.5 mmol) in propan-1-ol (50 mL) and the reaction mixture was heated at 100° C. for 1.5 hours. The resultant mixture was allowed to cool to room temperature before being partitioned between ethyl acetate and saturated aqueous sodium hydrogen carbonate solution. The layers were separated and the organic layer was washed with brine, dried over anhydrous sodium sulfate, filtered and concentrated under reduced pressure. The residue was purified by silica gel flash chromatography (4-5% methanol in DCM) to afford the title compound as a beige solid (1.0 g, 62% yield). $^1$H NMR (400 MHz, DMSO-$d_6$): δ 9.00 (d, J=2.6 Hz, 1H), 8.89 (d, J=1.4 Hz, 1H), 8.35 (dd, J=6.3, 1.5 Hz, 1H), 7.97 (s, 2H), 6.85 (dd, J=17.6, 11.0 Hz, 1H), 6.24 (d, J=17.6 Hz, 1H), 5.60 (d, J=11.0 Hz, 1H).

Step 5

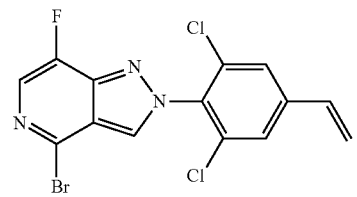 [SMILES: C=Cc1cc(Cl)c(-n2cc3c(Br)ncc(F)c3n2)c(Cl)c1]

4-Bromo-2-(2,6-dichloro-4-vinylphenyl)-7-fluoro-2H-pyrazolo[4,3-c]pyridine

To a suspension of 2-(2,6-dichloro-4-vinylphenyl)-7-fluoro-2H-pyrazolo[4,3-c]pyridine 5 oxide (1.0 g, 3.1 mmol) in DCM (15 mL) under an atmosphere of nitrogen at 0° C., was added phosphorus oxybromide (2.6 g, 9.0 mmol). The reaction mixture was stirred at 0° C. for 1 hour and then allowed to reach room temperature over 30 minutes. The resultant mixture was quenched with saturated aqueous sodium hydrogen carbonate solution and diluted with DCM. The layers were separated and the organic layer was washed with brine, dried over anhydrous sodium sulfate, filtered and concentrated under reduced pressure. The residue was purified by silica gel flash chromatography (20% ethyl acetate in cyclohexane) to afford the title compound as a white solid (304 mg, 25% yield). $^1$H NMR (400 MHz, DMSO-$d_6$): δ 9.41 (d, J=2.5 Hz, 1H), 8.19 (d, J=3.3 Hz, 1H), 7.99 (s, 2H), 6.85 (dd, J=17.6, 11.0 Hz, 1H), 6.25 (d, J=17.6 Hz, 1H), 5.60 (d, J=11.0 Hz, 1H).

Step 6

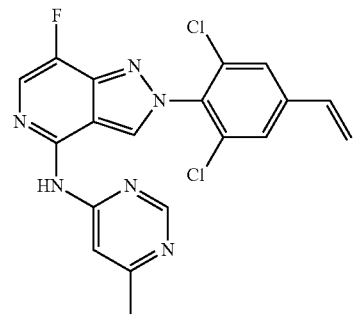 [SMILES: C=Cc1cc(Cl)c(-n2cc3c(Nc4cc(C)ncn4)ncc(F)c3n2)c(Cl)c1]

[2-(2,6-Dichloro-4-vinylphenyl)-7-fluoro-2H-pyrazolo[4,3-c]pyridin-4-yl]-(6-methylpyrimidin-4-yl)amine A mixture of 4-bromo-2-(2,6-dichloro-4-vinylphenyl)-7-fluoro-2H-pyrazolo[4,3-c]pyridine (295 mg, 0.76 mmol), 6-methylpyrimidin-4-ylamine (99 mg, 0.91 mmol), Pd$_2$(dba)$_3$ (17 mg, 0.019 mmol), Xantphos (44 mg, 0.076 mmol) and cesium carbonate (495 mg, 1.52 mmol) in dioxane (8.0 mL) was de-gassed and purged with nitrogen and the reaction mixture was heated at 80° C. in a sealed vial overnight. The resultant mixture was allowed to cool to room temperature, before being partitioned between ethyl acetate and water. The layers were separated and the organic layer was washed with brine, dried over anhydrous sodium sulfate, filtered and concentrated under reduced pressure. The residue was purified by silica gel flash chromatography (70-80% ethyl acetate in cyclohexane) to afford the title compound as a beige solid (197 mg, 62% yield). $^1$H NMR (400 MHz, DMSO-d$_6$): δ 10.69 (s, 1H), 9.24 (d, J=2.6 Hz, 1H), 8.67 (d, J=1.2 Hz, 1H), 8.36 (s, 1H), 7.98-7.93 (m, 3H), 6.88-6.78 (m, 1H), 6.22 (d, J=17.6 Hz, 1H), 5.58 (d, J=11.0 Hz, 1H), 2.43 (s, 3H).

Step 7

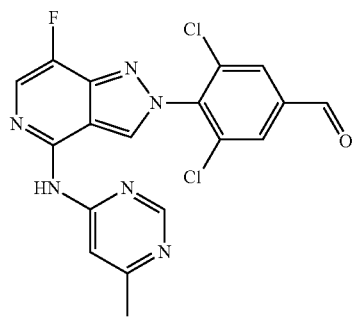 [SMILES: Cc1cc(Nc2ncc(F)c3nn(-c4c(Cl)cc(C=O)cc4Cl)cc23)ncn1]

3,5-Dichloro-4-[7-fluoro-4-(6-methylpyrimidin-4-ylamino)pyrazolo[4,3-c]pyridin-2-yl]benzaldehyde To a mixture of [2-(2,6-dichloro-4-vinylphenyl)-7-fluoro-2H-pyrazolo[4,3-c]pyridin-4-yl]-(6-methylpyrimidin-4-yl)amine (193 mg, 0.47 mmol) in acetone (10 mL) and water (2.5 mL) was added osmium (VIII) oxide (2.5% wt in tert-butanol, 0.465 mL), followed by sodium periodate (257 mg, 1.2 mmol) and the reaction mixture was stirred at room temperature overnight. The resultant mixture was partitioned between ethyl acetate and water and the layers were separated. The organic layer was washed with brine, dried over anhydrous sodium sulfate, filtered and concentrated under reduced pressure. The residue was purified by silica gel flash chromatography (80% ethyl acetate in cyclohexane) to afford the title compound as a yellow solid (129 mg, 66% yield). $^1$H NMR (400 MHz, DMSO-d$_6$): δ 10.77 (s, 1H), 10.10 (s, 1H), 9.35 (d, J=2.6 Hz, 1H), 8.70 (s, 1H), 8.37 (s, 1H), 8.31 (s, 2H), 8.01 (d, J=3.5 Hz, 1H), 2.45 (s, 3H).

Step 8

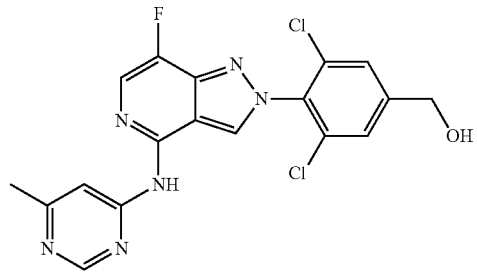 [SMILES: Cc1cc(Nc2ncc(F)c3nn(-c4c(Cl)cc(CO)cc4Cl)cc23)ncn1]

{3,5-Dichloro-4-[7-fluoro-4-(6-methylpyrimidin-4-ylamino)pyrazolo[4,3-c]pyridin-2-yl]phenyl}methanol hydrochloride salt To a solution of 3,5-dichloro-4-[7-fluoro-4-(6-methylpyrimidin-4-ylamino)pyrazolo[4,3-c]pyridin-2-yl]benzaldehyde (125 mg, 0.3 mmol) in ethanol (IMS grade, 5 mL) and THF (2 mL) was added sodium borohydride (14 mg, 0.36 mmol) and the reaction mixture was stirred at room temperature for 2 hours. The resultant mixture was partitioned between ethyl acetate and water and the layers were separated. The organic layer was washed with brine, dried over anhydrous sodium sulfate, filtered and concentrated under reduced pressure. The residue was purified by silica gel flash chromatography (0-1% methanol in ethyl acetate) to yield a solid, to which was added HCl (1.25 N in propan-2-ol, 10 mL) and the mixture was stirred at room temperature for 1 hour. The solid obtained was collected by filtration and dried to afford the title compound as an off-white solid (62 mg, 45% yield). $^1$H NMR (400 MHz, DMSO-d$_6$): δ 9.35 (br s, 1H), 8.97 (s, 1H), 8.36 (br s, 1H), 8.10 (d, J=3.5 Hz, 1H), 7.75 (s, 2H), 4.68 (s, 2H), 2.57 (s, 3H). LCMS (Method B): RT=2.89 min, m/z: 419 [M+H$^+$].

Method 2

Example 114

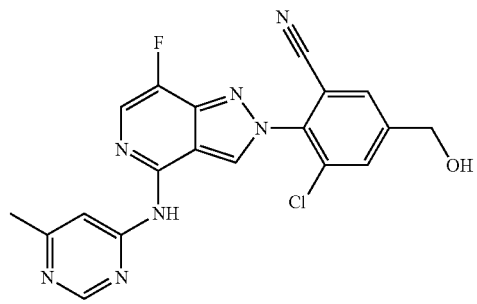 [SMILES: Cc1cc(Nc2ncc(F)c3nn(-c4c(Cl)cc(CO)cc4C#N)cc23)ncn1]

3-Chloro-2-[7-fluoro-4-(6-methylpyrimidin-4-ylamino)pyrazolo[4,3-c]pyridin-2-yl]-5-hydroxymethyl benzonitrile

Step 1

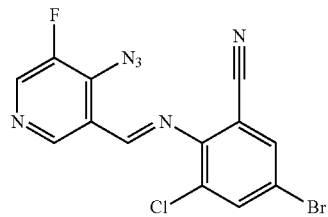 [SMILES: N#Cc1cc(Br)cc(Cl)c1/N=C/c1cncc(F)c1N=[N+]=[N-]]

2-{[1-(4-Azido-5-fluoropyridin-3-yl)meth-(E)-ylidene]amino}-5-bromo-3-chlorobenzonitrile A solution of 4-azido-5-fluoropyridine-3-carbaldehyde (3.75 g, 22.6 mmol) and 2-amino-5-bromo-3-chlorobenzonitrile (5.24 g, 22.6 mmol) in DCM (75 mL) was cooled to 0° C. under an atmosphere of nitrogen. Triethylamine (9.5 mL, 68 mmol) was added, followed by titanium (IV) chloride solution (1 N in DCM, 13.6 mL, 13.6 mmol) dropwise. The reaction mixture was stirred at 0° C. for 2 hours and then allowed to reach room temperature overnight. The resultant mixture was concentrated under reduced pressure and the residue was suspended in toluene and filtered through a pad of Celite®. The filtrate was concentrated under reduced pressure to afford the title compound which was used in the next step without further purification.

Step 2

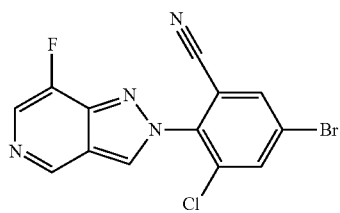 [SMILES: N#Cc1cc(Br)cc(Cl)c1-n1cc2cncc(F)c2n1]

5-Bromo-3-chloro-2-(7-fluoropyrazolo[4,3-c]pyridin-2-yl)benzonitrile

A solution of 2-{[1-(4-azido-5-fluoropyridin-3-yl)meth-(E)-ylidene]amino}-5-bromo-3-chlorobenzonitrile (~22.6 mmol) in toluene (100 mL) was heated under reflux for 5 hours. The resultant mixture was cooled to room temperature and concentrated under reduced pressure. The residue was triturated with diethyl ether and the solid obtained was collected by filtration and dried to afford the title compound as an off-white solid (4.61 g, 58% yield over two steps). $^1$H NMR (400 MHz, DMSO-$d_6$): δ 9.37 (d, J=2.7 Hz, 1H), 9.27 (d, J=2.6 Hz, 1H), 8.61-8.58 (m, 2H), 8.34 (d, J=3.8 Hz, 1H).

Step 3

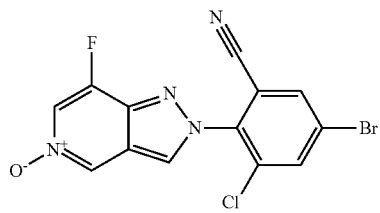 [SMILES: N#Cc1cc(Br)cc(Cl)c1-n1cc2c[n+]([O-])cc(F)c2n1]

5-Bromo-3-chloro-2-(7-fluoro-5-oxypyrazolo[4,3-c]pyridin-2-yl)benzonitrile

5-Bromo-3-chloro-2-(7-fluoropyrazolo[4,3-c]pyridin-2-yl)benzonitrile (4.6 g, 13.1 mmol) was dissolved in DCM (45 mL) and methyltrioxorhenium (324 mg, 1.3 mmol) was added, followed by 30% aqueous hydrogen peroxide solution (1.67 mL, 26.0 mmol) dropwise. The reaction mixture was stirred at room temperature overnight. The resultant mixture was quenched with saturated aqueous sodium thiosulfate solution and the layers were separated. The organic layer was washed with brine, dried over anhydrous sodium sulfate, filtered and concentrated under reduced pressure. The residue was purified by silica gel flash chromatography (5-10% methanol in DCM) to afford the title compound as a pale yellow solid (3.75 g, 78% yield). $^1$H NMR (400 MHz, DMSO-$d_6$): δ 9.07 (d, J=2.5 Hz, 1H), 8.92 (d, J=1.4 Hz, 1H), 8.58-8.55 (m, 2H), 8.37 (dd, J=6.3, 1.5 Hz, 1H).

Step 4

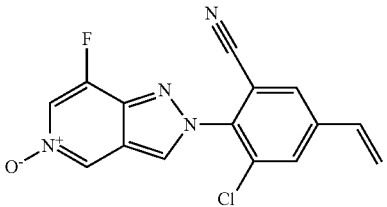 [SMILES: C=Cc1cc(Cl)c(-n2cc3c[n+]([O-])cc(F)c3n2)c(C#N)c1]

3-Chloro-2-(7-fluoro-5-oxypyrazolo[4,3-c]pyridin-2-yl)-5-vinylbenzonitrile

Triethylamine (7.0 mL, 50 mmol) was added to a mixture of 5-bromo-3-chloro-2-(7-fluoro-5-oxypyrazolo[4,3-c]pyridin-2-yl)benzonitrile (3.68 g, 10.0 mmol), potassium vinyl trifluoroborate (2.0 g, 15.0 mmol) and Pd(dppf)Cl$_2$.CHCl$_3$ (408 mg, 0.5 mmol) in propan-1-ol (50 mL) and the reaction mixture was heated at 100° C. for 1.5 hours. The resultant mixture was allowed to cool to room temperature before being partitioned between ethyl acetate and saturated aqueous sodium hydrogen carbonate solution. The layers were separated and the organic layer was washed with brine, dried over anhydrous sodium sulfate, filtered and concentrated under reduced pressure. The residue was purified by silica gel flash chromatography (4-6% methanol in DCM) to afford the title compound as a brown glass (945 mg, 30% yield). $^1$H NMR (400 MHz, DMSO-$d_6$): δ 9.11 (d, J=2.5 Hz, 1H), 8.93 (s, 1H), 8.40-8.36 (m, 2H), 8.32 (d, J=1.8 Hz, 1H), 6.93-6.84 (m, 1H), 6.31 (d, J=17.6 Hz, 1H), 5.66 (d, J=11.1 Hz, 1H).

Step 5

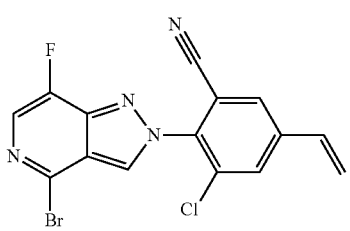 [SMILES: C=Cc1cc(Cl)c(-n2cc3c(Br)ncc(F)c3n2)c(C#N)c1]

2-(4-Bromo-7-fluoropyrazolo[4,3-c]pyridin-2-yl)-3-chloro-5-vinylbenzonitrile

Phosphorus oxybromide (2.6 g, 9.0 mmol) was added to a solution of 3-chloro-2-(7-fluoro-5-oxypyrazolo[4,3-c]pyridin-2-yl)-5-vinylbenzonitrile (936 mg, 3.0 mmol) in DCM (15 mL) and the reaction mixture was stirred at 0° C. for 3 hours. The resultant mixture was quenched with saturated aqueous sodium carbonate solution, diluted with DCM and the layers were separated. The organic layer was washed with brine, dried over anhydrous sodium sulfate, filtered and concentrated under reduced pressure. The residue was purified by silica gel flash chromatography (20% ethyl acetate in cyclohexane) to afford the title compound as a yellow oil (67 mg, 6% yield). $^1$H NMR (400 MHz, CDCl$_3$): δ 8.40 (d, J=2.2 Hz, 1H), 8.02 (d, J=3.0 Hz, 1H), 7.85 (d, J=1.9 Hz, 1H), 7.80 (d, J=1.9 Hz, 1H), 6.75 (dd, J=17.5, 10.9 Hz, 1H), 6.00 (d, J=17.5 Hz, 1H), 5.66 (d, J=10.9 Hz, 1H).

Step 6

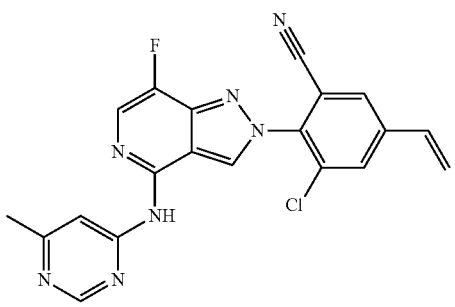 [SMILES: C=Cc1cc(Cl)c(-n2cc3c(Nc4cc(C)ncn4)ncc(F)c3n2)c(C#N)c1]

3-Chloro-2-[7-fluoro-4-(6-methylpyrimidin-4-ylamino)pyrazolo[4,3-c]pyridin-2-yl]-5-vinylbenzonitrile A mixture of 2-(4-bromo-7-fluoropyrazolo[4,3-c]pyridin-2-yl)-3-chloro-5-vinylbenzonitrile (67 mg, 0.18 mmol), 6-methylpyrimidin-4-ylamine (24 mg, 0.22 mmol), Pd$_2$(dba)$_3$ (4 mg, 0.005 mmol), Xantphos (10 mg, 0.018 mmol) and cesium carbonate (117 mg, 0.36 mmol) in dioxane (2.0 mL) was de-gassed and purged with nitrogen and the reaction mixture was heated at 80° C. in a sealed vial overnight. The resultant mixture was allowed to cool to room temperature, before being partitioned between ethyl acetate and water. The layers were separated and the organic layer was washed with brine, dried over anhydrous sodium sulfate, filtered and concentrated under reduced pressure. The residue was purified by silica gel flash chromatography (70% ethyl acetate in cyclohexane) to afford the title compound as a brown glass (42 mg, 58% yield). $^1$H NMR (400 MHz, CDCl$_3$): δ 8.72 (s, 1H), 8.55 (br s, 1H), 8.26 (br s, 1H), 7.98-7.75 (m, 3H), 6.80-6.68 (dd, J=17.6, 6.7 1H), 5.99 (d, J=17.5 Hz, 1H), 5.64 (d, J=10.9 Hz, 1H), 2.55 (s, 3H).

Step 7

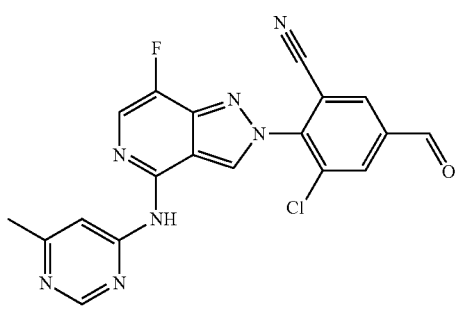 [SMILES: Cc1cc(Nc2ncc(F)c3nn(-c4c(Cl)cc(C=O)cc4C#N)cc23)ncn1]

3-Chloro-2-[7-fluoro-4-(6-methylpyrimidin-4-ylamino)pyrazolo[4,3-c]pyridin-2-yl]-5-formylbenzonitrile Osmium (VIII) oxide (2.5% wt in tert-butanol, 0.1 mL) was added to a solution of 3-chloro-2-[7-fluoro-4-(6-methylpyrimidin-4-ylamino)pyrazolo[4,3-c]pyridin-2-yl]-5-vinylbenzonitrile (42 mg, 0.1 mmol) in acetone (2.0 mL) and water (0.5 mL). Sodium periodate (47 mg, 0.22 mmol) was then added and the reaction mixture was stirred at room temperature overnight. The resultant mixture was partitioned between ethyl acetate and water and the layers were separated. The organic layer was washed with brine, dried over anhydrous sodium sulfate, filtered and concentrated under reduced pressure. The residue was purified by silica gel flash chromatography (70-80% ethyl acetate in cyclohexane) to afford the title compound as a yellow glass (24 mg, 60% yield). $^1$H NMR (400 MHz, DMSO-d$_6$): δ 10.89 (s, 1H), 10.12 (s, 1H), 9.55 (d, J=2.5 Hz, 1H), 8.72-8.62 (m, 3H), 8.37 (s, 1H), 8.03 (d, J=3.4 Hz, 1H), 2.45 (s, 3H).

Step 8

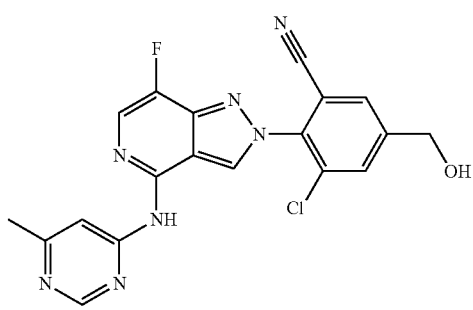 [SMILES: Cc1cc(Nc2ncc(F)c3nn(-c4c(Cl)cc(CO)cc4C#N)cc23)ncn1]

3-Chloro-2-[7-fluoro-4-(6-methylpyrimidin-4-ylamino)pyrazolo[4,3-c]pyridin-2-yl]-5-hydroxymethyl benzonitrile To a solution of 3-chloro-2-[7-fluoro-4-(6-methylpyrimidin-4-ylamino)pyrazolo[4,3-c]pyridin-2-yl]-5-formylbenzonitrile (24 mg, 0.06 mmol) in ethanol (IMS grade, 2.0 mL) and THF (2.0 mL) was added sodium borohydride (4 mg, 0.1 mmol) and the reaction mixture was stirred at room temperature for 2 hours. The resultant mixture was partitioned between ethyl acetate and water and the layers were separated. The organic layer was washed with brine, dried over anhydrous sodium sulfate, filtered and concentrated under reduced pressure. The residue was triturated with diethyl ether and the solid obtained was filtered and dried. This was then purified by silica gel flash chromatography (0-1% methanol in ethyl acetate) to afford the title compound as a white solid (4.0 mg, 16% yield). $^1$H NMR (400 MHz, DMSO-$d_6$): δ 10.82 (s, 1H), 9.46 (d, J=2.6 Hz, 1H), 8.71 (d, J=1.2 Hz, 1H), 8.38 (s, 1H), 8.09 (m, 2H), 8.03 (d, J=3.5 Hz, 1H), 5.76 (t, J=5.8 Hz, 1H), 4.71 (d, J=5.8 Hz, 2H), 2.46 (s, 3H). LCMS (Method B): RT=2.78 min, m/z: 410 [M+H$^+$].

TABLE 3

| Example | Structure | Name | Synth. Method | LCMS (ESI) m/z | LCMS Method | R$_T$ (min) | NMR |
|---|---|---|---|---|---|---|---|
| 115 | 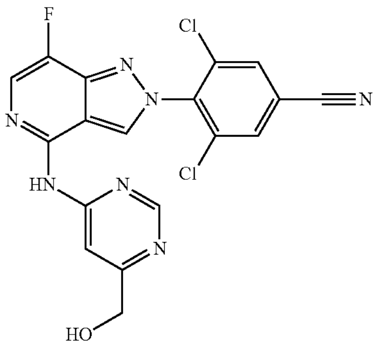 [SMILES: N#Cc1cc(Cl)c(-n2cc3c(Nc4cc(CO)ncn4)ncc(F)c3n2)c(Cl)c1] | 3,5-Dichloro-4-[7-fluoro-4-(6-hydroxymethyl-pyrimidin-4-ylamino)-pyrazolo-[4,3-c]pyridin-2-yl]-benzonitrile | 2 | 430 | B | 3.09 | $^1$H NMR (400 MHz, DMSO-$d_6$): δ 9.58 (br s, 1H), 8.97 (s, 1H), 8.53 (s, 2H), 8.37 (br s, 1H), 8.13 (d, J = 3.7 Hz, 1H), 4.66 (s, 2H). |
| 116 | 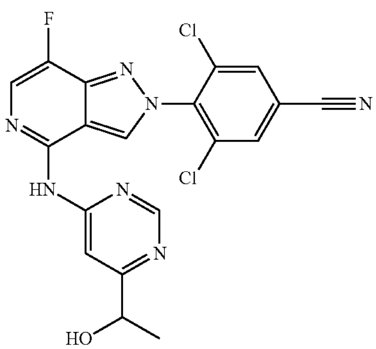 [SMILES: CC(O)c1cc(Nc2ncc(F)c3nn(-c4c(Cl)cc(C#N)cc4Cl)cc23)ncn1] | 3,5-Dichloro-4-{7-fluoro-4-[6-(1-hydroxyethyl)-pyrimidin-4-ylamino]-pyrazolo-[4,3-c]pyridin-2-yl}-benzonitrile | 2 | 444 | B | 3.23 | $^1$H NMR (400 MHz, DMSO-$d_6$): δ 10.81 (s, 1H), 9.33 (d, J = 2.6 Hz, 1H), 8.70 (d, J = 1.2 Hz, 1H), 8.56 (s, 1H), 8.51 (s, 2H), 8.00 (d, J = 3.4 Hz, 1H), 5.53 (d, J = 4.6 Hz, 1H), 4.68-4.60 (m, 1H), 1.39 (d, J = 6.6 Hz, 3H). |
| 117 | 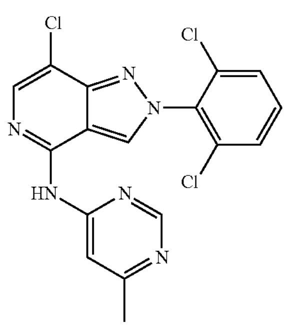 [SMILES: Cc1cc(Nc2ncc(Cl)c3nn(-c4c(Cl)cccc4Cl)cc23)ncn1] | [7-Chloro-2-(2,6-dichlorophenyl)-2H-pyrazolo[4,3-c]pyridin-4-yl]-(6-methylpyrimidin-4-yl)-amine | 2 | 405 | B | 3.54 | $^1$H NMR (400 MHz, DMSO-$d_6$): δ 9.37 (s, 1H), 9.18 (s, 1H), 8.46 (br s, 1H), 8.24 (s, 1H), 7.85-7.82 (m, 2H), 7.77-7.73 (m, 1H), 2.65 (s, 3H). |
| 118 | 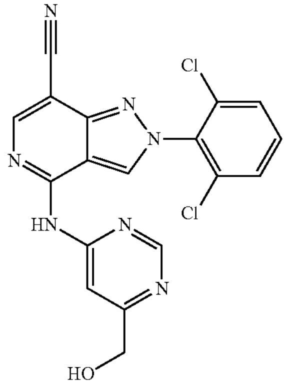 [SMILES: N#Cc1cnc(Nc2cc(CO)ncn2)c2cn(-c3c(Cl)cccc3Cl)nc12] | 2-(2,6-Dichlorophenyl)-4-(6-hydroxymethyl-pyrimidin-4-ylamino)-2H-pyrazolo[4,3-c]pyridine-7-carbonitrile | 2 | 412 | B | 3.48 | $^1$H NMR (400 MHz, DMSO-$d_6$): δ 11.36 (s, 1H), 9.39 (s, 1H), 8.81 (d, J = 1.2 Hz, 1H), 8.68 (s, 1H), 8.62 (s, 1H), 7.86-7.83 (m, 2H), 7.75 (dd, J = 9.1, 7.3 Hz, 1H), 5.67 (t, J = 5.8 Hz, 1H), 4.57 (d, J = 5.8 Hz, 2H). |

TABLE 3-continued

| Example | Structure | Name | Synth. Method | LCMS (ESI) m/z | LCMS Method | $R_T$ (min) | NMR |
|---|---|---|---|---|---|---|---|
| 119 | 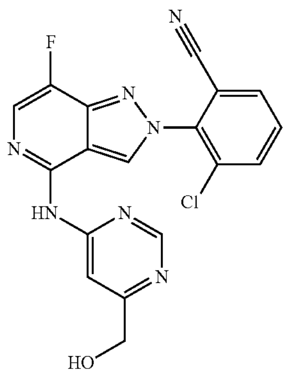 [SMILES: N#Cc1cccc(Cl)c1-n1cc2c(Nc3cc(CO)ncn3)ncc(F)c2n1] | 3-Chloro-2-[7-fluoro-4-(-6-hydroxymethyl-pyrimidin-4-ylamino)-pyrazolo[4,3-c]pyridin-2-yl]-benzonitrile | 2 | 396 | B | 2.79 | $^1$H NMR (400 MHz, DMSO-$d_6$): δ 10.84 (s, 1H), 9.46 (d, J = 2.6 Hz, 1H), 8.69 (d, J = 1.2 Hz, 1H), 8.57 (d, J = 1.2 Hz, 1H), 8.22-8.19 (m, 2H), 8.01 (d, J = 3.5 Hz, 1H), 7.90 (t, J = 8.1 Hz, 1H), 5.58 (t, J = 5.8 Hz, 1H), 4.52 (d, J = 5.8 Hz, 2H). |
| 120 | 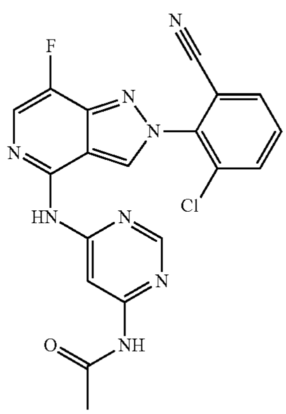 [SMILES: CC(=O)Nc1cc(Nc2ncc(F)c3nn(-c4c(Cl)cccc4C#N)cc23)ncn1] | N-{6-[2-(2-Chloro-6-cyanophenyl)-7-fluoro-2H-pyrazolo[4,3-c]pyridin-4-ylamino]-pyrimidin-4-yl}-acetamide | 2 | 423 | B | 2.98 | $^1$H NMR (400 MHz, DMSO-$d_6$): δ 10.69 (s, 1H), 10.60 (s, 1H), 9.39 (d, J = 2.6 Hz, 1H), 9.01 (d, J = 1.1 Hz, 1H), 8.48 (d, J = 1.1 Hz, 1H), 8.15 (d, J = 8.1 Hz, 2H), 7.91-7.83 (m, 2H), 2.09 (s, 3H). |
| 121 | 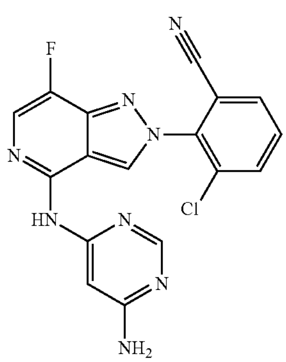 [SMILES: N#Cc1cccc(Cl)c1-n1cc2c(Nc3cc(N)ncn3)ncc(F)c2n1] | 2-[4-(6-Aminopyrimidin-4-ylamino)-7-fluoropyrazolo[4,3-c]pyridin-2-yl]-3-chloro-benzonitrile•HCl | 2 | 381 | B | 2.87 | $^1$H NMR (400 MHz, DMSO-$d_6$): δ 9.64 (d, J = 2.5 Hz, 1H), 8.59 (d, J = 0.8 Hz, 1H), 8.21-8.18 (m, 2H), 8.05 (d, J = 3.5 Hz, 1H), 7.94 (dd, J = 8.4, 7.8 Hz, 1H), 7.30 (br s, 1H). |
| 122 | 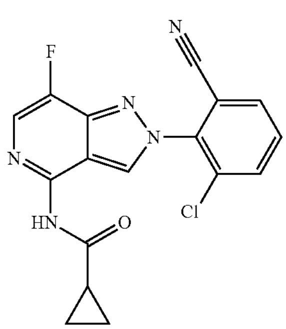 [SMILES: N#Cc1cccc(Cl)c1-n1cc2c(NC(=O)C3CC3)ncc(F)c2n1] | N-(2-(2-chloro-6-cyanophenyl)-7-fluoro-2H-pyrazolo-[4,3-c]pyridin-4-yl)-cyclopropanecarboxamide | 2 | 356 | B | 3.71 | $^1$H NMR (400 MHz, DMSO-$d_6$): δ 11.26 (s, 1H), 9.24 (d, J = 2.4 Hz, 1H), 8.18-8.14 (m, 2H), 8.03 (d, J = 3.1 Hz, 1H), 7.89 (t, J = 8.1 Hz, 1H), 2.14-2.07 (m, 1H), 0.92-0.87 (m, 4H). |

TABLE 3-continued

| Example | Structure | Name | Synth. Method | LCMS (ESI) m/z | LCMS Method | R_T (min) | NMR |
|---|---|---|---|---|---|---|---|
| 123 | 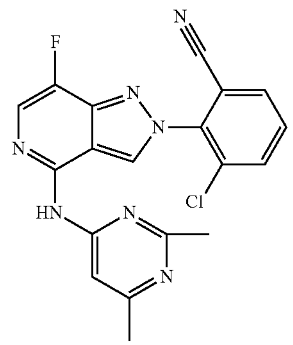 [SMILES: Cc1cc(Nc2ncc(F)c3nn(-c4c(Cl)cccc4C#N)cc23)nc(C)n1] | 3-Chloro-2-[4-(2,6-dimethylpyrimidin-4-ylamino)-7-fluoropyrazolo[4,3-c]pyridin-2-yl]benzonitrile | 2 | 394 | B | 3.01 | $^1$H NMR (400 MHz, DMSO-$d_6$): δ 12.18 (br s, 1H), 9.48 (d, J = 2.4 Hz, 1H), 8.24-8.20 (m, 3H), 8.15 (d, J = 3.3 Hz, 1H), 7.92 (dd, J = 8.5, 7.7 Hz, 1H), 2.67 (s, 3H), 2.61 (s, 3H). |
| 124 | 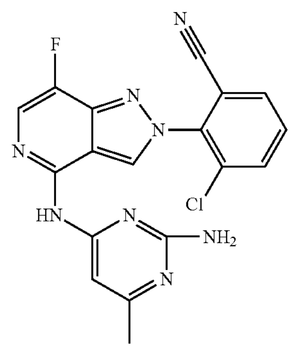 [SMILES: Cc1cc(Nc2ncc(F)c3nn(-c4c(Cl)cccc4C#N)cc23)nc(N)n1] | 2-[4-(2-Amino-6-methylpyrimidin-4-ylamino)-7-fluoropyrazolo[4,3-c]pyridin-2-yl]-3-chlorobenzonitrile | 2 | 395 | B | 2.89 | $^1$H NMR (400 MHz, DMSO-$d_6$): δ 9.83 (s, 1H), 8.28-8.17 (m, 3H), 7.94 (t, J = 8.1 Hz, 1H), 7.18 (s, 1H), 2.46 (s, 3H). |
| 125 | 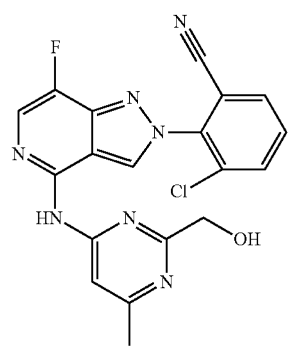 [SMILES: Cc1cc(Nc2ncc(F)c3nn(-c4c(Cl)cccc4C#N)cc23)nc(CO)n1] | 3-Chloro-2-[7-fluoro-4-(2-hydroxymethyl-6-methylpyrimidin-4-ylamino)-pyrazolo[4,3-c]pyridin-2-yl]-benzonitrile | 2 | 410 | B | 2.94 | $^1$H NMR (400 MHz, DMSO-$d_6$): δ 12.33 (br s, 1H), 9.62 (s, 1H), 8.22 (br s, 1H), 8.17 (d, J = 3.2 Hz, 1H), 8.12-8.03 (m, 2H), 7.98-7.90 (m, 1H), 4.74 (s, 2H), 2.64 (s, 3H). |
| 126 | 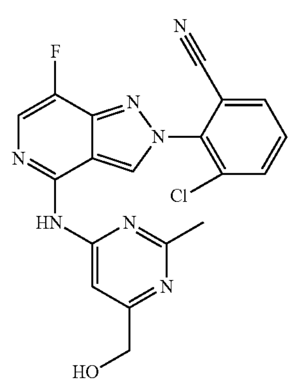 [SMILES: Cc1nc(CO)cc(Nc2ncc(F)c3nn(-c4c(Cl)cccc4C#N)cc23)n1] | 3-Chloro-2-[7-fluoro-4-(6-hydroxymethyl-2-methylpyrimidin-4-ylamino)-pyrazolo[4,3-c]pyridin-2-yl]-benzonitrile | 2 | 410 | B | 2.85 | $^1$H NMR (400 MHz, DMSO-$d_6$): δ 12.25 (br s, 1H), 9.55 (s, 1H), 8.26 (br s, 1H), 8.23 (d, J = 8.0 Hz, 2H), 8.18 (d, J = 3.4 Hz, 1H), 7.93 (t, J = 8.0 Hz, 2H), 4.71 (s, 2H), 2.67 (s, 3H). |

TABLE 3-continued

| Example | Structure | Name | Synth. Method | LCMS (ESI) m/z | LCMS Method | R_T (min) | NMR |
|---|---|---|---|---|---|---|---|
| 127 | 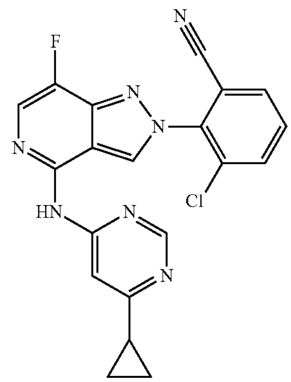 [SMILES: N#Cc1cccc(Cl)c1-n1cc2c(Nc3cc(C4CC4)ncn3)ncc(F)c2n1] | 3-Chloro-2-[4-(6-cyclopropyl-pyrimidin-4-ylamino)-7-fluoropyrazolo[4,3-c]pyridin-2-yl]-benzonitrile | 2 | 406 | B | 3.61 | $^1$H NMR (400 MHz, DMSO-$d_6$): δ 10.77 (br s, 1H), 9.46 (d, J = 2.6 Hz, 1H), 8.62 (d, J = 1.1 Hz, 1H), 8.43 (d, J = 1.1 Hz, 1H), 8.20 (d, J = 7.9 Hz, 2H), 8.02 (d, J = 3.5 Hz, 1H), 7.90 (t, J = 8.0 Hz, 1H), 2.08 (1H, quintet, J = 6.3 Hz, 1H), 1.03 (d, J = 6.3 Hz, 4H). |
| 128 | 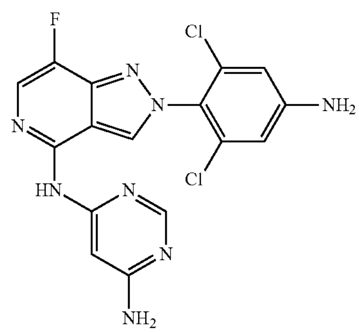 [SMILES: Nc1cc(Cl)c(-n2cc3c(Nc4cc(N)ncn4)ncc(F)c3n2)c(Cl)c1] | N-[2-(4-Amino-2,6-dichlorophenyl)-7-fluoro-2H-pyrazolo[4,3-c]pyridin-4-yl]-benzene-1,3-diamine | 5 | 405 | B | 2.91 | $^1$H NMR (400 MHz, DMSO-$d_6$): δ 9.27 (d, J = 2.5 Hz, 1H), 8.55 (d, J = 0.8 Hz, 1H), 7.98 (d, J = 3.6 Hz, 1H), 7.21 (s, 1H), 6.84 (s, 2H). |
| 129 | 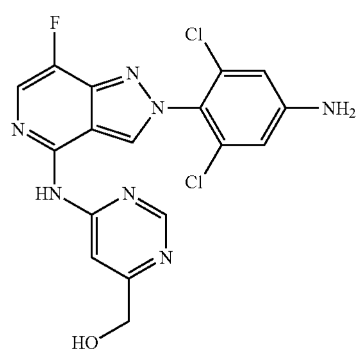 [SMILES: Nc1cc(Cl)c(-n2cc3c(Nc4cc(CO)ncn4)ncc(F)c3n2)c(Cl)c1] | {6-[2-(4-Amino-2,6-dichlorophenyl)-7-fluoro-2H-pyrazolo[4,3-c]pyridin-4-ylamino]-pyrimidin-4-yl}-methanol | 5 | 420 | B | 2.76 | $^1$H NMR (400 MHz, DMSO-$d_6$): δ 10.64 (s, 1H), 9.12 (d, J = 2.6 Hz, 1H), 8.69 (d, J = 1.2 Hz, 1H), 8.61 (s, 1H), 7.94 (d, J = 3.5 Hz, 1H), 6.80 (s, 2H), 6.28 (br s, 2H), 5.58 (t, J = 5.7 Hz, 1H), 4.52 (d, J = 5.4 Hz, 2H). |
| 130 | 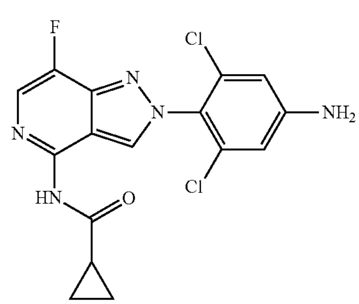 [SMILES: Nc1cc(Cl)c(-n2cc3c(NC(=O)C4CC4)ncc(F)c3n2)c(Cl)c1] | N-[2-(4-amino-2,6-dichlorophenyl)-7-fluoro-2H-pyrazolo[4,3-c]pyridin-4-yl)cyclo-propanecarboxamide | 5 | 380 | B | 3.43 | $^1$H NMR (400 MHz, DMSO-$d_6$): δ 11.12 (s, 1H), 8.78 (d, J = 2.5 Hz, 1H), 7.93 (d, J = 3.1 Hz, 1H), 6.77 (s, 2H), 6.22 (s, 2H), 2.13-2.02 (m, 1H), 0.91-0.81 (m, 4H). |

TABLE 3-continued

| Example | Structure | Name | Synth. Method | LCMS (ESI) m/z | LCMS Method | R$_T$ (min) | NMR |
|---|---|---|---|---|---|---|---|
| 131 | 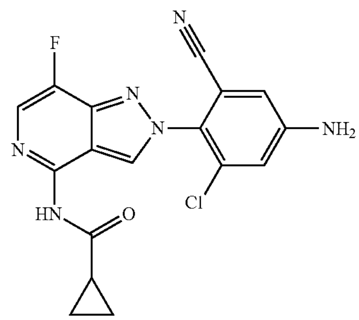 [SMILES: N#Cc1cc(N)cc(Cl)c1-n1cc2c(NC(=O)C3CC3)ncc(F)c2n1] | N-(2-(4-amino-2-chloro-6-cyanophenyl)-7-fluoro-2H-pyrazolo-[4,3-c]pyridin-4-yl)-cyclopropane-carboxamide | 5 | 371 | B | 3.71 | $^1$H NMR (400 MHz, DMSO-d$_6$): δ 11.22 (s, 1H), 8.59 (d, J = 2.2 Hz, 1H), 8.22 (d, J = 2.8 Hz, 1H), 7.09-7.03 (m, 2H), 6.45 (s, 2H), 2.17-2.08 (m, 1H), 0.97-0.87 (m, 4H). |
| 132 | 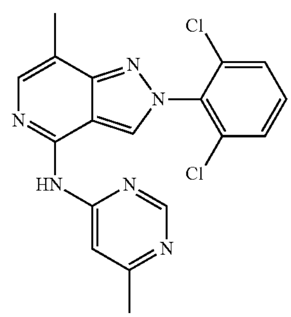 [SMILES: Cc1cc(Nc2ncc(C)c3nn(-c4c(Cl)cccc4Cl)cc23)ncn1] | 2-(2,6-dichlorophenyl)-7-methyl-N-(6-methylpyrimidin-4-yl)-2H-pyrazolo-[4,3-c]pyridin-4-amine | 2 | 385 | B | 3.04 | $^1$H NMR (400 MHz, DMSO-d$_6$): δ 9.51 (s, 1H), 9.05 (d, J = 1.1 Hz, 1H), 7.90-7.85 (m, 3H), 7.78 (dd, J = 9.2, 7.1 Hz, 1H), 7.48 (br s, 1H), 2.60 (s, 3H), 2.50 (d, J = 1.3 Hz, 3H). |
| 133 | 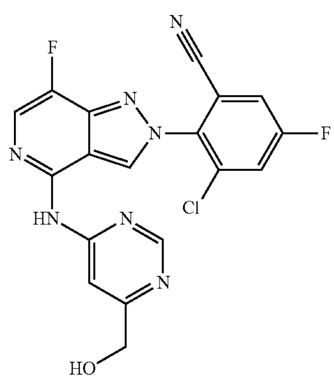 [SMILES: N#Cc1cc(F)cc(Cl)c1-n1cc2c(Nc3cc(CO)ncn3)ncc(F)c2n1] | 3-Chloro-5-fluoro-2-[7-fluoro-4-(6-hydroxymethyl-pyrimidin-4-ylamino)-pyrazolo[4,3-c]pyridin-2-yl]-benzonitrile | 2 | 414 | B | 2.94 | $^1$H NMR (400 MHz, DMSO-d$_6$): δ 10.88 (s, 1H), 9.45 (d, J = 2.6 Hz, 1H), 8.70 (d, J = 1.2 Hz, 1H), 8.56 (s, 1H), 8.37-8.29 (m, 2H), 8.01 (d, J = 3.4 Hz, 1H), 5.59 (br s, 1H), 4.52 (s, 2H). |
| 134 | 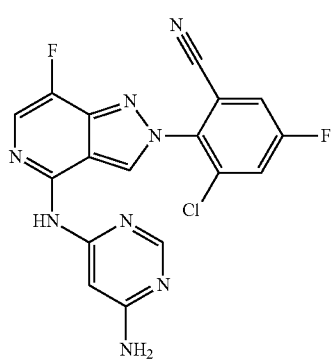 [SMILES: N#Cc1cc(F)cc(Cl)c1-n1cc2c(Nc3cc(N)ncn3)ncc(F)c2n1] | 2-[4-(6-Aminopyrimidin-4-ylamino)-7-fluoropyrazolo[4,3-c]pyridin-2-yl]-3-chloro-5-fluorobenzonitrile | 2 | 399 | B | 2.99 | $^1$H NMR (400 MHz, DMSO-d$_6$): δ 10.27 (s, 1H), 9.45 (d, J = 2.6 Hz, 1H), 8.36-8.30 (m, 2H), 8.15 (d, J = 1.0 Hz, 1H), 7.91 (d, J = 3.5 Hz, 1H), 7.59 (d, J = 1.1 Hz, 1H), 6.72 (s, 2H). |

TABLE 3-continued

| Example | Structure | Name | Synth. Method | LCMS (ESI) m/z | LCMS Method | R_T (min) | NMR |
|---|---|---|---|---|---|---|---|
| 135 | 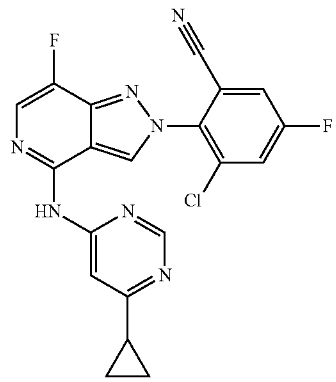 [SMILES: N#Cc1cc(F)cc(Cl)c1-n1cc2c(Nc3cc(C4CC4)ncn3)ncc(F)c2n1] | 3-Chloro-2-[4-(6-cyclopropyl-pyrimidin-4-ylamino)-7-fluoropyrazolo[4,3-c]pyridin-2-yl]-5-fluorobenzonitrile | 2 | 424 | B | 3.77 | $^1$H NMR (400 MHz, DMSO-d$_6$): δ 10.76 (s, 1H), 9.41 (d, J = 2.6 Hz, 1H), 8.59 (d, J = 1.2 Hz, 1H), 8.40 (d, J = 1.2 Hz, 1H), 8.33-8.26 (m, 2H), 7.99 (d, J = 3.4 Hz, 1H), 2.09-2.00 (m, 1H), 1.05-0.97 (m, 4H). |
| 136 | 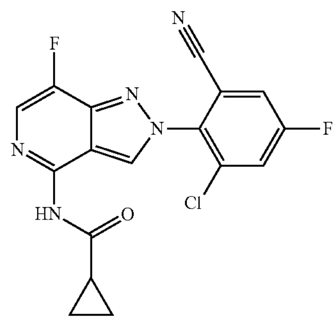 [SMILES: N#Cc1cc(F)cc(Cl)c1-n1cc2c(NC(=O)C3CC3)ncc(F)c2n1] | N-(2-(2-chloro-6-cyano-4-fluoro-phenyl)-7-fluoro-2H-pyrazolo[4,3-c]-pyridin-4-yl)cyclo-propanecarbox-amide | 2 | 374 | B | 3.94 | $^1$H NMR (400 MHz, DMSO-d$_6$): δ 11.27 (s, 1H), 9.23 (d, J = 2.5 Hz, 1H), 8.32-8.25 (m, 2 H), 8.02 (d, J = 3.1 Hz, 1H), 2.14-2.06 (m, 1H), 0.93-0.85 (m, 4H). |
| 137 | 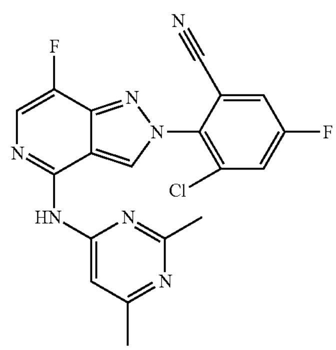 [SMILES: Cc1cc(Nc2ncc(F)c3nn(-c4c(Cl)cc(F)cc4C#N)cc23)nc(C)n1] | 3-Chloro-2-[4-(2,6-dimethylpyrimidin-4-ylamino)-7-fluoropyrazolo[4,3-c]pyridin-2-yl]-5-fluoro-benzonitrile•HCl | 2 | 412 | G | 6.51 | $^1$H NMR (400 MHz, DMSO-d$_6$): δ 9.49 (d, J = 2.4 Hz, 1H), 8.39-8.28 (m, 3H), 8.16 (d, J = 3.2 Hz, 1H), 2.68 (s, 3H), 2.62 (s, 3H). |
| 138 | 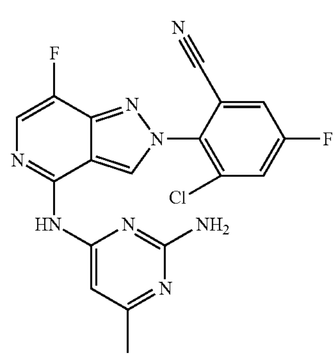 [SMILES: Cc1cc(Nc2ncc(F)c3nn(-c4c(Cl)cc(F)cc4C#N)cc23)nc(N)n1] | 2-[4-(2-Amino-6-methylpyrimidin-4-ylamino)-7-fluoro-pyrazolo[4,3-c]pyridin-2-yl]-3-chloro-5-fluoro-benzonitrile•HCl | 2 | 413 | B | 3.03 | $^1$H NMR (400 MHz, DMSO-d$_6$): δ 9.50 (br s, 1H), 8.39-8.33 (m, 2H), 8.13 (d, J = 3.4 Hz, 1H), 7.54 (br s, 1H), 2.40 (s, 3H). |

TABLE 3-continued

| Example | Structure | Name | Synth. Method | LCMS (ESI) m/z | LCMS Method | R$_T$ (min) | NMR |
|---|---|---|---|---|---|---|---|
| 139 | 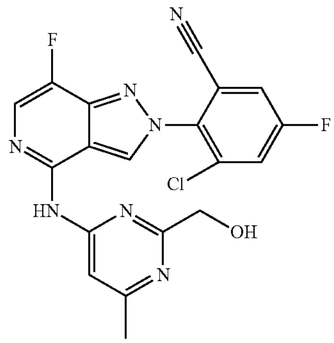 [SMILES: Cc1cc(Nc2ncc(F)c3nn(-c4c(Cl)cc(F)cc4C#N)cc23)nc(CO)n1] | 3-Chloro-5-fluoro-2-[7-fluoro-4-(2-hydroxymethyl-6-methylpyrimidin-4-ylamino)-pyrazolo[4,3-c]pyridin-2-yl]-benzonitrile•HCl | 2 | 428 | B | 3.07 | $^1$H NMR (400 MHz, DMSO-d$_6$): δ 10.77 (s, 1H), 9.47 (d, J = 3.2 Hz, 1H), 8.31-8.25 (m, 2H), 8.13 (s, 1H), 7.96 (d, J = 3.2 Hz, 1H), 5.01 (t, J = 5.6 Hz, 1H), 4.45 (d, J = 5.6 Hz, 2H), 2.39 (s, 3H). |
| 140 | 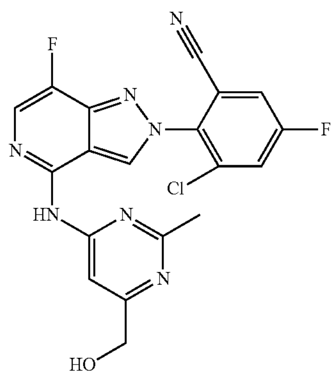 [SMILES: Cc1nc(CO)cc(Nc2ncc(F)c3nn(-c4c(Cl)cc(F)cc4C#N)cc23)n1] | 3-Chloro-5-fluoro-2-[7-fluoro-4-(6-hydroxymethyl-2-methylpyrimidin-4-ylamino)-pyrazolo[4,3-c]pyridin-2-yl]-benzonitrile•HCl | 2 | 428 | B | 2.99 | $^1$H NMR (400 MHz, DMSO-d$_6$): δ 12.18 (br s, 1H), 9.46 (s, 1H), 8.33-8.29 (m, 2H), 8.13 (d, J = 3.2 Hz, 1H), 7.96 (d, J = 3.4 Hz, 1H), 4.65 (br s, 2H), 2.62 (s, 3H). |
| 141 | 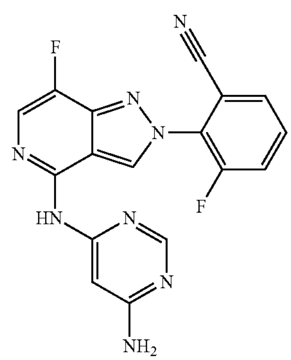 [SMILES: N#Cc1cccc(F)c1-n1cc2c(Nc3cc(N)ncn3)ncc(F)c2n1] | 2-[4-(6-Aminopyrimidin-4-ylamino)-7-fluoropyrazolo[4,3-c]pyridin-2-yl]-3-fluoro-benzonitrile•HCl | 2 | 365 | B | 2.75 | $^1$H NMR (400 MHz, DMSO-d$_6$): δ 9.70 (br s, 1H), 8.54 (s, 1H), 8.12-8.00 (m, 3H), 7.97-7.90 (m, 2H). |
| 142 | 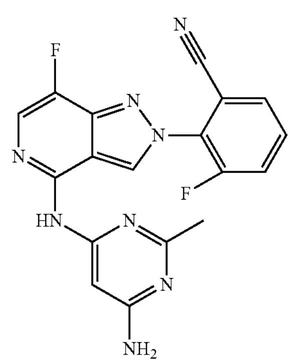 [SMILES: Cc1nc(N)cc(Nc2ncc(F)c3nn(-c4c(F)cccc4C#N)cc23)n1] | 2-[4-(6-Amino-2-methylpyrimidin-4-ylamino)-7-fluoropyrazolo[4,3-c]pyridin-2-yl]-3-fluoro-benzonitrile•HCl | 2 | 379 | G | 6.12 | $^1$H NMR (400 MHz, DMSO-d$_6$): δ 11.59 (br s, 1H), 9.65 (s, 1H), 8.41 (br s, 1H), 8.09-8.01 (m, 3H), 7.94-7.88 (m, 1H), 7.57 (br s, 2H), 2.49 (s, 3H). |

TABLE 3-continued

| Example | Structure | Name | Synth. Method | LCMS (ESI) m/z | LCMS Method | R$_T$ (min) | NMR |
|---|---|---|---|---|---|---|---|
| 143 | 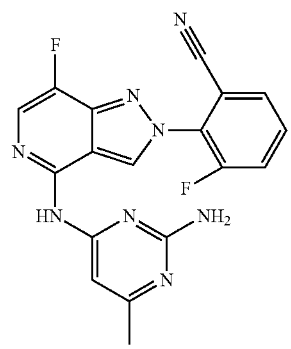 [SMILES: Cc1cc(Nc2ncc(F)c3nn(-c4c(F)cccc4C#N)cc23)nc(N)n1] | 2-[4-(2-Amino-6-methylpyrimidin-4-ylamino)-7-fluoropyrazolo[4,3-c]pyridin-2-yl]-3-fluoro-benzonitrile•HCl | 2 | 379 | B | 2.80 | $^1$H NMR (400 MHz, DMSO-d$_6$): δ 9.79 (s, 1H), 8.21 (d, J = 3.7 Hz, 1H), 8.14-8.05 (m, 2H), 8.00-7.92 (m, 1H), 7.29 (br s, 1H), 2.43 (s, 3H). |
| 144 | 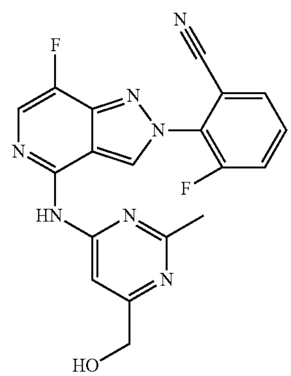 [SMILES: Cc1nc(CO)cc(Nc2ncc(F)c3nn(-c4c(F)cccc4C#N)cc23)n1] | 3-Fluoro-2-[7-fluoro-4-(6-hydroxymethyl-2-methylpyrimidin-4-ylamino)-pyrazolo[4,3-c]pyridin-2-yl]-benzonitrile•HCl | 2 | 394 | B | 2.74 | $^1$H NMR (400 MHz, DMSO-d$_6$): δ 12.29 (br s, 1H), 9.62 (s, 1H), 8.35 (br s, 1H), 8.17 (d, J = 3.3 Hz, 1H), 8.12-8.03 (m, 2H), 7.97-7.90 (m, 1H), 4.71 (s, 2H), 2.69 (s, 3H). |
| 145 | 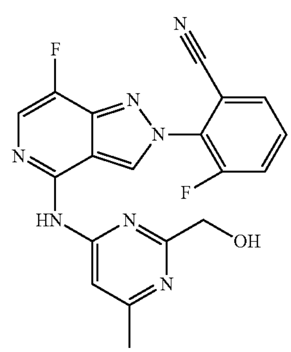 [SMILES: Cc1cc(Nc2ncc(F)c3nn(-c4c(F)cccc4C#N)cc23)nc(CO)n1] | 3-Fluoro-2-[7-fluoro-4-(2-hydroxymethyl-6-methylpyrimidin-4-ylamino)-pyrazolo[4,3-c]pyridin-2-yl]-benzonitrile•HCl | 2 | 394 | B | 2.79 | $^1$H NMR (400 MHz, DMSO-d$_6$): δ 12.32 (br s, 1H), 9.62 (s, 1H), 8.21 (br s, 1H), 8.17 (d, J = 3.1 Hz, 1H), 8.12-8.02 (m, 2H), 7.99-7.89 (m, 1H), 4.74 (s, 2H), 2.68 (s, 3H). |
| 146 | 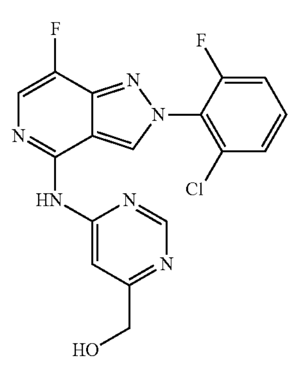 [SMILES: OCc1cc(Nc2ncc(F)c3nn(-c4c(F)cccc4Cl)cc23)ncn1] | {6-[2-(2-Chloro-6-fluorophenyl)-7-fluoro-2H-pyrazolo[4,3-c]pyridin-4-ylamino]pyrimidin-4-yl}methanol•HCl | 2 | 389 | B | 2.89 | $^1$H NMR (400 MHz, DMSO-d$_6$): δ 9.78 (br s, 1H), 9.01 (s, 1H), 8.33 (br s, 1H), 8.15 (d, J = 3.9 Hz, 1H), 7.86-7.78 (m, 1H), 7.76-7.64 (m, 2H), 4.69 (s, 2H). |

TABLE 3-continued

| Example | Structure | Name | Synth. Method | LCMS (ESI) m/z | LCMS Method | R_T (min) | NMR |
|---|---|---|---|---|---|---|---|
| 147 | 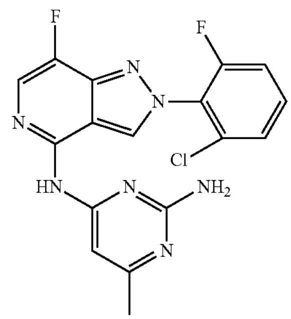 [SMILES: Cc1cc(Nc2ncc(F)c3nn(-c4c(F)cccc4Cl)cc23)nc(N)n1] | N⁴-[2-(2-Chloro-6-fluorophenyl)-7-fluoro-2H-pyrazolo[4,3-c]pyridin-4-yl]-6-methylpyrimidine-2,4-diamine•HCl | 2 | 388 | B | 3.00 | ¹H NMR (400 MHz, DMSO-d₆): δ 9.79 (s, 1H), 8.26 (d, J = 4.1 Hz, 1H), 7.86-7.78 (m, 1H), 7.75-7.65 (m, 2H), 7.20 (br s, 1H), 2.46 (s, 3H). |
| 148 | 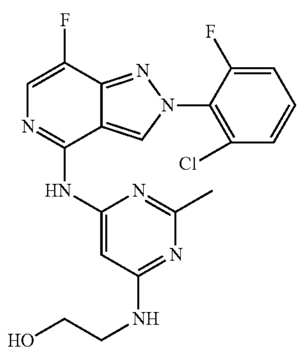 [SMILES: Cc1nc(NCCO)cc(Nc2ncc(F)c3nn(-c4c(F)cccc4Cl)cc23)n1] | 2-{6-[2-(2-Chloro-6-fluorophenyl)-7-fluoro-2H-pyiazolo[4,3-c]pyridin-4-ylamino]-2-methylpyrimidin-4-ylamino}-ethanol•HCl | 2 | 432 | B | 3.14 | ¹H NMR (400 MHz, DMSO-d₆): δ 9.45 (s, 1H), 8.04 (d, J = 3.2 Hz, 1H), 7.84-7.75 (m, 1H), 7.73-7.61 (m, 2H), 7.10 (br s, 1H), 3.67-3.59 (m, 2H), 3.59-3.49 (m, 2H), 2.59 (s, 3H). |
| 149 | 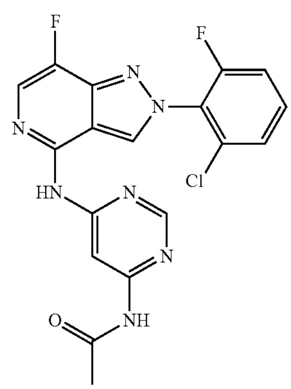 [SMILES: CC(=O)Nc1cc(Nc2ncc(F)c3nn(-c4c(F)cccc4Cl)cc23)ncn1] | N-{6-[2-(2-Chloro-6-fluorophenyl)-7-fluoro-2H-pyrazolo[4,3-c]pyridin-4-ylamino]-pyrimidin-4-yl}-acetamide•HCl | 2 | 416 | B | 3.09 | ¹H NMR (400 MHz, DMSO-d₆): δ 12.20 (br s, 1H), 11.03 (s, 1H), 9.70 (s, 1H), 8.72 (s, 1H), 8.57 (br s, 1H), 8.08 (d, J = 4.3 Hz, 1H), 8.53 (dt, J = 5.7, 8.5 Hz, 1H), 7.75-7.64 (m, 2H), 2.17 (s, 3H). |
| 150 | 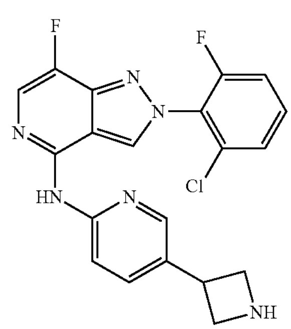 [SMILES: Fc1cccc(Cl)c1-n1cc2c(Nc3ccc(C4CNC4)cn3)ncc(F)c2n1] | (5-Azetidin-3-yl-pyridin-2-yl)-[2-(2-chloro-6-fluorophenyl)-7-fluoro-2H-pyrazolo[4,3-c]pyridin-4-yl]-amine•HCl | 2 | 413 | B | 2.36 | ¹H NMR (400 MHz, DMSO-d₆): δ 13.52 (br s, 1H), 10.24 (s, 1H), 9.43 (s, 1H), 9.22 (s, 1H), 8.46 (d, J = 2.1 Hz, 1H), 8.31-8.25 (m, 1H), 8.12-8.03 (m, 2H), 7.96 (dt, J = 5.8, 8.1 Hz, 1H), 7.77-7.66 (m, 2H), 4.34-1.21 (m, 3H), 4.19-4.07 (m, 2H). |

TABLE 3-continued

| Example | Structure | Name | Synth. Method | LCMS (ESI) m/z | LCMS Method | R$_T$ (min) | NMR |
|---|---|---|---|---|---|---|---|
| 151 | 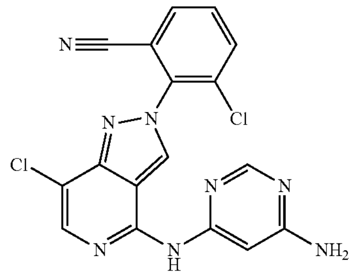 [SMILES: N#Cc1cccc(Cl)c1-n1cc2c(Nc3cc(N)ncn3)ncc(Cl)c2n1] | 2-(4-(6-aminopyrimidin-4-ylamino)-7-chloro-2H-pyrazolo[4,3-c]pyridin-2-yl)-3-chlorobenzonitrile | 2 | 397 | E | 3.71 | $^1$H NMR (400 MHz, DMSO-d$_6$) δ 10.32 (s, 1H), 9.45 (s, 1H), 8.29-8.09 (m, 3H), 7.98 (s, 1H), 7.89 (t, J = 8.1 Hz, 1H), 7.58 (s, 1H), 6.73 (s, 2H). |
| 152 | 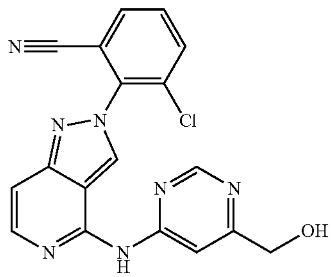 [SMILES: N#Cc1cccc(Cl)c1-n1cc2c(Nc3cc(CO)ncn3)nccc2n1] | 3-chloro-2-(4-(6-(hydroxymethyl)pyrimidin-4-ylamino)-2H-pyrazolo[4,3-c]pyridin-2-yl)benzonitrile | 2 | 378 | E | 3.16 | $^1$H NMR (400 MHz, DMSO-d$_6$) δ 10.76 (s, 1H), 9.35 (s, 1H), 8.71 (s, 2H), 8.24 (s, 1H), 8.18 (d, J = 8.0 Hz, 2H), 8.01 (s, 1H), 7.87 (t, J = 8.0 Hz, 1H), 7.26 (s, 1H), 6.57 (s, 1H), 5.57 (s, 1H), 4.53 (s, 3H). |
| 153 | 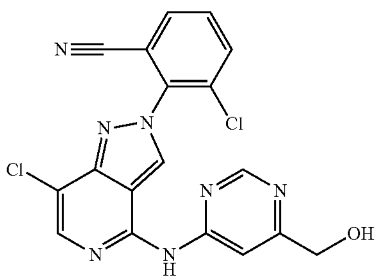 [SMILES: N#Cc1cccc(Cl)c1-n1cc2c(Nc3cc(CO)ncn3)ncc(Cl)c2n1] | 3-chloro-2-(7-chloro-4-(6-(hydroxymethyl)pyrimidin-4-ylamino)-2H-pyrazolo[4,3-c]pyridin-2-yl)benzonitrile | 2 | 412 | E | 3.52 | $^1$H NMR (400 MHz, DMSO-d$_6$) δ 10.94 (s, 1H), 9.47 (s, 1H), 8.73 (s, 1H), 8.60 (d, J = 10.3 Hz, 1H), 8.19 (t, J = 8.2 Hz, 2H), 8.09 (s, 1H), 7.90 (t, J = 8.0 Hz, 2H), 5.59 (s, 1H), 4.54 (d, J = 4.0 Hz, 3H). |
| 154 | 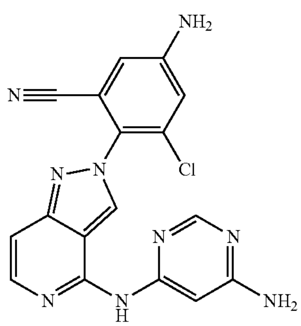 [SMILES: N#Cc1cc(N)cc(Cl)c1-n1cc2c(Nc3cc(N)ncn3)nccc2n1] | 5-amino-2-(4-(6-aminopyrimidin-4-ylamino)-2H-pyrazolo[4,3-c]pyridin-2-yl)-3-chlorobenzonitrile | 2 | 378 | E | 3.44 | $^1$H NMR (400 MHz, DMSO-d$_6$) δ 10.11 (s, 1H), 8.94 (s, 1H), 8.15 (s, 1H), 8.06 (d, J = 6.0 Hz, 1H), 7.63 (s, 1H), 7.08 (dd, J = 17.9, 2.3 Hz, 2H), 6.78 (d, J = 6.0 Hz, 1H), 6.64 (s, 2H), 6.38 (s, 2H). |
| 155 | 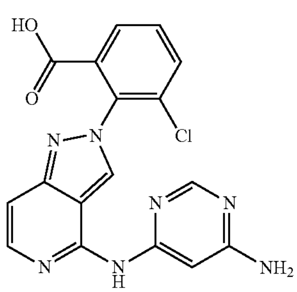 [SMILES: Nc1cc(Nc2nccc3nn(-c4c(Cl)cccc4C(=O)O)cc23)ncn1] | 2-(4-(6-aminopyrimidin-4-ylamino)-2H-pyrazolo[4,3-c]pyridin-2-yl)-3-chlorobenzoic acid | 2 | 382 | E | 3.42 | $^1$H NMR (400 MHz, DMSO-d$_6$) δ 9.87 (s, 1H), 9.00 (s, 1H), 8.12 (s, 1H), 7.83 (d, J = 6.2 Hz, 1H), 7.75 (s, 1H), 7.55-7.38 (m, 3H), 7.04 (d, J = 6.1 Hz, 1H), 6.61 (s, 2H). |

TABLE 3-continued

| Example | Structure | Name | Synth. Method | LCMS (ESI) m/z | LCMS Method | R$_T$ (min) | NMR |
|---|---|---|---|---|---|---|---|
| 156 | 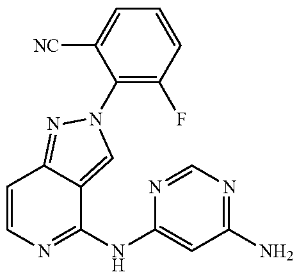 [SMILES: N#Cc1cccc(F)c1-n1cc2c(Nc3cc(N)ncn3)nccc2n1] | 2-(4-(6-aminopyrimidin-4-ylamino)-2H-pyrazolo[4,3-c]pyridin-2-yl)-3-fluorobenzonitrile | 2 | 347 | E | 3.21 | $^1$H NMR (400 MHz, DMSO-d$_6$) δ 10.15 (s, 1H), 9.43 (s, 1H), 8.17 (d, J = 16.9 Hz, 1H), 8.01 (dd, J = 14.2, 8.7 Hz, 2H), 7.93 (d, J = 6.0 Hz, 1H), 7.86 (td, J = 8.2, 5.1 Hz, 1H), 7.71 (s, 1H), 7.15 (d, J = 5.9 Hz, 1H), 6.68 (s, 2H). |
| 157 | 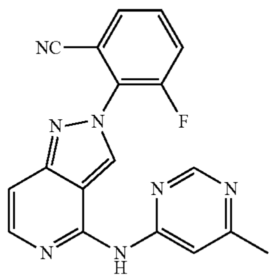 [SMILES: Cc1cc(Nc2nccc3nn(-c4c(F)cccc4C#N)cc23)ncn1] | 3-fluoro-2-(4-(6-methylpyrimidin-4-ylamino)-2H-pyrazolo[4,3-c]pyridin-2-yl)benzonitrile | 2 | 346 | E | 3.26 | $^1$H NMR (400 MHz, DMSO-d$_6$) δ 10.73 (s, 1H), 9.43 (s, 1H), 8.71 (s, 1H), 8.51 (s, 1H), 8.16-7.94 (m, 3H), 7.87 (td, J = 8.1, 5.1 Hz, 1H), 7.25 (d, J = 6.4 Hz, 1H), 2.46 (s, 3H). |
| 158 | 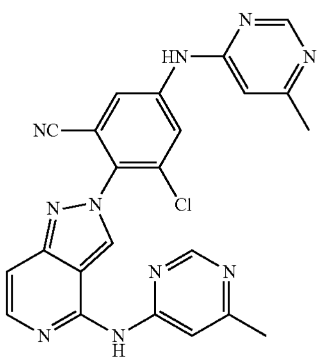 [SMILES: Cc1cc(Nc2cc(Cl)c(-n3cc4c(Nc5cc(C)ncn5)nccc4n3)c(C#N)c2)ncn1] | 3-chloro-5-(6-methylpyrimidin-4-ylamino)-2-(4-(6-methylpyrimidin-4-ylamino)-2H-pyrazolo[4,3-c]pyridin-2-yl)benzonitrile | 2 | 469 | E | 3.02 | $^1$H NMR (400 MHz, DMSO-d$_6$) δ 10.68 (s, 1H), 10.30 (s, 1H), 9.29 (s, 1H), 8.71 (d, J = 10.3 Hz, 2H), 8.51 (s, 1H), 8.45 (d, J = 2.0 Hz, 1H), 8.38 (d, J = 2.1 Hz, 1H), 8.01 (d, J = 6.4 Hz, 1H), 7.24 (d, J = 6.3 Hz, 1H), 6.79 (s, 1H), 2.46 (s, 3H), 2.40 (s, 4H). |
| 159 | 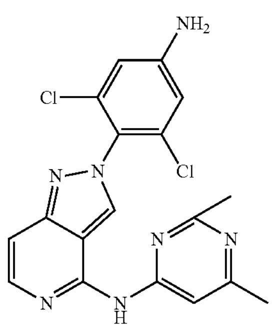 [SMILES: Cc1cc(Nc2nccc3nn(-c4c(Cl)cc(N)cc4Cl)cc23)nc(C)n1] | 2-(4-amino-2,6-dichlorophenyl)-N-(2,6-dimethylpyrimidin-4-yl)-2H-pyrazolo[4,3-c]pyridin-4-amine | 2 | 401 | E | 3.27 | $^1$H NMR (400 MHz, DMSO-d$_6$) δ 9.87 (d, J = 32.7 Hz, 1H), 9.00 (s, 1H), 7.86 (d, J = 6.4 Hz, 1H), 7.59 (d, J = 18.2 Hz, 1H), 7.07 (d, J = 6.4 Hz, 1H), 6.78 (s, 2H), 6.55 (d, J = 10.4 Hz, 2H), 6.23 (d, J = 24.6 Hz, 2H), 2.27 (s, 3H). |
| 160 | 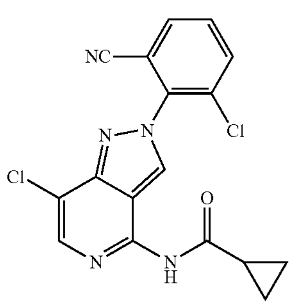 [SMILES: N#Cc1cccc(Cl)c1-n1cc2c(NC(=O)C3CC3)ncc(Cl)c2n1] | N-(7-chloro-2-(2-chloro-6-cyanophenyl)-2H-pyrazolo[4,3-c]pyridin-4-yl)cyclopropanecarboxamide | 2 | 372 | E | 4.14 | $^1$H NMR (400 MHz, DMSO-d$_6$) δ 11.34 (s, 1H), 9.28 (d, J = 15.0 Hz, 1H), 8.28-8.06 (m, 3H), 7.88 (t, J = 8.1 Hz, 1H), 2.21-2.05 (m, 1H), 0.99-0.79 (m, 4H). |

TABLE 3-continued

| Example | Structure | Name | Synth. Method | LCMS (ESI) m/z | LCMS Method | R$_T$ (min) | NMR |
|---|---|---|---|---|---|---|---|
| 161 | 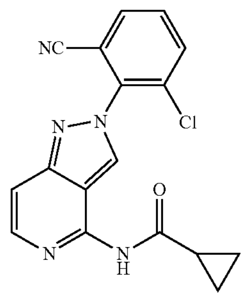 [SMILES: N#Cc1cccc(Cl)c1-n1cc2c(NC(=O)C3CC3)nccc2n1] | N-(2-(2-chloro-6-cyanophenyl)-2H-pyrazolo[4,3-c]pyridin-4-yl)cyclopropane-carboxamide | 2 | 338 | E | 3.18 | $^1$H NMR (400 MHz, DMSO-d$_6$) δ 11.19 (s, 1H), 9.08 (s, 1H), 8.15 (t, J = 8.6 Hz, 2H), 8.01 (d, J = 6.3 Hz, 1H), 7.90-7.74 (m, 1H), 7.38 (dd, J = 19.6, 6.1 Hz, 2H), 6.51 (s, 1H), 2.23-2.03 (m, 1H), 0.99-0.77 (m, 5H). |
| 162 | 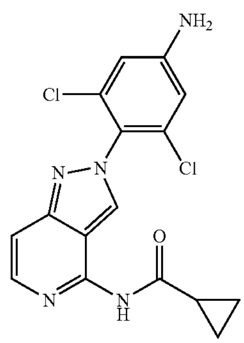 [SMILES: Nc1cc(Cl)c(-n2cc3c(NC(=O)C4CC4)nccc3n2)c(Cl)c1] | N-(2-(4-amino-2,6-dichlorophenyl)-2H-pyrazolo[4,3-c]pyridin-4-yl]cyclopropane-carboxamide | 2 | 362 | E | 3.45 | $^1$H NMR (400 MHz, DMSO-d$_6$) δ 11.07 (s, 1H), 8.64 (d, J = 21.9 Hz, 1H), 7.94 (d, J = 6.3 Hz, 1H), 7.32 (d, J = 6.3 Hz, 1H), 6.76 (s, 2H), 6.18 (s, 2H), 2.22-2.04 (m, 1H), 1.00-0.73 (m, 5H). |
| 163 | 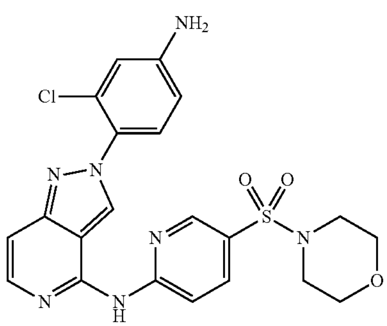 [SMILES: Nc1ccc(-n2cc3c(Nc4ccc(S(=O)(=O)N5CCOCC5)cn4)nccc3n2)c(Cl)c1] | 2-(4-amino-2-chlorophenyl)-N-(5-(morpholinosulfonyl)pyridin-2-yl)-2H-pyrazolo[4,3-c]pyridin-4-amine | 2 | 486 | E | 3.69 | $^1$H NMR (400 MHz, DMSO-d$_6$) δ 10.84 (s, 1H), 9.15 (s, 1H), 8.91 (d, J = 9.0 Hz, 1H), 8.64 (t, J = 16.0 Hz, 1H), 8.10 (d, J = 8.9 Hz, 1H), 7.93 (d, J = 6.3 Hz, 1H), 7.37 (t, J = 9.6 Hz, 1H), 7.24-7.12 (m, 1H), 6.80 (d, J = 2.2 Hz, 1H), 6.66 (dd, J = 8.6, 2.2 Hz, 2H), 5.89 (s, 2H), 3.74-3.55 (m, 6H), 2.93 (dd, J = 13.7, 9.3 Hz, 5H). |
| 164 | 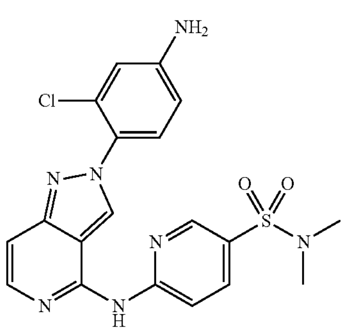 [SMILES: CN(C)S(=O)(=O)c1ccc(Nc2nccc3nn(-c4ccc(N)cc4Cl)cc23)nc1] | 6-(2-(4-amino-2-chlorophenyl)-2H-pyrazolo[4,3-c]pyridin-4-ylamino)-N,N-dimethylpyridine-3-sulfonamide | 2 | 444 | E | 3.70 | $^1$H NMR (400 MHz, DMSO-d$_6$) δ 10.80 (s, 1H), 9.15 (s, 1H), 8.87 (dd, J = 19.5, 9.0 Hz, 1H), 8.62 (d, J = 2.4 Hz, 1H), 8.12 (dd, J = 9.0, 2.4 Hz, 1H), 7.95 (t, J = 16.4 Hz, 1H), 7.34 (dd, J = 18.5, 8.4 Hz, 1H), 7.16 (t, J = 12.5 Hz, 1H), 6.80 (d, J = 2.2 Hz, 1H), 6.75-6.62 (m, 1H), 5.89 (s, 2H), 2.75-2.61 (b, 6H). |

TABLE 3-continued

| Example | Structure | Name | Synth. Method | LCMS (ESI) m/z | LCMS Method | $R_T$ (min) | NMR |
|---|---|---|---|---|---|---|---|
| 165 | 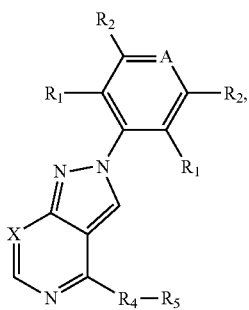 | 5-amino-3-chloro-2-(4-(6-methylpyrimidin-4-ylamino)-2H-pyrazolo[4,3-c]pyridin-2-yl)benzonitrile | 2 | 377 | E | 3.19 | $^1$H NMR (400 MHz, DMSO-$d_6$) δ 10.70 (s, 1H), 8.94 (s, 1H), 8.70 (d, J = 5.0 Hz, 1H), 8.42 (d, J = 6.1 Hz, 1H), 8.14 (d, J = 6.0 Hz, 1H), 7.09 (dd, J = 17.6, 2.5 Hz, 2H), 6.89 (d, J = 6.0 Hz, 1H), 6.40 (s, 2H), 2.44 (s, 3H). |

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as defined by the claims.

What is claimed is:

1. A compound of Formula I:

$$I$$

or pharmaceutically acceptable salts thereof, wherein
A is $CR^3$;
X is $CR^{15}$;
$R^1$ is independently hydrogen, halogen, $C_1$-$C_6$ alkyl, $C_2$-$C_6$ alkenyl, $C_2$-$C_6$ alkynyl, $C_3$-$C_6$ cycloalkyl, —$CF_3$, —$OR^6$, —$SR^6$, —$OCF_3$, —CN, —$NO_2$, —$C(O)R^6$, —$C(O)OR^6$, —$C(O)NR^6R^7$, —$S(O)_{1-2}R^6$, —$S(O)_{1-2}NR^6R^7$, —$NR^6SO_2R^7$, —$NR^6SO_2NR^6R^7$, —$NR^6C(O)R^7$, —$NR^6C(O)OR^7$, —$NR^6C(O)NR^6R^7$, —$OC(O)NR^6R^7$, —$NR^6R^7$, 3-6 membered heterocyclyl or phenyl, wherein both $R^1$ cannot be hydrogen at the same time, and wherein said alkyl, alkenyl and alkynyl are independently optionally substituted by halogen, oxo, —CN, —$OR^6$, —$NR^6R^7$ $C_3$-$C_6$ cycloalkyl, 3-6 membered heterocyclyl or phenyl, and said cycloalkyl, heterocyclyl and phenyl are independently optionally substituted by $R^{10}$;
$R^2$ and $R^3$ are each independently hydrogen, $C_1$-$C_6$ alkyl, $C_2$-$C_6$ alkenyl, $C_2$-$C_6$ alkynyl, halogen, —($C_0$-$C_3$ alkylene)CN, —($C_0$-$C_3$ alkylene)$OR^8$, —($C_0$-$C_3$ alkylene)$SR^8$, —($C_0$-$C_3$ alkylene)$NR^8R^9$, —($C_0$-$C_3$ alkylene)$CF_3$, —O($C_0$-$C_3$ alkylene)$CF_3$, —($C_0$-$C_3$ alkylene)$NO_2$, —($C_0$-$C_3$ alkylene)$C(O)R^8$, —($C_0$-$C_3$ alkylene)$C(O)OR^8$, —($C_0$-$C_3$ alkylene)$C(O)NR^8R^9$, —($C_0$-$C_3$ alkylene)$NR^8C(O)R^9$, —($C_0$-$C_3$ alkylene)$S(O)_{1-2}R^8$, —($C_0$-$C_3$ alkylene)$NR^8S(O)_{1-2}R^9$, —($C_0$-$C_3$ alkylene)$S(O)_{1-2}NR^8R^9$, —($C_0$-$C_3$ alkylene)($C_3$-$C_6$ cycloalkyl), —($C_0$-$C_3$ alkylene)(3-6-membered heterocyclyl), —($C_0$-$C_3$ alkylene)(5-6-membered heteroaryl) or —($C_0$-$C_3$ alkylene)phenyl, wherein $R^2$ and $R^3$ are each independently optionally substituted by $R^{10}$;
$R^4$ is hydrogen, —$NR^6$—, —$NR^6R^7$, —$NR^6C(O)$—, —$NR^6C(O)O$—, —$NR^6C(O)NR^7$—, —$NR^6S(O)_{1-2}$— or —$NR^6S(O)_{1-2}NR^7$—;
$R^5$ is absent, hydrogen, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3-10-membered heterocyclyl or 5-10-membered heteroaryl, wherein $R^5$ is optionally substituted by $R^{10}$;
$R^6$ and $R^7$ are each independently hydrogen, $C_1$-$C_6$ alkyl, $C_2$-$C_6$ alkenyl, $C_2$-$C_6$ alkynyl, $C_3$-$C_6$ cycloalkyl, 3-10 membered heterocyclyl or phenyl, wherein said alkyl, alkenyl and alkynyl are independently optionally substituted by halogen, oxo, —CN, —$OR^6$, —$NR^6R^7$, $C_3$-$C_6$ cycloalkyl, 3-6 membered heterocyclyl or phenyl, and said cycloalkyl, heterocyclyl and phenyl are independently optionally substituted by $R^{10}$; or
$R^6$ and $R^7$ are independently taken together with the atom to which they are attached to form a 3-10 membered heterocyclyl optionally substituted by halogen, oxo, —$OR^{11}$, —$NR^{11}R^{12}$, $C_1$-$C_6$ alkyl, $C_2$-$C_6$ alkenyl or $C_2$-$C_6$ alkynyl, wherein said alkyl, alkenyl and alkynyl are independently optionally substituted by halogen or oxo;
$R^8$ and $R^9$ are each independently hydrogen, $C_1$-$C_6$ alkyl, $C_2$-$C_6$ alkenyl, $C_2$-$C_6$ alkynyl, $C_3$-$C_6$ cycloalkyl, phenyl, 3-10-membered heterocyclyl, wherein said alkyl, alkenyl, alkynyl, cycloalkyl, phenyl and heterocyclyl are independently optionally substituted by $R^{10}$; or
$R^8$ and $R^9$ are independently taken together with the atom to which they are attached to form a 3-10 membered heterocyclyl optionally substituted by halogen, oxo, —$OR^{11}$, —$NR^{11}R^{12}$, $C_1$-$C_6$ alkyl, $C_2$-$C_6$ alkenyl or $C_2$-$C_6$ alkynyl, wherein said alkyl, alkenyl and alkynyl are independently optionally substituted by halogen or oxo;
$R^{10}$ is independently hydrogen, oxo, $C_1$-$C_{12}$ alkyl, $C_2$-$C_{12}$ alkenyl, $C_2$-$C_{12}$ alkynyl, halogen, —($C_0$-$C_3$ alkylene)CN, —($C_0$-$C_3$ alkylene)$OR^{11}$, —($C_0$-$C_3$ alkylene)$SR^{11}$, —($C_0$-$C_3$ alkylene)$NR^{11}R^{12}$, —($C_0$-$C_3$ alkylene)$CF_3$, —($C_0$-$C_3$ alkylene)$NO_2$, —($C_0$-$C_3$ alkylene)C═$NR^{11}$ (R¹²), —(C₀-C₃ alkylene)C=NR¹¹(OR¹²), —(C₀-C₃ alkylene)C(O)R¹¹, —(C₀-C₃ alkylene)C(O)OR¹¹, —(C₀-C₃ alkylene)C(O)NR¹¹R¹², —(C₀-C₃ alkylene)NR¹¹C(O)R¹², —(C₀-C₃ alkylene)S(O)₁₋₂R¹¹, —(C₀-C₃ alkylene)NR¹¹S(O)₁₋₂R¹², —(C₀-C₃ alkylene)S(O)₁₋₂NR¹¹R¹², —(C₀-C₃ alkylene)(C₃-C₆ cycloalkyl), —(C₀-C₃ alkylene)(3-10-membered heterocyclyl), —(C₀-C₃ alkylene)C(O)(3-10-membered heterocyclyl) or —(C₀-C₃ alkylene)(C₆-C₁₀ aryl), wherein R¹⁰ is independently optionally substituted by halogen, oxo, C₁-C₁₂ alkyl optionally substituted by oxo or halogen, C₂-C₁₂ alkenyl optionally substituted by oxo or halogen, C₂-C₁₂ alkynyl optionally substituted by oxo or halogen, —(C₀-C₃ alkylene)CN, —(C₀-C₃ alkylene)OR¹³, —(C₀-C₃ alkylene)SR¹³, —(C₀-C₃ alkylene)NR¹³R¹⁴, —(C₀-C₃ alkylene)CF₃, —(C₀-C₃ alkylene)NO₂, —(C₀-C₃ alkylene)C(O)R¹³, —(C₀-C₃ alkylene)C(O)OR¹³, —(C₀-C₃ alkylene)C(O)NR¹³R¹⁴, —(C₀-C₃ alkylene)NR¹³C(O)R¹⁴, —(C₀-C₃ alkylene)S(O)₁₋₂R¹³, —(C₀-C₃ alkylene)NR¹³S(O)₁₋₂R¹⁴, —(C₀-C₃ alkylene)S(O)₁₋₂NR¹³R¹⁴, —(C₀-C₃ alkylene)(C₃-C₆ cycloalkyl), —(C₀-C₃ alkylene)(3-6-membered heterocyclyl), —(C₀-C₃ alkylene)C(O)(3-6-membered heterocyclyl) or —(C₀-C₃ alkylene)phenyl;

R¹¹ and R¹² are each independently hydrogen, C₁-C₆ alkyl, C₂-C₆ alkenyl, C₂-C₆ alkynyl, C₃-C₆ cycloalkyl, phenyl or 3-6 membered heterocyclyl, wherein said alkyl, alkenyl, alkynyl, cycloalkyl, phenyl and heterocyclyl are independently optionally substituted by halogen, oxo, —CN, —OR¹⁶, —NR¹⁶R¹⁷ or C₁-C₆ alkyl optionally substituted by halogen or oxo; or R¹¹ and R¹² are taken together with the atom to which they attached to form a 3-6 membered heterocyclyl optionally substituted by halogen, oxo, —OR¹⁶, —NR¹⁶R¹⁷ or C₁-C₃ alkyl optionally substituted by halogen, oxo or OH;

R¹³ and R¹⁴ are each independently hydrogen or C₁-C₆ alkyl optionally substituted by halogen or oxo; or R¹³ and R¹⁴ are taken together with the atom to which they attached to form a 3-6 membered heterocyclyl optionally substituted by halogen, oxo or C₁-C₆ alkyl optionally substituted by halogen or oxo;

R¹⁵ is hydrogen, halogen, C₁-C₆ alkyl, C₂-C₆ alkenyl, C₂-C₆ alkynyl, —(C₀-C₃ alkylene)CN, —(C₀-C₃ alkylene)OR¹⁸, —(C₀-C₃ alkylene)SR¹⁸, —(C₀-C₃ alkylene)NR¹⁸R¹⁹, —(C₀-C₃ alkylene)CF₃, —O(C₀-C₃ alkylene)CF₃, —(C₀-C₃ alkylene)NO₂, —(C₀-C₃ alkylene)C(O)R¹⁸, —(C₀-C₃ alkylene)C(O)OR¹⁸, —(C₀-C₃ alkylene)C(O)NR¹⁸R¹⁹, —(C₀-C₃ alkylene)NR¹⁸C(O)R¹⁹, —(C₀-C₃ alkylene)S(O)₁₋₂R¹⁸, —(C₀-C₃ alkylene)NR¹⁸S(O)₁₋₂R¹⁹, —(C₀-C₃ alkylene)S(O)₁₋₂NR¹⁸R¹⁹, —(C₀-C₃ alkylene)(C₃-C₆ cycloalkyl), —(C₀-C₃ alkylene)(3-6-membered heterocyclyl) or —(C₀-C₃ alkylene)phenyl, wherein R¹⁵ is independently optionally substituted by halogen, oxo, —CN, —CF₃ or C₁-C₆ alkyl optionally substituted by oxo or halogen;

R¹⁶ and R¹⁷ are each independently hydrogen or C₁-C₆ alkyl optionally substituted by halogen or oxo; or R¹⁶ and R¹⁷ are taken together with the atom to which they attached to form a 3-6 membered heterocyclyl optionally substituted by halogen, oxo or C₁-C₆ alkyl optionally substituted by oxo or halogen; and R¹⁸ and R¹⁹ are each independently hydrogen or C₁-C₆ alkyl optionally substituted by halogen or oxo.

2. The compound of claim 1, wherein one R¹ is halogen and the other R¹ is hydrogen, halogen, C₁-C₆ alkyl, C₂-C₆ alkenyl, C₂-C₆ alkynyl, C₃-C₆ cycloalkyl, —CF₃, —OR⁶, —SR⁶, —OCF₃, —CN, —NO₂, —C(O)R⁶, —C(O)OR⁶, —C(O)NR⁶R⁷, —S(O)₁₋₂R⁶, —S(O)₁₋₂NR⁶R⁷, —NR⁶SO₂R⁷, —NR⁶SO₂NR⁶R⁷, —NR⁶C(O)R⁷, —NR⁶C(O)OR⁷, —NR⁶C(O)NR⁶R⁷, —OC(O)NR⁶R⁷, —NR⁶R⁷, 3-6 membered heterocyclyl or phenyl, wherein both R¹ cannot be hydrogen at the same time, and wherein said alkyl, alkenyl and alkynyl are independently optionally substituted by halogen, oxo, —CN, —OR⁶, —NR⁶R⁷ C₃-C₆ cycloalkyl, 3-6 membered heterocyclyl or phenyl, and said cycloalkyl, heterocyclyl and phenyl are independently optionally substituted by R¹⁰.

3. The compound of claim 1, wherein R¹ is independently Cl, F or —CN.

4. The compound of claim 1, wherein R² is hydrogen.

5. The compound of claim 1, wherein R³ is hydrogen, hydroxylmethyl, —C(O)H, ethenyl, —CN, —NH₂, F, Cl, I or —S(O)₂CH₃.

6. The compound of claim 1, wherein the portion of Formula I having the structure:

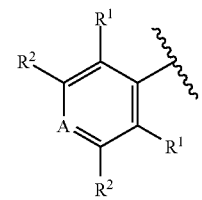

is selected from:

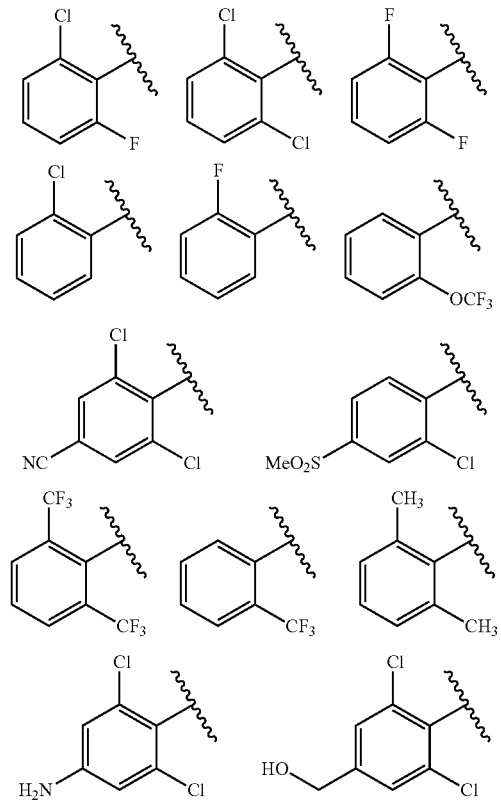

269

-continued

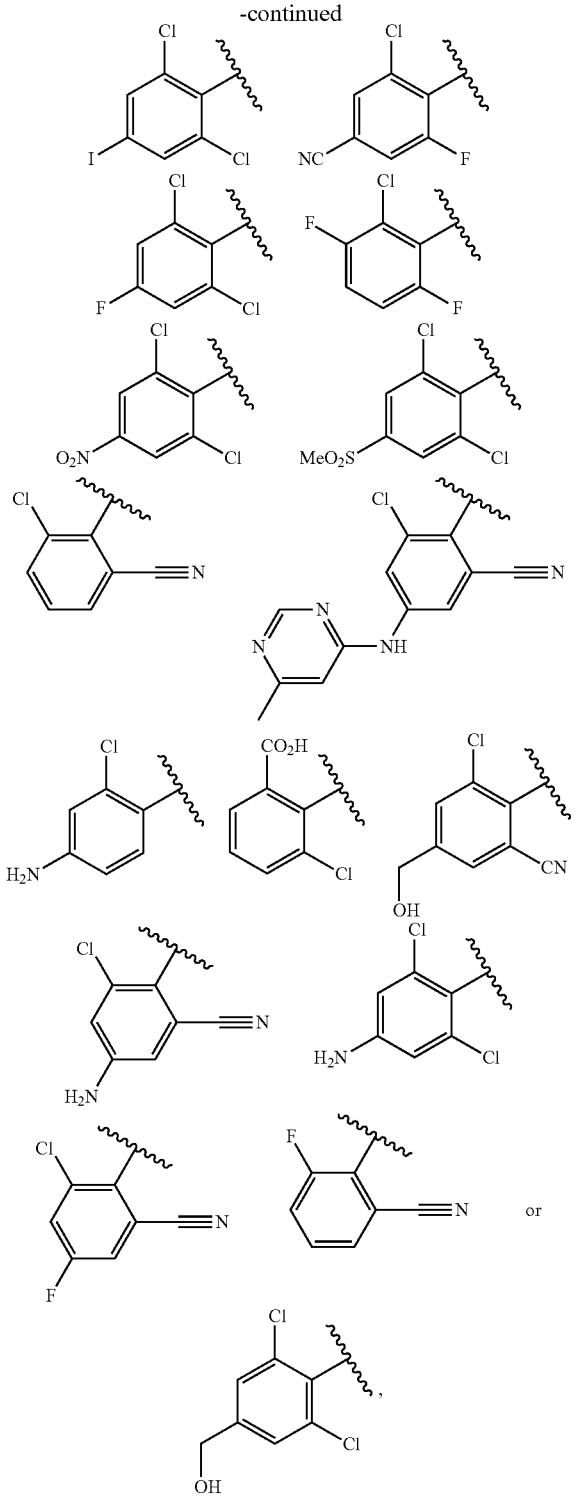

wherein the wavy lines represent the point of attachment in Formula I.

7. The compound of claim 1, wherein $R^4$ is hydrogen, —$NR^6$—, —$NR^6C(O)$—, —$NR^6C(O)O$— or —$NR^6C(O)NR^7$—.

8. The compound of claim 1, wherein $R^5$ is $C_1$-$C_6$ alkyl, $C_3$-$C_{10}$ cycloalkyl, phenyl, 3-10-membered heterocyclyl or 5-10-membered heteroaryl, wherein $R^5$ is optionally substituted by $R^{10}$.

9. The compound of claim 1, wherein $R^5$ is selected from methyl, ethyl, isopropyl, tert-butyl, —$CH_2OH$, —$CH_2NH_2$, —$CH_2N(CH_3)_2$, —$CH_2CH_2NH_2$, phenyl,

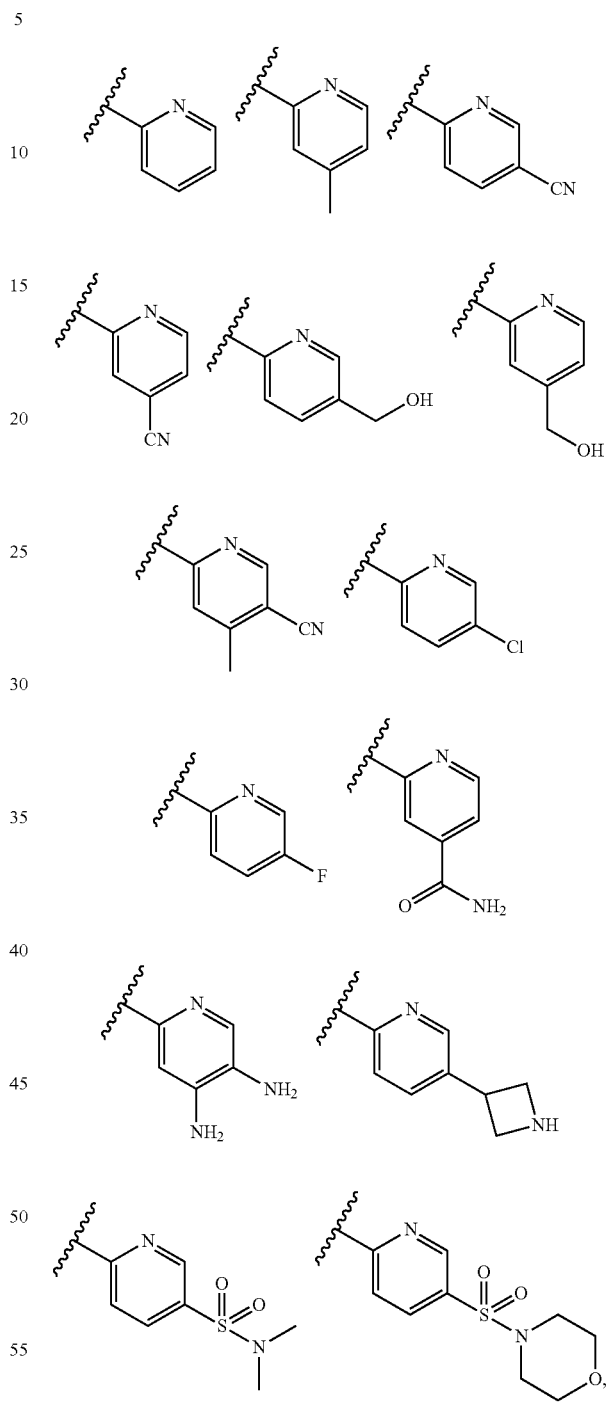

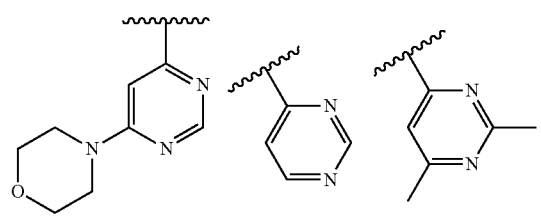

271
-continued
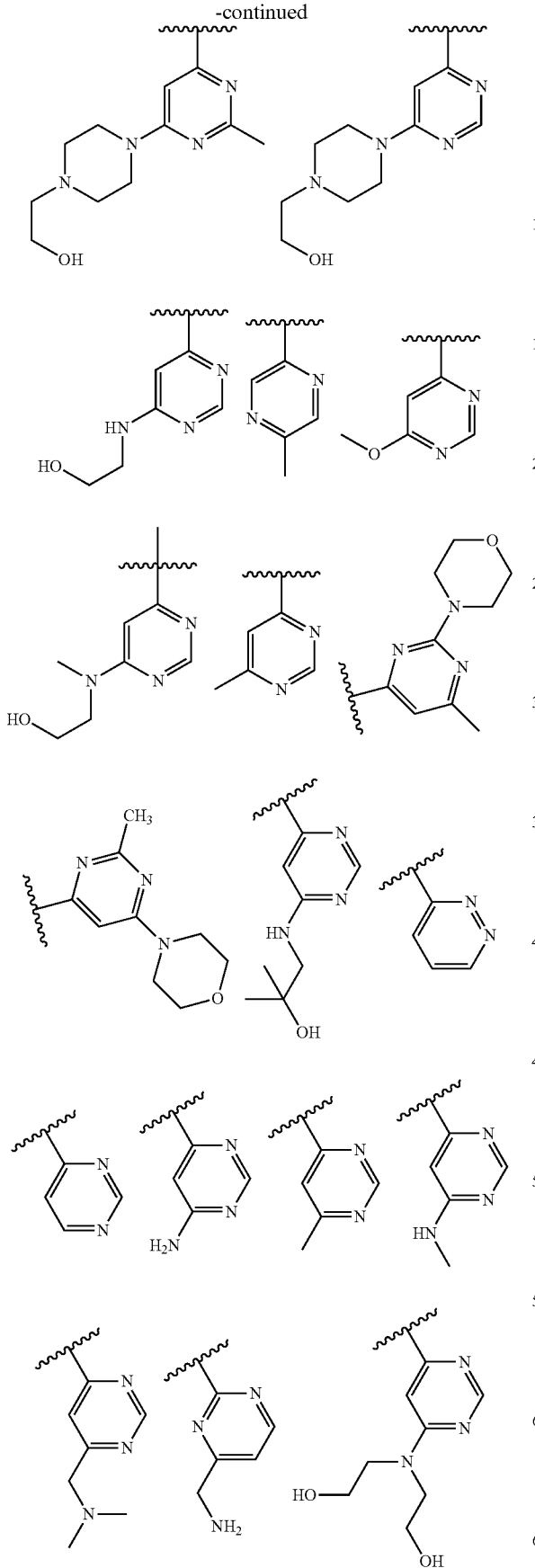
272
-continued
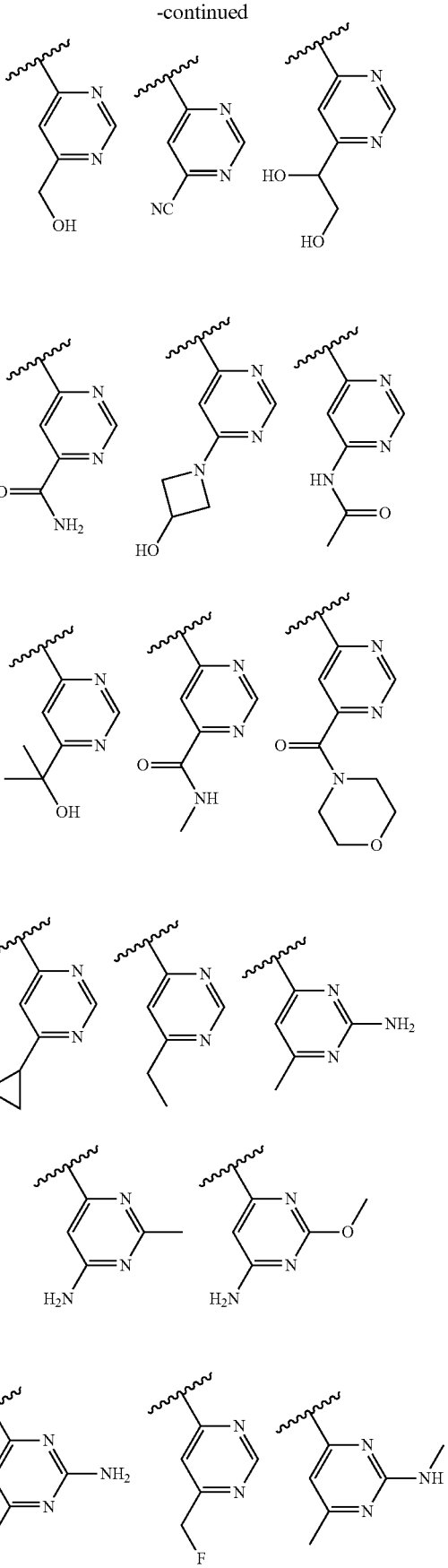

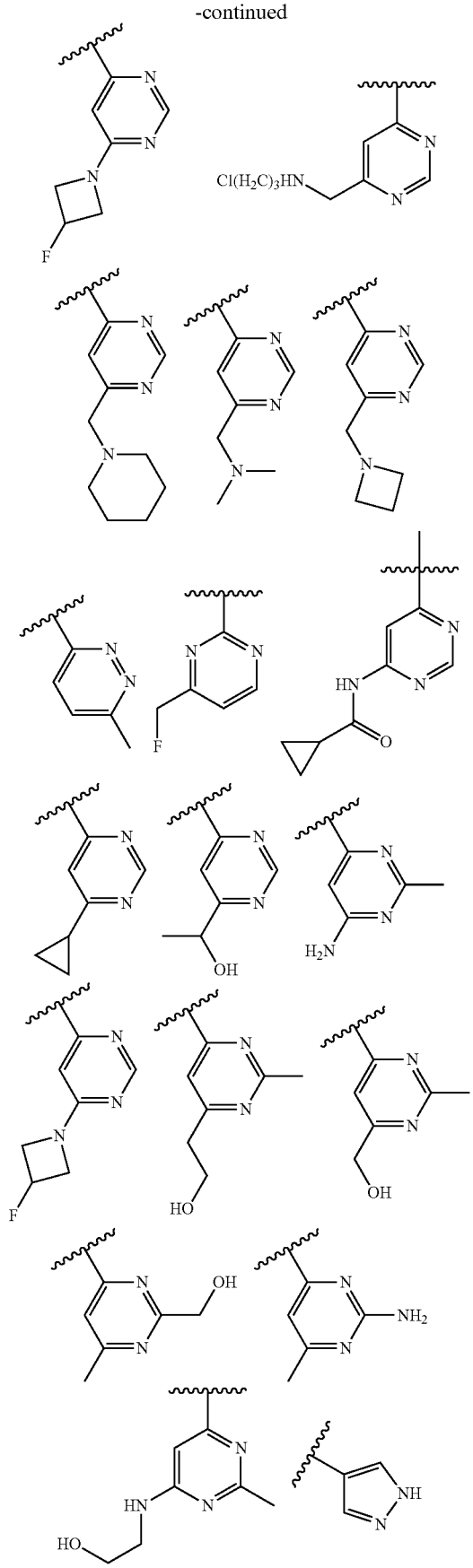

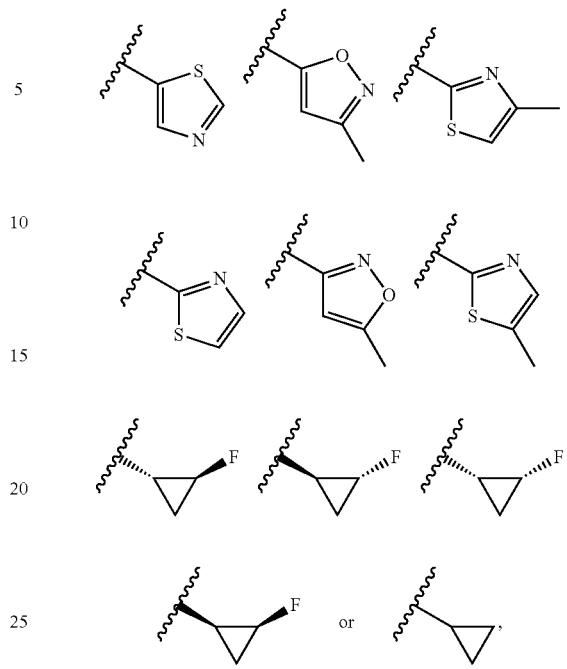

wherein the wavy line represents the point of attachment of $R^5$ in Formula I.

10. The compound of claim 1, wherein $R^8$ and $R^9$ are each independently hydrogen, $C_1$-$C_6$ alkyl, $C_2$-$C_6$ alkenyl or $C_2$-$C_6$ alkynyl, wherein said alkyl, alkenyl and alkynyl are independently optionally substituted by $R^{10}$; or $R^8$ and $R^9$ are independently taken together with the atom to which they are attached to form a 3-10 membered heterocyclyl optionally substituted by halogen, oxo, —$OR^{11}$, —$NR^{11}R^{12}$, $C_1$-$C_6$ alkyl, $C_2$-$C_6$ alkenyl or $C_2$-$C_6$ alkynyl, wherein said alkyl, alkenyl and alkynyl are independently optionally substituted by halogen or oxo.

11. The compound of claim 1, wherein $R^{11}$ is independently selected from F, Cl, —CN, methyl, ethyl, isopropyl, —$CH_2OH$, —$CH_2CH_2OH$, —$CH(OH)CH_2OH$, —$C(CH_3)_2OH$, —$CH_2NH_2$, —$CH_2N(CH_3)_2$, —$CF_3$, —OH, —$OCH_3$, —$NH_2$, —$NHCH_3$, —$NHC(O)CH_3$, —$N(CH_3)_2$, —$N(CH_2CH_2OH)_2$, —$NHCH_2CH_2OH$, —$N(CH_3)CH_2CH_2OH$, —$NHCH_2C(CH_3)_2OH$, —$N(CH_3)CH_2C(CH_3)_2OH$, —$C(O)NH_2$, —$C(O)NHCH_3$, —$C(O)N(CH_3)_2$,

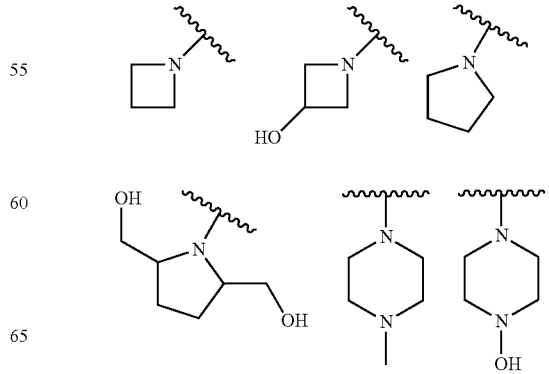

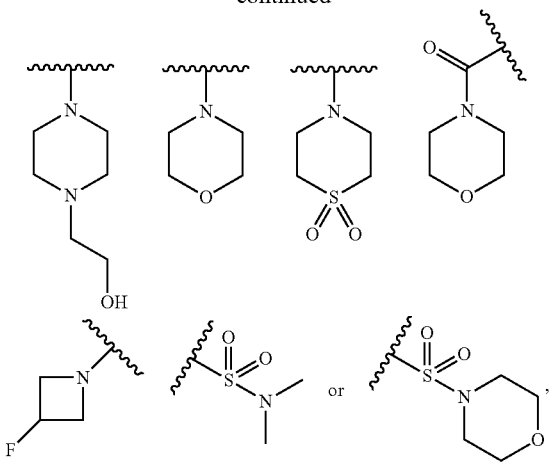

wherein the wavy line represents the point of attachment in Formula I.

12. The compound of claim 1, wherein $R^{11}$, $R^{12}$, $R^{13}$, $R^{14}$, $R^{16}$, $R^{17}$, $R^{18}$ and $R^{19}$ are independently selected from hydrogen or $C_1$-$C_6$ alkyl optionally substituted by oxo or halogen.

13. The compound of claim 1, wherein $R^{15}$ is hydrogen, F, Cl, Br, —CN, —OCH$_3$ or methyl.

14. The compound of claim 1, selected from
   i. N-(2-(2, 6-Dichlorophenyl)-2H-pyrazolo[4,3-c]pyridin-4-yl)cyclopropanecarboxamide;
   ii. [2-(2,6-Dichlorophenyl)-2H-pyrazolo[4,3-c]pyridine-4-yl]-(2,6-dimethylpyrimidin-4-yl)amine;
   iii. 6-[2-(2,6-Dichlorophenyl)-2H-pyrazolo[4,3-c]pyridin-4-ylamino]nicotinonitrile;
   iv. N-[2-(2,6-Dichlorophenyl)-2H-pyrazolo[4,3-c]pyridine-4-yl]-N'-methylpyrimidine-4,6-diamine;
   v. [2-(2,6-Dichlorophenyl)-2H-pyrazolo[4,3-c]pyridine-4-yl]-[6-(3-fluoroazetidin-1-yl)pyrimidin-4-yl]amine;
   vi. [2-(2,6-Dichlorophenyl)-2H-pyrazolo[4,3-c]pyridine-4-yl]carbamic acid methyl ester;
   vii. 1-[2-(2,6-Dichlorophenyl)-2H-pyrazolo[4,3-c]pyridine-4-yl]-3-methylurea;
   viii. N-[2-(2,6-Dichlorophenyl)-2H-pyrazolo[4,3-c]pyridin-4-yl]-pyridazine-3,6-diamine;
   ix. $N^4$-[2-(2,6-Dichlorophenyl)-2H-pyrazolo[4,3-c]pyridin-4-yl]-6-methyl-pyrimidine-2,4-diamine;
   x. N-[2-(2,6-Dichlorophenyl)-2H-pyrazolo[4,3-c]pyridin-4-yl]-2-methoxy-pyrimidine-4,6-diamine;
   xi. N-[2-(2,6-Dichlorophenyl)-2H-pyrazolo[4,3-c]pyridin-4-yl]-pyrimidine-2,4,6-triamine;
   xii. N-[2-(2,6-Dichlorophenyl)-2H-pyrazolo[4,3-c]pyridin-4-yl]-2-methyl-pyrimidine-4,6-diamine;
   xiii. $N^4$-[2-(2,6-Dichlorophenyl)-2H-pyrazolo[4,3-c]pyridin-4-yl]-6,$N^2$-dimethylpyrimidine-2,4-diamine;
   xiv. N-[2-(2,6-Dichlorophenyl)-2H-pyrazolo[4,3-c]pyridin-4-yl]-pyrimidine-4,6-diamine;
   xv. N-(2-(2-chloro-6-fluorophenyl)-2H-pyrazolo[4,3-c]pyridin-4-yl)cyclopropanecarboxamide;
   xvi. 6-[2-(2-Chloro-6-fluorophenyl)-2H-pyrazolo[4,3-c]pyridin-4-ylamino]isonicotinonitrile;
   xvii. 4-Bromo-2-(2-chloro-6-fluorophenyl)-2H-pyrazolo[4,3-c]pyridine;
   xviii. [2-(2,6-Dichloro-4-methanesulfonylphenyl)-2H-pyrazolo[4,3-c]pyridin-4-yl]-(2,6-dimethylpyrimidin-4-yl)amine;
   xix. 3,5-Dichloro-4-[4-(2,6-dimethylpyrimidin-4-ylamino)pyrazolo[4,3-c]pyridin-2-yl]benzonitrile;
   xx. 3,5-Dichloro-4-[4-(6-hydroxymethyl-pyrimidin-4-ylamino)-pyrazolo[4,3-c]pyridin-2-yl]-benzonitrile;
   xxi. 3,5-Dichloro-4-[4-(6-fluoromethyl-pyrimidin-4-ylamino)-pyrazolo[4,3-c]pyridin-2-yl]-benzonitrile;
   xxii. 4-[4-(6-Azetidin-1-ylmethylpyrimidin-4-ylamino)pyrazolo[4,3-c]pyridin-2-yl]-3,5-dichlorobenzonitrile;
   xxiii. 3,5-Dichloro-4-[4-(4-fluoromethylpyrimidin-2-ylamino)pyrazolo[4,3-c]pyridin-2-yl]benzonitrile;
   xxiv. 4-[4-(6-Amino-2-methylpyrimidin-4-ylamino)pyrazolo[4,3-c]pyridin-2-yl]-3,5-dichlorobenzonitrile;
   xxv. 4-[4-(6-Aminopyrimidin-4-ylamino)-pyrazolo[4,3-c]pyridin-2-yl]-3,5-dichloro-benzonitrile;
   xxvi. N-(6-((2-(2,6-dichloro-4-cyanophenyl)-2H-pyrazolo[4,3-c]pyridin-4-yl)amino)pyrimidin-4-yl)cyclopropanecarboxamide;
   xxvii. [2-(2,6-Dichloro-4-fluorophenyl)-2H-pyrazolo[4,3-c]pyridin-4-yl]-(6-methylpyrimidin-4-yl)amine;
   xxviii. {6-[2-(2,6-Dichloro-4-fluorophenyl)-2H-pyrazolo[4,3-c]pyridine-4-yl]-(4-methylpyridin-2-yl)}methanol;
   xxix. [2-(2,6-Dichloro-4-fluorophenyl)-2H-pyrazolo[4,3-c]pyridin-4-yl]-(6-fluoromethylpyrimidin-4-yl)amine;
   xxx. 3,5-Dichloro-4-[7-chloro-4-(6-methylpyrimidin-4-ylamino)pyrazolo[4,3-c]pyridin-2-yl]benzonitrile;
   xxxi. {6-[7-Chloro-2-(2,6-dichlorophenyl)-2H-pyrazolo[4,3-c]pyridin-4-ylamino]-pyrimidin-4-yl}-methanol;
   xxxii. N-[7-Chloro-2-(2,6-dichlorophenyl)-2H-pyrazolo[4,3-c]pyridin-4-yl]-pyrimidine-4,6-diamine;
   xxxiii. 3,5-Dichloro-4-[7-fluoro-4-(6-methyl-pyrimidin-4-ylamino)-pyrazolo[4,3-c]pyridin-2-yl]-benzonitrile;
   xxxiv. 4-[4-(6-Amino-pyrimidin-4-ylamino)-7-fluoro-pyrazolo[4,3-c]pyridin-2-yl]-3,5-dichlorobenzonitrile;
   xxxv. [2-(2,6-Dichlorophenyl)-7-fluoro-2H-pyrazolo[4,3-c]pyridin-4-yl]-(6-methyl-pyrimidin-4-yl)-amine;
   xxxvi. 4-[7-Bromo-4-(6-methyl-pyrimidin-4-ylamino)-pyrazolo[4,3-c]pyridin-2-yl]-3,5-dichlorobenzonitrile;
   xxxvii. {6-[7-Bromo-2-(2,6-dichloro-phenyl)-2H-pyrazolo[4,3-c]pyridin-4-ylamino]-pyrimidin-4-yl}-methanol;
   xxxviii. [7-Bromo-2-(2,6-dichlorophenyl)-2H-pyrazolo[4,3-c]pyridin-4-yl]-(6-methylpyrimidin-4-yl)-amine;
   xxxix. 2-(2,6-Dichlorophenyl)-4-(6-methylpyrimidin-4-ylamino)-2H-pyrazolo[4,3-c]pyridine-7-carbonitrile;
   xl. 4-(6-Aminopyrimidin-4-ylamino)-2-(2,6-dichlorophenyl)-2H-pyrazolo[4,3-c]pyridine-7-carbonitrile;
   xli. N-[7-Bromo-2-(2,6-dichlorophenyl)-2H-pyrazolo[4,3-c]pyridin-4-yl]-pyrimidine-4,6-diamine;
   xlii. {6-[2-(2,6-Dichlorophenyl)-7-methoxy-2H-pyrazolo[4,3-c]pyridin-4-ylamino]-pyrimidin-4-yl}-methanol;
   xliii. [2-(2,6-Dichloro-4-fluorophenyl)-7-fluoro-2H-pyrazolo[4,3-c]pyridin-4-yl]-(6-methylpyrimidin-4-yl)-amine;
   xliv. [2-(2,6-Dichlorophenyl)-2H-pyrazolo[4,3-c]pyridine-4-yl]pyrimidin-4-ylamine;
   xlv. 2-[2-(2,6-Dichlorophenyl)-2H-pyrazolo[4,3-c]pyridin-4-ylamino]isonicotinonitrile;
   xlvi. [2-(2,6-Dichlorophenyl)-2H-pyrazolo[4,3-c]pyridine-4-yl]-(6-methylpyrimidin-4-yl)amine;
   xlvii. [2-(2,6-Dichlorophenyl)-2H-pyrazolo[4,3-c]pyridin-4-yl]-(6-morpholin-4-ylpyrimidin-4-yl)amine;
   xlviii. {6-[2-(2,6-Dichlorophenyl)-2H-pyrazolo[4,3-c]pyridin-4-ylamino]pyrimidin-4-yl}methanol;
   xlix. 2-(4-(6-((2-(2,6-dichlorophenyl)-2H-pyrazolo[4,3-c]pyridin-4-yl)amino)pyrimidin-4-yl)piperazin-1-yl)ethan-1-ol
   l. 1-{6-[2-(2,6-Dichlorophenyl)-2H-pyrazolo[4,3-c]pyridin-4-ylamino]pyrimidin-4-yl}azetidin-3-ol;

li. {2-[2-(2,6-Dichlorophenyl)-2H-pyrazolo[4,3-c]pyridin-4-ylamino]pyridin-4-yl}methanol;
lii. [2-(2,6-Dichlorophenyl)-2H-pyrazolo[4,3-c]pyridin-4-yl]-(5-fluoropyridin-2-yl)amine;
liii. 6-[2-(2,6-Dichlorophenyl)-2H-pyrazolo[4,3-c]pyridin-4-ylamino]-4-methylnicotinonitrile;
liv. 6-[2-(2,6-Dichlorophenyl)-2H-pyrazolo[4,3-c]pyridin-4-ylamino]pyrimidine-4-carbonitrile;
lv. 2-[2-(2,6-Dichloro-phenyl)-2H-pyrazolo[4,3-c]pyridin-4-ylamino]-isonicotinamide;
lvi. [2-(2,6-Dichlorophenyl)-2H-pyrazolo[4,3-c]pyridin-4-yl]-(6-methoxypyrimidin-4-yl)amine;
lvii. [2-(2,6-Dichlorophenyl)-2H-pyrazolo[4,3-c]pyridin-4-yl]-(6-methylpyridazin-3-yl)amine;
lviii. [2-(2,6-Dichlorophenyl)-2H-pyrazolo[4,3-c]pyridin-4-yl]-(5-methylpyrazin-2-yl)amine;
lix. 6-[2-(2,6-Dichloro-phenyl)-2H-pyrazolo[4,3-c]pyridin-4-ylamino]-pyrimidine-4-carboxylic acid amide;
lx. N-{6-[2-(2,6-Dichloro-phenyl)-2H-pyrazolo[4,3-c]pyridin-4-ylamino]-pyrimidin-4-yl}-acetamide;
lxi. 2-{6-[2-(2,6-Dichlorophenyl)-2H-pyrazolo[4,3-c]pyridin-4-ylamino]pyrimidin-4ylamino}ethanol;
lxii. 1-{6-[2-(2,6-Dichlorophenyl)-2H-pyrazolo[4,3-c]pyridin-4-ylamino]pyrimidin-4-ylamino}-2-methylpropan-2-ol;
lxiii. [2-(2-Chloro-6-fluorophenyl)-2H-pyrazolo[4,3-c]pyridine-4-yl]-(6-methylpyrimidin-4-yl)amine;
lxiv. [2-(2-Chloro-6-fluorophenyl)-2H-pyrazolo[4,3-c]pyridine-4-yl]-(2,6-dimethylpyrimidin-4-yl)amine;
lxv. {6-[2-(2-Chloro-6-fluoro-phenyl)-2H-pyrazolo[4,3-c]pyridin-4-ylamino]-pyrimidin-4-yl}-methanol;
lxvi. {6-[2-(2,6-Dichloro-4-methanesulphonylphenyl)-2H-pyrazolo[4,3-c]pyridine-4-ylamino]pyrimidin-4-yl}methanol;
lxvii. N-(2-(2,6-dichloro-4-(methylsulfonyl)phenyl)-2H-pyrazolo[4,3-c]pyridin-4-yl)cyclopropanecarboxamide;
lxviii. 3,5-Dichloro-4-[4-(6-methylpyrimidin-4-ylamino)pyrazolo[4,3-c]pyridin-2-yl]benzonitrile;
lxix. N-(2-(2,6-dichloro-4-cyanophenyl)-2H-pyrazolo[4,3-c]pyridin-4-yl)cyclopropanecarboxamide;
lxx. 3,5-Dichloro-4-[4-(6-ethyl-pyrimidin-4-ylamino)-pyrazolo[4,3-c]pyridin-2-yl]-benzonitrile;
lxxi. 3,5-Dichloro-4-[4-(6-cyclopropylpyrimidin-4-ylamino)pyrazolo[4,3-c]pyridin-2-yl]benzonitrile;
lxxii. 3,5-Dichloro-4-[4-(6-dimethylaminomethylpyrimidin-4-ylamino)pyrazolo[4,3-c]pyridine-2-yl]benzonitrile;
lxxiii. 3,5-Dichloro-4-[4-(6-piperidin-1-ylmethylpyrimidin-4-ylamino)pyrazolo[4,3-c]pyridine-2-yl]benzonitrile;
lxxiv. [2-(2,6-Dichloro-4-fluorophenyl)-2H-pyrazolo[4,3-c]pyridine-4-yl]-(4-methylpyridin-2-yl)amine;
lxxv. [2-(2,6-Dichloro-4-fluorophenyl)-2H-pyrazolo[4,3-c]pyridine-4-yl]-(2,6-dimethylpyridin-2-yl)amine;
lxxvi. (5-Chloropyridin-2-yl)-[2-(2,6-dichloro-4-fluorophenyl)-2H-pyrazolo[4,3-c]pyridine-4-yl]amine;
lxxvii. 3,5-Dichloro-4-[7-chloro-4-(6-hydroxymethylpyrimidin-4-ylamino)pyrazolo[4,3-c]pyridin-2-yl]benzonitrile;
lxxviii. 3,5-Dichloro-4-[7-fluoro-4-(6-hydroxymethylpyrimidin-4-ylamino)-pyrazolo[4,3-c]pyridin-2-yl]-benzonitrile;
lxxix. {6-[2-(2,6-Dichloro-phenyl)-7-fluoro-2H-pyrazolo[4,3-c]pyridin-4-ylamino]-pyrimidin-4-yl}-methanol;
lxxx. {6-[2-(2,6-Dichloro-4-fluoro-phenyl)-7-fluoro-2H-pyrazolo[4,3-c]pyridin-4-ylamino]-pyrimdin-4-yl}-methanol;
lxxxi. N4-(2-(2-chloro-3,6-difluorophenyl)-2H-pyrazolo[4,3-c]pyridin-4-yl)pyrimidine-4,6-diamine;
lxxxii. 2-((6-(2-(2-chloro-3,6-difluorophenyl)-2H-pyrazolo[4,3-c]pyridin-4-ylamino)pyrimidin-4-yl)(methyl)amino)ethanol;
lxxxiii. 2-(4-(6-(2-(2-chloro-3,6-difluorophenyl)-2H-pyrazolo[4,3-c]pyridin-4-ylamino)pyrimidin-4-yl)piperazin-1-yl)ethanol;
lxxxiv. 3-(2-(2-chloro-3,6-difluorophenyl)-2H-pyrazolo[4,3-c]pyridin-4-ylamino)-1-methylpyridin-2(1H)-one;
lxxxv. 2-(2-(2-chloro-3,6-difluorophenyl)-2H-pyrazolo[4,3-c]pyridin-4-ylamino)pyrimidin-4(3H)-one;
lxxxvi. 2-(4-amino-2,6-dichlorophenyl)-N-(6-methylpyrimidin-4-yl)-2H-pyrazolo[4,3-c]pyridin-4-amine;
lxxxvii. N4-(2-(4-amino-2,6-dichlorophenyl)-2H-pyrazolo[4,3-c]pyridin-4-yl)pyrimidine-4,6-diamine;
lxxxviii. 3-chloro-2-(4-(6-methylpyrimidin-4-ylamino)-2H-pyrazolo[4,3-c]pyridin-2-yl)benzonitrile
lxxxix. 3-Chloro-2-[7-fluoro-4-(6-methylpyrimidin-4-ylamino)pyrazolo[4,3-c]pyridin-2-yl]-5-hydroxy methyl benzonitrile;
xc. {3,5-Dichloro-4-[7-fluoro-4-(6-methylpyrimidin-4-ylamino)pyrazolo[4,3-c]pyridin-2-yl]phenyl}methanol;
xci. {4-[2-(2-Chloro-6-fluoro-phenyl)-7-fluoro-2H-pyrazolo[4,3-c]pyridin-4-ylamino]-6-methyl-pyrimidin-2-yl}-methanol;
xcii. 4-[4-(6-Aminopyrimidin-4-ylamino)-7-chloropyrazolo[4,3-c]pyridin-2-yl]-3,5-dichlorobenzonitrile;
xciii. N-[2-(2,6-Dichlorophenyl)-7-fluoro-2H-pyrazolo[4,3-c]pyridin-4-yl]pyrimidine-4,6-diamine;
xciv. N-{6-[2-(2,6-Dichlorophenyl)-7-fluoro-2H-pyrazolo[4,3-c]pyridin-4-ylamino]-pyrimidin-4-yl}-acetamide;
xcv. 1-{6-[2-(2,6-Dichlorophenyl)-2H-pyrazolo[4,3-c]pyridin-4-ylamino]-pyrimidin-4-yl}-ethanol;
xcvi. (6-Cyclopropylpyrimidin-4-yl)-[2-(2,6-dichlorophenyl)-2H-pyrazolo[4,3-c]pyridin4-yl]-amine;
xcvii. 3-Chloro-2-[7-fluoro-4-(6-methylpyrimidin-4-ylamino)-pyrazolo[4,3-c]pyridin-2-yl]-benzonitrile;
xcviii. 3-Chloro-2-{7-fluoro-4-[6-(1-hydroxyethyl)-pyrimidin-4-ylamino]-pyrazolo[4,3-c]pyridin-2-yl}-benzonitrile;
xcix. 2-[4-(6-Amino-2-methylpyrimid-4-ylamino)-7-fluoropyrazolo[4,3-c]pyridin-2-yl]-3-chlorobenzonitrile;
c. 2-[4-(5-Azetidin-3-yl-pyridin-2-ylamino)-7-fluoropyrazolo[4,3-c]pyridin-2-yl]-3-chlorobenzonitrile;
ci. [2-(4-Amino-2,6-dichlorophenyl)-7-fluoro-2H-pyrazolo[4,3-c]pyridin-4-yl]-(6-methylpyrimidin-4-yl)-amine;
cii. 5-Amino-3-chloro-2-[7-fluoro-4-(6-methylpyrimidin-4-ylamino)-pyrazolo[4,3-c]pyridin-2-yl]benzonitrile;
ciii. 5-Amino-2-[4-(6-aminopyrimidin-4-ylamino)-7-fluoropyrazolo[4,3-c]pyridin-2-yl]-3-chlorobenzonitrile;
civ. N-[2-(2,6-Dichlorophenyl)-7-methyl-2H-pyrazolo[4,3-c]pyridin-4-yl]-pyrimidine-4,6-diamine;
cv. 3-Chloro-5-fluoro-2-[7-fluoro-4-(6-methylpyrimidin-4-ylamino)-pyrazolo[4,3-c]pyridin-2-yl]-benzonitrile;
cvi. 2-[4-(6-Amino-2-methylpyrimidin-4-ylamino)-7-fluoropyrazolo[4,3-c]pyridin-2-yl]-3-chloro-5-fluorobenzonitrile;

cvii. 3-Chloro-5-fluoro-2-{7-fluoro-4-[6-(3-fluoroazetidin-1-yl)pyrimidin-4-ylamino]pyrazolo[4,3-c]pyridin-2-yl}benzonitrile;

cviii. 3-Chloro-5-fluoro-2-{7-fluoro-4-[6-(2-hydroxyethylamino)-2-methylpyrimidin-4-ylamino]pyrazolo[4,3-c]pyridin-2-yl}benzonitrile;

cix. 2-[4-(2,6-Dimethylpyrimidin-4-ylamino)-7-fluoropyrazolo[4,3-c]pyridin-2-yl]-3-fluorobenzonitrile;

cx. N-[2-(2-Chloro-6-fluorophenyl)-7-fluoro-2H-pyrazolo[4,3-c]pyridin-4-yl]-2-methylpyrimidine-4,6-diamine;

cxi. [2-(2-Chloro-6-fluorophenyl)-7-fluoro-2H-pyrazolo[4,3-c]pyridin-4-yl]-(2,6-dimethylpyrimidin-4-yl)amine;

cxii. {6-[2-(2-Chloro-6-fluorophenyl)-7-fluoro-2H-pyrazolo[4,3-c]pyridin-4-ylamino]-2-methylpyrimidin-4-yl}-methanol;

cxiii. 3,5-Dichloro-4-[7-fluoro-4-(6-hydroxymethylpyrimidin-4-ylamino)-pyrazolo-[4,3-c]pyridin-2-yl]-benzonitrile;

cxiv. 3,5-Dichloro-4-{7-fluoro-4-[6-(1-hydroxyethyl)-pyrimidin-4-ylamino]-pyrazolo-[4,3-c]pyridin-2-yl}-benzonitrile;

cxv. [7-Chloro-2-(2,6-dichlorophenyl)-2H-pyrazolo[4,3-c]pyridin-4-yl]-(6-methylpyrimidin-4-yl)-amine;

cxvi. 2-(2,6-Dichlorophenyl)-4-(6-hydroxymethylpyrimidin-4-ylamino)-2H-pyrazolo[4,3-c]pyridine-7-carbonitrile;

cxvii. 3-Chloro-2-[7-fluoro-4-(-6-hydroxymethylpyrimidin-4-ylamino)-pyrazolo[4,3-c]pyridin-2-yl]-benzonitrile;

cxviii. N-{6-[2-(2-Chloro-6-cyanophenyl)-7-fluoro-2H-pyrazolo[4,3-c]pyridin-4-ylamino]-pyrimidin-4-yl}-acetamide;

cxix. 2-[4-(6-Aminopyrimidin-4-ylamino)-7-fluoropyrazolo[4,3-c]pyridin-2-yl]-3-chlorobenzonitrile;

cxx. N-(2-(2-chloro-6-cyanophenyl)-7-fluoro-2H-pyrazolo[4,3-c]pyridin-4-yl)cyclopropanecarboxamide;

cxxi. 3-Chloro-2-[4-(2,6-dimethylpyrimidin-4-ylamino)-7-fluoropyrazolo[4,3-c]pyridin-2-yl]benzonitrile;

cxii. 2-[4-(2-Amino-6-methylpyrimidin-4-ylamino)-7-fluoropyrazolo[4,3-c]pyridin-2-yl]-3-chlorobenzonitrile;

cxxiii. 3-Chloro-2-[7-fluoro-4-(2-hydroxymethyl-6-methylpyrimidin-4-ylamino)-pyrazolo[4,3-c]pyridin-2-yl]-benzonitrile;

cxxiv. 3-Chloro-2-[7-fluoro-4-(6-hydroxymethyl-2-methylpyrimidin-4-ylamino)-pyrazolo[4,3-c]pyridin-2-yl]-benzonitrile;

cxxv. 3-Chloro-2-[4-(6-cyclopropylpyrimidin-4-ylamino)-7-fluoropyrazolo[4,3-c]pyridin-2-yl]-benzonitrile;

cxxvi. N-[2-(4-Amino-2,6-dichlorophenyl)-7-fluoro-2H-pyrazolo[4,3-c]pyridin-4-yl]-benzene-1,3-diamine;

cxxvii. {6-[2-(4-Amino-2,6-dichlorophenyl)-7-fluoro-2H-pyrazolo[4,3-c]pyridin-4-ylamino]-pyrimidin-4-yl}-methanol;

cxxviii. N-(2-(4-amino-2,6-dichlorophenyl)-7-fluoro-2H-pyrazolo[4,3-c]pyridin-4-yl)cyclopropanecarboxamide;

cxxix. N-(2-(4-amino-2-chloro-6-cyanophenyl)-7-fluoro-2H-pyrazolo[4,3-c]pyridin-4-yl)cyclopropanecarboxamide;

cxxx. 2-(2,6-dichlorophenyl)-7-methyl-N-(6-methylpyrimidin-4-yl)-2H-pyrazolo[4,3-c]pyridin-4-amine;

cxxxi. 3-Chloro-5-fluoro-2-[7-fluoro-4-(6-hydroxymethyl-pyrimidin-4-ylamino)-pyrazolo[4,3-c]pyridin-2-yl]-benzonitrile;

cxxxii. 2-[4-(6-Aminopyrimidin-4-ylamino)-7-fluoropyrazolo[4,3-c]pyridin-2-yl]-3-chloro-5-fluorobenzonitrile;

cxxxiii. 3-Chloro-2-[4-(6-cyclopropylpyrimidin-4-ylamino)-7-fluoropyrazolo[4,3-c]pyridin-2-yl]-5-fluorobenzonitrile;

cxxxiv. N-(2-(2-chloro-6-cyano-4-fluorophenyl)-7-fluoro-2H-pyrazolo[4,3-c]pyridin-4-yl)cyclopropanecarboxamide;

cxxxv. 3-Chloro-2-[4-(2,6-dimethylpyrimidin-4-ylamino)-7-fluoropyrazolo[4,3-c]pyridin-2-yl]-5-fluorobenzonitrile;

cxxxvi. 2-[4-(2-Amino-6-methylpyrimidin-4-ylamino)-7-fluoro-pyrazolo[4,3-c]pyridin-2-yl]-3-chloro-5-fluorobenzonitrile;

cxxxvii. 3-Chloro-5-fluoro-2-[7-fluoro-4-(2-hydroxymethyl-6-methylpyrimidin-4-ylamino)-pyrazolo[4,3-c]pyridin-2-yl]-benzonitrile;

cxxxviii. 3-Chloro-5-fluoro-2-[7-fluoro-4-(6-hydroxymethyl-2-methylpyrimidin-4-ylamino)-pyrazolo[4,3-c]pyridin-2-yl]-benzonitrile;

cxxxix. 2-[4-(6-Aminopyrimidin-4-ylamino)-7-fluoropyrazolo[4,3-c]pyridin-2-yl]-3-fluorobenzonitrile;

cxl. 2-[4-(6-Amino-2-methylpyrimidin-4-ylamino)-7-fluoropyrazolo[4,3-c]pyridin-2-yl]-3-fluorobenzonitrile;

cxli. 2-[4-(2-Amino-6-methylpyrimidin-4-ylamino)-7-fluoropyrazolo[4,3-c]pyridin-2-yl]-3-fluorobenzonitrile;

cxlii. 3-Fluoro-2-[7-fluoro-4-(6-hydroxymethyl-2-methylpyrimidin-4-ylamino)-pyrazolo[4,3-c]pyridin-2-yl]-benzonitrile;

cxliii. 3-Fluoro-2-[7-fluoro-4-(2-hydroxymethyl-6-methylpyrimidin-4-ylamino)-pyrazolo[4,3-c]pyridin-2-yl]-benzonitrile;

cxliv. {6-[2-(2-Chloro-6-fluorophenyl)-7-fluoro-2H-pyrazolo[4,3-c]pyridin-4-ylamino]pyrimidin-4-yl}methanol;

cxlv. N$^4$-[2-(2-Chloro-6-fluorophenyl)-7-fluoro-2H-pyrazolo[4,3-c]pyridin-4-yl]-6-methylpyrimidine-2,4-diamine;

cxlvi. 2-{6-[2-(2-Chloro-6-fluorophenyl)-7-fluoro-2H-pyrazolo[4,3-c]pyridin-4-ylamino]-2-methylpyrimidin-4-ylamino}-ethanol;

cxlvii. N-{6-[2-(2-Chloro-6-fluorophenyl)-7-fluoro-2H-pyrazolo[4,3-c]pyridin-4-ylamino]-pyrimidin-4-yl}-acetamide;

cxlviii. (5-Azetidin-3-yl-pyridin-2-yl)-[2-(2-chloro-6-fluorophenyl)-7-fluoro-2H-pyrazolo[4,3-c]pyridin-4-yl]-amine;

cxlix. 2-(4-(6-aminopyrimidin-4-ylamino)-7-chloro-2H-pyrazolo[4,3-c]pyridin-2-yl)-3-chlorobenzonitrile;

cl. 3-chloro-2-(4-(6-(hydroxymethyl)pyrimidin-4-ylamino)-2H-pyrazolo[4,3-c]pyridin-2-yl)benzonitrile;

cli. 3-chloro-2-(7-chloro-4-(6-(hydroxymethyl)pyrimidin-4-ylamino)-2H-pyrazolo[4,3-c]pyridin-2-yl)benzonitrile;

clii. 5-amino-2-(4-(6-aminopyrimidin-4-ylamino)-2H-pyrazolo[4,3-c]pyridin-2-yl)-3-chlorobenzonitrile;

cliii. 2-(4-(6-aminopyrimidin-4-ylamino)-2H-pyrazolo[4,3-c]pyridin-2-yl)-3-chlorobenzoic acid;

cliv. 2-(4-(6-aminopyrimidin-4-ylamino)-2H-pyrazolo[4,3-c]pyridin-2-yl)-3-fluorobenzonitrile;

clv. 3-fluoro-2-(4-(6-methylpyrimidin-4-ylamino)-2H-pyrazolo[4,3-c]pyridin-2-yl)benzonitrile;
clvi. 3-chloro-5-(6-methylpyrimidin-4-ylamino)-2-(4-(6-methylpyrimidin-4-ylamino)-2H-pyrazolo[4,3-c]pyridin-2-yl)benzonitrile;
clvii. 2-(4-amino-2,6-dichlorophenyl)-N-(2,6-dimethylpyrimidin-4-yl)-2H-pyrazolo[4,3-c]pyridin-4-amine;
clviii. N-(7-chloro-2-(2-chloro-6-cyanophenyl)-2H-pyrazolo[4,3-c]pyridin-4-yl)cyclopropanecarboxamide;
clix. N-(2-(2-chloro-6-cyanophenyl)-2H-pyrazolo[4,3-c]pyridin-4-yl)cyclopropanecarboxamide;
clx. N-(2-(4-amino-2,6-dichlorophenyl)-2H-pyrazolo[4,3-c]pyridin-4-yl)cyclopropanecarboxamide;
clxi. 2-(4-amino-2-chlorophenyl)-N-(5-(morpholinosulfonyl)pyridin-2-yl)-2H-pyrazolo[4,3-c]pyridin-4-amine;
clxii. 6-(2-(4-amino-2-chlorophenyl)pyrazolo[4,3-c]pyridin-4-ylamino)-N,N-dimethylpyridine-3-sulfonamide; and
clxiii. 5-amino-3-chloro-2-(4-(6-methylpyrimidin-4-ylamino)-2H-pyrazolo[4,3-c]pyridin-2-yl)benzonitrile, or a pharmaceutically acceptable salt thereof.

15. A pharmaceutical composition comprising a compound of claim 1 and a pharmaceutically acceptable carrier, adjuvant or vehicle.

16. A method for the manufacture of a compound of claim 1, comprising reacting, in the presence of a base and exposure to heat, a compound of formula (iii):

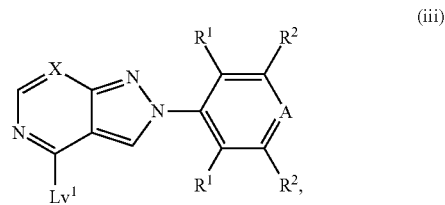

(iii)

wherein $Lv^1$ is a leaving group, with a compound of the formula $H-R^4-R^5$ under transition metal catalyzed conditions.

* * * * *